(12) United States Patent
Hofmeister et al.

(10) Patent No.: US 11,897,911 B2
(45) Date of Patent: Feb. 13, 2024

(54) NUCLEOTIDE PRECURSORS, NUCLEOTIDE ANALOGS AND OLIGOMERIC COMPOUNDS CONTAINING THE SAME

(71) Applicant: Sanofi, Paris (FR)

(72) Inventors: Armin Hofmeister, Frankfurt am Main (DE); Kerstin Jahn-Hofmann, Frankfurt am Main (DE)

(73) Assignee: Sanofi, Paris (FR)

( * ) Notice: Subject to any disclaimer, the term of this patent is extended or adjusted under 35 U.S.C. 154(b) by 406 days.

(21) Appl. No.: 16/978,603

(22) PCT Filed: Mar. 6, 2019

(86) PCT No.: PCT/EP2019/055546
§ 371 (c)(1),
(2) Date: Sep. 4, 2020

(87) PCT Pub. No.: WO2019/170731
PCT Pub. Date: Sep. 12, 2019

(65) Prior Publication Data
US 2021/0115075 A1   Apr. 22, 2021

(30) Foreign Application Priority Data

Mar. 7, 2018  (EP) ................................. 18305239
Nov. 15, 2018 (EP) ................................. 18306497

(51) Int. Cl.
*C07F 9/655* (2006.01)
*C07F 9/6558* (2006.01)
*C07F 9/6561* (2006.01)
*C07H 15/26* (2006.01)

(52) U.S. Cl.
CPC ...... *C07F 9/65583* (2013.01); *C07F 9/65616* (2013.01); *C07H 15/26* (2013.01)

(58) Field of Classification Search
CPC .................. C07F 9/65583; C07F 9/65616
See application file for complete search history.

(56) References Cited

U.S. PATENT DOCUMENTS

| | | | |
|---|---|---|---|
| 3,687,808 A | 8/1972 | Clercq et al. | |
| 4,469,863 A | 9/1984 | Ts'o et al. | |
| 4,476,301 A | 10/1984 | Imbach et al. | |
| 5,023,243 A | 6/1991 | Tullis | |
| 5,034,506 A | 7/1991 | Summerton et al. | |
| 5,166,315 A | 11/1992 | Summerton et al. | |
| 5,177,196 A | 1/1993 | Meyer, Jr. et al. | |
| 5,185,444 A | 2/1993 | Summerton et al. | |
| 5,188,897 A | 2/1993 | Suhadolnik et al. | |
| 5,192,749 A | 3/1993 | O-Yang et al. | |
| 5,194,599 A | 3/1993 | Froehler et al. | |
| 5,214,134 A | 5/1993 | Weis et al. | |
| 5,216,141 A | 6/1993 | Benner | |
| 5,235,033 A | 8/1993 | Summerton et al. | |
| 5,264,423 A | 11/1993 | Cohen et al. | |
| 5,264,562 A | 11/1993 | Matteucci | |
| 5,264,564 A | 11/1993 | Matteucci | |
| 5,276,019 A | 1/1994 | Cohen et al. | |
| 5,278,302 A | 1/1994 | Caruthers et al. | |
| 5,286,717 A | 2/1994 | Cohen et al. | |
| 5,321,131 A | 6/1994 | Agrawal et al. | |

(Continued)

FOREIGN PATENT DOCUMENTS

WO   1993023569 A1   11/1993
WO   1994002595 A1   2/1994

(Continued)

OTHER PUBLICATIONS

PubChem CID 130138745, National Center for Biotechnology Information. PubChem Compound Summary for CID 130138745, 5-(1,4-Dioxan-2-yl)pyrimidin-2-amine. https://pubchem.ncbi.nlm.nih.gov/compound/130138745. Accessed Jul. 22, 2022, create date Oct. 7, 2017. (Year: 2017).*

(Continued)

*Primary Examiner* — Laura L Stockton
(74) *Attorney, Agent, or Firm* — K&L Gates LLP

(57) ABSTRACT

The present disclosure relates to novel nucleotide precursors and nucleotide analogs that can be incorporated into oligonucleotides, including double-stranded oligonucleotides such as siRNAs. Oligonucleotides containing these analogs have superior biological activity, for example, increased in vitro stability and improved in vivo potency especially duration of action. The improved oligonucleotides are useful for silencing (e.g., reducing or eradicating) the expression of a target gene. In particular embodiments, this invention encompasses specific nucleotide analogs to be included in double-stranded RNAs (dsRNAs), and especially in siRNAs, that can hybridize to messenger RNAs (mRNAs) of interest, so as to reduce or block the expression of target genes of interest. The present compounds have general formula (I), wherein each of Ra, Rb, Rc and Rd is independently, H or a (C1-C6) alkyl group and B is a heterocyclic nucleobase.

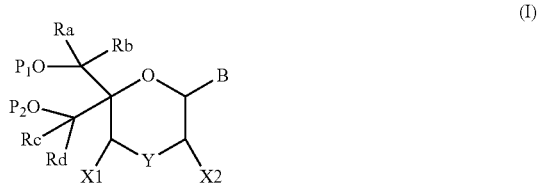

(I)

19 Claims, 18 Drawing Sheets
Specification includes a Sequence Listing.

(56) References Cited

U.S. PATENT DOCUMENTS

| | | |
|---|---|---|
| 5,399,676 A | 3/1995 | Froehler |
| 5,405,938 A | 4/1995 | Summerton et al. |
| 5,405,939 A | 4/1995 | Suhadolnik et al. |
| 5,432,272 A | 7/1995 | Benner |
| 5,434,257 A | 7/1995 | Matteucci et al. |
| 5,453,496 A | 9/1995 | Caruthers et al. |
| 5,455,233 A | 10/1995 | Spielvogel et al. |
| 5,466,677 A | 11/1995 | Baxter et al. |
| 5,470,967 A | 11/1995 | Huie et al. |
| 5,476,925 A | 12/1995 | Letsinger et al. |
| 5,489,677 A | 2/1996 | Sanghvi et al. |
| 5,519,126 A | 5/1996 | Hecht |
| 5,527,899 A | 6/1996 | Froehler |
| 5,536,821 A | 7/1996 | Agrawal et al. |
| 5,541,306 A | 7/1996 | Agrawal et al. |
| 5,541,307 A | 7/1996 | Cook et al. |
| 5,550,111 A | 8/1996 | Suhadolnik et al. |
| 5,561,225 A | 10/1996 | Maddry et al. |
| 5,563,253 A | 10/1996 | Agrawal et al. |
| 5,565,555 A | 10/1996 | Froehler et al. |
| 5,571,799 A | 11/1996 | Tkachuk et al. |
| 5,587,361 A | 12/1996 | Cook et al. |
| 5,596,086 A | 1/1997 | Matteucci et al. |
| 5,602,240 A | 2/1997 | De Mesmaeker et al. |
| 5,608,046 A | 3/1997 | Cook et al. |
| 5,610,289 A | 3/1997 | Cook et al. |
| 5,618,704 A | 4/1997 | Sanghvi et al. |
| 5,623,070 A | 4/1997 | Cook et al. |
| 5,625,050 A | 4/1997 | Beaton et al. |
| 5,633,360 A | 5/1997 | Bischofberger et al. |
| 5,646,269 A | 7/1997 | Matteucci et al. |
| 5,663,312 A | 9/1997 | Chaturvedula |
| 5,665,710 A | 9/1997 | Rahman et al. |
| 5,672,697 A | 9/1997 | Buhr et al. |
| 5,677,437 A | 10/1997 | Teng et al. |
| 5,677,439 A | 10/1997 | Weis et al. |
| 5,698,685 A | 12/1997 | Summerton et al. |
| 5,721,218 A | 2/1998 | Froehler |
| 5,792,608 A | 8/1998 | Swaminathan et al. |
| 5,889,136 A | 3/1999 | Scaringe et al. |
| 5,976,567 A | 11/1999 | Wheeler et al. |
| 5,981,501 A | 11/1999 | Wheeler et al. |
| 6,001,311 A | 12/1999 | Brennan |
| 6,008,400 A | 12/1999 | Scaringe et al. |
| 6,111,086 A | 8/2000 | Scaringe |
| 6,534,484 B1 | 3/2003 | Wheeler et al. |
| 6,586,410 B1 | 7/2003 | Wheeler et al. |
| 6,649,751 B2 | 11/2003 | Usman et al. |
| 6,673,918 B2 | 1/2004 | Bellon et al. |
| 6,686,463 B2 | 2/2004 | Beigelman et al. |
| 6,815,432 B2 | 11/2004 | Wheeler et al. |
| 6,989,442 B2 | 1/2006 | Vargeese |
| 6,995,259 B1 | 2/2006 | Vargeese et al. |
| 7,125,855 B2 | 10/2006 | Bhat et al. |
| 7,205,399 B1 | 4/2007 | Vargeese et al. |
| 2016/0186174 A1 | 6/2016 | Seth et al. |
| 2022/0372063 A1 | 11/2022 | Brunner et al. |

FOREIGN PATENT DOCUMENTS

| | | | |
|---|---|---|---|
| WO | 1996040964 A2 | 12/1996 | |
| WO | 1999054459 A2 | 10/1999 | |
| WO | 2004/044245 A1 | 5/2004 | |
| WO | 2011005860 A2 | 1/2011 | |
| WO | 2015179742 A1 | 11/2015 | |
| WO | WO-2017066793 A1 * | 4/2017 | ............ C07H 19/20 |
| WO | 2018013999 A1 | 1/2018 | |
| WO | 2019/170731 A1 | 9/2019 | |
| WO | 2021044004 A1 | 3/2021 | |

OTHER PUBLICATIONS

International Search Report and Written Opinion in corresponding International Patent Application No. PCT/EP2019/055546 dated May 22, 2019.
Akhtar, S. & Juliano, R. L. "Cellular uptake and intracellular fate of antisense oligonucleotides." Trends in Cell Biology vol. 2,5 (1992): 139-44.
Bellon, L. et al. "Amino-Linked Ribozymes: Post-Synthetic Conjugation of Half-Ribozymes." Nucleosides and Nucleotides, 16:7-9, (1997): 951-954.
Bellon, L. et al. "Post-synthetically ligated ribozymes: an alternative approach to iterative solid-phase synthesis." Bioconjugate Chemistry vol. 8,2 (1997): 204-12.
Bramsen, J. B. et al. "A screen of chemical modifications identifies position-specific modification by UNA to most potently reduce siRNA off-target effects." Nucleic Acids Research vol. 38,17 (2010): 5761-73. Epub: May 7, 2010.
Brennan, T. et al. "Two-dimensional parallel array technology as a new approach to automated combinatorial solid-phase organic synthesis." Biotechnology and Bioengineering vol. 61,1 (1998): 33-45.
Bäumer, N. et al. "Antibody-coupled siRNA as an efficient method for in vivo mRNA knockdown." Nature Protocols vol. 11,1 (2016): 22-36.
Caruthers, M. H. et al. "Chemical synthesis of deoxyoligonucleotides and deoxyoligonucleotide analogs." Methods in Enzymology vol. 211 (1992): 3-20.
Corey, D. R. & Abrams, J.M. "Morpholino antisense oligonucleotides: tools for investigating vertebrate development." Genome Biology vol. 2,5 (2001): Reviews1015.1-1015.3.
Cuellar, T. L. et al. "Systematic evaluation of antibody-mediated siRNA delivery using an industrial platform of THIOMAB-siRNA conjugates." Nucleic Acids Research vol. 43,2 (2015): 1189-203. Epub: Dec. 30, 2014.
Draz, M. S. et al. "Nanoparticle-mediated systemic delivery of siRNA for treatment of cancers and viral infections." Theranostics vol. 4,9 (2014): 872-92.
Gary, D. J. et al. "Polymer-based siRNA delivery: perspectives on the fundamental and phenomenological distinctions from polymer-based DNA delivery." Journal of Controlled Release : Official Journal of the Controlled Release Society vol. 121, 1-2 (2007): 64-73.
Huang, Y. "Preclinical and Clinical Advances of GalNAc-Decorated Nucleic Acid Therapeutics." Molecular Therapy—Nucleic Acids vol. 6 (2017): 116-132.
Ibtehaj, N. et al. "High-dose BAFF receptor specific mAb-siRNA conjugate generates Fas-expressing B cells in lymph nodes and high-affinity serum autoantibody in a myasthenia mouse model." Clinical Immunology (Orlando, Fla.) vol. 176 (2017): 122-130.
International Search Report and Written Opinion in corresponding International Patent Application No. PCT/EP2020/074800 dated Nov. 19, 2020.
Kanasty, R. et al. "Delivery materials for siRNA therapeutics." Nature Materials vol. 12,11 (2013): 967-77.
Kim, S. H. et al. "Local and systemic delivery of VEGF siRNA using polyelectrolyte complex micelles for effective treatment of cancer." Journal of Controlled Release : Official Journal of the Controlled Release Society vol. 129,2 (2008): 107-16.
Koshkin, A. A. et al. "LNA (Locked Nucleic Acids): Synthesis of the adenine, cytosine, guanine, 5-methylcytosine, thymine and uracil bicyclonucleoside monomers, oligomerisation, and unprecedented nucleic acid recognition." Tetrahedron vol. 54, 14 (1998): 3607-3630.
Leydier, C. et al. "4'-Thio-RNA: synthesis of mixed base 4'-thio-oligoribonucleotides, nuclease resistance, and base pairing properties with complementary single and double strand." Antisense Research and Development vol. 5,3 (1995): 167-74.
Li, C. et al. "Current multifunctional albumin-based nanoplatforms for cancer multi-mode therapy." Asian Journal of Pharmaceutical Sciences vol. 15,1 (2020): 1-12.
Mangos, M. M. et al. "Efficient RNase H-directed cleavage of RNA promoted by antisense DNA or 2'F-ANA constructs containing acyclic nucleotide inserts." Journal of the American Chemical Society vol. 125,3 (2003): 654-61.

(56) References Cited

OTHER PUBLICATIONS

Moore, M. J. et al. "Site-specific modification of pre-mRNA: the 2'-hydroxyl groups at the splice sites." Science vol. 256, 5059 (1992): 992-997.
Nair, J. K. et al. "Multivalent N-acetylgalactosamine-conjugated siRNA localizes in hepatocytes and elicits robust RNAi-mediated gene silencing." Journal of the American Chemical Society vol. 136,49 (2014): 16958-61.
Partridge, M. et al. "A simple method for delivering morpholino antisense oligos into the cytoplasm of cells." Antisense & Nucleic Acid Drug Development vol. 6,3 (1996): 169-75.
Podesta, J. E. & Kostarelos, K. "Chapter 17—Engineering cationic liposome siRNA complexes for in vitro and in vivo delivery." Methods in Enzymology vol. 464 (2009): 343-54.
Prakash, T. P. "An overview of sugar-modified oligonucleotides for antisense therapeutics." Chemistry & Biodiversity vol. 8,9 (2011): 1616-41.
Prakash, T. P. et al. "Solid-phase synthesis of 5'-triantennary N-acetylgalactosamine conjugated antisense oligonucleotides using phosphoramidite chemistry." Bioorganic & Medicinal Chemistry Letters vol. 25, 19 (2015): 4127-30.
Rajeev, K. G. et al. "Hepatocyte-specific delivery of siRNAs conjugated to novel non-nucleosidic trivalent N-acetylgalactosamine elicits robust gene silencing in vivo." Chembiochem : a European Journal of Chemical Biology vol. 16,6 (2015): 903-8.
Rozema, D. B. et al. "Dynamic PolyConjugates for targeted in vivo delivery of siRNA to hepatocytes." Proceedings of the National Academy of Sciences of the United States of America vol. 104,32 (2007): 12982-7.
Seglen, P. O. "Preparation of isolated rat liver cells." Methods in Cell Biology vol. 13 (1976): 29-83.
Shabarova, Z. A. et al. "Chemical ligation of DNA: the first non-enzymatic assembly of a biologically active gene." Nucleic Acids Research vol. 19,15 (1991): 4247-51.
Shemesh, C. S. et al. "Elucidation of the Biotransformation Pathways of a Galnac3-conjugated Antisense Oligonucleotide in Rats and Monkeys." Molecular Therapy—Nucleic Acids vol. 5,5 e319 (2016).
Stephenson, M. L., & Zamecnik, P. C. "Inhibition of Rous sarcoma viral RNA translation by a specific oligodeoxyribonucleotide." Proceedings of the National Academy of Sciences of the United States of America vol. 75,1 (1978): 285-8.
Sugo, T. et al. "Development of antibody-siRNA conjugate targeted to cardiac and skeletal muscles." Journal of Controlled Release : Official Journal of the Controlled Release Society vol. 237 (2016): 1-13.
Vaish, N. et al. "Improved specificity of gene silencing by siRNAs containing unlocked nucleobase analogs." Nucleic Acids Research vol. 39,5 (2011): 1823-32. Epub: Nov. 2, 2010.
Wan, C. et al. "Lipid nanoparticle delivery systems for siRNA-based therapeutics." Drug Delivery and Translational Research vol. 4,1 (2014): 74-83.
Wang, J. et al. "Delivery of siRNA therapeutics: barriers and carriers." The AAPS Journal vol. 12,4 (2010): 492-503.
Whitehead, K. A. et al. "Knocking down barriers: advances in siRNA delivery." Nature Reviews—Drug Discovery vol. 8,2 (2009): 129-38.
Wincott, F. E. & Usman, N. "A practical method for the production of RNA and ribozymes." Methods in Molecular Biology (Clifton, N.J.) vol. 74 (1997): 59-68.
Wincott, F. et al. "Synthesis, deprotection, analysis and purification of RNA and ribozymes." Nucleic Acids Research vol. 23,14 (1995): 2677-84.
Wittrup, A. & Lieberman, J. "Knocking down disease: a progress report on siRNA therapeutics." Nature Reviews—Genetics vol. 16,9 (2015): 543-52.
Xia, C. et al. "Antibody-mediated targeting of siRNA via the human insulin receptor using avidin-biotin technology." Molecular Pharmaceutics vol. 6,3 (2009): 747-51.
Yu, R. Z. et al. "Disposition and Pharmacology of a GalNAc3-conjugated ASO Targeting Human Lipoprotein (a) in Mice." Mol Ther—Nucleic Acids, vol. 5 (2016): e317. Epub: May 3, 2016.
Zimmermann, T. S. et al. "Clinical Proof of Concept for a Novel Hepatocyte-Targeting GalNAc-siRNA Conjugate." Molecular Therapy : The Journal of the American Society of Gene Therapy vol. 25,1 (2017): 71-78.

\* cited by examiner

SEQUENCE LISTING

<160> NUMBER OF SEQ ID NOS: 118

<210> SEQ ID NO 1
<211> LENGTH: 21
<212> TYPE: RNA
<213> ORGANISM: Artificial Sequence
<220> FEATURE:
<223> OTHER INFORMATION: ss1
<220> FEATURE:
<221> NAME/KEY: variation
<222> LOCATION: 20
<223> OTHER INFORMATION: The nucleotide in position 20 and the
    nucleotide in position 21 are linked through a phosphoramidite
    bond
<220> FEATURE:
<221> NAME/KEY: variation
<222> LOCATION: 21
<223> OTHER INFORMATION: The nucleotide in position 20 and the
    nucleotide in position 21 are linked through a phosphoramidite
    bond

<400> SEQUENCE: 1
ggaugaagug gagauuagut t                                            21

<210> SEQ ID NO 2
<211> LENGTH: 21
<212> TYPE: RNA
<213> ORGANISM: Artificial Sequence
<220> FEATURE:
<223> OTHER INFORMATION: ss2
<220> FEATURE:
<221> NAME/KEY: variation
<222> LOCATION: 19
<223> OTHER INFORMATION: U in position 19 a lU3b nucleotide analog
<220> FEATURE:
<221> NAME/KEY: variation

```
<222> LOCATION: 20
<223> OTHER INFORMATION: The nucleotide in position 20 and the
      nucleotide in position 21 are linked through a phosphoramidite
      bond
<220> FEATURE:
<221> NAME/KEY: variation
<222> LOCATION: 21
<223> OTHER INFORMATION: The nucleotide in position 20 and the
      nucleotide in position 21 are linked through a phosphoramidite
      bond

<400> SEQUENCE: 2
ggaugaagug gagauuagut t                                              21

<210> SEQ ID NO 3
<211> LENGTH: 21
<212> TYPE: RNA
<213> ORGANISM: Artificial Sequence
<220> FEATURE:
<223> OTHER INFORMATION: ss3
<220> FEATURE:
<221> NAME/KEY: variation
<222> LOCATION: 16
<223> OTHER INFORMATION: U in position 16 and 19 is a lU3b nucleotide
      analog
<220> FEATURE:
<221> NAME/KEY: variation
<222> LOCATION: 19
<223> OTHER INFORMATION: U in position 16 and 19 is a lU3b nucleotide
      analog
<220> FEATURE:
<221> NAME/KEY: variation
<222> LOCATION: 20
<223> OTHER INFORMATION: The nucleotide in position 20 and the
      nucleotide in position 21 are linked through a phosphoramidite
      bond
<220> FEATURE:
<221> NAME/KEY: variation
<222> LOCATION: 21
<223> OTHER INFORMATION: The nucleotide in position 20 and the
      nucleotide in position 21 are linked through a phosphoramidite
      bond

<400> SEQUENCE: 3
ggaugaagug gagauuagut t                                              21

<210> SEQ ID NO 4
<211> LENGTH: 21
<212> TYPE: RNA
<213> ORGANISM: Artificial Sequence
<220> FEATURE:
<223> OTHER INFORMATION: ss4
<220> FEATURE:
<221> NAME/KEY: variation
<222> LOCATION: 15
<223> OTHER INFORMATION: U in position 15,16 and 19 is a lU3b nucleotide
      analog
<220> FEATURE:
<221> NAME/KEY: variation
<222> LOCATION: 16
<223> OTHER INFORMATION: U in position 15,16 and 19 is a lU3b nucleotide
      analog
<220> FEATURE:
<221> NAME/KEY: variation
<222> LOCATION: 19
<223> OTHER INFORMATION: U in position 15,16 and 19 is a lU3b nucleotide
      analog
<220> FEATURE:
<221> NAME/KEY: variation
<222> LOCATION: 20
<223> OTHER INFORMATION: The nucleotide in position 20 and the
      nucleotide in position 21 are linked through a phosphoramidite
      bond
<220> FEATURE:
<221> NAME/KEY: variation
```

```
<222> LOCATION: 21
<223> OTHER INFORMATION: The nucleotide in position 20 and the
      nucleotide in position 21 are linked through a phosphoramidite
      bond

<400> SEQUENCE: 4
ggaugaagug gagauuagut t                                           21

<210> SEQ ID NO 5
<211> LENGTH: 21
<212> TYPE: RNA
<213> ORGANISM: Artificial Sequence
<220> FEATURE:
<223> OTHER INFORMATION: ss5
<220> FEATURE:
<221> NAME/KEY: variation
<222> LOCATION: 9
<223> OTHER INFORMATION: U in position 9,15,16 and 19 is a lU3b
      nucleotide analog
<220> FEATURE:
<221> NAME/KEY: variation
<222> LOCATION: 15
<223> OTHER INFORMATION: U in position 9,15,16 and 19 is a lU3b
      nucleotide analog
<220> FEATURE:
<221> NAME/KEY: variation
<222> LOCATION: 16
<223> OTHER INFORMATION: U in position 9,15,16 and 19 is a lU3b
      nucleotide analog
<220> FEATURE:
<221> NAME/KEY: variation
<222> LOCATION: 19
<223> OTHER INFORMATION: U in position 9,15,16 and 19 is a lU3b
      nucleotide analog
<220> FEATURE:
<221> NAME/KEY: variation
<222> LOCATION: 20
<223> OTHER INFORMATION: The nucleotide in position 20 and the
      nucleotide in position 21 are linked through a phosphoramidite
      bond
<220> FEATURE:
<221> NAME/KEY: variation
<222> LOCATION: 21
<223> OTHER INFORMATION: The nucleotide in position 20 and the
      nucleotide in position 21 are linked through a phosphoramidite
      bond

<400> SEQUENCE: 5
ggaugaagug gagauuagut t                                           21

<210> SEQ ID NO 6
<211> LENGTH: 21
<212> TYPE: RNA
<213> ORGANISM: Artificial Sequence
<220> FEATURE:
<223> OTHER INFORMATION: ss6
<220> FEATURE:
<221> NAME/KEY: variation
<222> LOCATION: 4
<223> OTHER INFORMATION: U in position 4,9,15,16 and 19 is a lU3b
      nucleotide analog
<220> FEATURE:
<221> NAME/KEY: variation
<222> LOCATION: 9
<223> OTHER INFORMATION: U in position 4,9,15,16 and 19 is a lU3b
      nucleotide analog
<220> FEATURE:
<221> NAME/KEY: variation
<222> LOCATION: 15
<223> OTHER INFORMATION: U in position 4,9,15,16 and 19 is a lU3b
      nucleotide analog
<220> FEATURE:
<221> NAME/KEY: variation
<222> LOCATION: 16
<223> OTHER INFORMATION: U in position 4,9,15,16 and 19 is a lU3b
```

```
            nucleotide analog
<220> FEATURE:
<221> NAME/KEY: variation
<222> LOCATION: 19
<223> OTHER INFORMATION: U in position 4,9,15,16 and 19 is a 1U3b
      nucleotide analog
<220> FEATURE:
<221> NAME/KEY: variation
<222> LOCATION: 20
<223> OTHER INFORMATION: The nucleotide in position 20 and the
      nucleotide in position 21 are linked through a phosphoramidite
      bond
<220> FEATURE:
<221> NAME/KEY: variation
<222> LOCATION: 21
<223> OTHER INFORMATION: The nucleotide in position 20 and the
      nucleotide in position 21 are linked through a phosphoramidite
      bond

<400> SEQUENCE: 6
ggaugaagug gagauuagut t                                              21

<210> SEQ ID NO 7
<211> LENGTH: 21
<212> TYPE: RNA
<213> ORGANISM: Artificial Sequence
<220> FEATURE:
<223> OTHER INFORMATION: ss7
<220> FEATURE:
<221> NAME/KEY: variation
<222> LOCATION: 4
<223> OTHER INFORMATION: U in positions 4,9,14,16 and 19 represents a
      2'-O-methyl-uracile (mU)
<220> FEATURE:
<221> NAME/KEY: variation
<222> LOCATION: 9
<223> OTHER INFORMATION: U in positions 4,9,14,16 and 19 represents a
      2'-O-methyl-uracile (mU)
<220> FEATURE:
<221> NAME/KEY: variation
<222> LOCATION: 15
<223> OTHER INFORMATION: U in positions 4,9,14,16 and 19 represents a
      2'-O-methyl-uracile (mU)
<220> FEATURE:
<221> NAME/KEY: variation
<222> LOCATION: 16
<223> OTHER INFORMATION: U in positions 4,9,14,16 and 19 represents a
      2'-O-methyl-uracile (mU)
<220> FEATURE:
<221> NAME/KEY: variation
<222> LOCATION: 19
<223> OTHER INFORMATION: U in positions 4,9,14,16 and 19 represents a
      2'-O-methyl-uracile (mU)
<220> FEATURE:
<221> NAME/KEY: variation
<222> LOCATION: 20
<223> OTHER INFORMATION: The nucleotide in position 20 and the
      nucleotide in position 21 are linked through a phosphoramidite
      bond
<220> FEATURE:
<221> NAME/KEY: variation
<222> LOCATION: 21
<223> OTHER INFORMATION: The nucleotide in position 20 and the
      nucleotide in position 21 are linked through a phosphoramidite
      bond

<400> SEQUENCE: 7
ggaugaagug gagauuagut t                                              21

<210> SEQ ID NO 8
<211> LENGTH: 21
<212> TYPE: RNA
<213> ORGANISM: Artificial Sequence
<220> FEATURE:
<223> OTHER INFORMATION: ss8
```

-continued

```
<220> FEATURE:
<221> NAME/KEY: variation
<222> LOCATION: 19
<223> OTHER INFORMATION: U in position 19 is a 1U3 nucleotide analog
<220> FEATURE:
<221> NAME/KEY: variation
<222> LOCATION: 20
<223> OTHER INFORMATION: The nucleotide in position 20 and the
      nucleotide in position 21 are linked through a phosphoramidite
      bond
<220> FEATURE:
<221> NAME/KEY: variation
<222> LOCATION: 21
<223> OTHER INFORMATION: The nucleotide in position 20 and the
      nucleotide in position 21 are linked through a phosphoramidite
      bond

<400> SEQUENCE: 8
ggaugaagug gagauuagut t                                             21

<210> SEQ ID NO 9
<211> LENGTH: 21
<212> TYPE: RNA
<213> ORGANISM: Artificial Sequence
<220> FEATURE:
<223> OTHER INFORMATION: ss9
<220> FEATURE:
<221> NAME/KEY: variation
<222> LOCATION: 16
<223> OTHER INFORMATION: U in position 16 and 19 is a 1U3 nucleotide
      analog
<220> FEATURE:
<221> NAME/KEY: variation
<222> LOCATION: 19
<223> OTHER INFORMATION: U in position 16 and 19 is a 1U3 nucleotide
      analog
<220> FEATURE:
<221> NAME/KEY: variation
<222> LOCATION: 20
<223> OTHER INFORMATION: The nucleotide in position 20 and the
      nucleotide in position 21 are linked through a phosphoramidite
      bond
<220> FEATURE:
<221> NAME/KEY: variation
<222> LOCATION: 21
<223> OTHER INFORMATION: The nucleotide in position 20 and the
      nucleotide in position 21 are linked through a phosphoramidite
      bond

<400> SEQUENCE: 9
ggaugaagug gagauuagut t                                             21

<210> SEQ ID NO 10
<211> LENGTH: 21
<212> TYPE: RNA
<213> ORGANISM: Artificial Sequence
<220> FEATURE:
<223> OTHER INFORMATION: ss10
<220> FEATURE:
<221> NAME/KEY: variation
<222> LOCATION: 15
<223> OTHER INFORMATION: U in position 15,16 and 19 is a 1U3 nucleotide
      analog
<220> FEATURE:
<221> NAME/KEY: variation
<222> LOCATION: 16
<223> OTHER INFORMATION: U in position 15,16 and 19 is a 1U3 nucleotide
      analog
<220> FEATURE:
<221> NAME/KEY: variation
<222> LOCATION: 19
<223> OTHER INFORMATION: U in position 15,16 and 19 is a 1U3 nucleotide
      analog
<220> FEATURE:
<221> NAME/KEY: variation
```

```
<222> LOCATION: 20
<223> OTHER INFORMATION: The nucleotide in position 20 and the
      nucleotide in position 21 are linked through a phosphoramidite
      bond
<220> FEATURE:
<221> NAME/KEY: variation
<222> LOCATION: 21
<223> OTHER INFORMATION: The nucleotide in position 20 and the
      nucleotide in position 21 are linked through a phosphoramidite
      bond

<400> SEQUENCE: 10
ggaugaagug gagauuagut t                                              21

<210> SEQ ID NO 11
<211> LENGTH: 21
<212> TYPE: RNA
<213> ORGANISM: Artificial Sequence
<220> FEATURE:
<223> OTHER INFORMATION: ss11
<220> FEATURE:
<221> NAME/KEY: variation
<222> LOCATION: 9
<223> OTHER INFORMATION: U in position 9,15,16 and 19 is a lU3
      nucleotide analog
<220> FEATURE:
<221> NAME/KEY: variation
<222> LOCATION: 15
<223> OTHER INFORMATION: U in position 9,15,16 and 19 is a lU3
      nucleotide analog
<220> FEATURE:
<221> NAME/KEY: variation
<222> LOCATION: 16
<223> OTHER INFORMATION: U in position 9,15,16 and 19 is a lU3
      nucleotide analog
<220> FEATURE:
<221> NAME/KEY: variation
<222> LOCATION: 19
<223> OTHER INFORMATION: U in position 9,15,16 and 19 is a lU3
      nucleotide analog
<220> FEATURE:
<221> NAME/KEY: variation
<222> LOCATION: 20
<223> OTHER INFORMATION: The nucleotide in position 20 and the
      nucleotide in position 21 are linked through a phosphoramidite
      bond
<220> FEATURE:
<221> NAME/KEY: variation
<222> LOCATION: 21
<223> OTHER INFORMATION: The nucleotide in position 20 and the
      nucleotide in position 21 are linked through a phosphoramidite
      bond

<400> SEQUENCE: 11
ggaugaagug gagauuagut t                                              21

<210> SEQ ID NO 12
<211> LENGTH: 21
<212> TYPE: RNA
<213> ORGANISM: Artificial Sequence
<220> FEATURE:
<223> OTHER INFORMATION: ss12
<220> FEATURE:
<221> NAME/KEY: variation
<222> LOCATION: 4
<223> OTHER INFORMATION: U in position 4,9,15,16 and 19 is a lU3
      nucleotide analog
<220> FEATURE:
<221> NAME/KEY: variation
<222> LOCATION: 9
<223> OTHER INFORMATION: U in position 4,9,15,16 and 19 is a lU3
      nucleotide analog
<220> FEATURE:
<221> NAME/KEY: variation
<222> LOCATION: 15
```

```
<223> OTHER INFORMATION: U in position 4,9,15,16 and 19 is a lU3
      nucleotide analog
<220> FEATURE:
<221> NAME/KEY: variation
<222> LOCATION: 16
<223> OTHER INFORMATION: U in position 4,9,15,16 and 19 is a lU3
      nucleotide analog
<220> FEATURE:
<221> NAME/KEY: variation
<222> LOCATION: 19
<223> OTHER INFORMATION: U in position 4,9,15,16 and 19 is a lU3
      nucleotide analog
<220> FEATURE:
<221> NAME/KEY: variation
<222> LOCATION: 20
<223> OTHER INFORMATION: The nucleotide in position 20 and the
      nucleotide in position 21 are linked through a phosphoramidite
      bond
<220> FEATURE:
<221> NAME/KEY: variation
<222> LOCATION: 21
<223> OTHER INFORMATION: The nucleotide in position 20 and the
      nucleotide in position 21 are linked through a phosphoramidite
      bond

<400> SEQUENCE: 12
ggaugaagug gagauuagut t                                            21

<210> SEQ ID NO 13
<211> LENGTH: 21
<212> TYPE: RNA
<213> ORGANISM: Artificial Sequence
<220> FEATURE:
<223> OTHER INFORMATION: as1
<220> FEATURE:
<221> NAME/KEY: variation
<222> LOCATION: 20
<223> OTHER INFORMATION: The nucleotide in position 20 and the
      nucleotide in position 21 are linked through a phosphoramidite
      bond
<220> FEATURE:
<221> NAME/KEY: variation
<222> LOCATION: 21
<223> OTHER INFORMATION: The nucleotide in position 20 and the
      nucleotide in position 21 are linked through a phosphoramidite
      bond

<400> SEQUENCE: 13
acuaaucucc acuucaucct t                                            21

<210> SEQ ID NO 14
<211> LENGTH: 21
<212> TYPE: RNA
<213> ORGANISM: Artificial Sequence
<220> FEATURE:
<223> OTHER INFORMATION: as2
<220> FEATURE:
<221> NAME/KEY: variation
<222> LOCATION: 3
<223> OTHER INFORMATION: U in position 3 represents a 2'-O-methyl-
      uracile (mU)
<220> FEATURE:
<221> NAME/KEY: variation
<222> LOCATION: 10
<223> OTHER INFORMATION: C in position 10 and 15 represents a mC
      nucleotide analog
<220> FEATURE:
<221> NAME/KEY: variation
<222> LOCATION: 15
<223> OTHER INFORMATION: C in position 10 and 15 represents a mC
      nucleotide analog
<220> FEATURE:
<221> NAME/KEY: variation
<222> LOCATION: 20
<223> OTHER INFORMATION: The nucleotide in position 20 and the
```

```
      nucleotide in position 21 are linked through a phosphoramidite
      bond
<220> FEATURE:
<221> NAME/KEY: variation
<222> LOCATION: 21
<223> OTHER INFORMATION: The nucleotide in position 20 and the
      nucleotide in position 21 are linked through a phosphoramidite
      bond

<400> SEQUENCE: 14
acuaaucucc acuucaucct t                                              21

<210> SEQ ID NO 15
<211> LENGTH: 21
<212> TYPE: RNA
<213> ORGANISM: Artificial Sequence
<220> FEATURE:
<223> OTHER INFORMATION: ss13
<220> FEATURE:
<221> NAME/KEY: variation
<222> LOCATION: 1
<223> OTHER INFORMATION: C in position 1,5,7,14 and 17 represents a mC
      nucleotide analog
<220> FEATURE:
<221> NAME/KEY: variation
<222> LOCATION: 2
<223> OTHER INFORMATION: U in position 2,3,8,12,15 and 16 represents a
      2'-O-methyl-uracile (mU)
<220> FEATURE:
<221> NAME/KEY: variation
<222> LOCATION: 3
<223> OTHER INFORMATION: U in position 2,3,8,12,15 and 16 represents a
      2'-O-methyl-uracile (mU)
<220> FEATURE:
<221> NAME/KEY: variation
<222> LOCATION: 5
<223> OTHER INFORMATION: C in position 1,5,7,14 and 17 represents a mC
      nucleotide analog
<220> FEATURE:
<221> NAME/KEY: variation
<222> LOCATION: 7
<223> OTHER INFORMATION: C in position 1,5,7,14 and 17 represents a mC
      nucleotide analog
<220> FEATURE:
<221> NAME/KEY: variation
<222> LOCATION: 8
<223> OTHER INFORMATION: U in position 2,3,8,12,15 and 16 represents a
      2'-O-methyl-uracile (mU)
<220> FEATURE:
<221> NAME/KEY: variation
<222> LOCATION: 12
<223> OTHER INFORMATION: U in position 2,3,8,12,15 and 16 represents a
      2'-O-methyl-uracile (mU)
<220> FEATURE:
<221> NAME/KEY: variation
<222> LOCATION: 14
<223> OTHER INFORMATION: C in position 1,5,7,14 and 17 represents a mC
      nucleotide analog
<220> FEATURE:
<221> NAME/KEY: variation
<222> LOCATION: 15
<223> OTHER INFORMATION: U in position 2,3,8,12,15 and 16 represents a
      2'-O-methyl-uracile (mU)
<220> FEATURE:
<221> NAME/KEY: variation
<222> LOCATION: 16
<223> OTHER INFORMATION: U in position 2,3,8,12,15 and 16 represents a
      2'-O-methyl-uracile (mU)
<220> FEATURE:
<221> NAME/KEY: variation
<222> LOCATION: 17
<223> OTHER INFORMATION: C in position 1,5,7,14 and 17 represents a mC
      nucleotide analog
<220> FEATURE:
<221> NAME/KEY: variation
<222> LOCATION: 19
<223> OTHER INFORMATION: The nucleotide in position 19 and the
```

```
      nucleotide in position 20 are linked through a phosphoramidite
      bond
<220> FEATURE:
<221> NAME/KEY: variation
<222> LOCATION: 20
<223> OTHER INFORMATION: The nucleotide in position 19 and the
      nucleotide in position 20 are linked through a phosphoramidite
      bond
<220> FEATURE:
<221> NAME/KEY: variation
<222> LOCATION: 20
<223> OTHER INFORMATION: The nucleotide in position 20 and the
      nucleotide in position 21 are linked through a phosphoramidite
      bond
<220> FEATURE:
<221> NAME/KEY: variation
<222> LOCATION: 21
<223> OTHER INFORMATION: The nucleotide in position 20 and the
      nucleotide in position 21 are linked through a phosphoramidite
      bond

<400> SEQUENCE: 15
cuuacgcuga guacuucgat t                                               21

<210> SEQ ID NO 16
<211> LENGTH: 21
<212> TYPE: RNA
<213> ORGANISM: Artificial Sequence
<220> FEATURE:
<223> OTHER INFORMATION: ss14
<220> FEATURE:
<221> NAME/KEY: variation
<222> LOCATION: 1
<223> OTHER INFORMATION: C in position 1,5,7,14 and 17 represents a mC
      nucleotide analog
<220> FEATURE:
<221> NAME/KEY: variation
<222> LOCATION: 2
<223> OTHER INFORMATION: U in position 2,3,8,12 and 15 represents a
      2'-O-methyl-uracile (mU)
<220> FEATURE:
<221> NAME/KEY: variation
<222> LOCATION: 3
<223> OTHER INFORMATION: U in position 2,3,8,12 and 15 represents a
      2'-O-methyl-uracile (mU)
<220> FEATURE:
<221> NAME/KEY: variation
<222> LOCATION: 5
<223> OTHER INFORMATION: C in position 1,5,7,14 and 17 represents a mC
      nucleotide analog
<220> FEATURE:
<221> NAME/KEY: variation
<222> LOCATION: 7
<223> OTHER INFORMATION: C in position 1,5,7,14 and 17 represents a mC
      nucleotide analog
<220> FEATURE:
<221> NAME/KEY: variation
<222> LOCATION: 8
<223> OTHER INFORMATION: U in position 2,3,8,12 and 15 represents a
      2'-O-methyl-uracile (mU)
<220> FEATURE:
<221> NAME/KEY: variation
<222> LOCATION: 12
<223> OTHER INFORMATION: U in position 2,3,8,12 and 15 represents a
      2'-O-methyl-uracile (mU)
<220> FEATURE:
<221> NAME/KEY: variation
<222> LOCATION: 14
<223> OTHER INFORMATION: C in position 1,5,7,14 and 17 represents a mC
      nucleotide analog
<220> FEATURE:
<221> NAME/KEY: variation
<222> LOCATION: 15
<223> OTHER INFORMATION: U in position 2,3,8,12 and 15 represents a
      2'-O-methyl-uracile (mU)
<220> FEATURE:
<221> NAME/KEY: variation
```

```
<222> LOCATION: 16
<223> OTHER INFORMATION: U in position 16 is a lU1b nucleotide analog
<220> FEATURE:
<221> NAME/KEY: variation
<222> LOCATION: 17
<223> OTHER INFORMATION: C in position 1,5,7,14 and 17 represents a mC
      nucleotide analog
<220> FEATURE:
<221> NAME/KEY: variation
<222> LOCATION: 19
<223> OTHER INFORMATION: The nucleotide in position 19 and the
      nucleotide in position 20 are linked through a phosphoramidite
      bond
<220> FEATURE:
<221> NAME/KEY: variation
<222> LOCATION: 20
<223> OTHER INFORMATION: The nucleotide in position 19 and the
      nucleotide in position 20 are linked through a phosphoramidite
      bond
<220> FEATURE:
<221> NAME/KEY: variation
<222> LOCATION: 20
<223> OTHER INFORMATION: The nucleotide in position 20 and the
      nucleotide in position 21 are linked through a phosphoramidite
      bond
<220> FEATURE:
<221> NAME/KEY: variation
<222> LOCATION: 21
<223> OTHER INFORMATION: The nucleotide in position 20 and the
      nucleotide in position 21 are linked through a phosphoramidite
      bond

<400> SEQUENCE: 16
cuuacgcuga guacuucgat t                                              21

<210> SEQ ID NO 17
<211> LENGTH: 21
<212> TYPE: RNA
<213> ORGANISM: Artificial Sequence
<220> FEATURE:
<223> OTHER INFORMATION: ss15
<220> FEATURE:
<221> NAME/KEY: variation
<222> LOCATION: 1
<223> OTHER INFORMATION: C in position 1,5,7,14 and 17 represents a mC
      nucleotide analog
<220> FEATURE:
<221> NAME/KEY: variation
<222> LOCATION: 2
<223> OTHER INFORMATION: U in position 2,3,8 and 12 represents a
      2'-O-methyl-uracile (mU)
<220> FEATURE:
<221> NAME/KEY: variation
<222> LOCATION: 3
<223> OTHER INFORMATION: U in position 2,3,8 and 12 represents a
      2'-O-methyl-uracile (mU)
<220> FEATURE:
<221> NAME/KEY: variation
<222> LOCATION: 5
<223> OTHER INFORMATION: C in position 1,5,7,14 and 17 represents a mC
      nucleotide analog
<220> FEATURE:
<221> NAME/KEY: variation
<222> LOCATION: 7
<223> OTHER INFORMATION: C in position 1,5,7,14 and 17 represents a mC
      nucleotide analog
<220> FEATURE:
<221> NAME/KEY: variation
<222> LOCATION: 8
<223> OTHER INFORMATION: U in position 2,3,8 and 12 represents a
      2'-O-methyl-uracile (mU)
<220> FEATURE:
<221> NAME/KEY: variation
<222> LOCATION: 12
<223> OTHER INFORMATION: U in position 2,3,8 and 12 represents a
      2'-O-methyl-uracile (mU)
<220> FEATURE:
```

```
<221> NAME/KEY: variation
<222> LOCATION: 14
<223> OTHER INFORMATION: C in position 1,5,7,14 and 17 represents a mC
      nucleotide analog
<220> FEATURE:
<221> NAME/KEY: variation
<222> LOCATION: 15
<223> OTHER INFORMATION: U in position 15 and 16 is a lU1b nucleotide
      analog
<220> FEATURE:
<221> NAME/KEY: variation
<222> LOCATION: 16
<223> OTHER INFORMATION: U in position 15 and 16 is a lU1b nucleotide
      analog
<220> FEATURE:
<221> NAME/KEY: variation
<222> LOCATION: 17
<223> OTHER INFORMATION: C in position 1,5,7,14 and 17 represents a mC
      nucleotide analog
<220> FEATURE:
<221> NAME/KEY: variation
<222> LOCATION: 19
<223> OTHER INFORMATION: The nucleotide in position 19 and the
      nucleotide in position 20 are linked through a phosphoramidite
      bond
<220> FEATURE:
<221> NAME/KEY: variation
<222> LOCATION: 20
<223> OTHER INFORMATION: The nucleotide in position 19 and the
      nucleotide in position 20 are linked through a phosphoramidite
      bond
<220> FEATURE:
<221> NAME/KEY: variation
<222> LOCATION: 20
<223> OTHER INFORMATION: The nucleotide in position 20 and the
      nucleotide in position 21 are linked through a phosphoramidite
      bond
<220> FEATURE:
<221> NAME/KEY: variation
<222> LOCATION: 21
<223> OTHER INFORMATION: The nucleotide in position 20 and the
      nucleotide in position 21 are linked through a phosphoramidite
      bond

<400> SEQUENCE: 17
cuuacgcuga guacuucgat t                                               21

<210> SEQ ID NO 18
<211> LENGTH: 21
<212> TYPE: RNA
<213> ORGANISM: Artificial Sequence
<220> FEATURE:
<223> OTHER INFORMATION: ss16
<220> FEATURE:
<221> NAME/KEY: variation
<222> LOCATION: 1
<223> OTHER INFORMATION: C in position 1,5,7,14 and 17 represents a mC
      nucleotide analog
<220> FEATURE:
<221> NAME/KEY: variation
<222> LOCATION: 2
<223> OTHER INFORMATION: U in position 2,3 and 8 represents a 2'-O-
      methyl-uracile (mU)
<220> FEATURE:
<221> NAME/KEY: variation
<222> LOCATION: 3
<223> OTHER INFORMATION: U in position 2,3 and 8 represents a 2'-O-
      methyl-uracile (mU)
<220> FEATURE:
<221> NAME/KEY: variation
<222> LOCATION: 5
<223> OTHER INFORMATION: C in position 1,5,7,14 and 17 represents a mC
      nucleotide analog
<220> FEATURE:
<221> NAME/KEY: variation
<222> LOCATION: 7
<223> OTHER INFORMATION: C in position 1,5,7,14 and 17 represents a mC
```

```
      nucleotide analog
<220> FEATURE:
<221> NAME/KEY: variation
<222> LOCATION: 8
<223> OTHER INFORMATION: U in position 2,3 and 8 represents a 2'-O-
      methyl-uracile (mU)
<220> FEATURE:
<221> NAME/KEY: variation
<222> LOCATION: 12
<223> OTHER INFORMATION: U in position 12, and 16 is a lU1b nucleotide
      analog
<220> FEATURE:
<221> NAME/KEY: variation
<222> LOCATION: 14
<223> OTHER INFORMATION: C in position 1,5,7,14 and 17 represents a mC
      nucleotide analog
<220> FEATURE:
<221> NAME/KEY: variation
<222> LOCATION: 15
<223> OTHER INFORMATION: U in position 12, and 16 is a lU1b nucleotide
      analog
<220> FEATURE:
<221> NAME/KEY: variation
<222> LOCATION: 16
<223> OTHER INFORMATION: U in position 12, and 16 is a lU1b nucleotide
      analog
<220> FEATURE:
<221> NAME/KEY: variation
<222> LOCATION: 17
<223> OTHER INFORMATION: C in position 1,5,7,14 and 17 represents a mC
      nucleotide analog
<220> FEATURE:
<221> NAME/KEY: variation
<222> LOCATION: 19
<223> OTHER INFORMATION: The nucleotide in position 19 and the
      nucleotide in position 20 are linked through a phosphoramidite
      bond
<220> FEATURE:
<221> NAME/KEY: variation
<222> LOCATION: 20
<223> OTHER INFORMATION: The nucleotide in position 19 and the
      nucleotide in position 20 are linked through a phosphoramidite
      bond
<220> FEATURE:
<221> NAME/KEY: variation
<222> LOCATION: 20
<223> OTHER INFORMATION: The nucleotide in position 20 and the
      nucleotide in position 21 are linked through a phosphoramidite
      bond
<220> FEATURE:
<221> NAME/KEY: variation
<222> LOCATION: 21
<223> OTHER INFORMATION: The nucleotide in position 20 and the
      nucleotide in position 21 are linked through a phosphoramidite
      bond

<400> SEQUENCE: 18
cuuacgcuga guacuucgat t                                              21

<210> SEQ ID NO 19
<211> LENGTH: 21
<212> TYPE: RNA
<213> ORGANISM: Artificial Sequence
<220> FEATURE:
<223> OTHER INFORMATION: ss17
<220> FEATURE:
<221> NAME/KEY: variation
<222> LOCATION: 1
<223> OTHER INFORMATION: C in position 1,5,7,14 and 17 represents a mC
      nucleotide analog
<220> FEATURE:
<221> NAME/KEY: variation
<222> LOCATION: 2
<223> OTHER INFORMATION: U in position 2 and 3 represents a 2'-O-methyl-
      uracile (mU)
<220> FEATURE:
<221> NAME/KEY: variation
```

```
<222> LOCATION: 3
<223> OTHER INFORMATION: U in position 2 and 3 represents a 2'-O-methyl-
      uracile (mU)
<220> FEATURE:
<221> NAME/KEY: variation
<222> LOCATION: 5
<223> OTHER INFORMATION: C in position 1,5,7,14 and 17 represents a mC
      nucleotide analog
<220> FEATURE:
<221> NAME/KEY: variation
<222> LOCATION: 7
<223> OTHER INFORMATION: C in position 1,5,7,14 and 17 represents a mC
      nucleotide analog
<220> FEATURE:
<221> NAME/KEY: variation
<222> LOCATION: 8
<223> OTHER INFORMATION: U in position 8,12,15 and 16 is a lU1b
      nucleotide analog
<220> FEATURE:
<221> NAME/KEY: variation
<222> LOCATION: 12
<223> OTHER INFORMATION: U in position 8,12,15 and 16 is a lU1b
      nucleotide analog
<220> FEATURE:
<221> NAME/KEY: variation
<222> LOCATION: 14
<223> OTHER INFORMATION: C in position 1,5,7,14 and 17 represents a mC
      nucleotide analog
<220> FEATURE:
<221> NAME/KEY: variation
<222> LOCATION: 15
<223> OTHER INFORMATION: U in position 8,12,15 and 16 is a lU1b
      nucleotide analog
<220> FEATURE:
<221> NAME/KEY: variation
<222> LOCATION: 16
<223> OTHER INFORMATION: U in position 8,12,15 and 16 is a lU1b
      nucleotide analog
<220> FEATURE:
<221> NAME/KEY: variation
<222> LOCATION: 17
<223> OTHER INFORMATION: C in position 1,5,7,14 and 17 represents a mC
      nucleotide analog
<220> FEATURE:
<221> NAME/KEY: variation
<222> LOCATION: 19
<223> OTHER INFORMATION: The nucleotide in position 19 and the
      nucleotide in position 20 are linked through a phosphoramidite
      bond
<220> FEATURE:
<221> NAME/KEY: variation
<222> LOCATION: 20
<223> OTHER INFORMATION: The nucleotide in position 19 and the
      nucleotide in position 20 are linked through a phosphoramidite
      bond
<220> FEATURE:
<221> NAME/KEY: variation
<222> LOCATION: 20
<223> OTHER INFORMATION: The nucleotide in position 20 and the
      nucleotide in position 21 are linked through a phosphoramidite
      bond
<220> FEATURE:
<221> NAME/KEY: variation
<222> LOCATION: 21
<223> OTHER INFORMATION: The nucleotide in position 20 and the
      nucleotide in position 21 are linked through a phosphoramidite
      bond

<400> SEQUENCE: 19
cuuacgcuga guacuucgat t                                            21

<210> SEQ ID NO 20
<211> LENGTH: 21
<212> TYPE: RNA
<213> ORGANISM: Artificial Sequence
<220> FEATURE:
<223> OTHER INFORMATION: ss18
```

```
<220> FEATURE:
<221> NAME/KEY: variation
<222> LOCATION: 1
<223> OTHER INFORMATION: C in position 1,5,7,14 and 17 represents a mC
      nucleotide analog
<220> FEATURE:
<221> NAME/KEY: variation
<222> LOCATION: 2
<223> OTHER INFORMATION: U in position 2 represents a 2'-O-methyl-
      uracile (mU)
<220> FEATURE:
<221> NAME/KEY: variation
<222> LOCATION: 3
<223> OTHER INFORMATION: U in position 3,8,12,15 and 16 is a lU1b
      nucleotide analog
<220> FEATURE:
<221> NAME/KEY: variation
<222> LOCATION: 5
<223> OTHER INFORMATION: C in position 1,5,7,14 and 17 represents a mC
      nucleotide analog
<220> FEATURE:
<221> NAME/KEY: variation
<222> LOCATION: 7
<223> OTHER INFORMATION: C in position 1,5,7,14 and 17 represents a mC
      nucleotide analog
<220> FEATURE:
<221> NAME/KEY: variation
<222> LOCATION: 8
<223> OTHER INFORMATION: U in position 3,8,12,15 and 16 is a lU1b
      nucleotide analog
<220> FEATURE:
<221> NAME/KEY: variation
<222> LOCATION: 12
<223> OTHER INFORMATION: U in position 3,8,12,15 and 16 is a lU1b
      nucleotide analog
<220> FEATURE:
<221> NAME/KEY: variation
<222> LOCATION: 14
<223> OTHER INFORMATION: C in position 1,5,7,14 and 17 represents a mC
      nucleotide analog
<220> FEATURE:
<221> NAME/KEY: variation
<222> LOCATION: 15
<223> OTHER INFORMATION: U in position 3,8,12,15 and 16 is a lU1b
      nucleotide analog
<220> FEATURE:
<221> NAME/KEY: variation
<222> LOCATION: 16
<223> OTHER INFORMATION: U in position 3,8,12,15 and 16 is a lU1b
      nucleotide analog
<220> FEATURE:
<221> NAME/KEY: variation
<222> LOCATION: 17
<223> OTHER INFORMATION: C in position 1,5,7,14 and 17 represents a mC
      nucleotide analog
<220> FEATURE:
<221> NAME/KEY: variation
<222> LOCATION: 19
<223> OTHER INFORMATION: The nucleotide in position 19 and the
      nucleotide in position 20 are linked through a phosphoramidite
      bond
<220> FEATURE:
<221> NAME/KEY: variation
<222> LOCATION: 20
<223> OTHER INFORMATION: The nucleotide in position 19 and the
      nucleotide in position 20 are linked through a phosphoramidite
      bond
<220> FEATURE:
<221> NAME/KEY: variation
<222> LOCATION: 20
<223> OTHER INFORMATION: The nucleotide in position 20 and the
      nucleotide in position 21 are linked through a phosphoramidite
      bond
<220> FEATURE:
<221> NAME/KEY: variation
<222> LOCATION: 21
<223> OTHER INFORMATION: The nucleotide in position 20 and the
      nucleotide in position 21 are linked through a phosphoramidite
      bond
```

<400> SEQUENCE: 20
cuuacgcuga guacuucgat t                                              21

<210> SEQ ID NO 21
<211> LENGTH: 21
<212> TYPE: RNA
<213> ORGANISM: Artificial Sequence
<220> FEATURE:
<223> OTHER INFORMATION: ss19
<220> FEATURE:
<221> NAME/KEY: variation
<222> LOCATION: 1
<223> OTHER INFORMATION: C in position 1,5,7,14 and 17 represents a mC
      nucleotide analog
<220> FEATURE:
<221> NAME/KEY: variation
<222> LOCATION: 2
<223> OTHER INFORMATION: U in position 2,3,8,12,15 and 16 is a lU1b
      nucleotide analog
<220> FEATURE:
<221> NAME/KEY: variation
<222> LOCATION: 3
<223> OTHER INFORMATION: U in position 2,3,8,12,15 and 16 is a lU1b
      nucleotide analog
<220> FEATURE:
<221> NAME/KEY: variation
<222> LOCATION: 5
<223> OTHER INFORMATION: C in position 1,5,7,14 and 17 represents a mC
      nucleotide analog
<220> FEATURE:
<221> NAME/KEY: variation
<222> LOCATION: 7
<223> OTHER INFORMATION: C in position 1,5,7,14 and 17 represents a mC
      nucleotide analog
<220> FEATURE:
<221> NAME/KEY: variation
<222> LOCATION: 8
<223> OTHER INFORMATION: U in position 2,3,8,12,15 and 16 is a lU1b
      nucleotide analog
<220> FEATURE:
<221> NAME/KEY: variation
<222> LOCATION: 12
<223> OTHER INFORMATION: U in position 2,3,8,12,15 and 16 is a lU1b
      nucleotide analog
<220> FEATURE:
<221> NAME/KEY: variation
<222> LOCATION: 14
<223> OTHER INFORMATION: C in position 1,5,7,14 and 17 represents a mC
      nucleotide analog
<220> FEATURE:
<221> NAME/KEY: variation
<222> LOCATION: 15
<223> OTHER INFORMATION: U in position 2,3,8,12,15 and 16 is a lU1b
      nucleotide analog
<220> FEATURE:
<221> NAME/KEY: variation
<222> LOCATION: 16
<223> OTHER INFORMATION: U in position 2,3,8,12,15 and 16 is a lU1b
      nucleotide analog
<220> FEATURE:
<221> NAME/KEY: variation
<222> LOCATION: 17
<223> OTHER INFORMATION: C in position 1,5,7,14 and 17 represents a mC
      nucleotide analog
<220> FEATURE:
<221> NAME/KEY: variation
<222> LOCATION: 19
<223> OTHER INFORMATION: The nucleotide in position 19 and the
      nucleotide in position 20 are linked through a phosphoramidite
      bond
<220> FEATURE:
<221> NAME/KEY: variation
<222> LOCATION: 20
<223> OTHER INFORMATION: The nucleotide in position 19 and the
      nucleotide in position 20 are linked through a phosphoramidite
      bond

```
<220> FEATURE:
<221> NAME/KEY: variation
<222> LOCATION: 20
<223> OTHER INFORMATION: The nucleotide in position 20 and the
      nucleotide in position 21 are linked through a phosphoramidite
      bond
<220> FEATURE:
<221> NAME/KEY: variation
<222> LOCATION: 21
<223> OTHER INFORMATION: The nucleotide in position 20 and the
      nucleotide in position 21 are linked through a phosphoramidite
      bond

<400> SEQUENCE: 21
cuuacgcuga guacuucgat t                                              21

<210> SEQ ID NO 22
<211> LENGTH: 21
<212> TYPE: RNA
<213> ORGANISM: Artificial Sequence
<220> FEATURE:
<223> OTHER INFORMATION: ss20
<220> FEATURE:
<221> NAME/KEY: variation
<222> LOCATION: 1
<223> OTHER INFORMATION: C in position 1,5,7,14 and 17 represents a mC
      nucleotide analog
<220> FEATURE:
<221> NAME/KEY: variation
<222> LOCATION: 2
<223> OTHER INFORMATION: U in position 2,3,8,12 and 15 represents a
      2'-O-methyl-uracile (mU)
<220> FEATURE:
<221> NAME/KEY: variation
<222> LOCATION: 3
<223> OTHER INFORMATION: U in position 2,3,8,12 and 15 represents a
      2'-O-methyl-uracile (mU)
<220> FEATURE:
<221> NAME/KEY: variation
<222> LOCATION: 5
<223> OTHER INFORMATION: C in position 1,5,7,14 and 17 represents a mC
      nucleotide analog
<220> FEATURE:
<221> NAME/KEY: variation
<222> LOCATION: 7
<223> OTHER INFORMATION: C in position 1,5,7,14 and 17 represents a mC
      nucleotide analog
<220> FEATURE:
<221> NAME/KEY: variation
<222> LOCATION: 8
<223> OTHER INFORMATION: U in position 2,3,8,12 and 15 represents a
      2'-O-methyl-uracile (mU)
<220> FEATURE:
<221> NAME/KEY: variation
<222> LOCATION: 12
<223> OTHER INFORMATION: U in position 2,3,8,12 and 15 represents a
      2'-O-methyl-uracile (mU)
<220> FEATURE:
<221> NAME/KEY: variation
<222> LOCATION: 14
<223> OTHER INFORMATION: C in position 1,5,7,14 and 17 represents a mC
      nucleotide analog
<220> FEATURE:
<221> NAME/KEY: variation
<222> LOCATION: 15
<223> OTHER INFORMATION: U in position 2,3,8,12 and 15 represents a
      2'-O-methyl-uracile (mU)
<220> FEATURE:
<221> NAME/KEY: variation
<222> LOCATION: 16
<223> OTHER INFORMATION: U in position 16 is a lU1 nucleotide analog
<220> FEATURE:
<221> NAME/KEY: variation
<222> LOCATION: 17
<223> OTHER INFORMATION: C in position 1,5,7,14 and 17 represents a mC
      nucleotide analog
<220> FEATURE:
```

```
<221> NAME/KEY: variation
<222> LOCATION: 19
<223> OTHER INFORMATION: The nucleotide in position 19 and the
      nucleotide in position 20 are linked through a phosphoramidite
      bond
<220> FEATURE:
<221> NAME/KEY: variation
<222> LOCATION: 20
<223> OTHER INFORMATION: The nucleotide in position 19 and the
      nucleotide in position 20 are linked through a phosphoramidite
      bond
<220> FEATURE:
<221> NAME/KEY: variation
<222> LOCATION: 20
<223> OTHER INFORMATION: The nucleotide in position 20 and the
      nucleotide in position 21 are linked through a phosphoramidite
      bond
<220> FEATURE:
<221> NAME/KEY: variation
<222> LOCATION: 21
<223> OTHER INFORMATION: The nucleotide in position 20 and the
      nucleotide in position 21 are linked through a phosphoramidite
      bond

<400> SEQUENCE: 22
cuuacgcuga guacuucgat t                                           21

<210> SEQ ID NO 23
<211> LENGTH: 21
<212> TYPE: RNA
<213> ORGANISM: Artificial Sequence
<220> FEATURE:
<223> OTHER INFORMATION: ss21
<220> FEATURE:
<221> NAME/KEY: variation
<222> LOCATION: 1
<223> OTHER INFORMATION: C in position 1,5,7,14 and 17 represents a mC
      nucleotide analog
<220> FEATURE:
<221> NAME/KEY: variation
<222> LOCATION: 2
<223> OTHER INFORMATION: U in position 2,3,8 and 12 represents a
      2'-O-methyl-uracile (mU)
<220> FEATURE:
<221> NAME/KEY: variation
<222> LOCATION: 3
<223> OTHER INFORMATION: U in position 2,3,8 and 12 represents a
      2'-O-methyl-uracile (mU)
<220> FEATURE:
<221> NAME/KEY: variation
<222> LOCATION: 5
<223> OTHER INFORMATION: C in position 1,5,7,14 and 17 represents a mC
      nucleotide analog
<220> FEATURE:
<221> NAME/KEY: variation
<222> LOCATION: 7
<223> OTHER INFORMATION: C in position 1,5,7,14 and 17 represents a mC
      nucleotide analog
<220> FEATURE:
<221> NAME/KEY: variation
<222> LOCATION: 8
<223> OTHER INFORMATION: U in position 2,3,8 and 12 represents a
      2'-O-methyl-uracile (mU)
<220> FEATURE:
<221> NAME/KEY: variation
<222> LOCATION: 12
<223> OTHER INFORMATION: U in position 2,3,8 and 12 represents a
      2'-O-methyl-uracile (mU)
<220> FEATURE:
<221> NAME/KEY: variation
<222> LOCATION: 14
<223> OTHER INFORMATION: C in position 1,5,7,14 and 17 represents a mC
      nucleotide analog
<220> FEATURE:
<221> NAME/KEY: variation
<222> LOCATION: 15
<223> OTHER INFORMATION: U in position 15 and 16 is a lU1 nucleotide
```

```
            analog
<220> FEATURE:
<221> NAME/KEY: variation
<222> LOCATION: 16
<223> OTHER INFORMATION: U in position 15 and 16 is a lU1 nucleotide
      analog
<220> FEATURE:
<221> NAME/KEY: variation
<222> LOCATION: 17
<223> OTHER INFORMATION: C in position 1,5,7,14 and 17 represents a mC
      nucleotide analog
<220> FEATURE:
<221> NAME/KEY: variation
<222> LOCATION: 19
<223> OTHER INFORMATION: The nucleotide in position 19 and the
      nucleotide in position 20 are linked through a phosphoramidite
      bond
<220> FEATURE:
<221> NAME/KEY: variation
<222> LOCATION: 20
<223> OTHER INFORMATION: The nucleotide in position 19 and the
      nucleotide in position 20 are linked through a phosphoramidite
      bond
<220> FEATURE:
<221> NAME/KEY: variation
<222> LOCATION: 20
<223> OTHER INFORMATION: The nucleotide in position 20 and the
      nucleotide in position 21 are linked through a phosphoramidite
      bond
<220> FEATURE:
<221> NAME/KEY: variation
<222> LOCATION: 21
<223> OTHER INFORMATION: The nucleotide in position 20 and the
      nucleotide in position 21 are linked through a phosphoramidite
      bond

<400> SEQUENCE: 23
cuuacgcuga guacuucgat t                                              21

<210> SEQ ID NO 24
<211> LENGTH: 21
<212> TYPE: RNA
<213> ORGANISM: Artificial Sequence
<220> FEATURE:
<223> OTHER INFORMATION: ss22
<220> FEATURE:
<221> NAME/KEY: variation
<222> LOCATION: 1
<223> OTHER INFORMATION: C in position 1,5,7,14 and 17 represents a mC
      nucleotide analog
<220> FEATURE:
<221> NAME/KEY: variation
<222> LOCATION: 2
<223> OTHER INFORMATION: U in position 2,3 and 8 represents a 2'-O-
      methyl-uracile (mU)
<220> FEATURE:
<221> NAME/KEY: variation
<222> LOCATION: 3
<223> OTHER INFORMATION: U in position 2,3 and 8 represents a 2'-O-
      methyl-uracile (mU)
<220> FEATURE:
<221> NAME/KEY: variation
<222> LOCATION: 5
<223> OTHER INFORMATION: C in position 1,5,7,14 and 17 represents a mC
      nucleotide analog
<220> FEATURE:
<221> NAME/KEY: variation
<222> LOCATION: 7
<223> OTHER INFORMATION: C in position 1,5,7,14 and 17 represents a mC
      nucleotide analog
<220> FEATURE:
<221> NAME/KEY: variation
<222> LOCATION: 8
<223> OTHER INFORMATION: U in position 2,3 and 8 represents a 2'-O-
      methyl-uracile (mU)
<220> FEATURE:
<221> NAME/KEY: variation
```

```
<222> LOCATION: 12
<223> OTHER INFORMATION: U in position 12,15 and 16 is a lU1 nucleotide
      analog
<220> FEATURE:
<221> NAME/KEY: variation
<222> LOCATION: 14
<223> OTHER INFORMATION: C in position 1,5,7,14 and 17 represents a mC
      nucleotide analog
<220> FEATURE:
<221> NAME/KEY: variation
<222> LOCATION: 15
<223> OTHER INFORMATION: U in position 12,15 and 16 is a lU1 nucleotide
      analog
<220> FEATURE:
<221> NAME/KEY: variation
<222> LOCATION: 16
<223> OTHER INFORMATION: U in position 12,15 and 16 is a lU1 nucleotide
      analog
<220> FEATURE:
<221> NAME/KEY: variation
<222> LOCATION: 17
<223> OTHER INFORMATION: C in position 1,5,7,14 and 17 represents a mC
      nucleotide analog
<220> FEATURE:
<221> NAME/KEY: variation
<222> LOCATION: 19
<223> OTHER INFORMATION: The nucleotide in position 19 and the
      nucleotide in position 20 are linked through a phosphoramidite
      bond
<220> FEATURE:
<221> NAME/KEY: variation
<222> LOCATION: 20
<223> OTHER INFORMATION: The nucleotide in position 19 and the
      nucleotide in position 20 are linked through a phosphoramidite
      bond
<220> FEATURE:
<221> NAME/KEY: variation
<222> LOCATION: 20
<223> OTHER INFORMATION: The nucleotide in position 20 and the
      nucleotide in position 21 are linked through a phosphoramidite
      bond
<220> FEATURE:
<221> NAME/KEY: variation
<222> LOCATION: 21
<223> OTHER INFORMATION: The nucleotide in position 20 and the
      nucleotide in position 21 are linked through a phosphoramidite
      bond

<400> SEQUENCE: 24
cuuacgcuga guacuucgat t                                            21

<210> SEQ ID NO 25
<211> LENGTH: 21
<212> TYPE: RNA
<213> ORGANISM: Artificial Sequence
<220> FEATURE:
<223> OTHER INFORMATION: ss23
<220> FEATURE:
<221> NAME/KEY: variation
<222> LOCATION: 1
<223> OTHER INFORMATION: C in position 1,5,7,14 and 17 represents a mC
      nucleotide analog
<220> FEATURE:
<221> NAME/KEY: variation
<222> LOCATION: 2
<223> OTHER INFORMATION: U in position 2 and 3 represents a 2'-O-methyl-
      uracile (mU)
<220> FEATURE:
<221> NAME/KEY: variation
<222> LOCATION: 3
<223> OTHER INFORMATION: U in position 2 and 3 represents a 2'-O-methyl-
      uracile (mU)
<220> FEATURE:
<221> NAME/KEY: variation
<222> LOCATION: 5
<223> OTHER INFORMATION: C in position 1,5,7,14 and 17 represents a mC
      nucleotide analog
```

```
<220> FEATURE:
<221> NAME/KEY: variation
<222> LOCATION: 7
<223> OTHER INFORMATION: C in position 1,5,7,14 and 17 represents a mC
      nucleotide analog
<220> FEATURE:
<221> NAME/KEY: variation
<222> LOCATION: 8
<223> OTHER INFORMATION: U in position 8,12,15 and 16 is a lU1
      nucleotide analog
<220> FEATURE:
<221> NAME/KEY: variation
<222> LOCATION: 12
<223> OTHER INFORMATION: U in position 8,12,15 and 16 is a lU1
      nucleotide analog
<220> FEATURE:
<221> NAME/KEY: variation
<222> LOCATION: 14
<223> OTHER INFORMATION: C in position 1,5,7,14 and 17 represents a mC
      nucleotide analog
<220> FEATURE:
<221> NAME/KEY: variation
<222> LOCATION: 15
<223> OTHER INFORMATION: U in position 8,12,15 and 16 is a lU1
      nucleotide analog
<220> FEATURE:
<221> NAME/KEY: variation
<222> LOCATION: 16
<223> OTHER INFORMATION: U in position 8,12,15 and 16 is a lU1
      nucleotide analog
<220> FEATURE:
<221> NAME/KEY: variation
<222> LOCATION: 17
<223> OTHER INFORMATION: C in position 1,5,7,14 and 17 represents a mC
      nucleotide analog
<220> FEATURE:
<221> NAME/KEY: variation
<222> LOCATION: 19
<223> OTHER INFORMATION: The nucleotide in position 19 and the
      nucleotide in position 20 are linked through a phosphoramidite
      bond
<220> FEATURE:
<221> NAME/KEY: variation
<222> LOCATION: 20
<223> OTHER INFORMATION: The nucleotide in position 19 and the
      nucleotide in position 20 are linked through a phosphoramidite
      bond
<220> FEATURE:
<221> NAME/KEY: variation
<222> LOCATION: 20
<223> OTHER INFORMATION: The nucleotide in position 20 and the
      nucleotide in position 21 are linked through a phosphoramidite
      bond
<220> FEATURE:
<221> NAME/KEY: variation
<222> LOCATION: 21
<223> OTHER INFORMATION: The nucleotide in position 20 and the
      nucleotide in position 21 are linked through a phosphoramidite
      bond

<400> SEQUENCE: 25
cuuacgcuga guacuucgat t                                              21

<210> SEQ ID NO 26
<211> LENGTH: 21
<212> TYPE: RNA
<213> ORGANISM: Artificial Sequence
<220> FEATURE:
<223> OTHER INFORMATION: ss24
<220> FEATURE:
<221> NAME/KEY: variation
<222> LOCATION: 1
<223> OTHER INFORMATION: C in position 1,5,7,14 and 17 represents a mC
      nucleotide analog
<220> FEATURE:
<221> NAME/KEY: variation
<222> LOCATION: 2
```

```
<223> OTHER INFORMATION: U in position 2 represents a 2'-O-methyl-
      uracile (mU)
<220> FEATURE:
<221> NAME/KEY: variation
<222> LOCATION: 3
<223> OTHER INFORMATION: U in position 3,8,12,15 and 16 is a lU1
      nucleotide analog
<220> FEATURE:
<221> NAME/KEY: variation
<222> LOCATION: 5
<223> OTHER INFORMATION: C in position 1,5,7,14 and 17 represents a mC
      nucleotide analog
<220> FEATURE:
<221> NAME/KEY: variation
<222> LOCATION: 7
<223> OTHER INFORMATION: C in position 1,5,7,14 and 17 represents a mC
      nucleotide analog
<220> FEATURE:
<221> NAME/KEY: variation
<222> LOCATION: 8
<223> OTHER INFORMATION: U in position 3,8,12,15 and 16 is a lU1
      nucleotide analog
<220> FEATURE:
<221> NAME/KEY: variation
<222> LOCATION: 12
<223> OTHER INFORMATION: U in position 3,8,12,15 and 16 is a lU1
      nucleotide analog
<220> FEATURE:
<221> NAME/KEY: variation
<222> LOCATION: 14
<223> OTHER INFORMATION: C in position 1,5,7,14 and 17 represents a mC
      nucleotide analog
<220> FEATURE:
<221> NAME/KEY: variation
<222> LOCATION: 15
<223> OTHER INFORMATION: U in position 3,8,12,15 and 16 is a lU1
      nucleotide analog
<220> FEATURE:
<221> NAME/KEY: variation
<222> LOCATION: 16
<223> OTHER INFORMATION: U in position 3,8,12,15 and 16 is a lU1
      nucleotide analog
<220> FEATURE:
<221> NAME/KEY: variation
<222> LOCATION: 17
<223> OTHER INFORMATION: C in position 1,5,7,14 and 17 represents a mC
      nucleotide analog
<220> FEATURE:
<221> NAME/KEY: variation
<222> LOCATION: 19
<223> OTHER INFORMATION: The nucleotide in position 19 and the
      nucleotide in position 20 are linked through a phosphoramidite
      bond
<220> FEATURE:
<221> NAME/KEY: variation
<222> LOCATION: 20
<223> OTHER INFORMATION: The nucleotide in position 19 and the
      nucleotide in position 20 are linked through a phosphoramidite
      bond
<220> FEATURE:
<221> NAME/KEY: variation
<222> LOCATION: 20
<223> OTHER INFORMATION: The nucleotide in position 20 and the
      nucleotide in position 21 are linked through a phosphoramidite
      bond
<220> FEATURE:
<221> NAME/KEY: variation
<222> LOCATION: 21
<223> OTHER INFORMATION: The nucleotide in position 20 and the
      nucleotide in position 21 are linked through a phosphoramidite
      bond

<400> SEQUENCE: 26
cuuacgcuga guacuucgat t                                              21

<210> SEQ ID NO 27
<211> LENGTH: 21
```

```
<212> TYPE: RNA
<213> ORGANISM: Artificial Sequence
<220> FEATURE:
<223> OTHER INFORMATION: ss25
<220> FEATURE:
<221> NAME/KEY: variation
<222> LOCATION: 1
<223> OTHER INFORMATION: C in position 1,5,7,14 and 17 represents a mC
      nucleotide analog
<220> FEATURE:
<221> NAME/KEY: variation
<222> LOCATION: 2
<223> OTHER INFORMATION: U in position 2,3,8,12,15 and 16 is a iPr-
      morpholine-U (2S,6R) (lU3)
<220> FEATURE:
<221> NAME/KEY: variation
<222> LOCATION: 3
<223> OTHER INFORMATION: U in position 2,3,8,12,15 and 16 is a iPr-
      morpholine-U (2S,6R) (lU3)
<220> FEATURE:
<221> NAME/KEY: variation
<222> LOCATION: 5
<223> OTHER INFORMATION: C in position 1,5,7,14 and 17 represents a mC
      nucleotide analog
<220> FEATURE:
<221> NAME/KEY: variation
<222> LOCATION: 7
<223> OTHER INFORMATION: C in position 1,5,7,14 and 17 represents a mC
      nucleotide analog
<220> FEATURE:
<221> NAME/KEY: variation
<222> LOCATION: 8
<223> OTHER INFORMATION: U in position 2,3,8,12,15 and 16 is a iPr-
      morpholine-U (2S,6R) (lU3)
<220> FEATURE:
<221> NAME/KEY: variation
<222> LOCATION: 12
<223> OTHER INFORMATION: U in position 2,3,8,12,15 and 16 is a iPr-
      morpholine-U (2S,6R) (lU3)
<220> FEATURE:
<221> NAME/KEY: variation
<222> LOCATION: 14
<223> OTHER INFORMATION: C in position 1,5,7,14 and 17 represents a mC
      nucleotide analog
<220> FEATURE:
<221> NAME/KEY: variation
<222> LOCATION: 15
<223> OTHER INFORMATION: U in position 2,3,8,12,15 and 16 is a iPr-
      morpholine-U (2S,6R) (lU3)
<220> FEATURE:
<221> NAME/KEY: variation
<222> LOCATION: 16
<223> OTHER INFORMATION: U in position 2,3,8,12,15 and 16 is a iPr-
      morpholine-U (2S,6R) (lU3)
<220> FEATURE:
<221> NAME/KEY: variation
<222> LOCATION: 17
<223> OTHER INFORMATION: C in position 1,5,7,14 and 17 represents a mC
      nucleotide analog
<220> FEATURE:
<221> NAME/KEY: variation
<222> LOCATION: 19
<223> OTHER INFORMATION: The nucleotide in position 19 and the
      nucleotide in position 20 are linked through a phosphoramidite
      bond
<220> FEATURE:
<221> NAME/KEY: variation
<222> LOCATION: 20
<223> OTHER INFORMATION: The nucleotide in position 19 and the
      nucleotide in position 20 are linked through a phosphoramidite
      bond
<220> FEATURE:
<221> NAME/KEY: variation
<222> LOCATION: 20
<223> OTHER INFORMATION: The nucleotide in position 20 and the
      nucleotide in position 21 are linked through a phosphoramidite
      bond
<220> FEATURE:
<221> NAME/KEY: variation
```

```
<222> LOCATION: 21
<223> OTHER INFORMATION: The nucleotide in position 20 and the
      nucleotide in position 21 are linked through a phosphoramidite
      bond

<400> SEQUENCE: 27
cuuacgcuga guacuucgat t                                              21

<210> SEQ ID NO 28
<211> LENGTH: 21
<212> TYPE: RNA
<213> ORGANISM: Artificial Sequence
<220> FEATURE:
<223> OTHER INFORMATION: as3
<220> FEATURE:
<221> NAME/KEY: variation
<222> LOCATION: 20
<223> OTHER INFORMATION: The nucleotide in position 20 and the
      nucleotide in position 21 are linked through a phosphoramidite
      bond
<220> FEATURE:
<221> NAME/KEY: variation
<222> LOCATION: 21
<223> OTHER INFORMATION: The nucleotide in position 20 and the
      nucleotide in position 21 are linked through a phosphoramidite
      bond

<400> SEQUENCE: 28
ucgaaguacu cagcguaagt t                                              21

<210> SEQ ID NO 29
<211> LENGTH: 21
<212> TYPE: RNA
<213> ORGANISM: Artificial Sequence
<220> FEATURE:
<223> OTHER INFORMATION: ss26
<220> FEATURE:
<221> NAME/KEY: variation
<222> LOCATION: 4
<223> OTHER INFORMATION: U in position 4,9,15,16 and 19 represents a
      2'-O-methyl-uracile (mU)
<220> FEATURE:
<221> NAME/KEY: variation
<222> LOCATION: 9
<223> OTHER INFORMATION: U in position 4,9,15,16 and 19 represents a
      2'-O-methyl-uracile (mU)
<220> FEATURE:
<221> NAME/KEY: variation
<222> LOCATION: 15
<223> OTHER INFORMATION: U in position 4,9,15,16 and 19 represents a
      2'-O-methyl-uracile (mU)
<220> FEATURE:
<221> NAME/KEY: variation
<222> LOCATION: 16
<223> OTHER INFORMATION: U in position 4,9,15,16 and 19 represents a
      2'-O-methyl-uracile (mU)
<220> FEATURE:
<221> NAME/KEY: variation
<222> LOCATION: 19
<223> OTHER INFORMATION: U in position 4,9,15,16 and 19 represents a
      2'-O-methyl-uracile (mU)

<400> SEQUENCE: 29
ggaugaagug gagauuagut t                                              21

<210> SEQ ID NO 30
<211> LENGTH: 21
<212> TYPE: RNA
<213> ORGANISM: Artificial Sequence
<220> FEATURE:
<223> OTHER INFORMATION: as5
<220> FEATURE:
<221> NAME/KEY: variation
```

-continued

```
<222> LOCATION: 3
<223> OTHER INFORMATION: U in position 3 represents a 2'-O-methyl-
      uracile (mU)
<220> FEATURE:
<221> NAME/KEY: variation
<222> LOCATION: 10
<223> OTHER INFORMATION: C in position 10 and 15 represents a mC
      nucleotide analog
<220> FEATURE:
<221> NAME/KEY: variation
<222> LOCATION: 15
<223> OTHER INFORMATION: C in position 10 and 15 represents a mC
      nucleotide analog

<400> SEQUENCE: 30
acuaaucucc acuucaucct t                                             21

<210> SEQ ID NO 31
<211> LENGTH: 20
<212> TYPE: RNA
<213> ORGANISM: Artificial Sequence
<220> FEATURE:
<223> OTHER INFORMATION: ss44
<220> FEATURE:
<221> NAME/KEY: variation
<222> LOCATION: 4
<223> OTHER INFORMATION: U in position 4,9,15,16 and 19 represents a
      2'-O-methyl-uracile (mU)
<220> FEATURE:
<221> NAME/KEY: variation
<222> LOCATION: 9
<223> OTHER INFORMATION: U in position 4,9,15,16 and 19 represents a
      2'-O-methyl-uracile (mU)
<220> FEATURE:
<221> NAME/KEY: variation
<222> LOCATION: 15
<223> OTHER INFORMATION: U in position 4,9,15,16 and 19 represents a
      2'-O-methyl-uracile (mU)
<220> FEATURE:
<221> NAME/KEY: variation
<222> LOCATION: 16
<223> OTHER INFORMATION: U in position 4,9,15,16 and 19 represents a
      2'-O-methyl-uracile (mU)
<220> FEATURE:
<221> NAME/KEY: variation
<222> LOCATION: 19
<223> OTHER INFORMATION: U in position 4,9,15,16 and 19 represents a
      2'-O-methyl-uracile (mU)
<220> FEATURE:
<221> NAME/KEY: variation
<222> LOCATION: 20
<223> OTHER INFORMATION: T in position 20 is a lT3 nucleotide analog

<400> SEQUENCE: 31
ggaugaagug gagauuagut                                               20

<210> SEQ ID NO 32
<211> LENGTH: 21
<212> TYPE: RNA
<213> ORGANISM: Artificial Sequence
<220> FEATURE:
<223> OTHER INFORMATION: ss27
<220> FEATURE:
<221> NAME/KEY: variation
<222> LOCATION: 4
<223> OTHER INFORMATION: U in position 4,9,15,16 and 19 represents a
      2'-O-methyl-uracile (mU)
<220> FEATURE:
<221> NAME/KEY: variation
<222> LOCATION: 9
<223> OTHER INFORMATION: U in position 4,9,15,16 and 19 represents a
      2'-O-methyl-uracile (mU)
<220> FEATURE:
<221> NAME/KEY: variation
<222> LOCATION: 15
```

```
<223> OTHER INFORMATION: U in position 4,9,15,16 and 19 represents a
      2'-O-methyl-uracile (mU)
<220> FEATURE:
<221> NAME/KEY: variation
<222> LOCATION: 16
<223> OTHER INFORMATION: U in position 4,9,15,16 and 19 represents a
      2'-O-methyl-uracile (mU)
<220> FEATURE:
<221> NAME/KEY: variation
<222> LOCATION: 19
<223> OTHER INFORMATION: U in position 4,9,15,16 and 19 represents a
      2'-O-methyl-uracile (mU)
<220> FEATURE:
<221> NAME/KEY: variation
<222> LOCATION: 20
<223> OTHER INFORMATION: T in position 20 and 21 is a lT3 nucleotide
      analog
<220> FEATURE:
<221> NAME/KEY: variation
<222> LOCATION: 21
<223> OTHER INFORMATION: T in position 20 and 21 is a lT3 nucleotide
      analog

<400> SEQUENCE: 32
ggaugaagug gagauuagut t                                                  21

<210> SEQ ID NO 33
<211> LENGTH: 23
<212> TYPE: RNA
<213> ORGANISM: Artificial Sequence
<220> FEATURE:
<223> OTHER INFORMATION: ss45
<220> FEATURE:
<221> NAME/KEY: variation
<222> LOCATION: 1
<223> OTHER INFORMATION: U in position 1,2,22 and 23 represents a
      2'-O-methyl-uracile (mU)
<220> FEATURE:
<221> NAME/KEY: variation
<222> LOCATION: 2
<223> OTHER INFORMATION: U in position 1,2,22 and 23 represents a
      2'-O-methyl-uracile (mU)
<220> FEATURE:
<221> NAME/KEY: variation
<222> LOCATION: 6
<223> OTHER INFORMATION: U in position 6,11,17,18 and 21 represents a
      2'-O-methyl-uracile (mU)
<220> FEATURE:
<221> NAME/KEY: variation
<222> LOCATION: 11
<223> OTHER INFORMATION: U in position 6,11,17,18 and 21 represents a
      2'-O-methyl-uracile (mU)
<220> FEATURE:
<221> NAME/KEY: variation
<222> LOCATION: 17
<223> OTHER INFORMATION: U in position 6,11,17,18 and 21 represents a
      2'-O-methyl-uracile (mU)
<220> FEATURE:
<221> NAME/KEY: variation
<222> LOCATION: 18
<223> OTHER INFORMATION: U in position 6,11,17,18 and 21 represents a
      2'-O-methyl-uracile (mU)
<220> FEATURE:
<221> NAME/KEY: variation
<222> LOCATION: 21
<223> OTHER INFORMATION: U in position 6,11,17,18 and 21 represents a
      2'-O-methyl-uracile (mU)
<220> FEATURE:
<221> NAME/KEY: variation
<222> LOCATION: 22
<223> OTHER INFORMATION: U in position 1,2,22 and 23 represents a
      2'-O-methyl-uracile (mU)
<220> FEATURE:
<221> NAME/KEY: variation
<222> LOCATION: 23
<223> OTHER INFORMATION: U in position 1,2,22 and 23 represents a
      2'-O-methyl-uracile (mU)
```

<400> SEQUENCE: 33
ttggaugaag uggagauuag utt                                          23

<210> SEQ ID NO 34
<211> LENGTH: 20
<212> TYPE: RNA
<213> ORGANISM: Artificial Sequence
<220> FEATURE:
<223> OTHER INFORMATION: ss46
<220> FEATURE:
<221> NAME/KEY: variation
<222> LOCATION: 4
<223> OTHER INFORMATION: U in position 4,9,15,16 and 19 represents a
      2'-O-methyl-uracile (mU)
<220> FEATURE:
<221> NAME/KEY: variation
<222> LOCATION: 9
<223> OTHER INFORMATION: U in position 4,9,15,16 and 19 represents a
      2'-O-methyl-uracile (mU)
<220> FEATURE:
<221> NAME/KEY: variation
<222> LOCATION: 15
<223> OTHER INFORMATION: U in position 4,9,15,16 and 19 represents a
      2'-O-methyl-uracile (mU)
<220> FEATURE:
<221> NAME/KEY: variation
<222> LOCATION: 16
<223> OTHER INFORMATION: U in position 4,9,15,16 and 19 represents a
      2'-O-methyl-uracile (mU)
<220> FEATURE:
<221> NAME/KEY: variation
<222> LOCATION: 19
<223> OTHER INFORMATION: U in position 4,9,15,16 and 19 represents a
      2'-O-methyl-uracile (mU)
<220> FEATURE:
<221> NAME/KEY: variation
<222> LOCATION: 20
<223> OTHER INFORMATION: T in position 20 is a 1T3b nucleotide analog

<400> SEQUENCE: 34
ggaugaagug gagauuagut                                              20

<210> SEQ ID NO 35
<211> LENGTH: 21
<212> TYPE: RNA
<213> ORGANISM: Artificial Sequence
<220> FEATURE:
<223> OTHER INFORMATION: 37
<220> FEATURE:
<221> NAME/KEY: variation
<222> LOCATION: 4
<223> OTHER INFORMATION: U in position 4,9,15,16 and 19 represents a
      2'-O-methyl-uracile (mU)
<220> FEATURE:
<221> NAME/KEY: variation
<222> LOCATION: 9
<223> OTHER INFORMATION: U in position 4,9,15,16 and 19 represents a
      2'-O-methyl-uracile (mU)
<220> FEATURE:
<221> NAME/KEY: variation
<222> LOCATION: 15
<223> OTHER INFORMATION: U in position 4,9,15,16 and 19 represents a
      2'-O-methyl-uracile (mU)
<220> FEATURE:
<221> NAME/KEY: variation
<222> LOCATION: 16
<223> OTHER INFORMATION: U in position 4,9,15,16 and 19 represents a
      2'-O-methyl-uracile (mU)
<220> FEATURE:
<221> NAME/KEY: variation
<222> LOCATION: 19
<223> OTHER INFORMATION: U in position 4,9,15,16 and 19 represents a
      2'-O-methyl-uracile (mU)
<220> FEATURE:

```
<221> NAME/KEY: variation
<222> LOCATION: 20
<223> OTHER INFORMATION: T in position 20 and 21 is a lT3b nucleotide
      analog
<220> FEATURE:
<221> NAME/KEY: variation
<222> LOCATION: 21
<223> OTHER INFORMATION: T in position 20 and 21 is a lT3b nucleotide
      analog

<400> SEQUENCE: 35
ggaugaagug gagauuagut t                                            21

<210> SEQ ID NO 36
<211> LENGTH: 23
<212> TYPE: RNA
<213> ORGANISM: Artificial Sequence
<220> FEATURE:
<223> OTHER INFORMATION: ss47
<220> FEATURE:
<221> NAME/KEY: variation
<222> LOCATION: 1
<223> OTHER INFORMATION: T in position 1,2,22 and 23 is a lT3b
      nucleotide analog
<220> FEATURE:
<221> NAME/KEY: variation
<222> LOCATION: 2
<223> OTHER INFORMATION: T in position 1,2,22 and 23 is a lT3b
      nucleotide analog
<220> FEATURE:
<221> NAME/KEY: variation
<222> LOCATION: 6
<223> OTHER INFORMATION: U in position 6,11,17,18 and 21 represents a
      2'-O-methyl-uracile (mU)
<220> FEATURE:
<221> NAME/KEY: variation
<222> LOCATION: 11
<223> OTHER INFORMATION: U in position 6,11,17,18 and 21 represents a
      2'-O-methyl-uracile (mU)
<220> FEATURE:
<221> NAME/KEY: variation
<222> LOCATION: 17
<223> OTHER INFORMATION: U in position 6,11,17,18 and 21 represents a
      2'-O-methyl-uracile (mU)
<220> FEATURE:
<221> NAME/KEY: variation
<222> LOCATION: 18
<223> OTHER INFORMATION: U in position 6,11,17,18 and 21 represents a
      2'-O-methyl-uracile (mU)
<220> FEATURE:
<221> NAME/KEY: variation
<222> LOCATION: 21
<223> OTHER INFORMATION: U in position 6,11,17,18 and 21 represents a
      2'-O-methyl-uracile (mU)
<220> FEATURE:
<221> NAME/KEY: variation
<222> LOCATION: 22
<223> OTHER INFORMATION: T in position 1,2,22 and 23 is a lT3b
      nucleotide analog
<220> FEATURE:
<221> NAME/KEY: variation
<222> LOCATION: 23
<223> OTHER INFORMATION: T in position 1,2,22 and 23 is a lT3b
      nucleotide analog

<400> SEQUENCE: 36
ttggaugaag uggagauuag utt                                          23

<210> SEQ ID NO 37
<211> LENGTH: 20
<212> TYPE: RNA
<213> ORGANISM: Artificial Sequence
<220> FEATURE:
<223> OTHER INFORMATION: ss48
<220> FEATURE:
```

```
<221> NAME/KEY: variation
<222> LOCATION: 4
<223> OTHER INFORMATION: U in position 4,9,15,16 and 19 represents a
      2'-O-methyl-uracile (mU)
<220> FEATURE:
<221> NAME/KEY: variation
<222> LOCATION: 9
<223> OTHER INFORMATION: U in position 4,9,15,16 and 19 represents a
      2'-O-methyl-uracile (mU)
<220> FEATURE:
<221> NAME/KEY: variation
<222> LOCATION: 15
<223> OTHER INFORMATION: U in position 4,9,15,16 and 19 represents a
      2'-O-methyl-uracile (mU)
<220> FEATURE:
<221> NAME/KEY: variation
<222> LOCATION: 16
<223> OTHER INFORMATION: U in position 4,9,15,16 and 19 represents a
      2'-O-methyl-uracile (mU)
<220> FEATURE:
<221> NAME/KEY: variation
<222> LOCATION: 19
<223> OTHER INFORMATION: U in position 4,9,15,16 and 19 represents a
      2'-O-methyl-uracile (mU)
<220> FEATURE:
<221> NAME/KEY: variation
<222> LOCATION: 20
<223> OTHER INFORMATION: T in position 20 is a lT1 nucleotide analog

<400> SEQUENCE: 37
ggaugaagug gagauuagut                                                 20

<210> SEQ ID NO 38
<211> LENGTH: 21
<212> TYPE: RNA
<213> ORGANISM: Artificial Sequence
<220> FEATURE:
<223> OTHER INFORMATION: ss49
<220> FEATURE:
<221> NAME/KEY: variation
<222> LOCATION: 4
<223> OTHER INFORMATION: U in position 4,9,15,16 and 19 represents a
      2'-O-methyl-uracile (mU)
<220> FEATURE:
<221> NAME/KEY: variation
<222> LOCATION: 9
<223> OTHER INFORMATION: U in position 4,9,15,16 and 19 represents a
      2'-O-methyl-uracile (mU)
<220> FEATURE:
<221> NAME/KEY: variation
<222> LOCATION: 15
<223> OTHER INFORMATION: U in position 4,9,15,16 and 19 represents a
      2'-O-methyl-uracile (mU)
<220> FEATURE:
<221> NAME/KEY: variation
<222> LOCATION: 16
<223> OTHER INFORMATION: U in position 4,9,15,16 and 19 represents a
      2'-O-methyl-uracile (mU)
<220> FEATURE:
<221> NAME/KEY: variation
<222> LOCATION: 19
<223> OTHER INFORMATION: U in position 4,9,15,16 and 19 represents a
      2'-O-methyl-uracile (mU)
<220> FEATURE:
<221> NAME/KEY: variation
<222> LOCATION: 20
<223> OTHER INFORMATION: T in position 20,21 is a lT1 nucleotide analog
<220> FEATURE:
<221> NAME/KEY: variation
<222> LOCATION: 21
<223> OTHER INFORMATION: T in position 20,21 is a lT1 nucleotide analog

<400> SEQUENCE: 38
ggaugaagug gagauuagut t                                               21
```

```
<210> SEQ ID NO 39
<211> LENGTH: 23
<212> TYPE: RNA
<213> ORGANISM: Artificial Sequence
<220> FEATURE:
<223> OTHER INFORMATION: ss50
<220> FEATURE:
<221> NAME/KEY: variation
<222> LOCATION: 1
<223> OTHER INFORMATION: T in position 1,2,22 and 23 is a lT1 nucleotide
      analog
<220> FEATURE:
<221> NAME/KEY: variation
<222> LOCATION: 2
<223> OTHER INFORMATION: T in position 1,2,22 and 23 is a lT1 nucleotide
      analog
<220> FEATURE:
<221> NAME/KEY: variation
<222> LOCATION: 6
<223> OTHER INFORMATION: U in position 6,11,17,18 and 21 represents a
      2'-O-methyl-uracile (mU)
<220> FEATURE:
<221> NAME/KEY: variation
<222> LOCATION: 11
<223> OTHER INFORMATION: U in position 6,11,17,18 and 21 represents a
      2'-O-methyl-uracile (mU)
<220> FEATURE:
<221> NAME/KEY: variation
<222> LOCATION: 17
<223> OTHER INFORMATION: U in position 6,11,17,18 and 21 represents a
      2'-O-methyl-uracile (mU)
<220> FEATURE:
<221> NAME/KEY: variation
<222> LOCATION: 18
<223> OTHER INFORMATION: U in position 6,11,17,18 and 21 represents a
      2'-O-methyl-uracile (mU)
<220> FEATURE:
<221> NAME/KEY: variation
<222> LOCATION: 21
<223> OTHER INFORMATION: U in position 6,11,17,18 and 21 represents a
      2'-O-methyl-uracile (mU)
<220> FEATURE:
<221> NAME/KEY: variation
<222> LOCATION: 22
<223> OTHER INFORMATION: T in position 1,2,22 and 23 is a lT1 nucleotide
      analog
<220> FEATURE:
<221> NAME/KEY: variation
<222> LOCATION: 23
<223> OTHER INFORMATION: T in position 1,2,22 and 23 is a lT1 nucleotide
      analog

<400> SEQUENCE: 39
ttggaugaag uggagauuag utt                                             23

<210> SEQ ID NO 40
<211> LENGTH: 20
<212> TYPE: RNA
<213> ORGANISM: Artificial Sequence
<220> FEATURE:
<223> OTHER INFORMATION: ss51
<220> FEATURE:
<221> NAME/KEY: variation
<222> LOCATION: 4
<223> OTHER INFORMATION: U in position 4,9,15,16 and 19 represents a
      2'-O-methyl-uracile (mU)
<220> FEATURE:
<221> NAME/KEY: variation
<222> LOCATION: 9
<223> OTHER INFORMATION: U in position 4,9,15,16 and 19 represents a
      2'-O-methyl-uracile (mU)
<220> FEATURE:
<221> NAME/KEY: variation
<222> LOCATION: 15
<223> OTHER INFORMATION: U in position 4,9,15,16 and 19 represents a
      2'-O-methyl-uracile (mU)
<220> FEATURE:
```

```
<221> NAME/KEY: variation
<222> LOCATION: 16
<223> OTHER INFORMATION: U in position 4,9,15,16 and 19 represents a
      2'-O-methyl-uracile (mU)
<220> FEATURE:
<221> NAME/KEY: variation
<222> LOCATION: 19
<223> OTHER INFORMATION: U in position 4,9,15,16 and 19 represents a
      2'-O-methyl-uracile (mU)
<220> FEATURE:
<221> NAME/KEY: variation
<222> LOCATION: 20
<223> OTHER INFORMATION: T in position 20 is a lT1b nucleotide analog

<400> SEQUENCE: 40
ggaugaagug gagauuagut                                                     20

<210> SEQ ID NO 41
<211> LENGTH: 21
<212> TYPE: RNA
<213> ORGANISM: Artificial Sequence
<220> FEATURE:
<223> OTHER INFORMATION: ss52
<220> FEATURE:
<221> NAME/KEY: variation
<222> LOCATION: 4
<223> OTHER INFORMATION: U in position 4,9,15,16 and 19 represents a
      2'-O-methyl-uracile (mU)
<220> FEATURE:
<221> NAME/KEY: variation
<222> LOCATION: 9
<223> OTHER INFORMATION: U in position 4,9,15,16 and 19 represents a
      2'-O-methyl-uracile (mU)
<220> FEATURE:
<221> NAME/KEY: variation
<222> LOCATION: 15
<223> OTHER INFORMATION: U in position 4,9,15,16 and 19 represents a
      2'-O-methyl-uracile (mU)
<220> FEATURE:
<221> NAME/KEY: variation
<222> LOCATION: 16
<223> OTHER INFORMATION: U in position 4,9,15,16 and 19 represents a
      2'-O-methyl-uracile (mU)
<220> FEATURE:
<221> NAME/KEY: variation
<222> LOCATION: 19
<223> OTHER INFORMATION: U in position 4,9,15,16 and 19 represents a
      2'-O-methyl-uracile (mU)
<220> FEATURE:
<221> NAME/KEY: variation
<222> LOCATION: 20
<223> OTHER INFORMATION: T in position 20 and 21 is a lT1b nucleotide
      analog
<220> FEATURE:
<221> NAME/KEY: variation
<222> LOCATION: 21
<223> OTHER INFORMATION: T in position 20 and 21 is a lT1b nucleotide
      analog

<400> SEQUENCE: 41
ggaugaagug gagauuagut t                                                   21

<210> SEQ ID NO 42
<211> LENGTH: 23
<212> TYPE: RNA
<213> ORGANISM: Artificial Sequence
<220> FEATURE:
<223> OTHER INFORMATION: ss53
<220> FEATURE:
<221> NAME/KEY: variation
<222> LOCATION: 1
<223> OTHER INFORMATION: T in position 1,2,22 and 23 is a lT1b
      nucleotide analog
<220> FEATURE:
<221> NAME/KEY: variation
```

```
<222> LOCATION: 2
<223> OTHER INFORMATION: T in position 1,2,22 and 23 is a lT1b
      nucleotide analog
<220> FEATURE:
<221> NAME/KEY: variation
<222> LOCATION: 6
<223> OTHER INFORMATION: U in position 6,11,17,18 and 21 represents a
      2'-O-methyl-uracile (mU)
<220> FEATURE:
<221> NAME/KEY: variation
<222> LOCATION: 11
<223> OTHER INFORMATION: U in position 6,11,17,18 and 21 represents a
      2'-O-methyl-uracile (mU)
<220> FEATURE:
<221> NAME/KEY: variation
<222> LOCATION: 17
<223> OTHER INFORMATION: U in position 6,11,17,18 and 21 represents a
      2'-O-methyl-uracile (mU)
<220> FEATURE:
<221> NAME/KEY: variation
<222> LOCATION: 18
<223> OTHER INFORMATION: U in position 6,11,17,18 and 21 represents a
      2'-O-methyl-uracile (mU)
<220> FEATURE:
<221> NAME/KEY: variation
<222> LOCATION: 21
<223> OTHER INFORMATION: U in position 6,11,17,18 and 21 represents a
      2'-O-methyl-uracile (mU)
<220> FEATURE:
<221> NAME/KEY: variation
<222> LOCATION: 22
<223> OTHER INFORMATION: T in position 1,2,22 and 23 is a lT1b
      nucleotide analog
<220> FEATURE:
<221> NAME/KEY: variation
<222> LOCATION: 23
<223> OTHER INFORMATION: T in position 1,2,22 and 23 is a lT1b
      nucleotide analog

<400> SEQUENCE: 42
ttggaugaag uggagauuag utt                                            23

<210> SEQ ID NO 43
<211> LENGTH: 20
<212> TYPE: RNA
<213> ORGANISM: Artificial Sequence
<220> FEATURE:
<223> OTHER INFORMATION: as6
<220> FEATURE:
<221> NAME/KEY: variation
<222> LOCATION: 3
<223> OTHER INFORMATION: U in position 3 represents a 2'-O-methyl-
      uracile (mU)
<220> FEATURE:
<221> NAME/KEY: variation
<222> LOCATION: 10
<223> OTHER INFORMATION: C in position 10 and 15 represents a mC
      nucleotide analog
<220> FEATURE:
<221> NAME/KEY: variation
<222> LOCATION: 15
<223> OTHER INFORMATION: C in position 10 and 15 represents a mC
      nucleotide analog
<220> FEATURE:
<221> NAME/KEY: variation
<222> LOCATION: 20
<223> OTHER INFORMATION: T in position 20 is a lT3 nucleotide analog

<400> SEQUENCE: 43
acuaaucucc acuucaucct                                                20

<210> SEQ ID NO 44
<211> LENGTH: 20
<212> TYPE: RNA
<213> ORGANISM: Artificial Sequence
```

```
<220> FEATURE:
<223> OTHER INFORMATION: as7
<220> FEATURE:
<221> NAME/KEY: variation
<222> LOCATION: 3
<223> OTHER INFORMATION: U in position 3 represents a 2'-O-methyl-
      uracile (mU)
<220> FEATURE:
<221> NAME/KEY: variation
<222> LOCATION: 10
<223> OTHER INFORMATION: C in position 10 and 15 represents a mC
      nucleotide analog
<220> FEATURE:
<221> NAME/KEY: variation
<222> LOCATION: 15
<223> OTHER INFORMATION: C in position 10 and 15 represents a mC
      nucleotide analog
<220> FEATURE:
<221> NAME/KEY: variation
<222> LOCATION: 20
<223> OTHER INFORMATION: T in position 20 is a lT3b nucleotide analog

<400> SEQUENCE: 44
acuaaucucc acuucaucct                                              20

<210> SEQ ID NO 45
<211> LENGTH: 20
<212> TYPE: RNA
<213> ORGANISM: Artificial Sequence
<220> FEATURE:
<223> OTHER INFORMATION: as8
<220> FEATURE:
<221> NAME/KEY: variation
<222> LOCATION: 3
<223> OTHER INFORMATION: U in position 3 represents a 2'-O-methyl-
      uracile (mU)
<220> FEATURE:
<221> NAME/KEY: variation
<222> LOCATION: 10
<223> OTHER INFORMATION: C in position 10 and 15 represents a mC
      nucleotide analog
<220> FEATURE:
<221> NAME/KEY: variation
<222> LOCATION: 15
<223> OTHER INFORMATION: C in position 10 and 15 represents a mC
      nucleotide analog
<220> FEATURE:
<221> NAME/KEY: variation
<222> LOCATION: 20
<223> OTHER INFORMATION: T in position 20 is a lT1 nucleotide analog

<400> SEQUENCE: 45
acuaaucucc acuucaucct                                              20

<210> SEQ ID NO 46
<211> LENGTH: 20
<212> TYPE: RNA
<213> ORGANISM: Artificial Sequence
<220> FEATURE:
<223> OTHER INFORMATION: as9
<220> FEATURE:
<221> NAME/KEY: variation
<222> LOCATION: 3
<223> OTHER INFORMATION: U in position 3 represents a 2'-O-methyl-
      uracile (mU)
<220> FEATURE:
<221> NAME/KEY: variation
<222> LOCATION: 10
<223> OTHER INFORMATION: C in position 10 and 15 represents a mC
      nucleotide analog
<220> FEATURE:
<221> NAME/KEY: variation
<222> LOCATION: 15
<223> OTHER INFORMATION: C in position 10 and 15 represents a mC
      nucleotide analog
```

```
<220> FEATURE:
<221> NAME/KEY: variation
<222> LOCATION: 20
<223> OTHER INFORMATION: T in position 20 is a 1T1b nucleotide analog

<400> SEQUENCE: 46
acuaaucucc acuucaucct                                                    20

<210> SEQ ID NO 47
<211> LENGTH: 21
<212> TYPE: RNA
<213> ORGANISM: Artificial Sequence
<220> FEATURE:
<223> OTHER INFORMATION: as10
<220> FEATURE:
<221> NAME/KEY: variation
<222> LOCATION: 3
<223> OTHER INFORMATION: U in position 3 represents a 2'-O-methyl-
      uracile (mU)
<220> FEATURE:
<221> NAME/KEY: variation
<222> LOCATION: 10
<223> OTHER INFORMATION: C in position 10 and 15 represents a mC
      nucleotide analog
<220> FEATURE:
<221> NAME/KEY: variation
<222> LOCATION: 15
<223> OTHER INFORMATION: C in position 10 and 15 represents a mC
      nucleotide analog
<220> FEATURE:
<221> NAME/KEY: variation
<222> LOCATION: 20
<223> OTHER INFORMATION: T in position 20 and 21 is a 1T3 nucleotide
      analog
<220> FEATURE:
<221> NAME/KEY: variation
<222> LOCATION: 21
<223> OTHER INFORMATION: T in position 20 and 21 is a 1T3 nucleotide
      analog

<400> SEQUENCE: 47
acuaaucucc acuucaucct t                                                  21

<210> SEQ ID NO 48
<211> LENGTH: 21
<212> TYPE: RNA
<213> ORGANISM: Artificial Sequence
<220> FEATURE:
<223> OTHER INFORMATION: as11
<220> FEATURE:
<221> NAME/KEY: variation
<222> LOCATION: 3
<223> OTHER INFORMATION: U in position 3 represents a 2'-O-methyl-
      uracile (mU)
<220> FEATURE:
<221> NAME/KEY: variation
<222> LOCATION: 10
<223> OTHER INFORMATION: C in position 10 and 15 represents a mC
      nucleotide analog
<220> FEATURE:
<221> NAME/KEY: variation
<222> LOCATION: 15
<223> OTHER INFORMATION: C in position 10 and 15 represents a mC
      nucleotide analog
<220> FEATURE:
<221> NAME/KEY: variation
<222> LOCATION: 20
<223> OTHER INFORMATION: T in position 20 and 21 is a 1T3b nucleotide
      analog
<220> FEATURE:
<221> NAME/KEY: variation
<222> LOCATION: 21
<223> OTHER INFORMATION: T in position 20 and 21 is a 1T3b nucleotide
      analog
```

```
<400> SEQUENCE: 48
acuaaucucc acuucaucct t                                              21

<210> SEQ ID NO 49
<211> LENGTH: 21
<212> TYPE: RNA
<213> ORGANISM: Artificial Sequence
<220> FEATURE:
<223> OTHER INFORMATION: as12
<220> FEATURE:
<221> NAME/KEY: variation
<222> LOCATION: 3
<223> OTHER INFORMATION: U in position 3 represents a 2'-O-methyl-
      uracile (mU)
<220> FEATURE:
<221> NAME/KEY: variation
<222> LOCATION: 10
<223> OTHER INFORMATION: C in position 10 and 15 represents a mC
      nucleotide analog
<220> FEATURE:
<221> NAME/KEY: variation
<222> LOCATION: 15
<223> OTHER INFORMATION: C in position 10 and 15 represents a mC
      nucleotide analog
<220> FEATURE:
<221> NAME/KEY: variation
<222> LOCATION: 20
<223> OTHER INFORMATION: T in position 20 and 21 is a lT1 nucleotide
      analog
<220> FEATURE:
<221> NAME/KEY: variation
<222> LOCATION: 21
<223> OTHER INFORMATION: T in position 20 and 21 is a lT1 nucleotide
      analog

<400> SEQUENCE: 49
acuaaucucc acuucaucct t                                              21

<210> SEQ ID NO 50
<211> LENGTH: 21
<212> TYPE: RNA
<213> ORGANISM: Artificial Sequence
<220> FEATURE:
<223> OTHER INFORMATION: as13
<220> FEATURE:
<221> NAME/KEY: variation
<222> LOCATION: 3
<223> OTHER INFORMATION: U in position 3 represents a 2'-O-methyl-
      uracile (mU)
<220> FEATURE:
<221> NAME/KEY: variation
<222> LOCATION: 10
<223> OTHER INFORMATION: C in position 10 and 15 represents a mC
      nucleotide analog
<220> FEATURE:
<221> NAME/KEY: variation
<222> LOCATION: 15
<223> OTHER INFORMATION: C in position 10 and 15 represents a mC
      nucleotide analog
<220> FEATURE:
<221> NAME/KEY: variation
<222> LOCATION: 20
<223> OTHER INFORMATION: T in position 20 and 21 is a lT1b nucleotide
      analog
<220> FEATURE:
<221> NAME/KEY: variation
<222> LOCATION: 21
<223> OTHER INFORMATION: T in position 20 and 21 is a lT1b nucleotide
      analog

<400> SEQUENCE: 50
acuaaucucc acuucaucct t                                              21
```

```
<210> SEQ ID NO 51
<211> LENGTH: 23
<212> TYPE: RNA
<213> ORGANISM: Artificial Sequence
<220> FEATURE:
<223> OTHER INFORMATION: ss28
<220> FEATURE:
<221> NAME/KEY: variation
<222> LOCATION: 4
<223> OTHER INFORMATION: U in position 4,9,15,16 and 19 represents a
      2'-O-methyl-uracile (mU)
<220> FEATURE:
<221> NAME/KEY: variation
<222> LOCATION: 9
<223> OTHER INFORMATION: U in position 4,9,15,16 and 19 represents a
      2'-O-methyl-uracile (mU)
<220> FEATURE:
<221> NAME/KEY: variation
<222> LOCATION: 15
<223> OTHER INFORMATION: U in position 4,9,15,16 and 19 represents a
      2'-O-methyl-uracile (mU)
<220> FEATURE:
<221> NAME/KEY: variation
<222> LOCATION: 16
<223> OTHER INFORMATION: U in position 4,9,15,16 and 19 represents a
      2'-O-methyl-uracile (mU)
<220> FEATURE:
<221> NAME/KEY: variation
<222> LOCATION: 19
<223> OTHER INFORMATION: U in position 4,9,15,16 and 19 represents a
      2'-O-methyl-uracile (mU)
<220> FEATURE:
<221> NAME/KEY: variation
<222> LOCATION: 20
<223> OTHER INFORMATION: T in position 20,21,22 and 23 is a lT3
      nucleotide analog
<220> FEATURE:
<221> NAME/KEY: variation
<222> LOCATION: 21
<223> OTHER INFORMATION: T in position 20,21,22 and 23 is a lT3
      nucleotide analog
<220> FEATURE:
<221> NAME/KEY: variation
<222> LOCATION: 22
<223> OTHER INFORMATION: T in position 20,21,22 and 23 is a lT3
      nucleotide analog
<220> FEATURE:
<221> NAME/KEY: variation
<222> LOCATION: 23
<223> OTHER INFORMATION: T in position 20,21,22 and 23 is a lT3
      nucleotide analog

<400> SEQUENCE: 51
ggaugaagug gagauuagut ttt                                      23

<210> SEQ ID NO 52
<211> LENGTH: 24
<212> TYPE: RNA
<213> ORGANISM: Artificial Sequence
<220> FEATURE:
<223> OTHER INFORMATION: ss29
<220> FEATURE:
<221> NAME/KEY: variation
<222> LOCATION: 4
<223> OTHER INFORMATION: U in position 4,9,15,16 and 19 represents a
      2'-O-methyl-uracile (mU)
<220> FEATURE:
<221> NAME/KEY: variation
<222> LOCATION: 9
<223> OTHER INFORMATION: U in position 4,9,15,16 and 19 represents a
      2'-O-methyl-uracile (mU)
<220> FEATURE:
<221> NAME/KEY: variation
<222> LOCATION: 15
<223> OTHER INFORMATION: U in position 4,9,15,16 and 19 represents a
      2'-O-methyl-uracile (mU)
<220> FEATURE:
```

```
<221> NAME/KEY: variation
<222> LOCATION: 16
<223> OTHER INFORMATION: U in position 4,9,15,16 and 19 represents a
      2'-O-methyl-uracile (mU)
<220> FEATURE:
<221> NAME/KEY: variation
<222> LOCATION: 19
<223> OTHER INFORMATION: U in position 4,9,15,16 and 19 represents a
      2'-O-methyl-uracile (mU)
<220> FEATURE:
<221> NAME/KEY: variation
<222> LOCATION: 20
<223> OTHER INFORMATION: T in position 20,21,22,23 and 24 is a lT3
      nucleotide analog
<220> FEATURE:
<221> NAME/KEY: variation
<222> LOCATION: 21
<223> OTHER INFORMATION: T in position 20,21,22,23 and 24 is a lT3
      nucleotide analog
<220> FEATURE:
<221> NAME/KEY: variation
<222> LOCATION: 22
<223> OTHER INFORMATION: T in position 20,21,22,23 and 24 is a lT3
      nucleotide analog
<220> FEATURE:
<221> NAME/KEY: variation
<222> LOCATION: 23
<223> OTHER INFORMATION: T in position 20,21,22,23 and 24 is a lT3
      nucleotide analog
<220> FEATURE:
<221> NAME/KEY: variation
<222> LOCATION: 24
<223> OTHER INFORMATION: T in position 20,21,22,23 and 24 is a lT3
      nucleotide analog

<400> SEQUENCE: 52
ggaugaagug gagauuagut tttt                                             24

<210> SEQ ID NO 53
<211> LENGTH: 25
<212> TYPE: RNA
<213> ORGANISM: Artificial Sequence
<220> FEATURE:
<223> OTHER INFORMATION: ss30
<220> FEATURE:
<221> NAME/KEY: variation
<222> LOCATION: 4
<223> OTHER INFORMATION: U in position 4,9,15,16 and 19 represents a
      2'-O-methyl-uracile (mU)
<220> FEATURE:
<221> NAME/KEY: variation
<222> LOCATION: 9
<223> OTHER INFORMATION: U in position 4,9,15,16 and 19 represents a
      2'-O-methyl-uracile (mU)
<220> FEATURE:
<221> NAME/KEY: variation
<222> LOCATION: 15
<223> OTHER INFORMATION: U in position 4,9,15,16 and 19 represents a
      2'-O-methyl-uracile (mU)
<220> FEATURE:
<221> NAME/KEY: variation
<222> LOCATION: 16
<223> OTHER INFORMATION: U in position 4,9,15,16 and 19 represents a
      2'-O-methyl-uracile (mU)
<220> FEATURE:
<221> NAME/KEY: variation
<222> LOCATION: 19
<223> OTHER INFORMATION: U in position 4,9,15,16 and 19 represents a
      2'-O-methyl-uracile (mU)
<220> FEATURE:
<221> NAME/KEY: variation
<222> LOCATION: 20
<223> OTHER INFORMATION: T in position 20,21,22,23,24 and 25 is a lT3
      nucleotide analog
<220> FEATURE:
<221> NAME/KEY: variation
<222> LOCATION: 21
```

```
<223> OTHER INFORMATION: T in position 20,21,22,23,24 and 25 is a lT3
      nucleotide analog
<220> FEATURE:
<221> NAME/KEY: variation
<222> LOCATION: 22
<223> OTHER INFORMATION: T in position 20,21,22,23,24 and 25 is a lT3
      nucleotide analog
<220> FEATURE:
<221> NAME/KEY: variation
<222> LOCATION: 23
<223> OTHER INFORMATION: T in position 20,21,22,23,24 and 25 is a lT3
      nucleotide analog
<220> FEATURE:
<221> NAME/KEY: variation
<222> LOCATION: 24
<223> OTHER INFORMATION: T in position 20,21,22,23,24 and 25 is a lT3
      nucleotide analog
<220> FEATURE:
<221> NAME/KEY: variation
<222> LOCATION: 25
<223> OTHER INFORMATION: T in position 20,21,22,23,24 and 25 is a lT3
      nucleotide analog

<400> SEQUENCE: 53
ggaugaagug gagauuagut ttttt                                          25

<210> SEQ ID NO 54
<211> LENGTH: 26
<212> TYPE: RNA
<213> ORGANISM: Artificial Sequence
<220> FEATURE:
<223> OTHER INFORMATION: ss31
<220> FEATURE:
<221> NAME/KEY: variation
<222> LOCATION: 4
<223> OTHER INFORMATION: U in position 4,9,15,16 and 19 represents a
      2'-O-methyl-uracile (mU)
<220> FEATURE:
<221> NAME/KEY: variation
<222> LOCATION: 9
<223> OTHER INFORMATION: U in position 4,9,15,16 and 19 represents a
      2'-O-methyl-uracile (mU)
<220> FEATURE:
<221> NAME/KEY: variation
<222> LOCATION: 15
<223> OTHER INFORMATION: U in position 4,9,15,16 and 19 represents a
      2'-O-methyl-uracile (mU)
<220> FEATURE:
<221> NAME/KEY: variation
<222> LOCATION: 16
<223> OTHER INFORMATION: U in position 4,9,15,16 and 19 represents a
      2'-O-methyl-uracile (mU)
<220> FEATURE:
<221> NAME/KEY: variation
<222> LOCATION: 19
<223> OTHER INFORMATION: U in position 4,9,15,16 and 19 represents a
      2'-O-methyl-uracile (mU)
<220> FEATURE:
<221> NAME/KEY: variation
<222> LOCATION: 20
<223> OTHER INFORMATION: T in position 20,21,22,23,24,25 and 26 is a lT3
      nucleotide analog
<220> FEATURE:
<221> NAME/KEY: variation
<222> LOCATION: 21
<223> OTHER INFORMATION: T in position 20,21,22,23,24,25 and 26 is a lT3
      nucleotide analog
<220> FEATURE:
<221> NAME/KEY: variation
<222> LOCATION: 22
<223> OTHER INFORMATION: T in position 20,21,22,23,24,25 and 26 is a lT3
      nucleotide analog
<220> FEATURE:
<221> NAME/KEY: variation
<222> LOCATION: 23
<223> OTHER INFORMATION: T in position 20,21,22,23,24,25 and 26 is a lT3
      nucleotide analog
```

```
<220> FEATURE:
<221> NAME/KEY: variation
<222> LOCATION: 24
<223> OTHER INFORMATION: T in position 20,21,22,23,24,25 and 26 is a 1T3
      nucleotide analog
<220> FEATURE:
<221> NAME/KEY: variation
<222> LOCATION: 25
<223> OTHER INFORMATION: T in position 20,21,22,23,24,25 and 26 is a 1T3
      nucleotide analog
<220> FEATURE:
<221> NAME/KEY: variation
<222> LOCATION: 26
<223> OTHER INFORMATION: T in position 20,21,22,23,24,25 and 26 is a 1T3
      nucleotide analog

<400> SEQUENCE: 54
ggaugaagug gagauuagut tttttt                                            26

<210> SEQ ID NO 55
<211> LENGTH: 27
<212> TYPE: RNA
<213> ORGANISM: Artificial Sequence
<220> FEATURE:
<223> OTHER INFORMATION: ss32
<220> FEATURE:
<221> NAME/KEY: variation
<222> LOCATION: 4
<223> OTHER INFORMATION: U in position 4,9,15,16 and 19 represents a
      2'-O-methyl-uracile (mU)
<220> FEATURE:
<221> NAME/KEY: variation
<222> LOCATION: 9
<223> OTHER INFORMATION: U in position 4,9,15,16 and 19 represents a
      2'-O-methyl-uracile (mU)
<220> FEATURE:
<221> NAME/KEY: variation
<222> LOCATION: 15
<223> OTHER INFORMATION: U in position 4,9,15,16 and 19 represents a
      2'-O-methyl-uracile (mU)
<220> FEATURE:
<221> NAME/KEY: variation
<222> LOCATION: 16
<223> OTHER INFORMATION: U in position 4,9,15,16 and 19 represents a
      2'-O-methyl-uracile (mU)
<220> FEATURE:
<221> NAME/KEY: variation
<222> LOCATION: 19
<223> OTHER INFORMATION: U in position 4,9,15,16 and 19 represents a
      2'-O-methyl-uracile (mU)
<220> FEATURE:
<221> NAME/KEY: variation
<222> LOCATION: 20
<223> OTHER INFORMATION: T in position 20,21,22,23,24,25,26 and 27 is a
      1T3 nucleotide analog
<220> FEATURE:
<221> NAME/KEY: variation
<222> LOCATION: 21
<223> OTHER INFORMATION: T in position 20,21,22,23,24,25,26 and 27 is a
      1T3 nucleotide analog
<220> FEATURE:
<221> NAME/KEY: variation
<222> LOCATION: 22
<223> OTHER INFORMATION: T in position 20,21,22,23,24,25,26 and 27 is a
      1T3 nucleotide analog
<220> FEATURE:
<221> NAME/KEY: variation
<222> LOCATION: 23
<223> OTHER INFORMATION: T in position 20,21,22,23,24,25,26 and 27 is a
      1T3 nucleotide analog
<220> FEATURE:
<221> NAME/KEY: variation
<222> LOCATION: 24
<223> OTHER INFORMATION: T in position 20,21,22,23,24,25,26 and 27 is a
      1T3 nucleotide analog
<220> FEATURE:
<221> NAME/KEY: variation
```

```
<222> LOCATION: 25
<223> OTHER INFORMATION: T in position 20,21,22,23,24,25,26 and 27 is a
      1T3 nucleotide analog
<220> FEATURE:
<221> NAME/KEY: variation
<222> LOCATION: 26
<223> OTHER INFORMATION: T in position 20,21,22,23,24,25,26 and 27 is a
      1T3 nucleotide analog
<220> FEATURE:
<221> NAME/KEY: variation
<222> LOCATION: 27
<223> OTHER INFORMATION: T in position 20,21,22,23,24,25,26 and 27 is a
      1T3 nucleotide analog

<400> SEQUENCE: 55
ggaugaagug gagauuagut tttttt                                               27

<210> SEQ ID NO 56
<211> LENGTH: 21
<212> TYPE: RNA
<213> ORGANISM: Artificial Sequence
<220> FEATURE:
<223> OTHER INFORMATION: ss33
<220> FEATURE:
<221> NAME/KEY: variation
<222> LOCATION: 4
<223> OTHER INFORMATION: U in position 4,9,15,16 and 19 represents a
      2'-O-methyl-uracile (mU)
<220> FEATURE:
<221> NAME/KEY: variation
<222> LOCATION: 9
<223> OTHER INFORMATION: U in position 4,9,15,16 and 19 represents a
      2'-O-methyl-uracile (mU)
<220> FEATURE:
<221> NAME/KEY: variation
<222> LOCATION: 15
<223> OTHER INFORMATION: U in position 4,9,15,16 and 19 represents a
      2'-O-methyl-uracile (mU)
<220> FEATURE:
<221> NAME/KEY: variation
<222> LOCATION: 16
<223> OTHER INFORMATION: U in position 4,9,15,16 and 19 represents a
      2'-O-methyl-uracile (mU)
<220> FEATURE:
<221> NAME/KEY: variation
<222> LOCATION: 19
<223> OTHER INFORMATION: U in position 4,9,15,16 and 19 represents a
      2'-O-methyl-uracile (mU)
<220> FEATURE:
<221> NAME/KEY: variation
<222> LOCATION: 20
<223> OTHER INFORMATION: T in position 20 is a 1T3 nucleotide analog
<220> FEATURE:
<221> NAME/KEY: variation
<222> LOCATION: 21
<223> OTHER INFORMATION: T in position 21 is a 1T3 nucleotide analog
      with an additional cholesterol substituent

<400> SEQUENCE: 56
ggaugaagug gagauuagut t                                                    21

<210> SEQ ID NO 57
<211> LENGTH: 23
<212> TYPE: RNA
<213> ORGANISM: Artificial Sequence
<220> FEATURE:
<223> OTHER INFORMATION: ss34
<220> FEATURE:
<221> NAME/KEY: variation
<222> LOCATION: 4
<223> OTHER INFORMATION: U in position 4,9,15,16 and 19 represents a
      2'-O-methyl-uracile (mU)
<220> FEATURE:
<221> NAME/KEY: variation
<222> LOCATION: 9
```

```
<223> OTHER INFORMATION: U in position 4,9,15,16 and 19 represents a
      2'-O-methyl-uracile (mU)
<220> FEATURE:
<221> NAME/KEY: variation
<222> LOCATION: 15
<223> OTHER INFORMATION: U in position 4,9,15,16 and 19 represents a
      2'-O-methyl-uracile (mU)
<220> FEATURE:
<221> NAME/KEY: variation
<222> LOCATION: 16
<223> OTHER INFORMATION: U in position 4,9,15,16 and 19 represents a
      2'-O-methyl-uracile (mU)
<220> FEATURE:
<221> NAME/KEY: variation
<222> LOCATION: 19
<223> OTHER INFORMATION: U in position 4,9,15,16 and 19 represents a
      2'-O-methyl-uracile (mU)
<220> FEATURE:
<221> NAME/KEY: variation
<222> LOCATION: 20
<223> OTHER INFORMATION: T in position 20,21 and 22 is a lT3 nucleotide
      analog
<220> FEATURE:
<221> NAME/KEY: variation
<222> LOCATION: 21
<223> OTHER INFORMATION: T in position 20,21 and 22 is a lT3 nucleotide
      analog
<220> FEATURE:
<221> NAME/KEY: variation
<222> LOCATION: 22
<223> OTHER INFORMATION: T in position 20,21 and 22 is a lT3 nucleotide
      analog
<220> FEATURE:
<221> NAME/KEY: variation
<222> LOCATION: 23
<223> OTHER INFORMATION: T in position 23 is a lT3 nucleotide analog
      with an additional cholesterol substituent

<400> SEQUENCE: 57
ggaugaagug gagauuagut ttt                                           23

<210> SEQ ID NO 58
<211> LENGTH: 25
<212> TYPE: RNA
<213> ORGANISM: Artificial Sequence
<220> FEATURE:
<223> OTHER INFORMATION: ss35
<220> FEATURE:
<221> NAME/KEY: variation
<222> LOCATION: 4
<223> OTHER INFORMATION: U in position 4,9,15,16 and 19 represents a
      2'-O-methyl-uracile (mU)
<220> FEATURE:
<221> NAME/KEY: variation
<222> LOCATION: 9
<223> OTHER INFORMATION: U in position 4,9,15,16 and 19 represents a
      2'-O-methyl-uracile (mU)
<220> FEATURE:
<221> NAME/KEY: variation
<222> LOCATION: 15
<223> OTHER INFORMATION: U in position 4,9,15,16 and 19 represents a
      2'-O-methyl-uracile (mU)
<220> FEATURE:
<221> NAME/KEY: variation
<222> LOCATION: 16
<223> OTHER INFORMATION: U in position 4,9,15,16 and 19 represents a
      2'-O-methyl-uracile (mU)
<220> FEATURE:
<221> NAME/KEY: variation
<222> LOCATION: 19
<223> OTHER INFORMATION: U in position 4,9,15,16 and 19 represents a
      2'-O-methyl-uracile (mU)
<220> FEATURE:
<221> NAME/KEY: variation
<222> LOCATION: 20
<223> OTHER INFORMATION: T in position 20,21,22,23 and 24 is a lT3
      nucleotide analog
```

```
<220> FEATURE:
<221> NAME/KEY: variation
<222> LOCATION: 21
<223> OTHER INFORMATION: T in position 20,21,22,23 and 24 is a lT3
      nucleotide analog
<220> FEATURE:
<221> NAME/KEY: variation
<222> LOCATION: 22
<223> OTHER INFORMATION: T in position 20,21,22,23 and 24 is a lT3
      nucleotide analog
<220> FEATURE:
<221> NAME/KEY: variation
<222> LOCATION: 23
<223> OTHER INFORMATION: T in position 20,21,22,23 and 24 is a lT3
      nucleotide analog
<220> FEATURE:
<221> NAME/KEY: variation
<222> LOCATION: 24
<223> OTHER INFORMATION: T in position 20,21,22,23 and 24 is a lT3
      nucleotide analog
<220> FEATURE:
<221> NAME/KEY: variation
<222> LOCATION: 25
<223> OTHER INFORMATION: T in position 25 is a lT3 nucleotide analog
      with an additional cholesterol substituent

<400> SEQUENCE: 58
ggaugaagug gagauuagut ttttt                                            25

<210> SEQ ID NO 59
<211> LENGTH: 27
<212> TYPE: RNA
<213> ORGANISM: Artificial Sequence
<220> FEATURE:
<223> OTHER INFORMATION: ss36
<220> FEATURE:
<221> NAME/KEY: variation
<222> LOCATION: 4
<223> OTHER INFORMATION: U in position 4,9,15,16 and 19 represents a
      2'-O-methyl-uracile (mU)
<220> FEATURE:
<221> NAME/KEY: variation
<222> LOCATION: 9
<223> OTHER INFORMATION: U in position 4,9,15,16 and 19 represents a
      2'-O-methyl-uracile (mU)
<220> FEATURE:
<221> NAME/KEY: variation
<222> LOCATION: 15
<223> OTHER INFORMATION: U in position 4,9,15,16 and 19 represents a
      2'-O-methyl-uracile (mU)
<220> FEATURE:
<221> NAME/KEY: variation
<222> LOCATION: 16
<223> OTHER INFORMATION: U in position 4,9,15,16 and 19 represents a
      2'-O-methyl-uracile (mU)
<220> FEATURE:
<221> NAME/KEY: variation
<222> LOCATION: 19
<223> OTHER INFORMATION: U in position 4,9,15,16 and 19 represents a
      2'-O-methyl-uracile (mU)
<220> FEATURE:
<221> NAME/KEY: variation
<222> LOCATION: 20
<223> OTHER INFORMATION: T in position 20,21,22,23,24,25 and 26 is a lT3
      nucleotide analog
<220> FEATURE:
<221> NAME/KEY: variation
<222> LOCATION: 21
<223> OTHER INFORMATION: T in position 20,21,22,23,24,25 and 26 is a lT3
      nucleotide analog
<220> FEATURE:
<221> NAME/KEY: variation
<222> LOCATION: 22
<223> OTHER INFORMATION: T in position 20,21,22,23,24,25 and 26 is a lT3
      nucleotide analog
<220> FEATURE:
<221> NAME/KEY: variation
```

```
<222> LOCATION: 23
<223> OTHER INFORMATION: T in position 20,21,22,23,24,25 and 26 is a lT3
      nucleotide analog
<220> FEATURE:
<221> NAME/KEY: variation
<222> LOCATION: 24
<223> OTHER INFORMATION: T in position 20,21,22,23,24,25 and 26 is a lT3
      nucleotide analog
<220> FEATURE:
<221> NAME/KEY: variation
<222> LOCATION: 25
<223> OTHER INFORMATION: T in position 20,21,22,23,24,25 and 26 is a lT3
      nucleotide analog
<220> FEATURE:
<221> NAME/KEY: variation
<222> LOCATION: 26
<223> OTHER INFORMATION: T in position 20,21,22,23,24,25 and 26 is a lT3
      nucleotide analog
<220> FEATURE:
<221> NAME/KEY: variation
<222> LOCATION: 27
<223> OTHER INFORMATION: T in position 27 is a lT3 nucleotide analog
      with an additional cholesterol substituent

<400> SEQUENCE: 59
ggaugaagug gagauuagut tttttt                                          27

<210> SEQ ID NO 60
<211> LENGTH: 21
<212> TYPE: RNA
<213> ORGANISM: Artificial Sequence
<220> FEATURE:
<223> OTHER INFORMATION: as4
<220> FEATURE:
<221> NAME/KEY: variation
<222> LOCATION: 3
<223> OTHER INFORMATION: U in position 3 represents a 2'-O-methyl-
      uracile (mU)
<220> FEATURE:
<221> NAME/KEY: variation
<222> LOCATION: 10
<223> OTHER INFORMATION: C in position 10 and 15 represents a mC
      nucleotide analog
<220> FEATURE:
<221> NAME/KEY: variation
<222> LOCATION: 15
<223> OTHER INFORMATION: C in position 10 and 15 represents a mC
      nucleotide analog
<220> FEATURE:
<221> NAME/KEY: variation
<222> LOCATION: 20
<223> OTHER INFORMATION: The nucleotide in position 20 and the
      nucleotide in position 21 are linked through a phosphoramidite
      bond
<220> FEATURE:
<221> NAME/KEY: variation
<222> LOCATION: 21
<223> OTHER INFORMATION: The nucleotide in position 20 and the
      nucleotide in position 21 are linked through a phosphoramidite
      bond
<220> FEATURE:
<221> NAME/KEY: variation
<222> LOCATION: 21
<223> OTHER INFORMATION: dT in position 21 with an additional
      cholesterol substituent

<400> SEQUENCE: 60
acuaaucucc acuucaucct t                                               21

<210> SEQ ID NO 61
<211> LENGTH: 23
<212> TYPE: RNA
<213> ORGANISM: Artificial Sequence
<220> FEATURE:
<223> OTHER INFORMATION: ss38
```

```
<220> FEATURE:
<221> NAME/KEY: variation
<222> LOCATION: 4
<223> OTHER INFORMATION: U in position 4,9,15,16 and 19 represents a
      2'-O-methyl-uracile (mU)
<220> FEATURE:
<221> NAME/KEY: variation
<222> LOCATION: 9
<223> OTHER INFORMATION: U in position 4,9,15,16 and 19 represents a
      2'-O-methyl-uracile (mU)
<220> FEATURE:
<221> NAME/KEY: variation
<222> LOCATION: 15
<223> OTHER INFORMATION: U in position 4,9,15,16 and 19 represents a
      2'-O-methyl-uracile (mU)
<220> FEATURE:
<221> NAME/KEY: variation
<222> LOCATION: 16
<223> OTHER INFORMATION: U in position 4,9,15,16 and 19 represents a
      2'-O-methyl-uracile (mU)
<220> FEATURE:
<221> NAME/KEY: variation
<222> LOCATION: 19
<223> OTHER INFORMATION: U in position 4,9,15,16 and 19 represents a
      2'-O-methyl-uracile (mU)
<220> FEATURE:
<221> NAME/KEY: variation
<222> LOCATION: 20
<223> OTHER INFORMATION: T in position 20,21,22 and 23 is a lT3b
      nucleotide analog
<220> FEATURE:
<221> NAME/KEY: variation
<222> LOCATION: 21
<223> OTHER INFORMATION: T in position 20,21,22 and 23 is a lT3b
      nucleotide analog
<220> FEATURE:
<221> NAME/KEY: variation
<222> LOCATION: 22
<223> OTHER INFORMATION: T in position 20,21,22 and 23 is a lT3b
      nucleotide analog
<220> FEATURE:
<221> NAME/KEY: variation
<222> LOCATION: 23
<223> OTHER INFORMATION: T in position 20,21,22 and 23 is a lT3b
      nucleotide analog

<400> SEQUENCE: 61
ggaugaagug gagauuagut ttt                                            23

<210> SEQ ID NO 62
<211> LENGTH: 25
<212> TYPE: RNA
<213> ORGANISM: Artificial Sequence
<220> FEATURE:
<223> OTHER INFORMATION: ss39
<220> FEATURE:
<221> NAME/KEY: variation
<222> LOCATION: 4
<223> OTHER INFORMATION: U in position 4,9,15,16 and 19 represents a
      2'-O-methyl-uracile (mU)
<220> FEATURE:
<221> NAME/KEY: variation
<222> LOCATION: 9
<223> OTHER INFORMATION: U in position 4,9,15,16 and 19 represents a
      2'-O-methyl-uracile (mU)
<220> FEATURE:
<221> NAME/KEY: variation
<222> LOCATION: 15
<223> OTHER INFORMATION: U in position 4,9,15,16 and 19 represents a
      2'-O-methyl-uracile (mU)
<220> FEATURE:
<221> NAME/KEY: variation
<222> LOCATION: 16
<223> OTHER INFORMATION: U in position 4,9,15,16 and 19 represents a
      2'-O-methyl-uracile (mU)
<220> FEATURE:
<221> NAME/KEY: variation
```

```
<222> LOCATION: 19
<223> OTHER INFORMATION: U in position 4,9,15,16 and 19 represents a
      2'-O-methyl-uracile (mU)
<220> FEATURE:
<221> NAME/KEY: variation
<222> LOCATION: 20
<223> OTHER INFORMATION: T in position 20,21,22,23,24 and 25 is a lT3b
      nucleotide analog
<220> FEATURE:
<221> NAME/KEY: variation
<222> LOCATION: 21
<223> OTHER INFORMATION: T in position 20,21,22,23,24 and 25 is a lT3b
      nucleotide analog
<220> FEATURE:
<221> NAME/KEY: variation
<222> LOCATION: 22
<223> OTHER INFORMATION: T in position 20,21,22,23,24 and 25 is a lT3b
      nucleotide analog
<220> FEATURE:
<221> NAME/KEY: variation
<222> LOCATION: 23
<223> OTHER INFORMATION: T in position 20,21,22,23,24 and 25 is a lT3b
      nucleotide analog
<220> FEATURE:
<221> NAME/KEY: variation
<222> LOCATION: 24
<223> OTHER INFORMATION: T in position 20,21,22,23,24 and 25 is a lT3b
      nucleotide analog
<220> FEATURE:
<221> NAME/KEY: variation
<222> LOCATION: 25
<223> OTHER INFORMATION: T in position 20,21,22,23,24 and 25 is a lT3b
      nucleotide analog

<400> SEQUENCE: 62
ggaugaagug gagauuagut ttttt                                           25

<210> SEQ ID NO 63
<211> LENGTH: 27
<212> TYPE: RNA
<213> ORGANISM: Artificial Sequence
<220> FEATURE:
<223> OTHER INFORMATION: ss40
<220> FEATURE:
<221> NAME/KEY: variation
<222> LOCATION: 4
<223> OTHER INFORMATION: U in position 4,9,15,16 and 19 represents a
      2'-O-methyl-uracile (mU)
<220> FEATURE:
<221> NAME/KEY: variation
<222> LOCATION: 9
<223> OTHER INFORMATION: U in position 4,9,15,16 and 19 represents a
      2'-O-methyl-uracile (mU)
<220> FEATURE:
<221> NAME/KEY: variation
<222> LOCATION: 15
<223> OTHER INFORMATION: U in position 4,9,15,16 and 19 represents a
      2'-O-methyl-uracile (mU)
<220> FEATURE:
<221> NAME/KEY: variation
<222> LOCATION: 16
<223> OTHER INFORMATION: U in position 4,9,15,16 and 19 represents a
      2'-O-methyl-uracile (mU)
<220> FEATURE:
<221> NAME/KEY: variation
<222> LOCATION: 19
<223> OTHER INFORMATION: U in position 4,9,15,16 and 19 represents a
      2'-O-methyl-uracile (mU)
<220> FEATURE:
<221> NAME/KEY: variation
<222> LOCATION: 20
<223> OTHER INFORMATION: T in position 20,21,22,23,24,25,26 and 27 is a
      lT3b nucleotide analog
<220> FEATURE:
<221> NAME/KEY: variation
<222> LOCATION: 21
<223> OTHER INFORMATION: T in position 20,21,22,23,24,25,26 and 27 is a
```

```
        1T3b nucleotide analog
<220> FEATURE:
<221> NAME/KEY: variation
<222> LOCATION: 22
<223> OTHER INFORMATION: T in position 20,21,22,23,24,25,26 and 27 is a
      1T3b nucleotide analog
<220> FEATURE:
<221> NAME/KEY: variation
<222> LOCATION: 23
<223> OTHER INFORMATION: T in position 20,21,22,23,24,25,26 and 27 is a
      1T3b nucleotide analog
<220> FEATURE:
<221> NAME/KEY: variation
<222> LOCATION: 24
<223> OTHER INFORMATION: T in position 20,21,22,23,24,25,26 and 27 is a
      1T3b nucleotide analog
<220> FEATURE:
<221> NAME/KEY: variation
<222> LOCATION: 25
<223> OTHER INFORMATION: T in position 20,21,22,23,24,25,26 and 27 is a
      1T3b nucleotide analog
<220> FEATURE:
<221> NAME/KEY: variation
<222> LOCATION: 26
<223> OTHER INFORMATION: T in position 20,21,22,23,24,25,26 and 27 is a
      1T3b nucleotide analog
<220> FEATURE:
<221> NAME/KEY: variation
<222> LOCATION: 27
<223> OTHER INFORMATION: T in position 20,21,22,23,24,25,26 and 27 is a
      1T3b nucleotide analog

<400> SEQUENCE: 63
ggaugaagug gagauuagut tttttt                                              27

<210> SEQ ID NO 64
<211> LENGTH: 21
<212> TYPE: RNA
<213> ORGANISM: Artificial Sequence
<220> FEATURE:
<223> OTHER INFORMATION: ss41
<220> FEATURE:
<221> NAME/KEY: variation
<222> LOCATION: 4
<223> OTHER INFORMATION: U in position 4,9,15,16 and 19 represents a
      2'-O-methyl-uracile (mU)
<220> FEATURE:
<221> NAME/KEY: variation
<222> LOCATION: 9
<223> OTHER INFORMATION: U in position 4,9,15,16 and 19 represents a
      2'-O-methyl-uracile (mU)
<220> FEATURE:
<221> NAME/KEY: variation
<222> LOCATION: 15
<223> OTHER INFORMATION: U in position 4,9,15,16 and 19 represents a
      2'-O-methyl-uracile (mU)
<220> FEATURE:
<221> NAME/KEY: variation
<222> LOCATION: 16
<223> OTHER INFORMATION: U in position 4,9,15,16 and 19 represents a
      2'-O-methyl-uracile (mU)
<220> FEATURE:
<221> NAME/KEY: variation
<222> LOCATION: 19
<223> OTHER INFORMATION: U in position 4,9,15,16 and 19 represents a
      2'-O-methyl-uracile (mU)
<220> FEATURE:
<221> NAME/KEY: variation
<222> LOCATION: 20
<223> OTHER INFORMATION: T in position 20 is a 1T3b nucleotide analog
<220> FEATURE:
<221> NAME/KEY: variation
<222> LOCATION: 21
<223> OTHER INFORMATION: T in position 21 is a 1T3b nucleotide analog
      with an additional cholesterol substituent

<400> SEQUENCE: 64
```
ggaugaagug gagauuagut t                                          21

<210> SEQ ID NO 65
<211> LENGTH: 23
<212> TYPE: RNA
<213> ORGANISM: Artificial Sequence
<220> FEATURE:
<223> OTHER INFORMATION: ss42
<220> FEATURE:
<221> NAME/KEY: variation
<222> LOCATION: 4
<223> OTHER INFORMATION: U in position 4,9,15,16 and 19 represents a
      2'-O-methyl-uracile (mU)
<220> FEATURE:
<221> NAME/KEY: variation
<222> LOCATION: 9
<223> OTHER INFORMATION: U in position 4,9,15,16 and 19 represents a
      2'-O-methyl-uracile (mU)
<220> FEATURE:
<221> NAME/KEY: variation
<222> LOCATION: 15
<223> OTHER INFORMATION: U in position 4,9,15,16 and 19 represents a
      2'-O-methyl-uracile (mU)
<220> FEATURE:
<221> NAME/KEY: variation
<222> LOCATION: 16
<223> OTHER INFORMATION: U in position 4,9,15,16 and 19 represents a
      2'-O-methyl-uracile (mU)
<220> FEATURE:
<221> NAME/KEY: variation
<222> LOCATION: 19
<223> OTHER INFORMATION: U in position 4,9,15,16 and 19 represents a
      2'-O-methyl-uracile (mU)
<220> FEATURE:
<221> NAME/KEY: variation
<222> LOCATION: 20
<223> OTHER INFORMATION: T in position 20,21 and 22 is a lT3b nucleotide
      analog
<220> FEATURE:
<221> NAME/KEY: variation
<222> LOCATION: 21
<223> OTHER INFORMATION: T in position 20,21 and 22 is a lT3b nucleotide
      analog
<220> FEATURE:
<221> NAME/KEY: variation
<222> LOCATION: 22
<223> OTHER INFORMATION: T in position 20,21 and 22 is a lT3b nucleotide
      analog
<220> FEATURE:
<221> NAME/KEY: variation
<222> LOCATION: 23
<223> OTHER INFORMATION: T in position 23 is a lT3b nucleotide analog
      with an additional cholesterol substituent

<400> SEQUENCE: 65
ggaugaagug gagauuagut ttt                                        23

<210> SEQ ID NO 66
<211> LENGTH: 25
<212> TYPE: RNA
<213> ORGANISM: Artificial Sequence
<220> FEATURE:
<223> OTHER INFORMATION: ss43
<220> FEATURE:
<221> NAME/KEY: variation
<222> LOCATION: 4
<223> OTHER INFORMATION: U in position 4,9,15,16 and 19 represents a
      2'-O-methyl-uracile (mU)
<220> FEATURE:
<221> NAME/KEY: variation
<222> LOCATION: 9
<223> OTHER INFORMATION: U in position 4,9,15,16 and 19 represents a
      2'-O-methyl-uracile (mU)
<220> FEATURE:
<221> NAME/KEY: variation
<222> LOCATION: 15
<223> OTHER INFORMATION: U in position 4,9,15,16 and 19 represents a
      2'-O-methyl-uracile (mU)
<220> FEATURE:
<221> NAME/KEY: variation
<222> LOCATION: 16
<223> OTHER INFORMATION: U in position 4,9,15,16 and 19 represents a
      2'-O-methyl-uracile (mU)
<220> FEATURE:
<221> NAME/KEY: variation
<222> LOCATION: 19
<223> OTHER INFORMATION: U in position 4,9,15,16 and 19 represents a
      2'-O-methyl-uracile (mU)
<220> FEATURE:
<221> NAME/KEY: variation
<222> LOCATION: 20
<223> OTHER INFORMATION: T in position 20,21,22,23 and 24 is a lT3b
      nucleotide analog
<220> FEATURE:
<221> NAME/KEY: variation
<222> LOCATION: 21
<223> OTHER INFORMATION: T in position 20,21,22,23 and 24 is a lT3b
      nucleotide analog
<220> FEATURE:
<221> NAME/KEY: variation
<222> LOCATION: 22
<223> OTHER INFORMATION: T in position 20,21,22,23 and 24 is a lT3b
      nucleotide analog
<220> FEATURE:
<221> NAME/KEY: variation
<222> LOCATION: 23
<223> OTHER INFORMATION: T in position 20,21,22,23 and 24 is a lT3b
      nucleotide analog
<220> FEATURE:
<221> NAME/KEY: variation
<222> LOCATION: 24
<223> OTHER INFORMATION: T in position 20,21,22,23 and 24 is a lT3b
      nucleotide analog
<220> FEATURE:
<221> NAME/KEY: variation
<222> LOCATION: 25
<223> OTHER INFORMATION: T in position 25 is a lT3b nucleotide analog
      with an additional cholesterol substituent

<400> SEQUENCE: 66
ggaugaagug gagauuagut ttttt                                         25

<210> SEQ ID NO 67
<211> LENGTH: 24
<212> TYPE: RNA
<213> ORGANISM: Artificial Sequence
<220> FEATURE:
<223> OTHER INFORMATION: ss1-1
<220> FEATURE:
<221> NAME/KEY: variation
<222> LOCATION: 1
<223> OTHER INFORMATION: T in position 1,2 and 3 is a lgT2 nucleotide
      analog
<220> FEATURE:
<221> NAME/KEY: variation
<222> LOCATION: 2
<223> OTHER INFORMATION: T in position 1,2 and 3 is a lgT2 nucleotide
      analog
<220> FEATURE:
<221> NAME/KEY: variation
<222> LOCATION: 3
<223> OTHER INFORMATION: T in position 1,2 and 3 is a lgT2 nucleotide
      analog
<220> FEATURE:
<221> NAME/KEY: variation
<222> LOCATION: 4
<223> OTHER INFORMATION: A in position 4 and 24 is a fA nucleotide
      analog
<220> FEATURE:
<221> NAME/KEY: variation
<222> LOCATION: 5
<223> OTHER INFORMATION: A in position 5,7,21 and 23 represents a mA

```
      nucleotide analog
<220> FEATURE:
<221> NAME/KEY: variation
<222> LOCATION: 6
<223> OTHER INFORMATION: C in position 6 and 13 is a fC nucleotide
      analog
<220> FEATURE:
<221> NAME/KEY: variation
<222> LOCATION: 7
<223> OTHER INFORMATION: A in position 5,7,21 and 23 represents a mA
      nucleotide analog
<220> FEATURE:
<221> NAME/KEY: variation
<222> LOCATION: 8
<223> OTHER INFORMATION: G in position 8,10 and 16 is a fG nucleotide
      analog
<220> FEATURE:
<221> NAME/KEY: variation
<222> LOCATION: 9
<223> OTHER INFORMATION: U in position 9,11 and 15 represents a 2'-O-
      methyl-uracile (mU)
<220> FEATURE:
<221> NAME/KEY: variation
<222> LOCATION: 10
<223> OTHER INFORMATION: G in position 8,10 and 16 is a fG nucleotide
      analog
<220> FEATURE:
<221> NAME/KEY: variation
<222> LOCATION: 11
<223> OTHER INFORMATION: U in position 9,11 and 15 represents a 2'-O-
      methyl-uracile (mU)
<220> FEATURE:
<221> NAME/KEY: variation
<222> LOCATION: 12
<223> OTHER INFORMATION: U in position 12,14,18,20 and 22 is a fU
      nucleotide analog
<220> FEATURE:
<221> NAME/KEY: variation
<222> LOCATION: 13
<223> OTHER INFORMATION: C in position 6 and 13 is a fC nucleotide
      analog
<220> FEATURE:
<221> NAME/KEY: variation
<222> LOCATION: 14
<223> OTHER INFORMATION: U in position 12,14,18,20 and 22 is a fU
      nucleotide analog
<220> FEATURE:
<221> NAME/KEY: variation
<222> LOCATION: 15
<223> OTHER INFORMATION: U in position 9,11 and 15 represents a 2'-O-
      methyl-uracile (mU)
<220> FEATURE:
<221> NAME/KEY: variation
<222> LOCATION: 16
<223> OTHER INFORMATION: G in position 8,10 and 16 is a fG nucleotide
      analog
<220> FEATURE:
<221> NAME/KEY: variation
<222> LOCATION: 17
<223> OTHER INFORMATION: C in position 17 and 19 represents a mC
      nucleotide analog
<220> FEATURE:
<221> NAME/KEY: variation
<222> LOCATION: 18
<223> OTHER INFORMATION: U in position 12,14,18,20 and 22 is a fU
      nucleotide analog
<220> FEATURE:
<221> NAME/KEY: variation
<222> LOCATION: 19
<223> OTHER INFORMATION: C in position 17 and 19 represents a mC
      nucleotide analog
<220> FEATURE:
<221> NAME/KEY: variation
<222> LOCATION: 20
<223> OTHER INFORMATION: U in position 12,14,18,20 and 22 is a fU
      nucleotide analog
<220> FEATURE:
<221> NAME/KEY: variation
<222> LOCATION: 21
```

```
<223> OTHER INFORMATION: A in position 5,7,21 and 23 represents a mA
      nucleotide analog
<220> FEATURE:
<221> NAME/KEY: variation
<222> LOCATION: 22
<223> OTHER INFORMATION: U in position 12,14,18,20 and 22 is a fU
      nucleotide analog
<220> FEATURE:
<221> NAME/KEY: variation
<222> LOCATION: 23
<223> OTHER INFORMATION: A in position 5,7,21 and 23 represents a mA
      nucleotide analog
<220> FEATURE:
<221> NAME/KEY: variation
<222> LOCATION: 24
<223> OTHER INFORMATION: A in position 4 and 24 is a fA nucleotide
      analog

<400> SEQUENCE: 67
tttaacagug uucuugcucu auaa                                          24

<210> SEQ ID NO 68
<211> LENGTH: 24
<212> TYPE: RNA
<213> ORGANISM: Artificial Sequence
<220> FEATURE:
<223> OTHER INFORMATION: ss1-2
<220> FEATURE:
<221> NAME/KEY: variation
<222> LOCATION: 1
<223> OTHER INFORMATION: The nucleotide in position 1 and the nucleotide
      in position 2 are linked through a phosphoramidite bond
<220> FEATURE:
<221> NAME/KEY: variation
<222> LOCATION: 1
<223> OTHER INFORMATION: A in position 1 and 21 is a fA nucleotide
      analog
<220> FEATURE:
<221> NAME/KEY: variation
<222> LOCATION: 2
<223> OTHER INFORMATION: The nucleotide in position 1 and the nucleotide
      in position 2 are linked through a phosphoramidite bond
<220> FEATURE:
<221> NAME/KEY: variation
<222> LOCATION: 2
<223> OTHER INFORMATION: The nucleotide in position 2 and the nucleotide
      in position 3 are linked through a phosphoramidite bond
<220> FEATURE:
<221> NAME/KEY: variation
<222> LOCATION: 2
<223> OTHER INFORMATION: A in position 2,4,18 and 20 represents a mA
      nucleotide analog
<220> FEATURE:
<221> NAME/KEY: variation
<222> LOCATION: 3
<223> OTHER INFORMATION: The nucleotide in position 2 and the nucleotide
      in position 3 are linked through a phosphoramidite bond
<220> FEATURE:
<221> NAME/KEY: variation
<222> LOCATION: 3
<223> OTHER INFORMATION: C in position 3 and 10 is a fC nucleotide
      analog
<220> FEATURE:
<221> NAME/KEY: variation
<222> LOCATION: 4
<223> OTHER INFORMATION: A in position 2,4,18 and 20 represents a mA
      nucleotide analog
<220> FEATURE:
<221> NAME/KEY: variation
<222> LOCATION: 5
<223> OTHER INFORMATION: G in position 5,7 and 13 is a fG nucleotide
      analog
<220> FEATURE:
<221> NAME/KEY: variation
<222> LOCATION: 6
<223> OTHER INFORMATION: U in position 6,8 and 12 represents a 2'-O-
      methyl-uracile (mU)
```

```
<220> FEATURE:
<221> NAME/KEY: variation
<222> LOCATION: 7
<223> OTHER INFORMATION: G in position 5,7 and 13 is a fG nucleotide
      analog
<220> FEATURE:
<221> NAME/KEY: variation
<222> LOCATION: 8
<223> OTHER INFORMATION: U in position 6,8 and 12 represents a 2'-O-
      methyl-uracile (mU)
<220> FEATURE:
<221> NAME/KEY: variation
<222> LOCATION: 9
<223> OTHER INFORMATION: U in position 9,11,15,17 and 19is a fU
      nucleotide analog
<220> FEATURE:
<221> NAME/KEY: variation
<222> LOCATION: 10
<223> OTHER INFORMATION: C in position 3 and 10 is a fC nucleotide
      analog
<220> FEATURE:
<221> NAME/KEY: variation
<222> LOCATION: 11
<223> OTHER INFORMATION: U in position 9,11,15,17 and 19is a fU
      nucleotide analog
<220> FEATURE:
<221> NAME/KEY: variation
<222> LOCATION: 12
<223> OTHER INFORMATION: U in position 6,8 and 12 represents a 2'-O-
      methyl-uracile (mU)
<220> FEATURE:
<221> NAME/KEY: variation
<222> LOCATION: 13
<223> OTHER INFORMATION: G in position 5,7 and 13 is a fG nucleotide
      analog
<220> FEATURE:
<221> NAME/KEY: variation
<222> LOCATION: 14
<223> OTHER INFORMATION: C in position 14 and 16 represents a mC
      nucleotide analog
<220> FEATURE:
<221> NAME/KEY: variation
<222> LOCATION: 15
<223> OTHER INFORMATION: U in position 9,11,15,17 and 19is a fU
      nucleotide analog
<220> FEATURE:
<221> NAME/KEY: variation
<222> LOCATION: 16
<223> OTHER INFORMATION: C in position 14 and 16 represents a mC
      nucleotide analog
<220> FEATURE:
<221> NAME/KEY: variation
<222> LOCATION: 17
<223> OTHER INFORMATION: U in position 9,11,15,17 and 19is a fU
      nucleotide analog
<220> FEATURE:
<221> NAME/KEY: variation
<222> LOCATION: 18
<223> OTHER INFORMATION: A in position 2,4,18 and 20 represents a mA
      nucleotide analog
<220> FEATURE:
<221> NAME/KEY: variation
<222> LOCATION: 19
<223> OTHER INFORMATION: U in position 9,11,15,17 and 19is a fU
      nucleotide analog
<220> FEATURE:
<221> NAME/KEY: variation
<222> LOCATION: 20
<223> OTHER INFORMATION: A in position 2,4,18 and 20 represents a mA
      nucleotide analog
<220> FEATURE:
<221> NAME/KEY: variation
<222> LOCATION: 21
<223> OTHER INFORMATION: A in position 1 and 21 is a fA nucleotide
      analog
<220> FEATURE:
<221> NAME/KEY: variation
<222> LOCATION: 22
<223> OTHER INFORMATION: T in position 22,23 and 24 is a lgT2 nucleotide
```

-continued

```
      analog
<220> FEATURE:
<221> NAME/KEY: variation
<222> LOCATION: 23
<223> OTHER INFORMATION: T in position 22,23 and 24 is a lgT2 nucleotide
      analog
<220> FEATURE:
<221> NAME/KEY: variation
<222> LOCATION: 24
<223> OTHER INFORMATION: T in position 22,23 and 24 is a lgT2 nucleotide
      analog

<400> SEQUENCE: 68
aacaguguuc uugcucuaua attt                                              24

<210> SEQ ID NO 69
<211> LENGTH: 24
<212> TYPE: RNA
<213> ORGANISM: Artificial Sequence
<220> FEATURE:
<223> OTHER INFORMATION: ss1-3
<220> FEATURE:
<221> NAME/KEY: variation
<222> LOCATION: 1
<223> OTHER INFORMATION: T in position 1,2 and 3 is a lgT5 nucleotide
      analog
<220> FEATURE:
<221> NAME/KEY: variation
<222> LOCATION: 2
<223> OTHER INFORMATION: T in position 1,2 and 3 is a lgT5 nucleotide
      analog
<220> FEATURE:
<221> NAME/KEY: variation
<222> LOCATION: 3
<223> OTHER INFORMATION: T in position 1,2 and 3 is a lgT5 nucleotide
      analog
<220> FEATURE:
<221> NAME/KEY: variation
<222> LOCATION: 4
<223> OTHER INFORMATION: A in position 4 and 24 is a fA nucleotide
      analog
<220> FEATURE:
<221> NAME/KEY: variation
<222> LOCATION: 5
<223> OTHER INFORMATION: A in position 5,7,21 and 23 represents a mA
      nucleotide analog
<220> FEATURE:
<221> NAME/KEY: variation
<222> LOCATION: 6
<223> OTHER INFORMATION: C in position 6 and 13 is a fC nucleotide
      analog
<220> FEATURE:
<221> NAME/KEY: variation
<222> LOCATION: 7
<223> OTHER INFORMATION: A in position 5,7,21 and 23 represents a mA
      nucleotide analog
<220> FEATURE:
<221> NAME/KEY: variation
<222> LOCATION: 8
<223> OTHER INFORMATION: G in position 8,10 and 16 is a fG nucleotide
      analog
<220> FEATURE:
<221> NAME/KEY: variation
<222> LOCATION: 9
<223> OTHER INFORMATION: U in position 9,11 and 15 represents a 2'-O-
      methyl-uracile (mU)
<220> FEATURE:
<221> NAME/KEY: variation
<222> LOCATION: 10
<223> OTHER INFORMATION: G in position 8,10 and 16 is a fG nucleotide
      analog
<220> FEATURE:
<221> NAME/KEY: variation
<222> LOCATION: 11
<223> OTHER INFORMATION: U in position 9,11 and 15 represents a 2'-O-
      methyl-uracile (mU)
<220> FEATURE:
```

```
<221> NAME/KEY: variation
<222> LOCATION: 12
<223> OTHER INFORMATION: U in position 12,14,18,20 and 22 is a fU
      nucleotide analog
<220> FEATURE:
<221> NAME/KEY: variation
<222> LOCATION: 13
<223> OTHER INFORMATION: C in position 6 and 13 is a fC nucleotide
      analog
<220> FEATURE:
<221> NAME/KEY: variation
<222> LOCATION: 14
<223> OTHER INFORMATION: U in position 12,14,18,20 and 22 is a fU
      nucleotide analog
<220> FEATURE:
<221> NAME/KEY: variation
<222> LOCATION: 15
<223> OTHER INFORMATION: U in position 9,11 and 15 represents a 2'-O-
      methyl-uracile (mU)
<220> FEATURE:
<221> NAME/KEY: variation
<222> LOCATION: 16
<223> OTHER INFORMATION: G in position 8,10 and 16 is a fG nucleotide
      analog
<220> FEATURE:
<221> NAME/KEY: variation
<222> LOCATION: 17
<223> OTHER INFORMATION: C in position 17 and 19 represents a mC
      nucleotide analog
<220> FEATURE:
<221> NAME/KEY: variation
<222> LOCATION: 18
<223> OTHER INFORMATION: U in position 12,14,18,20 and 22 is a fU
      nucleotide analog
<220> FEATURE:
<221> NAME/KEY: variation
<222> LOCATION: 19
<223> OTHER INFORMATION: C in position 17 and 19 represents a mC
      nucleotide analog
<220> FEATURE:
<221> NAME/KEY: variation
<222> LOCATION: 20
<223> OTHER INFORMATION: U in position 12,14,18,20 and 22 is a fU
      nucleotide analog
<220> FEATURE:
<221> NAME/KEY: variation
<222> LOCATION: 21
<223> OTHER INFORMATION: A in position 5,7,21 and 23 represents a mA
      nucleotide analog
<220> FEATURE:
<221> NAME/KEY: variation
<222> LOCATION: 22
<223> OTHER INFORMATION: U in position 12,14,18,20 and 22 is a fU
      nucleotide analog
<220> FEATURE:
<221> NAME/KEY: variation
<222> LOCATION: 23
<223> OTHER INFORMATION: A in position 5,7,21 and 23 represents a mA
      nucleotide analog
<220> FEATURE:
<221> NAME/KEY: variation
<222> LOCATION: 24
<223> OTHER INFORMATION: A in position 4 and 24 is a fA nucleotide
      analog

<400> SEQUENCE: 69
tttaacagug uucuugcucu auaa                                          24

<210> SEQ ID NO 70
<211> LENGTH: 24
<212> TYPE: RNA
<213> ORGANISM: Artificial Sequence
<220> FEATURE:
<223> OTHER INFORMATION: ss1-4
<220> FEATURE:
<221> NAME/KEY: variation
<222> LOCATION: 1
```

```
<223> OTHER INFORMATION: The nucleotide in position 1 and the nucleotide
      in position 2 are linked through a phosphoramidite bond
<220> FEATURE:
<221> NAME/KEY: variation
<222> LOCATION: 1
<223> OTHER INFORMATION: A in position 1 and 21 is a fA nucleotide
      analog
<220> FEATURE:
<221> NAME/KEY: variation
<222> LOCATION: 2
<223> OTHER INFORMATION: The nucleotide in position 1 and the nucleotide
      in position 2 are linked through a phosphoramidite bond
<220> FEATURE:
<221> NAME/KEY: variation
<222> LOCATION: 2
<223> OTHER INFORMATION: The nucleotide in position 2 and the nucleotide
      in position 3 are linked through a phosphoramidite bond
<220> FEATURE:
<221> NAME/KEY: variation
<222> LOCATION: 2
<223> OTHER INFORMATION: A in position 2,4,18 and 20 represents a mA
      nucleotide analog
<220> FEATURE:
<221> NAME/KEY: variation
<222> LOCATION: 3
<223> OTHER INFORMATION: The nucleotide in position 2 and the nucleotide
      in position 3 are linked through a phosphoramidite bond
<220> FEATURE:
<221> NAME/KEY: variation
<222> LOCATION: 3
<223> OTHER INFORMATION: C in position 3 and 10 is a fC nucleotide
      analog
<220> FEATURE:
<221> NAME/KEY: variation
<222> LOCATION: 4
<223> OTHER INFORMATION: A in position 2,4,18 and 20 represents a mA
      nucleotide analog
<220> FEATURE:
<221> NAME/KEY: variation
<222> LOCATION: 5
<223> OTHER INFORMATION: G in position 5,7 and 13 is a fG nucleotide
      analog
<220> FEATURE:
<221> NAME/KEY: variation
<222> LOCATION: 6
<223> OTHER INFORMATION: U in position 6,8 and 12 represents a 2'-O-
      methyl-uracile (mU)
<220> FEATURE:
<221> NAME/KEY: variation
<222> LOCATION: 7
<223> OTHER INFORMATION: G in position 5,7 and 13 is a fG nucleotide
      analog
<220> FEATURE:
<221> NAME/KEY: variation
<222> LOCATION: 8
<223> OTHER INFORMATION: U in position 6,8 and 12 represents a 2'-O-
      methyl-uracile (mU)
<220> FEATURE:
<221> NAME/KEY: variation
<222> LOCATION: 9
<223> OTHER INFORMATION: U in position 9,11,15,17 and 19 is a fU
      nucleotide analog
<220> FEATURE:
<221> NAME/KEY: variation
<222> LOCATION: 10
<223> OTHER INFORMATION: C in position 3 and 10 is a fC nucleotide
      analog
<220> FEATURE:
<221> NAME/KEY: variation
<222> LOCATION: 11
<223> OTHER INFORMATION: U in position 9,11,15,17 and 19 is a fU
      nucleotide analog
<220> FEATURE:
<221> NAME/KEY: variation
<222> LOCATION: 12
<223> OTHER INFORMATION: U in position 6,8 and 12 represents a 2'-O-
      methyl-uracile (mU)
<220> FEATURE:
<221> NAME/KEY: variation
```

```
<222> LOCATION: 13
<223> OTHER INFORMATION: G in position 5,7 and 13 is a fG nucleotide
      analog
<220> FEATURE:
<221> NAME/KEY: variation
<222> LOCATION: 14
<223> OTHER INFORMATION: C in position 14 and 16 represents a mC
      nucleotide analog
<220> FEATURE:
<221> NAME/KEY: variation
<222> LOCATION: 15
<223> OTHER INFORMATION: U in position 9,11,15,17 and 19 is a fU
      nucleotide analog
<220> FEATURE:
<221> NAME/KEY: variation
<222> LOCATION: 16
<223> OTHER INFORMATION: C in position 14 and 16 represents a mC
      nucleotide analog
<220> FEATURE:
<221> NAME/KEY: variation
<222> LOCATION: 17
<223> OTHER INFORMATION: U in position 9,11,15,17 and 19 is a fU
      nucleotide analog
<220> FEATURE:
<221> NAME/KEY: variation
<222> LOCATION: 18
<223> OTHER INFORMATION: A in position 2,4,18 and 20 represents a mA
      nucleotide analog
<220> FEATURE:
<221> NAME/KEY: variation
<222> LOCATION: 19
<223> OTHER INFORMATION: U in position 9,11,15,17 and 19 is a fU
      nucleotide analog
<220> FEATURE:
<221> NAME/KEY: variation
<222> LOCATION: 20
<223> OTHER INFORMATION: A in position 2,4,18 and 20 represents a mA
      nucleotide analog
<220> FEATURE:
<221> NAME/KEY: variation
<222> LOCATION: 21
<223> OTHER INFORMATION: A in position 1 and 21 is a fA nucleotide
      analog
<220> FEATURE:
<221> NAME/KEY: variation
<222> LOCATION: 22
<223> OTHER INFORMATION: T in position 22,23 and 24 is a lgT5 nucleotide
      analog
<220> FEATURE:
<221> NAME/KEY: variation
<222> LOCATION: 23
<223> OTHER INFORMATION: T in position 22,23 and 24 is a lgT5 nucleotide
      analog
<220> FEATURE:
<221> NAME/KEY: variation
<222> LOCATION: 24
<223> OTHER INFORMATION: T in position 22,23 and 24 is a lgT5 nucleotide
      analog

<400> SEQUENCE: 70
aacaguguuc uugcucuaua attt                                            24

<210> SEQ ID NO 71
<211> LENGTH: 24
<212> TYPE: RNA
<213> ORGANISM: Artificial Sequence
<220> FEATURE:
<223> OTHER INFORMATION: ss1-5
<220> FEATURE:
<221> NAME/KEY: variation
<222> LOCATION: 1
<223> OTHER INFORMATION: T in position 1, 2 and 3 is a lgT1 nucleotide
      analog
<220> FEATURE:
<221> NAME/KEY: variation
<222> LOCATION: 2
<223> OTHER INFORMATION: T in position 1, 2 and 3 is a lgT1 nucleotide
``` analog
<220> FEATURE:
<221> NAME/KEY: variation
<222> LOCATION: 3
<223> OTHER INFORMATION: T in position 1, 2 and 3 is a lgT1 nucleotide
analog
<220> FEATURE:
<221> NAME/KEY: variation
<222> LOCATION: 4
<223> OTHER INFORMATION: A in position 4 and 24 is a fA nucleotide
analog
<220> FEATURE:
<221> NAME/KEY: variation
<222> LOCATION: 5
<223> OTHER INFORMATION: A in position 5,7,21 and 23 represents a mA
nucleotide analog
<220> FEATURE:
<221> NAME/KEY: variation
<222> LOCATION: 6
<223> OTHER INFORMATION: C in position 6 and 13 is a fC nucleotide
analog
<220> FEATURE:
<221> NAME/KEY: variation
<222> LOCATION: 7
<223> OTHER INFORMATION: A in position 5,7,21 and 23 represents a mA
nucleotide analog
<220> FEATURE:
<221> NAME/KEY: variation
<222> LOCATION: 8
<223> OTHER INFORMATION: G in position 8,10 and 16 is a fG nucleotide
analog
<220> FEATURE:
<221> NAME/KEY: variation
<222> LOCATION: 9
<223> OTHER INFORMATION: U in position 9,11 and 15 represents a 2'-O-
methyl-uracile (mU)
<220> FEATURE:
<221> NAME/KEY: variation
<222> LOCATION: 10
<223> OTHER INFORMATION: G in position 8,10 and 16 is a fG nucleotide
analog
<220> FEATURE:
<221> NAME/KEY: variation
<222> LOCATION: 11
<223> OTHER INFORMATION: U in position 9,11 and 15 represents a 2'-O-
methyl-uracile (mU)
<220> FEATURE:
<221> NAME/KEY: variation
<222> LOCATION: 12
<223> OTHER INFORMATION: U in position 12,14,18,20 and 22 is a fU
nucleotide analog
<220> FEATURE:
<221> NAME/KEY: variation
<222> LOCATION: 13
<223> OTHER INFORMATION: C in position 6 and 13 is a fC nucleotide
analog
<220> FEATURE:
<221> NAME/KEY: variation
<222> LOCATION: 14
<223> OTHER INFORMATION: U in position 12,14,18,20 and 22 is a fU
nucleotide analog
<220> FEATURE:
<221> NAME/KEY: variation
<222> LOCATION: 15
<223> OTHER INFORMATION: U in position 9,11 and 15 represents a 2'-O-
methyl-uracile (mU)
<220> FEATURE:
<221> NAME/KEY: variation
<222> LOCATION: 16
<223> OTHER INFORMATION: G in position 8,10 and 16 is a fG nucleotide
analog
<220> FEATURE:
<221> NAME/KEY: variation
<222> LOCATION: 17
<223> OTHER INFORMATION: C in position 17 and 19 represents a mC
nucleotide analog
<220> FEATURE:
<221> NAME/KEY: variation
<222> LOCATION: 18

```
<223> OTHER INFORMATION: U in position 12,14,18,20 and 22 is a fU
      nucleotide analog
<220> FEATURE:
<221> NAME/KEY: variation
<222> LOCATION: 19
<223> OTHER INFORMATION: C in position 17 and 19 represents a mC
      nucleotide analog
<220> FEATURE:
<221> NAME/KEY: variation
<222> LOCATION: 20
<223> OTHER INFORMATION: U in position 12,14,18,20 and 22 is a fU
      nucleotide analog
<220> FEATURE:
<221> NAME/KEY: variation
<222> LOCATION: 21
<223> OTHER INFORMATION: A in position 5,7,21 and 23 represents a mA
      nucleotide analog
<220> FEATURE:
<221> NAME/KEY: variation
<222> LOCATION: 22
<223> OTHER INFORMATION: U in position 12,14,18,20 and 22 is a fU
      nucleotide analog
<220> FEATURE:
<221> NAME/KEY: variation
<222> LOCATION: 22
<223> OTHER INFORMATION: The nucleotide in position 22 and the
      nucleotide in position 23 are linked through a phosphoramidite
      bond
<220> FEATURE:
<221> NAME/KEY: variation
<222> LOCATION: 23
<223> OTHER INFORMATION: A in position 5,7,21 and 23 represents a mA
      nucleotide analog
<220> FEATURE:
<221> NAME/KEY: variation
<222> LOCATION: 23
<223> OTHER INFORMATION: The nucleotide in position 22 and the
      nucleotide in position 23 are linked through a phosphoramidite
      bond
<220> FEATURE:
<221> NAME/KEY: variation
<222> LOCATION: 23
<223> OTHER INFORMATION: The nucleotide in position 23 and the
      nucleotide in position 24 are linked through a phosphoramidite
      bond
<220> FEATURE:
<221> NAME/KEY: variation
<222> LOCATION: 24
<223> OTHER INFORMATION: A in position 4 and 24 is a fA nucleotide
      analog
<220> FEATURE:
<221> NAME/KEY: variation
<222> LOCATION: 24
<223> OTHER INFORMATION: The nucleotide in position 23 and the
      nucleotide in position 24 are linked through a phosphoramidite
      bond

<400> SEQUENCE: 71
tttaacagug uucuugcucu auaa                                            24

<210> SEQ ID NO 72
<211> LENGTH: 24
<212> TYPE: RNA
<213> ORGANISM: Artificial Sequence
<220> FEATURE:
<223> OTHER INFORMATION: ss1-6
<220> FEATURE:
<221> NAME/KEY: variation
<222> LOCATION: 1
<223> OTHER INFORMATION: T in position 1,2 and 3 is a lgT1 nucleotide
      analog
<220> FEATURE:
<221> NAME/KEY: variation
<222> LOCATION: 2
<223> OTHER INFORMATION: T in position 1,2 and 3 is a lgT1 nucleotide
      analog
<220> FEATURE:
```

```
<221> NAME/KEY: variation
<222> LOCATION: 3
<223> OTHER INFORMATION: T in position 1,2 and 3 is a lgT1 nucleotide
      analog
<220> FEATURE:
<221> NAME/KEY: variation
<222> LOCATION: 4
<223> OTHER INFORMATION: A in position 4 and 24 is a fA nucleotide
      analog
<220> FEATURE:
<221> NAME/KEY: variation
<222> LOCATION: 5
<223> OTHER INFORMATION: A in position 5,7,21 and 23 represents a mA
      nucleotide analog
<220> FEATURE:
<221> NAME/KEY: variation
<222> LOCATION: 6
<223> OTHER INFORMATION: C in position 6 and 13 is a fC nucleotide
      analog
<220> FEATURE:
<221> NAME/KEY: variation
<222> LOCATION: 7
<223> OTHER INFORMATION: A in position 5,7,21 and 23 represents a mA
      nucleotide analog
<220> FEATURE:
<221> NAME/KEY: variation
<222> LOCATION: 8
<223> OTHER INFORMATION: G in position 8,10 and 16 is a fG nucleotide
      analog
<220> FEATURE:
<221> NAME/KEY: variation
<222> LOCATION: 9
<223> OTHER INFORMATION: U in position 9,11 and 15 represents a 2'-O-
      methyl-uracile (mU)
<220> FEATURE:
<221> NAME/KEY: variation
<222> LOCATION: 10
<223> OTHER INFORMATION: G in position 8,10 and 16 is a fG nucleotide
      analog
<220> FEATURE:
<221> NAME/KEY: variation
<222> LOCATION: 11
<223> OTHER INFORMATION: U in position 9,11 and 15 represents a 2'-O-
      methyl-uracile (mU)
<220> FEATURE:
<221> NAME/KEY: variation
<222> LOCATION: 12
<223> OTHER INFORMATION: U in position 12,14,18,20 and 22 is a fU
      nucleotide analog
<220> FEATURE:
<221> NAME/KEY: variation
<222> LOCATION: 13
<223> OTHER INFORMATION: C in position 6 and 13 is a fC nucleotide
      analog
<220> FEATURE:
<221> NAME/KEY: variation
<222> LOCATION: 14
<223> OTHER INFORMATION: U in position 12,14,18,20 and 22 is a fU
      nucleotide analog
<220> FEATURE:
<221> NAME/KEY: variation
<222> LOCATION: 15
<223> OTHER INFORMATION: U in position 9,11 and 15 represents a 2'-O-
      methyl-uracile (mU)
<220> FEATURE:
<221> NAME/KEY: variation
<222> LOCATION: 16
<223> OTHER INFORMATION: G in position 8,10 and 16 is a fG nucleotide
      analog
<220> FEATURE:
<221> NAME/KEY: variation
<222> LOCATION: 17
<223> OTHER INFORMATION: C in position 17 and 19 represents a mC
      nucleotide analog
<220> FEATURE:
<221> NAME/KEY: variation
<222> LOCATION: 18
<223> OTHER INFORMATION: U in position 12,14,18,20 and 22 is a fU
      nucleotide analog
```

```
<220> FEATURE:
<221> NAME/KEY: variation
<222> LOCATION: 19
<223> OTHER INFORMATION: C in position 17 and 19 represents a mC
      nucleotide analog
<220> FEATURE:
<221> NAME/KEY: variation
<222> LOCATION: 20
<223> OTHER INFORMATION: U in position 12,14,18,20 and 22 is a fU
      nucleotide analog
<220> FEATURE:
<221> NAME/KEY: variation
<222> LOCATION: 21
<223> OTHER INFORMATION: A in position 5,7,21 and 23 represents a mA
      nucleotide analog
<220> FEATURE:
<221> NAME/KEY: variation
<222> LOCATION: 22
<223> OTHER INFORMATION: U in position 12,14,18,20 and 22 is a fU
      nucleotide analog
<220> FEATURE:
<221> NAME/KEY: variation
<222> LOCATION: 23
<223> OTHER INFORMATION: A in position 5,7,21 and 23 represents a mA
      nucleotide analog
<220> FEATURE:
<221> NAME/KEY: variation
<222> LOCATION: 24
<223> OTHER INFORMATION: A in position 4 and 24 is a fA nucleotide
      analog

<400> SEQUENCE: 72
tttaacagug uucuugcucu auaa                                           24

<210> SEQ ID NO 73
<211> LENGTH: 24
<212> TYPE: RNA
<213> ORGANISM: Artificial Sequence
<220> FEATURE:
<223> OTHER INFORMATION: ss1-7
<220> FEATURE:
<221> NAME/KEY: variation
<222> LOCATION: 1
<223> OTHER INFORMATION: The nucleotide in position 1 and the nucleotide
      in position 2 are linked through a phosphoramidite bond
<220> FEATURE:
<221> NAME/KEY: variation
<222> LOCATION: 1
<223> OTHER INFORMATION: A in position 1 and 21 is a fA nucleotide
      analog
<220> FEATURE:
<221> NAME/KEY: variation
<222> LOCATION: 2
<223> OTHER INFORMATION: The nucleotide in position 1 and the nucleotide
      in position 2 are linked through a phosphoramidite bond
<220> FEATURE:
<221> NAME/KEY: variation
<222> LOCATION: 2
<223> OTHER INFORMATION: The nucleotide in position 2 and the nucleotide
      in position 3 are linked through a phosphoramidite bond
<220> FEATURE:
<221> NAME/KEY: variation
<222> LOCATION: 2
<223> OTHER INFORMATION: A in position 2,4,18 and 20 represents a mA
      nucleotide analog
<220> FEATURE:
<221> NAME/KEY: variation
<222> LOCATION: 3
<223> OTHER INFORMATION: The nucleotide in position 2 and the nucleotide
      in position 3 are linked through a phosphoramidite bond
<220> FEATURE:
<221> NAME/KEY: variation
<222> LOCATION: 3
<223> OTHER INFORMATION: C in position 3 and 10 is a fC nucleotide
      analog
<220> FEATURE:
<221> NAME/KEY: variation
```

```
<222> LOCATION: 4
<223> OTHER INFORMATION: A in position 2,4,18 and 20 represents a mA
      nucleotide analog
<220> FEATURE:
<221> NAME/KEY: variation
<222> LOCATION: 5
<223> OTHER INFORMATION: G in position 5,7 and 13 is a fG nucleotide
      analog
<220> FEATURE:
<221> NAME/KEY: variation
<222> LOCATION: 6
<223> OTHER INFORMATION: U in position 6,8 and 12 represents a 2'-O-
      methyl-uracile (mU)
<220> FEATURE:
<221> NAME/KEY: variation
<222> LOCATION: 7
<223> OTHER INFORMATION: G in position 5,7 and 13 is a fG nucleotide
      analog
<220> FEATURE:
<221> NAME/KEY: variation
<222> LOCATION: 8
<223> OTHER INFORMATION: U in position 6,8 and 12 represents a 2'-O-
      methyl-uracile (mU)
<220> FEATURE:
<221> NAME/KEY: variation
<222> LOCATION: 9
<223> OTHER INFORMATION: U in position 9,11,15,17 and 19 is a fU
      nucleotide analog
<220> FEATURE:
<221> NAME/KEY: variation
<222> LOCATION: 10
<223> OTHER INFORMATION: C in position 3 and 10 is a fC nucleotide
      analog
<220> FEATURE:
<221> NAME/KEY: variation
<222> LOCATION: 11
<223> OTHER INFORMATION: U in position 9,11,15,17 and 19 is a fU
      nucleotide analog
<220> FEATURE:
<221> NAME/KEY: variation
<222> LOCATION: 12
<223> OTHER INFORMATION: U in position 6,8 and 12 represents a 2'-O-
      methyl-uracile (mU)
<220> FEATURE:
<221> NAME/KEY: variation
<222> LOCATION: 13
<223> OTHER INFORMATION: G in position 5,7 and 13 is a fG nucleotide
      analog
<220> FEATURE:
<221> NAME/KEY: variation
<222> LOCATION: 14
<223> OTHER INFORMATION: C in position 14 and 16 represents a mC
      nucleotide analog
<220> FEATURE:
<221> NAME/KEY: variation
<222> LOCATION: 15
<223> OTHER INFORMATION: U in position 9,11,15,17 is a fU
      nucleotide analog
<220> FEATURE:
<221> NAME/KEY: variation
<222> LOCATION: 16
<223> OTHER INFORMATION: C in position 14 and 16 represents a mC
      nucleotide analog
<220> FEATURE:
<221> NAME/KEY: variation
<222> LOCATION: 17
<223> OTHER INFORMATION: U in position 9,11,15,17 and 19 is a fU
      nucleotide analog
<220> FEATURE:
<221> NAME/KEY: variation
<222> LOCATION: 18
<223> OTHER INFORMATION: A in position 2,4,18 and 20 represents a mA
      nucleotide analog
<220> FEATURE:
<221> NAME/KEY: variation
<222> LOCATION: 19
<223> OTHER INFORMATION: U in position 9,11,15,17 and 19 is a fU
      nucleotide analog
<220> FEATURE:
```

<221> NAME/KEY: variation
<222> LOCATION: 20
<223> OTHER INFORMATION: A in position 2,4,18 and 20 represents a mA
       nucleotide analog
<220> FEATURE:
<221> NAME/KEY: variation
<222> LOCATION: 21
<223> OTHER INFORMATION: A in position 1 and 21 is a fA nucleotide
       analog
<220> FEATURE:
<221> NAME/KEY: variation
<222> LOCATION: 22
<223> OTHER INFORMATION: T in position 22,23 and 24 is a lgT1 nucleotide
       analog
<220> FEATURE:
<221> NAME/KEY: variation
<222> LOCATION: 23
<223> OTHER INFORMATION: T in position 22,23 and 24 is a lgT1 nucleotide
       analog
<220> FEATURE:
<221> NAME/KEY: variation
<222> LOCATION: 24
<223> OTHER INFORMATION: T in position 22,23 and 24 is a lgT1 nucleotide
       analog

<400> SEQUENCE: 73
aacaguguuc uugcucuaua attt                                          24

<210> SEQ ID NO 74
<211> LENGTH: 24
<212> TYPE: RNA
<213> ORGANISM: Artificial Sequence
<220> FEATURE:
<223> OTHER INFORMATION: ss1_8
<220> FEATURE:
<221> NAME/KEY: variation
<222> LOCATION: 1
<223> OTHER INFORMATION: T in position 1,2 and 3 is a lgT3 nucleotide
       analog
<220> FEATURE:
<221> NAME/KEY: variation
<222> LOCATION: 2
<223> OTHER INFORMATION: T in position 1,2 and 3 is a lgT3 nucleotide
       analog
<220> FEATURE:
<221> NAME/KEY: variation
<222> LOCATION: 3
<223> OTHER INFORMATION: T in position 1,2 and 3 is a lgT3 nucleotide
       analog
<220> FEATURE:
<221> NAME/KEY: variation
<222> LOCATION: 4
<223> OTHER INFORMATION: A in position 4 and 24 is a fA nucleotide
       analog
<220> FEATURE:
<221> NAME/KEY: variation
<222> LOCATION: 5
<223> OTHER INFORMATION: A in position 5,7,21 and 23 represents a mA
       nucleotide analog
<220> FEATURE:
<221> NAME/KEY: variation
<222> LOCATION: 6
<223> OTHER INFORMATION: C in position 6 and 13 is a fC nucleotide
       analog
<220> FEATURE:
<221> NAME/KEY: variation
<222> LOCATION: 7
<223> OTHER INFORMATION: A in position 5,7,21 and 23 represents a mA
       nucleotide analog
<220> FEATURE:
<221> NAME/KEY: variation
<222> LOCATION: 8
<223> OTHER INFORMATION: G in position 8,10 and 16 is a fG nucleotide
       analog
<220> FEATURE:
<221> NAME/KEY: variation
<222> LOCATION: 9

-continued

```
<223> OTHER INFORMATION: U in position 9,11 and 15 represents a 2'-O-
      methyl-uracile (mU)
<220> FEATURE:
<221> NAME/KEY: variation
<222> LOCATION: 10
<223> OTHER INFORMATION: G in position 8,10 and 16 is a fG nucleotide
      analog
<220> FEATURE:
<221> NAME/KEY: variation
<222> LOCATION: 11
<223> OTHER INFORMATION: U in position 9,11 and 15 represents a 2'-O-
      methyl-uracile (mU)
<220> FEATURE:
<221> NAME/KEY: variation
<222> LOCATION: 12
<223> OTHER INFORMATION: U in position 12,14,18,20 and 22 is a fU
      nucleotide analog
<220> FEATURE:
<221> NAME/KEY: variation
<222> LOCATION: 13
<223> OTHER INFORMATION: C in position 6 and 13 is a fC nucleotide
      analog
<220> FEATURE:
<221> NAME/KEY: variation
<222> LOCATION: 14
<223> OTHER INFORMATION: U in position 12,14,18,20 and 22 is a fU
      nucleotide analog
<220> FEATURE:
<221> NAME/KEY: variation
<222> LOCATION: 15
<223> OTHER INFORMATION: U in position 9,11 and 15 represents a 2'-O-
      methyl-uracile (mU)
<220> FEATURE:
<221> NAME/KEY: variation
<222> LOCATION: 16
<223> OTHER INFORMATION: G in position 8,10 and 16 is a fG nucleotide
      analog
<220> FEATURE:
<221> NAME/KEY: variation
<222> LOCATION: 17
<223> OTHER INFORMATION: C in position 17 and 19 represents a mC
      nucleotide analog
<220> FEATURE:
<221> NAME/KEY: variation
<222> LOCATION: 18
<223> OTHER INFORMATION: U in position 12,14,18,20 and 22 is a fU
      nucleotide analog
<220> FEATURE:
<221> NAME/KEY: variation
<222> LOCATION: 19
<223> OTHER INFORMATION: C in position 17 and 19 represents a mC
      nucleotide analog
<220> FEATURE:
<221> NAME/KEY: variation
<222> LOCATION: 20
<223> OTHER INFORMATION: U in position 12,14,18,20 and 22 is a fU
      nucleotide analog
<220> FEATURE:
<221> NAME/KEY: variation
<222> LOCATION: 21
<223> OTHER INFORMATION: A in position 5,7,21 and 23 represents a mA
      nucleotide analog
<220> FEATURE:
<221> NAME/KEY: variation
<222> LOCATION: 22
<223> OTHER INFORMATION: U in position 12,14,18,20 and 22 is a fU
      nucleotide analog
<220> FEATURE:
<221> NAME/KEY: variation
<222> LOCATION: 22
<223> OTHER INFORMATION: The nucleotide in position 22 and the
      nucleotide in position 23 are linked through a phosphoramidite
      bond
<220> FEATURE:
<221> NAME/KEY: variation
<222> LOCATION: 23
<223> OTHER INFORMATION: A in position 5,7,21 and 23 represents a mA
      nucleotide analog
<220> FEATURE:
```

```
<221> NAME/KEY: variation
<222> LOCATION: 23
<223> OTHER INFORMATION: The nucleotide in position 22 and the
      nucleotide in position 23 are linked through a phosphoramidite
      bond
<220> FEATURE:
<221> NAME/KEY: variation
<222> LOCATION: 23
<223> OTHER INFORMATION: The nucleotide in position 23 and the
      nucleotide in position 24 are linked through a phosphoramidite
      bond
<220> FEATURE:
<221> NAME/KEY: variation
<222> LOCATION: 24
<223> OTHER INFORMATION: A in position 4 and 24 is a fA nucleotide
      analog
<220> FEATURE:
<221> NAME/KEY: variation
<222> LOCATION: 24
<223> OTHER INFORMATION: The nucleotide in position 23 and the
      nucleotide in position 24 are linked through a phosphoramidite
      bond

<400> SEQUENCE: 74
tttaacagug uucuugcucu auaa                                          24

<210> SEQ ID NO 75
<211> LENGTH: 24
<212> TYPE: RNA
<213> ORGANISM: Artificial Sequence
<220> FEATURE:
<223> OTHER INFORMATION: ss1-9
<220> FEATURE:
<221> NAME/KEY: variation
<222> LOCATION: 1
<223> OTHER INFORMATION: T in position 1,2 and 3 is a lgT3 nucleotide
      analog
<220> FEATURE:
<221> NAME/KEY: variation
<222> LOCATION: 2
<223> OTHER INFORMATION: T in position 1,2 and 3 is a lgT3 nucleotide
      analog
<220> FEATURE:
<221> NAME/KEY: variation
<222> LOCATION: 3
<223> OTHER INFORMATION: T in position 1,2 and 3 is a lgT3 nucleotide
      analog
<220> FEATURE:
<221> NAME/KEY: variation
<222> LOCATION: 4
<223> OTHER INFORMATION: A in position 4 and 24 is a fA nucleotide
      analog
<220> FEATURE:
<221> NAME/KEY: variation
<222> LOCATION: 5
<223> OTHER INFORMATION: A in position 5,7,21 and 23 represents a mA
      nucleotide analog
<220> FEATURE:
<221> NAME/KEY: variation
<222> LOCATION: 6
<223> OTHER INFORMATION: C in position 6 and 13 is a fC nucleotide
      analog
<220> FEATURE:
<221> NAME/KEY: variation
<222> LOCATION: 7
<223> OTHER INFORMATION: A in position 5,7,21 and 23 represents a mA
      nucleotide analog
<220> FEATURE:
<221> NAME/KEY: variation
<222> LOCATION: 8
<223> OTHER INFORMATION: G in position 8,10 and 16 is a fG nucleotide
      analog
<220> FEATURE:
<221> NAME/KEY: variation
<222> LOCATION: 9
<223> OTHER INFORMATION: U in position 9,11 and 15 represents a 2'-O-
      methyl-uracile (mU)
```

```
<220> FEATURE:
<221> NAME/KEY: variation
<222> LOCATION: 10
<223> OTHER INFORMATION: G in position 8,10 and 16 is a fG nucleotide
      analog
<220> FEATURE:
<221> NAME/KEY: variation
<222> LOCATION: 11
<223> OTHER INFORMATION: U in position 9,11 and 15 represents a 2'-O-
      methyl-uracile (mU)
<220> FEATURE:
<221> NAME/KEY: variation
<222> LOCATION: 12
<223> OTHER INFORMATION: U in position 12,14,18,20 and 22 is a fU
      nucleotide analog
<220> FEATURE:
<221> NAME/KEY: variation
<222> LOCATION: 13
<223> OTHER INFORMATION: C in position 6 and 13 is a fC nucleotide
      analog
<220> FEATURE:
<221> NAME/KEY: variation
<222> LOCATION: 14
<223> OTHER INFORMATION: U in position 12,14,18,20 and 22 is a fU
      nucleotide analog
<220> FEATURE:
<221> NAME/KEY: variation
<222> LOCATION: 15
<223> OTHER INFORMATION: U in position 9,11 and 15 represents a 2'-O-
      methyl-uracile (mU)
<220> FEATURE:
<221> NAME/KEY: variation
<222> LOCATION: 16
<223> OTHER INFORMATION: G in position 8,10 and 16 is a fG nucleotide
      analog
<220> FEATURE:
<221> NAME/KEY: variation
<222> LOCATION: 17
<223> OTHER INFORMATION: C in position 17 and 19 represents a mC
      nucleotide analog
<220> FEATURE:
<221> NAME/KEY: variation
<222> LOCATION: 18
<223> OTHER INFORMATION: U in position 12,14,18,20 and 22 is a fU
      nucleotide analog
<220> FEATURE:
<221> NAME/KEY: variation
<222> LOCATION: 19
<223> OTHER INFORMATION: C in position 17 and 19 represents a mC
      nucleotide analog
<220> FEATURE:
<221> NAME/KEY: variation
<222> LOCATION: 20
<223> OTHER INFORMATION: U in position 12,14,18,20 and 22 is a fU
      nucleotide analog
<220> FEATURE:
<221> NAME/KEY: variation
<222> LOCATION: 21
<223> OTHER INFORMATION: A in position 5,7,21 and 23 represents a mA
      nucleotide analog
<220> FEATURE:
<221> NAME/KEY: variation
<222> LOCATION: 22
<223> OTHER INFORMATION: U in position 12,14,18,20 and 22 is a fU
      nucleotide analog
<220> FEATURE:
<221> NAME/KEY: variation
<222> LOCATION: 23
<223> OTHER INFORMATION: A in position 5,7,21 and 23 represents a mA
      nucleotide analog
<220> FEATURE:
<221> NAME/KEY: variation
<222> LOCATION: 24
<223> OTHER INFORMATION: A in position 4 and 24 is a fA nucleotide
      analog

<400> SEQUENCE: 75
tttaacagug uucuugcucu auaa                                            24
```

<210> SEQ ID NO 76
<211> LENGTH: 24
<212> TYPE: RNA
<213> ORGANISM: Artificial Sequence
<220> FEATURE:
<223> OTHER INFORMATION: ss1-10
<220> FEATURE:
<221> NAME/KEY: variation
<222> LOCATION: 1
<223> OTHER INFORMATION: The nucleotide in position 1 and the nucleotide
      in position 2 are linked through a phosphoramidite bond
<220> FEATURE:
<221> NAME/KEY: variation
<222> LOCATION: 1
<223> OTHER INFORMATION: A in position 1 and 21 is a fA nucleotide
      analog
<220> FEATURE:
<221> NAME/KEY: variation
<222> LOCATION: 2
<223> OTHER INFORMATION: The nucleotide in position 1 and the nucleotide
      in position 2 are linked through a phosphoramidite bond
<220> FEATURE:
<221> NAME/KEY: variation
<222> LOCATION: 2
<223> OTHER INFORMATION: The nucleotide in position 2 and the nucleotide
      in position 3 are linked through a phosphoramidite bond
<220> FEATURE:
<221> NAME/KEY: variation
<222> LOCATION: 2
<223> OTHER INFORMATION: A in position 2,4,18 and 20 represents a mA
      nucleotide analog
<220> FEATURE:
<221> NAME/KEY: variation
<222> LOCATION: 3
<223> OTHER INFORMATION: The nucleotide in position 2 and the nucleotide
      in position 3 are linked through a phosphoramidite bond
<220> FEATURE:
<221> NAME/KEY: variation
<222> LOCATION: 3
<223> OTHER INFORMATION: C in position 3 and 10 is a fC nucleotide
      analog
<220> FEATURE:
<221> NAME/KEY: variation
<222> LOCATION: 4
<223> OTHER INFORMATION: A in position 2,4,18 and 20 represents a mA
      nucleotide analog
<220> FEATURE:
<221> NAME/KEY: variation
<222> LOCATION: 5
<223> OTHER INFORMATION: G in position 5,7 and 13 is a fG nucleotide
      analog
<220> FEATURE:
<221> NAME/KEY: variation
<222> LOCATION: 6
<223> OTHER INFORMATION: U in position 6,8 and 12 represents a 2'-O-
      methyl-uracile (mU)
<220> FEATURE:
<221> NAME/KEY: variation
<222> LOCATION: 7
<223> OTHER INFORMATION: G in position 5,7 and 13 is a fG nucleotide
      analog
<220> FEATURE:
<221> NAME/KEY: variation
<222> LOCATION: 8
<223> OTHER INFORMATION: U in position 6,8 and 12 represents a 2'-O-
      methyl-uracile (mU)
<220> FEATURE:
<221> NAME/KEY: variation
<222> LOCATION: 9
<223> OTHER INFORMATION: U in position 9,11,15,17 and 19 is a fU
      nucleotide analog
<220> FEATURE:
<221> NAME/KEY: variation
<222> LOCATION: 10
<223> OTHER INFORMATION: C in position 3 and 10 is a fC nucleotide
      analog
<220> FEATURE:

```
<221> NAME/KEY: variation
<222> LOCATION: 11
<223> OTHER INFORMATION: U in position 9,11,15,17 and 19 is a fU
      nucleotide analog
<220> FEATURE:
<221> NAME/KEY: variation
<222> LOCATION: 12
<223> OTHER INFORMATION: U in position 6,8 and 12 represents a 2'-O-
      methyl-uracile (mU)
<220> FEATURE:
<221> NAME/KEY: variation
<222> LOCATION: 13
<223> OTHER INFORMATION: G in position 5,7 and 13 is a fG nucleotide
      analog
<220> FEATURE:
<221> NAME/KEY: variation
<222> LOCATION: 14
<223> OTHER INFORMATION: C in position 14 and 16 represents a mC
      nucleotide analog
<220> FEATURE:
<221> NAME/KEY: variation
<222> LOCATION: 15
<223> OTHER INFORMATION: U in position 9,11,15,17 and 19 is a fU
      nucleotide analog
<220> FEATURE:
<221> NAME/KEY: variation
<222> LOCATION: 16
<223> OTHER INFORMATION: C in position 14 and 16 represents a mC
      nucleotide analog
<220> FEATURE:
<221> NAME/KEY: variation
<222> LOCATION: 17
<223> OTHER INFORMATION: U in position 9,11,15,17 and 19 is a fU
      nucleotide analog
<220> FEATURE:
<221> NAME/KEY: variation
<222> LOCATION: 18
<223> OTHER INFORMATION: A in position 2,4,18 and 20 represents a mA
      nucleotide analog
<220> FEATURE:
<221> NAME/KEY: variation
<222> LOCATION: 19
<223> OTHER INFORMATION: U in position 9,11,15,17 and 19 is a fU
      nucleotide analog
<220> FEATURE:
<221> NAME/KEY: variation
<222> LOCATION: 20
<223> OTHER INFORMATION: A in position 2,4,18 and 20 represents a mA
      nucleotide analog
<220> FEATURE:
<221> NAME/KEY: variation
<222> LOCATION: 21
<223> OTHER INFORMATION: A in position 1 and 21 is a fA nucleotide
      analog
<220> FEATURE:
<221> NAME/KEY: variation
<222> LOCATION: 22
<223> OTHER INFORMATION: T in position 22,23 and 24 is a lgT3 nucleotide
      analog
<220> FEATURE:
<221> NAME/KEY: variation
<222> LOCATION: 23
<223> OTHER INFORMATION: T in position 22,23 and 24 is a lgT3 nucleotide
      analog
<220> FEATURE:
<221> NAME/KEY: variation
<222> LOCATION: 24
<223> OTHER INFORMATION: T in position 22,23 and 24 is a lgT3 nucleotide
      analog

<400> SEQUENCE: 76
aacaguguuc uugcucuaua attt                                          24

<210> SEQ ID NO 77
<211> LENGTH: 24
<212> TYPE: RNA
<213> ORGANISM: Artificial Sequence
```

-continued

```
<220> FEATURE:
<223> OTHER INFORMATION: ss1-11
<220> FEATURE:
<221> NAME/KEY: variation
<222> LOCATION: 1
<223> OTHER INFORMATION: T in position 1,2 and 3 is a lgT4 nucleotide
      analog
<220> FEATURE:
<221> NAME/KEY: variation
<222> LOCATION: 2
<223> OTHER INFORMATION: T in position 1,2 and 3 is a lgT4 nucleotide
      analog
<220> FEATURE:
<221> NAME/KEY: variation
<222> LOCATION: 3
<223> OTHER INFORMATION: T in position 1,2 and 3 is a lgT4 nucleotide
      analog
<220> FEATURE:
<221> NAME/KEY: variation
<222> LOCATION: 4
<223> OTHER INFORMATION: A in position 4 and 24 is a fA nucleotide
      analog
<220> FEATURE:
<221> NAME/KEY: variation
<222> LOCATION: 5
<223> OTHER INFORMATION: A in position 5,7,21 and 23 represents a mA
      nucleotide analog
<220> FEATURE:
<221> NAME/KEY: variation
<222> LOCATION: 6
<223> OTHER INFORMATION: C in position 6 and 13 is a fC nucleotide
      analog
<220> FEATURE:
<221> NAME/KEY: variation
<222> LOCATION: 7
<223> OTHER INFORMATION: A in position 5,7,21 and 23 represents a mA
      nucleotide analog
<220> FEATURE:
<221> NAME/KEY: variation
<222> LOCATION: 8
<223> OTHER INFORMATION: G in position 8,10 and 16 is a fG nucleotide
      analog
<220> FEATURE:
<221> NAME/KEY: variation
<222> LOCATION: 9
<223> OTHER INFORMATION: U in position 9,11 and 15 represents a 2'-O-
      methyl-uracile (mU)
<220> FEATURE:
<221> NAME/KEY: variation
<222> LOCATION: 10
<223> OTHER INFORMATION: G in position 8,10 and 16 is a fG nucleotide
      analog
<220> FEATURE:
<221> NAME/KEY: variation
<222> LOCATION: 11
<223> OTHER INFORMATION: U in position 9,11 and 15 represents a 2'-O-
      methyl-uracile (mU)
<220> FEATURE:
<221> NAME/KEY: variation
<222> LOCATION: 12
<223> OTHER INFORMATION: U in position 12,14,18,20 and 22 is a fU
      nucleotide analog
<220> FEATURE:
<221> NAME/KEY: variation
<222> LOCATION: 13
<223> OTHER INFORMATION: C in position 6 and 13 is a fC nucleotide
      analog
<220> FEATURE:
<221> NAME/KEY: variation
<222> LOCATION: 14
<223> OTHER INFORMATION: U in position 12,14,18,20 and 22 is a fU
      nucleotide analog
<220> FEATURE:
<221> NAME/KEY: variation
<222> LOCATION: 15
<223> OTHER INFORMATION: U in position 9,11 and 15 represents a 2'-O-
      methyl-uracile (mU)
<220> FEATURE:
<221> NAME/KEY: variation
```

```
<222> LOCATION: 16
<223> OTHER INFORMATION: G in position 8,10 and 16 is a fG nucleotide
      analog
<220> FEATURE:
<221> NAME/KEY: variation
<222> LOCATION: 17
<223> OTHER INFORMATION: C in position 17 and 19 represents a mC
      nucleotide analog
<220> FEATURE:
<221> NAME/KEY: variation
<222> LOCATION: 18
<223> OTHER INFORMATION: U in position 12,14,18,20 and 22 is a fU
      nucleotide analog
<220> FEATURE:
<221> NAME/KEY: variation
<222> LOCATION: 19
<223> OTHER INFORMATION: C in position 17 and 19 represents a mC
      nucleotide analog
<220> FEATURE:
<221> NAME/KEY: variation
<222> LOCATION: 20
<223> OTHER INFORMATION: U in position 12,14,18,20 and 22 is a fU
      nucleotide analog
<220> FEATURE:
<221> NAME/KEY: variation
<222> LOCATION: 21
<223> OTHER INFORMATION: A in position 5,7,21 and 23 represents a mA
      nucleotide analog
<220> FEATURE:
<221> NAME/KEY: variation
<222> LOCATION: 22
<223> OTHER INFORMATION: U in position 12,14,18,20 and 22 is a fU
      nucleotide analog
<220> FEATURE:
<221> NAME/KEY: variation
<222> LOCATION: 22
<223> OTHER INFORMATION: The nucleotide in position 22 and the
      nucleotide in position 23 are linked through a phosphoramidite
      bond
<220> FEATURE:
<221> NAME/KEY: variation
<222> LOCATION: 23
<223> OTHER INFORMATION: A in position 5,7,21 and 23 represents a mA
      nucleotide analog
<220> FEATURE:
<221> NAME/KEY: variation
<222> LOCATION: 23
<223> OTHER INFORMATION: The nucleotide in position 22 and the
      nucleotide in position 23 are linked through a phosphoramidite
      bond
<220> FEATURE:
<221> NAME/KEY: variation
<222> LOCATION: 23
<223> OTHER INFORMATION: The nucleotide in position 23 and the
      nucleotide in position 24 are linked through a phosphoramidite
      bond
<220> FEATURE:
<221> NAME/KEY: variation
<222> LOCATION: 24
<223> OTHER INFORMATION: A in position 4 and 24 is a fA nucleotide
      analog
<220> FEATURE:
<221> NAME/KEY: variation
<222> LOCATION: 24
<223> OTHER INFORMATION: The nucleotide in position 23 and the
      nucleotide in position 24 are linked through a phosphoramidite
      bond

<400> SEQUENCE: 77
tttaacagug uucuugcucu auaa                                            24

<210> SEQ ID NO 78
<211> LENGTH: 24
<212> TYPE: RNA
<213> ORGANISM: Artificial Sequence
<220> FEATURE:
<223> OTHER INFORMATION: ss1-12
```

```
<220> FEATURE:
<221> NAME/KEY: variation
<222> LOCATION: 1
<223> OTHER INFORMATION: The nucleotide in position 1 and the nucleotide
      in position 2 are linked through a phosphoramidite bond
<220> FEATURE:
<221> NAME/KEY: variation
<222> LOCATION: 1
<223> OTHER INFORMATION: A in position 1 and 21 is a fA nucleotide
      analog
<220> FEATURE:
<221> NAME/KEY: variation
<222> LOCATION: 2
<223> OTHER INFORMATION: The nucleotide in position 1 and the nucleotide
      in position 2 are linked through a phosphoramidite bond
<220> FEATURE:
<221> NAME/KEY: variation
<222> LOCATION: 2
<223> OTHER INFORMATION: The nucleotide in position 2 and the nucleotide
      in position 3 are linked through a phosphoramidite bond
<220> FEATURE:
<221> NAME/KEY: variation
<222> LOCATION: 2
<223> OTHER INFORMATION: A in position 2,4,18 and 20 represents a mA
      nucleotide analog
<220> FEATURE:
<221> NAME/KEY: variation
<222> LOCATION: 3
<223> OTHER INFORMATION: The nucleotide in position 2 and the nucleotide
      in position 3 are linked through a phosphoramidite bond
<220> FEATURE:
<221> NAME/KEY: variation
<222> LOCATION: 3
<223> OTHER INFORMATION: C in position 3 and 10 is a fC nucleotide
      analog
<220> FEATURE:
<221> NAME/KEY: variation
<222> LOCATION: 4
<223> OTHER INFORMATION: A in position 2,4,18 and 20 represents a mA
      nucleotide analog
<220> FEATURE:
<221> NAME/KEY: variation
<222> LOCATION: 5
<223> OTHER INFORMATION: G in position 5,7 and 13 is a fG nucleotide
      analog
<220> FEATURE:
<221> NAME/KEY: variation
<222> LOCATION: 6
<223> OTHER INFORMATION: U in position 6,8 and 12 represents a 2'-O-
      methyl-uracile (mU)
<220> FEATURE:
<221> NAME/KEY: variation
<222> LOCATION: 7
<223> OTHER INFORMATION: G in position 5,7 and 13 is a fG nucleotide
      analog
<220> FEATURE:
<221> NAME/KEY: variation
<222> LOCATION: 8
<223> OTHER INFORMATION: U in position 6,8 and 12 represents a 2'-O-
      methyl-uracile (mU)
<220> FEATURE:
<221> NAME/KEY: variation
<222> LOCATION: 9
<223> OTHER INFORMATION: U in position 9,11,15,17 and 19 is a fU
      nucleotide analog
<220> FEATURE:
<221> NAME/KEY: variation
<222> LOCATION: 10
<223> OTHER INFORMATION: C in position 3 and 10 is a fC nucleotide
      analog
<220> FEATURE:
<221> NAME/KEY: variation
<222> LOCATION: 11
<223> OTHER INFORMATION: U in position 9,11,15,17 and 19 is a fU
      nucleotide analog
<220> FEATURE:
<221> NAME/KEY: variation
<222> LOCATION: 12
<223> OTHER INFORMATION: U in position 6,8 and 12 represents a 2'-O-
```

```
            methyl-uracile (mU)
<220> FEATURE:
<221> NAME/KEY: variation
<222> LOCATION: 13
<223> OTHER INFORMATION: G in position 5,7 and 13 is a fG nucleotide
      analog
<220> FEATURE:
<221> NAME/KEY: variation
<222> LOCATION: 14
<223> OTHER INFORMATION: C in position 14 and 16 represents a mC
      nucleotide analog
<220> FEATURE:
<221> NAME/KEY: variation
<222> LOCATION: 15
<223> OTHER INFORMATION: U in position 9,11,15,17 and 19 is a fU
      nucleotide analog
<220> FEATURE:
<221> NAME/KEY: variation
<222> LOCATION: 16
<223> OTHER INFORMATION: C in position 14 and 16 represents a mC
      nucleotide analog
<220> FEATURE:
<221> NAME/KEY: variation
<222> LOCATION: 17
<223> OTHER INFORMATION: U in position 9,11,15,17 and 19 is a fU
      nucleotide analog
<220> FEATURE:
<221> NAME/KEY: variation
<222> LOCATION: 18
<223> OTHER INFORMATION: A in position 2,4,18 and 20 represents a mA
      nucleotide analog
<220> FEATURE:
<221> NAME/KEY: variation
<222> LOCATION: 19
<223> OTHER INFORMATION: U in position 9,11,15,17 and 19 is a fU
      nucleotide analog
<220> FEATURE:
<221> NAME/KEY: variation
<222> LOCATION: 20
<223> OTHER INFORMATION: A in position 2,4,18 and 20 represents a mA
      nucleotide analog
<220> FEATURE:
<221> NAME/KEY: variation
<222> LOCATION: 21
<223> OTHER INFORMATION: A in position 1 and 21 is a fA nucleotide
      analog
<220> FEATURE:
<221> NAME/KEY: variation
<222> LOCATION: 22
<223> OTHER INFORMATION: T in position 22,23 and 24 is a lgT4 nucleotide
      analog
<220> FEATURE:
<221> NAME/KEY: variation
<222> LOCATION: 23
<223> OTHER INFORMATION: T in position 22,23 and 24 is a lgT4 nucleotide
      analog
<220> FEATURE:
<221> NAME/KEY: variation
<222> LOCATION: 24
<223> OTHER INFORMATION: T in position 22,23 and 24 is a lgT4 nucleotide
      analog

<400> SEQUENCE: 78
aacaguguuc uugcucuaua attt                                           24

<210> SEQ ID NO 79
<211> LENGTH: 23
<212> TYPE: RNA
<213> ORGANISM: Artificial Sequence
<220> FEATURE:
<223> OTHER INFORMATION: as1-1
<220> FEATURE:
<221> NAME/KEY: variation
<222> LOCATION: 1
<223> OTHER INFORMATION: The nucleotide in position 1 and the nucleotide
      in position 2 are linked through a phosphoramidite bond
<220> FEATURE:
```

```
<221> NAME/KEY: variation
<222> LOCATION: 1
<223> OTHER INFORMATION: U in position 1,21,22 and 23 represents a
      2'-O-methyl-uracile (mU)
<220> FEATURE:
<221> NAME/KEY: variation
<222> LOCATION: 2
<223> OTHER INFORMATION: The nucleotide in position 1 and the nucleotide
      in position 2 are linked through a phosphoramidite bond
<220> FEATURE:
<221> NAME/KEY: variation
<222> LOCATION: 2
<223> OTHER INFORMATION: The nucleotide in position 2 and the nucleotide
      in position 3 are linked through a phosphoramidite bond
<220> FEATURE:
<221> NAME/KEY: variation
<222> LOCATION: 2
<223> OTHER INFORMATION: U in position 2,4,18 and 20 is a fU nucleotide
      analog
<220> FEATURE:
<221> NAME/KEY: variation
<222> LOCATION: 3
<223> OTHER INFORMATION: The nucleotide in position 2 and the nucleotide
      in position 3 are linked through a phosphoramidite bond
<220> FEATURE:
<221> NAME/KEY: variation
<222> LOCATION: 3
<223> OTHER INFORMATION: A in position 3,5,7,11 and 13 represents a mA
      nucleotide analog
<220> FEATURE:
<221> NAME/KEY: variation
<222> LOCATION: 4
<223> OTHER INFORMATION: U in position 2,4,18 and 20 is a fU nucleotide
      analog
<220> FEATURE:
<221> NAME/KEY: variation
<222> LOCATION: 5
<223> OTHER INFORMATION: A in position 3,5,7,11 and 13 represents a mA
      nucleotide analog
<220> FEATURE:
<221> NAME/KEY: variation
<222> LOCATION: 6
<223> OTHER INFORMATION: G in position 6 and 8 is a fG nucleotide analog
<220> FEATURE:
<221> NAME/KEY: variation
<222> LOCATION: 7
<223> OTHER INFORMATION: A in position 3,5,7,11 and 13 represents a mA
      nucleotide analog
<220> FEATURE:
<221> NAME/KEY: variation
<222> LOCATION: 8
<223> OTHER INFORMATION: G in position 6 and 8 is a fG nucleotide analog
<220> FEATURE:
<221> NAME/KEY: variation
<222> LOCATION: 9
<223> OTHER INFORMATION: C in position 9,15 and 17 represents a mC
      nucleotide analog
<220> FEATURE:
<221> NAME/KEY: variation
<222> LOCATION: 10
<223> OTHER INFORMATION: A in position 10,14 and 16 is a fA nucleotide
      analog
<220> FEATURE:
<221> NAME/KEY: variation
<222> LOCATION: 11
<223> OTHER INFORMATION: A in position 3,5,7,11 and 13 represents a mA
      nucleotide analog
<220> FEATURE:
<221> NAME/KEY: variation
<222> LOCATION: 12
<223> OTHER INFORMATION: G in position 12 and 19 represents a mG
      nucleotide analog
<220> FEATURE:
<221> NAME/KEY: variation
<222> LOCATION: 13
<223> OTHER INFORMATION: A in position 3,5,7,11 and 13 represents a mA
      nucleotide analog
<220> FEATURE:
<221> NAME/KEY: variation
```

```
<222> LOCATION: 14
<223> OTHER INFORMATION: A in position 10,14 and 16 is a fA nucleotide
      analog
<220> FEATURE:
<221> NAME/KEY: variation
<222> LOCATION: 15
<223> OTHER INFORMATION: C in position 9,15 and 17 represents a mC
      nucleotide analog
<220> FEATURE:
<221> NAME/KEY: variation
<222> LOCATION: 16
<223> OTHER INFORMATION: A in position 10,14 and 16 is a fA nucleotide
      analog
<220> FEATURE:
<221> NAME/KEY: variation
<222> LOCATION: 17
<223> OTHER INFORMATION: C in position 9,15 and 17 represents a mC
      nucleotide analog
<220> FEATURE:
<221> NAME/KEY: variation
<222> LOCATION: 18
<223> OTHER INFORMATION: U in position 2,4,18 and 20 is a fU nucleotide
      analog
<220> FEATURE:
<221> NAME/KEY: variation
<222> LOCATION: 19
<223> OTHER INFORMATION: G in position 12 and 19 represents a mG
      nucleotide analog (mG)
<220> FEATURE:
<221> NAME/KEY: variation
<222> LOCATION: 20
<223> OTHER INFORMATION: U in position 2,4,18 and 20 is a fU nucleotide
      analog
<220> FEATURE:
<221> NAME/KEY: variation
<222> LOCATION: 21
<223> OTHER INFORMATION: U in position 1,21,22 and 23 represents a
      2'-O-methyl-uracile (mU)
<220> FEATURE:
<221> NAME/KEY: variation
<222> LOCATION: 21
<223> OTHER INFORMATION: The nucleotide in position 21 and the
      nucleotide in position 22 are linked through a phosphoramidite
      bond
<220> FEATURE:
<221> NAME/KEY: variation
<222> LOCATION: 22
<223> OTHER INFORMATION: U in position 1,21,22 and 23 represents a
      2'-O-methyl-uracile (mU)
<220> FEATURE:
<221> NAME/KEY: variation
<222> LOCATION: 22
<223> OTHER INFORMATION: The nucleotide in position 21 and the
      nucleotide in position 22 are linked through a phosphoramidite
      bond
<220> FEATURE:
<221> NAME/KEY: variation
<222> LOCATION: 22
<223> OTHER INFORMATION: The nucleotide in position 22 and the
      nucleotide in position 23 are linked through a phosphoramidite
      bond
<220> FEATURE:
<221> NAME/KEY: variation
<222> LOCATION: 23
<223> OTHER INFORMATION: U in position 1,21,22 and 23 represents a
      2'-O-methyl-uracile (mU)
<220> FEATURE:
<221> NAME/KEY: variation
<222> LOCATION: 23
<223> OTHER INFORMATION: The nucleotide in position 22 and the
      nucleotide in position 23 are linked through a phosphoramidite
      bond

<400> SEQUENCE: 79
uuauagagca agaacacugu uuu                                          23

<210> SEQ ID NO 80
```

```
<211> LENGTH: 22
<212> TYPE: RNA
<213> ORGANISM: Artificial Sequence
<220> FEATURE:
<223> OTHER INFORMATION: ss2-0
<220> FEATURE:
<221> NAME/KEY: variation
<222> LOCATION: 1
<223> OTHER INFORMATION: T in position 1,2 and 3 is a lgT3 nucleotide
      analog
<220> FEATURE:
<221> NAME/KEY: variation
<222> LOCATION: 2
<223> OTHER INFORMATION: T in position 1,2 and 3 is a lgT3 nucleotide
      analog
<220> FEATURE:
<221> NAME/KEY: variation
<222> LOCATION: 3
<223> OTHER INFORMATION: T in position 1,2 and 3 is a lgT3 nucleotide
      analog
<220> FEATURE:
<221> NAME/KEY: variation
<222> LOCATION: 4
<223> OTHER INFORMATION: A in position 4 is a fA nucleotide analog
<220> FEATURE:
<221> NAME/KEY: variation
<222> LOCATION: 5
<223> OTHER INFORMATION: U in position 5 and 17 represents a 2'-O-
      methyl-uracile (mU)
<220> FEATURE:
<221> NAME/KEY: variation
<222> LOCATION: 6
<223> OTHER INFORMATION: C in position 6,10,14 and 18 is a fC nucleotide
      analog
<220> FEATURE:
<221> NAME/KEY: variation
<222> LOCATION: 7
<223> OTHER INFORMATION: G in position 7,11 and 19 represents a mG
      nucleotide analog
<220> FEATURE:
<221> NAME/KEY: variation
<222> LOCATION: 8
<223> OTHER INFORMATION: U in position 8,12,20 and 22 is a fU nucleotide
      analog
<220> FEATURE:
<221> NAME/KEY: variation
<222> LOCATION: 9
<223> OTHER INFORMATION: A in position 9,13 and 21 represents a mA
      nucleotide analog
<220> FEATURE:
<221> NAME/KEY: variation
<222> LOCATION: 10
<223> OTHER INFORMATION: C in position 6,10,14 and 18 is a fC nucleotide
      analog
<220> FEATURE:
<221> NAME/KEY: variation
<222> LOCATION: 11
<223> OTHER INFORMATION: G in position 7,11 and 19 represents a mG
      nucleotide analog
<220> FEATURE:
<221> NAME/KEY: variation
<222> LOCATION: 12
<223> OTHER INFORMATION: U in position 8,12,20 and 22 is a fU nucleotide
      analog
<220> FEATURE:
<221> NAME/KEY: variation
<222> LOCATION: 13
<223> OTHER INFORMATION: A in position 9,13 and 21 represents a mA
      nucleotide analog
<220> FEATURE:
<221> NAME/KEY: variation
<222> LOCATION: 14
<223> OTHER INFORMATION: C in position 6,10,14 and 18 is a fC nucleotide
      analog
<220> FEATURE:
<221> NAME/KEY: variation
<222> LOCATION: 15
<223> OTHER INFORMATION: C in position 15 represents a mC nucleotide
      analog
```

```
<220> FEATURE:
<221> NAME/KEY: variation
<222> LOCATION: 16
<223> OTHER INFORMATION: G in position 16 is a fG nucleotide analog
<220> FEATURE:
<221> NAME/KEY: variation
<222> LOCATION: 17
<223> OTHER INFORMATION: U in position 5 and 17 represents a 2'-O-
      methyl-uracile (mU)
<220> FEATURE:
<221> NAME/KEY: variation
<222> LOCATION: 18
<223> OTHER INFORMATION: C in position 6,10,14 and 18 is a fC nucleotide
      analog
<220> FEATURE:
<221> NAME/KEY: variation
<222> LOCATION: 19
<223> OTHER INFORMATION: G in position 7,11 and 19 represents a mG
      nucleotide analog
<220> FEATURE:
<221> NAME/KEY: variation
<222> LOCATION: 20
<223> OTHER INFORMATION: U in position 8,12,20 and 22 is a fU nucleotide
      analog
<220> FEATURE:
<221> NAME/KEY: variation
<222> LOCATION: 20
<223> OTHER INFORMATION: The nucleotide in position 20 and the
      nucleotide in position 21 are linked through a phosphoramidite
      bond
<220> FEATURE:
<221> NAME/KEY: variation
<222> LOCATION: 21
<223> OTHER INFORMATION: A in position 9,13 and 21 represents a mA
      nucleotide analog
<220> FEATURE:
<221> NAME/KEY: variation
<222> LOCATION: 21
<223> OTHER INFORMATION: The nucleotide in position 20 and the
      nucleotide in position 21 are linked through a phosphoramidite
      bond
<220> FEATURE:
<221> NAME/KEY: variation
<222> LOCATION: 21
<223> OTHER INFORMATION: The nucleotide in position 21 and the
      nucleotide in position 22 are linked through a phosphoramidite
      bond
<220> FEATURE:
<221> NAME/KEY: variation
<222> LOCATION: 22
<223> OTHER INFORMATION: U in position 8,12,20 and 22 is a fU nucleotide
      analog
<220> FEATURE:
<221> NAME/KEY: variation
<222> LOCATION: 22
<223> OTHER INFORMATION: The nucleotide in position 21 and the
      nucleotide in position 22 are linked through a phosphoramidite
      bond

<400> SEQUENCE: 80
tttaucguac guaccgucgu au                                             22

<210> SEQ ID NO 81
<211> LENGTH: 26
<212> TYPE: RNA
<213> ORGANISM: Artificial Sequence
<220> FEATURE:
<223> OTHER INFORMATION: ss2-2
<220> FEATURE:
<221> NAME/KEY: variation
<222> LOCATION: 1
<223> OTHER INFORMATION: T in position 1,2,3 is a lgT3 nucleotide analog
<220> FEATURE:
<221> NAME/KEY: variation
<222> LOCATION: 2
<223> OTHER INFORMATION: T in position 1,2,3 is a lgT3 nucleotide analog
<220> FEATURE:
```

```
<221> NAME/KEY: variation
<222> LOCATION: 3
<223> OTHER INFORMATION: T in position 1,2,3 is a lgT3 nucleotide analog
<220> FEATURE:
<221> NAME/KEY: variation
<222> LOCATION: 4
<223> OTHER INFORMATION: A in position 4 and 24 is a fA nucleotide
      analog
<220> FEATURE:
<221> NAME/KEY: variation
<222> LOCATION: 5
<223> OTHER INFORMATION: A in position 5,7,21 and 23 represents a mA
      nucleotide analog
<220> FEATURE:
<221> NAME/KEY: variation
<222> LOCATION: 6
<223> OTHER INFORMATION: C in position 6 and 13 is a fC nucleotide
      analog
<220> FEATURE:
<221> NAME/KEY: variation
<222> LOCATION: 7
<223> OTHER INFORMATION: A in position 5,7,21 and 23 represents a mA
      nucleotide analog
<220> FEATURE:
<221> NAME/KEY: variation
<222> LOCATION: 8
<223> OTHER INFORMATION: G in position 8,10 and 16 is a fG nucleotide
      analog
<220> FEATURE:
<221> NAME/KEY: variation
<222> LOCATION: 9
<223> OTHER INFORMATION: U in position 9,11 and 15 represents a 2'-O-
      methyl-uracile (mU)
<220> FEATURE:
<221> NAME/KEY: variation
<222> LOCATION: 10
<223> OTHER INFORMATION: G in position 8,10 and 16 is a fG nucleotide
      analog
<220> FEATURE:
<221> NAME/KEY: variation
<222> LOCATION: 11
<223> OTHER INFORMATION: U in position 9,11 and 15 represents a 2'-O-
      methyl-uracile (mU)
<220> FEATURE:
<221> NAME/KEY: variation
<222> LOCATION: 12
<223> OTHER INFORMATION: U in position 12,14,18,20 and 22 is a fU
      nucleotide analog
<220> FEATURE:
<221> NAME/KEY: variation
<222> LOCATION: 13
<223> OTHER INFORMATION: C in position 6 and 13 is a fC nucleotide
      analog
<220> FEATURE:
<221> NAME/KEY: variation
<222> LOCATION: 14
<223> OTHER INFORMATION: U in position 12,14,18,20 and 22 is a fU
      nucleotide analog
<220> FEATURE:
<221> NAME/KEY: variation
<222> LOCATION: 15
<223> OTHER INFORMATION: U in position 9,11 and 15 represents a 2'-O-
      methyl-uracile (mU)
<220> FEATURE:
<221> NAME/KEY: variation
<222> LOCATION: 16
<223> OTHER INFORMATION: G in position 8,10 and 16 is a fG nucleotide
      analog
<220> FEATURE:
<221> NAME/KEY: variation
<222> LOCATION: 17
<223> OTHER INFORMATION: C in position 17 and 19 represents a mC
      nucleotide analog
<220> FEATURE:
<221> NAME/KEY: variation
<222> LOCATION: 18
<223> OTHER INFORMATION: U in position 12,14,18,20 and 22 is a fU
      nucleotide analog
<220> FEATURE:
```

<221> NAME/KEY: variation
<222> LOCATION: 19
<223> OTHER INFORMATION: C in position 17 and 19 represents a mC
      nucleotide analog
<220> FEATURE:
<221> NAME/KEY: variation
<222> LOCATION: 20
<223> OTHER INFORMATION: U in position 12,14,18,20 and 22 is a fU
      nucleotide analog
<220> FEATURE:
<221> NAME/KEY: variation
<222> LOCATION: 21
<223> OTHER INFORMATION: A in position 5,7,21 and 23 represents a mA
      nucleotide analog
<220> FEATURE:
<221> NAME/KEY: variation
<222> LOCATION: 22
<223> OTHER INFORMATION: U in position 12,14,18,20 and 22 is a fU
      nucleotide analog
<220> FEATURE:
<221> NAME/KEY: variation
<222> LOCATION: 23
<223> OTHER INFORMATION: A in position 5,7,21 and 23 represents a mA
      nucleotide analog
<220> FEATURE:
<221> NAME/KEY: variation
<222> LOCATION: 24
<223> OTHER INFORMATION: A in position 4 and 24 is a fA nucleotide
      analog
<220> FEATURE:
<221> NAME/KEY: variation
<222> LOCATION: 25
<223> OTHER INFORMATION: T in position 25 and 26 is a lT1 nucleotide
      analog
<220> FEATURE:
<221> NAME/KEY: variation
<222> LOCATION: 26
<223> OTHER INFORMATION: T in position 25 and 26 is a lT1 nucleotide
      analog

<400> SEQUENCE: 81
tttaacagug uucuugcucu auaatt                                        26

<210> SEQ ID NO 82
<211> LENGTH: 26
<212> TYPE: RNA
<213> ORGANISM: Artificial Sequence
<220> FEATURE:
<223> OTHER INFORMATION: ss2-3
<220> FEATURE:
<221> NAME/KEY: variation
<222> LOCATION: 1
<223> OTHER INFORMATION: T in position 1,2 and 3 is a lgT3 nucleotide
      analog
<220> FEATURE:
<221> NAME/KEY: variation
<222> LOCATION: 2
<223> OTHER INFORMATION: T in position 1,2 and 3 is a lgT3 nucleotide
      analog
<220> FEATURE:
<221> NAME/KEY: variation
<222> LOCATION: 3
<223> OTHER INFORMATION: T in position 1,2 and 3 is a lgT3 nucleotide
      analog
<220> FEATURE:
<221> NAME/KEY: variation
<222> LOCATION: 4
<223> OTHER INFORMATION: A in position 4 and 24 is a fA nucleotide
      analog
<220> FEATURE:
<221> NAME/KEY: variation
<222> LOCATION: 5
<223> OTHER INFORMATION: A in position 5,7,21 and 23 represents a mA
      nucleotide analog
<220> FEATURE:
<221> NAME/KEY: variation
<222> LOCATION: 6

```
<223> OTHER INFORMATION: C in position 6 and 13 is a fC nucleotide
      analog
<220> FEATURE:
<221> NAME/KEY: variation
<222> LOCATION: 7
<223> OTHER INFORMATION: A in position 5,7,21 and 23 represents a mA
      nucleotide analog
<220> FEATURE:
<221> NAME/KEY: variation
<222> LOCATION: 8
<223> OTHER INFORMATION: G in position 8,10 and 16 is a fG nucleotide
      analog
<220> FEATURE:
<221> NAME/KEY: variation
<222> LOCATION: 9
<223> OTHER INFORMATION: U in position 9,11 and 15 represents a 2'-O-
      methyl-uracile (mU)
<220> FEATURE:
<221> NAME/KEY: variation
<222> LOCATION: 10
<223> OTHER INFORMATION: G in position 8,10 and 16 is a fG nucleotide
      analog
<220> FEATURE:
<221> NAME/KEY: variation
<222> LOCATION: 11
<223> OTHER INFORMATION: U in position 9,11 and 15 represents a 2'-O-
      methyl-uracile (mU)
<220> FEATURE:
<221> NAME/KEY: variation
<222> LOCATION: 12
<223> OTHER INFORMATION: U in position 12,14,18,20 and 22 is a fU
      nucleotide analog
<220> FEATURE:
<221> NAME/KEY: variation
<222> LOCATION: 13
<223> OTHER INFORMATION: C in position 6 and 13 is a fC nucleotide
      analog
<220> FEATURE:
<221> NAME/KEY: variation
<222> LOCATION: 14
<223> OTHER INFORMATION: U in position 12,14,18,20 and 22 is a fU
      nucleotide analog
<220> FEATURE:
<221> NAME/KEY: variation
<222> LOCATION: 15
<223> OTHER INFORMATION: U in position 9,11 and 15 represents a 2'-O-
      methyl-uracile (mU)
<220> FEATURE:
<221> NAME/KEY: variation
<222> LOCATION: 16
<223> OTHER INFORMATION: G in position 8,10 and 16 is a fG nucleotide
      analog
<220> FEATURE:
<221> NAME/KEY: variation
<222> LOCATION: 17
<223> OTHER INFORMATION: C in position 17 and 19 represents a mC
      nucleotide analog
<220> FEATURE:
<221> NAME/KEY: variation
<222> LOCATION: 18
<223> OTHER INFORMATION: U in position 12,14,18,20 and 22 is a fU
      nucleotide analog
<220> FEATURE:
<221> NAME/KEY: variation
<222> LOCATION: 19
<223> OTHER INFORMATION: C in position 17 and 19 represents a mC
      nucleotide analog
<220> FEATURE:
<221> NAME/KEY: variation
<222> LOCATION: 20
<223> OTHER INFORMATION: U in position 12,14,18,20 and 22 is a fU
      nucleotide analog
<220> FEATURE:
<221> NAME/KEY: variation
<222> LOCATION: 21
<223> OTHER INFORMATION: A in position 5,7,21 and 23 represents a mA
      nucleotide analog
<220> FEATURE:
<221> NAME/KEY: variation
```

-continued

```
<222> LOCATION: 22
<223> OTHER INFORMATION: U in position 12,14,18,20 and 22 is a fU
      nucleotide analog
<220> FEATURE:
<221> NAME/KEY: variation
<222> LOCATION: 23
<223> OTHER INFORMATION: A in position 5,7,21 and 23 represents a mA
      nucleotide analog
<220> FEATURE:
<221> NAME/KEY: variation
<222> LOCATION: 24
<223> OTHER INFORMATION: A in position 4 and 24 is a fA nucleotide
      analog
<220> FEATURE:
<221> NAME/KEY: variation
<222> LOCATION: 25
<223> OTHER INFORMATION: T in position 25 and 26 is a lT2 nucleotide
      analog
<220> FEATURE:
<221> NAME/KEY: variation
<222> LOCATION: 26
<223> OTHER INFORMATION: T in position 25 and 26 is a lT2 nucleotide
      analog

<400> SEQUENCE: 82
tttaacagug uucuugcucu auaatt                                          26

<210> SEQ ID NO 83
<211> LENGTH: 26
<212> TYPE: RNA
<213> ORGANISM: Artificial Sequence
<220> FEATURE:
<223> OTHER INFORMATION: ss2-4
<220> FEATURE:
<221> NAME/KEY: variation
<222> LOCATION: 1
<223> OTHER INFORMATION: T in position 1,2 and 3 is a lgT3 nucleotide
      analog
<220> FEATURE:
<221> NAME/KEY: variation
<222> LOCATION: 2
<223> OTHER INFORMATION: T in position 1,2 and 3 is a lgT3 nucleotide
      analog
<220> FEATURE:
<221> NAME/KEY: variation
<222> LOCATION: 3
<223> OTHER INFORMATION: T in position 1,2 and 3 is a lgT3 nucleotide
      analog
<220> FEATURE:
<221> NAME/KEY: variation
<222> LOCATION: 4
<223> OTHER INFORMATION: A in position 4 and 24 is a fA nucleotide
      analog
<220> FEATURE:
<221> NAME/KEY: variation
<222> LOCATION: 5
<223> OTHER INFORMATION: A in position 5,7,21 and 23 represents a mA
      nucleotide analog
<220> FEATURE:
<221> NAME/KEY: variation
<222> LOCATION: 6
<223> OTHER INFORMATION: C in position 6 and 13 is a fC nucleotide
      analog
<220> FEATURE:
<221> NAME/KEY: variation
<222> LOCATION: 7
<223> OTHER INFORMATION: A in position 5,7,21 and 23 represents a mA
      nucleotide analog
<220> FEATURE:
<221> NAME/KEY: variation
<222> LOCATION: 8
<223> OTHER INFORMATION: G in position 8,10 and 16 is a fG nucleotide
      analog
<220> FEATURE:
<221> NAME/KEY: variation
<222> LOCATION: 9
<223> OTHER INFORMATION: U in position 9,11 and 15 represents a 2'-O-
``` methyl-uracile (mU)
<220> FEATURE:
<221> NAME/KEY: variation
<222> LOCATION: 10
<223> OTHER INFORMATION: G in position 8,10 and 16 is a fG nucleotide
    analog
<220> FEATURE:
<221> NAME/KEY: variation
<222> LOCATION: 11
<223> OTHER INFORMATION: U in position 9,11 and 15 represents a 2'-O-
    methyl-uracile (mU)
<220> FEATURE:
<221> NAME/KEY: variation
<222> LOCATION: 12
<223> OTHER INFORMATION: U in position 12,14,18,20 and 22 is a fU
    nucleotide analog
<220> FEATURE:
<221> NAME/KEY: variation
<222> LOCATION: 13
<223> OTHER INFORMATION: C in position 6 and 13 is a fC nucleotide
    analog
<220> FEATURE:
<221> NAME/KEY: variation
<222> LOCATION: 14
<223> OTHER INFORMATION: U in position 12,14,18,20 and 22 is a fU
    nucleotide analog
<220> FEATURE:
<221> NAME/KEY: variation
<222> LOCATION: 15
<223> OTHER INFORMATION: U in position 9,11 and 15 represents a 2'-O-
    methyl-uracile (mU)
<220> FEATURE:
<221> NAME/KEY: variation
<222> LOCATION: 16
<223> OTHER INFORMATION: G in position 8,10 and 16 is a fG nucleotide
    analog
<220> FEATURE:
<221> NAME/KEY: variation
<222> LOCATION: 17
<223> OTHER INFORMATION: C in position 17 and 19 represents a mC
    nucleotide analog
<220> FEATURE:
<221> NAME/KEY: variation
<222> LOCATION: 18
<223> OTHER INFORMATION: U in position 12,14,18,20 and 22 is a fU
    nucleotide analog
<220> FEATURE:
<221> NAME/KEY: variation
<222> LOCATION: 19
<223> OTHER INFORMATION: C in position 17 and 19 represents a mC
    nucleotide analog
<220> FEATURE:
<221> NAME/KEY: variation
<222> LOCATION: 20
<223> OTHER INFORMATION: U in position 12,14,18,20 and 22 is a fU
    nucleotide analog
<220> FEATURE:
<221> NAME/KEY: variation
<222> LOCATION: 21
<223> OTHER INFORMATION: A in position 5,7,21 and 23 represents a mA
    nucleotide analog
<220> FEATURE:
<221> NAME/KEY: variation
<222> LOCATION: 22
<223> OTHER INFORMATION: U in position 12,14,18,20 and 22 is a fU
    nucleotide analog
<220> FEATURE:
<221> NAME/KEY: variation
<222> LOCATION: 23
<223> OTHER INFORMATION: A in position 5,7,21 and 23 represents a mA
    nucleotide analog
<220> FEATURE:
<221> NAME/KEY: variation
<222> LOCATION: 24
<223> OTHER INFORMATION: A in position 4 and 24 is a fA nucleotide
    analog
<220> FEATURE:
<221> NAME/KEY: variation
<222> LOCATION: 25

<223> OTHER INFORMATION: T in position 25 and 26 is a lT3 nucleotide
      analog
<220> FEATURE:
<221> NAME/KEY: variation
<222> LOCATION: 26
<223> OTHER INFORMATION: T in position 25 and 26 is a lT3 nucleotide
      analog

<400> SEQUENCE: 83
tttaacagug uucuugcucu auaatt                                           26

<210> SEQ ID NO 84
<211> LENGTH: 26
<212> TYPE: RNA
<213> ORGANISM: Artificial Sequence
<220> FEATURE:
<223> OTHER INFORMATION: ss2-5
<220> FEATURE:
<221> NAME/KEY: variation
<222> LOCATION: 1
<223> OTHER INFORMATION: T in position 1,2 and 3 is a lgT3 nucleotide
      analog
<220> FEATURE:
<221> NAME/KEY: variation
<222> LOCATION: 2
<223> OTHER INFORMATION: T in position 1,2 and 3 is a lgT3 nucleotide
      analog
<220> FEATURE:
<221> NAME/KEY: variation
<222> LOCATION: 3
<223> OTHER INFORMATION: T in position 1,2 and 3 is a lgT3 nucleotide
      analog
<220> FEATURE:
<221> NAME/KEY: variation
<222> LOCATION: 4
<223> OTHER INFORMATION: A in position 4 and 24 is a fA nucleotide
      analog
<220> FEATURE:
<221> NAME/KEY: variation
<222> LOCATION: 5
<223> OTHER INFORMATION: A in position 5,7,21 and 23 represents a mA
      nucleotide analog
<220> FEATURE:
<221> NAME/KEY: variation
<222> LOCATION: 6
<223> OTHER INFORMATION: C in position 6 and 13 is a fC nucleotide
      analog
<220> FEATURE:
<221> NAME/KEY: variation
<222> LOCATION: 7
<223> OTHER INFORMATION: A in position 5,7,21 and 23 represents a mA
      nucleotide analog
<220> FEATURE:
<221> NAME/KEY: variation
<222> LOCATION: 8
<223> OTHER INFORMATION: G in position 8,10 and 16 is a fG nucleotide
      analog
<220> FEATURE:
<221> NAME/KEY: variation
<222> LOCATION: 9
<223> OTHER INFORMATION: U in position 9,11 and 15 represents a 2'-O-
      methyl-uracile (mU)
<220> FEATURE:
<221> NAME/KEY: variation
<222> LOCATION: 10
<223> OTHER INFORMATION: G in position 8,10 and 16 is a fG nucleotide
      analog
<220> FEATURE:
<221> NAME/KEY: variation
<222> LOCATION: 11
<223> OTHER INFORMATION: U in position 9,11 and 15 represents a 2'-O-
      methyl-uracile (mU)
<220> FEATURE:
<221> NAME/KEY: variation
<222> LOCATION: 12
<223> OTHER INFORMATION: U in position 12,14,18,20 and 22 is a fU
      nucleotide analog

```
<220> FEATURE:
<221> NAME/KEY: variation
<222> LOCATION: 13
<223> OTHER INFORMATION: C in position 6 and 13 is a fC nucleotide
      analog
<220> FEATURE:
<221> NAME/KEY: variation
<222> LOCATION: 14
<223> OTHER INFORMATION: U in position 12,14,18,20 and 22 is a fU
      nucleotide analog
<220> FEATURE:
<221> NAME/KEY: variation
<222> LOCATION: 15
<223> OTHER INFORMATION: U in position 9,11 and 15 represents a 2'-O-
      methyl-uracile (mU)
<220> FEATURE:
<221> NAME/KEY: variation
<222> LOCATION: 16
<223> OTHER INFORMATION: G in position 8,10 and 16 is a fG nucleotide
      analog
<220> FEATURE:
<221> NAME/KEY: variation
<222> LOCATION: 17
<223> OTHER INFORMATION: C in position 17 and 19 represents a mC
      nucleotide analog
<220> FEATURE:
<221> NAME/KEY: variation
<222> LOCATION: 18
<223> OTHER INFORMATION: U in position 12,14,18,20 and 22 is a fU
      nucleotide analog
<220> FEATURE:
<221> NAME/KEY: variation
<222> LOCATION: 19
<223> OTHER INFORMATION: C in position 17 and 19 represents a mC
      nucleotide analog
<220> FEATURE:
<221> NAME/KEY: variation
<222> LOCATION: 20
<223> OTHER INFORMATION: U in position 12,14,18,20 and 22 is a fU
      nucleotide analog
<220> FEATURE:
<221> NAME/KEY: variation
<222> LOCATION: 21
<223> OTHER INFORMATION: A in position 5,7,21 and 23 represents a mA
      nucleotide analog
<220> FEATURE:
<221> NAME/KEY: variation
<222> LOCATION: 22
<223> OTHER INFORMATION: U in position 12,14,18,20 and 22 is a fU
      nucleotide analog
<220> FEATURE:
<221> NAME/KEY: variation
<222> LOCATION: 23
<223> OTHER INFORMATION: A in position 5,7,21 and 23 represents a mA
      nucleotide analog
<220> FEATURE:
<221> NAME/KEY: variation
<222> LOCATION: 24
<223> OTHER INFORMATION: A in position 4 and 24 is a fA nucleotide
      analog
<220> FEATURE:
<221> NAME/KEY: variation
<222> LOCATION: 25
<223> OTHER INFORMATION: T in position 25 and 26 is a lT4 nucleotide
      analog
<220> FEATURE:
<221> NAME/KEY: variation
<222> LOCATION: 26
<223> OTHER INFORMATION: T in position 25 and 26 is a lT4 nucleotide
      analog

<400> SEQUENCE: 84
tttaacagug uucuugcucu auaatt                                          26

<210> SEQ ID NO 85
<211> LENGTH: 26
<212> TYPE: RNA
```

```
<213> ORGANISM: Artificial Sequence
<220> FEATURE:
<223> OTHER INFORMATION: ss2-6
<220> FEATURE:
<221> NAME/KEY: variation
<222> LOCATION: 1
<223> OTHER INFORMATION: T in position 1,2 and 3 is a lgT3 nucleotide
      analog
<220> FEATURE:
<221> NAME/KEY: variation
<222> LOCATION: 2
<223> OTHER INFORMATION: T in position 1,2 and 3 is a lgT3 nucleotide
      analog
<220> FEATURE:
<221> NAME/KEY: variation
<222> LOCATION: 3
<223> OTHER INFORMATION: T in position 1,2 and 3 is a lgT3 nucleotide
      analog
<220> FEATURE:
<221> NAME/KEY: variation
<222> LOCATION: 4
<223> OTHER INFORMATION: A in position 4 and 24 is a fA nucleotide
      analog
<220> FEATURE:
<221> NAME/KEY: variation
<222> LOCATION: 5
<223> OTHER INFORMATION: A in position 5,7,21 and 23 represents a mA
      nucleotide analog
<220> FEATURE:
<221> NAME/KEY: variation
<222> LOCATION: 6
<223> OTHER INFORMATION: C in position 6 and 13 is a fC nucleotide
      analog
<220> FEATURE:
<221> NAME/KEY: variation
<222> LOCATION: 7
<223> OTHER INFORMATION: A in position 5,7,21 and 23 represents a mA
      nucleotide analog
<220> FEATURE:
<221> NAME/KEY: variation
<222> LOCATION: 8
<223> OTHER INFORMATION: G in position 8,10 and 16 is a fG nucleotide
      analog
<220> FEATURE:
<221> NAME/KEY: variation
<222> LOCATION: 9
<223> OTHER INFORMATION: U in position 9,11 and 15 represents a 2'-O-
      methyl-uracile (mU)
<220> FEATURE:
<221> NAME/KEY: variation
<222> LOCATION: 10
<223> OTHER INFORMATION: G in position 8,10 and 16 is a fG nucleotide
      analog
<220> FEATURE:
<221> NAME/KEY: variation
<222> LOCATION: 11
<223> OTHER INFORMATION: U in position 9,11 and 15 represents a 2'-O-
      methyl-uracile (mU)
<220> FEATURE:
<221> NAME/KEY: variation
<222> LOCATION: 12
<223> OTHER INFORMATION: U in position 12,14,18,20 and 22 is a fU
      nucleotide analog
<220> FEATURE:
<221> NAME/KEY: variation
<222> LOCATION: 13
<223> OTHER INFORMATION: C in position 6 and 13 is a fC nucleotide
      analog
<220> FEATURE:
<221> NAME/KEY: variation
<222> LOCATION: 14
<223> OTHER INFORMATION: U in position 12,14,18,20 and 22 is a fU
      nucleotide analog
<220> FEATURE:
<221> NAME/KEY: variation
<222> LOCATION: 15
<223> OTHER INFORMATION: U in position 9,11 and 15 represents a 2'-O-
      methyl-uracile (mU)
<220> FEATURE:
```

```
<221> NAME/KEY: variation
<222> LOCATION: 16
<223> OTHER INFORMATION: G in position 8,10 and 16 is a fG nucleotide
      analog
<220> FEATURE:
<221> NAME/KEY: variation
<222> LOCATION: 17
<223> OTHER INFORMATION: C in position 17 and 19 represents a mC
      nucleotide analog
<220> FEATURE:
<221> NAME/KEY: variation
<222> LOCATION: 18
<223> OTHER INFORMATION: U in position 12,14,18,20 and 22 is a fU
      nucleotide analog
<220> FEATURE:
<221> NAME/KEY: variation
<222> LOCATION: 19
<223> OTHER INFORMATION: C in position 17 and 19 represents a mC
      nucleotide analog
<220> FEATURE:
<221> NAME/KEY: variation
<222> LOCATION: 20
<223> OTHER INFORMATION: U in position 12,14,18,20 and 22 is a fU
      nucleotide analog
<220> FEATURE:
<221> NAME/KEY: variation
<222> LOCATION: 21
<223> OTHER INFORMATION: A in position 5,7,21 and 23 represents a mA
      nucleotide analog
<220> FEATURE:
<221> NAME/KEY: variation
<222> LOCATION: 22
<223> OTHER INFORMATION: U in position 12,14,18,20 and 22 is a fU
      nucleotide analog
<220> FEATURE:
<221> NAME/KEY: variation
<222> LOCATION: 23
<223> OTHER INFORMATION: A in position 5,7,21 and 23 represents a mA
      nucleotide analog
<220> FEATURE:
<221> NAME/KEY: variation
<222> LOCATION: 24
<223> OTHER INFORMATION: A in position 4 and 24 is a fA nucleotide
      analog
<220> FEATURE:
<221> NAME/KEY: variation
<222> LOCATION: 25
<223> OTHER INFORMATION: T in position 25 and 26 is a lT5 nucleotide
      analog
<220> FEATURE:
<221> NAME/KEY: variation
<222> LOCATION: 26
<223> OTHER INFORMATION: T in position 25 and 26 is a lT5 nucleotide
      analog

<400> SEQUENCE: 85
tttaacagug uucuugcucu auaatt                                          26

<210> SEQ ID NO 86
<211> LENGTH: 26
<212> TYPE: RNA
<213> ORGANISM: Artificial Sequence
<220> FEATURE:
<223> OTHER INFORMATION: ss2-7
<220> FEATURE:
<221> NAME/KEY: variation
<222> LOCATION: 1
<223> OTHER INFORMATION: T in position 1,2 and 3 is a lgT3 nucleotide
      analog
<220> FEATURE:
<221> NAME/KEY: variation
<222> LOCATION: 2
<223> OTHER INFORMATION: T in position 1,2 and 3 is a lgT3 nucleotide
      analog
<220> FEATURE:
<221> NAME/KEY: variation
<222> LOCATION: 3
```

```
<223> OTHER INFORMATION: T in position 1,2 and 3 is a lgT3 nucleotide
      analog
<220> FEATURE:
<221> NAME/KEY: variation
<222> LOCATION: 4
<223> OTHER INFORMATION: A in position 4 and 24 is a fA nucleotide
      analog
<220> FEATURE:
<221> NAME/KEY: variation
<222> LOCATION: 5
<223> OTHER INFORMATION: A in position 5,7,21 and 23 represents a mA
      nucleotide analog
<220> FEATURE:
<221> NAME/KEY: variation
<222> LOCATION: 6
<223> OTHER INFORMATION: C in position 6 and 13 is a fC nucleotide
      analog
<220> FEATURE:
<221> NAME/KEY: variation
<222> LOCATION: 7
<223> OTHER INFORMATION: A in position 5,7,21 and 23 represents a mA
      nucleotide analog
<220> FEATURE:
<221> NAME/KEY: variation
<222> LOCATION: 8
<223> OTHER INFORMATION: G in position 8,10 and 16 is a fG nucleotide
      analog
<220> FEATURE:
<221> NAME/KEY: variation
<222> LOCATION: 9
<223> OTHER INFORMATION: U in position 9,11 and 15 represents a 2'-O-
      methyl-uracile (mU)
<220> FEATURE:
<221> NAME/KEY: variation
<222> LOCATION: 10
<223> OTHER INFORMATION: G in position 8,10 and 16 is a fG nucleotide
      analog
<220> FEATURE:
<221> NAME/KEY: variation
<222> LOCATION: 11
<223> OTHER INFORMATION: U in position 9,11 and 15 represents a 2'-O-
      methyl-uracile (mU)
<220> FEATURE:
<221> NAME/KEY: variation
<222> LOCATION: 12
<223> OTHER INFORMATION: U in position 12,14,18,20 and 22 is a fU
      nucleotide analog
<220> FEATURE:
<221> NAME/KEY: variation
<222> LOCATION: 13
<223> OTHER INFORMATION: C in position 6 and 13 is a fC nucleotide
      analog
<220> FEATURE:
<221> NAME/KEY: variation
<222> LOCATION: 14
<223> OTHER INFORMATION: U in position 12,14,18,20 and 22 is a fU
      nucleotide analog
<220> FEATURE:
<221> NAME/KEY: variation
<222> LOCATION: 15
<223> OTHER INFORMATION: U in position 9,11 and 15 represents a 2'-O-
      methyl-uracile (mU)
<220> FEATURE:
<221> NAME/KEY: variation
<222> LOCATION: 16
<223> OTHER INFORMATION: G in position 8,10 and 16 is a fG nucleotide
      analog
<220> FEATURE:
<221> NAME/KEY: variation
<222> LOCATION: 17
<223> OTHER INFORMATION: C in position 17 and 19 represents a mC
      nucleotide analog
<220> FEATURE:
<221> NAME/KEY: variation
<222> LOCATION: 18
<223> OTHER INFORMATION: U in position 12,14,18,20 and 22 is a fU
      nucleotide analog
<220> FEATURE:
<221> NAME/KEY: variation
```

```
<222> LOCATION: 19
<223> OTHER INFORMATION: C in position 17 and 19 represents a mC
      nucleotide analog
<220> FEATURE:
<221> NAME/KEY: variation
<222> LOCATION: 20
<223> OTHER INFORMATION: U in position 12,14,18,20 and 22 is a fU
      nucleotide analog
<220> FEATURE:
<221> NAME/KEY: variation
<222> LOCATION: 21
<223> OTHER INFORMATION: A in position 5,7,21 and 23 represents a mA
      nucleotide analog
<220> FEATURE:
<221> NAME/KEY: variation
<222> LOCATION: 22
<223> OTHER INFORMATION: U in position 12,14,18,20 and 22 is a fU
      nucleotide analog
<220> FEATURE:
<221> NAME/KEY: variation
<222> LOCATION: 23
<223> OTHER INFORMATION: A in position 5,7,21 and 23 represents a mA
      nucleotide analog
<220> FEATURE:
<221> NAME/KEY: variation
<222> LOCATION: 24
<223> OTHER INFORMATION: A in position 4 and 24 is a fA nucleotide
      analog
<220> FEATURE:
<221> NAME/KEY: variation
<222> LOCATION: 25
<223> OTHER INFORMATION: T in position 25 and 26 is a lT6 nucleotide
      analog
<220> FEATURE:
<221> NAME/KEY: variation
<222> LOCATION: 26
<223> OTHER INFORMATION: T in position 25 and 26 is a lT6 nucleotide
      analog

<400> SEQUENCE: 86
tttaacagug uucuugcucu auaatt                                              26

<210> SEQ ID NO 87
<211> LENGTH: 26
<212> TYPE: RNA
<213> ORGANISM: Artificial Sequence
<220> FEATURE:
<223> OTHER INFORMATION: ss2-8
<220> FEATURE:
<221> NAME/KEY: variation
<222> LOCATION: 1
<223> OTHER INFORMATION: T in position 1,2 and 3 is a lgT3 nucleotide
      analog
<220> FEATURE:
<221> NAME/KEY: variation
<222> LOCATION: 2
<223> OTHER INFORMATION: T in position 1,2 and 3 is a lgT3 nucleotide
      analog
<220> FEATURE:
<221> NAME/KEY: variation
<222> LOCATION: 3
<223> OTHER INFORMATION: T in position 1,2 and 3 is a lgT3 nucleotide
      analog
<220> FEATURE:
<221> NAME/KEY: variation
<222> LOCATION: 4
<223> OTHER INFORMATION: A in position 4 and 24 is a fA nucleotide
      analog
<220> FEATURE:
<221> NAME/KEY: variation
<222> LOCATION: 5
<223> OTHER INFORMATION: A in position 5,7,21 and 23 represents a mA
      nucleotide analog
<220> FEATURE:
<221> NAME/KEY: variation
<222> LOCATION: 6
<223> OTHER INFORMATION: C in position 6 and 13 is a fC nucleotide
```

-continued

```
        analog
<220> FEATURE:
<221> NAME/KEY: variation
<222> LOCATION: 7
<223> OTHER INFORMATION: A in position 5,7,21 and 23 represents a mA
      nucleotide analog
<220> FEATURE:
<221> NAME/KEY: variation
<222> LOCATION: 8
<223> OTHER INFORMATION: G in position 8,10 and 16 is a fG nucleotide
      analog
<220> FEATURE:
<221> NAME/KEY: variation
<222> LOCATION: 9
<223> OTHER INFORMATION: U in position 9,11 and 15 represents a 2'-O-
      methyl-uracile (mU)
<220> FEATURE:
<221> NAME/KEY: variation
<222> LOCATION: 10
<223> OTHER INFORMATION: G in position 8,10 and 16 is a fG nucleotide
      analog
<220> FEATURE:
<221> NAME/KEY: variation
<222> LOCATION: 11
<223> OTHER INFORMATION: U in position 9,11 and 15 represents a 2'-O-
      methyl-uracile (mU)
<220> FEATURE:
<221> NAME/KEY: variation
<222> LOCATION: 12
<223> OTHER INFORMATION: U in position 12,14,18,20 and 22 is a fU
      nucleotide analog
<220> FEATURE:
<221> NAME/KEY: variation
<222> LOCATION: 13
<223> OTHER INFORMATION: C in position 6 and 13 is a fC nucleotide
      analog
<220> FEATURE:
<221> NAME/KEY: variation
<222> LOCATION: 14
<223> OTHER INFORMATION: U in position 12,14,18,20 and 22 is a fU
      nucleotide analog
<220> FEATURE:
<221> NAME/KEY: variation
<222> LOCATION: 15
<223> OTHER INFORMATION: U in position 9,11 and 15 represents a 2'-O-
      methyl-uracile (mU)
<220> FEATURE:
<221> NAME/KEY: variation
<222> LOCATION: 16
<223> OTHER INFORMATION: G in position 8,10 and 16 is a fG nucleotide
      analog
<220> FEATURE:
<221> NAME/KEY: variation
<222> LOCATION: 17
<223> OTHER INFORMATION: C in position 17 and 19 represents a mC
      nucleotide analog
<220> FEATURE:
<221> NAME/KEY: variation
<222> LOCATION: 18
<223> OTHER INFORMATION: U in position 12,14,18,20 and 22 is a fU
      nucleotide analog
<220> FEATURE:
<221> NAME/KEY: variation
<222> LOCATION: 19
<223> OTHER INFORMATION: C in position 17 and 19 represents a mC
      nucleotide analog
<220> FEATURE:
<221> NAME/KEY: variation
<222> LOCATION: 20
<223> OTHER INFORMATION: U in position 12,14,18,20 and 22 is a fU
      nucleotide analog
<220> FEATURE:
<221> NAME/KEY: variation
<222> LOCATION: 21
<223> OTHER INFORMATION: A in position 5,7,21 and 23 represents a mA
      nucleotide analog
<220> FEATURE:
<221> NAME/KEY: variation
<222> LOCATION: 22
```

<223> OTHER INFORMATION: U in position 12,14,18,20 and 22 is a fU
      nucleotide analog
<220> FEATURE:
<221> NAME/KEY: variation
<222> LOCATION: 23
<223> OTHER INFORMATION: A in position 5,7,21 and 23 represents a mA
      nucleotide analog
<220> FEATURE:
<221> NAME/KEY: variation
<222> LOCATION: 24
<223> OTHER INFORMATION: A in position 4 and 24 is a fA nucleotide
      analog
<220> FEATURE:
<221> NAME/KEY: variation
<222> LOCATION: 25
<223> OTHER INFORMATION: T in position 25 and 26 is a lT7 nucleotide
      analog
<220> FEATURE:
<221> NAME/KEY: variation
<222> LOCATION: 26
<223> OTHER INFORMATION: T in position 25 and 26 is a lT7 nucleotide
      analog

<400> SEQUENCE: 87
tttaacagug uucuugcucu auaatt                                        26

<210> SEQ ID NO 88
<211> LENGTH: 26
<212> TYPE: RNA
<213> ORGANISM: Artificial Sequence
<220> FEATURE:
<223> OTHER INFORMATION: ss2-9
<220> FEATURE:
<221> NAME/KEY: variation
<222> LOCATION: 1
<223> OTHER INFORMATION: T in position 1,2 and 3 is a lgT3 nucleotide
      analog
<220> FEATURE:
<221> NAME/KEY: variation
<222> LOCATION: 2
<223> OTHER INFORMATION: T in position 1,2 and 3 is a lgT3 nucleotide
      analog
<220> FEATURE:
<221> NAME/KEY: variation
<222> LOCATION: 3
<223> OTHER INFORMATION: T in position 1,2 and 3 is a lgT3 nucleotide
      analog
<220> FEATURE:
<221> NAME/KEY: variation
<222> LOCATION: 4
<223> OTHER INFORMATION: A in position 4 and 24 is a fA nucleotide
      analog
<220> FEATURE:
<221> NAME/KEY: variation
<222> LOCATION: 5
<223> OTHER INFORMATION: A in position 5,7,21 and 23 represents a mA
      nucleotide analog
<220> FEATURE:
<221> NAME/KEY: variation
<222> LOCATION: 6
<223> OTHER INFORMATION: C in position 6 and 13 is a fC nucleotide
      analog
<220> FEATURE:
<221> NAME/KEY: variation
<222> LOCATION: 7
<223> OTHER INFORMATION: A in position 5,7,21 and 23 represents a mA
      nucleotide analog
<220> FEATURE:
<221> NAME/KEY: variation
<222> LOCATION: 8
<223> OTHER INFORMATION: G in position 8,10 and 16 is a fG nucleotide
      analog
<220> FEATURE:
<221> NAME/KEY: variation
<222> LOCATION: 9
<223> OTHER INFORMATION: U in position 9,11 and 15 represents a 2'-O-
      methyl-uracile (mU)

```
<220> FEATURE:
<221> NAME/KEY: variation
<222> LOCATION: 10
<223> OTHER INFORMATION: G in position 8,10 and 16 is a fG nucleotide
      analog
<220> FEATURE:
<221> NAME/KEY: variation
<222> LOCATION: 11
<223> OTHER INFORMATION: U in position 9,11 and 15 represents a 2'-O-
      methyl-uracile (mU)
<220> FEATURE:
<221> NAME/KEY: variation
<222> LOCATION: 12
<223> OTHER INFORMATION: U in position 12,14,18,20 and 22 is a fU
      nucleotide analog
<220> FEATURE:
<221> NAME/KEY: variation
<222> LOCATION: 13
<223> OTHER INFORMATION: C in position 6 and 13 is a fC nucleotide
      analog
<220> FEATURE:
<221> NAME/KEY: variation
<222> LOCATION: 14
<223> OTHER INFORMATION: U in position 12,14,18,20 and 22 is a fU
      nucleotide analog
<220> FEATURE:
<221> NAME/KEY: variation
<222> LOCATION: 15
<223> OTHER INFORMATION: U in position 9,11 and 15 represents a 2'-O-
      methyl-uracile (mU)
<220> FEATURE:
<221> NAME/KEY: variation
<222> LOCATION: 16
<223> OTHER INFORMATION: G in position 8,10 and 16 is a fG nucleotide
      analog
<220> FEATURE:
<221> NAME/KEY: variation
<222> LOCATION: 17
<223> OTHER INFORMATION: C in position 17 and 19 represents a mC
      nucleotide analog
<220> FEATURE:
<221> NAME/KEY: variation
<222> LOCATION: 18
<223> OTHER INFORMATION: U in position 12,14,18,20 and 22 is a fU
      nucleotide analog
<220> FEATURE:
<221> NAME/KEY: variation
<222> LOCATION: 19
<223> OTHER INFORMATION: C in position 17 and 19 represents a mC
      nucleotide analog
<220> FEATURE:
<221> NAME/KEY: variation
<222> LOCATION: 20
<223> OTHER INFORMATION: U in position 12,14,18,20 and 22 is a fU
      nucleotide analog
<220> FEATURE:
<221> NAME/KEY: variation
<222> LOCATION: 21
<223> OTHER INFORMATION: A in position 5,7,21 and 23 represents a mA
      nucleotide analog
<220> FEATURE:
<221> NAME/KEY: variation
<222> LOCATION: 22
<223> OTHER INFORMATION: U in position 12,14,18,20 and 22 is a fU
      nucleotide analog
<220> FEATURE:
<221> NAME/KEY: variation
<222> LOCATION: 23
<223> OTHER INFORMATION: A in position 5,7,21 and 23 represents a mA
      nucleotide analog
<220> FEATURE:
<221> NAME/KEY: variation
<222> LOCATION: 24
<223> OTHER INFORMATION: A in position 4 and 24 is a fA nucleotide
      analog
<220> FEATURE:
<221> NAME/KEY: variation
<222> LOCATION: 25
<223> OTHER INFORMATION: T in position 25 and 26 is a lT8 nucleotide
```

-continued

```
      analog
<220> FEATURE:
<221> NAME/KEY: variation
<222> LOCATION: 26
<223> OTHER INFORMATION: T in position 25 and 26 is a lT8 nucleotide
      analog

<400> SEQUENCE: 88
tttaacagug uucuugcucu auaatt                                          26

<210> SEQ ID NO 89
<211> LENGTH: 26
<212> TYPE: RNA
<213> ORGANISM: Artificial Sequence
<220> FEATURE:
<223> OTHER INFORMATION: ss2-10
<220> FEATURE:
<221> NAME/KEY: variation
<222> LOCATION: 1
<223> OTHER INFORMATION: T in position 1,2 and 3 is a lgT3 nucleotide
      analog
<220> FEATURE:
<221> NAME/KEY: variation
<222> LOCATION: 2
<223> OTHER INFORMATION: T in position 1,2 and 3 is a lgT3 nucleotide
      analog
<220> FEATURE:
<221> NAME/KEY: variation
<222> LOCATION: 3
<223> OTHER INFORMATION: T in position 1,2 and 3 is a lgT3 nucleotide
      analog
<220> FEATURE:
<221> NAME/KEY: variation
<222> LOCATION: 4
<223> OTHER INFORMATION: A in position 4 and 24 is a fA nucleotide
      analog
<220> FEATURE:
<221> NAME/KEY: variation
<222> LOCATION: 5
<223> OTHER INFORMATION: A in position 5,7,21 and 23 represents a mA
      nucleotide analog
<220> FEATURE:
<221> NAME/KEY: variation
<222> LOCATION: 6
<223> OTHER INFORMATION: C in position 6 and 13 is a fC nucleotide
      analog
<220> FEATURE:
<221> NAME/KEY: variation
<222> LOCATION: 7
<223> OTHER INFORMATION: A in position 5,7,21 and 23 represents a mA
      nucleotide analog
<220> FEATURE:
<221> NAME/KEY: variation
<222> LOCATION: 8
<223> OTHER INFORMATION: G in position 8,10 and 16 is a fG nucleotide
      analog
<220> FEATURE:
<221> NAME/KEY: variation
<222> LOCATION: 9
<223> OTHER INFORMATION: U in position 9,11 and 15 represents a 2'-O-
      methyl-uracile (mU)
<220> FEATURE:
<221> NAME/KEY: variation
<222> LOCATION: 10
<223> OTHER INFORMATION: G in position 8,10 and 16 is a fG nucleotide
      analog
<220> FEATURE:
<221> NAME/KEY: variation
<222> LOCATION: 11
<223> OTHER INFORMATION: U in position 9,11 and 15 represents a 2'-O-
      methyl-uracile (mU)
<220> FEATURE:
<221> NAME/KEY: variation
<222> LOCATION: 12
<223> OTHER INFORMATION: U in position 12,14,18,20 and 22 is a fU
      nucleotide analog
<220> FEATURE:
```

```
<221> NAME/KEY: variation
<222> LOCATION: 13
<223> OTHER INFORMATION: C in position 6 and 13 is a fC nucleotide
      analog
<220> FEATURE:
<221> NAME/KEY: variation
<222> LOCATION: 14
<223> OTHER INFORMATION: U in position 12,14,18,20 and 22 is a fU
      nucleotide analog
<220> FEATURE:
<221> NAME/KEY: variation
<222> LOCATION: 15
<223> OTHER INFORMATION: U in position 9,11 and 15 represents a 2'-O-
      methyl-uracile (mU)
<220> FEATURE:
<221> NAME/KEY: variation
<222> LOCATION: 16
<223> OTHER INFORMATION: G in position 8,10 and 16 is a fG nucleotide
      analog
<220> FEATURE:
<221> NAME/KEY: variation
<222> LOCATION: 17
<223> OTHER INFORMATION: C in position 17 and 19 represents a mC
      nucleotide analog
<220> FEATURE:
<221> NAME/KEY: variation
<222> LOCATION: 18
<223> OTHER INFORMATION: U in position 12,14,18,20 and 22 is a fU
      nucleotide analog
<220> FEATURE:
<221> NAME/KEY: variation
<222> LOCATION: 19
<223> OTHER INFORMATION: C in position 17 and 19 represents a mC
      nucleotide analog
<220> FEATURE:
<221> NAME/KEY: variation
<222> LOCATION: 20
<223> OTHER INFORMATION: U in position 12,14,18,20 and 22 is a fU
      nucleotide analog
<220> FEATURE:
<221> NAME/KEY: variation
<222> LOCATION: 21
<223> OTHER INFORMATION: A in position 5,7,21 and 23 represents a mA
      nucleotide analog
<220> FEATURE:
<221> NAME/KEY: variation
<222> LOCATION: 22
<223> OTHER INFORMATION: U in position 12,14,18,20 and 22 is a fU
      nucleotide analog
<220> FEATURE:
<221> NAME/KEY: variation
<222> LOCATION: 23
<223> OTHER INFORMATION: A in position 5,7,21 and 23 represents a mA
      nucleotide analog
<220> FEATURE:
<221> NAME/KEY: variation
<222> LOCATION: 24
<223> OTHER INFORMATION: A in position 4 and 24 is a fA nucleotide
      analog
<220> FEATURE:
<221> NAME/KEY: variation
<222> LOCATION: 25
<223> OTHER INFORMATION: T in position 25 and 26 is a lT9 nucleotide
      analog
<220> FEATURE:
<221> NAME/KEY: variation
<222> LOCATION: 26
<223> OTHER INFORMATION: T in position 25 and 26 is a lT9 nucleotide
      analog

<400> SEQUENCE: 89
tttaacagug uucuugcucu auaatt                                          26

<210> SEQ ID NO 90
<211> LENGTH: 26
<212> TYPE: RNA
<213> ORGANISM: Artificial Sequence
```

```
<220> FEATURE:
<223> OTHER INFORMATION: ss2-11
<220> FEATURE:
<221> NAME/KEY: variation
<222> LOCATION: 1
<223> OTHER INFORMATION: T in position 1,2 and 3 is a lgT3 nucleotide
      analog
<220> FEATURE:
<221> NAME/KEY: variation
<222> LOCATION: 2
<223> OTHER INFORMATION: T in position 1,2 and 3 is a lgT3 nucleotide
      analog
<220> FEATURE:
<221> NAME/KEY: variation
<222> LOCATION: 3
<223> OTHER INFORMATION: T in position 1,2 and 3 is a lgT3 nucleotide
      analog
<220> FEATURE:
<221> NAME/KEY: variation
<222> LOCATION: 4
<223> OTHER INFORMATION: A in position 4 and 24 is a fA nucleotide
      analog
<220> FEATURE:
<221> NAME/KEY: variation
<222> LOCATION: 5
<223> OTHER INFORMATION: A in position 5,7,21 and 23 represents a mA
      nucleotide analog
<220> FEATURE:
<221> NAME/KEY: variation
<222> LOCATION: 6
<223> OTHER INFORMATION: C in position 6 and 13 is a fC nucleotide
      analog
<220> FEATURE:
<221> NAME/KEY: variation
<222> LOCATION: 7
<223> OTHER INFORMATION: A in position 5,7,21 and 23 represents a mA
      nucleotide analog
<220> FEATURE:
<221> NAME/KEY: variation
<222> LOCATION: 8
<223> OTHER INFORMATION: G in position 8,10 and 16 is a fG nucleotide
      analog
<220> FEATURE:
<221> NAME/KEY: variation
<222> LOCATION: 9
<223> OTHER INFORMATION: U in position 9,11 and 15 represents a 2'-O-
      methyl-uracile (mU)
<220> FEATURE:
<221> NAME/KEY: variation
<222> LOCATION: 10
<223> OTHER INFORMATION: G in position 8,10 and 16 is a fG nucleotide
      analog
<220> FEATURE:
<221> NAME/KEY: variation
<222> LOCATION: 11
<223> OTHER INFORMATION: U in position 9,11 and 15 represents a 2'-O-
      methyl-uracile (mU)
<220> FEATURE:
<221> NAME/KEY: variation
<222> LOCATION: 12
<223> OTHER INFORMATION: U in position 12,14,18,20 and 22 is a fU
      nucleotide analog
<220> FEATURE:
<221> NAME/KEY: variation
<222> LOCATION: 13
<223> OTHER INFORMATION: C in position 6 and 13 is a fC nucleotide
      analog
<220> FEATURE:
<221> NAME/KEY: variation
<222> LOCATION: 14
<223> OTHER INFORMATION: U in position 12,14,18,20 and 22 is a fU
      nucleotide analog
<220> FEATURE:
<221> NAME/KEY: variation
<222> LOCATION: 15
<223> OTHER INFORMATION: U in position 9,11 and 15 represents a 2'-O-
      methyl-uracile (mU)
<220> FEATURE:
<221> NAME/KEY: variation
```

```
<222> LOCATION: 16
<223> OTHER INFORMATION: G in position 8,10 and 16 is a fG nucleotide
      analog
<220> FEATURE:
<221> NAME/KEY: variation
<222> LOCATION: 17
<223> OTHER INFORMATION: C in position 17 and 19 represents a mC
      nucleotide analog
<220> FEATURE:
<221> NAME/KEY: variation
<222> LOCATION: 18
<223> OTHER INFORMATION: U in position 12,14,18,20 and 22 is a fU
      nucleotide analog
<220> FEATURE:
<221> NAME/KEY: variation
<222> LOCATION: 19
<223> OTHER INFORMATION: C in position 17 and 19 represents a mC
      nucleotide analog
<220> FEATURE:
<221> NAME/KEY: variation
<222> LOCATION: 20
<223> OTHER INFORMATION: U in position 12,14,18,20 and 22 is a fU
      nucleotide analog
<220> FEATURE:
<221> NAME/KEY: variation
<222> LOCATION: 21
<223> OTHER INFORMATION: A in position 5,7,21 and 23 represents a mA
      nucleotide analog
<220> FEATURE:
<221> NAME/KEY: variation
<222> LOCATION: 22
<223> OTHER INFORMATION: U in position 12,14,18,20 and 22 is a fU
      nucleotide analog
<220> FEATURE:
<221> NAME/KEY: variation
<222> LOCATION: 23
<223> OTHER INFORMATION: A in position 5,7,21 and 23 represents a mA
      nucleotide analog
<220> FEATURE:
<221> NAME/KEY: variation
<222> LOCATION: 24
<223> OTHER INFORMATION: A in position 4 and 24 is a fA nucleotide
      analog
<220> FEATURE:
<221> NAME/KEY: variation
<222> LOCATION: 25
<223> OTHER INFORMATION: T in position 25 and 26 is a lT10 nucleotide
      analog
<220> FEATURE:
<221> NAME/KEY: variation
<222> LOCATION: 26
<223> OTHER INFORMATION: T in position 25 and 26 is a lT10 nucleotide
      analog

<400> SEQUENCE: 90
tttaacagug uucuugcucu auaatt                                           26

<210> SEQ ID NO 91
<211> LENGTH: 21
<212> TYPE: RNA
<213> ORGANISM: Artificial Sequence
<220> FEATURE:
<223> OTHER INFORMATION: as2-0
<220> FEATURE:
<221> NAME/KEY: variation
<222> LOCATION: 1
<223> OTHER INFORMATION: The nucleotide in position 1 and the nucleotide
      in position 2 are linked through a phosphoramidite bond
<220> FEATURE:
<221> NAME/KEY: variation
<222> LOCATION: 1
<223> OTHER INFORMATION: A in position 1,6 and 18 is a fA nucleotide
      analog
<220> FEATURE:
<221> NAME/KEY: variation
<222> LOCATION: 2
<223> OTHER INFORMATION: The nucleotide in position 1 and the nucleotide
```

-continued

```
      in position 2 are linked through a phosphoramidite bond
<220> FEATURE:
<221> NAME/KEY: variation
<222> LOCATION: 2
<223> OTHER INFORMATION: The nucleotide in position 2 and the nucleotide
      in position 3 are linked through a phosphoramidite bond
<220> FEATURE:
<221> NAME/KEY: variation
<222> LOCATION: 2
<223> OTHER INFORMATION: U in position 2,10 and 14 is a fU nucleotide
      analog
<220> FEATURE:
<221> NAME/KEY: variation
<222> LOCATION: 3
<223> OTHER INFORMATION: The nucleotide in position 2 and the nucleotide
      in position 3 are linked through a phosphoramidite bond
<220> FEATURE:
<221> NAME/KEY: variation
<222> LOCATION: 3
<223> OTHER INFORMATION: A in position 3,11 and 15 represents a mA
      nucleotide analog
<220> FEATURE:
<221> NAME/KEY: variation
<222> LOCATION: 4
<223> OTHER INFORMATION: C in position 4,12 and 16 is a fC nucleotide
      analog
<220> FEATURE:
<221> NAME/KEY: variation
<222> LOCATION: 5
<223> OTHER INFORMATION: G in position 5,9,13 and 17 represents a mG
      nucleotide analog
<220> FEATURE:
<221> NAME/KEY: variation
<222> LOCATION: 6
<223> OTHER INFORMATION: A in position 1,6 and 18 is a fA nucleotide
      analog
<220> FEATURE:
<221> NAME/KEY: variation
<222> LOCATION: 7
<223> OTHER INFORMATION: C in position 7 represents a mC nucleotide
      analog
<220> FEATURE:
<221> NAME/KEY: variation
<222> LOCATION: 8
<223> OTHER INFORMATION: G in position 8 is a fG nucleotide analog
<220> FEATURE:
<221> NAME/KEY: variation
<222> LOCATION: 9
<223> OTHER INFORMATION: G in position 5,9,13 and 17 represents a mG
      nucleotide analog
<220> FEATURE:
<221> NAME/KEY: variation
<222> LOCATION: 10
<223> OTHER INFORMATION: U in position 2,10 and 14 is a fU nucleotide
      analog
<220> FEATURE:
<221> NAME/KEY: variation
<222> LOCATION: 11
<223> OTHER INFORMATION: A in position 3,11 and 15 represents a mA
      nucleotide analog
<220> FEATURE:
<221> NAME/KEY: variation
<222> LOCATION: 12
<223> OTHER INFORMATION: C in position 4,12 and 16 is a fC nucleotide
      analog
<220> FEATURE:
<221> NAME/KEY: variation
<222> LOCATION: 13
<223> OTHER INFORMATION: G in position 5,9,13 and 17 represents a mG
      nucleotide analog
<220> FEATURE:
<221> NAME/KEY: variation
<222> LOCATION: 14
<223> OTHER INFORMATION: U in position 2,10 and 14 is a fU nucleotide
      analog
<220> FEATURE:
<221> NAME/KEY: variation
<222> LOCATION: 15
<223> OTHER INFORMATION: A in position 3,11 and 15 represents a mA
``` nucleotide analog
<220> FEATURE:
<221> NAME/KEY: variation
<222> LOCATION: 16
<223> OTHER INFORMATION: C in position 4,12 and 16 is a fC nucleotide
      analog
<220> FEATURE:
<221> NAME/KEY: variation
<222> LOCATION: 17
<223> OTHER INFORMATION: G in position 5,9,13 and 17 represents a mG
      nucleotide analog
<220> FEATURE:
<221> NAME/KEY: variation
<222> LOCATION: 18
<223> OTHER INFORMATION: A in position 1,6 and 18 is a fA nucleotide
      analog
<220> FEATURE:
<221> NAME/KEY: variation
<222> LOCATION: 19
<223> OTHER INFORMATION: U in position 19 represents a 2'-O-methyl-
      uracile (mU)
<220> FEATURE:
<221> NAME/KEY: variation
<222> LOCATION: 19
<223> OTHER INFORMATION: The nucleotide in position 19 and the
      nucleotide in position 20 are linked through a phosphoramidite
      bond
<220> FEATURE:
<221> NAME/KEY: variation
<222> LOCATION: 20
<223> OTHER INFORMATION: The nucleotide in position 19 and the
      nucleotide in position 20 are linked through a phosphoramidite
      bond
<220> FEATURE:
<221> NAME/KEY: variation
<222> LOCATION: 20
<223> OTHER INFORMATION: The nucleotide in position 20 and the
      nucleotide in position 21 are linked through a phosphoramidite
      bond
<220> FEATURE:
<221> NAME/KEY: variation
<222> LOCATION: 21
<223> OTHER INFORMATION: The nucleotide in position 20 and the
      nucleotide in position 21 are linked through a phosphoramidite
      bond

<400> SEQUENCE: 91
auacgacggu acguacgaut t                                              21

<210> SEQ ID NO 92
<211> LENGTH: 23
<212> TYPE: RNA
<213> ORGANISM: Artificial Sequence
<220> FEATURE:
<223> OTHER INFORMATION: as2-2
<220> FEATURE:
<221> NAME/KEY: variation
<222> LOCATION: 1
<223> OTHER INFORMATION: The nucleotide in position 1 and the nucleotide
      in position 2 are linked through a phosphoramidite bond
<220> FEATURE:
<221> NAME/KEY: variation
<222> LOCATION: 1
<223> OTHER INFORMATION: U in position 1 and 21 represents a 2'-O-
      methyl-uracile (mU)
<220> FEATURE:
<221> NAME/KEY: variation
<222> LOCATION: 2
<223> OTHER INFORMATION: The nucleotide in position 1 and the nucleotide
      in position 2 are linked through a phosphoramidite bond
<220> FEATURE:
<221> NAME/KEY: variation
<222> LOCATION: 2
<223> OTHER INFORMATION: The nucleotide in position 2 and the nucleotide
      in position 3 are linked through a phosphoramidite bond
<220> FEATURE:
<221> NAME/KEY: variation

```
<222> LOCATION: 2
<223> OTHER INFORMATION: U in position 2,4,18 and 20 is a fU nucleotide
      analog
<220> FEATURE:
<221> NAME/KEY: variation
<222> LOCATION: 3
<223> OTHER INFORMATION: The nucleotide in position 2 and the nucleotide
      in position 3 are linked through a phosphoramidite bond
<220> FEATURE:
<221> NAME/KEY: variation
<222> LOCATION: 3
<223> OTHER INFORMATION: A in position 3,5,7,11 and 13 represents a mA
      nucleotide analog
<220> FEATURE:
<221> NAME/KEY: variation
<222> LOCATION: 4
<223> OTHER INFORMATION: U in position 2,4,18 and 20 is a fU nucleotide
      analog
<220> FEATURE:
<221> NAME/KEY: variation
<222> LOCATION: 5
<223> OTHER INFORMATION: A in position 3,5,7,11 and 13 represents a mA
      nucleotide analog
<220> FEATURE:
<221> NAME/KEY: variation
<222> LOCATION: 6
<223> OTHER INFORMATION: G in position 6 and 8 is a fG nucleotide analog
<220> FEATURE:
<221> NAME/KEY: variation
<222> LOCATION: 7
<223> OTHER INFORMATION: A in position 3,5,7,11 and 13 represents a mA
      nucleotide analog
<220> FEATURE:
<221> NAME/KEY: variation
<222> LOCATION: 8
<223> OTHER INFORMATION: G in position 6 and 8 is a fG nucleotide analog
<220> FEATURE:
<221> NAME/KEY: variation
<222> LOCATION: 9
<223> OTHER INFORMATION: C in position 9,15 and 17 represents a mC
      nucleotide analog
<220> FEATURE:
<221> NAME/KEY: variation
<222> LOCATION: 10
<223> OTHER INFORMATION: A in position 10,14 and 16 is a fA nucleotide
      analog
<220> FEATURE:
<221> NAME/KEY: variation
<222> LOCATION: 11
<223> OTHER INFORMATION: A in position 3,5,7,11 and 13 represents a mA
      nucleotide analog
<220> FEATURE:
<221> NAME/KEY: variation
<222> LOCATION: 12
<223> OTHER INFORMATION: G in position 12 and 19 represents a mG
      nucleotide analog
<220> FEATURE:
<221> NAME/KEY: variation
<222> LOCATION: 13
<223> OTHER INFORMATION: A in position 3,5,7,11 and 13 represents a mA
      nucleotide analog
<220> FEATURE:
<221> NAME/KEY: variation
<222> LOCATION: 14
<223> OTHER INFORMATION: A in position 10,14 and 16 is a fA nucleotide
      analog
<220> FEATURE:
<221> NAME/KEY: variation
<222> LOCATION: 15
<223> OTHER INFORMATION: C in position 9,15 and 17 represents a mC
      nucleotide analog
<220> FEATURE:
<221> NAME/KEY: variation
<222> LOCATION: 16
<223> OTHER INFORMATION: A in position 10,14 and 16 is a fA nucleotide
      analog
<220> FEATURE:
<221> NAME/KEY: variation
<222> LOCATION: 17
```

```
<223> OTHER INFORMATION: C in position 9,15 and 17 represents a mC
      nucleotide analog
<220> FEATURE:
<221> NAME/KEY: variation
<222> LOCATION: 18
<223> OTHER INFORMATION: U in position 2,4,18 and 20 is a fU nucleotide
      analog
<220> FEATURE:
<221> NAME/KEY: variation
<222> LOCATION: 19
<223> OTHER INFORMATION: G in position 12 and 19 represents a mG
      nucleotide analog
<220> FEATURE:
<221> NAME/KEY: variation
<222> LOCATION: 20
<223> OTHER INFORMATION: U in position 2,4,18 and 20 is a fU nucleotide
      analog
<220> FEATURE:
<221> NAME/KEY: variation
<222> LOCATION: 21
<223> OTHER INFORMATION: U in position 1 and 21 represents a 2'-O-
      methyl-uracile (mU)
<220> FEATURE:
<221> NAME/KEY: variation
<222> LOCATION: 22
<223> OTHER INFORMATION: T in position 22 and 23 is a lT1 nucleotide
      analog
<220> FEATURE:
<221> NAME/KEY: variation
<222> LOCATION: 23
<223> OTHER INFORMATION: T in position 22 and 23 is a lT1 nucleotide
      analog

<400> SEQUENCE: 92
uuauagagca agaacacugu utt                                              23

<210> SEQ ID NO 93
<211> LENGTH: 23
<212> TYPE: RNA
<213> ORGANISM: Artificial Sequence
<220> FEATURE:
<223> OTHER INFORMATION: as2-3
<220> FEATURE:
<221> NAME/KEY: variation
<222> LOCATION: 1
<223> OTHER INFORMATION: The nucleotide in position 1 and the nucleotide
      in position 2 are linked through a phosphoramidite bond
<220> FEATURE:
<221> NAME/KEY: variation
<222> LOCATION: 1
<223> OTHER INFORMATION: U in position 1 and 21 represents a 2'-O-
      methyl-uracile (mU)
<220> FEATURE:
<221> NAME/KEY: variation
<222> LOCATION: 2
<223> OTHER INFORMATION: The nucleotide in position 1 and the nucleotide
      in position 2 are linked through a phosphoramidite bond
<220> FEATURE:
<221> NAME/KEY: variation
<222> LOCATION: 2
<223> OTHER INFORMATION: The nucleotide in position 2 and the nucleotide
      in position 3 are linked through a phosphoramidite bond
<220> FEATURE:
<221> NAME/KEY: variation
<222> LOCATION: 2
<223> OTHER INFORMATION: U in position 2,4,18 and 20 is a fU nucleotide
      analog
<220> FEATURE:
<221> NAME/KEY: variation
<222> LOCATION: 3
<223> OTHER INFORMATION: The nucleotide in position 2 and the nucleotide
      in position 3 are linked through a phosphoramidite bond
<220> FEATURE:
<221> NAME/KEY: variation
<222> LOCATION: 3
<223> OTHER INFORMATION: A in position 3,5,7,11 and 13 represents a mA
      nucleotide analog
```

-continued

```
<220> FEATURE:
<221> NAME/KEY: variation
<222> LOCATION: 4
<223> OTHER INFORMATION: U in position 2,4,18 and 20 is a fU nucleotide
      analog
<220> FEATURE:
<221> NAME/KEY: variation
<222> LOCATION: 5
<223> OTHER INFORMATION: A in position 3,5,7,11 and 13 represents a mA
      nucleotide analog
<220> FEATURE:
<221> NAME/KEY: variation
<222> LOCATION: 6
<223> OTHER INFORMATION: G in position 6 and 8 is a fG nucleotide analog
<220> FEATURE:
<221> NAME/KEY: variation
<222> LOCATION: 7
<223> OTHER INFORMATION: A in position 3,5,7,11 and 13 represents a mA
      nucleotide analog
<220> FEATURE:
<221> NAME/KEY: variation
<222> LOCATION: 8
<223> OTHER INFORMATION: G in position 6 and 8 is a fG nucleotide analog
<220> FEATURE:
<221> NAME/KEY: variation
<222> LOCATION: 9
<223> OTHER INFORMATION: C in position 9,15 and 17 represents a mC
      nucleotide analog
<220> FEATURE:
<221> NAME/KEY: variation
<222> LOCATION: 10
<223> OTHER INFORMATION: A in position 10,14 and 16 is a fA nucleotide
      analog
<220> FEATURE:
<221> NAME/KEY: variation
<222> LOCATION: 11
<223> OTHER INFORMATION: A in position 3,5,7,11 and 13 represents a mA
      nucleotide analog
<220> FEATURE:
<221> NAME/KEY: variation
<222> LOCATION: 12
<223> OTHER INFORMATION: G in position 12 and 19 represents a mG
      nucleotide analog
<220> FEATURE:
<221> NAME/KEY: variation
<222> LOCATION: 13
<223> OTHER INFORMATION: A in position 3,5,7,11 and 13 represents a mA
      nucleotide analog
<220> FEATURE:
<221> NAME/KEY: variation
<222> LOCATION: 14
<223> OTHER INFORMATION: A in position 10,14 and 16 is a fA nucleotide
      analog
<220> FEATURE:
<221> NAME/KEY: variation
<222> LOCATION: 15
<223> OTHER INFORMATION: C in position 9,15 and 17 represents a mC
      nucleotide analog
<220> FEATURE:
<221> NAME/KEY: variation
<222> LOCATION: 16
<223> OTHER INFORMATION: A in position 10,14 and 16 is a fA nucleotide
      analog
<220> FEATURE:
<221> NAME/KEY: variation
<222> LOCATION: 17
<223> OTHER INFORMATION: C in position 9,15 and 17 represents a mC
      nucleotide analog
<220> FEATURE:
<221> NAME/KEY: variation
<222> LOCATION: 18
<223> OTHER INFORMATION: U in position 2,4,18 and 20 is a fU nucleotide
      analog
<220> FEATURE:
<221> NAME/KEY: variation
<222> LOCATION: 19
<223> OTHER INFORMATION: G in position 12 and 19 represents a mG
      nucleotide analog
<220> FEATURE:
```

<221> NAME/KEY: variation
<222> LOCATION: 20
<223> OTHER INFORMATION: U in position 2,4,18 and 20 is a fU nucleotide
      analog
<220> FEATURE:
<221> NAME/KEY: variation
<222> LOCATION: 21
<223> OTHER INFORMATION: U in position 1 and 21 represents a 2'-O-
      methyl-uracile (mU)
<220> FEATURE:
<221> NAME/KEY: variation
<222> LOCATION: 22
<223> OTHER INFORMATION: T in position 22 and 23 is a lT2 nucleotide
      analog
<220> FEATURE:
<221> NAME/KEY: variation
<222> LOCATION: 23
<223> OTHER INFORMATION: T in position 22 and 23 is a lT2 nucleotide
      analog

<400> SEQUENCE: 93
uuauagagca agaacacugu utt                                            23

<210> SEQ ID NO 94
<211> LENGTH: 23
<212> TYPE: RNA
<213> ORGANISM: Artificial Sequence
<220> FEATURE:
<223> OTHER INFORMATION: as2-4
<220> FEATURE:
<221> NAME/KEY: variation
<222> LOCATION: 1
<223> OTHER INFORMATION: The nucleotide in position 1 and the nucleotide
      in position 2 are linked through a phosphoramidite bond
<220> FEATURE:
<221> NAME/KEY: variation
<222> LOCATION: 1
<223> OTHER INFORMATION: U in position 1 and 21 represents a 2'-O-
      methyl-uracile (mU)
<220> FEATURE:
<221> NAME/KEY: variation
<222> LOCATION: 2
<223> OTHER INFORMATION: The nucleotide in position 1 and the nucleotide
      in position 2 are linked through a phosphoramidite bond
<220> FEATURE:
<221> NAME/KEY: variation
<222> LOCATION: 2
<223> OTHER INFORMATION: The nucleotide in position 2 and the nucleotide
      in position 3 are linked through a phosphoramidite bond
<220> FEATURE:
<221> NAME/KEY: variation
<222> LOCATION: 2
<223> OTHER INFORMATION: U in position 2,4,18 and 20 is a fU nucleotide
      analog
<220> FEATURE:
<221> NAME/KEY: variation
<222> LOCATION: 3
<223> OTHER INFORMATION: The nucleotide in position 2 and the nucleotide
      in position 3 are linked through a phosphoramidite bond
<220> FEATURE:
<221> NAME/KEY: variation
<222> LOCATION: 3
<223> OTHER INFORMATION: A in position 3,5,7,11 and 13 represents a mA
      nucleotide analog
<220> FEATURE:
<221> NAME/KEY: variation
<222> LOCATION: 4
<223> OTHER INFORMATION: U in position 2,4,18 and 20 is a fU nucleotide
      analog
<220> FEATURE:
<221> NAME/KEY: variation
<222> LOCATION: 5
<223> OTHER INFORMATION: A in position 3,5,7,11 and 13 represents a mA
      nucleotide analog
<220> FEATURE:
<221> NAME/KEY: variation
<222> LOCATION: 6

```
<223> OTHER INFORMATION: G in position 6 and 8 is a fG nucleotide analog
<220> FEATURE:
<221> NAME/KEY: variation
<222> LOCATION: 7
<223> OTHER INFORMATION: A in position 3,5,7,11 and 13 represents a mA
      nucleotide analog
<220> FEATURE:
<221> NAME/KEY: variation
<222> LOCATION: 8
<223> OTHER INFORMATION: G in position 6 and 8 is a fG nucleotide analog
<220> FEATURE:
<221> NAME/KEY: variation
<222> LOCATION: 9
<223> OTHER INFORMATION: C in position 9,15 and 17 represents a mC
      nucleotide analog
<220> FEATURE:
<221> NAME/KEY: variation
<222> LOCATION: 10
<223> OTHER INFORMATION: A in position 10,14 and 16 is a fA nucleotide
      analog
<220> FEATURE:
<221> NAME/KEY: variation
<222> LOCATION: 11
<223> OTHER INFORMATION: A in position 3,5,7,11 and 13 represents a mA
      nucleotide analog
<220> FEATURE:
<221> NAME/KEY: variation
<222> LOCATION: 12
<223> OTHER INFORMATION: G in position 12 and 19 represents a mG
      nucleotide analog
<220> FEATURE:
<221> NAME/KEY: variation
<222> LOCATION: 13
<223> OTHER INFORMATION: A in position 3,5,7,11 and 13 represents a mA
      nucleotide analog
<220> FEATURE:
<221> NAME/KEY: variation
<222> LOCATION: 14
<223> OTHER INFORMATION: A in position 10,14 and 16 is a fA nucleotide
      analog
<220> FEATURE:
<221> NAME/KEY: variation
<222> LOCATION: 15
<223> OTHER INFORMATION: C in position 9,15 and 17 represents a mC
      nucleotide analog
<220> FEATURE:
<221> NAME/KEY: variation
<222> LOCATION: 16
<223> OTHER INFORMATION: A in position 10,14 and 16 is a fA nucleotide
      analog
<220> FEATURE:
<221> NAME/KEY: variation
<222> LOCATION: 17
<223> OTHER INFORMATION: C in position 9,15 and 17 represents a mC
      nucleotide analog
<220> FEATURE:
<221> NAME/KEY: variation
<222> LOCATION: 18
<223> OTHER INFORMATION: U in position 2,4,18 and 20 is a fU nucleotide
      analog
<220> FEATURE:
<221> NAME/KEY: variation
<222> LOCATION: 19
<223> OTHER INFORMATION: G in position 12 and 19 represents a mG
      nucleotide analog
<220> FEATURE:
<221> NAME/KEY: variation
<222> LOCATION: 20
<223> OTHER INFORMATION: U in position 2,4,18 and 20 is a fU nucleotide
      analog
<220> FEATURE:
<221> NAME/KEY: variation
<222> LOCATION: 21
<223> OTHER INFORMATION: U in position 1 and 21 represents a 2'-O-
      methyl-uracile (mU)
<220> FEATURE:
<221> NAME/KEY: variation
<222> LOCATION: 22
<223> OTHER INFORMATION: T in position 22 and 23 is a lT3 nucleotide
```

```
        analog
<220> FEATURE:
<221> NAME/KEY: variation
<222> LOCATION: 23
<223> OTHER INFORMATION: T in position 22 and 23 is a 1T3 nucleotide
        analog

<400> SEQUENCE: 94
uuauagagca agaacacugu utt                                              23

<210> SEQ ID NO 95
<211> LENGTH: 23
<212> TYPE: RNA
<213> ORGANISM: Artificial Sequence
<220> FEATURE:
<223> OTHER INFORMATION: as2-5
<220> FEATURE:
<221> NAME/KEY: variation
<222> LOCATION: 1
<223> OTHER INFORMATION: The nucleotide in position 1 and the nucleotide
        in position 2 are linked through a phosphoramidite bond
<220> FEATURE:
<221> NAME/KEY: variation
<222> LOCATION: 1
<223> OTHER INFORMATION: U in position 1 and 21 represents a 2'-O-
        methyl-uracile (mU)
<220> FEATURE:
<221> NAME/KEY: variation
<222> LOCATION: 2
<223> OTHER INFORMATION: The nucleotide in position 1 and the nucleotide
        in position 2 are linked through a phosphoramidite bond
<220> FEATURE:
<221> NAME/KEY: variation
<222> LOCATION: 2
<223> OTHER INFORMATION: The nucleotide in position 2 and the nucleotide
        in position 3 are linked through a phosphoramidite bond
<220> FEATURE:
<221> NAME/KEY: variation
<222> LOCATION: 2
<223> OTHER INFORMATION: U in position 2,4,18 and 20 is a fU nucleotide
        analog
<220> FEATURE:
<221> NAME/KEY: variation
<222> LOCATION: 3
<223> OTHER INFORMATION: The nucleotide in position 2 and the nucleotide
        in position 3 are linked through a phosphoramidite bond
<220> FEATURE:
<221> NAME/KEY: variation
<222> LOCATION: 3
<223> OTHER INFORMATION: A in position 3,5,7,11 and 13 represents a mA
        nucleotide analog
<220> FEATURE:
<221> NAME/KEY: variation
<222> LOCATION: 4
<223> OTHER INFORMATION: U in position 2,4,18 and 20 is a fU nucleotide
        analog
<220> FEATURE:
<221> NAME/KEY: variation
<222> LOCATION: 5
<223> OTHER INFORMATION: A in position 3,5,7,11 and 13 represents a mA
        nucleotide analog
<220> FEATURE:
<221> NAME/KEY: variation
<222> LOCATION: 6
<223> OTHER INFORMATION: G in position 6 and 8 is a fG nucleotide analog
<220> FEATURE:
<221> NAME/KEY: variation
<222> LOCATION: 7
<223> OTHER INFORMATION: A in position 3,5,7,11 and 13 represents a mA
        nucleotide analog
<220> FEATURE:
<221> NAME/KEY: variation
<222> LOCATION: 8
<223> OTHER INFORMATION: G in position 6 and 8 is a fG nucleotide analog
<220> FEATURE:
<221> NAME/KEY: variation
<222> LOCATION: 9
```

```
<223> OTHER INFORMATION: C in position 9,15 and 17 represents a mC
      nucleotide analog
<220> FEATURE:
<221> NAME/KEY: variation
<222> LOCATION: 10
<223> OTHER INFORMATION: A in position 10,14 and 16 is a fA nucleotide
      analog
<220> FEATURE:
<221> NAME/KEY: variation
<222> LOCATION: 11
<223> OTHER INFORMATION: A in position 3,5,7,11 and 13 represents a mA
      nucleotide analog
<220> FEATURE:
<221> NAME/KEY: variation
<222> LOCATION: 12
<223> OTHER INFORMATION: G in position 12 and 19 represents a mG
      nucleotide analog
<220> FEATURE:
<221> NAME/KEY: variation
<222> LOCATION: 13
<223> OTHER INFORMATION: A in position 3,5,7,11 and 13 represents a mA
      nucleotide analog
<220> FEATURE:
<221> NAME/KEY: variation
<222> LOCATION: 14
<223> OTHER INFORMATION: A in position 10,14 and 16 is a fA nucleotide
      analog
<220> FEATURE:
<221> NAME/KEY: variation
<222> LOCATION: 15
<223> OTHER INFORMATION: C in position 9,15 and 17 represents a mC
      nucleotide analog
<220> FEATURE:
<221> NAME/KEY: variation
<222> LOCATION: 16
<223> OTHER INFORMATION: A in position 10,14 and 16 is a fA nucleotide
      analog
<220> FEATURE:
<221> NAME/KEY: variation
<222> LOCATION: 17
<223> OTHER INFORMATION: C in position 9,15 and 17 represents a mC
      nucleotide analog
<220> FEATURE:
<221> NAME/KEY: variation
<222> LOCATION: 18
<223> OTHER INFORMATION: U in position 2,4,18 and 20 is a fU nucleotide
      analog
<220> FEATURE:
<221> NAME/KEY: variation
<222> LOCATION: 19
<223> OTHER INFORMATION: G in position 12 and 19 represents a mG
      nucleotide analog
<220> FEATURE:
<221> NAME/KEY: variation
<222> LOCATION: 20
<223> OTHER INFORMATION: U in position 2,4,18 and 20 is a fU nucleotide
      analog
<220> FEATURE:
<221> NAME/KEY: variation
<222> LOCATION: 21
<223> OTHER INFORMATION: U in position 1 and 21 represents a 2'-O-
      methyl-uracile (mU)
<220> FEATURE:
<221> NAME/KEY: variation
<222> LOCATION: 22
<223> OTHER INFORMATION: T in position 22 and 23 is a lT4 nucleotide
      analog
<220> FEATURE:
<221> NAME/KEY: variation
<222> LOCATION: 23
<223> OTHER INFORMATION: T in position 22 and 23 is a lT4 nucleotide
      analog

<400> SEQUENCE: 95
uuauagagca agaacacugu utt                                           23

<210> SEQ ID NO 96
```

```
<211> LENGTH: 23
<212> TYPE: RNA
<213> ORGANISM: Artificial Sequence
<220> FEATURE:
<223> OTHER INFORMATION: as2-6
<220> FEATURE:
<221> NAME/KEY: variation
<222> LOCATION: 1
<223> OTHER INFORMATION: The nucleotide in position 1 and the nucleotide
      in position 2 are linked through a phosphoramidite bond
<220> FEATURE:
<221> NAME/KEY: variation
<222> LOCATION: 1
<223> OTHER INFORMATION: U in position 1 and 21 represents a 2'-O-
      methyl-uracile (mU)
<220> FEATURE:
<221> NAME/KEY: variation
<222> LOCATION: 2
<223> OTHER INFORMATION: The nucleotide in position 1 and the nucleotide
      in position 2 are linked through a phosphoramidite bond
<220> FEATURE:
<221> NAME/KEY: variation
<222> LOCATION: 2
<223> OTHER INFORMATION: The nucleotide in position 2 and the nucleotide
      in position 3 are linked through a phosphoramidite bond
<220> FEATURE:
<221> NAME/KEY: variation
<222> LOCATION: 2
<223> OTHER INFORMATION: U in position 2,4,18 and 20 is a fU nucleotide
      analog
<220> FEATURE:
<221> NAME/KEY: variation
<222> LOCATION: 3
<223> OTHER INFORMATION: The nucleotide in position 2 and the nucleotide
      in position 3 are linked through a phosphoramidite bond
<220> FEATURE:
<221> NAME/KEY: variation
<222> LOCATION: 3
<223> OTHER INFORMATION: A in position 3,5,7,11 and 13 represents a mA
      nucleotide analog
<220> FEATURE:
<221> NAME/KEY: variation
<222> LOCATION: 4
<223> OTHER INFORMATION: U in position 2,4,18 and 20 is a fU nucleotide
      analog
<220> FEATURE:
<221> NAME/KEY: variation
<222> LOCATION: 5
<223> OTHER INFORMATION: A in position 3,5,7,11 and 13 represents a mA
      nucleotide analog
<220> FEATURE:
<221> NAME/KEY: variation
<222> LOCATION: 6
<223> OTHER INFORMATION: G in position 6 and 8 is a fG nucleotide analog
<220> FEATURE:
<221> NAME/KEY: variation
<222> LOCATION: 7
<223> OTHER INFORMATION: A in position 3,5,7,11 and 13 represents a mA
      nucleotide analog
<220> FEATURE:
<221> NAME/KEY: variation
<222> LOCATION: 8
<223> OTHER INFORMATION: G in position 6 and 8 is a fG nucleotide analog
<220> FEATURE:
<221> NAME/KEY: variation
<222> LOCATION: 9
<223> OTHER INFORMATION: C in position 9,15 and 17 represents a mC
      nucleotide analog
<220> FEATURE:
<221> NAME/KEY: variation
<222> LOCATION: 10
<223> OTHER INFORMATION: A in position 10,14 and 16 is a fA nucleotide
      analog
<220> FEATURE:
<221> NAME/KEY: variation
<222> LOCATION: 11
<223> OTHER INFORMATION: A in position 3,5,7,11 and 13 represents a mA
      nucleotide analog
<220> FEATURE:
```

```
<221> NAME/KEY: variation
<222> LOCATION: 12
<223> OTHER INFORMATION: G in position 12 and 19 represents a mG
      nucleotide analog
<220> FEATURE:
<221> NAME/KEY: variation
<222> LOCATION: 13
<223> OTHER INFORMATION: A in position 3,5,7,11 and 13 represents a mA
      nucleotide analog
<220> FEATURE:
<221> NAME/KEY: variation
<222> LOCATION: 14
<223> OTHER INFORMATION: A in position 10,14 and 16 is a fA nucleotide
      analog
<220> FEATURE:
<221> NAME/KEY: variation
<222> LOCATION: 15
<223> OTHER INFORMATION: C in position 9,15 and 17 represents a mC
      nucleotide analog
<220> FEATURE:
<221> NAME/KEY: variation
<222> LOCATION: 16
<223> OTHER INFORMATION: A in position 10,14 and 16 is a fA nucleotide
      analog
<220> FEATURE:
<221> NAME/KEY: variation
<222> LOCATION: 17
<223> OTHER INFORMATION: C in position 9,15 and 17 represents a mC
      nucleotide analog
<220> FEATURE:
<221> NAME/KEY: variation
<222> LOCATION: 18
<223> OTHER INFORMATION: U in position 2,4,18 and 20 is a fU nucleotide
      analog
<220> FEATURE:
<221> NAME/KEY: variation
<222> LOCATION: 19
<223> OTHER INFORMATION: G in position 12 and 19 represents a mG
      nucleotide analog
<220> FEATURE:
<221> NAME/KEY: variation
<222> LOCATION: 20
<223> OTHER INFORMATION: U in position 2,4,18 and 20 is a fU nucleotide
      analog
<220> FEATURE:
<221> NAME/KEY: variation
<222> LOCATION: 21
<223> OTHER INFORMATION: U in position 1 and 21 represents a 2'-O-
      methyl-uracile (mU)
<220> FEATURE:
<221> NAME/KEY: variation
<222> LOCATION: 22
<223> OTHER INFORMATION: T in position 22 and 23 is a lT5 nucleotide
      analog
<220> FEATURE:
<221> NAME/KEY: variation
<222> LOCATION: 23
<223> OTHER INFORMATION: T in position 22 and 23 is a lT5 nucleotide
      analog

<400> SEQUENCE: 96
uuauagagca agaacacugu utt                                              23

<210> SEQ ID NO 97
<211> LENGTH: 23
<212> TYPE: RNA
<213> ORGANISM: Artificial Sequence
<220> FEATURE:
<223> OTHER INFORMATION: as2-7
<220> FEATURE:
<221> NAME/KEY: variation
<222> LOCATION: 1
<223> OTHER INFORMATION: The nucleotide in position 1 and the nucleotide
      in position 2 are linked through a phosphoramidite bond
<220> FEATURE:
<221> NAME/KEY: variation
<222> LOCATION: 1
```

```
<223> OTHER INFORMATION: U in position 1 and 21 represents a 2'-O-
      methyl-uracile (mU)
<220> FEATURE:
<221> NAME/KEY: variation
<222> LOCATION: 2
<223> OTHER INFORMATION: The nucleotide in position 1 and the nucleotide
      in position 2 are linked through a phosphoramidite bond
<220> FEATURE:
<221> NAME/KEY: variation
<222> LOCATION: 2
<223> OTHER INFORMATION: The nucleotide in position 2 and the nucleotide
      in position 3 are linked through a phosphoramidite bond
<220> FEATURE:
<221> NAME/KEY: variation
<222> LOCATION: 2
<223> OTHER INFORMATION: U in position 2,4,18 and 20 is a fU nucleotide
      analog
<220> FEATURE:
<221> NAME/KEY: variation
<222> LOCATION: 3
<223> OTHER INFORMATION: The nucleotide in position 2 and the nucleotide
      in position 3 are linked through a phosphoramidite bond
<220> FEATURE:
<221> NAME/KEY: variation
<222> LOCATION: 3
<223> OTHER INFORMATION: A in position 3,5,7,11 and 13 represents a mA
      nucleotide analog
<220> FEATURE:
<221> NAME/KEY: variation
<222> LOCATION: 4
<223> OTHER INFORMATION: U in position 2,4,18 and 20 is a fU nucleotide
      analog
<220> FEATURE:
<221> NAME/KEY: variation
<222> LOCATION: 5
<223> OTHER INFORMATION: A in position 3,5,7,11 and 13 represents a mA
      nucleotide analog
<220> FEATURE:
<221> NAME/KEY: variation
<222> LOCATION: 6
<223> OTHER INFORMATION: G in position 6 and 8 is a fG nucleotide analog
<220> FEATURE:
<221> NAME/KEY: variation
<222> LOCATION: 7
<223> OTHER INFORMATION: A in position 3,5,7,11 and 13 represents a mA
      nucleotide analog
<220> FEATURE:
<221> NAME/KEY: variation
<222> LOCATION: 8
<223> OTHER INFORMATION: G in position 6 and 8 is a fG nucleotide analog
<220> FEATURE:
<221> NAME/KEY: variation
<222> LOCATION: 9
<223> OTHER INFORMATION: C in position 9,15 and 17 represents a mC
      nucleotide analog
<220> FEATURE:
<221> NAME/KEY: variation
<222> LOCATION: 10
<223> OTHER INFORMATION: A in position 10,14 and 16 is a fA nucleotide
      analog
<220> FEATURE:
<221> NAME/KEY: variation
<222> LOCATION: 11
<223> OTHER INFORMATION: A in position 3,5,7,11 and 13 represents a mA
      nucleotide analog
<220> FEATURE:
<221> NAME/KEY: variation
<222> LOCATION: 12
<223> OTHER INFORMATION: G in position 12 and 19 represents a mG
      nucleotide analog
<220> FEATURE:
<221> NAME/KEY: variation
<222> LOCATION: 13
<223> OTHER INFORMATION: A in position 3,5,7,11 and 13 represents a mA
      nucleotide analog
<220> FEATURE:
<221> NAME/KEY: variation
<222> LOCATION: 14
<223> OTHER INFORMATION: A in position 10,14 and 16 is a fA nucleotide
```

```
                    analog
<220> FEATURE:
<221> NAME/KEY: variation
<222> LOCATION: 15
<223> OTHER INFORMATION: C in position 9,15 and 17 represents a mC
      nucleotide analog
<220> FEATURE:
<221> NAME/KEY: variation
<222> LOCATION: 16
<223> OTHER INFORMATION: A in position 10,14 and 16 is a fA nucleotide
      analog
<220> FEATURE:
<221> NAME/KEY: variation
<222> LOCATION: 17
<223> OTHER INFORMATION: C in position 9,15 and 17 represents a mC
      nucleotide analog
<220> FEATURE:
<221> NAME/KEY: variation
<222> LOCATION: 18
<223> OTHER INFORMATION: U in position 2,4,18 and 20 is a fU nucleotide
      analog
<220> FEATURE:
<221> NAME/KEY: variation
<222> LOCATION: 19
<223> OTHER INFORMATION: G in position 12 and 19 represents a mG
      nucleotide analog
<220> FEATURE:
<221> NAME/KEY: variation
<222> LOCATION: 20
<223> OTHER INFORMATION: U in position 2,4,18 and 20 is a fU nucleotide
      analog
<220> FEATURE:
<221> NAME/KEY: variation
<222> LOCATION: 21
<223> OTHER INFORMATION: U in position 1 and 21 represents a 2'-O-
      methyl-uracile (mU)
<220> FEATURE:
<221> NAME/KEY: variation
<222> LOCATION: 22
<223> OTHER INFORMATION: T in position 22 and 23 is a lT6 nucleotide
      analog
<220> FEATURE:
<221> NAME/KEY: variation
<222> LOCATION: 23
<223> OTHER INFORMATION: T in position 22 and 23 is a lT6 nucleotide
      analog

<400> SEQUENCE: 97
uuauagagca agaacacugu utt                                             23

<210> SEQ ID NO 98
<211> LENGTH: 23
<212> TYPE: RNA
<213> ORGANISM: Artificial Sequence
<220> FEATURE:
<223> OTHER INFORMATION: as2-7
<220> FEATURE:
<221> NAME/KEY: variation
<222> LOCATION: 1
<223> OTHER INFORMATION: The nucleotide in position 1 and the nucleotide
      in position 2 are linked through a phosphoramidite bond
<220> FEATURE:
<221> NAME/KEY: variation
<222> LOCATION: 1
<223> OTHER INFORMATION: U in position 1 and 21 represents a 2'-O-
      methyl-uracile (mU)
<220> FEATURE:
<221> NAME/KEY: variation
<222> LOCATION: 2
<223> OTHER INFORMATION: The nucleotide in position 1 and the nucleotide
      in position 2 are linked through a phosphoramidite bond
<220> FEATURE:
<221> NAME/KEY: variation
<222> LOCATION: 2
<223> OTHER INFORMATION: The nucleotide in position 2 and the nucleotide
      in position 3 are linked through a phosphoramidite bond
<220> FEATURE:
```

```
<221> NAME/KEY: variation
<222> LOCATION: 2
<223> OTHER INFORMATION: U in position 2,4,18 and 20 is a fU nucleotide
      analog
<220> FEATURE:
<221> NAME/KEY: variation
<222> LOCATION: 3
<223> OTHER INFORMATION: The nucleotide in position 2 and the nucleotide
      in position 3 are linked through a phosphoramidite bond
<220> FEATURE:
<221> NAME/KEY: variation
<222> LOCATION: 3
<223> OTHER INFORMATION: A in position 3,5,7,11 and 13 represents a mA
      nucleotide analog
<220> FEATURE:
<221> NAME/KEY: variation
<222> LOCATION: 4
<223> OTHER INFORMATION: U in position 2,4,18 and 20 is a fU nucleotide
      analog
<220> FEATURE:
<221> NAME/KEY: variation
<222> LOCATION: 5
<223> OTHER INFORMATION: A in position 3,5,7,11 and 13 represents a mA
      nucleotide analog
<220> FEATURE:
<221> NAME/KEY: variation
<222> LOCATION: 6
<223> OTHER INFORMATION: G in position 6 and 8 is a fG nucleotide analog
<220> FEATURE:
<221> NAME/KEY: variation
<222> LOCATION: 7
<223> OTHER INFORMATION: A in position 3,5,7,11 and 13 represents a mA
      nucleotide analog
<220> FEATURE:
<221> NAME/KEY: variation
<222> LOCATION: 8
<223> OTHER INFORMATION: G in position 6 and 8 is a fG nucleotide analog
<220> FEATURE:
<221> NAME/KEY: variation
<222> LOCATION: 9
<223> OTHER INFORMATION: C in position 9,15 and 17 represents a mC
      nucleotide analog
<220> FEATURE:
<221> NAME/KEY: variation
<222> LOCATION: 10
<223> OTHER INFORMATION: A in position 10,14 and 16 is a fA nucleotide
      analog
<220> FEATURE:
<221> NAME/KEY: variation
<222> LOCATION: 11
<223> OTHER INFORMATION: A in position 3,5,7,11 and 13 represents a mA
      nucleotide analog
<220> FEATURE:
<221> NAME/KEY: variation
<222> LOCATION: 12
<223> OTHER INFORMATION: G in position 12 and 19 represents a mG
      nucleotide analog
<220> FEATURE:
<221> NAME/KEY: variation
<222> LOCATION: 13
<223> OTHER INFORMATION: A in position 3,5,7,11 and 13 represents a mA
      nucleotide analog
<220> FEATURE:
<221> NAME/KEY: variation
<222> LOCATION: 14
<223> OTHER INFORMATION: A in position 10,14 and 16 is a fA nucleotide
      analog
<220> FEATURE:
<221> NAME/KEY: variation
<222> LOCATION: 15
<223> OTHER INFORMATION: C in position 9,15 and 17 represents a mC
      nucleotide analog
<220> FEATURE:
<221> NAME/KEY: variation
<222> LOCATION: 16
<223> OTHER INFORMATION: A in position 10,14 and 16 is a fA nucleotide
      analog
<220> FEATURE:
<221> NAME/KEY: variation
```

```
<222> LOCATION: 17
<223> OTHER INFORMATION: C in position 9,15 and 17 represents a mC
      nucleotide analog
<220> FEATURE:
<221> NAME/KEY: variation
<222> LOCATION: 18
<223> OTHER INFORMATION: U in position 2,4,18 and 20 is a fU nucleotide
      analog
<220> FEATURE:
<221> NAME/KEY: variation
<222> LOCATION: 19
<223> OTHER INFORMATION: G in position 12 and 19 represents a mG
      nucleotide analog
<220> FEATURE:
<221> NAME/KEY: variation
<222> LOCATION: 20
<223> OTHER INFORMATION: U in position 2,4,18 and 20 is a fU nucleotide
      analog
<220> FEATURE:
<221> NAME/KEY: variation
<222> LOCATION: 21
<223> OTHER INFORMATION: U in position 1 and 21 represents a 2'-O-
      methyl-uracile (mU)
<220> FEATURE:
<221> NAME/KEY: variation
<222> LOCATION: 22
<223> OTHER INFORMATION: T in position 22 and 23 is a lT7 nucleotide
      analog
<220> FEATURE:
<221> NAME/KEY: variation
<222> LOCATION: 23
<223> OTHER INFORMATION: T in position 22 and 23 is a lT7 nucleotide
      analog

<400> SEQUENCE: 98
uuauagagca agaacacugu utt                                          23

<210> SEQ ID NO 99
<211> LENGTH: 23
<212> TYPE: RNA
<213> ORGANISM: Artificial Sequence
<220> FEATURE:
<223> OTHER INFORMATION: as2-9
<220> FEATURE:
<221> NAME/KEY: variation
<222> LOCATION: 1
<223> OTHER INFORMATION: The nucleotide in position 1 and the nucleotide
      in position 2 are linked through a phosphoramidite bond
<220> FEATURE:
<221> NAME/KEY: variation
<222> LOCATION: 1
<223> OTHER INFORMATION: U in position 1 and 21 represents a 2'-O-
      methyl-uracile (mU)
<220> FEATURE:
<221> NAME/KEY: variation
<222> LOCATION: 2
<223> OTHER INFORMATION: The nucleotide in position 1 and the nucleotide
      in position 2 are linked through a phosphoramidite bond
<220> FEATURE:
<221> NAME/KEY: variation
<222> LOCATION: 2
<223> OTHER INFORMATION: The nucleotide in position 2 and the nucleotide
      in position 3 are linked through a phosphoramidite bond
<220> FEATURE:
<221> NAME/KEY: variation
<222> LOCATION: 2
<223> OTHER INFORMATION: U in position 2,4,18 and 20 is a fU nucleotide
      analog
<220> FEATURE:
<221> NAME/KEY: variation
<222> LOCATION: 3
<223> OTHER INFORMATION: The nucleotide in position 2 and the nucleotide
      in position 3 are linked through a phosphoramidite bond
<220> FEATURE:
<221> NAME/KEY: variation
<222> LOCATION: 3
<223> OTHER INFORMATION: A in position 3,5,7,11 and 13 represents a mA
``` nucleotide analog
<220> FEATURE:
<221> NAME/KEY: variation
<222> LOCATION: 4
<223> OTHER INFORMATION: U in position 2,4,18 and 20 is a fU nucleotide
     analog
<220> FEATURE:
<221> NAME/KEY: variation
<222> LOCATION: 5
<223> OTHER INFORMATION: A in position 3,5,7,11 and 13 represents a mA
     nucleotide analog
<220> FEATURE:
<221> NAME/KEY: variation
<222> LOCATION: 6
<223> OTHER INFORMATION: G in position 6 and 8 is a fG nucleotide analog
<220> FEATURE:
<221> NAME/KEY: variation
<222> LOCATION: 7
<223> OTHER INFORMATION: A in position 3,5,7,11 and 13 represents a mA
     nucleotide analog
<220> FEATURE:
<221> NAME/KEY: variation
<222> LOCATION: 8
<223> OTHER INFORMATION: G in position 6 and 8 is a fG nucleotide analog
<220> FEATURE:
<221> NAME/KEY: variation
<222> LOCATION: 9
<223> OTHER INFORMATION: C in position 9,15 and 17 represents a mC
     nucleotide analog
<220> FEATURE:
<221> NAME/KEY: variation
<222> LOCATION: 10
<223> OTHER INFORMATION: A in position 10,14 and 16 is a fA nucleotide
     analog
<220> FEATURE:
<221> NAME/KEY: variation
<222> LOCATION: 11
<223> OTHER INFORMATION: A in position 3,5,7,11 and 13 represents a mA
     nucleotide analog
<220> FEATURE:
<221> NAME/KEY: variation
<222> LOCATION: 12
<223> OTHER INFORMATION: G in position 12 and 19 represents a mG
     nucleotide analog
<220> FEATURE:
<221> NAME/KEY: variation
<222> LOCATION: 13
<223> OTHER INFORMATION: A in position 3,5,7,11 and 13 represents a mA
     nucleotide analog
<220> FEATURE:
<221> NAME/KEY: variation
<222> LOCATION: 14
<223> OTHER INFORMATION: A in position 10,14 and 16 is a fA nucleotide
     analog
<220> FEATURE:
<221> NAME/KEY: variation
<222> LOCATION: 15
<223> OTHER INFORMATION: C in position 9,15 and 17 represents a mC
     nucleotide analog
<220> FEATURE:
<221> NAME/KEY: variation
<222> LOCATION: 16
<223> OTHER INFORMATION: A in position 10,14 and 16 is a fA nucleotide
     analog
<220> FEATURE:
<221> NAME/KEY: variation
<222> LOCATION: 17
<223> OTHER INFORMATION: C in position 9,15 and 17 represents a mC
     nucleotide analog
<220> FEATURE:
<221> NAME/KEY: variation
<222> LOCATION: 18
<223> OTHER INFORMATION: U in position 2,4,18 and 20 is a fU nucleotide
     analog
<220> FEATURE:
<221> NAME/KEY: variation
<222> LOCATION: 19
<223> OTHER INFORMATION: G in position 12 and 19 represents a mG
     nucleotide analog

```
<220> FEATURE:
<221> NAME/KEY: variation
<222> LOCATION: 20
<223> OTHER INFORMATION: U in position 2,4,18 and 20 is a fU nucleotide
      analog
<220> FEATURE:
<221> NAME/KEY: variation
<222> LOCATION: 21
<223> OTHER INFORMATION: U in position 1 and 21 represents a 2'-O-
      methyl-uracile (mU)
<220> FEATURE:
<221> NAME/KEY: variation
<222> LOCATION: 22
<223> OTHER INFORMATION: T in position 22 and 23 is a lT9 nucleotide
      analog
<220> FEATURE:
<221> NAME/KEY: variation
<222> LOCATION: 23
<223> OTHER INFORMATION: T in position 22 and 23 is a lT9 nucleotide
      analog

<400> SEQUENCE: 99
uuauagagca agaacacugu utt                                              23

<210> SEQ ID NO 100
<211> LENGTH: 24
<212> TYPE: RNA
<213> ORGANISM: Artificial Sequence
<220> FEATURE:
<223> OTHER INFORMATION: ss3-1
<220> FEATURE:
<221> NAME/KEY: variation
<222> LOCATION: 1
<223> OTHER INFORMATION: The nucleotide in position 1 and the nucleotide
      in position 2 are linked through a phosphoramidite bond
<220> FEATURE:
<221> NAME/KEY: variation
<222> LOCATION: 1
<223> OTHER INFORMATION: A in position 1 and 21 is a fA nucleotide
      analog
<220> FEATURE:
<221> NAME/KEY: variation
<222> LOCATION: 2
<223> OTHER INFORMATION: The nucleotide in position 1 and the nucleotide
      in position 2 are linked through a phosphoramidite bond
<220> FEATURE:
<221> NAME/KEY: variation
<222> LOCATION: 2
<223> OTHER INFORMATION: The nucleotide in position 2 and the nucleotide
      in position 3 are linked through a phosphoramidite bond
<220> FEATURE:
<221> NAME/KEY: variation
<222> LOCATION: 2
<223> OTHER INFORMATION: A in position 2,4,18 and 20 represents a mA
      nucleotide analog
<220> FEATURE:
<221> NAME/KEY: variation
<222> LOCATION: 3
<223> OTHER INFORMATION: The nucleotide in position 2 and the nucleotide
      in position 3 are linked through a phosphoramidite bond
<220> FEATURE:
<221> NAME/KEY: variation
<222> LOCATION: 3
<223> OTHER INFORMATION: C in position 3 and 10 is a fC nucleotide
      analog
<220> FEATURE:
<221> NAME/KEY: variation
<222> LOCATION: 4
<223> OTHER INFORMATION: A in position 2,4,18 and 20 represents a mA
      nucleotide analog
<220> FEATURE:
<221> NAME/KEY: variation
<222> LOCATION: 5
<223> OTHER INFORMATION: G in position 5,7 and 13 is a fG nucleotide
      analog
<220> FEATURE:
<221> NAME/KEY: variation
```

```
<222> LOCATION: 6
<223> OTHER INFORMATION: U in position 6,8 and 12 represents a 2'-O-
      methyl-uracile (mU)
<220> FEATURE:
<221> NAME/KEY: variation
<222> LOCATION: 7
<223> OTHER INFORMATION: G in position 5,7 and 13 is a fG nucleotide
      analog
<220> FEATURE:
<221> NAME/KEY: variation
<222> LOCATION: 8
<223> OTHER INFORMATION: U in position 6,8 and 12 represents a 2'-O-
      methyl-uracile (mU)
<220> FEATURE:
<221> NAME/KEY: variation
<222> LOCATION: 9
<223> OTHER INFORMATION: U in position 9,11,15,17 and 19 is a fU
      nucleotide analog
<220> FEATURE:
<221> NAME/KEY: variation
<222> LOCATION: 10
<223> OTHER INFORMATION: C in position 3 and 10 is a fC nucleotide
      analog
<220> FEATURE:
<221> NAME/KEY: variation
<222> LOCATION: 11
<223> OTHER INFORMATION: U in position 9,11,15,17 and 19 is a fU
      nucleotide analog
<220> FEATURE:
<221> NAME/KEY: variation
<222> LOCATION: 12
<223> OTHER INFORMATION: U in position 6,8 and 12 represents a 2'-O-
      methyl-uracile (mU)
<220> FEATURE:
<221> NAME/KEY: variation
<222> LOCATION: 13
<223> OTHER INFORMATION: G in position 5,7 and 13 is a fG nucleotide
      analog
<220> FEATURE:
<221> NAME/KEY: variation
<222> LOCATION: 14
<223> OTHER INFORMATION: C in position 14 and 16 represents a mC
      nucleotide analog
<220> FEATURE:
<221> NAME/KEY: variation
<222> LOCATION: 15
<223> OTHER INFORMATION: U in position 9,11,15,17 and 19 is a fU
      nucleotide analog
<220> FEATURE:
<221> NAME/KEY: variation
<222> LOCATION: 16
<223> OTHER INFORMATION: C in position 14 and 16 represents a mC
      nucleotide analog
<220> FEATURE:
<221> NAME/KEY: variation
<222> LOCATION: 17
<223> OTHER INFORMATION: U in position 9,11,15,17 and 19 is a fU
      nucleotide analog
<220> FEATURE:
<221> NAME/KEY: variation
<222> LOCATION: 18
<223> OTHER INFORMATION: A in position 2,4,18 and 20 represents a mA
      nucleotide analog
<220> FEATURE:
<221> NAME/KEY: variation
<222> LOCATION: 19
<223> OTHER INFORMATION: U in position 9,11,15,17 and 19 is a fU
      nucleotide analog
<220> FEATURE:
<221> NAME/KEY: variation
<222> LOCATION: 20
<223> OTHER INFORMATION: A in position 2,4,18 and 20 represents a mA
      nucleotide analog
<220> FEATURE:
<221> NAME/KEY: variation
<222> LOCATION: 21
<223> OTHER INFORMATION: A in position 1 and 21 is a fA nucleotide
      analog
<220> FEATURE:
```

```
<221> NAME/KEY: variation
<222> LOCATION: 22
<223> OTHER INFORMATION: T in position 22,23 and 24 is a lgT5 nucleotide
      analog
<220> FEATURE:
<221> NAME/KEY: variation
<222> LOCATION: 23
<223> OTHER INFORMATION: T in position 22,23 and 24 is a lgT5 nucleotide
      analog
<220> FEATURE:
<221> NAME/KEY: variation
<222> LOCATION: 24
<223> OTHER INFORMATION: T in position 22,23 and 24 is a lgT5 nucleotide
      analog

<400> SEQUENCE: 100
aacaguguuc uugcucuaua attt                                              24

<210> SEQ ID NO 101
<211> LENGTH: 24
<212> TYPE: RNA
<213> ORGANISM: Artificial Sequence
<220> FEATURE:
<223> OTHER INFORMATION: ss3-2
<220> FEATURE:
<221> NAME/KEY: variation
<222> LOCATION: 1
<223> OTHER INFORMATION: The nucleotide in position 1 and the nucleotide
      in position 2 are linked through a phosphoramidite bond
<220> FEATURE:
<221> NAME/KEY: variation
<222> LOCATION: 1
<223> OTHER INFORMATION: A in position 1 and 21 is a fA nucleotide
      analog
<220> FEATURE:
<221> NAME/KEY: variation
<222> LOCATION: 2
<223> OTHER INFORMATION: The nucleotide in position 1 and the nucleotide
      in position 2 are linked through a phosphoramidite bond
<220> FEATURE:
<221> NAME/KEY: variation
<222> LOCATION: 2
<223> OTHER INFORMATION: The nucleotide in position 2 and the nucleotide
      in position 3 are linked through a phosphoramidite bond
<220> FEATURE:
<221> NAME/KEY: variation
<222> LOCATION: 2
<223> OTHER INFORMATION: A in position 2,4,18 and 20 represents a mA
      nucleotide analog
<220> FEATURE:
<221> NAME/KEY: variation
<222> LOCATION: 3
<223> OTHER INFORMATION: The nucleotide in position 2 and the nucleotide
      in position 3 are linked through a phosphoramidite bond
<220> FEATURE:
<221> NAME/KEY: variation
<222> LOCATION: 3
<223> OTHER INFORMATION: C in position 3 and 10 is a fC nucleotide
      analog
<220> FEATURE:
<221> NAME/KEY: variation
<222> LOCATION: 4
<223> OTHER INFORMATION: A in position 2,4,18 and 20 represents a mA
      nucleotide analog
<220> FEATURE:
<221> NAME/KEY: variation
<222> LOCATION: 5
<223> OTHER INFORMATION: G in position 5,7 and 13 is a fG nucleotide
      analog
<220> FEATURE:
<221> NAME/KEY: variation
<222> LOCATION: 6
<223> OTHER INFORMATION: U in position 6,8 and 12 represents a 2'-O-
      methyl-uracile (mU)
<220> FEATURE:
<221> NAME/KEY: variation
<222> LOCATION: 7
```

-continued

```
<223> OTHER INFORMATION: G in position 5,7 and 13 is a fG nucleotide
      analog
<220> FEATURE:
<221> NAME/KEY: variation
<222> LOCATION: 8
<223> OTHER INFORMATION: U in position 6,8 and 12 represents a 2'-O-
      methyl-uracile (mU)
<220> FEATURE:
<221> NAME/KEY: variation
<222> LOCATION: 9
<223> OTHER INFORMATION: U in position 9,11,15,17 and 19 is a fU
      nucleotide analog
<220> FEATURE:
<221> NAME/KEY: variation
<222> LOCATION: 10
<223> OTHER INFORMATION: C in position 3 and 10 is a fC nucleotide
      analog
<220> FEATURE:
<221> NAME/KEY: variation
<222> LOCATION: 11
<223> OTHER INFORMATION: U in position 9,11,15,17 and 19 is a fU
      nucleotide analog
<220> FEATURE:
<221> NAME/KEY: variation
<222> LOCATION: 12
<223> OTHER INFORMATION: U in position 6,8 and 12 represents a 2'-O-
      methyl-uracile (mU)
<220> FEATURE:
<221> NAME/KEY: variation
<222> LOCATION: 13
<223> OTHER INFORMATION: G in position 5,7 and 13 is a fG nucleotide
      analog
<220> FEATURE:
<221> NAME/KEY: variation
<222> LOCATION: 14
<223> OTHER INFORMATION: C in position 14 and 16 represents a mC
      nucleotide analog
<220> FEATURE:
<221> NAME/KEY: variation
<222> LOCATION: 15
<223> OTHER INFORMATION: U in position 9,11,15,17 and 19 is a fU
      nucleotide analog
<220> FEATURE:
<221> NAME/KEY: variation
<222> LOCATION: 16
<223> OTHER INFORMATION: C in position 14 and 16 represents a mC
      nucleotide analog
<220> FEATURE:
<221> NAME/KEY: variation
<222> LOCATION: 17
<223> OTHER INFORMATION: U in position 9,11,15,17 and 19 is a fU
      nucleotide analog
<220> FEATURE:
<221> NAME/KEY: variation
<222> LOCATION: 18
<223> OTHER INFORMATION: A in position 2,4,18 and 20 represents a mA
      nucleotide analog
<220> FEATURE:
<221> NAME/KEY: variation
<222> LOCATION: 19
<223> OTHER INFORMATION: U in position 9,11,15,17 and 19 is a fU
      nucleotide analog
<220> FEATURE:
<221> NAME/KEY: variation
<222> LOCATION: 20
<223> OTHER INFORMATION: A in position 2,4,18 and 20 represents a mA
      nucleotide analog
<220> FEATURE:
<221> NAME/KEY: variation
<222> LOCATION: 21
<223> OTHER INFORMATION: A in position 1 and 21 is a fA nucleotide
      analog
<220> FEATURE:
<221> NAME/KEY: variation
<222> LOCATION: 22
<223> OTHER INFORMATION: T in position 22,23 and 24 is a lgT6 nucleotide
      analog
<220> FEATURE:
<221> NAME/KEY: variation
```

```
<222> LOCATION: 23
<223> OTHER INFORMATION: T in position 22,23 and 24 is a lgT6 nucleotide
      analog
<220> FEATURE:
<221> NAME/KEY: variation
<222> LOCATION: 24
<223> OTHER INFORMATION: T in position 22,23 and 24 is a lgT6 nucleotide
      analog

<400> SEQUENCE: 101
aacaguguuc uugcucuaua attt                                           24

<210> SEQ ID NO 102
<211> LENGTH: 24
<212> TYPE: RNA
<213> ORGANISM: Artificial Sequence
<220> FEATURE:
<223> OTHER INFORMATION: ss3-3
<220> FEATURE:
<221> NAME/KEY: variation
<222> LOCATION: 1
<223> OTHER INFORMATION: The nucleotide in position 1 and the nucleotide
      in position 2 are linked through a phosphoramidite bond
<220> FEATURE:
<221> NAME/KEY: variation
<222> LOCATION: 1
<223> OTHER INFORMATION: A in position 1 and 21 is a fA nucleotide
      analog
<220> FEATURE:
<221> NAME/KEY: variation
<222> LOCATION: 2
<223> OTHER INFORMATION: The nucleotide in position 1 and the nucleotide
      in position 2 are linked through a phosphoramidite bond
<220> FEATURE:
<221> NAME/KEY: variation
<222> LOCATION: 2
<223> OTHER INFORMATION: The nucleotide in position 2 and the nucleotide
      in position 3 are linked through a phosphoramidite bond
<220> FEATURE:
<221> NAME/KEY: variation
<222> LOCATION: 2
<223> OTHER INFORMATION: A in position 2,4,18 and 20 represents a mA
      nucleotide analog
<220> FEATURE:
<221> NAME/KEY: variation
<222> LOCATION: 3
<223> OTHER INFORMATION: The nucleotide in position 2 and the nucleotide
      in position 3 are linked through a phosphoramidite bond
<220> FEATURE:
<221> NAME/KEY: variation
<222> LOCATION: 3
<223> OTHER INFORMATION: C in position 3 and 10 is a fC nucleotide
      analog
<220> FEATURE:
<221> NAME/KEY: variation
<222> LOCATION: 4
<223> OTHER INFORMATION: A in position 2,4,18 and 20 represents a mA
      nucleotide analog
<220> FEATURE:
<221> NAME/KEY: variation
<222> LOCATION: 5
<223> OTHER INFORMATION: G in position 5,7 and 13 is a fG nucleotide
      analog
<220> FEATURE:
<221> NAME/KEY: variation
<222> LOCATION: 6
<223> OTHER INFORMATION: U in position 6,8 and 12 represents a 2'-O-
      methyl-uracile (mU)
<220> FEATURE:
<221> NAME/KEY: variation
<222> LOCATION: 7
<223> OTHER INFORMATION: G in position 5,7 and 13 is a fG nucleotide
      analog
<220> FEATURE:
<221> NAME/KEY: variation
<222> LOCATION: 8
<223> OTHER INFORMATION: U in position 6,8 and 12 represents a 2'-O-
```

```
      methyl-uracile (mU)
<220> FEATURE:
<221> NAME/KEY: variation
<222> LOCATION: 9
<223> OTHER INFORMATION: U in position 9,11,15,17 and 19 is a fU
      nucleotide analog
<220> FEATURE:
<221> NAME/KEY: variation
<222> LOCATION: 10
<223> OTHER INFORMATION: C in position 3 and 10 is a fC nucleotide
      analog
<220> FEATURE:
<221> NAME/KEY: variation
<222> LOCATION: 11
<223> OTHER INFORMATION: U in position 9,11,15,17 and 19 is a fU
      nucleotide analog
<220> FEATURE:
<221> NAME/KEY: variation
<222> LOCATION: 12
<223> OTHER INFORMATION: U in position 6,8 and 12 represents a 2'-O-
      methyl-uracile (mU)
<220> FEATURE:
<221> NAME/KEY: variation
<222> LOCATION: 13
<223> OTHER INFORMATION: G in position 5,7 and 13 is a fG nucleotide
      analog
<220> FEATURE:
<221> NAME/KEY: variation
<222> LOCATION: 14
<223> OTHER INFORMATION: C in position 14 and 16 represents a mC
      nucleotide analog
<220> FEATURE:
<221> NAME/KEY: variation
<222> LOCATION: 15
<223> OTHER INFORMATION: U in position 9,11,15,17 and 19 is a fU
      nucleotide analog
<220> FEATURE:
<221> NAME/KEY: variation
<222> LOCATION: 16
<223> OTHER INFORMATION: C in position 14 and 16 represents a mC
      nucleotide analog
<220> FEATURE:
<221> NAME/KEY: variation
<222> LOCATION: 17
<223> OTHER INFORMATION: U in position 9,11,15,17 and 19 is a fU
      nucleotide analog
<220> FEATURE:
<221> NAME/KEY: variation
<222> LOCATION: 18
<223> OTHER INFORMATION: A in position 2,4,18 and 20 represents a mA
      nucleotide analog
<220> FEATURE:
<221> NAME/KEY: variation
<222> LOCATION: 19
<223> OTHER INFORMATION: U in position 9,11,15,17 and 19 is a fU
      nucleotide analog
<220> FEATURE:
<221> NAME/KEY: variation
<222> LOCATION: 20
<223> OTHER INFORMATION: A in position 2,4,18 and 20 represents a mA
      nucleotide analog
<220> FEATURE:
<221> NAME/KEY: variation
<222> LOCATION: 21
<223> OTHER INFORMATION: A in position 1 and 21 is a fA nucleotide
      analog
<220> FEATURE:
<221> NAME/KEY: variation
<222> LOCATION: 22
<223> OTHER INFORMATION: T in position 22,23 and 24 is a lgT7 nucleotide
      analog
<220> FEATURE:
<221> NAME/KEY: variation
<222> LOCATION: 23
<223> OTHER INFORMATION: T in position 22,23 and 24 is a lgT7 nucleotide
      analog
<220> FEATURE:
<221> NAME/KEY: variation
<222> LOCATION: 24
```

```
<223> OTHER INFORMATION: T in position 22,23 and 24 is a lgT7 nucleotide
      analog

<400> SEQUENCE: 102
aacaguguuc uugcucuaua attt                                              24

<210> SEQ ID NO 103
<211> LENGTH: 24
<212> TYPE: RNA
<213> ORGANISM: Artificial Sequence
<220> FEATURE:
<223> OTHER INFORMATION: ss3-4
<220> FEATURE:
<221> NAME/KEY: variation
<222> LOCATION: 1
<223> OTHER INFORMATION: The nucleotide in position 1 and the nucleotide
      in position 2 are linked through a phosphoramidite bond
<220> FEATURE:
<221> NAME/KEY: variation
<222> LOCATION: 1
<223> OTHER INFORMATION: A in position 1 and 21 is a fA nucleotide
      analog
<220> FEATURE:
<221> NAME/KEY: variation
<222> LOCATION: 2
<223> OTHER INFORMATION: The nucleotide in position 1 and the nucleotide
      in position 2 are linked through a phosphoramidite bond
<220> FEATURE:
<221> NAME/KEY: variation
<222> LOCATION: 2
<223> OTHER INFORMATION: The nucleotide in position 2 and the nucleotide
      in position 3 are linked through a phosphoramidite bond
<220> FEATURE:
<221> NAME/KEY: variation
<222> LOCATION: 2
<223> OTHER INFORMATION: A in position 2,4,18 and 20 represents a mA
      nucleotide analog
<220> FEATURE:
<221> NAME/KEY: variation
<222> LOCATION: 3
<223> OTHER INFORMATION: The nucleotide in position 2 and the nucleotide
      in position 3 are linked through a phosphoramidite bond
<220> FEATURE:
<221> NAME/KEY: variation
<222> LOCATION: 3
<223> OTHER INFORMATION: C in position 3 and 10 is a fC nucleotide
      analog
<220> FEATURE:
<221> NAME/KEY: variation
<222> LOCATION: 4
<223> OTHER INFORMATION: A in position 2,4,18 and 20 represents a mA
      nucleotide analog
<220> FEATURE:
<221> NAME/KEY: variation
<222> LOCATION: 5
<223> OTHER INFORMATION: G in position 5,7 and 13 is a fG nucleotide
      analog
<220> FEATURE:
<221> NAME/KEY: variation
<222> LOCATION: 6
<223> OTHER INFORMATION: U in position 6,8 and 12 represents a 2'-O-
      methyl-uracile (mU)
<220> FEATURE:
<221> NAME/KEY: variation
<222> LOCATION: 7
<223> OTHER INFORMATION: G in position 5,7 and 13 is a fG nucleotide
      analog
<220> FEATURE:
<221> NAME/KEY: variation
<222> LOCATION: 8
<223> OTHER INFORMATION: U in position 6,8 and 12 represents a 2'-O-
      methyl-uracile (mU)
<220> FEATURE:
<221> NAME/KEY: variation
<222> LOCATION: 9
<223> OTHER INFORMATION: U in position 9,11,15,17 and 19 is a fU
      nucleotide analog
```

```
<220> FEATURE:
<221> NAME/KEY: variation
<222> LOCATION: 10
<223> OTHER INFORMATION: C in position 3 and 10 is a fC nucleotide
      analog
<220> FEATURE:
<221> NAME/KEY: variation
<222> LOCATION: 11
<223> OTHER INFORMATION: U in position 9,11,15,17 and 19 is a fU
      nucleotide analog
<220> FEATURE:
<221> NAME/KEY: variation
<222> LOCATION: 12
<223> OTHER INFORMATION: U in position 6,8 and 12 represents a 2'-O-
      methyl-uracile (mU)
<220> FEATURE:
<221> NAME/KEY: variation
<222> LOCATION: 13
<223> OTHER INFORMATION: G in position 5,7 and 13 is a fG nucleotide
      analog
<220> FEATURE:
<221> NAME/KEY: variation
<222> LOCATION: 14
<223> OTHER INFORMATION: C in position 14 and 16 represents a mC
      nucleotide analog
<220> FEATURE:
<221> NAME/KEY: variation
<222> LOCATION: 15
<223> OTHER INFORMATION: U in position 9,11,15,17 and 19 is a fU
      nucleotide analog
<220> FEATURE:
<221> NAME/KEY: variation
<222> LOCATION: 16
<223> OTHER INFORMATION: C in position 14 and 16 represents a mC
      nucleotide analog
<220> FEATURE:
<221> NAME/KEY: variation
<222> LOCATION: 17
<223> OTHER INFORMATION: U in position 9,11,15,17 and 19 is a fU
      nucleotide analog
<220> FEATURE:
<221> NAME/KEY: variation
<222> LOCATION: 18
<223> OTHER INFORMATION: A in position 2,4,18 and 20 represents a mA
      nucleotide analog
<220> FEATURE:
<221> NAME/KEY: variation
<222> LOCATION: 19
<223> OTHER INFORMATION: U in position 9,11,15,17 and 19 is a fU
      nucleotide analog
<220> FEATURE:
<221> NAME/KEY: variation
<222> LOCATION: 20
<223> OTHER INFORMATION: A in position 2,4,18 and 20 represents a mA
      nucleotide analog
<220> FEATURE:
<221> NAME/KEY: variation
<222> LOCATION: 21
<223> OTHER INFORMATION: A in position 1 and 21 is a fA nucleotide
      analog
<220> FEATURE:
<221> NAME/KEY: variation
<222> LOCATION: 22
<223> OTHER INFORMATION: T in position 22,23 and 24 is a lgT8 nucleotide
      analog
<220> FEATURE:
<221> NAME/KEY: variation
<222> LOCATION: 23
<223> OTHER INFORMATION: T in position 22,23 and 24 is a lgT8 nucleotide
      analog
<220> FEATURE:
<221> NAME/KEY: variation
<222> LOCATION: 24
<223> OTHER INFORMATION: T in position 22,23 and 24 is a lgT8 nucleotide
      analog

<400> SEQUENCE: 103
aacaguguuc uugcucuaua attt                                              24
```

```
<210> SEQ ID NO 104
<211> LENGTH: 24
<212> TYPE: RNA
<213> ORGANISM: Artificial Sequence
<220> FEATURE:
<223> OTHER INFORMATION: ss3-5
<220> FEATURE:
<221> NAME/KEY: variation
<222> LOCATION: 1
<223> OTHER INFORMATION: The nucleotide in position 1 and the nucleotide
      in position 2 are linked through a phosphoramidite bond
<220> FEATURE:
<221> NAME/KEY: variation
<222> LOCATION: 1
<223> OTHER INFORMATION: A in position 1 and 21 is a fA nucleotide
      analog
<220> FEATURE:
<221> NAME/KEY: variation
<222> LOCATION: 2
<223> OTHER INFORMATION: The nucleotide in position 1 and the nucleotide
      in position 2 are linked through a phosphoramidite bond
<220> FEATURE:
<221> NAME/KEY: variation
<222> LOCATION: 2
<223> OTHER INFORMATION: The nucleotide in position 2 and the nucleotide
      in position 3 are linked through a phosphoramidite bond
<220> FEATURE:
<221> NAME/KEY: variation
<222> LOCATION: 2
<223> OTHER INFORMATION: A in position 2,4,18 and 20 represents a mA
      nucleotide analog
<220> FEATURE:
<221> NAME/KEY: variation
<222> LOCATION: 3
<223> OTHER INFORMATION: The nucleotide in position 2 and the nucleotide
      in position 3 are linked through a phosphoramidite bond
<220> FEATURE:
<221> NAME/KEY: variation
<222> LOCATION: 3
<223> OTHER INFORMATION: C in position 3 and 10 is a fC nucleotide
      analog
<220> FEATURE:
<221> NAME/KEY: variation
<222> LOCATION: 4
<223> OTHER INFORMATION: A in position 2,4,18 and 20 represents a mA
      nucleotide analog
<220> FEATURE:
<221> NAME/KEY: variation
<222> LOCATION: 5
<223> OTHER INFORMATION: G in position 5,7 and 13 is a fG nucleotide
      analog
<220> FEATURE:
<221> NAME/KEY: variation
<222> LOCATION: 6
<223> OTHER INFORMATION: U in position 6,8 and 12 represents a 2'-O-
      methyl-uracile (mU)
<220> FEATURE:
<221> NAME/KEY: variation
<222> LOCATION: 7
<223> OTHER INFORMATION: G in position 5,7 and 13 is a fG nucleotide
      analog
<220> FEATURE:
<221> NAME/KEY: variation
<222> LOCATION: 8
<223> OTHER INFORMATION: U in position 6,8 and 12 represents a 2'-O-
      methyl-uracile (mU)
<220> FEATURE:
<221> NAME/KEY: variation
<222> LOCATION: 9
<223> OTHER INFORMATION: U in position 9,11,15,17 and 19 is a fU
      nucleotide analog
<220> FEATURE:
<221> NAME/KEY: variation
<222> LOCATION: 10
<223> OTHER INFORMATION: C in position 3 and 10 is a fC nucleotide
      analog
<220> FEATURE:
```

```
<221> NAME/KEY: variation
<222> LOCATION: 11
<223> OTHER INFORMATION: U in position 9,11,15,17 and 19 is a fU
      nucleotide analog
<220> FEATURE:
<221> NAME/KEY: variation
<222> LOCATION: 12
<223> OTHER INFORMATION: U in position 6,8 and 12 represents a 2'-O-
      methyl-uracile (mU)
<220> FEATURE:
<221> NAME/KEY: variation
<222> LOCATION: 13
<223> OTHER INFORMATION: G in position 5,7 and 13 is a fG nucleotide
      analog
<220> FEATURE:
<221> NAME/KEY: variation
<222> LOCATION: 14
<223> OTHER INFORMATION: C in position 14 and 16 represents a mC
      nucleotide analog
<220> FEATURE:
<221> NAME/KEY: variation
<222> LOCATION: 15
<223> OTHER INFORMATION: U in position 9,11,15,17 and 19 is a fU
      nucleotide analog
<220> FEATURE:
<221> NAME/KEY: variation
<222> LOCATION: 16
<223> OTHER INFORMATION: C in position 14 and 16 represents a mC
      nucleotide analog
<220> FEATURE:
<221> NAME/KEY: variation
<222> LOCATION: 17
<223> OTHER INFORMATION: U in position 9,11,15,17 and 19 is a fU
      nucleotide analog
<220> FEATURE:
<221> NAME/KEY: variation
<222> LOCATION: 18
<223> OTHER INFORMATION: A in position 2,4,18 and 20 represents a mA
      nucleotide analog
<220> FEATURE:
<221> NAME/KEY: variation
<222> LOCATION: 19
<223> OTHER INFORMATION: U in position 9,11,15,17 and 19 is a fU
      nucleotide analog
<220> FEATURE:
<221> NAME/KEY: variation
<222> LOCATION: 20
<223> OTHER INFORMATION: A in position 2,4,18 and 20 represents a mA
      nucleotide analog
<220> FEATURE:
<221> NAME/KEY: variation
<222> LOCATION: 21
<223> OTHER INFORMATION: A in position 1 and 21 is a fA nucleotide
      analog
<220> FEATURE:
<221> NAME/KEY: variation
<222> LOCATION: 22
<223> OTHER INFORMATION: T in position 22,23 and 24 is a lgT9 nucleotide
      analog
<220> FEATURE:
<221> NAME/KEY: variation
<222> LOCATION: 23
<223> OTHER INFORMATION: T in position 22,23 and 24 is a lgT9 nucleotide
      analog
<220> FEATURE:
<221> NAME/KEY: variation
<222> LOCATION: 24
<223> OTHER INFORMATION: T in position 22,23 and 24 is a lgT9 nucleotide
      analog

<400> SEQUENCE: 104
aacaguguuc uugcucuaua attt                                            24

<210> SEQ ID NO 105
<211> LENGTH: 24
<212> TYPE: RNA
<213> ORGANISM: Artificial Sequence
```

```
<220> FEATURE:
<223> OTHER INFORMATION: ss3-6
<220> FEATURE:
<221> NAME/KEY: variation
<222> LOCATION: 1
<223> OTHER INFORMATION: T in position 1,2 and 3 is a lgT5 nucleotide
      analog
<220> FEATURE:
<221> NAME/KEY: variation
<222> LOCATION: 2
<223> OTHER INFORMATION: T in position 1,2 and 3 is a lgT5 nucleotide
      analog
<220> FEATURE:
<221> NAME/KEY: variation
<222> LOCATION: 3
<223> OTHER INFORMATION: T in position 1,2 and 3 is a lgT5 nucleotide
      analog
<220> FEATURE:
<221> NAME/KEY: variation
<222> LOCATION: 4
<223> OTHER INFORMATION: A in position 4 and 24 is a fA nucleotide
      analog
<220> FEATURE:
<221> NAME/KEY: variation
<222> LOCATION: 5
<223> OTHER INFORMATION: A in position 5,7,21 and 23 represents a mA
      nucleotide analog
<220> FEATURE:
<221> NAME/KEY: variation
<222> LOCATION: 6
<223> OTHER INFORMATION: C in position 6 and 13 is a fC nucleotide
      analog
<220> FEATURE:
<221> NAME/KEY: variation
<222> LOCATION: 7
<223> OTHER INFORMATION: A in position 5,7,21 and 23 represents a mA
      nucleotide analog
<220> FEATURE:
<221> NAME/KEY: variation
<222> LOCATION: 8
<223> OTHER INFORMATION: G in position 8,10 and 16 is a fG nucleotide
      analog
<220> FEATURE:
<221> NAME/KEY: variation
<222> LOCATION: 9
<223> OTHER INFORMATION: U in position 9,11 and 15 represents a 2'-O-
      methyl-uracile (mU)
<220> FEATURE:
<221> NAME/KEY: variation
<222> LOCATION: 10
<223> OTHER INFORMATION: G in position 8,10 and 16 is a fG nucleotide
      analog
<220> FEATURE:
<221> NAME/KEY: variation
<222> LOCATION: 11
<223> OTHER INFORMATION: U in position 9,11 and 15 represents a 2'-O-
      methyl-uracile (mU)
<220> FEATURE:
<221> NAME/KEY: variation
<222> LOCATION: 12
<223> OTHER INFORMATION: U in position 12,14,18,20 and 22 is a fU
      nucleotide analog
<220> FEATURE:
<221> NAME/KEY: variation
<222> LOCATION: 13
<223> OTHER INFORMATION: C in position 6 and 13 is a fC nucleotide
      analog
<220> FEATURE:
<221> NAME/KEY: variation
<222> LOCATION: 14
<223> OTHER INFORMATION: U in position 12,14,18,20 and 22 is a fU
      nucleotide analog
<220> FEATURE:
<221> NAME/KEY: variation
<222> LOCATION: 15
<223> OTHER INFORMATION: U in position 9,11 and 15 represents a 2'-O-
      methyl-uracile (mU)
<220> FEATURE:
<221> NAME/KEY: variation
```

```
<222> LOCATION: 16
<223> OTHER INFORMATION: G in position 8,10 and 16 is a fG nucleotide
      analog
<220> FEATURE:
<221> NAME/KEY: variation
<222> LOCATION: 17
<223> OTHER INFORMATION: C in position 17 and 19 represents a mC
      nucleotide analog
<220> FEATURE:
<221> NAME/KEY: variation
<222> LOCATION: 18
<223> OTHER INFORMATION: U in position 12,14,18,20 and 22 is a fU
      nucleotide analog
<220> FEATURE:
<221> NAME/KEY: variation
<222> LOCATION: 19
<223> OTHER INFORMATION: C in position 17 and 19 represents a mC
      nucleotide analog
<220> FEATURE:
<221> NAME/KEY: variation
<222> LOCATION: 20
<223> OTHER INFORMATION: U in position 12,14,18,20 and 22 is a fU
      nucleotide analog
<220> FEATURE:
<221> NAME/KEY: variation
<222> LOCATION: 21
<223> OTHER INFORMATION: A in position 5,7,21 and 23 represents a mA
      nucleotide analog
<220> FEATURE:
<221> NAME/KEY: variation
<222> LOCATION: 22
<223> OTHER INFORMATION: U in position 12,14,18,20 and 22 is a fU
      nucleotide analog
<220> FEATURE:
<221> NAME/KEY: variation
<222> LOCATION: 22
<223> OTHER INFORMATION: The nucleotide in position 22 and the
      nucleotide in position 23 are linked through a phosphoramidite
      bond
<220> FEATURE:
<221> NAME/KEY: variation
<222> LOCATION: 23
<223> OTHER INFORMATION: A in position 5,7,21 and 23 represents a mA
      nucleotide analog
<220> FEATURE:
<221> NAME/KEY: variation
<222> LOCATION: 23
<223> OTHER INFORMATION: The nucleotide in position 22 and the
      nucleotide in position 23 are linked through a phosphoramidite
      bond
<220> FEATURE:
<221> NAME/KEY: variation
<222> LOCATION: 23
<223> OTHER INFORMATION: The nucleotide in position 23 and the
      nucleotide in position 24 are linked through a phosphoramidite
      bond
<220> FEATURE:
<221> NAME/KEY: variation
<222> LOCATION: 24
<223> OTHER INFORMATION: A in position 4 and 24 is a fA nucleotide
      analog
<220> FEATURE:
<221> NAME/KEY: variation
<222> LOCATION: 24
<223> OTHER INFORMATION: The nucleotide in position 23 and the
      nucleotide in position 24 are linked through a phosphoramidite
      bond

<400> SEQUENCE: 105
tttaacagug uucuugcucu auaa                                            24

<210> SEQ ID NO 106
<211> LENGTH: 24
<212> TYPE: RNA
<213> ORGANISM: Artificial Sequence
<220> FEATURE:
<223> OTHER INFORMATION: ss3-7
```

-continued

```
<220> FEATURE:
<221> NAME/KEY: variation
<222> LOCATION: 1
<223> OTHER INFORMATION: T in position 1,2 and 3 is a lgT6 nucleotide
      analog
<220> FEATURE:
<221> NAME/KEY: variation
<222> LOCATION: 2
<223> OTHER INFORMATION: T in position 1,2 and 3 is a lgT6 nucleotide
      analog
<220> FEATURE:
<221> NAME/KEY: variation
<222> LOCATION: 3
<223> OTHER INFORMATION: T in position 1,2 and 3 is a lgT6 nucleotide
      analog
<220> FEATURE:
<221> NAME/KEY: variation
<222> LOCATION: 4
<223> OTHER INFORMATION: A in position 4 and 24 is a fA nucleotide
      analog
<220> FEATURE:
<221> NAME/KEY: variation
<222> LOCATION: 5
<223> OTHER INFORMATION: A in position 5,7,21 and 23 represents a mA
      nucleotide analog
<220> FEATURE:
<221> NAME/KEY: variation
<222> LOCATION: 6
<223> OTHER INFORMATION: C in position 6 and 13 is a fC nucleotide
      analog
<220> FEATURE:
<221> NAME/KEY: variation
<222> LOCATION: 7
<223> OTHER INFORMATION: A in position 5,7,21 and 23 represents a mA
      nucleotide analog
<220> FEATURE:
<221> NAME/KEY: variation
<222> LOCATION: 8
<223> OTHER INFORMATION: G in position 8,10 and 16 is a fG nucleotide
      analog
<220> FEATURE:
<221> NAME/KEY: variation
<222> LOCATION: 9
<223> OTHER INFORMATION: U in position 9,11 and 15 represents a 2'-O-
      methyl-uracile (mU)
<220> FEATURE:
<221> NAME/KEY: variation
<222> LOCATION: 10
<223> OTHER INFORMATION: G in position 8,10 and 16 is a fG nucleotide
      analog
<220> FEATURE:
<221> NAME/KEY: variation
<222> LOCATION: 11
<223> OTHER INFORMATION: U in position 9,11 and 15 represents a 2'-O-
      methyl-uracile (mU)
<220> FEATURE:
<221> NAME/KEY: variation
<222> LOCATION: 12
<223> OTHER INFORMATION: U in position 12,14,18,20 and 22 is a fU
      nucleotide analog
<220> FEATURE:
<221> NAME/KEY: variation
<222> LOCATION: 13
<223> OTHER INFORMATION: C in position 6 and 13 is a fC nucleotide
      analog
<220> FEATURE:
<221> NAME/KEY: variation
<222> LOCATION: 14
<223> OTHER INFORMATION: U in position 12,14,18,20 and 22 is a fU
      nucleotide analog
<220> FEATURE:
<221> NAME/KEY: variation
<222> LOCATION: 15
<223> OTHER INFORMATION: U in position 9,11 and 15 represents a 2'-O-
      methyl-uracile (mU)
<220> FEATURE:
<221> NAME/KEY: variation
<222> LOCATION: 16
<223> OTHER INFORMATION: G in position 8,10 and 16 is a fG nucleotide
```

```
        analog
<220> FEATURE:
<221> NAME/KEY: variation
<222> LOCATION: 17
<223> OTHER INFORMATION: C in position 17 and 19 represents a mC
      nucleotide analog
<220> FEATURE:
<221> NAME/KEY: variation
<222> LOCATION: 18
<223> OTHER INFORMATION: U in position 12,14,18,20 and 22 is a fU
      nucleotide analog
<220> FEATURE:
<221> NAME/KEY: variation
<222> LOCATION: 19
<223> OTHER INFORMATION: C in position 17 and 19 represents a mC
      nucleotide analog
<220> FEATURE:
<221> NAME/KEY: variation
<222> LOCATION: 20
<223> OTHER INFORMATION: U in position 12,14,18,20 and 22 is a fU
      nucleotide analog
<220> FEATURE:
<221> NAME/KEY: variation
<222> LOCATION: 21
<223> OTHER INFORMATION: A in position 5,7,21 and 23 represents a mA
      nucleotide analog
<220> FEATURE:
<221> NAME/KEY: variation
<222> LOCATION: 22
<223> OTHER INFORMATION: U in position 12,14,18,20 and 22 is a fU
      nucleotide analog
<220> FEATURE:
<221> NAME/KEY: variation
<222> LOCATION: 22
<223> OTHER INFORMATION: The nucleotide in position 22 and the
      nucleotide in position 23 are linked through a phosphoramidite
      bond
<220> FEATURE:
<221> NAME/KEY: variation
<222> LOCATION: 23
<223> OTHER INFORMATION: A in position 5,7,21 and 23 represents a mA
      nucleotide analog
<220> FEATURE:
<221> NAME/KEY: variation
<222> LOCATION: 23
<223> OTHER INFORMATION: The nucleotide in position 22 and the
      nucleotide in position 23 are linked through a phosphoramidite
      bond
<220> FEATURE:
<221> NAME/KEY: variation
<222> LOCATION: 23
<223> OTHER INFORMATION: The nucleotide in position 23 and the
      nucleotide in position 24 are linked through a phosphoramidite
      bond
<220> FEATURE:
<221> NAME/KEY: variation
<222> LOCATION: 24
<223> OTHER INFORMATION: A in position 4 and 24 is a fA nucleotide
      analog
<220> FEATURE:
<221> NAME/KEY: variation
<222> LOCATION: 24
<223> OTHER INFORMATION: The nucleotide in position 23 and the
      nucleotide in position 24 are linked through a phosphoramidite
      bond

<400> SEQUENCE: 106
tttaacagug uucuugcucu auaa                                          24

<210> SEQ ID NO 107
<211> LENGTH: 24
<212> TYPE: RNA
<213> ORGANISM: Artificial Sequence
<220> FEATURE:
<223> OTHER INFORMATION: ss3-8
<220> FEATURE:
<221> NAME/KEY: variation
```

```
<222> LOCATION: 1
<223> OTHER INFORMATION: T in position 1,2 and 3 is a lgT7 nucleotide
      analog
<220> FEATURE:
<221> NAME/KEY: variation
<222> LOCATION: 2
<223> OTHER INFORMATION: T in position 1,2 and 3 is a lgT7 nucleotide
      analog
<220> FEATURE:
<221> NAME/KEY: variation
<222> LOCATION: 3
<223> OTHER INFORMATION: T in position 1,2 and 3 is a lgT7 nucleotide
      analog
<220> FEATURE:
<221> NAME/KEY: variation
<222> LOCATION: 4
<223> OTHER INFORMATION: A in position 4 and 24 is a fA nucleotide
      analog
<220> FEATURE:
<221> NAME/KEY: variation
<222> LOCATION: 5
<223> OTHER INFORMATION: A in position 5,7,21 and 23 represents a mA
      nucleotide analog
<220> FEATURE:
<221> NAME/KEY: variation
<222> LOCATION: 6
<223> OTHER INFORMATION: C in position 6 and 13 is a fC nucleotide
      analog
<220> FEATURE:
<221> NAME/KEY: variation
<222> LOCATION: 7
<223> OTHER INFORMATION: A in position 5,7,21 and 23 represents a mA
      nucleotide analog
<220> FEATURE:
<221> NAME/KEY: variation
<222> LOCATION: 8
<223> OTHER INFORMATION: G in position 8,10 and 16 is a fG nucleotide
      analog
<220> FEATURE:
<221> NAME/KEY: variation
<222> LOCATION: 9
<223> OTHER INFORMATION: U in position 9,11 and 15 represents a 2'-O-
      methyl-uracile (mU)
<220> FEATURE:
<221> NAME/KEY: variation
<222> LOCATION: 10
<223> OTHER INFORMATION: G in position 8,10 and 16 is a fG nucleotide
      analog
<220> FEATURE:
<221> NAME/KEY: variation
<222> LOCATION: 11
<223> OTHER INFORMATION: U in position 9,11 and 15 represents a 2'-O-
      methyl-uracile (mU)
<220> FEATURE:
<221> NAME/KEY: variation
<222> LOCATION: 12
<223> OTHER INFORMATION: U in position 12,14,18,20 and 22 is a fU
      nucleotide analog
<220> FEATURE:
<221> NAME/KEY: variation
<222> LOCATION: 13
<223> OTHER INFORMATION: C in position 6 and 13 is a fC nucleotide
      analog
<220> FEATURE:
<221> NAME/KEY: variation
<222> LOCATION: 14
<223> OTHER INFORMATION: U in position 12,14,18,20 and 22 is a fU
      nucleotide analog
<220> FEATURE:
<221> NAME/KEY: variation
<222> LOCATION: 15
<223> OTHER INFORMATION: U in position 9,11 and 15 represents a 2'-O-
      methyl-uracile (mU)
<220> FEATURE:
<221> NAME/KEY: variation
<222> LOCATION: 16
<223> OTHER INFORMATION: G in position 8,10 and 16 is a fG nucleotide
      analog
<220> FEATURE:
```

```
<221> NAME/KEY: variation
<222> LOCATION: 17
<223> OTHER INFORMATION: C in position 17 and 19 represents a mC
      nucleotide analog
<220> FEATURE:
<221> NAME/KEY: variation
<222> LOCATION: 18
<223> OTHER INFORMATION: U in position 12,14,18,20 and 22 is a fU
      nucleotide analog
<220> FEATURE:
<221> NAME/KEY: variation
<222> LOCATION: 19
<223> OTHER INFORMATION: C in position 17 and 19 represents a mC
      nucleotide analog
<220> FEATURE:
<221> NAME/KEY: variation
<222> LOCATION: 20
<223> OTHER INFORMATION: U in position 12,14,18,20 and 22 is a fU
      nucleotide analog
<220> FEATURE:
<221> NAME/KEY: variation
<222> LOCATION: 21
<223> OTHER INFORMATION: A in position 5,7,21 and 23 represents a mA
      nucleotide analog
<220> FEATURE:
<221> NAME/KEY: variation
<222> LOCATION: 22
<223> OTHER INFORMATION: U in position 12,14,18,20 and 22 is a fU
      nucleotide analog
<220> FEATURE:
<221> NAME/KEY: variation
<222> LOCATION: 22
<223> OTHER INFORMATION: The nucleotide in position 22 and the
      nucleotide in position 23 are linked through a phosphoramidite
      bond
<220> FEATURE:
<221> NAME/KEY: variation
<222> LOCATION: 23
<223> OTHER INFORMATION: A in position 5,7,21 and 23 represents a mA
      nucleotide analog
<220> FEATURE:
<221> NAME/KEY: variation
<222> LOCATION: 23
<223> OTHER INFORMATION: The nucleotide in position 22 and the
      nucleotide in position 23 are linked through a phosphoramidite
      bond
<220> FEATURE:
<221> NAME/KEY: variation
<222> LOCATION: 23
<223> OTHER INFORMATION: The nucleotide in position 23 and the
      nucleotide in position 24 are linked through a phosphoramidite
      bond
<220> FEATURE:
<221> NAME/KEY: variation
<222> LOCATION: 24
<223> OTHER INFORMATION: A in position 4 and 24 is a fA nucleotide
      analog
<220> FEATURE:
<221> NAME/KEY: variation
<222> LOCATION: 24
<223> OTHER INFORMATION: The nucleotide in position 23 and the
      nucleotide in position 24 are linked through a phosphoramidite
      bond

<400> SEQUENCE: 107
tttaacagug uucuugcucu auaa                                         24

<210> SEQ ID NO 108
<211> LENGTH: 24
<212> TYPE: RNA
<213> ORGANISM: Artificial Sequence
<220> FEATURE:
<223> OTHER INFORMATION: ss3-9
<220> FEATURE:
<221> NAME/KEY: variation
<222> LOCATION: 1
<223> OTHER INFORMATION: T in position 1,2 and 3 is a lgT8 nucleotide
``` analog
<220> FEATURE:
<221> NAME/KEY: variation
<222> LOCATION: 2
<223> OTHER INFORMATION: T in position 1,2 and 3 is a lgT8 nucleotide
      analog
<220> FEATURE:
<221> NAME/KEY: variation
<222> LOCATION: 3
<223> OTHER INFORMATION: T in position 1,2 and 3 is a lgT8 nucleotide
      analog
<220> FEATURE:
<221> NAME/KEY: variation
<222> LOCATION: 4
<223> OTHER INFORMATION: A in position 4 and 24 is a fA nucleotide
      analog
<220> FEATURE:
<221> NAME/KEY: variation
<222> LOCATION: 5
<223> OTHER INFORMATION: A in position 5,7,21 and 23 represents a mA
      nucleotide analog
<220> FEATURE:
<221> NAME/KEY: variation
<222> LOCATION: 6
<223> OTHER INFORMATION: C in position 6 and 13 is a fC nucleotide
      analog
<220> FEATURE:
<221> NAME/KEY: variation
<222> LOCATION: 7
<223> OTHER INFORMATION: A in position 5,7,21 and 23 represents a mA
      nucleotide analog
<220> FEATURE:
<221> NAME/KEY: variation
<222> LOCATION: 8
<223> OTHER INFORMATION: G in position 8,10 and 16 is a fG nucleotide
      analog
<220> FEATURE:
<221> NAME/KEY: variation
<222> LOCATION: 9
<223> OTHER INFORMATION: U in position 9,11 and 15 represents a 2'-O-
      methyl-uracile (mU)
<220> FEATURE:
<221> NAME/KEY: variation
<222> LOCATION: 10
<223> OTHER INFORMATION: G in position 8,10 and 16 is a fG nucleotide
      analog
<220> FEATURE:
<221> NAME/KEY: variation
<222> LOCATION: 11
<223> OTHER INFORMATION: U in position 9,11 and 15 represents a 2'-O-
      methyl-uracile (mU)
<220> FEATURE:
<221> NAME/KEY: variation
<222> LOCATION: 12
<223> OTHER INFORMATION: U in position 12,14,18,20 and 22 is a fU
      nucleotide analog
<220> FEATURE:
<221> NAME/KEY: variation
<222> LOCATION: 13
<223> OTHER INFORMATION: C in position 6 and 13 is a fC nucleotide
      analog
<220> FEATURE:
<221> NAME/KEY: variation
<222> LOCATION: 14
<223> OTHER INFORMATION: U in position 12,14,18,20 and 22 is a fU
      nucleotide analog
<220> FEATURE:
<221> NAME/KEY: variation
<222> LOCATION: 15
<223> OTHER INFORMATION: U in position 9,11 and 15 represents a 2'-O-
      methyl-uracile (mU)
<220> FEATURE:
<221> NAME/KEY: variation
<222> LOCATION: 16
<223> OTHER INFORMATION: G in position 8,10 and 16 is a fG nucleotide
      analog
<220> FEATURE:
<221> NAME/KEY: variation
<222> LOCATION: 17

<223> OTHER INFORMATION: C in position 17 and 19 represents a mC
       nucleotide analog
<220> FEATURE:
<221> NAME/KEY: variation
<222> LOCATION: 18
<223> OTHER INFORMATION: U in position 12,14,18,20 and 22 is a fU
       nucleotide analog
<220> FEATURE:
<221> NAME/KEY: variation
<222> LOCATION: 19
<223> OTHER INFORMATION: C in position 17 and 19 represents a mC
       nucleotide analog
<220> FEATURE:
<221> NAME/KEY: variation
<222> LOCATION: 20
<223> OTHER INFORMATION: U in position 12,14,18,20 and 22 is a fU
       nucleotide analog
<220> FEATURE:
<221> NAME/KEY: variation
<222> LOCATION: 21
<223> OTHER INFORMATION: A in position 5,7,21 and 23 represents a mA
       nucleotide analog
<220> FEATURE:
<221> NAME/KEY: variation
<222> LOCATION: 22
<223> OTHER INFORMATION: U in position 12,14,18,20 and 22 is a fU
       nucleotide analog
<220> FEATURE:
<221> NAME/KEY: variation
<222> LOCATION: 22
<223> OTHER INFORMATION: The nucleotide in position 22 and the
       nucleotide in position 23 are linked through a phosphoramidite
       bond
<220> FEATURE:
<221> NAME/KEY: variation
<222> LOCATION: 23
<223> OTHER INFORMATION: A in position 5,7,21 and 23 represents a mA
       nucleotide analog
<220> FEATURE:
<221> NAME/KEY: variation
<222> LOCATION: 23
<223> OTHER INFORMATION: The nucleotide in position 22 and the
       nucleotide in position 23 are linked through a phosphoramidite
       bond
<220> FEATURE:
<221> NAME/KEY: variation
<222> LOCATION: 23
<223> OTHER INFORMATION: The nucleotide in position 23 and the
       nucleotide in position 24 are linked through a phosphoramidite
       bond
<220> FEATURE:
<221> NAME/KEY: variation
<222> LOCATION: 24
<223> OTHER INFORMATION: A in position 4 and 24 is a fA nucleotide
       analog
<220> FEATURE:
<221> NAME/KEY: variation
<222> LOCATION: 24
<223> OTHER INFORMATION: The nucleotide in position 23 and the
       nucleotide in position 24 are linked through a phosphoramidite
       bond

<400> SEQUENCE: 108
tttaacagug uucuugcucu auaa                                           24

<210> SEQ ID NO 109
<211> LENGTH: 24
<212> TYPE: RNA
<213> ORGANISM: Artificial Sequence
<220> FEATURE:
<223> OTHER INFORMATION: ss3-10
<220> FEATURE:
<221> NAME/KEY: variation
<222> LOCATION: 1
<223> OTHER INFORMATION: T in position 1,2 and 3 is a lgT9 nucleotide
       analog
<220> FEATURE:

-continued

```
<221> NAME/KEY: variation
<222> LOCATION: 2
<223> OTHER INFORMATION: T in position 1,2 and 3 is a lgT9 nucleotide
      analog
<220> FEATURE:
<221> NAME/KEY: variation
<222> LOCATION: 3
<223> OTHER INFORMATION: T in position 1,2 and 3 is a lgT9 nucleotide
      analog
<220> FEATURE:
<221> NAME/KEY: variation
<222> LOCATION: 4
<223> OTHER INFORMATION: A in position 4 and 24 is a fA nucleotide
      analog
<220> FEATURE:
<221> NAME/KEY: variation
<222> LOCATION: 5
<223> OTHER INFORMATION: A in position 5,7,21 and 23 represents a mA
      nucleotide analog
<220> FEATURE:
<221> NAME/KEY: variation
<222> LOCATION: 6
<223> OTHER INFORMATION: C in position 6 and 13 is a fC nucleotide
      analog
<220> FEATURE:
<221> NAME/KEY: variation
<222> LOCATION: 7
<223> OTHER INFORMATION: A in position 5,7,21 and 23 represents a mA
      nucleotide analog
<220> FEATURE:
<221> NAME/KEY: variation
<222> LOCATION: 8
<223> OTHER INFORMATION: G in position 8,10 and 16 is a fG nucleotide
      analog
<220> FEATURE:
<221> NAME/KEY: variation
<222> LOCATION: 9
<223> OTHER INFORMATION: U in position 9,11 and 15 represents a 2'-O-
      methyl-uracile (mU)
<220> FEATURE:
<221> NAME/KEY: variation
<222> LOCATION: 10
<223> OTHER INFORMATION: G in position 8,10 and 16 is a fG nucleotide
      analog
<220> FEATURE:
<221> NAME/KEY: variation
<222> LOCATION: 11
<223> OTHER INFORMATION: U in position 9,11 and 15 represents a 2'-O-
      methyl-uracile (mU)
<220> FEATURE:
<221> NAME/KEY: variation
<222> LOCATION: 12
<223> OTHER INFORMATION: U in position 12,14,18,20 and 22 is a fU
      nucleotide analog
<220> FEATURE:
<221> NAME/KEY: variation
<222> LOCATION: 13
<223> OTHER INFORMATION: C in position 6 and 13 is a fC nucleotide
      analog
<220> FEATURE:
<221> NAME/KEY: variation
<222> LOCATION: 14
<223> OTHER INFORMATION: U in position 12,14,18,20 and 22 is a fU
      nucleotide analog
<220> FEATURE:
<221> NAME/KEY: variation
<222> LOCATION: 15
<223> OTHER INFORMATION: U in position 9,11 and 15 represents a 2'-O-
      methyl-uracile (mU)
<220> FEATURE:
<221> NAME/KEY: variation
<222> LOCATION: 16
<223> OTHER INFORMATION: G in position 8,10 and 16 is a fG nucleotide
      analog
<220> FEATURE:
<221> NAME/KEY: variation
<222> LOCATION: 17
<223> OTHER INFORMATION: C in position 17 and 19 represents a mC
      nucleotide analog
```

```
<220> FEATURE:
<221> NAME/KEY: variation
<222> LOCATION: 18
<223> OTHER INFORMATION: U in position 12,14,18,20 and 22 is a fU
      nucleotide analog
<220> FEATURE:
<221> NAME/KEY: variation
<222> LOCATION: 19
<223> OTHER INFORMATION: C in position 17 and 19 represents a mC
      nucleotide analog
<220> FEATURE:
<221> NAME/KEY: variation
<222> LOCATION: 20
<223> OTHER INFORMATION: U in position 12,14,18,20 and 22 is a fU
      nucleotide analog
<220> FEATURE:
<221> NAME/KEY: variation
<222> LOCATION: 21
<223> OTHER INFORMATION: A in position 5,7,21 and 23 represents a mA
      nucleotide analog
<220> FEATURE:
<221> NAME/KEY: variation
<222> LOCATION: 22
<223> OTHER INFORMATION: U in position 12,14,18,20 and 22 is a fU
      nucleotide analog
<220> FEATURE:
<221> NAME/KEY: variation
<222> LOCATION: 22
<223> OTHER INFORMATION: The nucleotide in position 22 and the
      nucleotide in position 23 are linked through a phosphoramidite
      bond
<220> FEATURE:
<221> NAME/KEY: variation
<222> LOCATION: 23
<223> OTHER INFORMATION: A in position 5,7,21 and 23 represents a mA
      nucleotide analog
<220> FEATURE:
<221> NAME/KEY: variation
<222> LOCATION: 23
<223> OTHER INFORMATION: The nucleotide in position 22 and the
      nucleotide in position 23 are linked through a phosphoramidite
      bond
<220> FEATURE:
<221> NAME/KEY: variation
<222> LOCATION: 23
<223> OTHER INFORMATION: The nucleotide in position 23 and the
      nucleotide in position 24 are linked through a phosphoramidite
      bond
<220> FEATURE:
<221> NAME/KEY: variation
<222> LOCATION: 24
<223> OTHER INFORMATION: A in position 4 and 24 is a fA nucleotide
      analog
<220> FEATURE:
<221> NAME/KEY: variation
<222> LOCATION: 24
<223> OTHER INFORMATION: The nucleotide in position 23 and the
      nucleotide in position 24 are linked through a phosphoramidite
      bond

<400> SEQUENCE: 109
tttaacagug uucuugcucu auaa                                           24

<210> SEQ ID NO 110
<211> LENGTH: 26
<212> TYPE: RNA
<213> ORGANISM: Artificial Sequence
<220> FEATURE:
<223> OTHER INFORMATION: ss3-11
<220> FEATURE:
<221> NAME/KEY: variation
<222> LOCATION: 1
<223> OTHER INFORMATION: T in position 1,2 and 3 is a lgT3 nucleotide
      analog
<220> FEATURE:
<221> NAME/KEY: variation
<222> LOCATION: 2
```

```
<223> OTHER INFORMATION: T in position 1,2 and 3 is a lgT3 nucleotide
      analog
<220> FEATURE:
<221> NAME/KEY: variation
<222> LOCATION: 3
<223> OTHER INFORMATION: T in position 1,2 and 3 is a lgT3 nucleotide
      analog
<220> FEATURE:
<221> NAME/KEY: variation
<222> LOCATION: 4
<223> OTHER INFORMATION: A in position 4 is a fA nucleotide analog
<220> FEATURE:
<221> NAME/KEY: variation
<222> LOCATION: 5
<223> OTHER INFORMATION: U in position 5 and 17 represents a 2'-O-
      methyl-uracile (mU)
<220> FEATURE:
<221> NAME/KEY: variation
<222> LOCATION: 6
<223> OTHER INFORMATION: C in position 6,10,14 and 18 is a fC nucleotide
      analog
<220> FEATURE:
<221> NAME/KEY: variation
<222> LOCATION: 7
<223> OTHER INFORMATION: G in position 7,11 and 19 represents a mG
      nucleotide analog
<220> FEATURE:
<221> NAME/KEY: variation
<222> LOCATION: 8
<223> OTHER INFORMATION: U in position 8,12,20 and 22 is a fU nucleotide
      analog
<220> FEATURE:
<221> NAME/KEY: variation
<222> LOCATION: 9
<223> OTHER INFORMATION: A in position 9,13 and 21 represents a mA
      nucleotide analog
<220> FEATURE:
<221> NAME/KEY: variation
<222> LOCATION: 10
<223> OTHER INFORMATION: C in position 6,10,14 and 18 is a fC nucleotide
      analog
<220> FEATURE:
<221> NAME/KEY: variation
<222> LOCATION: 11
<223> OTHER INFORMATION: G in position 7,11 and 19 represents a mG
      nucleotide analog
<220> FEATURE:
<221> NAME/KEY: variation
<222> LOCATION: 12
<223> OTHER INFORMATION: U in position 8,12,20 and 22 is a fU nucleotide
      analog
<220> FEATURE:
<221> NAME/KEY: variation
<222> LOCATION: 13
<223> OTHER INFORMATION: A in position 9,13 and 21 represents a mA
      nucleotide analog
<220> FEATURE:
<221> NAME/KEY: variation
<222> LOCATION: 14
<223> OTHER INFORMATION: C in position 6,10,14 and 18 is a fC nucleotide
      analog
<220> FEATURE:
<221> NAME/KEY: variation
<222> LOCATION: 15
<223> OTHER INFORMATION: C in position 15 represents a mC nucleotide
      analog
<220> FEATURE:
<221> NAME/KEY: variation
<222> LOCATION: 16
<223> OTHER INFORMATION: G in position 16 is a fG nucleotide analog
<220> FEATURE:
<221> NAME/KEY: variation
<222> LOCATION: 17
<223> OTHER INFORMATION: U in position 5 and 17 represents a 2'-O-
      methyl-uracile (mU)
<220> FEATURE:
<221> NAME/KEY: variation
<222> LOCATION: 18
<223> OTHER INFORMATION: C in position 6,10,14 and 18 is a fC nucleotide
```

-continued

```
      analog
<220> FEATURE:
<221> NAME/KEY: variation
<222> LOCATION: 19
<223> OTHER INFORMATION: G in position 7,11 and 19 represents a mG
      nucleotide analog
<220> FEATURE:
<221> NAME/KEY: variation
<222> LOCATION: 20
<223> OTHER INFORMATION: U in position 8,12,20 and 22 is a fU nucleotide
      analog
<220> FEATURE:
<221> NAME/KEY: variation
<222> LOCATION: 21
<223> OTHER INFORMATION: A in position 9,13 and 21 represents a mA
      nucleotide analog
<220> FEATURE:
<221> NAME/KEY: variation
<222> LOCATION: 22
<223> OTHER INFORMATION: U in position 8,12,20 and 22 is a fU nucleotide
      analog
<220> FEATURE:
<221> NAME/KEY: variation
<222> LOCATION: 23
<223> OTHER INFORMATION: A in position 23 represents a mA nucleotide
      analog
<220> FEATURE:
<221> NAME/KEY: variation
<222> LOCATION: 24
<223> OTHER INFORMATION: A in position 24 is a fA nucleotide analog
<220> FEATURE:
<221> NAME/KEY: variation
<222> LOCATION: 25
<223> OTHER INFORMATION: T in position 25 and 26 is a lT4 nucleotide
      analog
<220> FEATURE:
<221> NAME/KEY: variation
<222> LOCATION: 26
<223> OTHER INFORMATION: T in position 25 and 26 is a lT4 nucleotide
      analog

<400> SEQUENCE: 110
tttaucguac guaccgucgu auaatt                                          26

<210> SEQ ID NO 111
<211> LENGTH: 26
<212> TYPE: RNA
<213> ORGANISM: Artificial Sequence
<220> FEATURE:
<223> OTHER INFORMATION: ss4-3
<220> FEATURE:
<221> NAME/KEY: variation
<222> LOCATION: 1
<223> OTHER INFORMATION: T in position 1 is a lgT6 nucleotide analog
<220> FEATURE:
<221> NAME/KEY: variation
<222> LOCATION: 2
<223> OTHER INFORMATION: T in position 2 is a lgT6 nucleotide analog
<220> FEATURE:
<221> NAME/KEY: variation
<222> LOCATION: 3
<223> OTHER INFORMATION: T in position 3 is a lgT6 nucleotide analog
<220> FEATURE:
<221> NAME/KEY: variation
<222> LOCATION: 4
<223> OTHER INFORMATION: A in position 4 is a fA nucleotide analog
<220> FEATURE:
<221> NAME/KEY: variation
<222> LOCATION: 5
<223> OTHER INFORMATION: A in position 5 represents a mA nucleotide
      analog
<220> FEATURE:
<221> NAME/KEY: variation
<222> LOCATION: 6
<223> OTHER INFORMATION: C in position 6 is a fC nucleotide analog
<220> FEATURE:
<221> NAME/KEY: variation
```

-continued

```
<222> LOCATION: 7
<223> OTHER INFORMATION: A in position 7 represents a mA nucleotide
      analog
<220> FEATURE:
<221> NAME/KEY: variation
<222> LOCATION: 8
<223> OTHER INFORMATION: G in position 8 is a fG nucleotide analog
<220> FEATURE:
<221> NAME/KEY: variation
<222> LOCATION: 9
<223> OTHER INFORMATION: U in position 9 represents a 2'-O-methyl-
      uracile (mU)
<220> FEATURE:
<221> NAME/KEY: variation
<222> LOCATION: 10
<223> OTHER INFORMATION: G in position 10 is a fG nucleotide analog
<220> FEATURE:
<221> NAME/KEY: variation
<222> LOCATION: 11
<223> OTHER INFORMATION: U in position 11 represents a 2'-O-methyl-
      uracile (mU)
<220> FEATURE:
<221> NAME/KEY: variation
<222> LOCATION: 12
<223> OTHER INFORMATION: U in position 12 is a fU nucleotide analog
<220> FEATURE:
<221> NAME/KEY: variation
<222> LOCATION: 13
<223> OTHER INFORMATION: C in position 13 is a fC nucleotide analog
<220> FEATURE:
<221> NAME/KEY: variation
<222> LOCATION: 14
<223> OTHER INFORMATION: U in position 14 is a fU nucleotide analog
<220> FEATURE:
<221> NAME/KEY: variation
<222> LOCATION: 15
<223> OTHER INFORMATION: U in position 15 represents a 2'-O-methyl-
      uracile (mU)
<220> FEATURE:
<221> NAME/KEY: variation
<222> LOCATION: 16
<223> OTHER INFORMATION: G in position 16 is a fG nucleotide analog
<220> FEATURE:
<221> NAME/KEY: variation
<222> LOCATION: 17
<223> OTHER INFORMATION: C in position 17 represents a mC nucleotide
      analog
<220> FEATURE:
<221> NAME/KEY: variation
<222> LOCATION: 18
<223> OTHER INFORMATION: U in position 18 is a fU nucleotide analog
<220> FEATURE:
<221> NAME/KEY: variation
<222> LOCATION: 19
<223> OTHER INFORMATION: C in position 19 represents a mC nucleotide
      analog
<220> FEATURE:
<221> NAME/KEY: variation
<222> LOCATION: 20
<223> OTHER INFORMATION: U in position 20 is a fU nucleotide analog
<220> FEATURE:
<221> NAME/KEY: variation
<222> LOCATION: 21
<223> OTHER INFORMATION: A in position 21 represents a mA nucleotide
      analog
<220> FEATURE:
<221> NAME/KEY: variation
<222> LOCATION: 22
<223> OTHER INFORMATION: U in position 22 is a fU nucleotide analog
<220> FEATURE:
<221> NAME/KEY: variation
<222> LOCATION: 23
<223> OTHER INFORMATION: A in position 23 represents a mA nucleotide
      analog
<220> FEATURE:
<221> NAME/KEY: variation
<222> LOCATION: 24
<223> OTHER INFORMATION: A in position 24 is a fA nucleotide analog
<220> FEATURE:
```

```
<221> NAME/KEY: variation
<222> LOCATION: 25
<223> OTHER INFORMATION: T in position 25 is a lT4 nucleotide analog
<220> FEATURE:
<221> NAME/KEY: variation
<222> LOCATION: 26
<223> OTHER INFORMATION: T in position 26 is a lT4 nucleotide analog

<400> SEQUENCE: 111
tttaacagug uucuugcucu auaatt                                          26

<210> SEQ ID NO 112
<211> LENGTH: 26
<212> TYPE: RNA
<213> ORGANISM: Artificial Sequence
<220> FEATURE:
<223> OTHER INFORMATION: ss4-4
<220> FEATURE:
<221> NAME/KEY: variation
<222> LOCATION: 1
<223> OTHER INFORMATION: T in position 1 is a lgT7 nucleotide analog
<220> FEATURE:
<221> NAME/KEY: variation
<222> LOCATION: 2
<223> OTHER INFORMATION: T in position 2 is a lgT7 nucleotide analog
<220> FEATURE:
<221> NAME/KEY: variation
<222> LOCATION: 3
<223> OTHER INFORMATION: T in position 3 is a lgT7 nucleotide analog
<220> FEATURE:
<221> NAME/KEY: variation
<222> LOCATION: 4
<223> OTHER INFORMATION: A in position 4 is a fA nucleotide analog
<220> FEATURE:
<221> NAME/KEY: variation
<222> LOCATION: 5
<223> OTHER INFORMATION: A in position 5 represents a mA nucleotide
      analog
<220> FEATURE:
<221> NAME/KEY: variation
<222> LOCATION: 6
<223> OTHER INFORMATION: C in position 6 is a fC nucleotide analog
<220> FEATURE:
<221> NAME/KEY: variation
<222> LOCATION: 7
<223> OTHER INFORMATION: A in position 7 represents a mA nucleotide
      analog
<220> FEATURE:
<221> NAME/KEY: variation
<222> LOCATION: 8
<223> OTHER INFORMATION: G in position 8 is a fG nucleotide analog
<220> FEATURE:
<221> NAME/KEY: variation
<222> LOCATION: 9
<223> OTHER INFORMATION: U in position 9 represents a 2'-O-methyl-
      uracile (mU)
<220> FEATURE:
<221> NAME/KEY: variation
<222> LOCATION: 10
<223> OTHER INFORMATION: G in position 10 is a fG nucleotide analog
<220> FEATURE:
<221> NAME/KEY: variation
<222> LOCATION: 11
<223> OTHER INFORMATION: U in position 11 represents a 2'-O-methyl-
      uracile (mU)
<220> FEATURE:
<221> NAME/KEY: variation
<222> LOCATION: 12
<223> OTHER INFORMATION: U in position 12 is a fU nucleotide analog
<220> FEATURE:
<221> NAME/KEY: variation
<222> LOCATION: 13
<223> OTHER INFORMATION: C in position 13 is a fC nucleotide analog
<220> FEATURE:
<221> NAME/KEY: variation
<222> LOCATION: 14
<223> OTHER INFORMATION: U in position 14 is a fU nucleotide analog
```

```
<220> FEATURE:
<221> NAME/KEY: variation
<222> LOCATION: 15
<223> OTHER INFORMATION: U in position 15 represents a 2'-O-methyl-
      uracile (mU)
<220> FEATURE:
<221> NAME/KEY: variation
<222> LOCATION: 16
<223> OTHER INFORMATION: G in position 16 is a fG nucleotide analog
<220> FEATURE:
<221> NAME/KEY: variation
<222> LOCATION: 17
<223> OTHER INFORMATION: C in position 17 represents a mC nucleotide
      analog
<220> FEATURE:
<221> NAME/KEY: variation
<222> LOCATION: 18
<223> OTHER INFORMATION: U in position 18 is a fU nucleotide analog
<220> FEATURE:
<221> NAME/KEY: variation
<222> LOCATION: 19
<223> OTHER INFORMATION: C in position 19 represents a mC nucleotide
      analog
<220> FEATURE:
<221> NAME/KEY: variation
<222> LOCATION: 20
<223> OTHER INFORMATION: U in position 20 is a fU nucleotide analog
<220> FEATURE:
<221> NAME/KEY: variation
<222> LOCATION: 21
<223> OTHER INFORMATION: A in position 21 represents a mA nucleotide
      analog
<220> FEATURE:
<221> NAME/KEY: variation
<222> LOCATION: 22
<223> OTHER INFORMATION: U in position 22 is a fU nucleotide analog
<220> FEATURE:
<221> NAME/KEY: variation
<222> LOCATION: 23
<223> OTHER INFORMATION: A in position 23 represents a mA nucleotide
      analog
<220> FEATURE:
<221> NAME/KEY: variation
<222> LOCATION: 24
<223> OTHER INFORMATION: A in position 24 is a fA nucleotide analog
<220> FEATURE:
<221> NAME/KEY: variation
<222> LOCATION: 25
<223> OTHER INFORMATION: T in position 25 is a lT4 nucleotide analog
<220> FEATURE:
<221> NAME/KEY: variation
<222> LOCATION: 26
<223> OTHER INFORMATION: T in position 26 is a lT4 nucleotide analog

<400> SEQUENCE: 112
tttaacagug uucuugcucu auaatt                                           26

<210> SEQ ID NO 113
<211> LENGTH: 26
<212> TYPE: RNA
<213> ORGANISM: Artificial Sequence
<220> FEATURE:
<223> OTHER INFORMATION: ss4-5
<220> FEATURE:
<221> NAME/KEY: variation
<222> LOCATION: 1
<223> OTHER INFORMATION: T in position 1 is a lgT7 nucleotide analog
<220> FEATURE:
<221> NAME/KEY: variation
<222> LOCATION: 2
<223> OTHER INFORMATION: T in position 2 is a lgT3 nucleotide analog
<220> FEATURE:
<221> NAME/KEY: variation
<222> LOCATION: 3
<223> OTHER INFORMATION: T in position 3 is a lgT3 nucleotide analog
<220> FEATURE:
<221> NAME/KEY: variation
```

```
<222> LOCATION: 4
<223> OTHER INFORMATION: A in position 4 is a fA nucleotide analog
<220> FEATURE:
<221> NAME/KEY: variation
<222> LOCATION: 5
<223> OTHER INFORMATION: A in position 5 represents a mA nucleotide
      analog
<220> FEATURE:
<221> NAME/KEY: variation
<222> LOCATION: 6
<223> OTHER INFORMATION: C in position 6 is a fC nucleotide analog
<220> FEATURE:
<221> NAME/KEY: variation
<222> LOCATION: 7
<223> OTHER INFORMATION: A in position 7 represents a mA nucleotide
      analog
<220> FEATURE:
<221> NAME/KEY: variation
<222> LOCATION: 8
<223> OTHER INFORMATION: G in position 8 is a fG nucleotide analog
<220> FEATURE:
<221> NAME/KEY: variation
<222> LOCATION: 9
<223> OTHER INFORMATION: U in position 9 represents a 2'-O-methyl-
      uracile (mU)
<220> FEATURE:
<221> NAME/KEY: variation
<222> LOCATION: 10
<223> OTHER INFORMATION: G in position 10 is a fG nucleotide analog
<220> FEATURE:
<221> NAME/KEY: variation
<222> LOCATION: 11
<223> OTHER INFORMATION: U in position 11 represents a 2'-O-methyl-
      uracile (mU)
<220> FEATURE:
<221> NAME/KEY: variation
<222> LOCATION: 12
<223> OTHER INFORMATION: U in position 12 is a fU nucleotide analog
<220> FEATURE:
<221> NAME/KEY: variation
<222> LOCATION: 13
<223> OTHER INFORMATION: C in position 13 is a fC nucleotide analog
<220> FEATURE:
<221> NAME/KEY: variation
<222> LOCATION: 14
<223> OTHER INFORMATION: U in position 14 is a fU nucleotide analog
<220> FEATURE:
<221> NAME/KEY: variation
<222> LOCATION: 15
<223> OTHER INFORMATION: U in position 15 represents a 2'-O-methyl-
      uracile (mU)
<220> FEATURE:
<221> NAME/KEY: variation
<222> LOCATION: 16
<223> OTHER INFORMATION: G in position 16 is a fG nucleotide analog
<220> FEATURE:
<221> NAME/KEY: variation
<222> LOCATION: 17
<223> OTHER INFORMATION: C in position 17 represents a mC nucleotide
      analog
<220> FEATURE:
<221> NAME/KEY: variation
<222> LOCATION: 18
<223> OTHER INFORMATION: U in position 18 is a fU nucleotide analog
<220> FEATURE:
<221> NAME/KEY: variation
<222> LOCATION: 19
<223> OTHER INFORMATION: C in position 19 represents a mC nucleotide
      analog
<220> FEATURE:
<221> NAME/KEY: variation
<222> LOCATION: 20
<223> OTHER INFORMATION: U in position 20 is a fU nucleotide analog
<220> FEATURE:
<221> NAME/KEY: variation
<222> LOCATION: 21
<223> OTHER INFORMATION: A in position 21 represents a mA nucleotide
      analog
<220> FEATURE:
```

```
<221> NAME/KEY: variation
<222> LOCATION: 22
<223> OTHER INFORMATION: U in position 22 is a fU nucleotide analog
<220> FEATURE:
<221> NAME/KEY: variation
<222> LOCATION: 23
<223> OTHER INFORMATION: A in position 23 represents a mA nucleotide
      analog
<220> FEATURE:
<221> NAME/KEY: variation
<222> LOCATION: 24
<223> OTHER INFORMATION: A in position 24 is a fA nucleotide analog
<220> FEATURE:
<221> NAME/KEY: variation
<222> LOCATION: 24
<223> OTHER INFORMATION: The nucleotide in position 24 and the
      nucleotide in position 25 are linked through a phosphoramidite
      bond
<220> FEATURE:
<221> NAME/KEY: variation
<222> LOCATION: 25
<223> OTHER INFORMATION: T in position 25 is a lT4 nucleotide analog
<220> FEATURE:
<221> NAME/KEY: variation
<222> LOCATION: 25
<223> OTHER INFORMATION: The nucleotide in position 25 and the
      nucleotide in position 26 are linked through a phosphoramidite
      bond
<220> FEATURE:
<221> NAME/KEY: variation
<222> LOCATION: 26
<223> OTHER INFORMATION: T in position 26 is a lT4 nucleotide analog

<400> SEQUENCE: 113
tttaacagug uucuugcucu auaatt                                          26

<210> SEQ ID NO 114
<211> LENGTH: 24
<212> TYPE: RNA
<213> ORGANISM: Artificial Sequence
<220> FEATURE:
<223> OTHER INFORMATION: ss4-6
<220> FEATURE:
<221> NAME/KEY: variation
<222> LOCATION: 1
<223> OTHER INFORMATION: T in position 1 is a lgT7 nucleotide analog
<220> FEATURE:
<221> NAME/KEY: variation
<222> LOCATION: 2
<223> OTHER INFORMATION: T in position 2 is a lgT7 nucleotide analog
<220> FEATURE:
<221> NAME/KEY: variation
<222> LOCATION: 3
<223> OTHER INFORMATION: T in position 3 is a lgT7 nucleotide analog
<220> FEATURE:
<221> NAME/KEY: variation
<222> LOCATION: 4
<223> OTHER INFORMATION: A in position 4 is a fA nucleotide analog
<220> FEATURE:
<221> NAME/KEY: variation
<222> LOCATION: 5
<223> OTHER INFORMATION: A in position 5 represents a mA nucleotide
      analog
<220> FEATURE:
<221> NAME/KEY: variation
<222> LOCATION: 6
<223> OTHER INFORMATION: C in position 6 is a fC nucleotide analog
<220> FEATURE:
<221> NAME/KEY: variation
<222> LOCATION: 7
<223> OTHER INFORMATION: A in position 7 represents a mA nucleotide
      analog
<220> FEATURE:
<221> NAME/KEY: variation
<222> LOCATION: 8
<223> OTHER INFORMATION: G in position 8 is a fG nucleotide analog
<220> FEATURE:
```

```
<221> NAME/KEY: variation
<222> LOCATION: 9
<223> OTHER INFORMATION: U in position 9 represents a 2'-O-methyl-
      uracile (mU)
<220> FEATURE:
<221> NAME/KEY: variation
<222> LOCATION: 10
<223> OTHER INFORMATION: G in position 10 is a fG nucleotide analog
<220> FEATURE:
<221> NAME/KEY: variation
<222> LOCATION: 11
<223> OTHER INFORMATION: U in position 11 represents a 2'-O-methyl-
      uracile (mU)
<220> FEATURE:
<221> NAME/KEY: variation
<222> LOCATION: 12
<223> OTHER INFORMATION: U in position 12 is a fU nucleotide analog
<220> FEATURE:
<221> NAME/KEY: variation
<222> LOCATION: 13
<223> OTHER INFORMATION: C in position 13 is a fC nucleotide analog
<220> FEATURE:
<221> NAME/KEY: variation
<222> LOCATION: 14
<223> OTHER INFORMATION: U in position 14 is a fU nucleotide analog
<220> FEATURE:
<221> NAME/KEY: variation
<222> LOCATION: 15
<223> OTHER INFORMATION: U in position 15 represents a 2'-O-methyl-
      uracile (mU)
<220> FEATURE:
<221> NAME/KEY: variation
<222> LOCATION: 16
<223> OTHER INFORMATION: G in position 16 is a fG nucleotide analog
<220> FEATURE:
<221> NAME/KEY: variation
<222> LOCATION: 17
<223> OTHER INFORMATION: C in position 17 represents a mC nucleotide
      analog
<220> FEATURE:
<221> NAME/KEY: variation
<222> LOCATION: 18
<223> OTHER INFORMATION: U in position 18 is a fU nucleotide analog
<220> FEATURE:
<221> NAME/KEY: variation
<222> LOCATION: 19
<223> OTHER INFORMATION: C in position 19 represents a mC nucleotide
      analog
<220> FEATURE:
<221> NAME/KEY: variation
<222> LOCATION: 20
<223> OTHER INFORMATION: U in position 20 is a fU nucleotide analog
<220> FEATURE:
<221> NAME/KEY: variation
<222> LOCATION: 21
<223> OTHER INFORMATION: A in position 21 represents a mA nucleotide
      analog
<220> FEATURE:
<221> NAME/KEY: variation
<222> LOCATION: 22
<223> OTHER INFORMATION: U in position 22 is a fU nucleotide analog
<220> FEATURE:
<221> NAME/KEY: variation
<222> LOCATION: 23
<223> OTHER INFORMATION: T in position 23 is a lT4 nucleotide analog
<220> FEATURE:
<221> NAME/KEY: variation
<222> LOCATION: 24
<223> OTHER INFORMATION: T in position 24 is a lT4 nucleotide analog

<400> SEQUENCE: 114
tttaacagug uucuugcucu autt                                          24

<210> SEQ ID NO 115
<211> LENGTH: 24
<212> TYPE: RNA
<213> ORGANISM: Artificial Sequence
```

-continued

```
<220> FEATURE:
<223> OTHER INFORMATION: ss4-7
<220> FEATURE:
<221> NAME/KEY: variation
<222> LOCATION: 1
<223> OTHER INFORMATION: T in position 1 is a lgT7 nucleotide analog
<220> FEATURE:
<221> NAME/KEY: variation
<222> LOCATION: 2
<223> OTHER INFORMATION: T in position 2 is a lgT7 nucleotide analog
<220> FEATURE:
<221> NAME/KEY: variation
<222> LOCATION: 3
<223> OTHER INFORMATION: T in position 3 is a lgT7 nucleotide analog
<220> FEATURE:
<221> NAME/KEY: variation
<222> LOCATION: 4
<223> OTHER INFORMATION: A in position 4 is a fA nucleotide analog
<220> FEATURE:
<221> NAME/KEY: variation
<222> LOCATION: 5
<223> OTHER INFORMATION: A in position 5 represents a mA nucleotide
      analog
<220> FEATURE:
<221> NAME/KEY: variation
<222> LOCATION: 6
<223> OTHER INFORMATION: C in position 6 is a fC nucleotide analog
<220> FEATURE:
<221> NAME/KEY: variation
<222> LOCATION: 7
<223> OTHER INFORMATION: A in position 7 represents a mA nucleotide
      analog
<220> FEATURE:
<221> NAME/KEY: variation
<222> LOCATION: 8
<223> OTHER INFORMATION: G in position 8 is a fG nucleotide analog
<220> FEATURE:
<221> NAME/KEY: variation
<222> LOCATION: 9
<223> OTHER INFORMATION: U in position 9 represents a 2'-O-methyl-
      uracile (mU)
<220> FEATURE:
<221> NAME/KEY: variation
<222> LOCATION: 10
<223> OTHER INFORMATION: G in position 10 is a fG nucleotide analog
<220> FEATURE:
<221> NAME/KEY: variation
<222> LOCATION: 11
<223> OTHER INFORMATION: U in position 11 represents a 2'-O-methyl-
      uracile (mU)
<220> FEATURE:
<221> NAME/KEY: variation
<222> LOCATION: 12
<223> OTHER INFORMATION: U in position 12 is a fU nucleotide analog
<220> FEATURE:
<221> NAME/KEY: variation
<222> LOCATION: 13
<223> OTHER INFORMATION: C in position 13 is a fC nucleotide analog
<220> FEATURE:
<221> NAME/KEY: variation
<222> LOCATION: 14
<223> OTHER INFORMATION: U in position 14 is a fU nucleotide analog
<220> FEATURE:
<221> NAME/KEY: variation
<222> LOCATION: 15
<223> OTHER INFORMATION: U in position 15 represents a 2'-O-methyl-
      uracile (mU)
<220> FEATURE:
<221> NAME/KEY: variation
<222> LOCATION: 16
<223> OTHER INFORMATION: G in position 16 is a fG nucleotide analog
<220> FEATURE:
<221> NAME/KEY: variation
<222> LOCATION: 17
<223> OTHER INFORMATION: C in position 17 represents a mC nucleotide
      analog
<220> FEATURE:
<221> NAME/KEY: variation
<222> LOCATION: 18
```

```
<223> OTHER INFORMATION: U in position 18 is a fU nucleotide analog
<220> FEATURE:
<221> NAME/KEY: variation
<222> LOCATION: 19
<223> OTHER INFORMATION: C in position 19 represents a mC nucleotide
      analog
<220> FEATURE:
<221> NAME/KEY: variation
<222> LOCATION: 20
<223> OTHER INFORMATION: U in position 20 is a fU nucleotide analog
<220> FEATURE:
<221> NAME/KEY: variation
<222> LOCATION: 21
<223> OTHER INFORMATION: A in position 21 represents a mA nucleotide
      analog
<220> FEATURE:
<221> NAME/KEY: variation
<222> LOCATION: 22
<223> OTHER INFORMATION: The nucleotide in position 22 and the
      nucleotide in position 23 are linked through a phosphoramidite
      bond
<220> FEATURE:
<221> NAME/KEY: variation
<222> LOCATION: 22
<223> OTHER INFORMATION: U in position 22 is a fU nucleotide analog
<220> FEATURE:
<221> NAME/KEY: variation
<222> LOCATION: 23
<223> OTHER INFORMATION: The nucleotide in position 23 and the
      nucleotide in position 24 are linked through a phosphoramidite
      bond
<220> FEATURE:
<221> NAME/KEY: variation
<222> LOCATION: 23
<223> OTHER INFORMATION: T in position 23 is a lT4 nucleotide analog
<220> FEATURE:
<221> NAME/KEY: variation
<222> LOCATION: 24
<223> OTHER INFORMATION: T in position 24 is a lT4 nucleotide analog

<400> SEQUENCE: 115
tttaacagug uucuugcucu autt                                           24

<210> SEQ ID NO 116
<211> LENGTH: 24
<212> TYPE: RNA
<213> ORGANISM: Artificial Sequence
<220> FEATURE:
<223> OTHER INFORMATION: ss4-8
<220> FEATURE:
<221> NAME/KEY: variation
<222> LOCATION: 1
<223> OTHER INFORMATION: T in position 1 is a lgT7 nucleotide analog
<220> FEATURE:
<221> NAME/KEY: variation
<222> LOCATION: 2
<223> OTHER INFORMATION: T in position 2 is a lgT7 nucleotide analog
<220> FEATURE:
<221> NAME/KEY: variation
<222> LOCATION: 3
<223> OTHER INFORMATION: T in position 3 is a lgT7 nucleotide analog
<220> FEATURE:
<221> NAME/KEY: variation
<222> LOCATION: 4
<223> OTHER INFORMATION: A in position 4 is a fA nucleotide analog
<220> FEATURE:
<221> NAME/KEY: variation
<222> LOCATION: 5
<223> OTHER INFORMATION: A in position 5 represents a mA nucleotide
      analog
<220> FEATURE:
<221> NAME/KEY: variation
<222> LOCATION: 6
<223> OTHER INFORMATION: C in position 6 is a fC nucleotide analog
<220> FEATURE:
<221> NAME/KEY: variation
<222> LOCATION: 7
```

```
<223> OTHER INFORMATION: A in position 7 represents a mA nucleotide
      analog
<220> FEATURE:
<221> NAME/KEY: variation
<222> LOCATION: 8
<223> OTHER INFORMATION: G in position 8 is a fG nucleotide analog
<220> FEATURE:
<221> NAME/KEY: variation
<222> LOCATION: 9
<223> OTHER INFORMATION: U in position 9 represents a 2'-O-methyl-
      uracile (mU)
<220> FEATURE:
<221> NAME/KEY: variation
<222> LOCATION: 10
<223> OTHER INFORMATION: G in position 10 is a fG nucleotide analog
<220> FEATURE:
<221> NAME/KEY: variation
<222> LOCATION: 11
<223> OTHER INFORMATION: U in position 11 represents a 2'-O-methyl-
      uracile (mU)
<220> FEATURE:
<221> NAME/KEY: variation
<222> LOCATION: 12
<223> OTHER INFORMATION: U in position 12 is a fU nucleotide analog
<220> FEATURE:
<221> NAME/KEY: variation
<222> LOCATION: 13
<223> OTHER INFORMATION: C in position 13 is a fC nucleotide analog
<220> FEATURE:
<221> NAME/KEY: variation
<222> LOCATION: 14
<223> OTHER INFORMATION: U in position 14 is a fU nucleotide analog
<220> FEATURE:
<221> NAME/KEY: variation
<222> LOCATION: 15
<223> OTHER INFORMATION: U in position 15 represents a 2'-O-methyl-
      uracile (mU)
<220> FEATURE:
<221> NAME/KEY: variation
<222> LOCATION: 16
<223> OTHER INFORMATION: G in position 16 is a fG nucleotide analog
<220> FEATURE:
<221> NAME/KEY: variation
<222> LOCATION: 17
<223> OTHER INFORMATION: C in position 17 represents a mC nucleotide
      analog
<220> FEATURE:
<221> NAME/KEY: variation
<222> LOCATION: 18
<223> OTHER INFORMATION: U in position 18 is a fU nucleotide analog
<220> FEATURE:
<221> NAME/KEY: variation
<222> LOCATION: 19
<223> OTHER INFORMATION: C in position 19 represents a mC nucleotide
      analog
<220> FEATURE:
<221> NAME/KEY: variation
<222> LOCATION: 20
<223> OTHER INFORMATION: U in position 20 is a fU nucleotide analog
<220> FEATURE:
<221> NAME/KEY: variation
<222> LOCATION: 21
<223> OTHER INFORMATION: A in position 21 represents a mA nucleotide
      analog
<220> FEATURE:
<221> NAME/KEY: variation
<222> LOCATION: 22
<223> OTHER INFORMATION: U in position 22 is a fU nucleotide analog
<220> FEATURE:
<221> NAME/KEY: variation
<222> LOCATION: 23
<223> OTHER INFORMATION: A in position 23 is a lA4 nucleotide analog
<220> FEATURE:
<221> NAME/KEY: variation
<222> LOCATION: 24
<223> OTHER INFORMATION: A in position 24 is a lA4 nucleotide analog

<400> SEQUENCE: 116
```
tttaacagug uucuugcucu auaa                                                24

<210> SEQ ID NO 117
<211> LENGTH: 24
<212> TYPE: RNA
<213> ORGANISM: Artificial Sequence
<220> FEATURE:
<223> OTHER INFORMATION: ss4-9
<220> FEATURE:
<221> NAME/KEY: variation
<222> LOCATION: 1
<223> OTHER INFORMATION: T in position 1 is a lgT7 nucleotide analog
<220> FEATURE:
<221> NAME/KEY: variation
<222> LOCATION: 2
<223> OTHER INFORMATION: T in position 2 is a lgT7 nucleotide analog
<220> FEATURE:
<221> NAME/KEY: variation
<222> LOCATION: 3
<223> OTHER INFORMATION: T in position 3 is a lgT7 nucleotide analog
<220> FEATURE:
<221> NAME/KEY: variation
<222> LOCATION: 4
<223> OTHER INFORMATION: A in position 4 is a fA nucleotide analog
<220> FEATURE:
<221> NAME/KEY: variation
<222> LOCATION: 5
<223> OTHER INFORMATION: A in position 5 represents a mA nucleotide
      analog
<220> FEATURE:
<221> NAME/KEY: variation
<222> LOCATION: 6
<223> OTHER INFORMATION: C in position 6 is a fC nucleotide analog
<220> FEATURE:
<221> NAME/KEY: variation
<222> LOCATION: 7
<223> OTHER INFORMATION: A in position 7 represents a mA nucleotide
      analog
<220> FEATURE:
<221> NAME/KEY: variation
<222> LOCATION: 8
<223> OTHER INFORMATION: G in position 8 is a fG nucleotide analog
<220> FEATURE:
<221> NAME/KEY: variation
<222> LOCATION: 9
<223> OTHER INFORMATION: U in position 9 represents a 2'-O-methyl-
      uracile (mU)
<220> FEATURE:
<221> NAME/KEY: variation
<222> LOCATION: 10
<223> OTHER INFORMATION: G in position 10 is a fG nucleotide analog
<220> FEATURE:
<221> NAME/KEY: variation
<222> LOCATION: 11
<223> OTHER INFORMATION: U in position 11 represents a 2'-O-methyl-
      uracile (mU)
<220> FEATURE:
<221> NAME/KEY: variation
<222> LOCATION: 12
<223> OTHER INFORMATION: U in position 12 is a fU nucleotide analog
<220> FEATURE:
<221> NAME/KEY: variation
<222> LOCATION: 13
<223> OTHER INFORMATION: C in position 13 is a fC nucleotide analog
<220> FEATURE:
<221> NAME/KEY: variation
<222> LOCATION: 14
<223> OTHER INFORMATION: U in position 14 is a fU nucleotide analog
<220> FEATURE:
<221> NAME/KEY: variation
<222> LOCATION: 15
<223> OTHER INFORMATION: U in position 15 represents a 2'-O-methyl-
      uracile (mU)
<220> FEATURE:
<221> NAME/KEY: variation
<222> LOCATION: 16
<223> OTHER INFORMATION: G in position 16 is a fG nucleotide analog
<220> FEATURE:

```
<221> NAME/KEY: variation
<222> LOCATION: 17
<223> OTHER INFORMATION: C in position 17 represents a mC nucleotide
      analog
<220> FEATURE:
<221> NAME/KEY: variation
<222> LOCATION: 18
<223> OTHER INFORMATION: U in position 18 is a fU nucleotide analog
<220> FEATURE:
<221> NAME/KEY: variation
<222> LOCATION: 19
<223> OTHER INFORMATION: C in position 19 represents a mC nucleotide
      analog
<220> FEATURE:
<221> NAME/KEY: variation
<222> LOCATION: 20
<223> OTHER INFORMATION: U in position 20 is a fU nucleotide analog
<220> FEATURE:
<221> NAME/KEY: variation
<222> LOCATION: 21
<223> OTHER INFORMATION: A in position 21 represents a mA nucleotide
      analog
<220> FEATURE:
<221> NAME/KEY: variation
<222> LOCATION: 22
<223> OTHER INFORMATION: The nucleotide in position 22 and the
      nucleotide in position 23 are linked through a phosphoramidite
      bond
<220> FEATURE:
<221> NAME/KEY: variation
<222> LOCATION: 22
<223> OTHER INFORMATION: U in position 22 is a fU nucleotide analog
<220> FEATURE:
<221> NAME/KEY: variation
<222> LOCATION: 23
<223> OTHER INFORMATION: The nucleotide in position 23 and the
      nucleotide in position 24 are linked through a phosphoramidite
      bond
<220> FEATURE:
<221> NAME/KEY: variation
<222> LOCATION: 23
<223> OTHER INFORMATION: A in position 23 is a lA4 nucleotide analog
<220> FEATURE:
<221> NAME/KEY: variation
<222> LOCATION: 24
<223> OTHER INFORMATION: A in position 24 is a lA4 nucleotide analog

<400> SEQUENCE: 117
tttaacagug uucuugcucu auaa                                            24

<210> SEQ ID NO 118
<211> LENGTH: 20
<212> TYPE: PRT
<213> ORGANISM: Unknown
<220> FEATURE:
<223> OTHER INFORMATION: peptide with high selectivity for
      cardiomyocytes in vivo

<400> SEQUENCE: 118

Trp Leu Ser Glu Ala Gly Pro Val Val Thr Val Arg Ala Leu Arg Gly
1               5                   10                  15

Thr Gly Ser Trp
            20
```

NUCLEOTIDE PRECURSORS, NUCLEOTIDE ANALOGS AND OLIGOMERIC COMPOUNDS CONTAINING THE SAME

CROSS REFERENCE TO RELATED APPLICATIONS

This application is a National Phase application under 35 U.S.C. § 371 of International Application No. PCT/EP2019/055546, filed Mar. 6, 2019, which claims the priority benefit of EP Application Nos. 18305239.8, filed Mar. 7, 2018 and 18306497.1, filed Nov. 15, 2018.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 183952003600SEQLIST.TXT, date recorded: Aug. 28, 2020, size: 227 KB).

FIELD OF THE DISCLOSURE

This disclosure relates to the field of targeted gene silencing with small interfering RNAs (siRNAs), and more particularly to nucleotide precursors and analogs to be used in siRNAs.

BACKGROUND

The concept of using synthetic oligonucleotides to control the expression of specific genes dates back to the late 1970s when targeted gene silencing using a short synthetic oligonucleotide was first demonstrated (Stephenson et al., 1978, Proc Natl Acad Sci USA, 75:285-288). Subsequent to Stephenson's discovery, elucidation of the RNA interference pathway for modulation of gene expression and the role of siRNAs in the process has vastly expanded scientists' understanding of posttranscriptional gene expression control in eukaryotic cells.

Synthetic oligonucleotides include single stranded oligonucleotides such as antisense oligonucleotides ("ASOs"), antimiRs and antagomiRs and double stranded oligonucleotides such as siRNAs. ASOs and siRNAs both work by binding a target RNA through Watson-Crick base pairing, but their mechanisms of action are different. In antisense technology, ASOs form a DNA-RNA duplex with the target RNA and inhibit mRNA-translation by a blocking mechanism or cause RNase H-dependent degradation of the targeted RNA. In RNA interference technology, siRNAs bind to the RNA-induced silencing complex ("RISC"), where one strand (the "passenger strand" or "sense strand") is displaced and the remaining strand (the "guide strand" or "antisense strand") cooperates with RISC to bind a complementary RNA (the target RNA); once bound, the target RNA is cleaved by RNA endonuclease Argonaute (AGO) in RISC and then further degraded by RNA exonucleases.

The most significant obstacles for developing oligonucleotide therapeutics, including siRNA therapeutics, include (i) poor stability of the compounds, (ii) low efficiency of in vivo delivery to target cells, and (iii) side effects such as "off target" gene silencing and unintended immunostimulation. To address some of these obstacles, researches have attempted various oligonucleotide chemical modifications. These modifications can be classified into three categories, namely (i) sugar modifications, (ii) internucleotide linkage modifications, and (iii) nucleobase modifications.

Chemical modifications to the sugar group include modifications at the 2'-carbon atom or the 2'-hydroxy group of the ribose ring. The 2'-OMe (methoxy) nucleotide analog is one of the most widely used modifications. 2'-F (fluoro) nucleotides and 2'-O-methoxyethyl nucleotides have also been used. Although the majority of sugar alterations are localized at the 2'-position, modifications at other positions such as the 4'-position have also been reported-(Leydler at al., 1995, Antisense Res Dev, 5:161-174).

Other chemical modifications of the sugar group include linking the 2'-oxygen and 4'-carbon of the ribose scaffold in a nucleoside, creating a so-called locked nucleic acid ("LNA"). LNAs also are referred to as bicyclic nucleic acids and have been shown to have increased RNA-binding affinity (Koshin et al, 1998, Tetrahedron, 54:3607-3630; Prakash et al., 2011, Chem. Biodivers, 8:1616-1641), leading in a significant increase of their melting temperature in the resulting double stranded oligonucleotides. However, fully LNA-modified oligomers longer than eight nucleotides tend to aggregate. Contrasting with the rigid nature of the LNA modification, the highly flexible unlocked nucleic acid ("UNA") modification has also been developed for application in oligonucleotide therapeutics. UNA nucleosides do not have the C2'-C3'-bond of the ribose sugar. Due to their open chain structure, UNAs are not conformationally restrained and have been used to modulate oligonucleotide flexibility (Mangos et al., 2003, J Am Chem Soc, 125:654-661). UNA inserts can reduce duplex melting temperature (Tm) by 5° C.-10° C. per insert in some cases. Further, UNA inserts can facilitate antisense strand selection by RISC, and UNA modifications to the seed region of an siRNA guide strand can reduce off-target events (Vaish et al., 2011, Nucleic Acids Res, 39:1823-1832). UNA- and LNA-containing siRNAs have been reported by Bramsen et al. (2010, Nucleic Acids Research, 38(17):5761-5773).

Further, expanded sugar ring systems also have been developed and applied in gene silencing technology. Such systems include six-membered morpholino ring systems, where the ribose moiety of a nucleoside is replaced by a morpholine ring. Morpholino-based nucleosides form internucleotide linkage within oligonucleotides containing them through the nitrogen atom of the morpholine subunit. Phosphorodiamidate morpholino-based oligonucleotides ("PMO") have been used in antisense technology (Corey et al., 2001, Genome Biology, 2(5): reviews 1015.1-1015; Partridge et al., 1996, Antisense Nucleic Acid Drug Dev, 6:169-175). However, due to low binding affinity to complementary RNA, antisense PMOs need to be relatively long, e.g., 25 bases long (Corey et al., supra). Examples of morpholino subunits are also disclosed in U.S. Pat. Nos. 5,034,506; 5,166,315; 5,185,444; 5,698,685; and U.S. Patent Publication US2016US/0186174.

Chemical modifications may also be performed on internucleotide linkages by replacing the 3'-5' phosphodiester linkage with more stable moieties to reduce susceptibility to nuclease degradation. A widely used modification is a partial or complete replacement of the phosphodiester backbone with phosphorothioate linkages, in which a sulfur atom is used in place of the oxygen atom. An alternative backbone modification that confers increased biological stability to nucleic acids is the boranophosphate linkage. In boranophosphate oligonucleotides, the non-bridging phosphodiester oxygen is replaced with an isoelectronic borane (—$BH_3$) moiety.

However, most of the aforementioned phosphodiester modifications such as phosphorothioates create a chiral phosphorous in the internucleotide linkage, leading to diastereomeric mixtures of the obtained oligonucleotides. Since the number of diastereomeric oligonucleotides may double with each modified phosphodiester linkage, the resulting number of diastereomers increases exponentially with an increasing number of modified phosphodiester linkages. The individual diastereomers may exhibit different degrees of nuclease resistance and different hybridizing properties to the target mRNA. In addition, purification and chemical analytics of diastereomeric mixtures is complex. Thus, in some cases, it may be desirable to avoid the use of phosphodiester modifications such as phosphorothioates and the resulting diastereomeric oligonucleotide mixture.

Other significant challenges in RNA interference technology are targeted delivery and cellular uptake of siRNAs. The cellular membrane is a bilayer of negatively charged phospholipids and is an entry barrier for siRNAs, which also are negatively charged. Some groups have used N-acetylgalactosamine (GalNAc) to target siRNA attached thereto to hepatocytes, which express the GalNAc-binding asialoglycoprotein receptor (ASGPR) and can internalize the ASGPR-bound siRNA-GalNAc conjugate into through endocytosis (See, e.g., Nair et al., 2014, J Am Chem Soc, 136:16958-16961).

While progress has been made in RNA interference technology, there remains a need in the field for siRNA oligonucleotides with improved stability and delivery to their target cells.

SUMMARY OF THE DISCLOSURE

The present application discloses compounds of formula (I)

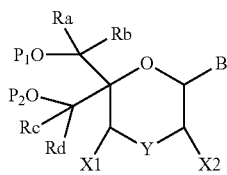

wherein:
B is a heterocyclic nucleobase;
P1 and P2 are each, independently, H, a reactive phosphorus group or a protecting group;
Y is O, NH, NR1 or N—C(=O)—R1, wherein R1 is:
  a (C1-C20) alkyl group, optionally substituted by one or more groups selected from an halogen atom, a (C1-C6) alkyl group, a (C3-C8) cycloalkyl group, a (C3-C14) heterocycle, a (C6-C14) aryl group, a (C5-C14) heteroaryl group, —O—Z1, —N(Z1)(Z2), —S—Z1, —CN, —C(=J)-O—Z1, —O—C(=J)-Z1, —C(=J)-N(Z1)(Z2), and —N(Z1)-C(=J)-Z2, wherein
  J is O or S,
  each of Z1 and Z2 is, independently, H, a (C1-C6) alkyl group, optionally substituted by one or more groups selected from a halogen atom and a (C1-C6) alkyl group,
  a (C3-C8) cycloalkyl group, optionally substituted by one or more groups selected from a halogen atom and a (C1-C6) alkyl group, or a group —[C(=O)]m-R2-(O—CH₂—CH₂)p-R3, wherein:
  m is an integer meaning 0 or 1,
  p is an integer ranging from 0 to 10,
  R2 is a (C1-C20) alkylene group optionally substituted by a (C1-C6) alkyl group, —O—Z3, —N(Z3)(Z4), —S—Z3, —CN, —C(=K)—O—Z3, —O—C(=K)—Z3, C(=K)—N(Z3)(Z4), and N(Z3)-C(=K)—Z4, wherein
  K is O or S,
  each of Z3 and Z4 is, independently, H, a (C1-C6) alkyl group, optionally substituted by one or more groups selected from a halogen atom and a (C1-C6) alkyl group,
  and
  R3 is selected from the group consisting of a hydrogen atom, a (C1-C6) alkyl group, a (C1-C6) alkoxy group, a (C3-C8) cycloalkyl group, a (C3-C14) heterocycle, a (C6-C14) aryl group or a (C5-C14) heteroaryl group,
or
R3 is a cell targeting moiety,
X1 and X2 are each, independently, a hydrogen atom, a —(C1-C6) alkyl group, and
each of Ra, Rb, Rc and Rd is, independently, H or a (C1-C6) alkyl group.

In some embodiments of a compound of formula (I), Y is NR1, wherein R1 is an optionally substituted (C1-C20) alkyl group, and P1, P2, Ra, Rb, Rc, Rd, X1, X2 and B are as defined for the general formula (I).

In some embodiments of a compound of formula (I), Y is NR1, wherein R1 is a non-substituted (C1-C16) alkyl group, which includes an alkyl group selected from a group consisting of methyl, isopropyl, butyl, octyl, hexadecyl, and P1, P2, Ra, Rb, Rc, Rd, X1, X2 and B have the same meaning as defined for the general formula (I).

In some embodiments of a compound of formula (I), Y is NR1, wherein R1 is a (C3-C8) cycloalkyl group, optionally substituted by one or more groups selected from a halogen atom and a (C1-C6) alkyl group, and P1, P2, Ra, Rb, Rc, Rd, X1, X2 and B have the same meaning as defined for the general formula (I).

In some embodiments of a compound of formula (I), Y is NR1, wherein R1 is a cyclohexyl group, and P1, P2, Ra, Rb, Rc, Rd, X1, X2 and B have the same meaning as defined for the general formula (I).

In some embodiments of a compound of formula (I), Y is NR1, wherein R1 is a (C1-C20) alkyl group which is substituted by a (C6-C14) aryl group, and P1, P2, Ra, Rb, Rc, Rd, X1, X2 and B have the same meaning as defined for the general formula (I).

In some embodiments of a compound of formula (I), Y is NR1, wherein R1 is a (C1-C20) alkyl group which is substituted by a phenyl group, and P1, P2, Ra, Rb, Rc, Rd, X1, X2 and B have the same meaning as defined for the general formula (I).

In some embodiments of a compound of formula (I), Y is NR1, wherein R1 is a methyl group which is substituted by a phenyl group and P1, P2, Ra, Rb, Rc, Rd, X1, X2 and B have the same meaning as defined for the general formula (I).

In some embodiments of a compound of formula (I), Y is N—C(=O)—R1, wherein R1 is an optionally-substituted (C1-C20) alkyl group, and P1, P2, Ra, Rb, Rc, Rd, X1, X2 and B have the same meaning as defined for the general formula (I).

In some embodiments of a compound of formula (I), Y is N—C(=O)—R1, wherein R1 is selected from a group consisting of methyl and pentadecyl and P1, P2, Ra, Rb, Rc, Rd, X1, X2 and B have the same meaning as defined for the general formula (I).

In some further embodiments of a compound of formula (I), Y is NR1 with R1 being a group —[C(=O)]m-R2-(O—CH$_2$—CH$_2$)p-R3, wherein
m is an integer meaning 0 or 1,
p is an integer ranging from 0 to 10,
R2 is a (C1-C20) alkylene group optionally substituted by a (C1-C6) alkyl group, —O—Z3, —N(Z3)(Z4), —S—Z3, —CN, —C(=K)—O—Z3, —C(=K)—Z3, —C(=K)—N(Z3)(Z4), —N(Z3)-C(=K)—Z4, wherein
K is O or S,
each of Z3 and Z4 is, independently, H, a (C1-C6) alkyl group, optionally substituted by one or more groups selected from a halogen atom and a (C1-C6) alkyl group,
and
R3 is a cell targeting moiety,
X1 and X2 are each, independently, a hydrogen atom, a (C1-C6) alkyl group, and
each of Ra, Rb, Rc and Rd is, independently, H or a (C1-C6) alkyl group.

In some of these further embodiments of a compound of formula (I), R1 is the group —[C(=O)]m-R2-(O—CH$_2$—CH$_2$)p-R3, m is 0, p is 0, R3 is a cell targeting moiety, B, P1, P2, Ra, Rb, Rc, Rd, X1, X2, and R2 are as in the general definition of the compound of formula (I).

In some of these further embodiments of a compound of formula (I), R2 is an ethylene group, p is 0 and X1 and X2 are both an hydrogen atom.

In some of these further embodiments of a compound of formula (I), R2 is a pentylene group and X1 and X2 are both an hydrogen atom.

In some of these further embodiments of a compound of formula (I), R2 is a (C12) alkylene group and X3 and X4 are both an hydrogen atom.

In some of these further embodiments of a compound of formula (I), R1 is the group —[C(=O)]m-R2-(O—CH$_2$—CH$_2$)p-R3, m is 0, p is selected from the group of integers consisting of 1, 2, 3 and 4, R3 is a cell targeting moiety and B, P1, P2, Ra, Rb, Rc, Rd, X1, X2 and R2, are as in the general definition of the compound of formula (I).

In some of these further embodiments of a compound of formula (I), R2 is an ethylene group, p is 1 and X1 and X2 are both an hydrogen atom.

In some of these further embodiments of a compound of formula (I), R2 is an ethylene group, p is 2 and X1 and X2 are both an hydrogen atom.

In some of these further embodiments of a compound of formula (I), R2 is an ethylene group, p is 3 and X1 and X2 are both an hydrogen atom.

In some of these further embodiments of a compound of formula (I), R2 is an ethylene group, p is 4 and X1 and X2 are both an hydrogen atom.

In some of these further embodiments of a compound of formula (I), m is 1, p is 0, R3 is a cell targeting moiety, and R2, B, P1, P2, Ra, Rb, Rc, Rd, X1, X2, are as in the general definition of the compound of formula (I).

In some of these further embodiments of a compound of formula (I), R2 is a butylene, X1 and X2 both represent a hydrogen atom and B, P1, P2, Ra, Rb, Rc and Rd are as defined for the general formula (I).

In some of these further embodiments of a compound of formula (I), R2 is a (C11) alkylene, X1 and X2 both represent a hydrogen atom and B, P1, P2, Ra, Rb, Rc and Rd are as defined for the general formula (I).

In some of these further embodiments of a compound of formula (I), R2 is a methylene, X1 and X2 both represent a hydrogen atom and B, P1, P2, Ra, Rb, Rc and Rd are as defined for the general formula (I).

In some of these further embodiments of a compound of formula (I), m is 1, p is selected from the group of integers consisting of 1 and 2, R3 is a cell targeting moiety, R2, B, P1, P2, Ra, Rb, Rc, Rd, X1, X2, are as in the general definition of the compound of formula (I).

In some of these further embodiments of a compound of formula (I), R2 is a methylene group, p is 2, R3 is a cell targeting moiety, B, P1, P2, Ra, Rb, Rc, Rd, X1, X2, are as defined for the general formula (I).

In some of these further embodiments of a compound of formula (I), R2 is a methylene group, p is 1, R3 is a cell targeting moiety, B, P1, P2, Ra, Rb, Rc, Rd, X1, X2 are as defined for the general formula (I).

In some of these further embodiments of a compound of formula (I), R3 is a compound of formula (III):

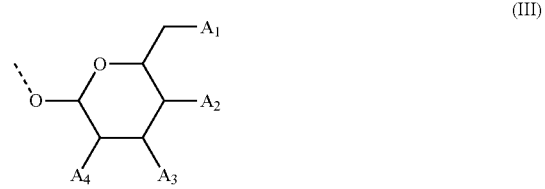

wherein A1, A2 and A3 are O—C(=O)—R4,
wherein R4 is a (C1-C6)-alkyl or a (C6-C10)-aryl group;
A4 is O—C(=O)—R4 or NHC(=O)—R5, with R4 being defined as above and R5 is (C1-C6)-alkyl group, optionally substituted by an halogen atom.

In some of these further embodiments of a compound of formula (I), R3 is a compound of formula (III) wherein A1, A2 and A3 are O—C(=O)—R4, wherein R4 is a (C1-C6)-alkyl or a (C6-C10)-aryl group; A4 is O—C(=O)—R4 or NHC(=O)—R5, wherein R4 being defined as above and R5 is (C1-C6)-alkyl group, optionally substituted by an halogen atom.

In some of these further embodiments of a compound of formula (I), R3 is a compound of formula (III) wherein A1, A2 and A3 are O—C(=O)—R4, wherein R4 is a methyl group, A4 is O—C(=O)—R4 or NHC(=O)—R5, wherein each of R4 and R5 is a methyl group.

In some embodiments of a compound of formula (I), B is optionally protected and is selected from a group consisting of a pyrimidine, a substituted pyrimidine, a purine and a substituted purine.

In some embodiments of a compound of formula (I), one of P1 or P2 is a O-4,4'-dimethoxytrityl group and the other of P1 and P2 is H, a reactive phosphorus group or a protecting group, and Y, B, Ra, Rb, Rc and Rd are as defined in formula (I).

In some embodiments of a compound of formula (I), one of P1 and P2 is a 2-cyanoethyl-N,N-diisopropylphosphoramidite group and the other P1 and P2 is a protecting group, and Y, B, Ra, Rb, Rc and Rd are as defined in formula (I).

In some embodiments of a compound of formula (I), one of P1 and P2 is a 2-cyanoethyl-N,N-diisopropylphosphoramidite group and the other P1 and P2 is 0-4,4'-dimethoxytrityl group and Y, B, Ra, Rb, Rc and Rd are as defined in formula (I).

This invention also pertains to an oligonucleotide comprising one or more nucleotides of formula (II):

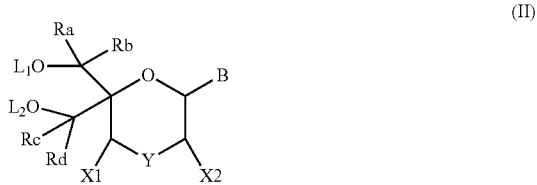

(II)

wherein:
B is a heterocyclic nucleobase;
one of L1 and L2 is an internucleoside linking group linking the compound of formula (II) to the oligomeric compound and the other of L1 and L2 is H, a protecting group, a phosphorus moiety or an internucleoside linking group linking the compound of formula (II) to the oligomeric compound,
Y is O, NH, NR1 or N—C(=O)—R1, wherein R1 is:
  a (C1-C20) alkyl group, optionally substituted by one or more groups selected from an halogen atom, a (C1-C6) alkyl group, a (C3-C8) cycloalkyl group, a (C3-C14) heterocycle, a (C6-C14) aryl group, a (C5-C14) heteroaryl group, —O—Z1, —N(Z1)(Z2), —S—Z1, —CN, —C(=J)-O—Z1, —O—C(=J)-Z1, —C(=J)-N(Z1)(Z2), and —N(Z1)-C(=J)-Z2, wherein
  J is O or S,
  each of Z1 and Z2 is, independently, H, a $(C_1-C_6)$ alkyl group, optionally substituted by one or more groups selected from a halogen atom and a (C1-C6) alkyl group,
  a (C3-C8) cycloalkyl group, optionally substituted by one or more groups selected from a halogen atom and a $(C_1-C_6)$ alkyl group, or
  a group —[C(=O)]m-R2-(O—CH$_2$—CH$_2$)p-R3, wherein
  m is an integer meaning 0 or 1,
  p is an integer ranging from 0 to 10,
  R2 is a (C1-C20) alkylene group optionally substituted by a (C1-C6) alkyl group, —O—Z3, —N(Z3)(Z4), —S—Z3, —CN, —C(=K)—O—Z3, —O—C(=K)—Z3, —C(=K)—N(Z3)(Z4), and —N(Z3)-C(=K)—Z4, wherein
  K is O or S,
  each of Z3 and Z4 is, independently, H, a (C1-C6) alkyl group, optionally substituted by one or more groups selected from a halogen atom and a (C1-C6) alkyl group,
  and
  R3 is selected from the group consisting of a hydrogen atom, a (C1-C6) alkyl group, a (C1-C6) alkoxy group, a (C3-C8) cycloalkyl group, a (C3-C14) heterocycle, a (C6-C14) aryl group or a (C5-C14) heteroaryl group,
  or R3 is a cell targeting moiety,
X1 and X2 are each, independently, a hydrogen atom, a (C1-C6) alkyl group, and
each of Ra, Rb, Rc and Rd is, independently, H or a (C1-C6) alkyl group,
or a pharmaceutically acceptable salt thereof.

In some embodiments of the said oligonucleotide, in one or more compounds of formula (II), Y is NR1, R1 is a non-substituted (C1-C20) alkyl group, and L1, L2, Ra, Rb, Rc, Rd, X1, X2 R2, R3 and B have the same meaning as defined for the general formula (II), or a pharmaceutically acceptable salt thereof.

In some embodiments of the said oligonucleotide, in one or more compounds of formula (II), Y is NR1, R1 is a non-substituted $(C_1-C_{16})$ alkyl group, which includes an alkyl group selected from a group comprising methyl, isopropyl, butyl, octyl, hexadecyl, and L1, L2, Ra, Rb, Rc, Rd, X1, X2 R2, R3 and B have the same meaning as defined in formula (II), or a pharmaceutically acceptable salt thereof.

In some embodiments of the said oligonucleotide, in one or more compounds of formula (II), Y is NR1, R1 is a (C3-C8) cycloalkyl group, optionally substituted by one or more groups selected from a halogen atom and a (C1-C6) alkyl group, and L1, L2, Ra, Rb, Rc, Rd, X1, X2, R2, R3 and B or a pharmaceutically acceptable salt thereof.

In some embodiments of the said oligonucleotide, in one or more compounds of formula (II), Y is NR1, R1 is a cyclohexyl group, and L1, L2, Ra, Rb, Rc, Rd, X1, X2, R2, R3 and B have the same meaning as defined in formula (II), or a pharmaceutically acceptable salt thereof.

In some embodiments of the said oligonucleotide, in one or more compounds of formula (II), Y is NR1, R1 is a (C1-C20) alkyl group substituted by a (C6-C14) aryl group and L1, L2, Ra, Rb, Rc, Rd, X1, X2, R2, R3 and B have the same meaning as defined in formula (II), or a pharmaceutically acceptable salt thereof.

In some embodiments of the said oligonucleotide, in one or more compounds of formula (II), Y is NR1, R1 is a methyl group substituted by a phenyl group, and L1, L2, Ra, Rb, Rc, Rd, X1, X2, R2, R3 and B have the same meaning as defined in formula (II), or a pharmaceutically acceptable salt thereof.

In some embodiments of the said oligonucleotide, in one or more compounds of formula (II), Y is N—C(=O)—R1, R1 is an optionally substituted (C1-C20) alkyl group, and L1, L2, Ra, Rb, Rc, Rd, X1, X2, R2, R3 and B have the same meaning as defined in formula (II), or a pharmaceutically acceptable salt thereof.

In some embodiments of the said oligonucleotide, in one or more compounds of formula (II), Y is N—C(=O)—R1, R1 is selected from a group comprising methyl and pentadecyl and L1, L2, Ra, Rb, Rc, Rd, X1, X2, R2, R3 and B have the same meaning as defined in formula (II), or a pharmaceutically acceptable salt thereof.

In some embodiments of the said oligonucleotide, in one or more compounds of formula (II), B is selected from a group comprising a pyrimidine, a substituted pyrimidine, a purine and a substituted purine, or a pharmaceutically acceptable salt thereof.

In some embodiments of the said oligonucleotide, in one or more compounds of formula (II), the said internucleoside linking group is independently selected from the group consisting of phosphodiester, phosphotriester, phosphorothioate, phosphorodithioate, alkyl-phosphonate and phosphoramidate backbone linking groups.

In some embodiments, the said oligonucleotide comprises from 2 to 10 compounds of formula (II).

In some embodiments, the said oligonucleotide comprises one or more targeted nucleotides.

In some embodiments of the said oligonucleotide, in one or more compounds of formula (II), R3 is of the formula (III):

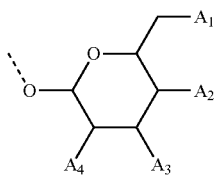

(III)

wherein A1, A2 and A3 are OH
A4 is OH or NHC(=O)—R5, R5 is (C1-C6)-alkyl group, optionally substituted by an halogen atom.

In some embodiments of the said oligonucleotide, in one or more compounds of formula (II), R3 is N-acetyl-galactosamine.

This invention also concerns a double-stranded oligonucleotide comprising one or more compounds of formula (II) described in the present disclosure, or a pharmaceutically acceptable salt thereof.

This invention also concerns a siRNA comprising one or more compounds of formula (II) described in the present disclosure, or a pharmaceutically acceptable salt thereof.

This disclosure also pertains to methods for obtaining the nucleotide precursors, the nucleotide analogs and the single-stranded or the double-stranded oligonucleotides specified herein.

DETAILED DESCRIPTION

Figure 1:
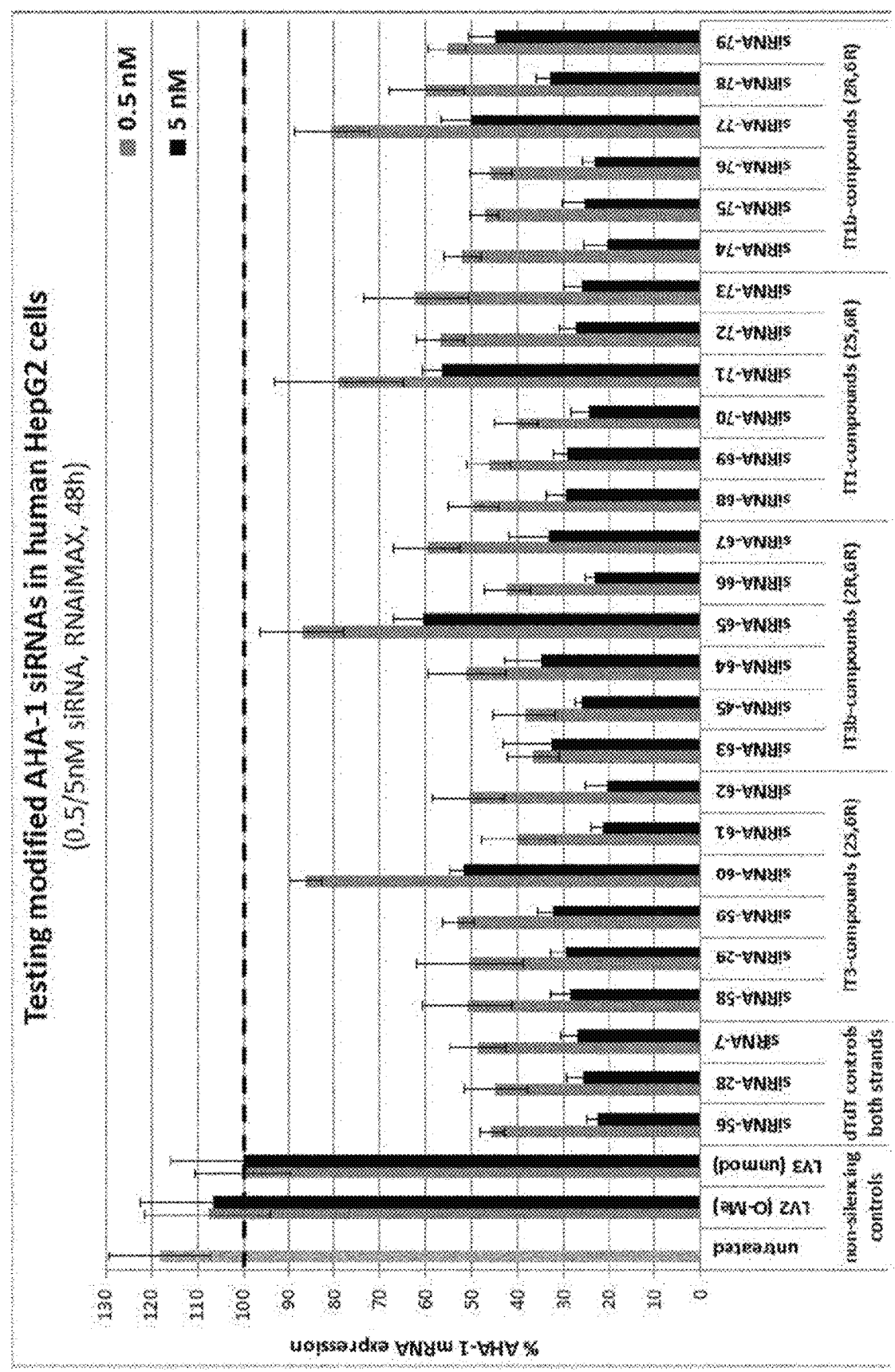
FIG. 1: In vitro knock-down of siRNAs 58 to 79 with IT3, IT3b, IT1 and IT1b-overhangs
  Ordinate: percent AHA-1 expression in transfected HepG2 cells relative to the control-siRNAs
  Abscissa: siRNA-#, concentration

The present disclosure invention provides novel nucleotide analogs that can be incorporated into oligonucleotides, including double-stranded oligonucleotides such as siRNAs. Oligonucleotides containing these analogs have superior biological activity, for example, improved in vitro stability and in vivo duration of action. The improved oligonucleotides are useful for silencing (e.g., reducing or eradicating) the expression of a target gene. In particular embodiments, this invention encompasses specific nucleotide analogs to be included in double-stranded RNAs (dsRNAs), and especially in siRNAs, that can hybridize to messenger RNAs (mRNAs) of interest, so as to reduce or block the expression of target genes of interest. In some embodiments, the present invention provides nucleotide analogs wherein the ribose sugar ring has been replaced by a six-membered heterocyclic ring. As described further in detail below, the six-membered heterocyclic group may be a dioxane or a morpholino ring. Where the heterocyclic group is a morpholino-ring, the nitrogen atom is either substituted or non-substituted. In some embodiments, the six-membered heterocyclic group may be substituted by linear or cyclic groups and/or targeting moieties.

Definitions

The terms used in this specification generally have their ordinary meanings in the art. Certain terms are discussed below, or elsewhere in the present disclosure, to provide additional guidance in describing the products and methods of the presently disclosed subject matter.

The following definitions apply in the context of the present disclosure:

As used in this specification and the appended claims, the singular forms "a", "an" and "the" include plural referents unless the content clearly dictates otherwise.

The term "about" as used herein refers to the usual error range for the respective value readily known to the skilled person in this technical field. Reference to "about" a value or parameter herein includes (and describes) embodiments that are directed to that value or parameter per se. In some embodiments, the term "about" refers to ±10% of a given value. However, whenever the value in question refers to an indivisible object, such as a nucleotide or other object that would lose its identity once subdivided, then "about" refers to ±1 of the indivisible object.

It is understood that aspects and embodiments of the present disclosure described herein include "having," "comprising," "consisting of," and "consisting essentially of" aspects and embodiments. The words "have" and "comprise," or variations such as "has," "having," "comprises," or "comprising," will be understood to imply the inclusion of the stated element(s) (such as a composition of matter or a method step) but not the exclusion of any other elements. The term "consisting of" implies the inclusion of the stated element(s), to the exclusion of any additional elements. The term "consisting essentially of" implies the inclusion of the stated elements, and possibly other element(s) where the other element(s) do not materially affect the basic and novel characteristic(s) of the invention.

An "alkyl," unless otherwise specified, means an aliphatic hydrocarbon group which may be linear or branched, having 1 to 20 (e.g., 1-5, 1-10, or 1-15) carbon atoms in the chain. "Branched" means that one or more alkyl groups such as a methyl, ethyl or propyl group are attached to a linear alkyl chain. Exemplary linear or branched alkyl groups include methyl, ethyl, n-propyl, i-propyl, n-butyl, t-butyl, n-pentyl, 3-pentyl, octyl, nonyl, and decyl.

A "cycloalkyl" means a cyclic saturated alkyl group as defined above. Examples are, but not limited to, cyclopropyl, cyclobutyl, cyclopentyl, cyclohexyl, cycloheptyl, and cyclooctyl.

An "alkoxy" is defined as a —OR group, wherein R is an alkyl group as defined above, including a cycloalkyl group. Examples are, but not limited to, methoxy, ethoxy, 1-propoxy, 2-propoxy, butoxy, and pentoxy.

A "halogen atom" refers to a fluorine, chlorine, bromine, or iodine atom. In some embodiments, a fluorine or chlorine atom may be preferred.

An "aryl," unless otherwise specified, means an aromatic monocyclic or multicyclic hydrocarbon ring system of 6 to 14 carbon atoms, e.g., 6 to 10 carbon atoms. Exemplary aryl groups include phenyl and naphthyl groups.

A "heterocycle" or "heterocyclic" refers to a saturated, partially unsaturated or unsaturated, carbocyclic group containing at least one heteroatom selected from the group of oxygen, nitrogen, selenium, phosphorus, and sulfur. The nitrogen, selenium, phosphorus or sulfur may optionally be oxidized and the nitrogen may optionally be quaternized. For example, the heterocycle can be a stable ring wherein at least one member of the ring is a heteroatom. In some embodiments, the heterocycle may have 3 to 14 e.g., 5 to 7, or 5 to 10) members and may have one, two, or multiple rings (i.e., mono-, bi- or multi-cyclic rings). In particular embodiments, the heteroatoms are oxygen, nitrogen and sulfur. The number of heteroatoms may vary, e.g., from one to three. Suitable heterocycles are also disclosed in *The Handbook of Chemistry and Physics*, 76th Edition, CRC Press, Inc., 1995-1996, pppp. 2-25 to 2-26, the disclosure of which is hereby incorporated by reference. In some embodiments, the heterocycles are non-aromatic heterocycles, which include, but are not limited to, pyrrolidinyl, pyrazolidinyl, imidazolidinyl, oxiranyl, tetrahydrofuranyl, dioxolanyl, tetrahydro-pyranyl, dioxanyl, dioxolanyl, piperidyl, piperazinyl, morpholinyl, pyranyl, imidazolinyl, pyrrolinyl, pyrazolinyl, thiazolidinyl, tetrahydrothiopyranyl, dithianyl, thiomorpholinyl, dihydro-pyranyl, tetrahydropyranyl, dihydropyranyl, tetrahydro-pyridyl, dihydropyridyl, tetrahydropyrinidinyl, dihydrothiopyranyl, and azepanyl, as well as the fused systems resulting from the condensation with a phenyl group.

A "heteroaryl" refers to an aromatic heterocyclic ring with 5 to 14 (e.g., 5 to 7, or 5 to 10) members and may be a mono-, bi- or multi-cyclic ring. The number of heteroatoms may typically vary from one to three heteroatoms, for example, selected from N and O. Examples of heteroaryl groups include pyrrolyl, pyridyl, pyrazolyl, thienyl, pyrimidinyl, pyrazinyl, tetrazolyl, indolyl, quinolinyl, purinyl, imidazolyl, thienyl, thiazolyl, benzothiazolyl, furanyl, benzofuranyl, 1,2,4-thiadiazolyl, oxadiazol, isothiazolyl, triazoyl, tetrazolyl, isoquinolyl, benzothienyl, isobenzofuryl, pyrazolyl, carbazolyl, benzimidazolyl, isoxazolyl, and pyridyl-N-oxide, as well as the fused systems resulting from the condensation with a phenyl group. In particular embodiments, a heteroaryl is a 5- or 6-membered heteroaryl comprising one or more heteroatoms, e.g., one to three heteroatoms selected from N and O. a "Alkyl", "cycloalkyl", "alkenyl", "alkynyl", "aryl", "heteroaryl", and "heterocyclyl" refer also to the corresponding "alkylene", "cycloalkylene", "alkenylene", "alkynylene", "arylene", "heteroarylene", and "heterocyclene" which are formed by the removal of two hydrogen atoms.

The term "heterocyclic nucleobase" means any nitrogen-containing heterocyclic moiety capable of forming Watson-Crick-type hydrogen bonds and stacking interactions in pairing with a complementary nucleobase or nucleobase analog (i.e., derivatives of nucleobases) when that nucleobase is incorporated into a polymeric structure.

Unless otherwise specified, the term "heterocyclic nucleobase" refers herein to an optionally substituted, nitrogen-containing heterocyclic group that can be attached to an optionally substituted dioxane ring or to an optionally substituted morpholino ring, according to the present disclosure. In some embodiments, the heterocyclic nucleobase can be selected from an optionally substituted purine-base or an optionally substituted pyrimidine-base. The term "purine-base" is used herein in its ordinary sense as understood by those skilled in the art, and includes its tautomers. Similarly, the term "pyrimidine-base" is used herein in its ordinary sense as understood by those skilled in the art, and includes its tautomers. A non-limiting list of optionally substituted purine-bases includes purine, adenine, guanine, hypoxanthine, xanthine, alloxanthine, 7-alkylguanine (e.g., 7-methylguanine), theobromine, caffeine, uric acid and isoguanine. Examples of pyrimidine-bases include, but are not limited to, cytosine, thymine, uracil, 5,6-dihydrouracil and 5-alkylcytosine (e.g., 5-methylcytosine). Other non-limiting examples of heterocyclic nucleobases include diaminopurine, 8-oxo-$N_6$ alkyladenine (e.g., 8-oxo-$N_6$ methyladenine), 7-deazaxanthine, 7-deazaguanine, 7-deazaadenine, $N_4$,N ethanocytosin, $N_6$,$N_6$-ethano-2,6-diaminopurine, 5-halouracil (e.g., 5-fluorouracil and 5-bromouracil), pseudoisocytosine, isocytosine, isoguanine, 1,2,4-triazole-3-carboxamides and other heterocyclic nucleobases described in U.S. Pat. Nos. 5,432,272 and 7,125,855, which are incorporated herein by reference disclosing additional heterocyclic bases. In some embodiments, a heterocyclic nucleobase can be optionally substituted with an amine- or an enol protecting group(s).

The terms "protecting group" and "protecting groups" as used herein refer to any atom or group of atoms that is added to a molecule in order to prevent existing groups in the molecule from undergoing unwanted chemical reactions. A "protecting group" may be a labile chemical moiety that is known in the art to protect reactive groups, such as hydroxyl, amino and thiol groups, against undesired or untimely reactions during chemical synthesis. Protecting groups are typically used selectively and/or orthogonally to protect sites during reactions at other reactive sites and can then be removed to leave the unprotected group as is or available for further reactions.

Examples of protecting group moieties are described in T. W. Greene and P. G. M. Wuts, Protective Groups in Organic Synthesis, 3. Ed. John Wiley & Sons, 1999, and in J. F. W. McOmie, Protective Groups in Organic Chemistry Plenum Press, 1973, both of which are hereby incorporated by reference for the limited purpose of disclosing suitable protecting groups. The protecting group moiety may be chosen in such a way, that they are stable to certain reaction conditions and readily removed at a convenient stage using methodology known from the art.

A non-limiting list of protecting groups include benzyl; substituted benzyl; alkylcarbonyls and alkoxycarbonyls (e.g., t-butoxycarbonyl (BOC), acetyl, or isobutyryl); arylalkylcarbonyls and arylalkoxycarbonyls (e.g., benzyloxycarbonyl); substituted methyl ether (e.g. methoxymethyl ether); substituted ethyl ether; a substituted benzyl ether; tetrahydropyranyl ether; silyls (e.g., trimethylsilyl, triethylsilyl, triisopropylsilyl, t-butyldimethylsilyl, tri-iso-propylsilyloxymethyl, [2-(trimethylsilyl)ethoxy]methyl or t-butyldiphenylsilyl); esters (e.g. benzoate ester); carbonates (e.g. methoxymethylcarbonate); sulfonates (e.g. tosylate or mesylate); acyclic ketal (e.g. dimethyl acetal); cyclic ketals (e.g., 1,3-dioxane, 1,3-dioxolanes, and those described herein); acyclic acetal; cyclic acetal (e.g., those described herein); acyclic hemiacetal; cyclic hemiacetal; cyclic dithioketals (e.g., 1,3-dithiane or 1,3-dithiolane); orthoesters (e.g., those described herein) and triarylmethyl groups (e.g., trityl; monomethoxytrityl (MMTr); 4,4'-dimethoxytrityl (DMTr); 4,4',4''-trimethoxytrityl (TMTr); and those described herein).

Preferred protecting groups are selected from a group comprising acetyl (Ac), benzoyl (Bzl), isobutyryl (iBu), phenylacetyl, dimethoxytrityl (DMT), methoxytrityl (MMT), triphenylmethyl (Trt), N,N-dimethylformamidine and 2-cyanoethyl (CE).

Unless indicated otherwise, the abbreviations for any protective groups, amino acids and other compounds are in accordance with their common usage, recognized abbreviations, or the IUPAC-UB Commission on Biochemical Nomenclature (See, Biochem. 11:942-944 (1972).

As used herein, the term "solid support" (also called resins) means the insoluble particles, typically 50-200 μm in diameter, to which the oligonucleotide is bound during synthesis.

Many types of solid support have been used, but controlled pore glass (CPG) and polystyrene (highly cross-linked polystyrene beads) have proved to be particularly useful. Controlled pore glass is rigid and non-swelling with deep pores (pore sizes between 500 and 1000 Å) in which oligonucleotide synthesis takes place. Solid supports for conventional oligonucleotide synthesis are commercially available and typically manufactured with a loading of 20-40 μmol of nucleoside per gram of resin in the case of CPG solid support. Polystyrene-based solid supports show higher loadings with up to 300 μmol per gram of resin. Solid support materials with standard nucleotides already attached are commercially available, amino-functionalized CPG and polystyrene materials are used for the synthesis of non-commercial building blocks as it will be shown later for the herein described building blocks.

Alternatively to solid supports, which already have attached the first nucleotide building block, commercially available universal solid support materials can be used as it will be described later in the present disclosure.

As used herein, the term "ribonucleotide" or "nucleotide" includes naturally occurring or modified nucleotide, as further detailed below, or a surrogate replacement moiety. A modified nucleotide is non-naturally occurring nucleotide and is also referred to herein as a "nucleotide analog." One of ordinary skill in the art would understand that guanine, cytosine, adenine, uracil, or thymine in a nucleotide may be replaced by other moieties without substantially altering the base pairing properties of an oligonucleotide comprising a nucleotide bearing such replacement moiety. For example, without limitation, a nucleotide comprising inosine as its base may base-pair with nucleotides containing adenine, cytosine, or uracil. Hence, nucleotides containing uracil, guanine, or adenine may be replaced in the nucleotide sequences of the present disclosure by a nucleotide containing, for example, inosine. Sequences comprising such replacement moieties are included as embodiments of the present disclosure.

As used herein, a "cell targeting moiety" means a molecular group ensuring increased delivery of an siRNA, which encompasses (i) increased specificity of an siRNA to bind to selected target receptors (e.g., target proteins), including increased specificity of an siRNA to bind to cells expressing the selected target receptor; (ii) increased uptake of an siRNA by the target cells; and/or (iii) increased ability of an siRNA to be appropriately processed once it has entered into a target cell, such as increasing the intracellular release of an siRNA, e.g., by facilitating the translocation of the siRNA from transport vesicles into the cytoplasm. Thus, a cell targeting moiety is used to direct and/or deliver an oligonucleotide to a particular cell, tissue, organ, etc. A cell targeting moiety comprised in a nucleotide, a nucleotide analog or in an oligonucleotide imparts to the said nucleotide, nucleotide analog or oligonucleotide characteristics such that the said nucleotide, nucleotide analog or oligonucleotide is preferentially recognized, bound, internalized, processed, activated, etc. by the targeted cell type(s) relative to non-targeted cell types. For example, endothelial cells have a high affinity for the peptide cell targeting moiety Arg-Gly-Asp (RGD); cancer and kidney cells preferentially interact with compounds having a folic acid moiety; immune cells have an affinity for mannose; and cardiomyocytes have an affinity for the peptide WLSEAGPVVTVRALRGTGSW (SEQ ID NO: 118) (see, e.g., Biomaterials ZV-8081-8087, 2010). Other cell targeting/delivery moieties are known in the art. Accordingly, compounds comprising a cell targeting moiety preferentially interact with and are taken up by the targeted cell type(s).

A cell targeting moiety encompasses cell targeting peptide groups and cell targeting non-peptide groups.

As used herein, "target cells" or "targeted cells" refers to cells of interest. The cells may be found in vitro, in vivo, in situ or in the tissue or organ of an organism. The organism may be an animal, preferably a mammal, more preferably a human, and most preferably a human patient.

As used herein, the term "TTR" refers to the transthyretin gene or protein. As used herein, the term "TTR" includes human TTR, the amino acid and nucleotide sequences of which may be found in, for example, EMBL database under the accession number CR456908; mouse TTR, the amino acid and nucleotide sequences of which may be found in, for example, GenBank database under the accession number AAH24702. Additional examples of TTR mRNA sequences are readily available in, e.g., GenBank.

As used herein, the term "AHA-1" refers to the AHSA1 gene or protein. As used herein, the term "AHA-1" includes human AHSA-1, the amino acid and nucleotide sequences of which may be found in, for example, EMBL database under the accession number AK300766.

As used herein, "target sequence" refers to a contiguous nucleotide sequence found in the RNA transcript of a target gene or portions thereof), including the mRNA, which is a product of RNA processing of a primary transcription product.

As used herein, and unless otherwise indicated, the term "complementary", when used to describe a first nucleotide sequence (e.g., an oligonucleotide) in relation to a second nucleotide sequence (e.g., an oligonucleotide), refers to the ability of the first nucleotide sequence to hybridize and form a duplex structure under certain conditions with the second nucleotide sequence, as will be understood by one of ordinary skill in the art. This includes base-pairing of the first nucleotide sequence to the second nucleotide sequence over the entire length of the first or second nucleotide sequence. Such sequences can be referred to as "fully complementary" with respect to each other herein. Where a first sequence is referred to as "substantially complementary" with respect to a second sequence herein, the two sequences can be fully complementary or they may have 70% or more nucleotide identity, while retaining the ability to hybridize under conditions most relevant to their ultimate target.

However, where two oligonucleotides are designed to form, upon hybridization, one or more single-stranded overhangs, such overhangs shall not be regarded as mismatches with regard to the determination of complementarity. For example, a double-stranded RNA (dsRNA) comprising a first oligonucleotide 21 nucleotides in length and a second oligonucleotide 23 nucleotides in length, wherein the second oligonucleotide comprises a sequence of 21 nucleotides that is fully complementary to the first oligonucleotide, may yet be referred to as "fully complementary" for the purpose of the present disclosure. "Complementary" sequences may also include, or be formed entirely from non-Watson-Crick base pairs and/or base pairs formed from non-natural and modified nucleotides, insofar as the above requirements with respect to their ability to hybridize are fulfilled. The terms "complementary", "fully complementary", and "substantially complementary" may be used with respect to the base matching between the sense strand and the antisense strand of a dsRNA, or between the antisense strand of a dsRNA and a target sequence, as it will be understood from the context of their use. As used herein, a polynucleotide which is "substantially complementary to at least a part of" an mRNA refers to a polynucleotide which is substantially complementary to a contiguous portion of the mRNA of interest. As used herein, the term "double-stranded RNA" or "dsRNA" refers to a complex of ribonucleic acid molecule(s), having a duplex structure comprising two anti-parallel and substantially complementary, as defined above, nucleic acid strands. The two strands forming the duplex structure may be different portions of one larger RNA molecule, or they may be separate RNA molecules. Where separate RNA molecules, such dsRNA may be referred to in the literature as short interfering RNA (siRNA). Where two strands are part of one larger molecule, and therefore are connected by an uninterrupted chain of nucleotides between the 3'-end of a first strand and the 5'-end of a second strand forming the duplex structure, the connecting RNA chain is referred to as a "hairpin loop", "short hairpin RNA", or "shRNA". Where the two strands are connected covalently by means other than an uninterrupted chain of nucleotides between the 3'-end of a first strand and the 5'-end of a second strand forming the duplex structure, the connecting structure is referred to as a "linker". The RNA strands may have the same or a different number of nucleotides. The maximum number of base pairs is the number of oligonucleotides in the shortest strand of the dsRNA minus any overhangs that are present in the duplex. In addition to the duplex structure, a dsRNA may comprise one or more nucleotide overhangs. In addition, as used herein, the term "dsRNA" may include chemical modifications to ribonucleotides, including substantial modifications at multiple nucleotides and including all types of modifications disclosed herein or known in the art. Any such modifications, as used in a siRNA type molecule, are encompassed by "dsRNA" for the purposes of the present disclosure. In some embodiments, the internucleotide linkages in the dsRNA may be modified, e.g., as described herein.

Within the scope of the present disclosure, the "percentage identity" between two sequences of nucleic acids means the percentage of identical nucleotides residues between the two sequences to be compared, obtained after optimal alignment, this percentage being purely statistical and the differences between the two sequences being distributed randomly along their length. The comparison of two nucleic acid sequences is traditionally carried out by comparing the sequences after having optimally aligned them, said comparison being able to be conducted by segment or by using an "alignment window". Optimal alignment of the sequences for comparison can be carried out, in addition to comparison by hand, by means of the local homology algorithm of Smith and Waterman (1981), by means of the local homology algorithm of Neddleman and Wunsch (1970), by means of the similarity search method of Pearson and Lipman (1988)), or by means of computer software using these algorithms (GAP, BESTFIT, FASTA and TFASTA in the Wisconsin Genetics Software Package, Genetics Computer Group, 575 Science Dr., Madison, WI, or by the comparison software BLAST NR or BLAST P).

The percentage identity between two nucleic acid sequences is determined by comparing the two optimally-aligned sequences in which the nucleic acid sequence to compare can have additions or deletions compared to the reference sequence for optimal alignment between the two sequences. Percentage identity is calculated by determining the number of positions at which the nucleotide residue is identical between the two sequences, preferably between the two complete sequences, dividing the number of identical positions by the total number of positions in the alignment window and multiplying the result by 100 to obtain the percentage identity between the two sequences.

As intended herein, nucleotide sequences having at least 70% nucleotide identity with a reference sequence encompass those having at least 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% nucleotide identity with the said reference sequence.

In some embodiments, the dsRNA comprises a modified ribonucleoside including a deoxyribonucleoside, including, for example, a deoxyribonucleoside overhang(s), one or more deoxyribonucleosides within the double-stranded portion of a dsRNA, and the like. However, it is self-evident that under no circumstances is a double-stranded DNA molecule encompassed by the term "dsRNA".

As used herein, the term "nucleotide overhang" refers to the unpaired nucleotide or nucleotides that protrude from the duplex structure of a dsRNA when a 3'-end of a first strand of the dsRNA extends beyond the 5' end of a second strand, or vice versa. "Blunt" or "blunt-end" means that there are no unpaired nucleotides at that end of the dsRNA, i.e., no nucleotide overhang. A "blunt-ended" dsRNA is a dsRNA that is double-stranded over its entire length, i.e., no nucleotide overhang at either end of the molecule. For clarity, chemical caps or non-nucleotide chemical moieties conjugated to the 3' end and/or the 5' end of a strand of a dsRNA are not considered in determining whether a dsRNA has an overhang or is blunt-ended.

As used herein, the term "antisense strand" in a dsRNA refers to the strand of the dsRNA containing a sequence that is substantially complementary to a target sequence. The other strand in the dsRNA is the "sense strand".

As used herein, the term "introducing into a cell" means facilitating uptake or absorption into the cell, as would be understood by one of ordinary skill in the art. Absorption or uptake of dsRNA can occur through unaided diffusive or active cellular processes, or by auxiliary agents or devices. The meaning of this term is not to be limited to a cell in vitro; a dsRNA may also be "introduced into a cell", wherein the cell is part of a living organism. In such an instance, introduction into the cell will include delivery to the organism. For example, for in vivo delivery, dsRNA can be injected into a tissue site or administered systemically. In vivo delivery can also be mediated by a beta-glucan delivery system (See, e.g., Tesz, G. J. et al., 2011, Biochem J. 436(2):351-62). In vitro introduction into a cell includes methods known in the art such as electroporation and lipofection. Further approaches are described herein below or known in the art.

As used herein, the terms "inhibit the expression of" or "inhibiting expression of" insofar as they refer to a target gene, refer to the at least partial suppression of the expression of the target gene, as manifested by a reduction of the amount of mRNA transcribed from the target gene. As used herein, the term "inhibiting" is used interchangeably with "reducing", "silencing", "downregulating", "suppressing", "knock-down" and other similar terms, and include any level of inhibition. The degree of inhibition is usually expressed in terms of (((mRNA in control cells)−(mRNA in treated cells))/(mRNA in control cells))·100%. Alternatively, the degree of inhibition may be given in terms of a reduction of a parameter that is functionally linked to a target gene transcription, e.g., the amount of protein encoded by the target gene which is secreted by a cell, or the number of cells displaying a certain phenotype, e.g., apoptosis. In principle, target gene silencing may be determined in any cell expressing the target, either constitutively or by genomic engineering, and by any appropriate assay. However, when a reference is needed in order to determine whether a given dsRNA inhibits the expression of the target gene by a certain degree and therefore is encompassed by the present disclosure, the assays provided in the Examples below shall serve as such a reference.

As used herein, in the context of a target gene expression, the terms "treat", "treatment" and the like refer to relief from or alleviation of pathological processes mediated by the expression of a target gene. In the context of the present disclosure, insofar as it relates to any of the other conditions recited herein below (other than pathological processes mediated by target expression), the terms "treat", "treatment", and the like refer to relieving or alleviating one or more symptoms associated with such condition.

As used herein, the terms "prevent" or "delay progression of" (and grammatical variants thereof) with respect to a disease or disorder relate to prophylactic treatment of a disease, e.g., in an individual suspected to have the disease, or at risk for developing the disease. Prevention may include, but is not limited to, preventing or delaying onset or progression of the disease and/or maintaining one or more symptoms of the disease at a desired or sub-pathological level.

As used herein, the terms "therapeutically effective amount" and "prophylactically effective amount" refer to an amount that provides a therapeutic benefit in the treatment, prevention, or management of pathological processes mediated by target gene expression, or an overt symptom of pathological processes mediated by the expression of a target gene. The specific amount that is therapeutically effective can be readily determined by an ordinary medical practitioner, and may vary depending on factors such as the type and stage of pathological processes mediated by the target gene expression, the patient's medical history and age, and the administration of other therapeutic agents that inhibit biological processes mediated by the target gene.

As used herein, the term "individual" or "subject" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In some embodiments, the individual or subject is a human.

The terms "internucleoside linkage," "internucleoside linking group," "internucleotide linkage", or "internucleotide linking group" are used herein interchangeably and refer to any linker or linkage between two nucleoside (i.e., a heterocyclic base moiety and a sugar moiety) units, as is known in the art, including, for example, but not as limitation, phosphate, analogs of phosphate, phosphorothioate, phosphonate, guanidium, hydroxylamine, hydroxyhydrazinyl, amide, carbamate, alkyl, and substituted alkyl linkages. A "internucleoside linking group" may be involved in the linkage between two nucleosides, between two nucleoside analogs or between a nucleoside and a nucleoside analog.

Internucleoside linkages constitute the backbone of a nucleic acid molecule. An internucleoside linking group refers to a chemical group linking two adjacent nucleoside residues comprised in a nucleic acid molecule, which encompasses (i) a chemical group linking two adjacent nucleoside residues, (ii) a chemical group linking a nucleoside residue with an adjacent nucleoside analog residue and (iii) a chemical group linking a first nucleoside analog residue with a second nucleoside analog residue, which nucleoside analog residues may be identical or may be distinct. Nucleoside analog residues encompass compounds of formula (II) that are disclosed herein. In one aspect, a nucleotide of an siNA molecule of the invention may be linked to an adjacent nucleotide through a linkage between the 3'-carbon of the sugar moiety of the first nucleotide and the 5'-carbon of the sugar moiety of the second nucleotide (herein referred to as a 3' internucleoside linkage). A 3'-5' internucleoside linkage, as used herein, refers to an internucleoside linkage that links two adjacent nucleoside units, wherein the linkage is between the 3'-carbon of the sugar moiety of the first nucleoside and the 5'-carbon of the sugar moiety of the second nucleoside. In another aspect, a nucleotide (including a nucleotide analog) of an siNA molecule of the invention may be linked to an adjacent nucleotide (including a nucleotide analog) through a linkage between the 2'-carbon of the sugar moiety of the first nucleotide and the 5'-carbon of the sugar moiety of the second nucleotide (herein referred to as a 2' internucleoside linkage). A 2'-5' internucleoside linkage, as used herein, refers to an internucleoside linkage that links two adjacent nucleoside units, wherein the linkage is between the 2' carbon of the sugar moiety of the first nucleoside and the 5'-carbon of the sugar moiety of the second nucleoside.

As used herein, the term "internucleoside linking group" encompasses phosphorus- and non-phosphorus-containing internucleoside linking groups.

In some embodiments, a phosphorus-containing internucleoside linking group encompasses phosphodiesters, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and boranophosphates having normal 3'-5' linkages, and 2'-5' linked analogs thereof.

Representative U.S. patents that teach the preparation of the above phosphorus-containing internucleoside linkages include U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,194,599; 5,565,555; 5,527,899; 5,721,218; 5,672,697 and 5,625,050, each of which is herein incorporated by reference.

In one embodiment, non-phosphodiester backbone linkage is selected from a group consisting of phosphorothioate, phosphorodithioate, alkyl-phosphonate and phosphoramidate backbone linking groups.

In one embodiment, a phosphorus-containing internucleoside linking group encompasses phosphodiesters, phosphotriesters and phosphorothioates.

In some embodiments, oligonucleotides of the invention comprise one or more internucleoside linking groups that do not contain a phosphorus atom. Such oligonucleotides include, but are not limited to, those that are formed by short chain alkyl or cycloalkyl internucleoside linking groups, mixed heteroatom and alkyl or cycloalkyl internucleoside linking groups, or one or more short chain heteroatomic or heterocyclic internucleoside linking groups. These include those having siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative U.S. patents that teach the preparation of the above non-phosphorus containing internucleoside linking group include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439, each of which is herein incorporated by reference.

In one embodiment, oligonucleotides of the invention comprise one or more neutral internucleoside linking groups that are non-ionic. Neutral internucleoside linking groups encompass nonionic linking groups comprising siloxane (dialkylsiloxane), carboxylate ester, carboxamide, sulfide, sulfonate ester and amides (See for example: Carbohydrate Modifications in Antisense Research; Y. S. Sanghvi and P. D. Cook Eds. ACS Symposium Series 580; Chapters 3 and 4, (pp. 40-65)). Further neutral internucleoside linking groups encompass nonionic linkages comprising mixed N, O, S and $CH_2$ component parts.

Compounds of Formula (I)

The present invention relates to compounds of general formula (I):

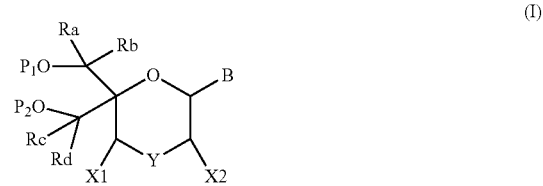

(I)

Wherein:

B is a heterocyclic nucleobase;

P1 and P2 are each, independently, H, a reactive phosphorus group or a protecting group;

Y is O, NH, NR1 or N—C(=O)—R1, wherein R1 is:
a ($C_1$-$C_{20}$) alkyl group, optionally non-substituted or substituted by one or more groups selected from an halogen atom, a (C1-C6) alkyl group, a (C3-C8) cycloalkyl group, a (C3-C14) heterocycle, a (C6-C14) aryl group, a (C5-C14) heteroaryl group —O—Z1, —N(Z1)(Z2), —S—Z1, —CN, —C(=J)-O—Z1, —O—C(=J)-Z1, —C(=J)-N(Z1)(Z2), and —N(Z1)-C(=J)-Z2, wherein J is O or S, each of Z1 and Z2 is, independently, H, a (C1-C6) alkyl group, optionally substituted by one or more groups selected from a halogen atom and a (C1-C6) alkyl group, a (C3-C8) cycloalkyl group, optionally substituted by one or more groups selected from a halogen atom and a (C1-C6) alkyl group, or a group —[C(=O)]m-R2-(O—$CH_2$—$CH_2$)p-R3, wherein m is an integer meaning 0 or 1, p is an integer ranging from 0 to 10, R2 is a (C1-C20) alkylene group optionally substituted by a (C1-C6) alkyl group, —O—Z3, —N(Z3)(Z4), —S—Z3, —CN, —C(=K)—O—Z3, —C(=K)—Z3, —C(=K)—N(Z3)(Z4), —N(Z3)-C(=K)—Z4, wherein K is O or S, each of Z3 and Z4 is, independently, H, a (C1-C6) alkyl group, optionally substituted by one or more groups selected from a halogen atom and a (C1-C6) alkyl group, and
R3 is selected from the group consisting of a hydrogen atom, a (C1-C6) alkyl group,
a (C1-C6) alkoxy group, a (C3-C8) cycloalkyl group, a (C3-C14) heterocycle, a (C6-C14) aryl group or a (C5-C14) heteroaryl group,
or
R3 is a cell targeting moiety,
X1 and X2 are each, independently, a hydrogen atom, a —(C1-C6) alkyl group, and
each of Ra, Rb, Rc and Rd is, independently, H or a (C1-C6) alkyl group.

A compound of formula (I) is encompassed by the term "nucleotide precursor" for the purpose of the present disclosure. A compound of formula (I) wherein group R3 is present and denotes a cell targeting moiety is encompassed by the term "targeted nucleotide precursor" for the purpose of the present disclosure.

Compounds of formula (I) and (II) disclosed herein encompass stereoisomers thereof, which include the (2S,6R) stereoisomer thereof and the (2R,6R) stereoisomer thereof, as specifically described in the following formula, that specifies position numbering and chiral centers of the compounds of formula (I) and (II):

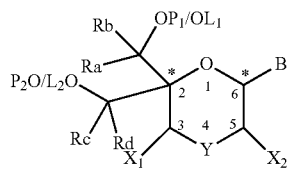

(I)

As it will be shown in the Examples herein, when incorporated in an oligonucleotide, the (2S,6R) stereoisomer of a compound of formula (I) and the (2R,6R) stereoisomer of a compound of formula (I) are endowed with the same ability to generate an siRNA allowing a good inhibition of a target mRNA.

As described above, the inventors have conceived specific nucleotide precursors of formula (I) comprising either a dioxane ring or a morpholino ring that are useful as building block units for synthesizing gene silencing oligonucleotides, and especially for synthesizing siRNAs.

Thus, in some embodiments of a compound of formula (I), which may be termed "dioxane analog" herein, Y is O. An embodiment of such a nucleotide precursor in the present disclosure is termed pre-lB1, wherein B is as defined in formula (I), e.g. pre-lT1, when B consists of a thymidinyl group.

In other embodiments of a compound of formula (I), which may be termed "morpholino analog" herein, Y is NH, NR1 or NC(=O)R1.

In morpholino analogs of formula (I), the nitrogen atom is preferably functionalized, so as to improve properties of the resulting morpholino analog-containing oligonucleotide, and especially the resulting morpholino analog-containing siRNA.

In some embodiments of a compound of formula (I), the compounds are morpholino analogs of the present disclosure that do not comprise a cell targeting moiety. According to these embodiments, group R3, when present, does not represent a cell targeting moiety.

Thus, in some preferred embodiments of a morpholino analog of formula (I), Y is NH, NR1 or N—C(=O)—R1, with R1 being as defined for the general formula (I).

In some embodiments wherein Y is NR1, R1 is:
a (C1-C20) alkyl group optionally substituted by one or more groups selected from an halogen atom, a (C1-C6) alkyl group, a (C3-C8) cycloalkyl group, a (C3-C14) heterocycle, a (C6-C14) aryl group, a (C5-C14) heteroaryl group, —O—Z1, —N(Z1)(Z2), —S—Z1, —CN, —C(=J)-O—Z1, —O—C(=J)-Z1, —C(=J)-N(Z1)(Z2), and —N(Z1)-C(=J)-Z2, wherein
J is O or S, and
each of Z1 and Z2 is, independently, H, a (C1-C6) alkyl group, optionally substituted by one or more groups selected from a halogen atom and a (C1-C6) alkyl group, or
a (C3-C8) cycloalkyl group optionally substituted by one or more groups selected from a halogen atom and a (C1-C6) alkyl group,
a group —[C(=O)]m-R2-(O—CH$_2$—CH$_2$)p-R3, wherein
m is an integer meaning 0 or 1
p is an integer ranging from 0 to 10
R2 is a (C1-C20) alkylene group optionally substituted by a (C1-C6) alkyl group, —O—Z3, —N(Z3)(Z4), —S—Z3, —CN, —C(=K)—O—Z3, —C(=K)—Z3, —C(=K)—N(Z3)(Z4), —N(Z3)-C(=K)—Z4, wherein
K is O or S,
each of Z3 and Z4 is, independently, H, a (C1-C6) alkyl group, optionally substituted by one or more groups selected from a halogen atom and a (C1-C6) alkyl group,
and
R3 is selected from the group consisting of a hydrogen atom, a (C1-C6)-alkyl, a (C1-C6)-alkoxy, a (C3-C8) cycloalkyl group, a (C3-C14) heterocycle, a (C6-C14) aryl group or a (C5-C14) heteroaryl group,
X1 and X2 are each, independently, a hydrogen atom, a (C1-C6) alkyl group
each of Ra, Rb, Rc and Rd is, independently, H or a (C1-C6) alkyl group.

As intended herein, a (C1-C20) alkyl group, which may be either a non-substituted alkyl group or a substituted alkyl group, includes C1, C2, C3, C4, C5, C6, C7, C8, C9, C10, C11, C12, C13, C14, C15, C16, C17, C18, C19 and C20 alkyl groups.

As intended herein, a (C1-C6) alkyl group, which may be either a non-substituted alkyl group or a substituted alkyl group, includes C1, C2, C3, C4, C5 and C6 alkyl groups.

As intended herein, a (C3-C8) cycloalkyl group, which may be either a non-substituted cycloalkyl group or a substituted cycloalkyl group, includes C3, C4, C5, C6, C7 and C8 cycloalkyl groups.

As intended herein, a (C3-C14) heterocycle, which may be either a non-substituted or a substituted heterocycle, includes C3, C4, C5, C6, C7, C8, C9, C10, C11, C12, C13 and C14 heterocycles.

As intended herein, a (C6-C14) aryl group, which may be either a non-substituted aryl group or a substituted aryl group, includes C6, C7, C8, C9, C10, C11, C12, C13 and C14 aryl groups.

As intended herein, a (C5-C14) heteroaryl group, which may be either a non-substituted heteroaryl group or a substituted heteroaryl group, includes C5, C6, C7, C8, C9, C10, C11, C12, C13 and C14 heteroaryl groups.

In some embodiments of a compound of formula (I) wherein Y is NR1, R1 is an optionally substituted (C1-C20)

alkyl group, and P1, P2, Ra, Rb, Rc, Rd, X1, X2 and B are as defined for the general formula (I).

In some of these embodiments wherein Y is NR1, R1 is a non-substituted (C1-C20) alkyl group.

In some of the embodiments wherein Y is NR1, R1 is a non-substituted (C1-C16) alkyl group, which includes an alkyl group selected from a group comprising methyl, isopropyl, butyl, octyl, hexadecyl and P1, P2, Ra, Rb, Rc, Rd, X1, X2 and B have the same meaning as defined for the general formula (I).

In some embodiments wherein Y is NR1, R1 is a methyl group, Ra, Rb, Rc, Rd, X1 and X2 are a hydrogen atom, and P1 and P2 are as defined for the general formula (I). An embodiment of such a nucleotide precursor in the present disclosure is termed pre-lB2, with B having the same meaning than in general formula (I); for example, an embodiment of such a nucleotide precursor in the present disclosure is termed pre-lT2 when B consists of a thymidinyl group.

In some embodiments wherein Y is NR1, R1 is an isopropyl group, Ra, Rb, Rc, Rd, X1 and X2 are a hydrogen atom, and P1 and P2 are as defined for the general formula (I). An embodiment of such a nucleotide precursor in the present disclosure is termed pre-lB3, with B having the same meaning than in general formula (I); for example, an embodiment of such a nucleotide precursor in the present disclosure is termed pre-lT3, wherein B consists of a thymidinyl group, pre-lU3, wherein B consists of a uracil group, pre-lG3 when B consists of a guanyl group, pre-lC3, wherein B consists of a cytosyl group, and pre-lA3, wherein B consists of a adenyl group.

In some embodiments wherein Y is NR1, R1 is a butyl group, Ra, Rb, Rc, Rd, X1 and X2 are a hydrogen atom, and P1 and P2 are as defined for the general formula (I). An embodiment of such a nucleotide precursor in the present disclosure is termed pre-lB6, with B having the same meaning than in general formula (I); for example, an embodiment of such a nucleotide precursor in the present disclosure is termed pre-lT6, wherein B consists of a thymidinyl group.

In some embodiments wherein Y is NR1, R1 is an octyl group, Ra, Rb, Rc, Rd, X1 and X2 are a hydrogen atom, and P1 and P2 are as defined for the general formula (I). An embodiment of such a nucleotide precursor in the present disclosure is termed pre-lB7, with B having the same meaning than in general formula (I); for example, an embodiment of such a nucleotide precursor in the present disclosure is termed pre-lT7, wherein B consists of a thymidinyl group.

In some embodiments wherein Y is NR1, R1 is a linear C16-alkyl group, Ra, Rb, Rc, Rd, X1 and X2 are a hydrogen atom, and P1 and P2 are as defined for the general formula (I). An embodiment of such a nucleotide precursor in the present disclosure is termed pre-lB8, with B having the same meaning than in general formula (I); for example, an embodiment of such a nucleotide precursor in the present disclosure is termed pre-lT8, wherein B consists of a thymidinyl group.

In further embodiments of a compound of formula (I) wherein Y is NR1, R1 is a (C1-C20) alkyl group which is substituted as defined in the general formula (I), which includes a C1, C2 or C3 alkyl group which is substituted as defined in the general formula (I).

In some of these further embodiments, R1 is an (C1-C20) alkyl group which is substituted by one or more groups selected from an halogen atom, a (C1-C6) alkyl group, a (C3-C8) cycloalkyl group, a (C3-C14) heterocycle, a (C6-C14) aryl group and a (C5-C14) heteroaryl group and P1, P2, Ra, Rb, Rc, Rd, X1, X2 and B have the same meaning as defined for the general formula (I).

In some of these further embodiments, R1 is an (C1-C20) alkyl group which is substituted by a (C6-C14) aryl group, and P1, P2, Ra, Rb, Rc, Rd, X1, X2 and B have the same meaning as defined for the general formula (I).

In some embodiments of a compound of formula (I) wherein Y is NR1, R1 is a (C1-C20) alkyl group which is substituted by a (C6-C14) aryl group. These embodiments encompass a compound of formula (I) wherein Y is NR1, R1 is a methylene group which is substituted by an aryl group. These embodiments also encompass a compound of formula (I) wherein Y is NR1, R1 is a (C1-C20) alkyl group which is substituted by a phenyl group.

In some embodiments of a compound of formula (I) wherein Y is NR1, R1 is a methyl group which is substituted by a non-substituted phenyl group, Ra, Rb, Rc, Rd, X1 and X2 are each a hydrogen atom, and P1 and P2 are as defined in the general formula (I). An embodiment of such a nucleotide precursor in the present disclosure is termed pre-lB5, with B having the same meaning than in general formula (I); for example, an embodiment of such a nucleotide precursor in the present disclosure is termed pre-lT5, wherein B consists of a thymidinyl group.

In further embodiments of a compound formula (I) wherein Y is NR1, R1 is a (C3-C8) cycloalkyl group, optionally substituted by one or more groups selected from a halogen atom and a (C1-C6) alkyl group, and P1, P2, Ra, Rb, Rc, Rd, X1, X2 and B have the same meaning as defined for the general formula (I).

In some of these further embodiments of a compound of formula (I) wherein Y is NR1, R1 is a cyclohexyl.

In some of these further embodiments, of a compound of formula (I) wherein Y is NR1, R1 is a non-substituted cyclohexyl, Ra, Rb, Rc, Rd, X1, X2 are each a hydrogen atom, and P1 and P2 are as defined for the general formula (I).

An embodiment of such a nucleotide precursor in the present disclosure is termed pre-lB4, with B having the same meaning than in general formula (I); for example, an embodiment of such a nucleotide precursor in the present disclosure is termed pre-lT4, wherein B consists of a thymidinyl group.

In some other embodiments of a morpholino analog of formula (I), Y is N—C(=O)—R1, wherein R1 is a (C1-C20) alkyl group, wherein optionally substituted by one or more groups selected from an halogen atom, a (C1-C6) alkyl group, a (C3-C8) cycloalkyl group, a (C3-C14) heterocycle, a (C6-C14) aryl group, a (C5-C14) heteroaryl group —O—Z1, —N(Z1)(Z2), —S—Z1, —CN, —C(=J)-O—Z1, —O—C(=J)-Z1, —C(=J)-N(Z1)(Z2), —N(Z1)-C(=J)-Z2, wherein J is O or S, each of Z1 and Z2 is, independently, H, a (C1-C6) alkyl group, optionally substituted by one or more groups selected from a halogen atom and a (C1-C6) alkyl group, and R1 is (C3-C8) cycloalkyl group, optionally substituted by one or more groups selected from an halogen atom or a (C1-C6) alkyl group, and P1, P2 Ra, Rb, Rc, Rd, X1, X2 and B have the same meaning as defined for the general formula (I).

In some of the embodiments wherein Y is N—C(=O)—R1, R1 is an optionally-substituted (C1-C20) alkyl group, which includes an optionally substituted (C1-C15) alkyl group, and P1, P2 Ra, Rb, Rc, Rd, X1, X2 and B have the same meaning as defined for the general formula (I).

According to some of these embodiments wherein Y is N—C(=O)—R1, R1 is selected from a group comprising methyl and pentadecyl groups, and P1, P2 Ra, Rb, Rc, Rd, X1, X2 and B have the same meaning as defined for the general formula (I).

These embodiments encompass compounds of formula (I) wherein Y is N—C(=O)—R1, R1 is methyl group, Ra, Rb, Rc, Rd, X1, X2 each represent a hydrogen atom and B, P1 and P2 are as defined in the general formula (I).

An embodiment of such a nucleotide precursor in the present disclosure is termed pre-lB9 with B having the same meaning than in general formula (I); for example, an embodiment of such a nucleotide analog in the present disclosure is termed pre-lT9, wherein B consists of a thymidinyl group. These embodiments also encompass compounds of formula (I) wherein Y is N—C(=O)—R1, R1 is a pentadecyl group, Ra, Rb, Rc, Rd, X1, X2 each represent a hydrogen atom and B, P1 and P2 are as defined in the general formula (I). An embodiment of such a nucleotide precursor in the present disclosure is termed pre-lB10 with B having the same meaning than in general formula (I); for example, an embodiment of such a nucleotide precursor in the present disclosure is termed pre-lT10, wherein B consists of a thymidinyl group.

In a compound of formula (I), B is a heterocyclic nucleobase moiety. As used herein, the term "heterocyclic nucleobase" refers to an optionally substituted nitrogen-containing heterocycle that is covalently linked to the dioxane ring or the morpholino ring. In some embodiments, the heterocyclic nucleobase can be selected from an optionally substituted purine-base and an optionally substituted pyrimidine-base. The term "purine-base" is used herein in its ordinary sense as understood by those skilled in the art and includes its tautomers. Similarly, the term "pyrimidine-base" is used herein in its ordinary sense as understood by those skilled in the art, and includes its tautomers. A non-limiting list of optionally substituted purine-bases includes purine, adenine, guanine, hypoxanthine, xanthine, alloxanthine, 7-alkylguanine (e.g. 7-methylguanine), theobromine, caffeine, uric acid and isoguanine. Examples of pyrimidine-bases include, but are not limited to, cytosine, thymine, uracil, 5,6-dihydrouracil and 5-alkylcytosine (e.g., 5-methylcytosine). Other non-limiting examples of heterocyclic bases include diaminopurine, 8-oxo-$N^6$alkyladenine (e.g., 8-oxo-$N^6$methyladenine), 7-deazaxanthine, 7-deazaguanine, 7-deazaadenine, $N^4N^4$ethanocytosin, $N^{<6>},N^{<6>}$-ethano-2,6-diaminopurine, 5-halouracil (e.g., 5-fluorouracil and 5-bromouracil), pseudoisocytosine, isocytosine, isoguanine, 1,2,4-triazole-3-carboxamides and other heterocyclic bases described in the U.S. Pat. Nos. 5,432,272 and 7,125,855, which are incorporated herein by reference for the limited purpose of disclosing additional heterocyclic bases. In some embodiments, a heterocyclic base can be optionally substituted with an amine or an enol protecting group(s). In some embodiments, B is selected from a group comprising a pyrimidine, a substituted pyrimidine, a purine and a substituted purine, which amino group thereof, when present, is optionally protected by a protecting group.

In preferred embodiments, B is selected from a group comprising Adenine, Thymine, Uracil, Guanine and Cytosine (i.e. Adenyl, Thyminyl, Uracyl, Guanyl and Cytosyl groups). Adenine, Guanine and Cytosine are optionally protected by amine protecting groups. Amine protecting groups encompass acyl-groups, as e.g. benzoyl, phenylacetyl and isobutyryl-protecting groups or formamidine protecting groups, as e.g. N,N-dimethyl-formamidine.

As already mentioned, in a compound of formula (I), groups P1 and P2 are each, independently, a hydrogen atom, a reactive phosphorus group or a protecting group.

As used herein, a "reactive phosphorus group" refers to a phosphorus-containing group comprised in a nucleotide unit or in a nucleotide analog unit and which may react with a hydroxyl group or an amine group comprised in another molecule, and especially in another nucleotide unit or in another nucleotide analog, through a nucleophilic attack reaction.

Generally, such a reaction generates an ester-type internucleoside linkage linking the said first nucleotide unit or the said first nucleotide analog unit to the said second nucleotide unit or to the said second nucleotide analog unit.

In some embodiments, a reactive phosphorus group can be selected from the group consisting of phosphoramidite, H-phosphonate, alkyl-phosphonate, phosphate or phosphate mimics include but not limited to: natural phosphate, phosphorothioate, phosphorodithioate, borano phosphate, borano thiophosphate, phosphonate, halogen substituted phosphonates and phosphates, phosphoramidates, phosphodiester, phosphotriester, thiophosphodiester, thiophosphotriester, diphosphates and triphosphates. Protecting groups encompass hydroxyl-, amine- and phosphoramidite protecting groups, which may be selected from a group comprising acetyl (Ac), benzoyl (Bzl), benzyl (Bn), isobutyryl (iBu), phenylacetyl, benzyloxymethyl acetal (BOM), beta-methoxyethoxymethyl ether (MEM), methoxymethylether (MOM), p-methoxybenzyl ether (PMB), methylthiomethyl ether, pivaloyl (Piv), tetrahydropyranyl (THP), triphenylmethyl (Trt), methoxytrityl [(4-methoxyohenyl)diphenylmethyl-] (MMT), dimethoxytrityl, [bis-(4-methoxyphenyl) phenylmethyl (DMT), trimethylsilyl ether (TMS), tert-butyldimethylsilyl ether (TBDMS), tri-isopropylsilyloxymethyl ether (TOM), tri-isopropylsilyl ether (TIPS), methyl ethers, ethoxyethyl ethers (EE) N,N-dimethylformamidine and 2-cynaonethyl (CE).

In some embodiments of a compound of formula (I) wherein Y, B, Ra, Rb, Rc, Rd, X1 and X2 are as defined for the general formula (I), one of P1 or P2 is a O-4,4'-dimethoxytrityl group (DMT) and the other of P1 and P2 is H, a reactive phosphorus group or a protecting group.

In some embodiments of a compound of formula (I) wherein Y, B, Ra, Rb, Rc, Rd, X1 and X2 are as defined for the general formula (I), one of P1 and P2 is a 2-cyanoethyl-N,N-diisopropylphosphoramidite group and the other P1 and P2 is a protecting group.

In some embodiments of a compound of formula (I) wherein Y, B, Ra, Rb, Rc, Rd, X1 and X2 are as defined for the general formula (I), one of P and P2 is a 2-cyanoethyl-N,N-diisopropylphosphoramidite group and the other of P1 and P2 is O-4,4'-dimethoxytrityl group Further, each of Ra, Rb, Rc and Rd are, independently, H or a (C1-C6) alkyl group, and preferably H or a non-substituted ($C_1$-$C_6$) alkyl group.

As used herein, a (C1-C6) alkyl group encompass alkyl groups selected from a group comprising C1, C2, C3, C4, C5 and C6 alkyl groups.

In most preferred embodiments, X1 and X2 both represent a hydrogen atom.

In most preferred embodiments, Ra, Rb, Rc and Rd both represent a hydrogen atom.

Embodiments of Compounds of Formula (I) Comprising targeted Nucleotide Analogs

As previously specified herein, the present disclosure encompasses compounds of formula (I) wherein:

B is a heterocyclic nucleobase;

P1 and P2 are each, independently, H, a reactive phosphorus group or a protecting group;

Y is NR1 with R1 being a group —[C(=O)]m-R2-(O—CH$_2$—CH$_2$)p-R3, wherein m is an integer meaning 0 or 1, p is an integer ranging from 0 to 10, R2 is a (C1-C20) alkylene group optionally substituted by a (C1-C6) alkyl group, —O—Z3, —N(Z3)(Z4), —S—Z3, —CN, —C(=K)—O—Z3, —C(=K)—Z3, —C(=K)—N(Z3)(Z4), —N(Z3)-C(=K)—Z4, wherein K is O or S, each of Z3 and Z4 is, independently, H, a (C1-C6) alkyl group, optionally substituted by one or more groups selected from a halogen atom and a (C1-C6) alkyl group, and R3 is a cell targeting moiety, X1 and X2 are each, independently, a hydrogen atom, a (C1-C6) alkyl group, and each of Ra, Rb, Rc and Rd is, independently, H or a (C1-C6) alkyl group.

These compounds of formula (I) are encompassed in a more general family of compounds that may be termed "targeted nucleotide precursors" in the present disclosure. Such compounds of formula (I) wherein group R3 is present and represents a cell targeting moiety may be termed a "targeted nucleotide precursor of formula (I)" or a "targeted nucleotide precursor (I)" in the present disclosure.

The compounds of formula (I) that do not comprise a group R3 representing a cell targeting moiety are not targeted nucleotide precursors, and are termed "non-targeted nucleotide precursors of formula (I)" or "non-targeted nucleotide precursors (I)" in the present disclosure.

In some embodiments of a targeted nucleotide precursors of formula (I), R1 is the group —[C(=O)]m-R2-(O—CH$_2$—CH$_2$)p-R3, m is 0, p is 0, R3 is a cell targeting moiety, B, P1, P2, Ra, Rb, Rc, Rd, X1, X2, and R2 are as in the general definition of the compound of formula (I). In some embodiments, R2 is an ethylene group and X1 and X2 are both an hydrogen atom. In some other of these embodiments, R2 is a pentylene group, and X1 and X2 are both an hydrogen atom. In some embodiments, R2 is a (C12) alkylene and X1 and X2 are both an hydrogen atom.

In some embodiments of a compound of formula (I) R1 is the group —[C(=O)]m-R2-(O—CH$_2$—CH$_2$)p-R3, m is 0, p is an integer selected from the group consisting of 1, 2, 3 and 4, R3 is a cell targeting moiety and B, P1, P2, Ra, Rb, Rc, Rd, X1, X2 and R2, are as in the general definition of the compound of formula (I). In some embodiments, R2 is an ethylene group, p is 1 and X1 and X2 are both an hydrogen atom. In some embodiments, R2 is an ethylene group, p is 2 and X1 and X2 are both an hydrogen atom. In some embodiments, R2 is an ethylene group, p is 3 and X1 and X2 are both an hydrogen atom. In some embodiments, R2 is an ethylene group, p is 4 and X1 and X2 are both an hydrogen atom.

In some embodiments of a compound of formula (I), R1 is the group —[C(=O)]m-R2-(O—CH$_2$—CH$_2$)p-R3, m is 1, p is 0, R3 is a cell targeting moiety, and R2, B, P1, P2, Ra, Rb, Rc, Rd, X1, X2, are as in the general definition of the compound of formula (I). In some of these embodiments, R2 is a butylene, X1 and X2 each represent a hydrogen atom and B, P1, P2, Ra, Rb, Rc and Rd are as defined for the general formula (I). In some further of these embodiments, R2 is a (C11) alkylene, X1 and X2 both represent a hydrogen atom and B, P1, P2, Ra, Rb, Rc and Rd are as defined for the general formula (I).) In some still further of these embodiments, R2 is a methylene, X1 and X2 both represent a hydrogen atom and B, P1, P2, Ra, Rb, Rc and Rd are as defined for the general formula (I).

In some embodiments of a compound of formula (I) wherein R1 is the group —[C(=O)]m-R2-(O—CH$_2$—CH$_2$) p-R3, m is 1, p is selected from the group of integers consisting of 1 and 2, R3 is a cell targeting moiety, R2, B, P1, P2, Ra, Rb, Rc, Rd, X1, X2, are as in the general definition of the compound of formula (I). In some of these embodiments, R2 is a methylene group, p is 2, R3 is a cell targeting moiety, B, P1, P2, Ra, Rb, Rc, Rd, X1, X2, are as defined for the general formula (I). In some other of these embodiments, R2 is a methylene group, p is 1, R3 is a cell targeting moiety, B, P1, P2, Ra, Rb, Rc, Rd, X1, X2 are as defined for the general formula (I).

In some embodiments of a compound of formula (I), Ra, Rb, Rc and Rd are an hydrogen atom.

In general, group R3 encompass any cell targeting moiety known in the art, including any cell targeting moiety specified in the present disclosure, which include the cell targeting moieties that are specified for the description of targeted oligonucleotides in the present disclosure.

In some embodiments of a compound of formula (I), R3 is of the formula (III)

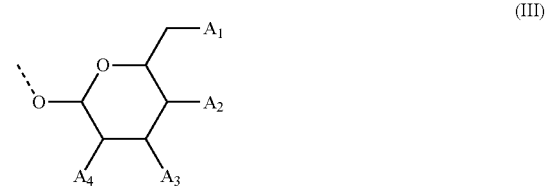

wherein

A1, A2 and A3 are OH or O—C(=O)—R4, wherein R4 is a (C1-C6)-alkyl or a (C6-C10)-aryl group.

A4 is OH, O—C(=O)—R4, NHC(=O)—R5, with R4 being defined as above and R5 is (C1-C6)-alkyl group, optionally substituted by an halogen atom.

In some preferred embodiments, A1, A2 and A3 are O—C(=O)—R4, wherein R4 is a (C1-C6)-alkyl or a (C6-C10)-aryl group.

In some preferred embodiments, A1, A2 and A3 are O—C(=O)—R4, R4 is a methyl or phenyl group.

In some preferred embodiments A1, A2 and A3 are O—C(=O)—R4, and R4 is methyl.

In some preferred embodiments, A4 is O—C(=O)—R4 or NHC(=O)—R5, wherein R4 is (C1-C6) alkyl or (C6-C10)-aryl group and R5 is (C1-C6)-alkyl group, optionally substituted by an halogen atom.

In some preferred embodiments, A1, A2 and A3 are O—C(=O)—R4, wherein R4 is methyl and A4 is O—C(=O)—R4 or NHC(=O)—R5, wherein each of R4 and R5 is methyl.

In some preferred embodiments, R3 is 3,4,6-Tri-O-acetyl-D-N-Acetylgalactosylamine of formula (III-A):

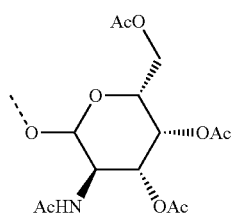
(III-A)

The present disclosure also relates to oligonucleotides comprising one or more nucleotide analogs that have been introduced in the oligonucleotides by using nucleotide analog precursors that are compounds of formula (I) specified herein.

As it will be detailed elsewhere in the present disclosure, the invention further pertains to single-stranded and double-stranded oligonucleotides, and especially siRNAs, comprising one or more compounds of formula (II).

Modified Oligonucleotides

Compounds of formula (I) disclosed herein are nucleotide analog building blocks, called also "nucleotide precursors" that have been conceived as monomer units of oligomeric compounds, particularly as monomer units of oligonucleotides, including as monomer units of double-stranded RNA ("dsRNA") oligomers, and especially as monomer units of siRNAs.

Incorporation of nucleotide precursors, described herein under compounds of formula (I) into an oligonucleotide leads to the corresponding monomer units of the oligonucleotides, described herein as compounds of formula (II).

The terms "oligomeric compound" and "oligonucleotide" may be interchangeably used herein.

Thus, this invention also pertains to oligonucleotides wherein one or more compounds of formula (I), either non-targeted, targeted, or non-targeted and targeted, have been incorporated therein, resulting in compounds of formula (II).

As it will be further detailed in the present disclosure, oligonucleotides according to the invention may be either under a single-stranded form or in a double-stranded form.

This invention relates to an oligonucleotide comprising one or more compounds of formula (II):

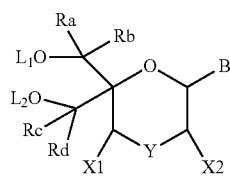
(II)

wherein, independently for each compound of formula (II):

B is a heterocyclic nucleobase;

one of L1 and L2 is an internucleoside linking group linking the compound of formula (II) to the oligomeric compound and the other of L1 and L2 is H, a protecting group, a phosphorus moiety or an internucleoside linking group linking the compound of formula (II) to the oligomeric compound Y is O, NH, NR1 or N—C(=O)—R1, wherein R1 is:
a (C1-C20) alkyl group,
optionally substituted by one or more groups selected from an halogen atom, a (C1-C6) alkyl group, a (C3-C8) cycloalkyl group, a (C3-C14) heterocycle, a (C6-C14) aryl group, a (C5-C14) heteroaryl group, —O—Z1, —N(Z1)(Z2), —S—Z1, —CN, —C(=J)-O—Z1, —O—C(=J)-Z1, —C(=J)-N(Z1)(Z2), —N(Z1)-C(=J)-Z2, wherein
J is O or S,
each of Z1 and Z2 is, independently, H, a (C1-C6) alkyl group, optionally substituted by one or more groups selected from a halogen atom and a (C1-C6) alkyl group,
a (C3-C8) cycloalkyl group, optionally substituted by one or more groups selected from a halogen atom and a (C1-C6) alkyl group,
a group —[C(=O)]m-R2-(O—CH2—CH2)p-R3, wherein
m is an integer meaning 0 or 1,
p is an integer ranging from 0 to 10,
R2 is a (C1-C20) alkylene group optionally substituted by a (C1-C6) alkyl group, —O—Z3, —N(Z3)(Z4), —S—Z3, —CN, —C(=K)—O—Z3, —O—C(=K)—Z3, —C(=K)—N(Z3)(Z4), and —N(Z3)-C(=K)—Z4, wherein
K is O or S,
each of Z3 and Z4 is, independently, H, a (C1-C6) alkyl group, optionally substituted by one or more groups selected from a halogen atom and a (C1-C6) alkyl group,
and
R3 is selected from the group consisting of a hydrogen atom, a (C1-C6) alkyl group, a (C1-C6) alkoxy group, a (C3-C8) cycloalkyl group, a (C3-C14) heterocycle, a (C6-C14) aryl group or a (C5-C14) heteroaryl group,
or
R3 is a cell targeting moiety,
X1 and X2 are each, independently, a hydrogen atom, a (C1-C6) alkyl group, and
each of Ra, Rb, Rc and Rd is, independently, H or a (C1-C6) alkyl group,
or a pharmaceutically acceptable salt thereof.

In some preferred embodiments of an oligonucleotide as described herein, in a compound of formula (II), Y is O.

In some other preferred embodiments of an oligonucleotide as described herein, in a compound of formula (II), Y is NR1 or N—C(=O)—R1, with R1 being as defined for the general formula (I).

In some embodiments wherein Y is NR1, R1 is a (C1-C20) alkyl group optionally substituted by one or more groups selected from an halogen atom, a (C1-C6) alkyl group, a (C3-C8) cycloalkyl group, a (C3-C14) heterocycle, a (C6-C14) aryl group, a (C5-C4) heteroaryl group, —O—Z1, —N(Z1)(Z2), —S—Z1, —CN, —C(=J)-O—Z1, —O—C(=J)-Z1, —C(=J)-N(Z1)(Z2), —N(Z1)-C(=J)-Z2, wherein
J is O or S,
each of Z1 and Z2 is, independently, H, a (C1-C6) alkyl group, optionally substituted by one or more groups selected from a halogen atom and a (C1-C6) alkyl group, in the form of the base or of an addition salt with an acid.

In some of these embodiments wherein Y is NR1, R1 is a non-substituted (C1-C20) alkyl group and L1, L2, Ra, Rb, Rc, Rd, X1, X2, R2, R3 and B have the same meaning as defined for the general formula (II), or a pharmaceutically acceptable salt thereof.

In some of the embodiments wherein Y is NR1, R1 is a non-substituted (C1-C16) alkyl group, which includes an alkyl group selected from a group comprising methyl, isopropyl, butyl, octyl, hexadecyl, and L1, L2 Ra, Rb, Rc, Rd, X1, X2 and B have the same meanings as defined for the general formula (II).

In some embodiments wherein Y is NR1, R1 is a methyl group, Ra, Rb, Rc, Rd, X1 and X2 are a hydrogen atom, and L1 and L2 are as defined for the general formula (II).

In some embodiments wherein Y is NR1, R1 is an isopropyl group, Ra, Rb, Rc, Rd, X1 and X2 are a hydrogen atom, and L1 and L2 are as defined for the general formula (II).

In some embodiments, wherein Y is NR1, R1 is a methyl group substituted by a phenyl group, and L1, L2, Ra, Rb, Rc, Rd, X1, X2, R2, R3 and B have the same meaning as defined for the general formula (II), or a pharmaceutically acceptable salt thereof.

In some embodiments wherein Y is NR1, R1 is a butyl group, Ra, Rb, Rc, Rd, X1 and X2 are a hydrogen atom, and L1 and L2 are as defined for the general formula (II).

In some embodiments wherein Y is NR1, R1 is an octyl group, Ra, Rb, Rc, Rd, X1 and X2 are a hydrogen atom, and L1 and L2 are as defined for the general formula (II).

In some embodiments wherein Y is NR1, R1 is a linear C16 alkyl group, Ra, Rb, Rc, Rd, X1 and X2 are a hydrogen atom, and L1 and L2 are as defined for the general formula (II).

In further embodiments of a compound of formula (II) wherein Y is NR1, R1 is a (C1-C20) alkyl group which is substituted as defined in the general formula (II), which includes a C1, C2 or C3 alkyl group which is substituted as defined in the general formula (II).

In some of these further embodiments, R1 is an (C1-C20) alkyl group which is substituted by one or more groups selected from an halogen atom, a (C1-C6) alkyl group, a (C3-C8) cycloalkyl group, a (C3-C14) heterocycle, a (C6-C14) aryl group and a (C5-C14) heteroaryl group.

In some of these further embodiments, R1 is an (C1-C20) alkyl group which is substituted by a (C6-C14) aryl group and L1, L2 Ra, Rb, Rc, Rd, X1, X2 and B have the same meaning as defined for the general formula (II).

In some embodiments of a compound of formula (II) wherein Y is NR1, R1 is a (C1-C20) alkyl group which is substituted by a (C6-C14) aryl group. These embodiments encompass a compound of formula (II) wherein Y is NR1, R1 is a methylene group which is substituted by an aryl group. These embodiments also encompass a compound of formula (II) wherein Y is NR1, R1 is a (C1-C20) alkyl group which is substituted by a phenyl group.

In some embodiments of a compound of formula (II) wherein Y is NR1, R1 is a methyl group which is substituted by a non-substituted phenyl group, Ra, Rb, Rc, Rd are each a hydrogen atom, and L1 and L2 are as defined in the general formula (II).

In further embodiments of a compound formula (II) wherein Y is NR1, R1 is a (C3-C8) cycloalkyl group, optionally substituted by one or more groups selected from a halogen atom and a (C1-C6) alkyl group, and L1, L2 Ra, Rb, Rc, Rd, X1, X2 and B have the same meaning as defined for the general formula (II).

In some of these further embodiments of a compound of formula (II) wherein Y is NR1, R1 is a cyclohexyl group, and L1, L2, Ra, Rb, Rc, Rd, X1, X2, R2, R3 and B have the same meaning have the same meaning as defined for the general formula (II), or a pharmaceutically acceptable salt thereof.

In some of these further embodiments, of a compound formula (II) wherein Y is NR1, R1 is a non-substituted cyclohexyl, Ra, Rb, Rc, Rd, X1, X2 are each a hydrogen atom, and L1 and L2 are as defined for the general formula (II).

In some other embodiments of an oligonucleotide of formula (II), Y is N—C(═O)—R1, wherein R1 is a (C1-C20) alkyl group, R1 is selected from a group comprising methyl and pentadecyl and L1, L2, Ra, Rb, Rc, Rd, X1, X2, R2, R3 and B have the same meaning as defined for the general formula (II), or a pharmaceutically acceptable salt thereof.

In some other embodiments of an oligonucleotide of formula (II), Y is N—C(═O)—R1, wherein R1 is a (C1-C20) alkyl group, optionally substituted by one or more groups selected from an halogen atom, a (C1-C6) alkyl group, a (C3-C8) cycloalkyl group, a (C3-C14) heterocycle, a (C6-C14) aryl group, a (C5-C14) heteroaryl group, —O—Z1, —N(Z1)(Z2), —S—Z1, —CN, —C(═J)-O—Z1, —O—C(═J)-Z1, —C(═J)-N(Z1)(Z2), and —N(Z1)-C(═J)-Z2, wherein J is O or S, and each of Z1 and Z2 is, independently, H, a (C1-C6) alkyl group, optionally substituted by one or more groups selected from a halogen atom and a (C1-C6) alkyl group, and L1, L2, Ra, Rb, Rc, Rd, X1, X2 and B have the same meanings as defined for the general formula (II)

In some of the embodiments wherein Y is N—C(═O)—R1, R1 is an optionally substituted (C1-C20) alkyl group, which includes an optionally-substituted (C1-C15) alkyl group, and L1, L2, Rb, Rc, Rd, X1, X2 and B have the same meanings as defined for the general formula (II).

In some of the embodiments wherein Y is N—C(═O)—R1, R1 is a non-substituted (C1-C20) alkyl group, which includes a non-substituted (C1-C15) alkyl group, and L1, L2 Ra, Rb, Rc, Rd, X1, X2 and B have the same meanings as defined for the general formula (II).

According to some of these embodiments wherein Y is N—C(═O)—R1, R1 is selected from a group comprising methyl and pentadecyl, and L1 and L2 and B have the same meanings as defined for the general formula (II). These embodiments encompass compounds of formula (II) wherein Y is N—C(═O)—R1, R1 is methyl group, Ra, Rb, Rc, Rd, X1, X2 each represent a hydrogen atom and B, L1 and L2 are as defined in the general formula (II). These embodiments also encompass compounds of formula (II) wherein Y is N—C(═O)—R1, R1 is a pentadecyl group, Ra, Rb, Rc, Rd, X1, X2 each represent a hydrogen atom and B, L1 and L2 are as defined in the general formula (II).

The compounds of formula (II) can exist in the form of free base or of addition salts with acids. The compounds of formula (II) can also exist in form of their pharmaceutically acceptable salts, that also come within the present disclosure.

Embodiments of Oligonucleotides Comprising Targeted Nucleotide Analogs of Formula (II)

As previously specified herein, the present disclosure also encompasses compounds of formula (II) wherein:

B is a heterocyclic nucleobase;

one of L1 and L2 is an internucleoside linking group linking the compound of formula (II) to the oligomeric compound and the other of L1 and L2 is H, a protecting group, a phosphorus moiety or an internucleoside linking group linking the compound of formula (II) to the oligomeric compound;

Y is NR1 an R is a group —[C(=O)]m-R2-(O—CH$_2$—CH$_2$)p-R3, wherein
  m is an integer meaning 0 or 1,
  p is an integer ranging from 0 to 10,
  R2 is a (C1-C20) alkylene group optionally substituted by a (C1-C6) alkyl group, —O—Z3, —N(Z3)(Z4), —S—Z3, —CN, —C(=K)—O—Z3, —C(=K)—Z3, —C(=K)—N(Z3)(Z4), —N(Z3)-C(=K)—Z4, wherein
    K is O or S,
    each of Z3 and Z4 is, independently, H, a (C1-C6) alkyl group, optionally substituted by one or more groups selected from a halogen atom and a (C1-C6) alkyl group,
    and
    R3 is a cell targeting moiety,
  X1 and X2 are each, independently, a hydrogen atom, a (C1-C6) alkyl group, and
  each of Ra, Rb, Rc and Rd is, independently, H or a (C1-C6) alkyl group, in the form of the base or of an addition salt with an acid.

These compounds of formula (II) are encompassed in a more general family of compounds that may be termed "targeted nucleotide analogs" in the present disclosure.

In some embodiments of a targeted nucleotide analogs of formula (II) wherein R1 is the group —[C(=O)]m-R2-(O—CH$_2$—CH$_2$)p-R3, m is 0, p is 0, R3 is a cell targeting moiety, B, P1, P2, Ra, Rb, Rc, Rd, X1, X2, and R2 are as in the general definition of the compound of formula (II).

In some embodiments, R2 is an ethylene group and X1 and X2 are both an hydrogen atom, B, P1, P2, Ra, Rb, Rc, Rd, are as in the general definition of the compound of formula (II).

In some other of these embodiments, R2 is a pentylene group and X1 and X2 are both an hydrogen atom, B, P1, P2, Ra, Rb, Rc, Rd, are as in the general definition of the compound of formula (II).

In some other of these embodiments, R2 is a (C12) alkylene group and X1 and X2 are both an hydrogen atom, B, P1, P2, Ra, Rb, Rc, Rd, are as in the general definition of the compound of formula (II).

In some embodiments of a compound of formula (II) wherein R1 is the group —[C(=O)]m-R2-(O—CH$_2$—CH$_2$)p-R3, m is 0, p is selected from the group of integers consisting of 1, 2, 3 and 4, R3 is a cell targeting moiety and B, L1, L2, Ra, Rb, Rc, Rd, X1, X2 and R2, are as in the general definition of the compound of formula (II). In some of these embodiments, R2 is an ethylene group, p is 1 and X1 and X2 are both an hydrogen atom. In still further of these embodiments, R2 is an ethylene group, p is 2 and X1 and X2 are both an hydrogen atom. In yet further of these embodiments, R2 is an ethylene group, p is 3 and X1 and X2 are both an hydrogen atom. In still other of these embodiments, R2 is an ethylene group, p is 4 and X1 and X2 are both an hydrogen atom.

In some embodiments of a compound of formula (II) wherein R1 is the group —[C(=O)]m-R2-(O—CH$_2$—CH$_2$)p-R3, m is 1, p is 0, R3 is a cell targeting moiety, and R2, B, L1, L2, Ra, Rb, Rc, Rd, X1, X2, are as in the general definition of the compound of formula (II).

In some of these embodiments, R2 is a butylene, X1 and X2 both represent a hydrogen atom and B, L1, L2, Ra, Rb, Rc and Rd are as defined for the general formula (II).

In some further of these embodiments, R2 is a (C11) alkylene, X1 and X2 both represent a hydrogen atom and B, L1, L2, Ra, Rb, Rc and Rd are as defined for the general formula (II).

In still some further of these embodiments, R2 is a methylene, X1 and X2 both represent a hydrogen atom and B, L1, L2, Ra, Rb, Rc and Rd are as defined for the general formula (II).

In some embodiments of a compound of formula (II) wherein R1 is the group —[C(=O)]m-R2-(O—CH$_2$—CH$_2$)p-R3, m is 1, p is selected from the group of integers consisting of 1 and 2, R3 is a cell targeting moiety, R2, B, L1, L2, Ra, Rb, Rc, Rd, X1, X2, are as in the general definition of the compound of formula (II).

In some of these embodiments, R2 is a methylene group, p is 2, R3 is a cell targeting moiety, B, L1, L2, Ra, Rb, Rc, Rd, X1, X2, are as defined for the general formula (II).

In some other of these embodiments, R2 is a methylene group, p is 1, R3 is a cell targeting moiety, B, L1, L2, Ra, Rb, Rc, Rd, X1, X2 are as defined for the general formula (II).

In general, group R3 encompass any cell targeting moiety known in the art, including any cell targeting moiety specified in the present disclosure, which include the cell targeting moieties that are specified for the description of targeted oligonucleotides in the present disclosure.

In some embodiments of a compound of formula (II), R3 is of the formula (III):

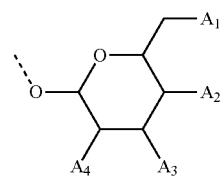

wherein A1, A2 and A3 are OH,
A4 is OH or NHC(=O)—R5, wherein R5 is a (C1-C6) alkyl group, optionally substituted by an halogen atom.

In some embodiments, R3 is N-acetyl-galactosamine of formula (III-B):

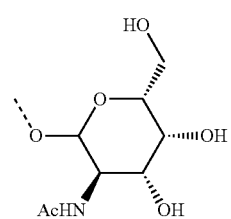

According to the present disclosure, reference to "GalNAc" or "N-acetyl galactosamine" includes both the β-form: 2-(Acetylamino)-2-deoxy-β-D-galactopyranose and the α-form: 2-(Acetylamino)-2-deoxy-α-D-galactopyranose. In certain embodiments, both the β-form: 2-(Acetylamino)-2-deoxy-β-D-galactopyranose and α-form; 2-(Acetylamino)-2-deoxy-α-D-galactopyranose may be used interchangeably.

In an oligonucleotide of formula (II), B is a heterocyclic nucleobase moiety. As used herein, the term "heterocyclic nucleobase" refers to an optionally substituted nitrogen-containing heterocycle that is covalently linked to the dioxane ring or the morpholino ring. In some embodiments, the heterocyclic nucleobase can be selected from an optionally substituted purine-base, an optionally substituted pyrimidine-base. The term "purine-base" is used herein in its ordinary sense as understood by those skilled in the art, and includes its tautomers. Similarly, the term "pyrimidine-base" is used herein in its ordinary sense as understood by those skilled in the art, and includes its tautomers. A non-limiting list of optionally substituted purine-bases includes purine, adenine, guanine, hypoxanthine, xanthine, alloxanthine, 7-alkylguanine (e.g. 7-methylguanine), theobromine, caffeine, uric acid and isoguanine. Examples of pyrimidine-bases include, but are not limited to, cytosine, thymine, uracil, 5,6-dihydrouracil and 5-alkylcytosine (e.g., 5-methylcytosine). Other non-limiting examples of heterocyclic bases include diaminopurine, 8-oxo-$N^6$alkyladenine (e.g., 8-oxo-$N^6$methyladenine), 7-deazaxanthine, 7-deazaguanine, 7-deazaadenine, $N^4N^4$ethanocytosin, $N^{<6>},N^{<6>}$-ethano-2,6-diaminopurine, 5-halouracil (e.g., 5-fluorouracil and 5-bromouracil), pseudoisocytosine, isocytosine, isoguanine, 1,2,4-triazole-3-carboxamides and other heterocyclic bases described in U.S. Pat. Nos. 5,432,272 and 7,125,855, which are incorporated herein by reference for disclosing additional heterocyclic bases.

In some embodiments, B is selected from a group comprising a pyrimidine, a substituted pyrimidine, a purine and a substituted purine.

In preferred embodiments, B is selected from a group comprising Adenine, Thymine, Uracil, Guanine and Cytosine (i.e., Adenyl, Thyminyl, Uracyl, Guanyl and Cytosyl groups).

As already mentioned, in an oligonucleotide of formula (II), one group among groups L1 and L2 is an internucleoside linking group linking the compound of formula (II) to the oligomeric compound and the other group among L1 and L2 groups is H, a protecting group, or an internucleoside linking group linking the compound of formula (II) to the oligomeric compound.

As will be shown in the examples, compounds of formula (I), when incorporated in a first oligonucleotide forming a duplex with a second oligonucleotide having a complementary sequence, showed a substantial decrease in the Tm value of the resulting nucleotide analog-containing oligonucleotide. The Tm-value of the resulting duplex decreases with increasing numbers of compounds of formula (II). Illustratively, for a starting 21-mer oligonucleotide having a Tm value of about 74° C., the Tm value may decrease to as low as about 50° C. for a resulting modified oligonucleotide comprising five compounds of formula (II) located at various positions within the resulting modified oligonucleotide. Thus, a decrease in the Tm value occurs when incorporating one or more compounds of formula (I) comprising a dioxane ring or one or more compounds of formula (I) comprising a morpholino ring. However, in most embodiments, such a decreased Tm value still ensures an appropriate duplex formation and then an appropriate duplex uptake in the RISC complex before hybridization of the antisense strand of the resulting siRNA to the desired target sequence.

The examples herein show that oligonucleotides wherein have been incorporated one or more compounds of formula (I) allow generating siRNA duplex structures that possess a stability that is required for ensuring an efficient inhibition of a target gene.

Highly unexpectedly, the examples also show that a high metabolic stability of siRNA duplexes comprising one or more compounds of formula (II) is obtained, when the compounds of formula (II) are linked, one with another or one with a ribose-containing nucleotide, through conventional phosphodiester bonds. It has been unexpectedly shown that, when compounds of formula (II) are linked through conventional phosphodiester bonds within an oligonucleotide, forming a strand of a siRNA, the resulting siRNA duplex possesses a higher stability against nuclease degradation than the same siRNA with phosphorothioate-linked deoxyribonucleotides instead of the compounds of formula (II). This unexpected stability increase has been especially shown for embodiments of siRNAs wherein compounds of formula (II) are present at an overhang of the sense strand and antisense strand thereof, including siRNAs wherein compounds of formula (II) are present at the 3'-end or 5'-end or both, 3'-end and 5'-end overhang of the sense strand thereof.

This high increase in metabolic stability of compounds of formula (II), when linked through a phosphodiester bond, is a clear technical advantage since stabilization through modified internucleotide linking phosphorous-groups such as phosphorothioates may be avoided. It is herein reminded that such non-conventional phosphorothioates introduce a chiral center, which leads to undesirable diastereomeric mixtures of the resulting siRNA. The latter may lower the siRNA specificity of the targeted sequence, leading to an increase of off-target events. It is also shown herein that siRNAs having one or more compounds of formula (II) have a good target gene silencing activity in vitro, even when the siRNAs are internalized by target cells in the absence of any transfection agent. As disclosed in the examples, embodiments of compounds of formula (II) exert a target gene silencing activity with an $IC_{50}$ value at a picomolar range.

In addition, the herein described examples of double stranded oligonucleotides incorporating one or more compounds of formula (II) with a targeting moiety attached to the morpholine-nitrogen (GalNAc residue), show a robust delivery into the liver, leading to an in vivo knock-down of the target mRNA and corresponding protein levels.

Unexpectedly it has been demonstrated a significant improvement of the in vivo behaviour of double stranded oligonucleotides (in particular the in vivo duration of action), when combining targeted compounds of formula (II) and non-targeted compounds of formula (II) within one double stranded oligonucleotide; this also may be shown wherein the sense strand does not contain any phosphorothioate groups. Even the additional attachment of non-targeted compounds of formula (II) as overhangs in the antisense strand without phosphorothioate stabilization shows a robust in vivo potency of the resulting siRNAs.

SiRNAs having incorporated one or more compounds of formula (I) in the sense strand, in the antisense strand or in both sense and antisense strands, and especially in the sense strand, also exert an efficient target gene silencing activity in vivo. The target gene silencing activity may be controlled according to (i) the embodiment(s) of the compounds of formula (I) present therein, (ii) the number of compounds of formula (I) present therein, and (iii) the location of the compound(s) of formula (I) within the sense strand or antisense strand of the siRNAs.

Importantly, siRNAs having incorporated one or more compounds of formula (II) are devoid of in vivo side effects at a dose range where those siRNAs are shown to exert a target gene silencing effect.

For the purpose of illustration, and without limiting the present disclosure, double-stranded oligonucleotides may also comprise one or more nucleotides on the sense and/or the antisense strands that are modified.

The modification may be selected from substitutions or insertions with analogues of nucleic acids or bases and chemical modification of the base, sugar or phosphate moieties. The selected modifications may each and individually be selected among 3'-terminal deoxy-thymine, 2'-O-methyl, a 2'-deoxy modification, a 2'-desoxy-fluoro, a 2'-amino modification, a 2'-alkyl modification, a phosphorothioate modification, a phosphoramidate modification, a 5'-phosphorothioate group modification, a 5'-phosphate or 5'-phosphate mimic modification and a cholesteryl derivative or a dodecanoic acid bisdecylamide group modification and/or the modified nucleotide may be any one of a locked nucleotide, an abasic nucleotide or a non-natural base comprising nucleotide. One of the preferred embodiments may be at least one modification being 2'-O-methyl and/or at least one modification being 2'-desoxy-fluoro.

Other examples of modified oligonucleotides, as used herein, can include one or more of the following: modification, e.g., replacement of one or both of the non-linking phosphate oxygens and/or of one or more of the linking phosphate oxygens; replacement of the phosphate moiety; modification or replacement of a naturally occurring base; replacement or modification of the ribose-phosphate backbone; modification of the 3'-end or 5'-end of the RNA, e.g., removal, modification or replacement of a terminal phosphate group or conjugation of a moiety, e.g., a fluorescently labeled moiety, to either the 3'- or 5'-end of RNA.

Methods for the Synthesis of Compounds of Formula (I)

Compounds of formula (I) may be prepared according to the detailed methods illustrated in the disclosure herein.

The present disclosure relates to a method for preparing a compound of formula (I-A), comprising the steps of:

a) oxidation of a compound of formula (X)

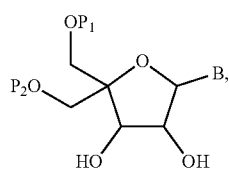

(X)

wherein B is a heterocyclic nucleobase and P1 and P2 each represents independently a protecting group as defined in the general formula (I) herein
by reaction of the compound of formula (X) with an oxidizing reagent, such as sodium periodate (NaIO$_4$), whereby the following compound of formula (XI) is obtained:

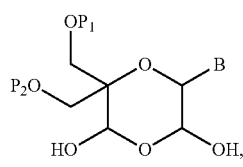

(XI)

and
b) subjecting the compound of formula (XI) to a step of reductive amination in the presence of the compound of formula (XII)

 (XII)

wherein R1 is as defined in the general formula (I) herein, for obtaining the compound of formula (I-A):

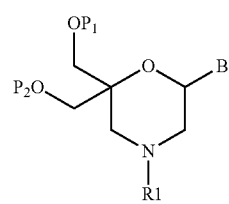

(I-A)

wherein B is a heterocyclic nucleobase and P1 and P2 each represent independently a protecting group as defined in the general formula (I).

The present disclosure also relates to a method for preparing a compound of formula (I-B) comprising the steps of:

a) oxidation of a compound of formula (X)

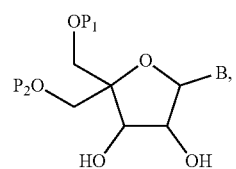

(X)

wherein B is a heterocyclic nucleobase and P1 and P2 each represents independently a protecting group as defined in the general formula (I) herein
by reaction of the compound of formula (X) with an oxidizing reagent, such as sodium periodate (NaIO$_4$), whereby the following compound of formula (XI) is obtained:

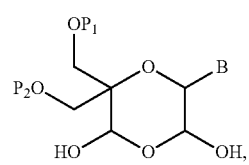

(XI)

and
b) subjecting the compound of formula (XI) to a step of reductive amination in the presence of an amine as e.g. ammonia or ammonium diborate for obtaining the compound of formula (XIII)

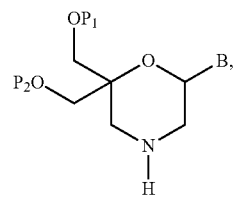

(XIII)

c) subjecting the compound of formula (XIII) to a step of amide coupling in the presence of the compound of formula (XIV)

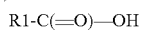 (XIV)

wherein R1 is as defined in the general formula (I) herein, for obtaining a compound of formula (I-B)

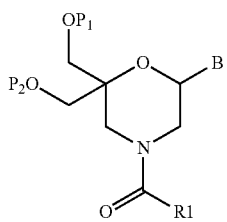
(I-B)

wherein B is a heterocyclic nucleobase and P1 and P2 each represents independently a protecting group as defined in the general formula (I) and R1 is as defined in the general formula (I).

d) subjecting the compound of formula (XIII) to a step of reductive amination in the presence of aldehydes or ketones for obtaining the compound of formula (I-A)

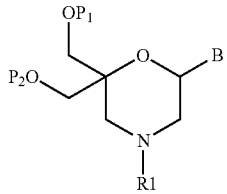
(I-A)

The present disclosure also relates to a method for preparing a compound of formula (I-C)

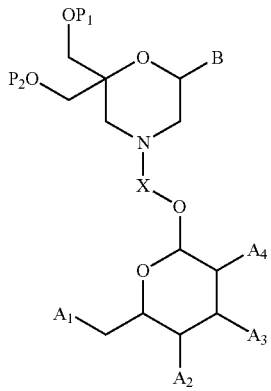
(I-C)

comprising the steps of reacting a compound of formula (XV)

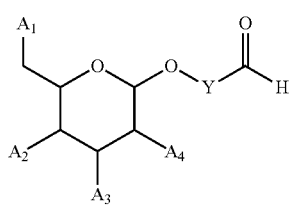
(XV)

wherein A1, A2, A3 and A4 are as defined in the formula (III) or (III-A) herein, —Y—CHO is transferred by the reductive amination reaction to —Y—CH2-, which equals X and X is a group of formula —(CH2-CH2-O)p-R2-, wherein p and R2 are as defined in the general formula (I), with the compound of formula (XIII)

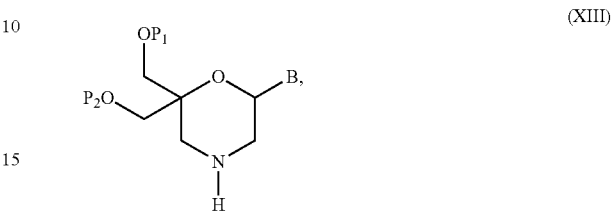
(XIII)

wherein P1, P2 and B are as defined in the general formula (I) herein, by reductive amination, for obtaining the compound of formula (I-C)

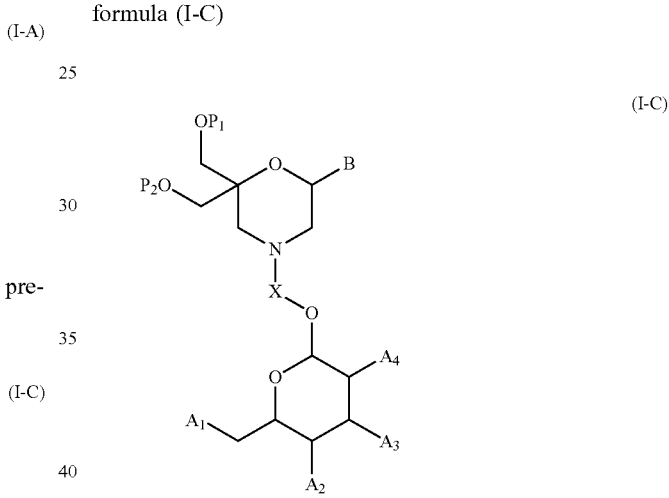
(I-C)

The above method is illustrated in Scheme 2 in the present disclosure.

The present disclosure also pertains to a method for obtaining a compound of formula (I-D)

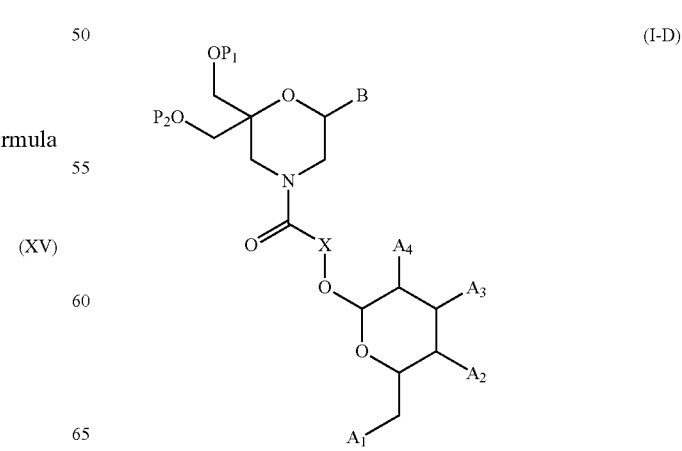
(I-D)

comprising the steps of:

a) reacting a compound of formula (XVI)

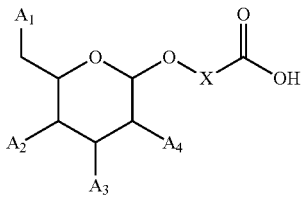
(XVI)

wherein A1, A2, A3 and A4 are as defined in the formula (III) or (III-A) herein and X is a group of formula —(CH2-CH2-O)p-R2-, wherein p and R2 are as defined in the general formula (I), with the compound of formula (XIII)

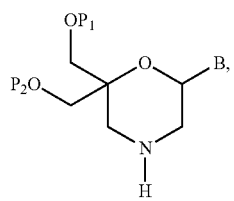
(XIII)

wherein P1, P2 and B are as defined in the general formula (I) herein, under peptide coupling conditions, for obtaining the compound of formula (I-D)

The above method is illustrated in Scheme 2 in the present disclosure.

The present disclosure further relates to a method for preparing a compound of formula (I-E) comprising the steps of:

a) reducing the compound of formula (XI)

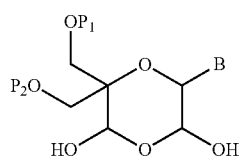
(XI)

wherein P1, P2 and B are as defined in the general formula (I), so as to obtain a compound of formula (XVII)

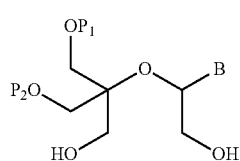
(XVII)

b) transferring the compound of formula (XVII) in the presence of a sulfonylating agent (e.g. p-toluene-sulfonyl-chloride Ts-Cl, methanesulfonylchloride Ms-Cl), so as to obtain the compound of formula (XVIII)

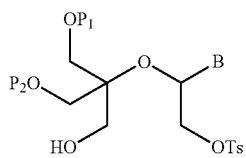
(XVIII)

wherein Ts represents a tosyl group, c) subjecting the compound of formula (XVIII) to a basic condition, so as to obtain the compound of formula (I-E)

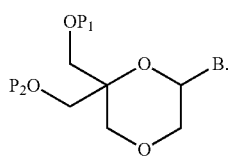
(I-E)

The above method is illustrated in Scheme 3 in the present disclosure.

The present disclosure also concerns an alternative method for preparing a compound of formula (I-E) comprising the steps of:

a) transferring the compound of formula (XVII)

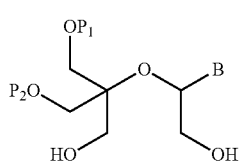
(XVII)

in the present of an excess of a sulfonylating agent (e.g. p-toluene-sulfonylchloride Ts-Cl, methanesulfonylchloride Ms-Cl), so as to obtain the compound of formula (XIX)

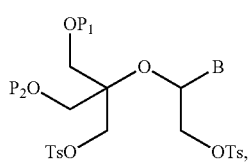
(XIX)

wherein Ts represents a tosyl group, b) deprotecting the compound of formula (XIX) by removal of group P1 for obtaining the compound of formula (XX)

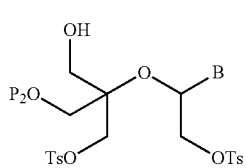
(XX)

c) subjecting the compound of formula (XX) to a basic condition, so as to obtain the compound of formula (XXI)

(XXI)

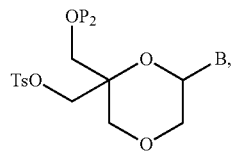

and d) replacing the tosyl group by the protecting group P1, so as to obtain the compound of formula (I-E)

(I-E)

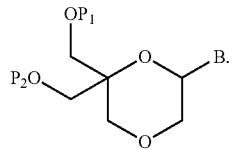

The above method is illustrated in Scheme 3 in the present disclosure.

Compounds of formula (I), (I-A), (I-B), (I-C), (I-D) and (I-E) may be prepared according to the detailed methods illustrated in the following schemes 1 to 8 disclosed herein.

Starting from commercially available ribose derivative G1, the two primary OH-groups can be differentiated by selective benzylation following standard literature protocols. Standard protecting group modification of the resulting benzylether G2 leads to the fully protected ribose analog G3, which can be used as a glycosyl donor in the presence of the nucleobases B (e.g.: T, U, $C^{Bzl}$, $G^{iBu}$, $A^{Bzl}$), yielding the nucleoside derivatives G4 (*Tetrahedron*, 1998, 54, 3607-3630).

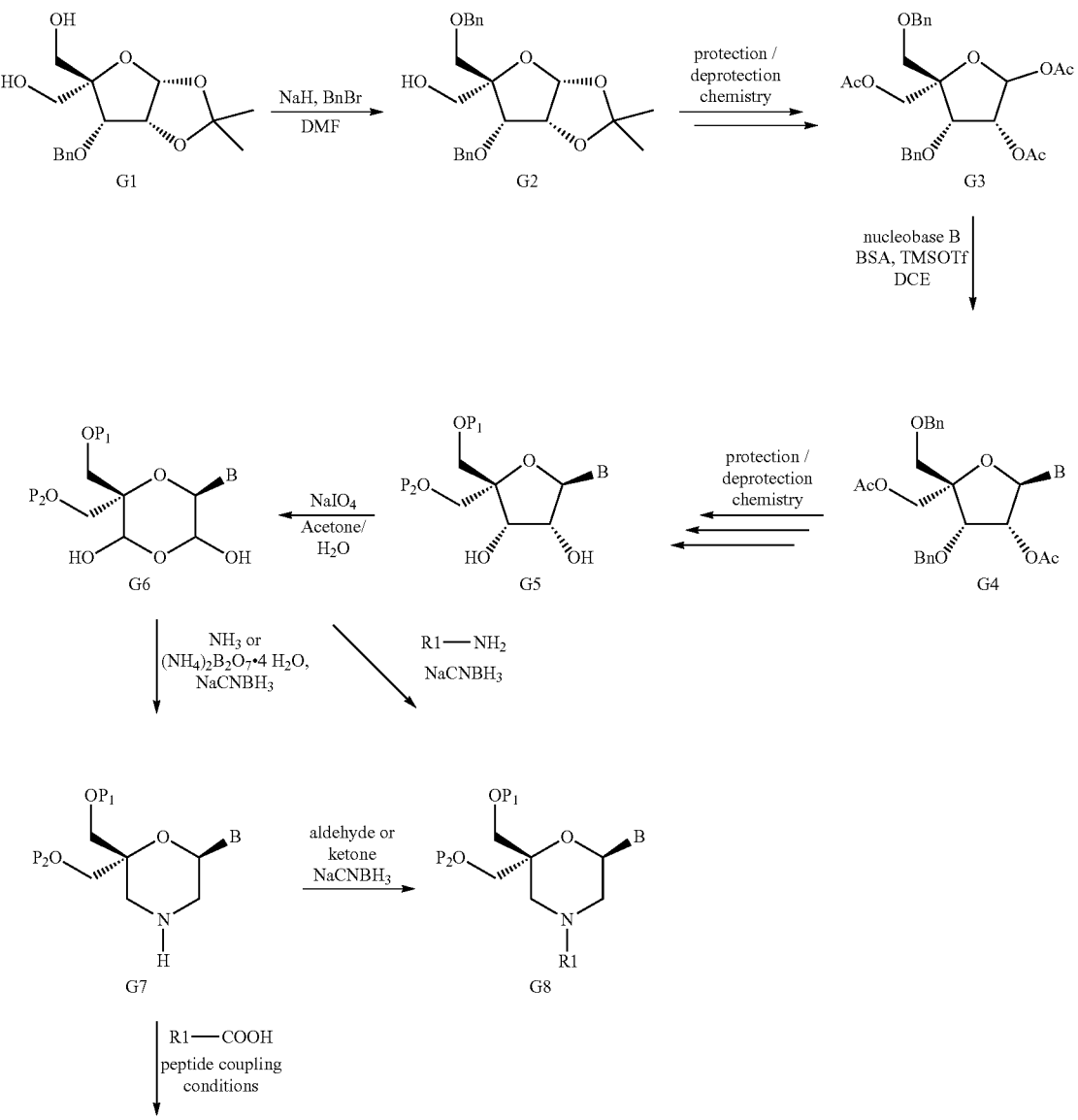

Scheme 1 Synthesis of compounds of formula (I) wherein Y in N

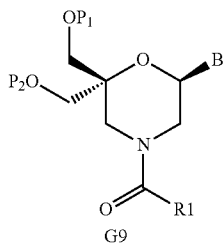

G9

Starting with the nucleoside analogs G4, modification of the protecting group pattern by standard procedures leads to the intermediates G5, with orthogonal protecting groups P1 and P2 as defined in general formula (I) on the two primary alcohols and unprotected OH-groups at C2' and C3' of the ribose scaffold. The cis-orientation of the dihydroxy-functionality in the G5-compounds allows the oxidative cleavage of the C—C-bond between C2' and C3' using $NaIO_4$ as oxidizing agent. The resulting dialdehyde can be isolated as monohydrate G6, which is transformed to the desired morpholine scaffolds by reductive amination reaction with a reducing agent, such as $NaCNBH_3$. Using an amine substrate such as ammonia or ammonium diborate leads to the morpholine intermediates G7 with a free NH-group in the morpholine scaffold. A second reductive amination reaction with the corresponding aldehydes or ketones in the presence of e.g. $NaCNBH_3$, yields in the alkylated morpholines G8, with R1 being as defined as in general formula (I). Alternatively, intermediates G6 can undergo a reductive amination reaction in the presence of the appropriate amines R1-$NH_2$, wherein R1 is as defined as in general formula (I), leading directly to the alkylated morpholines G8. The analogues acylated morpholines are obtained by standard peptide coupling reactions between the free morpholine building blocks G7 and the corresponding carboxylic acids R1-COOH, resulting in the amide intermediates G9.

Compounds G7, G8 and G9 consist of embodiments of a compound of formula (I) described in the present disclosure.

In analogy to the synthesis described in scheme 1 for the formation of compounds of the general formula (I), the herein described targeted compounds of general formula (I) can be prepared by reductive amination- or peptide coupling reactions using intermediate G7 as amine reagent.

Using peracetylated N-Acetylgalactosamine G11 as protected cell targeting moiety, the syntheses of the compounds of general formula (I) are described in following scheme 2.

Scheme 2: Synthesis of compounds of general formula (I) with amide (G14) and amine (G15) attachment, protected GalNAc as cell targeting moiety and different X linker groups, where X is created from the linker fragment —Y—CHO in (G13) and transformed to —Y—$CH_2$— after reductive amination.

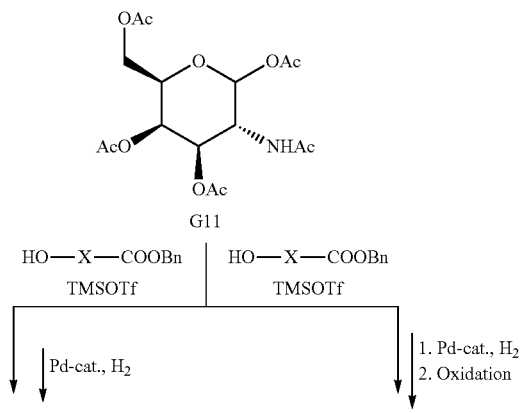

-continued

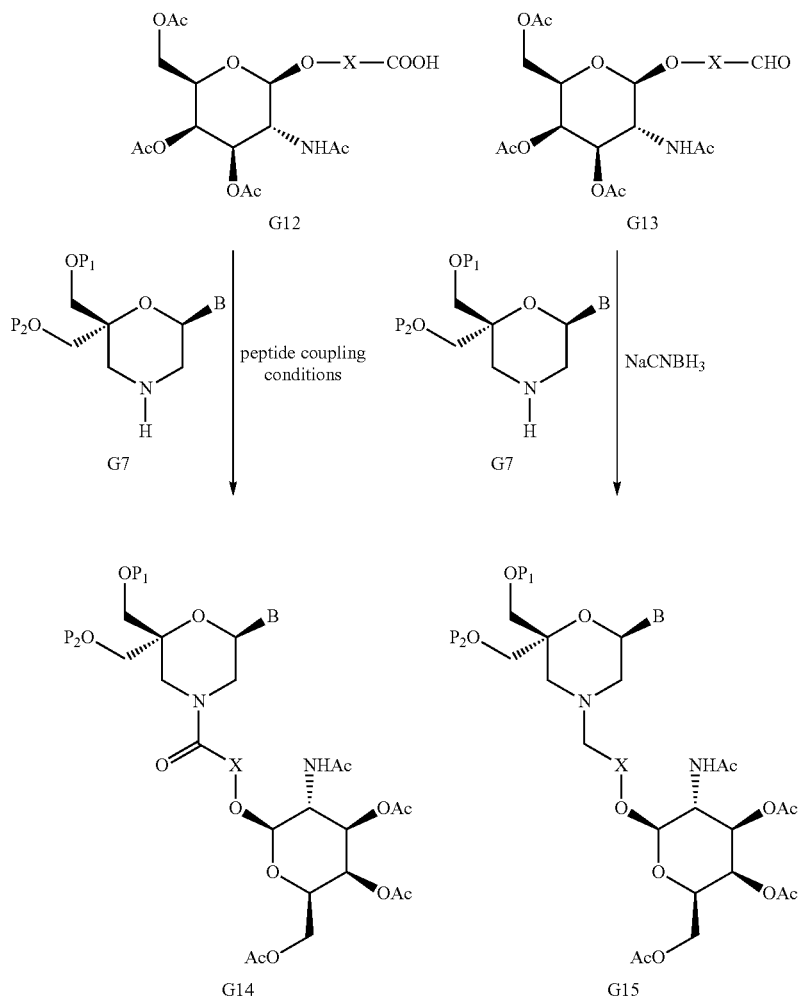

In the following, X is defined as the group —R2(OCH2-CH2)p- comprised in the group —[C(=O)]m-R2-(O—CH2-CH2)p-R3 as defined in the compounds of general formula (I).

Treating the peracetylated GalNAc-derivative G11 with o-hydroxycarboxylic acidesters (HO—X—COOBn) under standard glycosylation conditions leads, after ester cleavage, to the carboxylic acids G12, which form in the presence of the morpholine derivative G7 the desired amides G14 under peptide coupling conditions. Alternatively, glycosylation of G11 with O-hydroxy-benzylethers (HO—X—OBn) delivers, after benzylether cleavage and oxidation of the corresponding alcohols the aldehyde intermediates G13. Reductive amination with the morpholine G7 as amine component yields in the formation of the alkylated morpholines G15. Compounds G14 and G15 are compounds of formula (I) as described in the present disclosure.

A synthetic route to the compounds of general formula (I) in the dioxane series (Y is O) is shown in scheme 3.

Scheme 3: Synthetic route to compounds of general formula (I) wherein Y is O

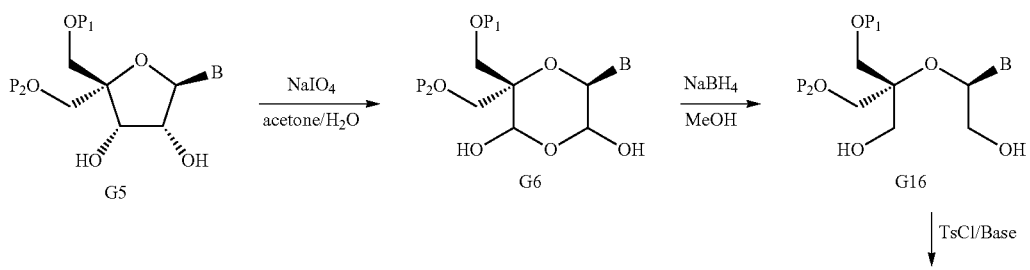

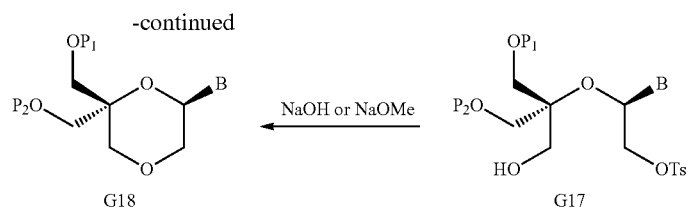

Starting with the already described cis-diol intermediate G5 and its oxidative cleavage to the building block G6 (see scheme 1), treatment with a reducing agent such as sodium boronhydride leads to the diol intermediate G16 with two primary OH-groups at the 2'- and 3'-C. In the presence of sulfonylating agent such as p-toluene sulfonylchloride in stoichiometric amounts under basic conditions, the 2'-OH-functionality can be selectively tosylated, forming the mono-tosylate G17. Under basic conditions, using e.g. aqueous NaOH or NaOMe in MeO, G17 undergoes nucleophilic substitution of the primary tosylate by the free OH-group at the 3'-C, which results in the formation of the desired dioxane scaffold G18.

Compound G18 consists of a compound of general formula (I) as described in the present disclosure.

Alternatively, the diol intermediate G16 can be bis-sulfonylated with for example an excess of p-toluene sulfonylchloride and increased reaction times, resulting in the bis-tosylate G19. After deprotection of one of the orthogonal protecting groups P1 or P2, the obtained primary alcohol G20 reacts in analogy to G17 (see scheme 3) under nucleophilic substitution and formation of the desired dioxane scaffold G21. The remaining tosylate can be replaced with sodium benzoate, yielding again a fully protected dioxane scaffold G18 with orthogonal protecting groups P1 and P2 at the primary hydroxyl groups.

The described building blocks of general formula (I) (G8, G9, G14, G15 and G18), with orthogonal protecting groups P1 and P2 are finally converted to the corresponding DMT-protected phosphoramidites, allowing their use as nucleotide precursors in the automated oligonucleotide synthesis.

For this purpose, the fully protected compounds of general formula (I) (G8, G9, G14, G15 and G18) are converted to the mono-DMT-protected intermediates G22 by standard protecting group modifications. Phosphitylation of the free OH-groups in the G22-building blocks by standard protocols results in the final DMT-protected phosphoramidites G23 as nucleotide precursors for the automated oligonucleotide synthesis.

Scheme 5: Synthesis of final phosphoramidite building blocks of compounds of general formula (I) and (V) for the automated oligonucleotide synthesis

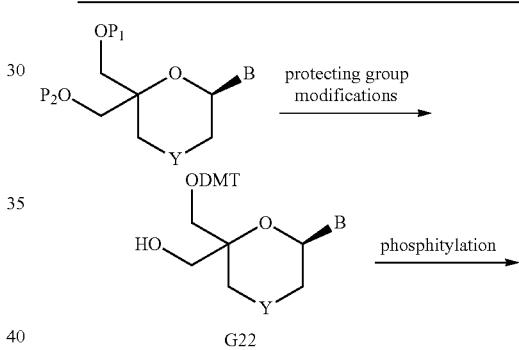

Scheme 4: Alternative synthesis for compounds of formula (I) wherein Y is O

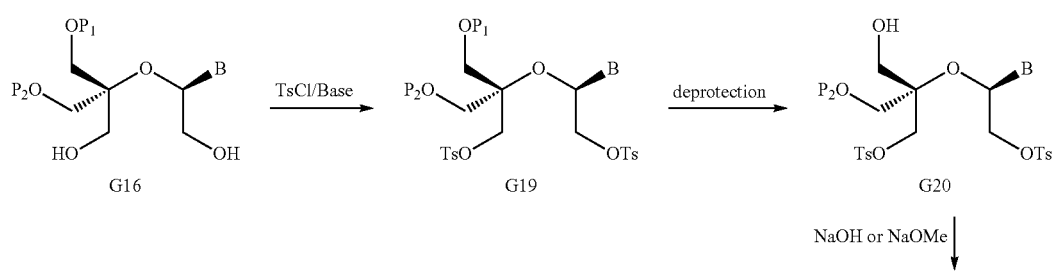

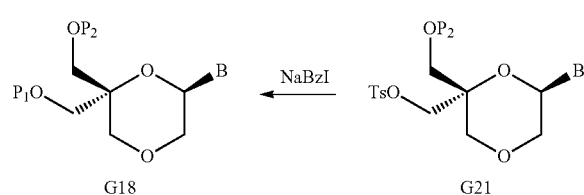

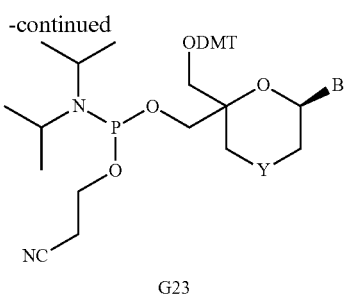

G23

Y =
N—R1: G8, G15
N—C(O)—R1: G9, G14
O: G18

Compound G23 is a compound of formula (I) wherein group P1 is a DMT protecting group and group P2 is a reactive phosphorous group consisting of a phosphoramidite group.

Depending on the protecting group modifications, which lead to the intermediates G22, (2S,6R)- and (2R,6R)-diastereomers of the compounds of general structures (I) can be synthesized.

Scheme 6: diastereomeric structures of compounds G23 of general formula (I)

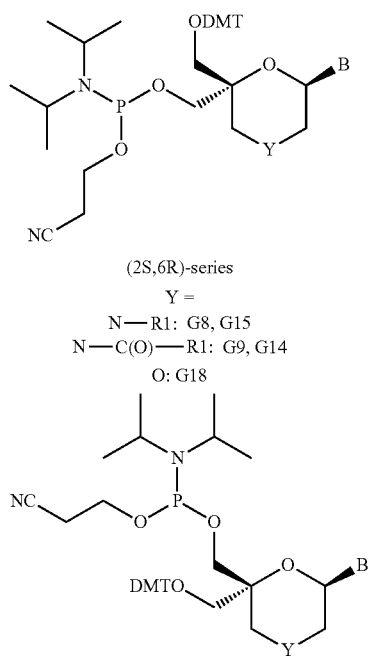

(2S,6R)-series
Y =
N—R1: G8, G15
N—C(O)—R1: G9, G14
O: G18

(2R,6R)-series
Y =
N—R1: G8, G15
N—C(O)—R1: G9, G14
O: G18

The starting nucleotides at the 3'-end of an oligonucleotide single strand can be prepared by standard procedures with a universal solid support material (see experimental part, synthesis of oligonucleotides), reacting with the corresponding phosphoramidites G23 as first nucleotide scaffolds in the automated synthesis.

Alternatively, solid support materials of the herein described compounds of general formula (I) can be synthesized as shown in general scheme 7.

Scheme 7: Synthesis of final CPG (controlled pore glass) solid support materials of compounds of general formula (I) for the automated oligonucleotide synthesis

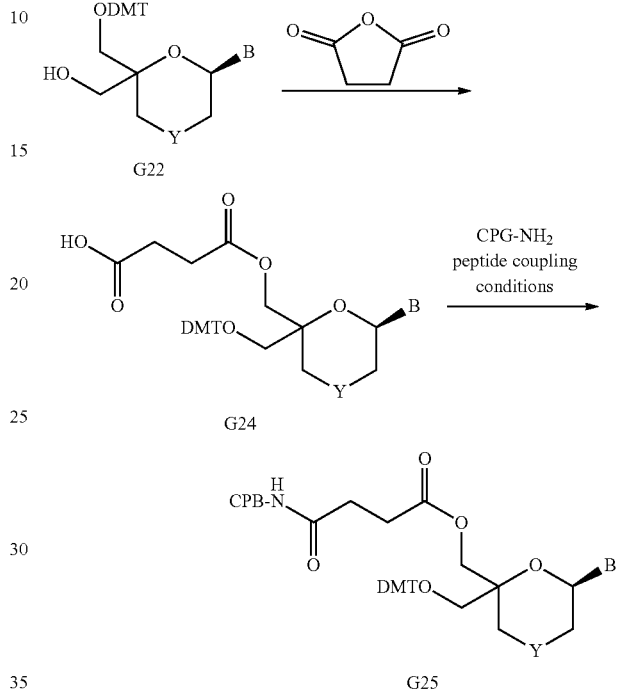

The alcohols G22 are acylated with an acylating agent such as succinic anhydride, yielding the corresponding succinates G24. The free carboxylic acid moieties are coupled with the free amino groups of the solid support material (CPG: controlled pore glass) under peptide coupling conditions, resulting in the desired solid supports G25, which can be used as starting materials in the automated oligonucleotide synthesis.

In analogy to the diastereoselective routes for the synthesis of phosphoramidites G23 (see scheme 6), both diastereomeric series of solid supports G25 can be synthesized (see scheme 8).

Scheme 8: diastereomeric structures of compounds G25

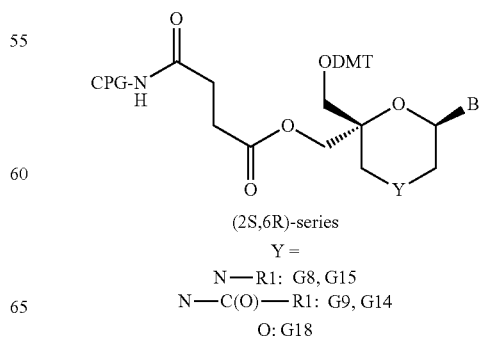

(2S,6R)-series
Y =
N—R1: G8, G15
N—C(O)—R1: G9, G14
O: G18

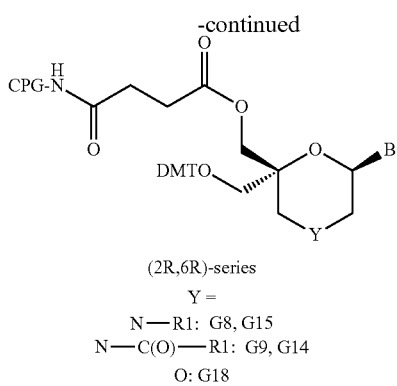

(2R,6R)-series

Y =

N—R1: G8, G15
N—C(O)—R1: G9, G14
O: G18

Succinate derivatives and solid support materials of compounds of general formula (I) are also a subject of the present disclosure, as defined in general formula (I'):

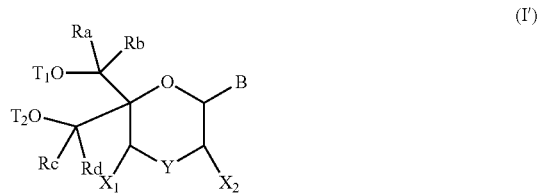

(I')

wherein T1 and T2 are each independently a protecting group, —C(=O)(CH2)r-COOH, or —C(=O)(CH2)r-C(=O)NH—R7, wherein R7 represents a solid support material, r is an integer selected from 2, 3 and 4, and wherein Y, B, X1, X2, Ra, Rb, Rc and Rd are as defined in general formula (I).

In some embodiments one of T1 and T2 is —C(=O)(CH2)r-COOH, and the other one is a protecting group.

In some embodiments, one of T1 and T2 is —C(=O)(CH2)rC(=O)NH—R7, wherein R7 is a CPG solid support or a polystyrene solid support, and the other one of T1 and T2 is a protecting group.

In some embodiments, r is 2.

Preparation of Oligonucleotides Comprising Compounds of Formula (II)

An oligonucleotide for use in accordance with the invention, which may also be termed "modified oligonucleotide" herein, may be prepared according to any useful technique, including the methods described herein, by using one or more compounds of formula (I) as some of the starting building block(s) to be incorporated at selected position(s) of the growing chain of the final oligonucleotide, thus generating an oligonucleotide comprising one or more compounds of formula (II), the one or more compounds of formula (II) being located at the selected position(s) of the final oligonucleotide.

Compounds of formula (I) may be synthesized as described in the present disclosure.

A modified oligonucleotide of the present invention may be double-stranded with or without overhangs, or comprise at least a double-stranded portion. A double-stranded modified oligonucleotide may be formed from a single oligonucleotide chain comprising therein a first nucleotide sequence (e.g., a sense nucleotide sequence) and a second nucleotide sequence (e.g., an antisense nucleotide sequence) that is complementary to the first nucleotide sequence and hybridizes thereto, and wherein the second nucleotide sequence is also complementary to a target RNA sequence, the inhibition of which is sought. According to these embodiments, the first nucleotide sequence and the second nucleotide sequence may be on separate chains within the modified oligonucleotide; or on the same chain but separated by a spacer or an additional nucleotide sequence of an appropriate length so as to form an hairpin loop once the first nucleotide sequence hybridizes to the second nucleotide sequence.

In some embodiments, a modified oligonucleotide of the present invention is single-stranded, and may comprise either the sense- or antisense strand of a double-stranded RNA such as a siRNA.

Oligonucleotides of the present invention such as those comprising one or more compounds of formula (II) may be chemically synthesized using protocols known in the art. See, e.g., Caruthers et al., 1992, Methods in Enzymology, 211: 3-19; Thompson et al., International PCT Publication No. WO 99/54459; Wincott et al., 1995, Nucleic Acids Res., 23:2677-2684; Wincott et al., 1997, Methods Mol. Bio., 74:59; Brennan et al., 1998, Biotechnol Bioeng., 61:33-45; and Brennan, U.S. Pat. No. 6,001,311. The synthesis of oligonucleotides makes use of common nucleic acid protecting and coupling groups, such as dimethoxytrityl at the 5'-end, and phosphoramidites at the 3'-end. In certain embodiments, oligonucleotides comprising compounds of formula (II) are synthesized, deprotected, and analyzed according to methods described in U.S. Pat. Nos. 6,995,259; 6,686,463; 6,673,918; 6,649,751; 6,989,442; and 7,205,399.

In a non-limiting synthesis example, small scale syntheses are conducted on a 394 Applied Biosystems, Inc./Thermo Fischer Scientific Inc. synthesizer.

Alternatively, oligonucleotides comprising one or more compounds of formula (II) can be synthesized separately and joined together post synthesis, for example, by ligation (Moore et al., 1992, Science 256:9923; Draper et al., International PCT Publication No. WO 93/23569; Shabarova et al., 1991, Nucleic Acids Research 19:4247; Bellon et al., 1997, Nucleosides & Nucleotides, 16:951; Bellon et al., 1997, Bioconjugate Chem., 8:204), or by hybridization following synthesis and/or deprotection. Various modified oligonucleotides according to the present disclosure may also be synthesized using the teachings of Scaringe et al., U.S. Pat. Nos. 5,889,136; 6,008,400; and 6,111,086.

Double-Stranded RNAs (dsRNAs)

An important aspect of the present invention is the provision of compounds of formula (I) that allow the preparation of modified oligonucleotides comprising one or more compounds of formula (II). The modified oligonucleotides may be used for generating double-stranded oligonucleotides, e.g. siRNAs that specifically hybridize to a selected target mRNA.

An oligomeric compound of formula (II) may be termed a "ribonucleic acid" or "RNA", in consideration of (i) the ribose sugar moiety that is contained in most of the nucleotide monomer units comprised therein and (ii) the kind of nucleobases comprised therein. Thus, certain aspects of the present disclosure relate to double-stranded ribonucleic acid (dsRNA) molecules targeting an mRNA of interest. A dsRNA of the present invention may comprise a modified oligonucleotide comprising one or more compounds of formula (II).

In some embodiments, the dsRNA comprises two strands, a sense strand comprising a first sequence and an antisense strand comprising a second sequence, wherein the first strand and the second strand are sufficiently complementary to form a duplex structure. In some embodiments, the sense strand comprises a first sequence that is substantially complementary or fully complementary to the second sequence in the antisense strand. In some embodiments, the second sequence in the antisense strand is substantially complementary or fully complementary to a target sequence, e.g., a sequence of an mRNA transcribed from a target gene.

In some embodiments, the sense strand and the antisense strand of the dsRNA are in two separate molecules. In some embodiments, the duplex region is formed between the first sequence in the sense strand and the second sequence in the antisense strand of the two separate molecules. In some embodiments, the dsRNA is an siRNA. In some embodiments, the two separate molecules are not covalently linked to one another. In some embodiments, the two separate molecules are covalently linked to one another. In some embodiments, the two separate molecules are covalently linked to one another by means other than a hairpin loop. In some embodiments, the two separate molecules are covalently linked to one another via a connecting structure (herein referred to as a "covalent linker").

In some embodiments, each of the sense and antisense strands may range from 9-36 nucleotides in length. For example, each strand may be between 12-30 nucleotides in length, 14-30 nucleotides in length, 15-30 nucleotides in length, 25-30 nucleotides in length, 27-30 nucleotides in length, 15-26 nucleotides in length, 15-23 nucleotides in length, 15-22 nucleotides in length, 15-21 nucleotides in length, 15-20 nucleotides in length, 15-19 nucleotides in length, 15-18 nucleotides in length, 15-17 nucleotides in length, 17-30 nucleotides in length, 17-23 nucleotides in length, 17-21 nucleotides in length, 17-19 nucleotides in length, 18-30 nucleotides in length, 18-26 nucleotides in length, 18-25 nucleotides in length, 18-23 nucleotides in length, 18-22 nucleotides in length, 18-21 nucleotides in length, 18-20 nucleotides in length, 19-30 nucleotides in length, 19-25 nucleotides in length, 19-24 nucleotides in length, 19-23 nucleotides in length, 19-22 nucleotides in length, 19-21 nucleotides in length, 19-20 nucleotides in length, 20-30 nucleotides in length, 20-26 nucleotides in length, 20-25 nucleotides in length, 20-24 nucleotides in length, 20-23 nucleotides in length, 20-22 nucleotides in length, 20-21 nucleotides in length, 21-30 nucleotides in length, 21-26 nucleotides in length, 21-25 nucleotides in length, 21-24 nucleotides in length, 21-23 nucleotides in length, or 21-22 nucleotides in length. In some embodiments, each strand is greater than or equal to 9, 10, 11, 12, 13, 14, 15, 16, 17, 18, 19, 20, 21, 22, 23, 24, 25, 26, 27, 28, 29, 30, 31, 32, 33, 34, or 35 nucleotides in length. In some embodiments, each strand is less than or equal to 10, 11, 12, 13, 14, 15, 16, 17, 18, 19, 20, 21, 22, 23, 24, 25, 26, 27, 28, 29, 30, 31, 32, 33, 34, 35, or 36 nucleotides in length. That is, each strand can be any of a range of nucleotide lengths having an upper limit of 10, 11, 12, 13, 14, 15, 16, 17, 18, 19, 20, 21, 22, 23, 24, 25, 26, 27, 28, 29, 30, 31, 32, 33, 34, 35, or 36, and an independently selected lower limit of 9, 10, 11, 12, 13, 14, 15, 16, 17, 18, 19, 20, 21, 22, 23, 24, 25, 26, 27, 28, 29, 30, 31, 32, 33, 34, or 35, wherein the lower limit is less than the upper limit. In some embodiments, each strand is 9, 10, 11, 12, 13, 14, 15, 16, 17, 18, 19, 20, 21, 22, 23, 24, 25, 26, 27, 28, 29, 30, 31, 32, 33, 34, 35, or 36 nucleotides in length. In some embodiments, the sense strand and antisense strand are the same number of nucleotides in length. In some embodiments, the sense strand and antisense strand are a different number of nucleotides in length.

Overhangs

In some embodiments, a dsRNA of the present disclosure comprises one or more overhangs at the 3'-end, 5'-end, or both ends of one or both of the sense and antisense strands. In some embodiments, the one or more overhangs improve the stability with a lower number of PS-groups in the overhangs.

In some embodiments, the overhang comprises one or more, two or more, three or more, four or more, five or more, or six or more nucleotides. For example, the overhang may comprise 1-8 nucleotides, 2-8 nucleotides, 3-8 nucleotides, 4-8 nucleotides, 5-8 nucleotides, 1-5 nucleotides, 2-5 nucleotides, 3-5 nucleotides, 4-5 nucleotides, 1-4 nucleotides, 2-4 nucleotides, 3-4 nucleotides, 1-3 nucleotides, 2-3 nucleotides, or 1-2 nucleotides. In some embodiments, the overhang is one, two, three, four, five, or six nucleotides in length.

In some embodiments, an overhang of the present disclosure comprises one or more ribonucleotides. In some embodiments, an overhang of the present disclosure comprises one or more deoxyribonucleotides. In some embodiments, the overhang comprises one or more thymines. In some embodiments, the dsRNA comprises an overhang located at the 3'-end of the antisense strand. In some embodiments, the dsRNA comprises a blunt end at the 5'-end of the antisense strand. In some embodiments, the dsRNA comprises an overhang located at the 3'-end of the antisense strand and a blunt end at the 5'-end of the antisense strand. In some embodiments, the dsRNA comprises an overhang located at the 3'-end of the sense strand. In some embodiments, the dsRNA comprises a blunt end at the 5'-end of the sense strand. In some embodiments, the dsRNA comprises an overhang located at the 3'-end of the sense strand and a blunt end at the 5'-end of the sense strand. In some embodiments, the dsRNA comprises overhangs located at both of the 3'-ends of the sense and antisense strands of the dsRNA.

In some embodiments, the dsRNA comprises an overhang located at the 5'-end of the antisense strand. In some embodiments, the dsRNA comprises a blunt end at the 3'-end of the antisense strand. In some embodiments, the dsRNA comprises an overhang located at the 5'-end of the antisense strand and a blunt end at the 3'-end of the antisense strand. In some embodiments, the dsRNA comprises an overhang located at the 5'-end of the sense strand. In some embodiments, the dsRNA comprises a blunt end at the 3'-end of the sense strand. In some embodiments, the dsRNA comprises an overhang located at the 5'-end of the sense strand and a blunt end at the 3'-end of the sense strand. In some embodiments, the dsRNA comprises overhangs located at both strands of the dsRNA.

In some embodiments, the overhang is the result of the sense strand being longer than the antisense strand. In some embodiments, the overhang is the result of the antisense strand being longer than the sense strand. In some embodiments, the overhang is the result of sense and antisense strands of the same length being staggered. In some embodiments, the overhang forms a mismatch with the target mRNA. In some embodiments, the overhang is complementary to the target mRNA.

In some embodiments, a dsRNA of the present disclosure comprises a sense strand comprising a first sequence and an antisense strand comprising a second sequence, wherein the first and second sequences are substantially complementary or complementary. In some embodiments, the first and second sequences are substantially complementary or complementary and form a duplex region of a dsRNA. In some embodiments, the duplex region of the dsRNA is 9-36 nucleotide pairs in length. For example, the duplex region may be between 12-30 nucleotide pairs in length, 14-30 nucleotide pairs in length, 15-30 nucleotide pairs in length, 15-26 nucleotide pairs in length, 15-23 nucleotide pairs in length, 15-22 nucleotide pairs in length, 15-21 nucleotide pairs in length, 15-20 nucleotide pairs in length, 15-19 nucleotide pairs in length, 15-18 nucleotide pairs in length, 15-17 nucleotide pairs in length, 17-30 nucleotide pairs in length, 27-30 nucleotide pairs in length, 17-23 nucleotide pairs in length, 17-21 nucleotide pairs in length, 17-19 nucleotide pairs in length, 18-30 nucleotide pairs in length, 18-26 nucleotide pairs in length, 18-25 nucleotide pairs in length, 18-24 nucleotide pairs in length, 18-23 nucleotide pairs in length, 18-22 nucleotide pairs in length, 18-21 nucleotide pairs in length, 18-20 nucleotide pairs in length, 19-30 nucleotide pairs in length, 19-25 nucleotide pairs in length, 19-24 nucleotide pairs in length, 19-23 nucleotide pairs in length, 19-22 nucleotide pairs in length, 19-21 nucleotide pairs in length, 19-20 nucleotide pairs in length, 20-30 nucleotide pairs in length, 20-26 nucleotide pairs in length, 20-25 nucleotide pairs in length, 20-24 nucleotide pairs in length, 20-23 nucleotide pairs in length, 20-22 nucleotide pairs in length, 20-21 nucleotide pairs in length, 21-30 nucleotide pairs in length, 21-26 nucleotide pairs in length, 21-25 nucleotide pairs in length, 21-24 nucleotide pairs in length, 21-23 nucleotide pairs in length, or 21-22 nucleotide pairs in length. In some embodiments, the duplex region of the dsRNA is greater than or equal to 9, 10, 11, 12, 13, 14, 15, 16, 17, 18, 19, 20, 21, 22, 23, 24, 25, 26, 27, 28, 29, 30, 31, 32, 33, 34, or 35 nucleotide pairs in length. In some embodiments, the duplex region of the dsRNA is less than or equal to 10, 11, 12, 13, 14, 15, 16, 17, 18, 19, 20, 21, 22, 23, 24, 25, 26, 27, 28, 29, 30, 31, 32, 33, 34, 35, or 36 nucleotide pairs in length. That is, the duplex region of the dsRNA can be any of a range of nucleotide pairs in length having an upper limit of 10, 11, 12, 13, 14, 15, 16, 17, 18, 19, 20, 21, 22, 23, 24, 25, 26, 27, 28, 29, 30, 31, 32, 33, 34, 35, or 36, and an independently selected lower limit of 9, 10, 11, 12, 13, 14, 15, 16, 17, 18, 19, 20, 21, 22, 23, 24, 25, 26, 27, 28, 29, 30, 31, 32, 33, 34, or 35, wherein the lower limit is less than the upper limit. In some embodiments, the duplex region is 9, 10, 11, 12, 13, 14, 15, 16, 17, 18, 19, 20, 21, 22, 23, 24, 25, 26, 27, 28, 29, 30, 31, 32, 33, 34, 35, or 36 nucleotide pairs in length. If more than one dsRNA is used, the duplex region of each dsRNA may be the same or different lengths than the one or more additional dsRNAs.

Location of Compounds of Formula (H) in Double-Stranded RNAs (dsRNAs)

As illustrated in the examples herein, nucleotide analogs of formula (II) may be present at various locations of each strand of a double-stranded oligonucleotide, namely at various locations of each strand of a double-stranded ribonucleotide.

Compounds of formula (II) wherein group R3 is present and represents a cell targeting moiety may be termed a "targeted nucleotide analog of formula (II)" or a "targeted nucleotide analog (II)" in the present disclosure.

The compounds of formula (II) that do not comprise a group R3 representing a cell targeting moiety are not targeted nucleotide analogs, and are termed "a non-targeted nucleotide analog of formula (II)" or "a non-targeted nucleotide analog (II)" in the present disclosure.

Location of non-targeted nucleotide analogs of formula (II) In particular embodiments, nucleotide analogs of formula (II) are located at the 3'-end, at the 5'-end, or both at the 3'-end and at the 5'-end of a nucleic acid strand of a dsRNA, such as the 3'-end or at the 5'-end of a nucleic acid strand of a siRNA. In some of these particular embodiments, nucleotide analogs of formula (II) are exclusively located at the 3'-end of a nucleic acid strand of a dsRNA, such as exclusively located at the 3'-end of a nucleic acid strand of a siRNA.

In some of these particular embodiments, nucleotide analogs of formula (II) are located at the 3'-end of the sense strand of a siRNA. In some other embodiments, nucleotide analogs of formula (II) are located at the 3'-end of the antisense strand of a siRNA. In still other embodiments, nucleotide analogs of formula (II) are located both at the 3'-end of the sense strand of a siRNA and at the 3'-end of the antisense strand of the siRNA.

In some of these particular embodiments, nucleotide analogs of formula (II) are located (i) both at the 3'-end and at the 5'-end of the sense strand of a siRNA and (ii) are located at the 3'-end of the antisense strand of the siRNA.

In some embodiments, 2 to 10 (e.g., 2 to 5) nucleotide analogs of formula (II) are present in an oligonucleotide. As used herein, 2 to 10 nucleotide analogs of formula (II) encompass 2, 3, 4, 5, 6, 7, 8, 9 and 10 nucleotide analogs of formula (II).

Location of targeted nucleotide analogs of formula (I) As illustrated in the examples herein, targeted nucleotide analogs of formula (II) may be present at various locations of each strand of a double-stranded oligonucleotide. For example, targeted nucleotide analogs of formula (II) are located at the 3'-end or at the 5'-end of a nucleic acid strand, such as the 3'-end or at the 5'-end of a nucleic acid strand of an siRNA. In some of these embodiments, targeted nucleotide analogs of formula (II) are located at the 3'-end or at the 5'-end of a sense strand of an siRNA.

In some preferred embodiments, targeted nucleotide analogs of formula (II) are located in an overhang of a dsRNA, such as of an siRNA. For example, the targeted nucleotide analogs of formula (II) are located in an overhang, such as the 5'-overhang, of the sense strand of an siRNA.

In some embodiments, 2 to 10 (e.g., 2 to 5) targeted nucleotide analogs of formula (II) are present in an oligonucleotide. As used herein, 2 to 10 targeted nucleotide analogs of formula (II) encompass 2, 3, 4, 5, 6, 7, 8, 9 and 10 targeted nucleotide analogs of formula (II).

Targeted Oligonucleotides

A targeted oligonucleotide according to the present disclosure is an oligonucleotide comprising at least a nucleotide analog of formula (II) and further comprising a cell targeting moiety comprised in a targeted nucleotide within the said oligonucleotide.

In some embodiments, a targeted nucleotide comprised in a targeted oligonucleotide according to the present disclosure has the structure of formula (II). Thus, in some embodiments, targeted oligonucleotides according to the present disclosure comprise one or more targeted nucleotide analogs of formula (II).

In some other embodiments, a targeted nucleotide comprised in a targeted oligonucleotide according to the present disclosure is selected among the targeted nucleotides that are known in the art. Thus, in some embodiments, targeted oligonucleotides according to the present disclosure comprise one or more non-targeted nucleotide analogs of formula (II) and one or more targeted nucleotides having a structure different from formula (II).

In still other embodiments, targeted oligonucleotides encompass those comprising (i) one or more non-targeted nucleotide analogs of formula (II) and (ii) one or more targeted nucleotide analogs of formula (II).

As disclosed elsewhere in the present disclosure, a non-targeted nucleotide analog of formula (II) encompasses embodiments wherein Y is O, embodiments wherein Y is NR1, embodiments wherein Y is NH and embodiments wherein Y is N—C(=O)—R1. Non-targeted nucleotides encompass notably nucleotide analogs of formula (II) wherein Y is selected in the group consisting of NR1 and N—C(=O)—R1 and wherein R1 is a a group —[C(=O)]m-R2-(O—CH$_2$—CH$_2$)p-R3, wherein m, p and R2 are defined as disclosed for general formula (II), and wherein group R3 is selected from the group consisting of a hydrogen atom, a (C1-C6) alkyl group, a (C1-C6) alkoxy group, a (C3-C8) cycloalkyl group, a (C3-C14) heterocycle, a (C6-C14) aryl group, and a (C5-C14) heteroaryl group.

As disclosed elsewhere in the present disclosure, a targeted nucleotide analog of formula (II) has group R3 as a cell targeting moiety. Cell targeting moieties are disclosed elsewhere in the present disclosure.

In some embodiments, a targeted oligonucleotide according to the present disclosure is a single-stranded oligonucleotide.

In some other embodiments, a targeted oligonucleotide according to the present disclosure is a double-stranded oligonucleotide.

In some embodiments of a targeted oligonucleotide according to the present disclosure, either being a single-stranded or a double-stranded oligonucleotide, an oligonucleotide strand thereof comprises one or more targeted nucleotide analogs of formula (II) which may be located at various locations within the said oligonucleotide strand, e.g. internally and/or at the 3' end or 5' end thereof.

As used herein, a nucleotide analog is defined as being located at the 3' end or at the 5' end end of an oligonucleotide strand when (i) the said nucleotide analog is the nucleotide located at the said 3' end or 5' end or when (ii) the said nucleotide analog is a nucleotide comprised in a continuous chain of successive nucleotide analogs having an end nucleotide located at the 3' end or at the 5' end of the said oligonucleotide strand.

In some embodiments of a targeted oligonucleotide according to the present disclosure, either being a single-stranded or a double-stranded oligonucleotide, an oligonucleotide strand thereof comprises one or more targeted nucleotide analogs of formula (II) which are located either at the 3' end or at the 5' end, or at both ends, of the said oligonucleotide strand.

In some embodiments of a targeted oligonucleotide according to the present disclosure, either being a single-stranded or a double-stranded oligonucleotide, an oligonucleotide strand thereof comprises from 1 to 10 targeted nucleotide analogs of formula (II) which are located either at the 3' end, or at the 5' end of the said strand, or at one or more other locations within the said strand.

In some embodiments, the said targeted oligonucleotide further comprises from 1 to 10 non-targeted nucleotide analogs of formula (II) which may be located at various locations within the said oligonucleotide strand, e.g. internally and/or at the 3' end or 5' end thereof.

In some embodiments of a targeted oligonucleotide according to the present disclosure, either being a single-stranded or a double-stranded oligonucleotide, an oligonucleotide strand thereof comprises (A) one or more targeted nucleotide analogs of formula (II) which are located either at the 3' end or at the 5' end, or at both ends, of the said oligonucleotide strand and (B) one or more non-targeted nucleotide analogs of formula (II) which are located either at the 3' end or at the 5' end, or at both ends, of the said oligonucleotide strand, with the targeted nucleotide analogs of formula (II) and the non-targeted nucleotide analogs of formula (II) being located at distinct positions within the said oligonucleotide strand.

In some embodiments of a targeted oligonucleotide according to the present disclosure, either being a single-stranded or a double-stranded oligonucleotide, an oligonucleotide strand thereof comprises from 1 to 10 targeted nucleotide analogs of formula (II) which are located either at the 3' end, or at the 5' end of the said strand. In some embodiments, the said targeted oligonucleotide further comprises from 1 to 10 non-targeted nucleotide analogs of formula (II) which are located at the opposite end of the said oligonucleotide strand. Thus, according to these embodiments, the number of targeted nucleotide analogs of formula (II) at the selected end of the oligonucleotide strand may be 1, 2, 3, 4, 5, 6, 7, 8, 9 or 10. According to some of these embodiments, the number of non-targeted nucleotide analogs of formula (II) at the selected end of the oligonucleotide strand, if present, may be 1, 2, 3, 4, 5, 6, 7, 8, 9 or 10.

In particular embodiments, the said one or more targeted nucleotide analogs of formula (II) are linked, one to the other so as to form a continuous chain of these targeted nucleotide analogs at the selected end of the oligonucleotide strand.

In particular embodiments, the said one or more targeted nucleotide analogs of formula (II) are located at the 5' end of a strand of a targeted oligonucleotide, either being single-stranded or double-stranded oligonucleotide. In some of these embodiments, the 5' end nucleotide is a targeted nucleotide analog of formula (II).

In some embodiments of a targeted oligonucleotide according to the present disclosure, either being a single-stranded or a double-stranded oligonucleotide, an oligonucleotide strand thereof comprises one or more non-targeted nucleotide analogs of formula (II) either at the 3' end or at the 5' end thereof, and especially at an end opposite to the end comprising one or more targeted nucleotide analogs of formula (II).

In some embodiments of a targeted oligonucleotide according to the present disclosure, either being a single-stranded or a double-stranded oligonucleotide, an oligonucleotide strand thereof comprises from 1 to 10 non-targeted nucleotide analogs of formula (II) either at the 3' end or at the 5' end, and comprises preferably from 1 to 10 non-targeted nucleotide analogs of formula (II) at the opposite end thereof. Thus, in these embodiments, the number of non-targeted nucleotide analogs of formula (II) at the selected end of the oligonucleotide strand may be 1, 2, 3, 4, 5, 6, 7, 8, 9 or 10. According to some of these embodiments, the number of targeted nucleotide analogs of formula (II) at the selected end of the oligonucleotide strand, if present, may be 1, 2, 3, 4, 5, 6, 7, 8, 9 or 10.

In particular embodiments, the said one or more non-targeted nucleotide analogs of formula (II) are linked, one to the other so as to form a continuous chain of these non-targeted nucleotide analogs at the selected end of the oligonucleotide strand.

In particular embodiments, the said one or more non-targeted nucleotide analogs of formula (II) are located at the 3' end of an oligonucleotide strand of a targeted oligonucleotide. In further embodiments, the 3' end nucleotide is a targeted nucleotide analog of formula (II).

Thus, the present disclosure encompasses single-stranded targeted oligonucleotides comprising (i) one or more targeted nucleotide analogs of formula (II), preferably from 1 to 10 targeted nucleotide analogs of formula (II), which may be consecutive in the oligonucleotide chain and which are located at the 5' end of the said single-stranded targeted oligonucleotides. In some of these embodiments, the said single-stranded targeted oligonucleotides further comprise (ii) one or more non-targeted nucleotide analogs of formula (II), e.g., from 1 to 10 non-targeted nucleotide analogs of formula (II) which may be consecutive in the oligonucleotide chain and which are located at the 3' end of the said single-stranded targeted oligonucleotides.

Illustrations of single-stranded targeted oligonucleotides comprising (i) three targeted nucleotide analogs of formula (II) at the 5' end thereof and (ii) two non-targeted nucleotide analogs of formula (II) at the 3' end thereof are disclosed in the examples herein.

The present disclosure also encompasses double-stranded oligonucleotides wherein (i) a first strand is a targeted oligonucleotide comprising one or more targeted nucleotide analogs of formula (II) and one or more non-targeted nucleotide analogs of formula (II), as described above, and wherein (ii) a second strand is another targeted oligonucleotide comprising one or more targeted nucleotide analogs of formula (II) and one or more non-targeted nucleotide analogs of formula (II).

The present disclosure further encompasses double-stranded oligonucleotides wherein at least one strand thereof is a targeted oligonucleotide as described above, such as a targeted oligonucleotide comprising one or more targeted nucleotide analogs of formula (II) and one or more non-targeted nucleotide analogs of formula (II), as described above, and (ii) a second strand is either of a non-targeted oligonucleotide or a targeted oligonucleotide.

The present disclosure further encompasses double-stranded oligonucleotides wherein (i) a first strand is a targeted oligonucleotide comprising one or more targeted nucleotide analogs of formula (II) and one or more non-targeted nucleotide analogs of formula (II), as described above, and (ii) a second strand is a non-targeted oligonucleotide comprising one or more non-targeted nucleotide analogs of formula (II).

The present disclosure also describes an siRNA comprising:
  a sense strand comprising (i) one or more targeted nucleotide analogs of formula (II), especially from 1 to 10 targeted nucleotide analogs of formula (II) which are located at the 5' end thereof and (ii) one or more non-targeted nucleotide analogs of formula (II), especially from 1 to 10 non-targeted nucleotide analogs of formula (II) which are located at the 3' end thereof, and
  an antisense strand, which is either a non-targeted oligonucleotide or a targeted oligonucleotide.

The present disclosure also describes an siRNA comprising:
  a sense strand comprising (i) one or more targeted nucleotide analogs of formula (II), especially from 1 to 10 targeted nucleotide analogs of formula (II) which are located at the 3' end thereof, and
  an antisense strand that does not comprise any nucleotide analog of formula (II).

The present disclosure further describes an siRNA comprising:
  a sense strand comprising (i) one or more targeted nucleotide analogs of formula (II), especially from 1 to 10 targeted nucleotide analogs of formula (II) which are located at the 5' end thereof and (ii) one or more non-targeted nucleotide analogs of formula (II), especially from 1 to 10 non-targeted nucleotide analogs of formula (II) which are located at the 3' end thereof, and an antisense strand comprising one or more non-targeted nucleotide analogs of formula (II), especially from 1 to 10 non-targeted nucleotide analogs of formula (II) which are located at the 3' end thereof.

The present disclosure further describes an siRNA comprising:
  a sense strand comprising (i) one or more non-targeted nucleotide analogs of formula (II), especially from 1 to 10 non-targeted nucleotide analogs of formula (II) which are located at the 3' end thereof, and
  an antisense strand, wherein the said antisense strand most preferably does not comprise any non-targeted nor targeted analog of formula (II).

The present disclosure further describes an siRNA comprising:
  a sense strand comprising (i) one or more non-targeted nucleotide analogs of formula (II), especially from 1 to 10 non-targeted nucleotide analogs of formula (II) which are located at the 3' end thereof, and
  an antisense strand comprising (i) one or more non-targeted nucleotide analogs of formula (II), especially from 1 to 10 non-targeted nucleotide analogs of formula (II) which are located at the 3' end thereof.

The present disclosure further describes an siRNA comprising:
  a sense strand comprising (i) one or more non-targeted nucleotide analogs of formula (II), especially from 1 to 10 non-targeted nucleotide analogs of formula (II) which are located at the 3' end thereof and (ii), and one or more non-targeted nucleotide analogs of formula (II), especially from 1 to 10 non-targeted nucleotide analogs of formula (II) which are located at the 5' end thereof
  an antisense strand, wherein the said antisense strand most preferably does not comprise any non-targeted nor targeted analog of formula (II).

The present disclosure further describes an siRNA comprising:
  a sense strand comprising (i) one or more non-targeted nucleotide analogs of formula (II), especially from 1 to 10 non-targeted nucleotide analogs of formula (II) which are located at the 3' end thereof and (ii), and one or more non-targeted nucleotide analogs of formula (II), especially from 1 to 10 non-targeted nucleotide analogs of formula (II) which are located at the 5' end thereof
  an antisense strand comprising (i) one or more non-targeted nucleotide analogs of formula (II), especially from 1 to 10 non-targeted nucleotide analogs of formula (II) which are located at the 3' end thereof.

The present disclosure further describes an siRNA comprising:
  a sense strand wherein the said sense strand most preferably does not comprise any non-targeted nor targeted analog of formula (II).
  an antisense strand comprising (i) one or more targeted nucleotide analogs of formula (II), especially from 1 to 10 non-targeted nucleotide analogs of formula (II.

Further Embodiments of Targeted Oligonucleotides

An oligonucleotide comprising one or more compounds of formula (II), especially one or more non-targeted nucleotide analog of formula (II), may further comprise one or more modified nucleotides ("targeted nucleotides") allowing the targeting of the oligonucleotide towards target cells or cell receptor proteins. For example, the oligonucleotide is double-stranded wherein one or both oligonucleotide strands comprise one or more compounds of formula (II), and wherein one or both oligonucleotide strands further comprise one or more targeted nucleotides. Such a double-stranded oligonucleotide may also be termed a "dsRNA conjugate" for the purpose of the present disclosure.

Targeted Nucleotides

In some embodiments of targeted oligonucleotides based on formula (II), a targeting ligand (e.g., a cell targeting moiety) is directly and covalently bound to the nitrogen atom of the morpholino group. In some other embodiments, the ligand is covalently bound to the nitrogen atom of the morpholino group via a linker group. By way of example, a targeted nucleotide analog of formula (II) may comprise, e.g., a compound of formula (II) wherein Y is NR1, and R1 is a group —[C(=O)]m-R2-(O—CH$_2$—CH$_2$)p-R3 with R3 being a cell targeting moiety, and wherein B, L1, L2, m, p, R2, X1, X2, Ra, Rb, Rc and Rd are as defined for the general formula (II).

Cell Targeting Moiety

A targeted nucleotide herein may be linked to one or more ligands targeting specific cells or tissue. Such a ligand is also called "cell targeting moiety." The ligand encompasses any molecular group that increases efficiency of the delivery of the resulting oligonucleotide such as an siRNA into cells, e.g., by improving specific cell targeting, improving the oligonucleotide's cell internalization, and/or improving intracellular mRNA targeting. The ligand may be selected from a group comprising receptor specific peptide, receptor-specific protein (e.g., monoclonal antibodies or fusion proteins), and receptor-specific small molecule ligands (e.g., carbohydrates such as GalNAc groups).

Ligands may be naturally occurring, or recombinant or synthetic. For example, the ligand may be a protein, a carbohydrate, a lipopolysaccharide, a lipid, a synthetic polymer, a polyamine, an alpha helical peptide, a lectin, a vitamin, or a cofactor. In some embodiments, the ligand is one or more dyes, crosslinkers, polycyclic aromatic hydrocarbons, peptide conjugates (e.g., RGD peptides, antennapedia peptide, Tat peptide), polyethylene glycol (PEG), enzymes, haptens, transport/absorption facilitators, synthetic ribonucleases (e.g., imidazole, bisimidazole, histamine, or imidazole clusters), human serum albumin (HSA), or LDL.

By way of example, the ligand may be one or more proteins, glycoproteins, peptides, or molecules having a specific affinity for a co-ligand. Such ligands may include a thyrotropin, melanotropin, glycoprotein, surfactant protein A, mucin carbohydrate, lactose (e.g., multivalent lactose), galactose (e.g., multivalent galactose), N-acetyl-galactosamine (e.g., multivalent N-acetyl-galactosamine), N-acetyl-glucosamine (e.g., multivalent N-acetyl-glucosamine), mannose (e.g., multivalent mannose), fucose (e.g., multivalent fucose), glycosylated polyaminoacids, transferrin, bisphosphonate, polyglutamate, polyaspartate, a lipid, cholesterol, a steroid, bile acid, folate, vitamin B12, and biotin.

In some embodiments, the cell targeting moiety is one or more dyes, crosslinkers, polycyclic aromatic hydrocarbons, peptide conjugates (e.g., antennapedia peptide, Tat peptide), polyethylene glycol (PEG), enzymes, haptens, transport/absorption facilitators, synthetic ribonucleases (e.g., imidazole, bisimidazole, histamine, or imidazole clusters), human serum albumin (HSA), or LDL.

In some embodiments, the ligand may be one or more cholesterol derivatives or lipophilic moieties. Any lipophilic compound may include, without limitation, cholesterol or a cholesterol derivative; cholic acid; a vitamin (such as folate, vitamin A, vitamin E (tocopherol), biotin, pyridoxal; bile or fatty acid conjugates, including both saturated and non-saturated (such as lauroyl ($C_{12}$), myristoyl ($C_{14}$) and palmitoyl ($C_{16}$), stearoyl ($C_{18}$) and docosanyl ($C_{22}$), lithocholic acid and/or lithocholic acid oleylamine conjugate (lithocholic-oleyl, $C_{43}$); polymeric backbones or scaffolds (such as PEG, triethylene glycol (TEG), hexaethylene glycol (HEG), poly(lactic-co-glycolic acid) (PLGA), poly(lactide-co-glycolide) (PLG), hydrodynamic polymers; steroids (such as dihydrotestosterone); terpene (such as triterpene); cationic lipids or peptides; and/or a lipid or lipid-based molecule. Such a lipid or lipid-based molecule may bind a serum protein, e.g., human serum albumin (HSA). A lipid based ligand may be used to modulate (e.g., control) the binding of the conjugate to a target tissue. For example, a lipid or lipid-based ligand that binds to HSA more strongly will be less likely to be targeted to the kidney and therefore less likely to be cleared from the body. The target tissue may be the liver, including parenchymal cells of the liver.

The polyaminoacids, transferrin, cell targeting ligands or moieties may also be antibodies that bind to receptors on specific cell types such as hepatocytes. Exemplary cell receptor-specific monoclonal antibodies are those disclosed by X1a et al. (2009, Mol Pharm, 63(3):747-751); Cuellar et al. (2015, Nucleic Acids Research, 43(2):1189-1203); Baumer et al. (2016, Nat Protocol, 11(1):22-36); Ibtejah et al. (2017, Clin Immunol, 176:122-130); and Sugo et al. (2016, J Control Release, 237:1-13).

The cell targeting ligands or moieties also encompass monovalent or multivalent (e.g., trivalent) GalNAc groups, such as those disclosed by Prakash et al. (2015, Bioorg Med Chem Lett, 25(19):4127-4130); Zu et al. (2016, Mol Ther—Nucleic Acids, e317, doi: 10.1038/mnta.2016.26); Zimmermann et al. (2017, Mol Ther, 25(1):71-78); Shemesh et al. (2016, Mol Ther Nucleic Acids, 5:e319-doi:10.1038/mnta.2016.31); Huang et al. (2016, Mol Ther—Nucleic Acids, 6:116-132); Rozema et al. (2007, Proc Natl Acad Sci USA, 104(32):12982-12987); Rajeev et al. (2015, Chembiochem, 16(6):903-908); and Nair et al. (2014, J Am Chem Soc, 136(49):16958-16961).

Preparation of Modified dsRNAs dsRNAs of the present disclosure may be chemically/physically linked to one or more ligands, moieties or conjugates. In some embodiments, the dsRNA is conjugated/attached to one or more ligands via a linker. Any linker known in the art may be used, including, for example, multivalent branched linkers. Conjugating a ligand to a dsRNA may alter its distribution, enhance its cellular absorption and/or targeting to a particular tissue and/or uptake by one or more specific cell types (e.g., liver cells), and/or enhance the lifetime of the dsRNA agent. In some embodiments, a hydrophobic ligand is conjugated to the dsRNA to facilitate direct permeation across the cellular membrane and/or uptake by the cells (e.g., liver cells).

In some embodiments of a dsRNA conjugate, one or more nucleotides may comprise a targeting moiety-bearing group, such as one or more nucleotides comprise a targeting moiety-bearing group wherein a targeting moiety is covalently linked to the nucleotide backbone, possibly via a linking group. According to these embodiments, one or more nucleotides of a dsRNA are conjugated to a targeting moiety-bearing group comprising a targeting moiety and wherein the targeting moiety may be, a ligand (e.g., a cell penetrating moiety or agent) that enhances intracellular delivery of the compositions.

Ligand-conjugated dsRNAs and ligand-molecule bearing sequence-specific linked nucleosides and nucleotides of the present disclosure may be assembled by any method known in the art, including, for example, by assembly on a suitable DNA synthesizer utilizing standard nucleotide precursors, or nucleotide or nucleoside conjugate precursors that already bear the linking moiety, ligand-nucleotide, or nucleoside-conjugated precursors that already bear the ligand molecule, or non-nucleoside ligand-bearing building blocks.

Ligand-conjugated dsRNAs of the present disclosure may be synthesized by any method known in the art, including, for example, by the use of a dsRNA bearing a pendant reactive functionality such as that derived from the attachment of a linking molecule onto the dsRNA. In some embodiments, this reactive oligonucleotide may be reacted directly with commercially-available ligands, ligands that are synthesized bearing any of a variety of protecting groups, or ligands that have a linking moiety attached thereto. In some embodiments, the methods facilitate the synthesis of ligand-conjugated dsRNA by the use of nucleoside monomers that have been appropriately conjugated with ligands and that may further be attached to a solid support material. In some embodiments, a dsRNA bearing an aralkyl ligand attached to the 3'-end of the dsRNA is prepared by first covalently attaching a monomer building block to a controlled-pore-glass support via an aminoalkyl group; then, nucleotides are bonded via standard solid-phase synthesis techniques to the monomer building-block bound to the solid support. The monomer building-block may be a nucleoside or other organic compound that is compatible with solid-phase synthesis.

Compositions

Certain aspects of the present disclosure relate to compositions (e.g., pharmaceutical compositions) comprising a dsRNA as described herein. In some embodiments, the composition (e.g., pharmaceutical composition) further comprises a pharmaceutically acceptable carrier. In some embodiments, the composition (e.g., pharmaceutical composition) is useful for treating a disease or disorder associated with the expression or activity of the targeted gene.

Compositions (e.g., pharmaceutical compositions) of the present disclosure are formulated based upon the mode of delivery, including, for example, compositions formulated for delivery to the liver via parenteral delivery.

The compositions (e.g., pharmaceutical composition) of the present disclosure may be administered in dosages sufficient to inhibit expression of the targeted gene. In some embodiments, a suitable dose of a dsRNA is in the range of 0.01 mg/kg-400 mg/kg body weight of the recipient.

One of ordinary skill in the art will appreciate that certain factors may influence the dosage and timing required to effectively treat a subject, including, but not limited to, severity of the disease or disorder, previous treatments, the general health and/or age of the subject, and one or more other diseases being present. Moreover, treatment of a subject with a therapeutically effective amount of a pharmaceutical composition can include a single treatment or a series of treatments. Estimates of effective dosages and in vivo half-lives for dsRNAs as disclosed herein may be made using conventional methodologies or on the basis of in vivo testing using an appropriate animal model.

dsRNA molecules of the present disclosure can be formulated in a pharmaceutically acceptable carrier or diluent. Pharmaceutically acceptable carriers can be liquid or solid, and may be selected with the planned manner of administration in mind so as to provide for the desired bulk, consistency, and other pertinent transport and chemical properties. Any known pharmaceutically acceptable carrier or diluent may be used, including, for example, water, saline solution, binding agents (e.g., polyvinylpyrrolidone or hydroxypropyl methylcellulose), fillers (e.g., lactose and other sugars, gelatin, or calcium sulfate), lubricants (e.g., starch, polyethylene glycol, or sodium acetate), disintegrates (e.g., starch or sodium starch glycolate), calcium salts (e.g., calcium sulfate, calcium chloride, calcium phosphate, etc.) and wetting agents (e.g., sodium lauryl sulfate).

dsRNA molecules of the present disclosure can be formulated into compositions (e.g., pharmaceutical compositions) containing the dsRNA admixed, encapsulated, conjugated, or otherwise associated with other molecules, molecular structures, or mixtures of nucleic acids. For example, a composition comprising one or more dsRNAs as described herein can contain other therapeutic agents such as other lipid lowering agents (e.g., statins). In some embodiments, the composition (e.g., pharmaceutical composition) further comprises a delivery vehicle (as described herein).

Vectors and dsRNA Delivery

A dsRNA of the present disclosure may be delivered directly or indirectly. In some embodiments, the dsRNA is delivered directly by administering a composition (e.g., pharmaceutical composition) comprising the dsRNA to a subject. In some embodiments, the dsRNA is delivered indirectly by administering one or more vectors described herein.

Delivery

A dsRNA of the present disclosure may be delivered by any method known in the art, including, for example, by adapting a method of delivering a nucleic acid molecule for use with a dsRNA (See e.g., Akhtar, S. et al. (1992) *Trends Cell. Biol.* 2(5): 139-144; WO 94/02595), or via additional methods known in the art (See e.g., Kanasty, R. et al. (2013) *Nature Materials* 12: 967-977; Wittrup, A. and Lieberman, J. (2015) *Nature Reviews Genetics* 16: 543-552; Whitehead, K. et al. (2009) *Nature Reviews Drug Discovery* 8: 129-138; Gary, D. et al. (2007) 121 (1-2): 64-73; Wang. J. et al. (2010) *AAPS J.* 12(4): 492-503; Draz, M. et al. (2014) *Theranostics* 4(9): 872-892; Wan, C. et al. (2013) *Drug Deliv. And Transl. Res.* 4(1): 74-83; Erdmann, V. A. and Barciszewski, J. (eds.) (2010) "*RNA Technologies and Their Applications*", Springer-Verlag Berlin Heidelberg, DOI 10.1007/978-3-642-12168-5; Xu, C. and Wang, J. (2015) *Asian Journal of Pharmaceutical Sciences* 10(1): 1-12).

In some embodiments, a dsRNA of the present disclosure is delivered by a delivery vehicle comprising the dsRNA. In some embodiments, the delivery vehicle is a liposome, lipoplex, complex, or nanoparticle.

Liposomal Formulations

Liposomes are unilamellar or multilamellar vesicles which have a membrane formed from a lipophilic material and an aqueous interior. In some embodiments, a liposome is a vesicle composed of amphiphilic lipids arranged in a spherical bilayer or bilayers. The aqueous portion contains the composition to be delivered. Cationic liposomes possess the advantage of being able to fuse to the cell wall. Advantages of liposomes include, e.g., liposomes obtained from natural phospholipids are biocompatible and biodegradable; liposomes can incorporate a wide range of water and lipid soluble drugs; liposomes can protect encapsulated drugs in their internal compartments from metabolism and degradation (Rosoff, in Pharmaceutical Dosage Forms, Lieberman, Rieger and Banker (Eds.), 1988, Marcel Dekker, Inc., New York, N.Y., volume 1, p. 245). Important considerations in the preparation of liposome formulations are the lipid surface charge, vesicle size and the aqueous volume of the liposomes. For example, engineered cationic liposomes and sterically stabilized liposomes can be used to deliver the dsRNA. See, e.g., Podesta et al. (2009) Methods Enzymol. 464, 343-54; U.S. Pat. No. 5,665,710.

Nucleic Acid-Lipid Particles

In some embodiments, a dsRNA of the present disclosure is fully encapsulated in a lipid formulation, e.g., to form a nucleic acid-lipid particle, e.g., a SPLP, pSPLP, or SNALP. As used herein, the term "SNALP" refers to a stable nucleic acid-lipid particle, including SPLP. As used herein, the term "SPLP" refers to a nucleic acid-lipid particle comprising plasmid DNA encapsulated within a lipid vesicle. Nucleic acid-lipid particles, e.g., SNALPs, typically contain a cationic lipid, a non-cationic lipid, cholesterol and a lipid that prevents aggregation of the particle and increases circulation time (e.g., a PEG-lipid conjugate). SNALPs and SPLPs are useful for systemic applications, as they exhibit extended circulation lifetimes following intravenous (i.v.) injection and accumulate at distal sites (e.g., sites physically separated from the administration site). SPLPs include "pSPLP", which include an encapsulated condensing agent-nucleic acid complex as set forth in PCT Publication No. WO 00/03683.

In some embodiments, dsRNAs when present in the nucleic acid-lipid particles are resistant in aqueous solution to degradation with a nuclease. Nucleic acid-lipid particles and their methods of preparation are disclosed in, e.g., U.S. Pat. Nos. 5,976,567; 5,981,501; 6,534,484; 6,586,410; and 6,815,432; and PCT Publication No. WO 96/40964.

In some embodiments, the nucleic acid-lipid particles comprise a cationic lipid. Any cationic lipid or mixture thereof known in the art may be used. In some embodiments, the nucleic acid-lipid particles comprise a non-cationic lipid. Any non-cationic lipid or mixture thereof known in the art may be used. In some embodiments, the nucleic acid-lipid particle comprises a conjugated lipid (e.g., to prevent aggregation). Any conjugated lipid known in the art may be used.

Additional Formulations

Factors that are important to consider in order to successfully deliver a dsRNA molecule in vivo include: (1) biological stability of the delivered molecule, (2) preventing nonspecific effects, and (3) accumulation of the delivered molecule in the target tissue. The nonspecific effects of a dsRNA can be minimized by local administration, for example by direct injection or implantation into a tissue or topically administering the preparation. For administering a dsRNA systemically for the treatment of a disease, the dsRNA may be modified or alternatively delivered using a drug delivery system; both methods act to prevent the rapid degradation of the dsRNA by endo and exo-nucleases in vivo. Modification of the RNA or the pharmaceutical carrier may also permit targeting of the dsRNA composition to the target tissue and avoid undesirable off-target effects. As described above, dsRNA molecules may be modified by chemical conjugation to lipophilic groups such as cholesterol to enhance cellular uptake and prevent degradation. In some embodiments, the dsRNA is delivered using drug delivery systems such as a nanoparticle, a dendrimer, a polymer, liposomes, or a cationic delivery system. Positively charged cationic delivery systems facilitate binding of a dsRNA molecule (negatively charged) and also enhance interactions at the negatively charged cell membrane to permit efficient uptake of a dsRNA by the cell. Cationic lipids, dendrimers, or polymers can either be bound to dsRNA, or induced to form a vesicle or micelle (See e.g., Kim S. H. et al. (2008) *Journal of Controlled Release* 129(2):107-116) that encases a dsRNA.

The formation of vesicles or micelles further prevents degradation of the dsRNA when administered systemically. Methods for making and administering cationic-dsRNA complexes are known in the art. In some embodiments, a dsRNA forms a complex with cyclodextrin for systemic administration.

Methods of Using dsRNA

Certain aspects of the present disclosure relate to methods for inhibiting the expression of a targeted gene in a mammal comprising administering an effective amount of one or more dsRNAs of the present disclosure, one or more vectors of the present disclosure, or a composition (e.g., pharmaceutical composition) of the present disclosure comprising one or more dsRNAs of the present disclosure. Certain aspects of the present disclosure relate to methods of treating and/or preventing one or more target gene-mediated diseases or disorders comprising administering one or more dsRNAs of the present disclosure and/or one or more vectors of the present disclosure and/or a composition (e.g., pharmaceutical composition) comprising one or more dsRNAs of the present disclosure. In some embodiments, downregulating target gene expression in a subject alleviates one or more symptoms of a targeted gene-mediated disease or disorder in the subject.

In some embodiments, expression of the target gene in the subject is inhibited by at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 99%, or about 100% after treatment as compared to pretreatment levels. In some embodiments, expression of the target gene is inhibited by at least about 1.1 fold, at least about 1.5 fold, at least about 2 fold, at least about 2.5 fold, at least about 3 fold, at least about 3.5 fold, at least about 4 fold, at least about 4.5 fold, at least about 5 fold, at least about 5.5 fold, at least about 6 fold, at least about 6.5 fold, at least about 7 fold, at least about 7.5 fold, at least about 8 fold, at least about 8.5 fold, at least about 9 fold, at least about 9.5 fold, at least about 10 fold, at least about 25 fold, at least about 50 fold, at least about 75 fold, or at least about 100 fold after treatment as compared to pretreatment levels. In some embodiments, the target gene is inhibited in the liver of the subject.

In some embodiments, the subject is human. In some embodiments, the subject has or has been diagnosed with a target gene-mediated disorder or disease. In some embodiments, the subject is suspected to have a target gene-mediated disorder or disease. In some embodiments, the subject is at risk for developing a target gene-mediated disorder or disease.

As it is understood from the content of the present disclosure, a dsRNA as described herein has its main characteristics lying in the presence of one or more nucleotide analogs of formula (II) comprised therein, which nucleotide analogs of formula (II) possess specific structural features of the "sugar-like" group thereof. A dsRNA as described herein is generally conceived for targeting a selected nucleic acid sequence comprised in a target nucleic acid of interest. Especially, embodiments of a dsRNA described herein consisting of siRNAs comprise an antisense strand that specifically hybridizes with a nucleic acid sequence comprised in a target nucleic acid of interest. A dsRNA or composition (e.g., pharmaceutical composition) described herein may be for use in the treatment of target gene-mediated disorder or disease. In particular, a dsRNA or composition (e.g., pharmaceutical composition) described herein, and especially a dsRNA comprising one or more targeted nucleotide analogs, and especially one or more targeted nucleotide analogs of formula (II), may be for use in the treatment of target gene-mediated disorder or disease wherein liver-targeting is needed.

Certain aspects of the present disclosure also relate to a method of delivery of nucleic acids to hepatocytes comprising contacting the hepatocyte with a dsRNA described herein.

A dsRNA or composition (e.g., pharmaceutical composition) described herein may be administered by any means known in the art, including, without limitation, oral or parenteral routes, including intravenous, intramuscular, subcutaneous, pulmonary, transdermal, and airway (aerosol) administration. Typically, when treating a mammal with hyperlipidemia, the dsRNA molecules are administered systemically via parenteral means. In some embodiments, the dsRNAs and/or compositions are administered by subcutaneous administration. In some embodiments, the dsRNAs and/or compositions are administered by intravenous administration. In some embodiments, the dsRNAs and/or compositions are administered by pulmonary administration.

A treatment or preventative effect of a dsRNA is evident when there is a statistically significant improvement in one or more parameters of disease status, or by a failure to worsen or to develop symptoms where they would otherwise be anticipated. For example, a favorable change of at least 10%, 15%, 20%, 25%, 30%, 35%, 40%, 45%, 50% or more in a measurable parameter of disease may be indicative of effective treatment. Efficacy for a given dsRNA or composition comprising the dsRNA may also be judged using an experimental animal model for the given disease or disorder known in the art. When using an experimental animal model, efficacy of treatment is evidenced when a statistically significant reduction in a marker or symptom is observed.

Kits and Articles of Manufacture

Certain aspects of the present disclosure relate to an article of manufacture or a kit comprising one or more of the dsRNAs, vector(s), or composition(s) (e.g., pharmaceutical composition(s) as described herein useful for the treatment and/or prevention of a target gene-mediated disorder or disease as described above. The article of manufacture or kit may further comprise a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating or preventing the disease and may have a sterile access port (for example the container may be an intravenous solution bag or a vial having a stopper pierceable by a hypodermic injection needle). At least one active agent in the composition is a dsRNA described herein. The label or package insert indicates that the composition is used for treating a target-mediated disorder or disease. Moreover, the article of manufacture or kit may comprise (a) a first container with a composition contained therein, wherein the composition comprises a dsRNA described herein; and (b) a second container with a composition contained therein, wherein the composition comprises a second therapeutic agent. The article of manufacture or kit in this embodiment of the present disclosure may further comprise a package insert indicating that the compositions can be used to treat a particular disease. Alternatively, or additionally, the article of manufacture or kit may further comprise a second (or third) container comprising a pharmaceutically acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

Nucleic acid sequences are disclosed in the present specification and especially in the examples herein, that serve as references. The same sequences are also presented in a sequence listing formatted according to standard requirements for the purpose of patent matters. In case of any sequence discrepancy with the standard sequence listing, the sequences described in the present specification shall be the reference.

Without limiting the present disclosure, a number of embodiments of the present disclosure are described below for the purpose of illustration.

EXAMPLES

Abbreviations Used

AcOH: acetic acid
FA: formic acid
ACN: acetonitrile
DCM: dichloromethane
DMA: dimethylacetamide
DCE: dichloroethane
DMF: dimethylformamide
DMSO: dimethylsulfoxide
EtOAc: ethyl acetate
EtOH: ethanol
$Et_2O$: diethylether
iPrOH: isopropanol
THF: tetrahydrofuran
MeOH: methanol
NMP: N-methyl-2-pyrrolidone
PE: petrol ether
Pyr: pyridine
iPr: isopropyl
cHex: cyclohexyl
MTB: methyl-tert.-butyl
DIPEA: diisopropylethylamine
DMAP: 4-(dimethylamino)-pyridine
HBTU: (2-(1H-Benzotriazol-1-yl)-1,1,3,3-tetramethyl-uronium-hexafluorophosphate)
TBTU: O-(Benzotriazol-1-yl)-N,N,N',N'-tetramethyluronium tetrafluoroborate
DDTT: 3-((N,N-dimethyl-aminomethylidene)amino)-3H-1,2,4-dithiazole-5-thione
$NEt_3$: triethylamine
NEM: N-ethyl-morpholine
BSA: N,O-bis-trimethylsilyl acetamide
TMSOTf: trimethylsilyltrifluormethanesulfonate Ts: p-toluenesulfonyl
Tf: trifluormethanesulfonyl trifluoromethanesulfonate
TFA: trifluoroacetic acid
DCA: dichloroacetic acid
TEA: triethylammonium
TIPS: triisopropylsilyl
TBDMS: tert-butyldimethylsilyl
DMT: 4,4'-dimethoxytrityl
Bzl: benzoyl
Bn: benzyl
BOM: benzyloxymethyl
Ac: acetyl
IBu: isobutyryl
Boc: tert-butyloxycarbonyl
Fmoc: fluorenylmethyloxycarbonyl
Fmoc-OSu: N-(9-Fluorenylmethoxycarbonyloxy)succinimide
CE: cyanoethyl
CPG: controlled pore glass
T: thymine
U: uracile
C: cytosine
A: adenine
G: guanine
I: hypoxanthinehypoxanthine
$T^{BOM}$: N-benzyloxymethyl-thymine
$U^{BOM}$: N-benzyloxymethyl-uracile
$U^{Bzl}$: N-benzoyl-uracile
$C^{Bzl}$: N-benzoyl-cytosine
$A^{Bzl}$: N-benzoyl-adenine
$G^{iBu}$: N-isobutyryl-guanine
GalNAc: D-N-acetylgalactosamine
FR: flow rate
HPLC: high pressure liquid chromatography
MS-TOF: Mass spectrometry-time of flight
LC-MS: High-pressure liquid chromatography-Mass spectrometry
$R_t$: retention time
RT: room temperature
Hal: halogen
ELSD: evaporative light scattering detector
quant.: quantitative
sat.: saturated
i. vac.: in vacuum
n.d.: not determined
TLC: thin layer chromatography
h: hour
min: minutes
Tm: melting temperature
r: ribonucleotide
d: desoxy-ribonucleotide
m: 2'-OMe-nucleotide
f: 2'-desoxy-fluoro-nucleotide
-ss: sense strand
as: antisense strand
-ds: double strand
chol: cholesterol
PO: phosphodiester linkage
* or PS: phosphorothiate linkage
mpk: mg/kg
M: molar
: number, no FBS: fetal bovine serum
ATP: adenosine-triphosphate
pre-lB: precursor nucleotide
pre-lgB: targeted precursor nucleotide
lB: nucleotide analog
lgB: targeted nucleotide analog

EXAMPLES

Nomenclature has been established according to IUPAC rules.

A. Synthesis of Nucleotide Analogs of Formula (I) Wherein X is N

Unless otherwise indicated the following LC-MS methods have been used:

A:
Column: Waters ACQUITY UPLC BEH C18, 1.7 µm, 21×50 mm
Eluent: (H$_2$O+0.05% FA)/(ACN+0.035% FA) 95:5 (0 min) to 5:95 (2 min) to 5:95 (2.6 min) to 95:5 (2.7 min) to 95:5 (3.0 min), 0.9 ml/min 55° C.

B-1:
Column: Phenomenex Luna C18, 3.0 µm, 2.0×10 mm
Eluent: (H$_2$O+0.05% TFA)/ACN 93:7 (0 min) to 5:95 (1.20 min) to 5:95 ACN (1.40 min) to 93:7 (1.50 min); 1.1 ml/min, room temperature.

B-2:
Column: Phenomenex Luna C18, 3.0 µm, 2.0×10 mm
Eluent: (H$_2$O+0.05% TFA)/ACN 93:7 (0 min) to 5:95 (1.00 min) to 5:95 ACN (1.45 min) to 93:7 (1.50 min); 1.1 ml/min, room temperature.

B-3:
Column: Phenomenex Luna C18, 3.0 µm, 2.0×10 mm
Eluent: (H$_2$O+0.05% TFA)/ACN 20:80 (0 min) to 5:95 (0.60 min) to 5:95 ACN (1.45 min) to 80:20 (1.50 min); 1.1 ml/min, room temperature.

C:
Column: Waters ACQUITY UPLC BEH C18, 1.7 m, 2.1×50 mm
Eluent: (H$_2$O+0.05% FA)/(ACN+0.035% FA) 98:2 (0 min) to 98:2 (0.2 min) to 2:98 (3.8 min) to 2:98 (4.3 min) to 98:2 (4.5 min), 1.0 ml/min, 55° C.

D:
Column: Chromolith@Flash RP-18E 2×25 mm
Eluent: (H$_2$O+0.0375% TFA)/(ACN+0.01875% TFA) 95:5 (0 min) to 5:95 (0.80 min) to 5:95 (1.20 min) to 95:5 (1.21 min) to 95:5 (1.55 min), 1.5 ml/min, 50° C.

E:
Column: Kinetex EVO C18E 2.1×30 mm, 5 µm
Eluent: (H$_2$O+0.0375% TFA)/(ACN+0.01875% TFA) 95:5 (0 min) to 5:95 (0.80 min) to 5:95 (1.20 min) to 95:5 (1.21 min) to 95:5 (1.55 min), 1.5 ml/min, 50° C.

Example A.1

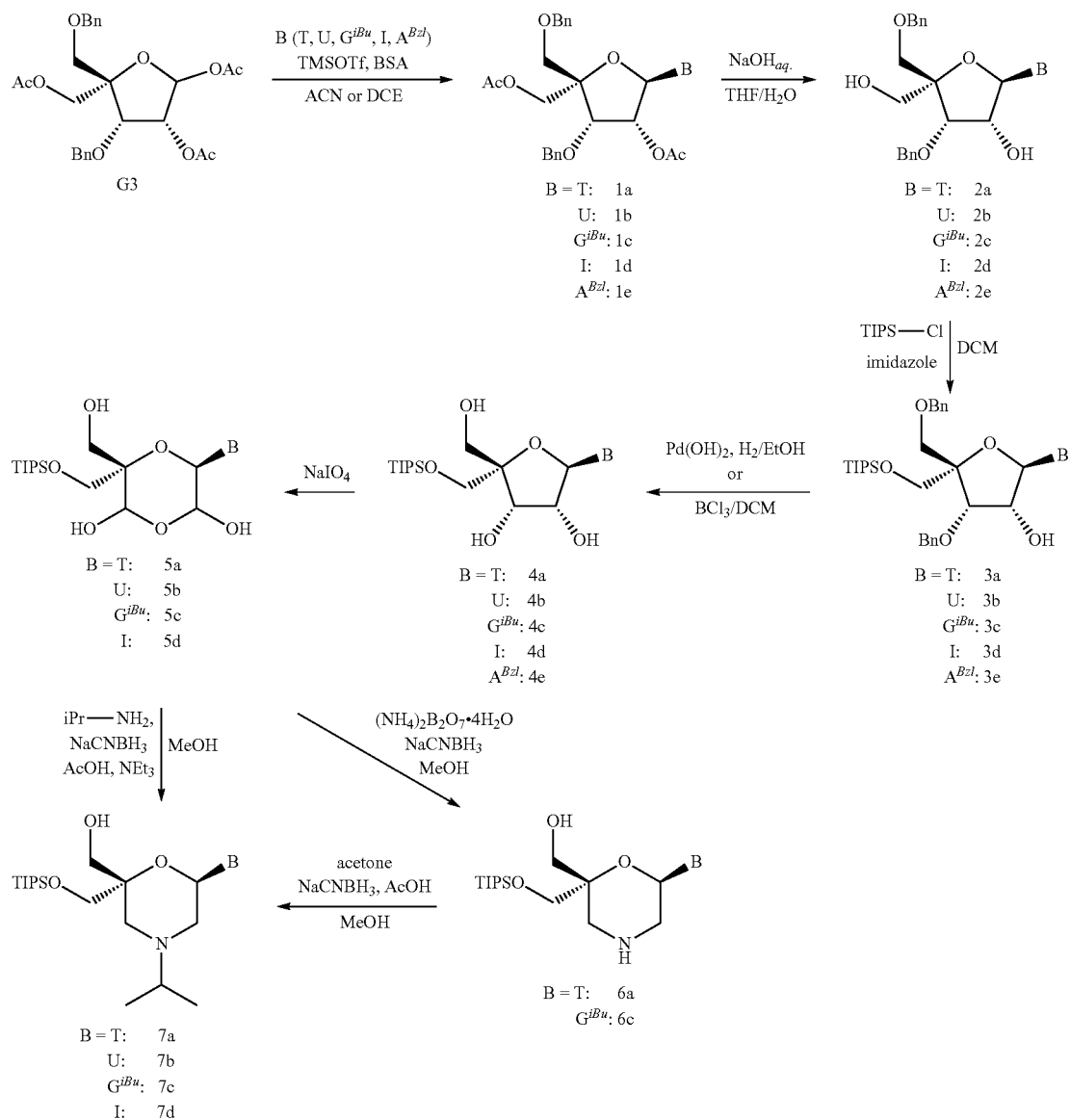

Synthetic Scheme 1

1a: [(2S,3S,4R,5R)-4-acetoxy-3-benzyloxy-2-(benzyloxymethyl)-5-(5-methyl-2,4-dioxo-pyrimidin-1-yl)tetrahydrofuran-2-yl]methyl Acetate 42.5 g (87.4 mmol) of the starting material G3 and 22.3 g (174.7 mmol) thymine were dissolved in 500 ml dry ACN under an atmosphere of argon. After adding 106.6 g (128.2 ml, 524.1 mmol) BSA, the solution was stirred for 1 h at 80° C. After cooling the solution to 50° C., 31.8 g (25.9 ml, 141.5 mmol) TMSOTf were added and heating was continued for 1 h at 80° C. The solvent was evaporated i.vac. and the residue was dissolved in EtOAc and washed with sat. NaHCO$_3$-solution, H$_2$O and sat. NaCl-solution. After drying with MgSO$_4$, the organic layer was evaporated and the crude product was purified by silica gel chromatography (10 to 100% ethyl acetate in n-heptane), yielding the desired thymidine derivative 1a as colourless foam (40.9 g, 84.7%).

LCMS-Method A:
UV-wavelength [nm]=220: R$_t$[min]=1.82
Ionization method: ES$^-$: [M–H]$^-$=551.3
1H-NMR (CDC$_3$, 400 MHz) δ[ppm]: 8.55 (s, 1H) 7.51-7.17 (m, 12H), 6.23 (d, J=5.27 Hz, 1H), 5.44 (t, J=5.65 Hz, 1H), 4.72-4.35 (m, 6H), 4.19 (d, J=12.17 Hz, 1H), 3.79 (d, J=10.16 Hz, 1H), 3.53 (d, J=10.16 Hz, 1H) 2.17-2.06 (m, 6H), 1.55 (d, J=0.75 Hz, 3H).

1b: [(2S,3S,4R,5R)-4-acetoxy-3-benzyloxy-2-(benzyloxymethyl)-5-(2,4-dioxopyrimidin-1-yl)-tetrahydrofuran-2-yl]methyl Acetate 10.0 g (20.55 mmol) of G3 and 3.49 g (30.8 mmol) uracile were dissolved 200 ml dry ACN. After adding 20.09 g (30.15 ml, 123.3 mmol) BSA, the solution was stirred at 81° C. for 1 h. After cooling the solution to 0° C., 7.48 g (6.10 ml, 33.3 mmol) TMSOTf were added and the mixture was heated to 65° C. Stirring was continued at this temperature for 1 h, when complete conversion was achieved. At room temperature, 500 ml sat. NaHCO$_3$-solution were added and the mixture was extracted with 500 ml EtOAc. The organic layer was separated and washed with H$_2$O and sat. NaCl-solution. After drying with MgSO$_4$, the crude product was purified on silicagel (20 to 100% EtOAc in n-heptane), which gave the protected nucleoside analog 1b in 82.3% yield (9.11 g) as colourless foam.

LCMS-Method A:
UV-wavelength [nm]=220: R$_t$[min]=1.82
Ionization method: ES$^+$: [M+H]$^+$=539.1
1H-NMR (CDC$_3$, 400 MHz) δ[ppm]: 8.97 (s, 1H), 7.66 (d, J=8.0 Hz, 1H), 7.38-7.35 (m, 10H), 6.19 (d, J=4.0 Hz, 1H), 5.38-5.30 (m, 2H), 4.63 (d, J=12.0 Hz, 1H), 4.46-4.41 (m, 5H), 4.19 (d, J=12.0 Hz, 1H), 3.79 (d, J=12.0 Hz, 1H), 3.51 (d, J=12.0 Hz, 1H), 2.12 (s, 3H), 2.07 (s, 3H).

1c: [(2S,3S,4R,5R)-4-acetoxy-3-benzyloxy-2-(benzyloxymethyl)-5-[2-(2-methylpropanoyl-amino)-6-oxo-1H-purin-9-yl]tetrahydrofuran-2-yl]methyl Acetate To a solution of compound G3 (148.5 g, 0.30 mol) in 6.68 l DCE was added N-isobutyryl-guanine (135 g, 0.61 mol) and BSA (311.85 mL, 1.2 mol) at 15° C. under N$_2$-atmosphere. The mixture was stirred at 85° C. for 3 h. Then TMSOTf (183.4 g, 0.90 mol) was added at 85° C. and stirring was continued for 3 h, when TLC showed complete conversion. The mixture was cooled to room temperature and poured into 6.5 l sat. NaHCO$_3$-solution. The organic layer was separated and the aqueous phase was extracted twice with 5 l DCM. The organic layers were combined and dried over anhydrous Na$_2$SO$_4$, filtered and concentrated. The obtained crude product was purified by preparative HPLC (0.1% TFA/ACN), yielding compound 1c (128 g, 64%) as a white solid.

1H-NMR (DMSO-d6, 400 MHz) δ[ppm]: 12.09 (s, 1H), 11.62 (s, 1H), 8.14 (s, 1H), 7.41-7.30 (m, 10H), 6.12 (d, J=6.4 Hz, 1H), 5.90 (t, J$_1$=J$_2$=5.6 Hz, 1H), 4.71 (d, J=5.2 Hz, 1H), 4.63-4.55 (m, 4H), 4.34 (d, J=5.6 Hz, 1H), 4.23 (d, J=5.6 Hz, 1H), 3.71-3.66 (m, 2H), 3.18 (d, J=4.8 Hz, 1H), 2.76-2.51 (m, 1H), 2.05 (s, 3H), 1.99 (s, 3H), 1.20-1.12 (s, 6H).

1d: [(2S,3S,4R,5R)-4-acetoxy-3-benzyloxy-2-(benzyloxymethyl)-5-(6-oxo-1H-purin-9-yl)-tetrahydrofuran-2-yl]methyl Acetate Starting with 10.0 g (20.55 mmol) G3 and 3.32 g (23.66 mmol) hypoxanthine as nucleobase, the title compound was synthesized following the protocol described for 1c. After silicagel purification (10 to 100% EtOAc/MeOH (9:1) in n-heptane), the title compound 1d was isolated as colourless foam (9.53 g, 81.1%).

LCMS-Method A:
UV-wavelength [nm]=220: R$_t$[min]=1.73
Ionization method: ES$^+$: [M+H]$^+$=563.3
1H-NMR (DMSO-d6, 400 MHz) δ[ppm]: 12.42 (s, 1H), 8.22 (s, 1H), 8.01 (s, 1H), 7.25-7.39 (m, 10H), 6.21 (d, J=4.89 Hz, 1H), 5.90-5.97 (m, 1H), 4.78 (d, J=5.75 Hz, 1H), 4.45-4.61 (m, 4H), 4.32-4.41 (m, 1H), 4.17-4.25 (m, 1H), 3.59-3.74 (m, 2H), 2.04 (m, 3H), 1.98 (m, 3H).

1e: [(2S,3S,4R,5R)-4-acetoxy-5-(6-benzamidopurin-9-yl)-3-benzyloxy-2-(benzyloxymethyl)-tetrahydrofuran-2-yl]methyl Acetate To a mixture of compound G3 (164 g, 0.337 mol) and N-benzoyl adenine (121 g, 0.506 mol) in 6.56 l DCE was added BSA (274 g, 1.348 mol) dropwise at room temperature and the mixture was stirred at 90° C. for 1.5 h. After dropwise addition of TMSOTf (225 g, 1.011 mol) at 40-50° C., the mixture was stirred at 90° C. for 1 h. The mixture was quenched with 15 l sat. NaHCO$_3$-solution and the layers were separated. The aqueous layer was extracted 2× with 3 l EtOAc and the combined organic layers were dried over anhydrous Na$_2$SO$_4$, filtered and concentrated in vacuo. The crude product was purified by flash chromatography (PE/EtOAc 1:2) to give compound 1e as an anomeric mixture (224.4 g) as yellow oil. The mixture was purified by two reverse flash chromatographies (neutral) to give pure compound 1e (75.5 g, 33.7%) as colourless foam.

1H-NMR (DMSO-d6, 400 MHz) δ[ppm]: 11.25 (s, 1H), 8.72 (s, 1H), 8.62 (s, 1H), 8.05 (d, J=7.40 Hz, 2H), 7.71-7.62 (m, 1H), 7.60-7.50 (m, 2H), 7.43-7.21 (m, 10H), 6.38 (d, J=4.77 Hz, 1H), 6.12 (t, J=5.33 Hz, 1H), 4.88 (d, J=5.77 Hz, 1H), 4.63 (s, 2H), 4.56-4.45 (m, 2H), 4.41 (d, J=11.92 Hz, 1H), 4.25 (d, J=11.80 Hz, 1H), 3.75-3.59 (m, 2H), 2.06 (s, 3H), 2.00 (s, 3H).

2a: 1-[(2R,3R,4S,5R)-4-benzyloxy-5-(benzyloxymethyl)-3-hydroxy-5-(hydroxymethyl)-tetrahydrofuran-2-yl]-5-methyl-pyrimidine-2,4-dione To a solution of 40.9 g (74.0 mmol) 1a in 500 ml THF/EtOH (4:1) were added 221.9 ml (443.8 mmol) of an aqueous NaOH-solution (2 N) at 0° C. After removing the ice bath, the mixture was stirred for 2 h to reach complete conversion. The solution was brought to neutral pH at 0° C. by adding a 2 N HCl-solution. The solvent was concentrated i.vac. and the remaining aqueous phase was extracted twice with 250 ml of DCM. The combined organic layers were dried with MgSO$_4$ and evaporated to yield 34.8 g (quant.) of the deprotected product 2a, which was used in the following step without further purification.

LCMS-Method A:
UV-wavelength [nm]=220: R$_t$[min]=1.64
Ionization method: ES$^+$: [M+H]$^+$=469.2
1H-NMR (CDCl$_3$, 400 MHz) δ[ppm]: 9.24-8.77 (m, 1H), 7.45 (br s, 1H), 7.41-7.30 (m, 8H), 7.27 (br d, J=7.78 Hz, 2H), 6.04 (br d, J=4.02 Hz, 1H), 4.86 (br d, J=11.67 Hz, 1H), 4.63-4.51 (m, 3H), 4.45-4.31 (m, 2H), 4.31-3.96 (m, 1H), 3.84 (br d, J=11.29 Hz, 1H), 3.76-3.64 (m, 2H), 3.58 (d, J=10.42 Hz, 1H), 2.96-2.62 (m, 1H), 1.63-1.51 (m, 3H).

2b: 1-[(2R,3R,4S,5R)-4-benzyloxy-5-(benzyloxymethyl)-3-hydroxy-5-(hydroxymethyl)-tetrahydrofuran-2-yl]pyrimidine-2,4-dione 9.10 g (16.9 mmol) of 1b were dissolved in 240 ml THF/EtOH (3:1). At 0° C., 8.49 ml (84.5 mmol) of a 1 M NaOH solution were added and the solution was stirred, allowing to reach room temperature. After 1 h, citric acid was added until a pH of 7 was reached and the solvent was evaporated. The aqueous residue was extracted with EtOAc. The organic layer was separated and washed with sat. NaCl-solution. After drying with MgSO$_4$, the solvent was removed, yielding 7.66 g (99.7%) of the crude product as colourless foam, which was used without further purification.

LCMS-Method A:
UV-wavelength [nm]=220: R$_t$[min]=1.63
Ionization method: ES$^+$: [M+H]$^+$=455.1
1H-NMR (DMSO-d6, 400 MHz) δ[ppm]: 11.29 (s, 1H), 7.69 (d, J=8.2 Hz, 1H), 7.27-7.41 (m, 10H), 5.88 (d, J=5.7 Hz, 1H), 5.57 (d, J=7.2 Hz, 1H), 5.37 (d, J=8.1 Hz, 1H), 4.98 (t, J=5.4 Hz, 1H), 4.80 (d, J=11.7 Hz, 1H), 4.46-4.58 (m, 3H), 4.27-4.37 (m, 1H), 4.00-4.14 (m, 1H), 3.50-3.69 (m, 4H).

2c: N-[9-[(2R,3R,4S,5R)-4-benzyloxy-5-(benzyloxymethyl)-3-hydroxy-5-(hydroxymethyl)-tetrahydrofuran-2-yl]-6-oxo-1H-purin-2-yl]-2-methyl-propanamide To a solution of compound 1c (72 g, 0.11 mol) in 1.7 l THF/EtOH (4:1) was added dropwise a 1 M NaOH-solution (443 mL) at 0° C. The solution was stirred at 0° C. for 1 h to reach complete conversion. The pH was adjusted to 7 by adding 1 N HCl and the solvent was removed. The residue was dissolved in H$_2$O (500 mL) and extracted with 3×500 ml DCM. The organic layers were combined, dried over anhydrous Na$_2$SO$_4$ and concentrated to give compound 2c (113 g, quant.) as a colourless solid, which was used in the next step without further purification.
1H-NMR (DMSO-d6, 400 MHz) δ[ppm]: 12.07 (s, 1H), 11.66 (s, 1H), 8.10 (s, 1H), 7.42-7.30 (m, 10H), 5.92 (d, J=6.8 Hz, 1H), 4.99 (s, 1H), 4.87-4.84 (m, 2H), 4.63 (d, J=15.6 Hz, 1H), 4.56 (s, 2H), 4.24 (d, J=4.8 Hz, 1H), 3.69-3.62 (m, 4H), 2.76-2.73 (m, 1H), 1.13-1.04 (m, 7H).

2d: 9-[(2R,3R,4S,5R)-4-benzyloxy-5-(benzyloxymethyl)-3-hydroxy-5-(hydroxymethyl)-tetrahydrofuran-2-yl]-1H-purin-6-one Following the procedure described for 2b, 9.34 g (16.65 mmol) 1d were deprotected to yield 7.76 g (97.4%) of the title compound 2d as crude product, which was used without additional purification.
LCMS-Method A:
UV-wavelength [nm]=220: R$_t$[min]=1.53
Ionization method: ES$^+$: [M+H]$^+$=479.3
1H-NMR (DMSO-d6, 400 MHz) δ[ppm]: 8.16 (s, 1H), 7.97-8.04 (m, 1H), 7.27-7.41 (m, 10H), 5.97 (d, J=5.75 Hz, 1H), 5.75 (s, 1H), 5.03 (br s, 1H), 4.79-4.92 (m, 2H), 4.47-4.62 (m, 3H), 4.24-4.34 (m, 1H), 3.55-3.70 (m, 4H).

2e: N-[9-[(2R,3R,4S,5R)-4-benzyloxy-5-(benzyloxymethyl)-3-hydroxy-5-(hydroxymethyl)-tetrahydrofuran-2-yl]purin-6-yl]benzamide Following the procedure described for 2b, 144 g (216 mmol) 1e were deprotected to yield 126 g (quant., crude) of the title compound 2e as colourless foam, which was used without additional purification.
1H-NMR (DMSO-d6, 400 MHz) δ[ppm]: 11.23 (s, 1H), 8.73 (s, 1H), 8.59 (s, 1H), 8.05 (br d, J=7.46 Hz, 2H), 7.71-7.63 (m, 1H), 7.61-7.52 (m, 2H), 7.49-7.23 (m, 10H), 6.16 (d, J=5.75 Hz, 1H), 5.85 (d, J=7.46 Hz, 1H), 5.14-4.99 (m, 2H), 4.86 (d, J=11.86 Hz, 1H), 4.63 (d, J=11.74 Hz, 1H), 4.53 (s, 2H), 4.38 (d, J=5.14 Hz, 1H), 3.79-3.57 (m, 4H).

3a: 1-[(2R,3R,4S,5S)-4-benzyloxy-5-(benzyloxymethyl)-3-hydroxy-5-(triisopropylsilyloxy-methyl)tetrahydrofuran-2-yl]-5-methyl-pyrimidine-2,4-dione 34.7 g (74.2 mmol) of the starting compound 2a and 16.8 g (244.7 mmol) imidazole were dissolved in 300 ml dry DCM. At room temperature, a solution of 16.2 g (18.0 ml, 81.6 mmol) TIPS-chloride in 200 ml DCM was added and the reaction was stirred for 19 h. After quenching with EtOH, the solvent was evaporated and the residue was dissolved in EtOAc. The organic solution was washed with H$_2$O, 1 N HCl, H$_2$O and sat. NaHCO$_3$-solution, followed by sat. NaCl-solution. After drying with MgSO$_4$, the solvent was removed and the crude product (47.1 g) was purified by silicagel chromatography (10 to 100% EtOAc in n-heptane), which gave the desired TIPS-protected product 3a as colourless foam (37.5 g, 80.9%).
LCMS-Method A:
UV-wavelength [nm]=220: R$_t$[min]=2.22
Ionization method: ES$^+$: [M+H]$^+$=625.3
1H-NMR (CDC$_3$, 400 MHz) δ[ppm]: 8.52 (s, 1H), 7.35-7.13 (m, 11H), 5.88 (d, J=3.89 Hz, 1H), 4.72-4.63 (m, 1H), 4.60-4.51 (m, 1H), 4.46 (s, 2H), 4.34-4.26 (m, 1H), 4.22 (d, J=6.27 Hz, 1H), 3.90 (d, J=10.92 Hz, 1H), 3.77 (d, J=1.00 Hz, 2H), 3.63-3.51 (m, 2H), 1.52 (d, J=0.88 Hz, 3H), 1.12-0.90 (m, 21H).

3b: 1-[(2R,3R,4S,5S)-4-benzyloxy-5-(benzyloxymethyl)-3-hydroxy-5-(triisopropylsilyloxy-methyl)tetrahydrofuran-2-yl]pyrimidine-2,4-dione Starting with 7.66 g (16.8 mmol) of 2b, the title compound was prepared as described in the protocol for 3a, yielding 8.69 g (84.5%) of the desired silylated product 3b after silicagel chromatography (20 to 80% EtOAc in n-heptane).
LCMS-Method A:
UV-wavelength [nm]=220: R$_t$[min]=2.23
Ionization method: ES$^+$: [M+H]$^+$=611.2
1H-NMR (CDC$_3$, 400 MHz) δ[ppm]: 9.04 (s, 1H), 7.63 (d, J=8.0 Hz, 1H), 7.37-7.34 (m, 8H), 7.26-7.24 (m, 2H), 5.96 (d, J=4.0 Hz, 1H), 5.37 (d, J=8.0 Hz, 1H), 4.77 (d, J=12.0 Hz, 1H), 4.62 (d, J=12.0 Hz, 1H), 4.49 (s, 2H), 4.26 (d, J=8.0 Hz, 1H), 3.83 (dd, J=8.0, 10.0 Hz, 2H), 3.63 (dd, J=8.0, 10.0 Hz, 2H), 1.15-1.04 (m, 21H).

3c: N-[9-[(2R,3R,4S,5S)-4-benzyloxy-5-(benzyloxymethyl)-3-hydroxy-5-(triisopropylsilyloxy-methyl)tetrahydrofuran-2-yl]-6-oxo-1H-purin-2-yl]-2-methyl-propanamide To a solution of compound 2c (75 g, 133 mmol) in anhydrous DCM (1568 mL) was added imidazole (38 g, 559 mmol) and TIPSCl (35.9 g, 186 mmol) at 0° C. under N$_2$-atmosphere. After stirring for 12 h at 10 to 15° C., the solution was poured into ice-water (2 L) and extracted with DCM (3×1.5 l). The organic layers were combined and washed with brine (1 l), dried over anhydrous Na$_2$SO$_4$, filtered and concentrated. The residue was purified by column chromatography on silica gel (PE/EtOAc 2:1 to EtOAc), yielding 65 g (68%) of the title compound 3c as a white foam.
1H-NMR (DMSO-d6, 400 MHz) δ[ppm]: 12.07 (s, 1H), 11.61 (s, 1H), 8.14 (s, 1H), 7.37-7.22 (m, 10H), 5.89 (d, J=6.8 Hz, 1H), 5.72 (d, J=5.6 Hz, 1H), 4.94-4.93 (m, 2H), 4.90-4.53 (m, 3H), 4.19 (d, J=4.4 Hz, 1H), 3.92-3.88 (m, 2H), 3.85-3.71 (m, 2H), 2.78-2.71 (m, 1H), 1.13-1.05 (m, 6H), 1.00-0.94 (m, 21H).

3d: 9-[(2R,3R,4S,5S)-4-benzyloxy-5-(benzyloxymethyl)-3-hydroxy-5-(triisopropylsilyloxy-methyl)tetrahydrofuran-2-yl]-1H-purin-6-one Starting with 7.75 g (16.2 mmol) of 2d, the title compound was prepared as described in the protocol for 3a, yielding 8.60 g (83.6%) of the desired silylated product 3d after silicagel chromatography (0 to 100% EtOAc/MeOH (9:1) in n-heptane).

LCMS-Method A:
UV-wavelength [nm]=220: $R_t$[min]=2.19
Ionization method: ES$^+$: [M+H]$^+$=635.5
1H-NMR (DMSO-d6, 400 MHz) δ[ppm]: 12.38 (br s, 1H), 8.22 (s, 1H), 8.03 (s, 1H), 7.26-7.39 (m, 10H), 5.94 (d, J=6.85 Hz, 1H), 5.67 (d, J=6.48 Hz, 1H), 4.98-4.74 (m, 2H), 4.61-4.48 (m, 3H), 4.24 (d, J=4.89 Hz, 1H), 3.97-3.82 (m, 2H), 3.69 (s, 2H), 0.80-1.18 (m, 21H).

3e: N-[9-[(2R,3R,4S,5S)-4-benzyloxy-5-(benzyloxymethyl)-3-hydroxy-5-(triisopropylsilyloxymethyl)tetrahydrofuran-2-yl]purin-6-yl]benzamide To a mixture of compound 2e (135 g, 0.232 mol) and imidazole (47.4 g, 0.696 mol) in 1.35 l DCM was added a solution of TIPSCl (80.6 g, 0.418 mol) in 1.35 l DCM at room temperature. The mixture was stirred for 24 h. After quenching with 400 ml of EtOH, the mixture was washed with 1.5 l water. The aqueous layer was extracted twice with 1 l EtOAc and the combined organic layers were dried over anhydrous Na$_2$SO$_4$, filtered and concentrated in vacuo. The crude product was purified by flash chromatography (PE/EtOAc 2:1) to yield the silylether 3e (145 g, 84.8%) as white foam.

1H-NMR (DMSO-d6, 400 MHz) δ[ppm]: 11.23 (s, 1H), 8.74 (s, 1H), 8.63 (s, 1H), 8.06 (d, J=7.28 Hz, 2H), 7.71-7.62 (m, 1H), 7.60-7.51 (m, 2H), 7.44-7.23 (m, 10H), 6.13 (d, J=6.78 Hz, 1H), 5.77 (d, J=6.40 Hz, 1H), 5.21-5.10 (m, 1H), 4.94 (d, J=11.92 Hz, 1H), 4.66-4.50 (m, 3H), 4.30 (d, J=4.77 Hz, 1H), 4.00-3.86 (m, 2H), 3.74 (s, 2H), 1.11-0.89 (m, 21H).

4a: 1-[(2R,3R,4S,5S)-3,4-dihydroxy-5-(hydroxymethyl)-5-(triisopropylsilyloxymethyl)-tetrahydrofuran-2-yl]-5-methyl-pyrimidine-2,4-dione In an autoclave, a solution of 13.4 g (21.4 mmol) of the bis-benzyl ether 3a in 100 ml EtOH was degassed and purged with argon. After adding a catalytical amount of Pd(OH)$_2$ (20% on carbon), the solution was set under H$_2$-atmosphere of 4 bar for 1 h. The Pd-catalyst was filtered off and the filtrate was evaporated, which gave 9.74 g (quant.) of the desired debenzylated product as colourless foam.

LCMS-Method A:
UV-wavelength [nm]=220: $R_t$[min]=1.84
Ionization method: ES$^+$: [M+H]$^+$=445.3
1H-NMR (CDC$_3$, 400 MHz) δ[ppm]: 8.85 (s, 1H), 7.25 (d, J=1.00 Hz, 1H), 5.58 (d, J=6.15 Hz, 1H), 4.71-4.61 (m, 1H), 4.51-4.44 (m, 1H), 4.02-3.95 (m, 1H), 3.94-3.89 (m, 1H), 3.88-3.77 (m, 3H), 3.76-3.67 (m, 1H), 3.22 (br dd, J=6.71, 3.83 Hz, 1H), 1.93 (d, J=1.00 Hz, 3H), 1.00-1.24 (m, 21H).

4b: 1-[(2R,3R,4S,5S)-3,4-dihydroxy-5-(hydroxymethyl)-5-(triisopropylsilyloxymethyl)-tetrahydrofuran-2-yl]pyrimidine-2,4-dione Starting with 8.69 g (14.2 mmol) of 3b, the title compound was prepared as described in the protocol for 4a, yielding 6.21 g (quant., crude) of the desired product 4b, which was used without purification.

LCMS-Method A:
UV-wavelength [nm]=220: $R_t$[min]=1.78
Ionization method: ES$^+$: [M+H]$^+$=431.1
1H-NMR (DMSO-d6, 400 MHz) δ[ppm]: 11.29 (s, 1H), 7.91 (d, J=8.0 Hz, 1H), 5.87 (d, J=8.0 Hz, 1H), 5.69 (d, J=8.0 Hz, 1H), 5.28 (d, J=8.0 Hz, 1H), 5.12 (t, J=4.0 Hz, 1H), 5.00 (d, J=4.0 Hz, 1H), 4.19 (dd, J=8.0, 12.0 Hz, 1H), 4.05 (t, J=4.0 Hz, 2H), 3.81 (dd, J=8.0, 12.0 Hz, 2H), 3.62 (d, J=4.0 Hz, 2H), 1.05-1.00 (m, 21H).

4c: N-[9-[(2R,3R,4S,5S)-3,4-dihydroxy-5-(hydroxymethyl)-5-(triisopropylsilyloxymethyl)-tetrahydrofuran-2-yl]-6-oxo-1H-purin-2-yl]-2-methylpropanamide To a solution of compound 3c (95 g, 0.132 mol) in anhydrous DCM (300 mL) was added BCl$_3$ (921 mL) at −70° C. under N$_2$-atmosphere. The reaction solution was stirred between −75 and −60° C. for 2 h, when full conversion was detected by TLC. To the mixture were added approx. 200 ml of a saturated solution of NH$_3$ in MeOH. The pH was adjusted to 10-11 and the solvents were removed under reduced pressure. The crude product was purified by column chromatography on silica gel (PE/EtOAc 20:1 to 4:1), yielding the debenzylated product 4c (51 g, yield, 71.6%) as a yellow solid.

1H-NMR (DMSO-d6, 400 MHz) δ[ppm]: 11.86 (s, 2H), 8.27 (s, 1H), 5.83 (d, J=7.2 Hz, 1H), 5.42 (s, 1H), 5.06 (s, 2H), 4.64 (s, 1H), 4.17 (d, J=4.0 Hz, 1H), 3.89 (d, J=10.8 Hz, 1H), 3.79 (d, J=10.4 Hz, 1H), 3.67 (s, 2H), 2.80-2.73 (m, 1H), 1.17-1.08 (m, 6H), 1.02-0.92 (m, 21H).

4d: 9-[(2R,3R,4S,5S)-3,4-dihydroxy-5-(hydroxymethyl)-5-(triisopropylsilyloxymethyl)-tetrahydrofuran-2-yl]-1H-purin-6-one 8.59 g (13.53 mmol) of the starting compound 3d were dissolved in 200 ml DCM. After cooling to −70 to −50° C., 74.4 ml (74.4 mmol) of a 1 M solution of BCl$_3$ in toluene were added over a period of 15 min. After stirring for additional 15 min at −70° C., the cooling bath was removed and stirring was continued for another 30 min at room temperature. The reaction solution was then added dropwise into 180 ml of a 7 M solution of NH$_3$ in MeOH. After stirring for 20 min, the mixture was evaporated and the residue dissolved 100 ml of DCM/iPrOH (4:1). After washing with sat. NaHCO$_3$-solution, the layers were separated and the aqueous layer was extracted 3× with DCM/iPrOH (4:1). The combined organic layers were dried with MgSO$_4$, filtered and evaporated. The crude product was purified by silicagel chromatography (0 to 10% MeOH in DCM) yielding 4.14 g (67.3%) of the title compound 4d as colourless foam.

LCMS-Method A:
UV-wavelength [nm]=220: $R_t$[min]=1.74
Ionization method: ES$^-$: [M−H]$^-$=453.4
1H-NMR (DMSO-d6, 400 MHz) δ[ppm]: 12.38 (m, 1H), 8.33 (s, 1H), 8.07 (s, 1H), 5.87 (d, J=7.34 Hz, 1H), 5.37 (d, J=6.97 Hz, 1H), 5.01-5.14 (m, 2H), 4.64-4.76 (m, 1H), 4.15-4.20 (m, 1H), 3.81-3.93 (m, 2H), 3.65 (d, J=5.14 Hz, 2H), 0.94-1.14 (m, 21H).

4e: N-[9-[(2R,3R,4S,5S)-3,4-dihydroxy-5-(hydroxymethyl)-5-(triisopropylsilyloxymethyl)-tetrahydrofuran-2-yl]purin-6-yl]benzamide To a solution of compound 3e (31 g, 42.0 mmol) in 620 ml DCM was added BCl$_3$ (252 mL, 0.252 mol) dropwise at −70° C. The mixture was stirred at −70° C. under N$_2$ for 30 min and warmed to 15° C. After stirring for another 30 min at this temperature, the reaction mixture was poured carefully into 600 ml 7 M NH₃ in MeOH, while keeping the temperature below −20° C. After evaporation, the residue was dissolved in 3 l DCM/iPrOH (4:1) and washed with 1 l water and sat. NaHCO₃-solution. The combined aqueous layers were extracted with 2×1 l DCM/iPrOH (4:1) and the combined organic layers were dried over anhydrous Na₂SO₄, filtered and concentrated in vacuo. The residue was purified by flash chromatography (PE/EtOAc 1:4) to give compound 4e (16.9 g, yield 72.2%) as white solid.

1H-NMR (DMSO-d6, 400 MHz) δ[ppm]: 11.23 (s, 1H), 8.77 (s, 1H), 8.72 (s, 1H), 8.06 (d, J=7.28 Hz, 2H), 7.70-7.61 (m, 1H), 7.60-7.51 (m, 2H), 6.06 (d, J=7.53 Hz, 1H), 5.48 (d, J=6.90 Hz, 1H), 5.22-5.11 (m, 2H), 4.93-4.83 (m, 1H), 4.24 (t, J=4.77 Hz, 1H), 3.92 (q, J=10.67 Hz, 2H), 3.78-3.62 (m, 2H), 1.14-1.01 (m, 21H).

5a: 1-[(2R,6S)-3,5-dihydroxy-6-(hydroxymethyl)-6-(triisopropylsilyloxymethyl)-1,4-dioxan-2-yl]-5-methyl-pyrimidine-2,4-dione 2.93 g (6.6 mmol) of the starting material 4a were dissolved in 120 ml acetone/H₂O (4:1). A solution of 1.69 g (7.9 mmol) NaIO₄ in 50 ml H₂O was added and the mixture was stirred at room temperature for 1 h. The precipitate was filtered off and the filtrate was concentrated i.vac. The remaining aqueous solution was extracted with 200 ml EtOAc. After washing the organic layer with H₂O and sat. NaCl-solution, it was dried with MgSO₄ and the solvent was removed under reduced pressure, which gave 2.86 g (94.1%) of the desired product as colourless solid, which was used without further purification.

LCMS-Method B-1:
UV-wavelength [nm]=220: R_t[min]=1.04
Ionization method: ES⁺: [M+H—H₂O]⁺=443.2

5b: 1-[(2R,6S)-3,5-dihydroxy-6-(hydroxymethyl)-6-(triisopropylsilyloxymethyl)-1,4-dioxan-2-yl]pyrimidine-2,4-dione Starting with 6.21 g (14.4 mmol) 4b, the title compound was made following the protocol described in 4a, which gave 6.38 g (99%) of the desired product 5b as crude product, which was used without additional purification.

LCMS-Method B-1:
UV-wavelength [nm]=220: R_t[min]=1.00
Ionization method: ES⁺: [M+H–H₂O]⁺=429.5

5c: N-[9-[(2R,6S)-3,5-dihydroxy-6-(hydroxymethyl)-6-(triisopropylsilyloxymethyl)-1,4-dioxan-2-yl]-6-oxo-1H-purin-2-yl]-2-methyl-propanamide To a solution of compound 4c (25 g, 46 mmol) in a mixed solvent of acetone (485 ml) and water (145 ml) was added a solution of NaIO₄ (13.9 g, 65 mmol) in water (150 ml) at 25° C. and the mixture was stirred for 12 h. After the solvents were evaporated i. vac., the residue was dissolved in EtOAc (500 ml) and washed with sat. NaHCO₃-solution (500 ml) and brine (500 ml). The organic layer was dried with Na₂SO₄, filtered and concentrated in vacuo to give crude 5c (25.7 g, quant.) as a white solid, which was used without further purifi-cation.

1H-NMR (DMSO-d6, 400 MHz) δ[ppm]: 12.05 (br s, 1H), 11.79 (s, 1H), 8.17 (s, 1H), 7.52 (d, J=5.62 Hz, 1H), 6.23 (s, 1H), 5.34 (d, J=5.62 Hz, 1H), 5.23 (s, 1H), 4.46 (d, J=9.54 Hz, 1H), 4.15-4.04 (m, 1H), 3.93 (d, J=9.78 Hz, 1H), 3.85 (d, J=10.03 Hz, 1H), 3.71 (d, J=10.03 Hz, 1H), 2.85-2.66 (m, 1H), 1.12 (d, J=6.85 Hz, 6H), 1.07-0.95 (m, 21H).

5d: 9-[(2R,6S)-3,5-dihydroxy-6-(hydroxymethyl)-6-(triisopropylsilyloxymethyl)-1,4-dioxan-2-yl]-1H-purin-6-one 4.14 g (9.1 mmol) of the starting material 4d were dissolved in 120 ml acetone/H₂O (4:1). A solution of 2.63 g (12.3 mmol) NaIO₄ in 50 ml H₂O was added and the mixture was stirred at room temperature for 18 h. The precipitate was filtered off and the filtrate was concentrated i.vac. To the remaining aqueous solution were added 100 ml sat. NaHCO₃-solution and the aqueous layer was extracted twice with 100 ml DCM/iPrOH (4:1). The organic layers were dried with MgSO₄ and the solvent was removed under reduced pressure, which gave 4.27 g (99.7%) of the desired product 5d as colourless foam, which was used without further purification.

LCMS-Method A:
UV-wavelength [nm]=220: R_t[min]=1.82
Ionization method: ES⁺: [M+H–H₂O]⁺=453.3

6a: 1-[(2R,6S)-6-(hydroxymethyl)-6-(triisopropylsilyloxymethyl)morpholin-2-yl]-5-methyl-pyrimidine-2,4-dione To a solution of compound 5a (31 g, 67 mmol) in anhydrous MeOH (527 ml) was added (NH₄)₂B₂O₇.4H₂O (19.5 g, 74 mmol) at room temperature under N₂-atmosphere. The mixture was stirred for 2 h, followed by the addition of AcOH (8.08 g, 134 mmol), 4 Å molecular sieves (62 g) and NaBH₃CN (8.44 g, 134 mmol). The mixture was stirred at room temperature for 12 h under N₂-atmosphere until TLC showed complete consumption of the starting material. The solvent was removed in vacuo and the residue was dissolved in water (200 ml) and extracted with DCM (3×200 ml). The combined organic layers were dried with Na₂SO₄ and concentrated in vacuo. The residue was purified by column chromatography on silica gel (DCM/MeOH 50:1 to 10:1) yielding compound 6a (19.5 g, 67%) as a colourless solid.

1H-NMR (DMSO-d6, 400 MHz) δ[ppm]: 11.27 (br s, 1H), 7.71-7.52 (m, 1H), 5.90-5.68 (m, 1H), 4.68-4.46 (m, 1H), 4.05-3.83 (m, 2H), 3.40 (br d, J=5.38 Hz, 2H), 2.83 (br d, J=9.78 Hz, 1H), 2.79-2.72 (m, 1H), 2.66 (br d, J=12.96 Hz, 2H), 1.79 (s, 3H), 1.22-0.83 (m, 23H).

6c: N-[9-[(2R,6S)-6-(hydroxymethyl)-6-(triisopropylsilyloxymethyl)morpholin-2-yl]-6-oxo-1H-purin-2-yl]-2-methyl-propanamide Starting with 25.7 g (46.4 mmol) of compound 5c, the title compound was synthesized following the protocol described for 6a, yielding the desired morpholine 6c as colourless solid (7.5 g, 30.6%).

1H-NMR (DMSO-d6, 400 MHz) δ[ppm]: 11.56 (br s, 1H), 8.13-8.25 (m, 1H), 5.67-5.81 (m, 2H), 4.56 (br s, 1H), 4.08 (br d, J=9.54 Hz, 1H), 3.83 (br d, J=9.29 Hz, 1H), 3.39-3.48 (m, 2H), 3.10 (br d, J=9.54 Hz, 1H), 2.65-2.93 (m, 4H), 1.12 (br d, J=6.60 Hz, 7H), 0.96-1.07 (m, 21H).

7a: 1-[(2R,6S)-6-(hydroxymethyl)-4-isopropyl-6-(triisopropylsilyloxymethyl)morpholin-2-yl]-5-methyl-pyrimidine-2,4-dione (from 6a)

To a solution of compound 6a (19.5 g, 45.7 mmol) in anhydrous MeOH (390 ml) was added 4 Å molecular sieves (39 g), acetone (13.25 g, 228 mmol) and NaBH$_3$CN (14.4 g, 228 mmol) at room temperature under N$_2$-atmosphere. After stirring for 2 h, the mixture was adjusted to pH=5 to 6 with AcOH (about 2.0 ml), and stirring was continued for 12 h, when complete consumption of the starting material was detected by TLC. The solvent was removed in vacuo and the residue was dissolved in water (500 ml). After extraction with DCM (3×500 ml), the organic layers were combined, dried over Na$_2$SO$_4$ and concentrated in vacuo. After purification by silicagel chromatography (DCM/MeOH 50:1 to 10:1) the title compound 7a was obtained as colourless solid (17 g, 81%).

7a: 1-[(2R,6S)-6-(hydroxymethyl)-4-isopropyl-6-(triisopropylsilyloxymethyl)morpholin-2-yl]-5-methyl-pyrimidine-2,4-dione (from 5a)

2.85 g (6.2 mmol) of the starting compound 5a, 1.26 g (1.74 ml, 12.4 mmol) NEt$_3$, 3.73 g (3.56 ml, 61.9 mmol) AcOH and 924 mg (1.34 ml, 15.5 mmol) isopropylamine were dissolved in 60 ml dry MeOH. At room temperature, 1.64 g (24.8 mmol) sodium cyanoborohydride were added and the solution was stirred for 2 h at 60° C. After cooling down to room temperature, the reaction mixture was poured into 100 ml sat. NaHCO$_3$-solution and the solvent was concentrated under reduced pressure. The remaining aqueous phase was extracted with EtOAc, which was washed with sat. NaHCO$_3$-solution and sat. NaCl-solution. After drying with MgSO$_4$, the solvent was evaporated and the crude product (3.0 g) was purified by silicagel chromatography (10 to 80% ethyl acetate in n-heptane), yielding 1.76 g (60.7%) of the desired morpholine 7a as colourless solid.

LCMS-Method A:

UV-wavelength [nm]=220: R$_t$[min]=1.80

Ionization method: ES$^+$: [M+H]$^+$=470.2

1H-NMR (DMSO-d6, 400 MHz) δ[ppm]: 11.30 (s, 1H), 7.63 (s, 1H), 5.77 (dd, J=10.42, 2.89 Hz, 1H), 4.61 (t, J=5.90 Hz, 1H), 4.00 (d, J=9.29 Hz, 1H), 3.74 (d, J=9.03 Hz, 1H), 3.53-3.41 (m, 2H), 2.83-2.63 (m, 3H), 2.26 (br d, J=11.29 Hz, 1H), 2.21-2.07 (m, 1H), 1.80 (s, 3H), 1.14-1.00 (m, 21H), 0.97 (d, J=6.53 Hz, 6H).

7b: 1-[(2R,6S)-6-(hydroxymethyl)-4-isopropyl-6-(triisopropylsilyloxymethyl)morpholin-2-yl]pyrimidine-2,4-dione (from 5b)

To a solution of 5b (6.38 g, 14.3 mmol) in 150 ml MeOH were added 8.62 g (8.23 ml, 142.8 mmol) AcOH, 2.90 g (3.98 ml, 28.6 mmol) NEt$_3$ and 2.13 g (3.09 ml, 35.7 mmol) isopropylamine at room temperature. After 1 h, 3.78 g (57.1 mmol) sodium cyanoborohydride were added and stirring was continued for 1 h at room temperature followed by one additional hour at 65° C. The mixture was cooled to room temperature and 150 ml sat. NaHCO$_3$-solution were added and the MeOH was evaporated i. vac. The aqueous solution was extracted with 350 ml EtOAc and the organic layer was washed with sat. NaHCO$_3$- and sat. NaCl-solution. After drying with MgSO$_4$, the solvent was removed and the crude product was purified by silicagel chromatography (0 to 5% MeOH in DCM), which gave 3.18 g (48.9%) of the title compound 7b as colourless solid.

LCMS-Method A:

UV-wavelength [nm]=220: R$_t$[min]=1.76

Ionization method: ES$^+$: [M+H]$^+$=456.4

1H-NMR (DMSO-d6, 400 MHz) δ[ppm]: 11.32 (b s, 1H), 7.77 (d, J=8.07 Hz, 1H), 5.75 (dd, J=9.90, 2.81 Hz, 1H), 5.61 (d, J=8.07 Hz, 1H), 4.62 (t, J=5.93 Hz, 1H), 3.99 (d, J=9.29 Hz, 1H), 3.74 (d, J=9.17 Hz, 1H), 3.45 (dd, J=10.33, 6.05 Hz, 2H), 2.82 (br d, J=10.27 Hz, 1H), 2.64-2.77 (m, 2H), 2.24 (d, J=11.37 Hz, 1H), 2.03-2.13 (m, 1H), 1.00-1.10 (m, 21H), 0.96 (m, 6H).

7c: N-[9-[(2R,6S)-6-(hydroxymethyl)-4-isopropyl-6-(triisopropylsilyloxymethyl)morpholin-2-yl]-6-oxo-1H-purin-2-yl]-2-methyl-propanamide (from 6c)

Starting with 7.5 g (14.0 mmol) 6c, the title compound was synthesized following the protocol described for 7a (from 6a). After final purification on silicagel (PE/EtOAc 4:1 to 1:1), 7c was isolated as colourless solid (5.13 g, 63%).

1H-NMR (DMSO-d6, 400 MHz) δ[ppm]: 12.09 (s, 1H), 11.56 (s, 1H), 8.22 (s, 1H), 5.80 (dd, J=9.79, 2.76 Hz, 1H), 4.60 (t, J=6.27 Hz, 1H), 4.09 (d, J=8.78 Hz, 1H), 3.71 (d, J=8.78 Hz, 1H), 3.48 (d, J=6.27 Hz, 2H), 2.98 (br d, J=10.04 Hz, 1H), 2.89-2.65 (m, 3H), 2.43 (t, J=10.42 Hz, 1H), 2.34 (d, J=11.29 Hz, 1H), 1.13 (d, J=6.78 Hz, 6H), 1.08-1.01 (m, 21H), 0.99 (d, J=6.27 Hz, 6H).

7d: 9-[(2R,6S)-6-(hydroxymethyl)-4-isopropyl-6-(triisopropylsilyloxymethyl)morpholin-2-yl]-1H-purin-6-one (from 5d)

4.27 g (9.1 mmol) of the starting compound 5d were dissolved in 100 ml MeOH. After adding 1.84 g (2.53 ml, 18.1 mmol) NEt$_3$, 5.44 g (5.19 ml, 90.6 mmol) AcOH and 808 mg (1.17 ml, 13.6 mmol) isopropyl amine, the solution was stirred for 1 h at room temperature. 1.80 g (27.2 mmol) sodium cyanoborohydride were added and the reaction was stirred at room temperature for 30 min and another 30 min at 60° C., when complete conversion was detected. To the reaction mixture 100 ml of sat. NaHCO$_3$-solution were added and the MeOH was evaporated. The remaining aqueous phase was extracted with 250 ml EtOAc. The organic layer was washed with sat. NaHCO$_3$- and NaCl-solution, dried with MgSO$_4$ and evaporated. The crude product was purified by silicagel chromatography (0 to 5% MeOH in DCM), yielding the title compound 7d as colourless solid (2.68 g, 61.7%).

LCMS-Method A:

UV-wavelength [nm]=220: R$_t$[min]=1.80

Ionization method: ES$^+$: [M+H]$^+$=480.4

1H-NMR (DMSO-d6, 400 MHz) δ[ppm]: 12.35 (br s, 1H), 8.31 (s, 1H), 8.06 (s, 1H), 5.91 (dd, J=9.90, 2.81 Hz, 1H), 4.57 (t, J=6.05 Hz, 1H), 4.11 (d, J=9.05 Hz, 1H), 3.77 (d, J=9.05 Hz, 1H), 3.40-3.50 (m, 2H), 2.94-3.02 (m, 1H), 2.67-2.87 (m, 2H), 2.54-2.63 (m, 1H), 2.33 (d, J=11.37 Hz, 1H), 0.97-1.11 (m, 27H).

Example A.2

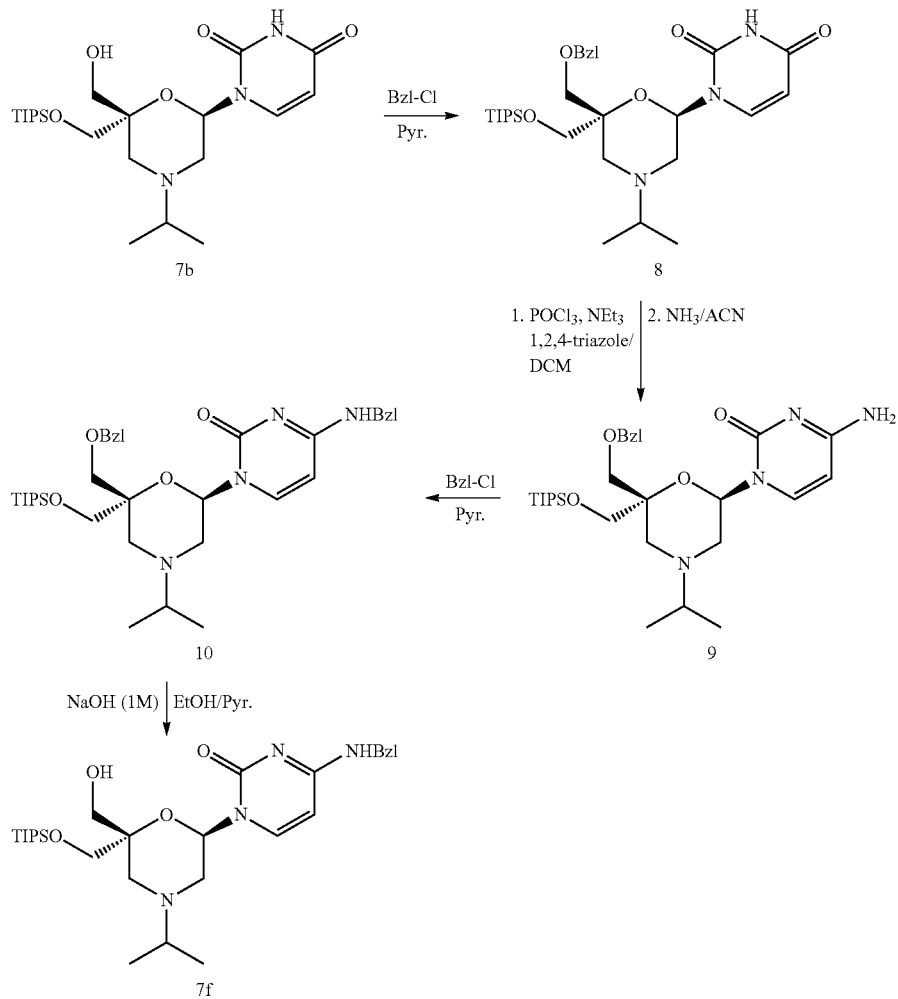

Synthetic Scheme 2

8: [(2S,6R)-6-(2,4-dioxopyrimidin-1-yl)-4-isopropyl-2-(triisopropylsilyloxymethyl)-morpholin-2-yl] methyl benzoate 6.00 g (13.2 mmol) of the starting material 7b were dissolved in 80 ml dry pyridine. At room temperature 2.80 g (2.32 ml, 19.75 mmol) benzoylchloride were added and the reaction was stirred for 20 h to achieve complete conversion. After evaporation of the solvent, the residue was dissolved in EtOAc, washed with 2×100 ml 10% citric acid-solution, H$_2$O, sat. NaHCO$_3$- and NaCl-solution. The organic layer was dried with MgSO$_4$ and evaporated, yielding 7.99 g (quant.) of the title compound as colourless foam, which was used without further purification.

LCMS-Method A:
UV-wavelength [nm]=220: R$_t$[min]=2.23
Ionization method: ES$^+$: [M+H]$^+$=560.5

9: [(2S,6R)-6-(4-amino-2-oxo-pyrimidin-1-yl)-4-isopropyl-2-(triisopropylsilyloxymethyl)-morpholin-2-yl]methyl Benzoate Starting compound 8 (7.99 g crude, 13.2 mmol) was dissolved in 200 ml dry ACN. After adding 22.88 g (31.4 ml, 223.8 mmol) NEt$_3$ and 11.13 g (158.0 mmol) 1H-1,2,4-triazole, the solution was cooled to 0° C. and a solution of 6.06 g (3.68 ml 39.5 mmol) POCl$_3$ in 50 ml dry ACN was added under vigorous stirring. The ice bath was removed and the solution was stirred for 2 h. Under reduced pressure, about 200 ml of the solvent were evaporated and the remaining solution was poured into 500 ml sat. NaCHO$_3$-solution/H$_2$O (1:1). The aqueous mixture was extracted 3× with 150 ml DCM and the combined organic extracts were dried with MgSO$_4$. After evaporation of the solvent, the crude intermediate (9.1 g, yellow foam) was dissolved in 200 ml ACN and 100 ml of an aqueous ammonia-solution (32%) were added. The reaction solution was stirred for 18 h at room temperature, when complete conversion was achieved. The solvents were removed under reduced pressure and 100 ml H₂O were added to the residue. Extraction with 2×200 ml DCM, drying the organic phases with MgSO₄ and evaporation of the solvent gave 7.65 g (quant.) of crude compound 9, which was used without additional purification.

LCMS-Method A:
UV-wavelength [nm]=220: R$_t$[min]=2.02
Ionization method: ES⁻: [M−H]⁻=557.4

10: [(2S,6R)-6-(4-benzamido-2-oxo-pyrimidin-1-yl)-4-isopropyl-2-(triisopropylsilyloxy-methyl)morpholin-2-yl]methyl Benzoate 7.64 g (13.2 mmol) of starting compound 9 were dissolved in 130 ml dry pyridine. At room temperature, 2.90 g (2.40 ml, 20.5 mmol) benzoylchloride were added and the solution was stirred for 20 h, when complete conversion was achieved. After evaporation of the solvent, the residue was dissolved in EtOAc, washed with 2×100 ml 10% citric acid-solution, H₂O, sat. NaHOC₃- and NaCl-solution. The organic layer was dried with MgSO₄ and evaporated, yielding 8.88 g of the crude product, which was purified by silicagel chromatography (0 to 100% EtOAc in n-heptane), yielding 6.69 g (76.7%) of the title compound (10) as light yellow foam.

LCMS-Method A:
UV-wavelength [nm]=220: R$_t$[min]=2.29
Ionization method: ES⁻: [M−H]⁻=661.5

7f: N-[1-[(2R,6S)-6-(hydroxymethyl)-4-isopropyl-6-(triisopropylsilyloxymethyl)morpholin-2-yl]-2-oxo-pyrimidin-4-yl]benzamide 3.63 g (5.48 mmol) of compound 10 were dissolved in 45 ml pyridine/EtOH (2:1). At 0° C., 27.4 ml (27.4 mmol) of a 1 M NaOH-solution were added. The solution was stirred 30 min at 0° C. and another 3 h at room temperature, to achieve complete conversion. The pH was adjusted to about 6 by adding citric acid monohydrate (approx. 2.0 g). The organic solvents were removed at 35° C. and the aqueous solution was extracted with EtOAc. The organic phase was washed 3× with 150 ml 10% citric acid solution, H₂O, sat. NaHCO₃- and NaCl-solution. After drying with MgSO₄, the solvent was evaporated. The obtained crude product (2.73 g, yellow foam) was purified by silicagel chromatography (10 to 70% EtOAc in n-heptane), which gave 2.25 g (73.4%) of the title compound (7f) as light yellow foam.

LCMS-Method A:
UV-wavelength [nm]=220: R$_t$[min]=1.89
Ionization method: ES⁺: [M+H]⁺=559.5

Example A.3

Synthetic Scheme 3

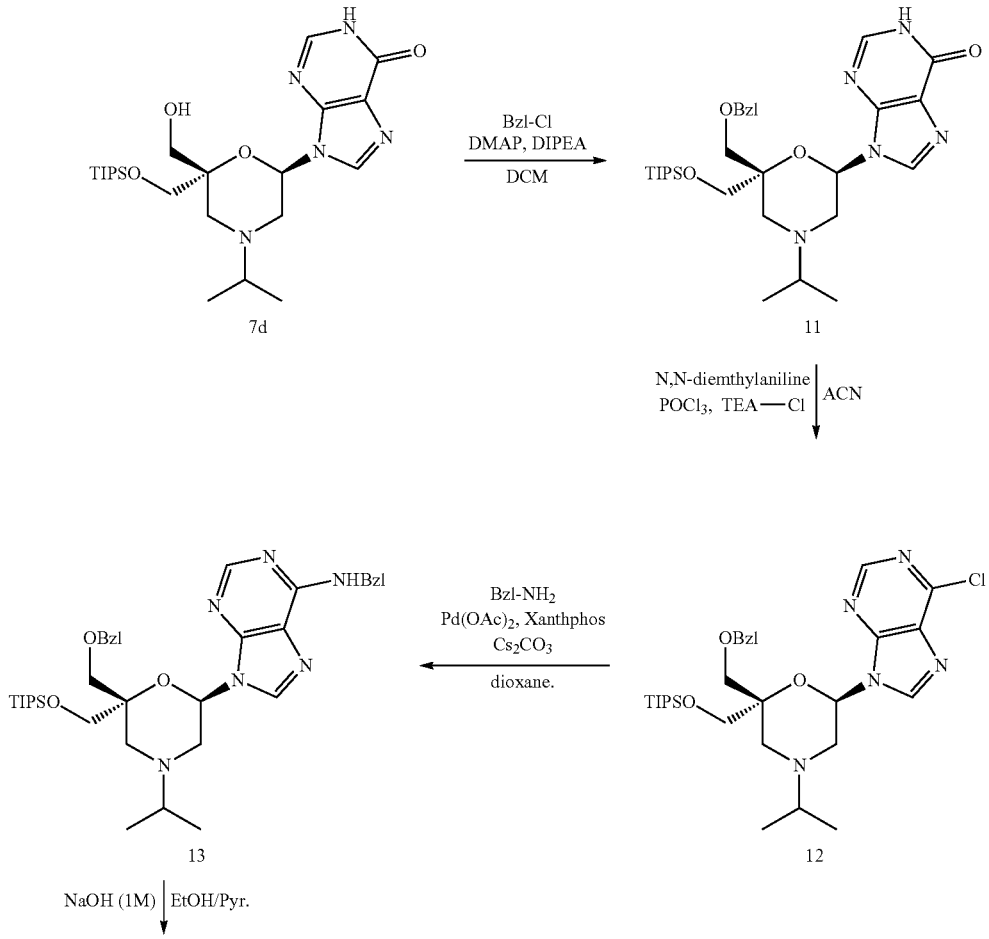

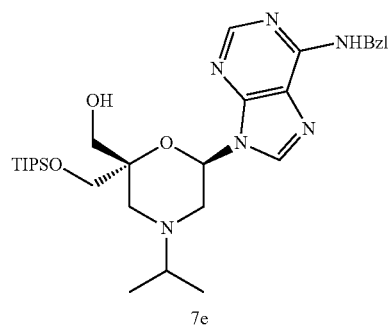

7e

11: [(2S,6R)-4-isopropyl-6-(6-oxo-H-purin-9-yl)-2-(triisopropylsilyloxymethyl)morpholin-2-yl]methyl Benzoate 2.68 g (5.59 mmol) of the starting material 7d, 2.53 g (3.42 ml, 19.55 mmol) DIPEA and 0.34 g (2.79 mmol) DMAP were dissolved in 50 ml dry DCM. At room temperature, 1.18 g (0.97 ml, 8.38 mmol) benzoylchloride were added and the reaction was stirred for 18 h to achieve complete conversion. After adding 20 ml MeOH, the solvent was evaporated and the residue was dissolved in EtOAc, washed with 2×100 ml 10% citric acid-solution, sat. $NaHCO_3$- and NaCl-solution. The organic layer phase was dried with $MgSO_4$ and evaporated, yielding 3.47 g (quant., crude) of the title compound (11) as colourless foam, which was used without further purification.

LCMS-Method A:
UV-wavelength [nm]=220: $R_t$[min]=2.18
Ionization method: $ES^+$: $[M+H]^+$=584.4

12: [(2S,6R)-6-(6-chloropurin-9-yl)-4-isopropyl-2-(triisopropylsilyloxymethyl)morpholin-2-yl]methyl Benzoate Starting compound 11 (2.86 g crude, 4.90 mmol), N,N-dimethylaniline (1.28 g, 1.34 ml, 10.53 mmol) and tetraethylammonium chloride (1.24 g, 7.35 mmol) were dissolved in 30 ml dry ACN. Under stirring, 1.70 g (1.03 ml, 11.07 mmol) $POCl_3$ were added at room temperature and the solution was refluxed for 3 h. After cooling to room temperature, the mixture was poured into 150 ml sat. $NaHCO_3$-solution and 3.0 g solid $NaHCO_3$ were additionally added. The reaction was stirred for 30 min and extracted with 100 ml DCM. The layers were separated and the aqueous phase was extracted 2× with 50 ml DCM. The combined organic layers were dried with $MgSO_4$ and evaporated. After purification of the crude product on silicagel (0 to 50% EtOAc in n-heptane) 1.52 g (51.4%) of the title compound 12 could be isolated as light yellow foam.

LCMS-Method A:
UV-wavelength [nm]=220: $R_t$[min]=2.33
Ionization method: $ES^+$: $[M+H]^+$=602.4

13: [(2S,6R)-6-(6-benzamidopurin-9-yl)-4-isopropyl-2-(triisopropylsilyloxymethyl)morpholin-2-yl] methyl Benzoate Chloropurin 12 (1.54 g, 2.56 mmol), benzamide (646 mg, 3.84 mmol) and $Cs_2CO_3$ (1.25 g, 3.84 mmol) were dissolved in 30 ml dioxane. After adding $Pd(OAc)_2$ (43 mg, 191.8 µmol) and xantphos (111 mg, 191.8 µmol), the reaction solution was stirred under argon for 1 h at 100° C., to achieve complete conversion. The reaction was cooled to room temperature and diluted with 50 ml EtOAc. The solution was filtered and the filtrate was evaporated i. vac. The crude product (2.48 g) was purified on silicagel (10 to 100% EtOAc in n-heptane), which gave 1.29 g (73.4%) of the desired compound 13 as colourless foam.

LCMS-Method A:
UV-wavelength [nm]=220: $R_t$[min]=2.26
Ionization method: $ES^+$: $[M+H]^+$=687.6

7e: N-[9-[(2R,6S)-6-(hydroxymethyl)-4-isopropyl-6-(triisopropylsilyloxymethyl)morpholin-2-yl]purin-6-yl]benzamide 1.00 g (1.46 mmol) of the benzoate 13 were saponified following the protocol described for 7f. Without chromatographic purification, 731 mg (86.2%, crude) of the title compound 7e could be isolated as light yellow foam.

LCMS-Method A:
UV-wavelength [nm]=220: $R_t$[min]=1.97
Ionization method: $ES^+$: $[M+H]^+$=583.5

Example A.4

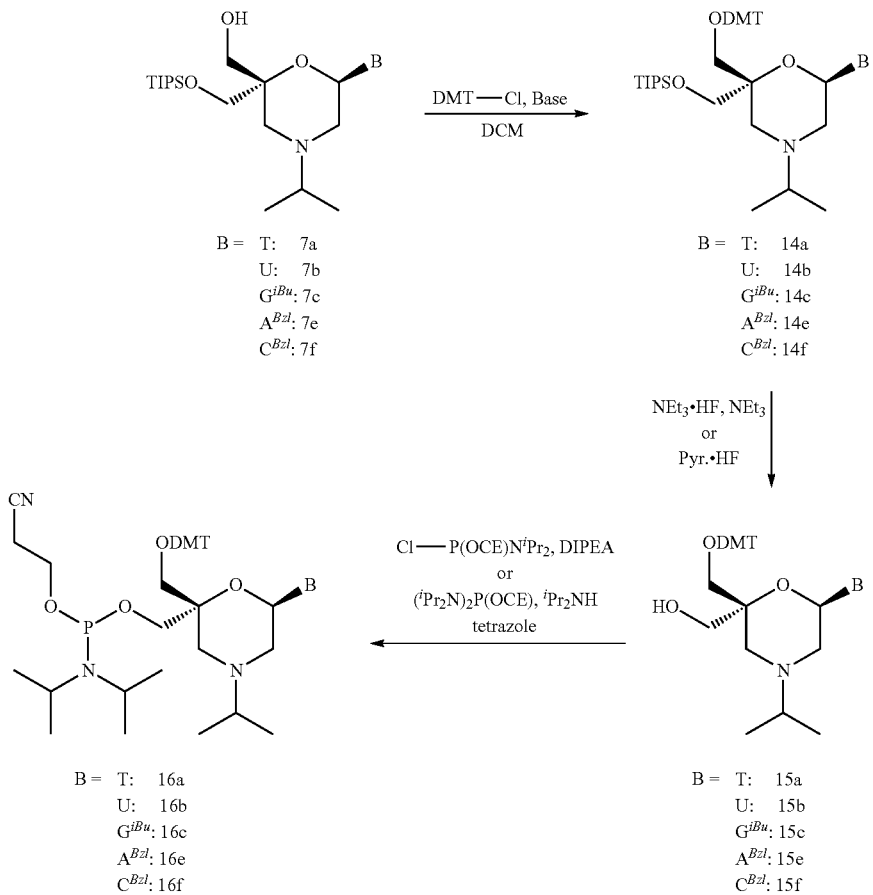

Synthetic Scheme 4

14a: 1-[(2R,6S)-6-[[bis(4-methoxyphenyl)-phenyl-methoxy]methyl]-4-isopropyl-6-(triisopropylsilyloxymethyl)morpholin-2-yl]-5-methyl-pyrimidine-2,4-dione 810 mg (1.7 mmol) of the primary alcohol 7a and 873 mg (1.20 ml, 8.6 mmol) NEt$_3$ were dissolved in 30 ml DCM. At room temperature, 716 mg (2.1 mmol) DMT-Cl were added and the reaction was stirred for 2 h at room temperature. After adding another 0.6 equivalents of DMT-Cl and stirring overnight, the reaction showed complete conversion. The solution of the crude product was directly transferred to a silica column and purified with 0 to 65% EtOAc in n-heptane, yielding 1.19 g (89.0%) of the desired product (14a) as light yellow foam.
LCMS-Method A:
UV-wavelength [nm]=220: R$_t$[min]=2.38
Ionization method: ES$^+$: [M+H]$^+$=772.5

14b: 1-[(2R,6S)-6-[[bis(4-methoxyphenyl)-phenyl-methoxy]methyl]-4-isopropyl-6-(triisopropylsilyloxymethyl)morpholin-2-yl]pyrimidine-2,4-dione 1.00 g (2.2 mmol) 7b and 1.42 g (1.92 ml, 11.0 mmol) DIPEA were dissolved in 30 ml DCM. 948 mg (2.7 mmol) DMT-Chloride were added and the reaction was stirred at room temperature overnight to achieve complete conversion. After adding Isolute-sorbent, the organic solvent was removed and the solid material was purified on silica (pre-conditioned with n-heptane+0.5% NEt$_3$, 0 to 75% EtOAc in n-heptane), yielding 1.61 g (96.8%) of the DMT-protected product (14b) as light yellow foam.
LCMS-Method A:
UV-wavelength [nm]=220: R$_t$[min]=2.34
Ionization method: ES$^+$: [M+H]$^+$=758.3

14c: N-[9-[(2R,6S)-6-[[bis(4-methoxyphenyl)-phenyl-methoxy]methyl]-4-isopropyl-6-(triisopropylsilyloxymethyl)morpholin-2-yl]-6-oxo-1H-purin-2-yl]-2-methyl-propanamide 1.00 g (1.77 mmol) of the starting compound 7c was protected following the protocol described for 14a. After purification on silicagel (0 to 5% MeOH in DCM), the desired product (14c) was isolated as yellow foam (1.46 g, 94.8%).
LCMS-Method C:
UV-wavelength [nm]=220: R$_t$[min]=3.66
Ionization method: ES$^+$: [M+H]$^+$=867.6

14e: N-[9-[(2R,6S)-6-[[bis(4-methoxyphenyl)-phenyl-methoxy]methyl]-4-isopropyl-6-(triisopropylsilyloxymethyl)morpholin-2-yl]purin-6-yl]benzamide 950 mg (1.63 mmol) of the starting material 7e were dissolved in 10 ml DCM/pyridine (1:1). After adding a solution of 733 mg (2.12 mmol) DMT-Cl in 20 ml DCM, the reaction was allowed to stir for 1.5 h to achieve complete conversion. After evaporation of the solvent, the residue was taken up in EtOAc and washed with H$_2$O, 2× with 10% citric acid solution and sat. NaHCO$_3$-solution. After drying with MgSO$_4$, the solvent was removed and the crude product purified on silica (pretreated with n-heptane+0.5% NEt$_3$; 0 to 50% EtOAc in n-heptane), yielding 1.20 g (83.2%) of the DMT-ether 14e as colourless foam.

LCMS-Method A:
UV-wavelength [nm]=220: R$_t$[min]=2.38
Ionization method: ES$^-$: [M−H]$^-$=883.5

14f: N-[1-[(2R,6S)-6-[[bis(4-methoxyphenyl)-phenyl-methoxy]methyl]-4-isopropyl-6-(triisopropylsilyloxymethyl)morpholin-2-yl]-2-oxo-pyrimidin-4-yl]benzamide 2.25 g (4.02 mmol) of the starting material 7f were protected following the protocol for 14e in dry pyridine. After final chromatography on silica (pretreated with n-heptane+0.5% NEt$_3$; 0 to 80% EtOAc in n-heptane), 3.35 g (96.9%) of the title compound (14f) were isolated as yellow foam.

LCMS-Method A:
UV-wavelength [nm]=220: R$_t$[min]=2.40
Ionization method: ES$^+$: [M+H]$^+$=861.6

15a: 1-[(2R,6R)-6-[[bis(4-methoxyphenyl)-phenyl-methoxy]methyl]-6-(hydroxymethyl)-4-isopropyl-morpholin-2-yl]-5-methyl-pyrimidine-2,4-dione 1.18 g (1.5 mmol) of the TIPS-protected morpholine 14a and 6.74 g (9.26 ml, 66.0 mmol) triethyl amine were dissolved in 30 ml THF. At room temperature, 12.23 g (12.4 ml, 73.6 mmol) NEt$_3$ 3 HF were added and the reaction was stirred at 65° C. for 1 h. After standing at room temperature overnight, 10 ml NMP were added and the reaction was stirred at 65° C. for additional 14 h to achieve complete conversion. The solvent was concentrated i.vac. and the remaining NMP-solution was added to a H$_2$O/sat. NaHCO$_3$-solution mixture (1:2). The aqueous solution was extracted with EtOAc and the organic layer was washed three times with H$_2$O and sat. NaCl-solution. After drying with MgSO$_4$, the crude product was purified by silicagel chromatography (preconditioned with 1% NEt$_3$ in n-heptane, 10 to 100% ethylacetate in n-heptane), which gave 645 mg (68.8%) of the desilylated product 15a as colourless foam.

LCMS-Method A:
UV-wavelength [nm]=220: R$_t$[min]=1.67
Ionization method: ES$^+$: [M+H]$^+$=616.4
1H-NMR (DMSO-d6, 400 MHz) δ[ppm]: 11.36 (s, 1H), 7.53-7.58 (m, 1H), 7.41 (d, J=7.34 Hz, 2H), 7.20-7.31 (m, 7H), 6.87 (d, J=8.80 Hz, 4H), 5.82 (dd, J=9.66, 2.93 Hz, 1H), 4.61 (br s, 1H), 3.67-3.79 (m, 8H), 3.07 (s, 1H), 2.97-3.10 (m, 1H), 2.80 (br d, J=9.78 Hz, 1H), 2.63-2.76 (m, 2H), 2.17-2.31 (m, 2H), 1.69 (s, 3H), 0.95 (d, J=6.60 Hz, 6H).

15b: 1-[(2R,6R)-6-[[bis(4-methoxyphenyl)-phenyl-methoxy]methyl]-6-(hydroxymethyl)-4-isopropyl-morpholin-2-yl]pyrimidine-2,4-dione 1.60 g (2.1 mmol) 14b were dissolved in 20 ml NMP. After adding 4.73 g (6.50 ml, 46.3 mmol) NEt$_3$ and 8.41 g (8.50 ml, 50.6 mmol) NEt$_3$.3HF, the mixture was stirred 15 h at room temperature followed by 5 h at 65° C. The mixture was cooled down to room temperature, followed by the addition of 250 ml sat. NaHCO$_3$-solution and 250 ml H$_2$O. After extraction with 250 ml EtOAc, the organic layer was washed with H$_2$O (2×) and sat. NaCl-solution. The organic phase was dried with MgSO$_4$ and purified on silica (preconditioned with n-heptane+0.5% NEt$_3$, 0 to 100% EtOAc in n-heptane), which gave the desired alcohol 15b as colourless foam (1.16 g, 91.1%).

LCMS-Method A:
UV-wavelength [nm]=220: R$_t$[min]=1.63
Ionization method: ES$^+$: [M+H]$^+$=602.3
1H-NMR (DMSO-d6, 400 MHz) δ[ppm]: 11.36 (br s, 1H), 7.63 (d, J=8.07 Hz, 1H), 7.40 (br d, J=7.82 Hz, 2H), 7.20-7.33 (m, 7H), 6.88 (d, J=8.56 Hz, 4H), 5.81 (br d, J=7.34 Hz, 1H), 5.62 (d, J=8.07 Hz, 1H), 4.62 (br s, 1H), 3.78-3.95 (m, 1H), 3.68-3.76 (m, 7H), 3.11 (d, J=9.05 Hz, 1H), 2.96 (br d, J=9.05 Hz, 1H), 2.82 (br d, =10.27 Hz, 1H), 2.60-2.76 (m, 2H), 2.10-2.22 (m, 2H), 0.94 (d, J=6.36 Hz, 6H).

15c: N-[9-[(2R,6R)-6-[[bis(4-methoxyphenyl)-phenyl-methoxy]methyl]-6-(hydroxymethyl)-4-isopropyl-morpholin-2-yl]-6-oxo-1H-purin-2-yl]-2-methyl-propanamide 1.44 g (1.66 mmol) of the TIPS-protected alcohol 14c were dissolved in 17 ml THF. After adding 1.27 g (1.15 ml, 8.30 mmol) of a 65% Pyr. HF-solution, the reaction mixture was stirred at room temperature for 1 h. Under vigorous stirring, 0.9 g NaHCO$_3$ and 10 ml H$_2$O were added and stirring was continued for 2 h. The THF was removed and the aqueous solution was extracted 10× with DCM/iPrOH (4:1). The combined organic layers were dried with MgSO$_4$ and evaporated, yielding 0.83 g (70.1%, crude) of 15c, which was used in the next steps without further purification.

LCMS-Method C:
UV-wavelength [nm]=220: R$_t$[min]=2.11
Ionization method: ES$^-$: [M−H]$^-$=709.5
1H-NMR (DMSO-d6, 400 MHz) δ[ppm]: 12.09 (s, 1H), 11.67 (s, 1H), 8.05 (s, 1H), 7.38 (d, J=7.34 Hz, 2H), 7.18-7.30 (m, 7H), 6.85 (d, J=8.80 Hz, 4H), 5.92 (dd, J=8.99, 3.00 Hz, 1H), 4.64 (t, J=5.14 Hz, 1H), 3.71-3.84 (m, 8H), 2.90-3.08 (m, 3H), 2.55-2.83 (m, 4H), 2.31-2.47 (m, 1H), 1.12 (dd, J=6.79, 3.36 Hz, 6H), 0.96 (d, J=6.48 Hz, 6H).

15e: N-[9-[(2R,6R)-6-[[bis(4-methoxyphenyl)-phenyl-methoxy]methyl]-6-(hydroxymethyl)-4-isopropyl-morpholin-2-yl]purin-6-yl]benzamide 1.20 g (1.35 mmol) of the starting compound 14e and 1.91 g (2.63 ml, 18.90 mmol) NEt$_3$ were dissolved in 20 ml THF. After adding 3.59 g (3.63 ml, 21.60 mmol) NEt$_3$.3HF, the solution was heated at 65° C., followed by the addition of another 0.95 g (1.32 ml, 9.45 mmol) NEt$_3$ and 1.80 g (1.82 ml, 10.8 mmol) NEt$_3$.3HF. The reaction mixture was stirred at 65° C. until complete conversion was achieved (approx. 10 h). After cooling to room temperature, the mixture was poured in 150 ml H$_2$O/sat. NaHCO$_3$-solution (1:1) and stirred for 30 min. The aqueous solution was extracted 3× with 50 DCM, dried with MgSO$_4$ and evaporated. After silicagel chromatography (10 to 100% EtOAc in n-heptane), 835 mg (84.9%) of the deprotected product 15e were isolated as colourless foam.

LCMS-Method A:
UV-wavelength [nm]=220: R$_t$[min]=1.74
Ionization method: ES$^+$: [M+H]$^+$=729.5

1H-NMR (DMSO-d6, 400 MHz) δ[ppm]: 11.21 (br s, 1H), 8.74 (s, 1H), 8.54 (s, 1H), 8.04 (d, J=7.62 Hz, 2H), 7.62-7.67 (m, 1H), 7.52-7.58 (m, 2H), 7.37 (d, J=7.34 Hz, 2H), 7.15-7.29 (m, 7H), 6.82 (d, J=7.95 Hz, 4H), 6.16 (dd, J=9.17, 2.93 Hz, 1H), 4.67 (t, J=5.20 Hz, 1H), 3.86-3.96 (m, 1H), 3.79 (dd, J=11.00, 5.87 Hz, 1H), 3.69-3.73 (m, 6H), 3.01-3.15 (m, 2H), 2.90-2.99 (m, 2H), 2.68-2.84 (m, 2H), 2.40 (m, 1H), 1.00 (d, J=6.60 Hz, 6H).

15f: N-[1-[(2R,6R)-6-[[bis(4-methoxyphenyl)-phenyl-methoxy]methyl]-6-(hydroxymethyl)-4-isopropyl-morpholin-2-yl]-2-oxo-pyrimidin-4-yl]benzamide 3.35 g (3.88 mmol) of the starting compound 14f were treated with NEt$_3$.3HF as described for 15e. After a reaction time of 20 h at 70° C., complete conversion was achieved. Working up and final purification as for 15e, gave 2.57 g (93.7%) of the title compound 15f as colorless foam.

LCMS-Method A:
UV-wavelength [nm]=220: R$_t$[min]=1.79
Ionization method: ES$^+$: [M+H]$^+$=705.4
1H-NMR (DMSO-d6, 400 MHz) δ[ppm]: 11.28 (br s, 1H), 8.10 (br d, J=7.58 Hz, 1H), 8.00 (d, J=7.69 Hz, 2H), 7.58-7.67 (m, 1H), 7.51 (t, J=7.64 Hz, 2H), 7.21-7.43 (m, 10H), 6.89 (d, J=8.80 Hz, 4H), 5.93 (dd, J=9.41, 2.69 Hz, 1H), 4.66 (t, J=5.26 Hz, 1H), 3.91 (dd, J=10.94, 4.22 Hz, 1H), 3.71-3.77 (m, 7H), 3.19 (d, J=9.05 Hz, 1H), 2.92-3.06 (m, 2H), 2.65-2.79 (m, 2H), 2.18 (d, J=11.49 Hz, 1H), 2.07 (t, J=10.21 Hz, 1H), 0.95 (d, J=6.36 Hz, 6H).

16a: 3-[[(2S,6R)-2-[[bis(4-methoxyphenyl)-phenyl-methoxy]methyl]-4-isopropyl-6-(5-methyl-2,4-dioxo-pyrimidin-1-yl)morpholin-2-yl]methoxy-(diisopropylamino)phosphanyl]oxypropanenitrile To a solution of 624 mg (1.0 mmol) 15a and 401.0 mg (513 µl, 3.0 mmol) N,N-diisopropylethylamine in 15 ml dry DCM, 370.9 mg (349.6 µl, 1.5 mmol) 2-cyanoethyl-N,N-diisopropylchlorophosphoramidite were added at room temperature under an argon atmosphere. After stirring for 1 h, the reaction was quenched by adding 200 µl n-butanol and stirring was continued for 10 min. The reaction solution was washed with H$_2$O and the aqueous phase was extracted once with DCM. After drying the organic layers with MgSO$_4$, the solvent was removed and the crude product was purified by silicagel chromatography (preconditioned with 0.5% NEt$_3$ in n-heptane, 10 to 100% methyl-tert. butyl ether in n-heptane), yielding 668 mg (80.8%) of the desired phosphoramidite (mixture of diastereomers) 16a as colourless foam.

LCMS-Method B-2:
UV-wavelength [nm]=220: R$_t$[min]=0.82
Ionization method: ES$^+$: [M]$^+$=733.1 (M-iPr$_2$N+OH+H+)
1H-NMR (DMSO-d6, 400 MHz) δ[ppm]: 11.37, 11.36 (2×s, 1H), 7.60, 7.56 (2×s, 1H), 7.41 (m, 2H), 7.20-7.32 (m, 7H), 6.83-6.90 (m, 4H), 5.88 (m, 1H), 3.84-4.05 (m, 2H), 3.74 (s, 6H), 3.54-3.73 (m, 2H), 3.40-3.54 (m, 2H), 3.14 (m, 1H), 2.95-3.05 (m, 2H), 2.57-2.84 (m, 5H), 2.15-2.37 (m, 2H), 1.76, 1.73 (2×s, 3H), 0.93-1.14 (m, 18H).
31P-NMR (DMSO-d6, 162 MHz) δ[ppm]: 148.1, 147.6.

16b: 3-[[(2S,6R)-2-[[bis(4-methoxyphenyl)-phenyl-methoxy]methyl]-6-(2,4-dioxopyrimidin-1-yl)-4-isopropyl-morpholin-2-yl]methoxy-(diisopropylamino)phosphanyl]oxypropanenitrile The title compound was prepared following the protocol described for 16a. Starting with 1.95 g (3.2 mmol) of primary alcohol 15b, 1.70 g (65.7%) of the desired phosphoramidite 16b were isolated as colourless foam after purification on silicagel (pre-conditioned with n-heptane+0.5% NEt$_3$, 0 to 80% EtOAc in n-heptane).

LCMS-Method A:
UV-wavelength [nm]=220: R$_t$[min]=1.85
Ionization method: ES$^+$: [M]$^+$=719.2 (M-$^i$Pr$_2$N+OH+H$^+$)
1H-NMR (DMSO-d6, 400 MHz) δ[ppm]: 11.36 (br s, 1H), 7.67, 7.63 (2×d, J=8.19 Hz, 1H), 7.35-7.44 (m, 2H), 7.20-7.32 (m, 7H), 6.84-6.89 (m, 4H), 5.81-5.89 (m, 1H), 5.67, 5.63 (2×d, J=8.13 Hz, 1H), 3.89-4.08 (m, 2H), 3.73 (s, 6H), 3.54-3.72 (m, 2H), 3.41-3.54 (m, 2H), 3.16 (d, J=9.05 Hz, 1H), 2.96 (t, J=9.05 Hz, 1H), 2.84 (br d, J=10.15 Hz, 1H), 2.55-2.76 (m, 4H), 2.10-2.33 (m, 2H), 0.89-1.12 (m, 18H).
31P-NMR (DMSO-d6, 162 MHz) δ[ppm]: 148.3, 147.6.

16c: N-[9-[(2R,6S)-6-[[bis(4-methoxyphenyl)-phenyl-methoxy]methyl]-6-[[2-cyanoethoxy-(diisopropylamino)phosphanyl]oxymethyl]-4-isopropyl-morpholin-2-yl]-6-oxo-1H-purin-2-yl]-2-methyl-propanamide 100 mg (141 µmol) of the alcohol 15c, 0.2 g molecular sieves (4 Å) and 12.7 mg (70 µmol) diisopropylammonium tetrazolide were dissolved in 2.5 ml dry DCM. Under an Ar-atmosphere, 42.8 mg (45 µl, 138 µmol) 2-cyanoethyl-N,N,N',N'-tetraisopropylphosphoro-diamidite were added and the solution was stirred for 2 h at room temperature to achieve complete conversion. After adding sat. NaHCO$_3$-solution, the organic phase was separated and the aqueous phase extracted with DCM. The combined organic layers were washed with sat. NaCl-solution, dried with MgSO$_4$ and evaporated. The crude product was purified on silica (pre-conditioned with DCM+0.5% NEt$_3$, 0 to 10% MeH in DCM), yielding 87 mg (67.9%) of the title compound (16c) as colourless foam.

LCMS-Method C:
UV-wavelength [nm]=220: R$_t$[min]=2.50, 2.52
Ionization method: ES$^+$: [M-$^i$Pr$_2$N+OH+H]$^+$=828.3
1H-NMR (DMSO-d6, 400 MHz) δ[ppm]: 12.08 (br s, 1H), 11.62 (br s, 1H), 8.09, 8.04 (2×s, 1H), 7.33-7.40 (m, 2H), 7.18-7.29 (m, 7H), 6.81-6.87 (m, 4H), 5.91 (m, 1H), 3.93-4.07 (m, 2H), 3.73 (s, 6H), 3.54-3.72 (m, 2H), 3.39-3.50 (m, 2H), 3.11 (m, 1H), 2.92-3.07 (m, 2H), 2.54-2.81 (m, 6H), 2.26-2.38 (m, 1H), 0.94-1.16 (m, 18H), 0.83-0.91 (m, 6H).
31P-NMR (DMSO-d6, 162 MHz) δ[ppm]: 147.5, 146.7.

16e: N-[9-[(2R,6S)-6-[[bis(4-methoxyphenyl)-phenyl-methoxy]methyl]-6-[[2-cyanoethoxy-(diisopropylamino)phosphanyl]oxymethyl]-4-isopropyl-morpholin-2-yl]purin-6-yl]benzamide 820 mg (1.13 mmol) of 15e and 584 mg (3.38 mmol) diisopropylammonium tetrazolide were dissolved in 20 ml dry DCM. Under an atmosphere of Ar, 524 mg (1.69 mmol) 2-cyanoethyl-N,N,N',N'-tetraisopropylphosphorodiamidite were added and the solution was stirred at room temperature. After stirring overnight, 50 ml H$_2$O were added and the layers were separated. The aqueous layer was extracted 1× with 30 ml DCM and the combined organic phases dried with MgSO$_4$. After evaporation of the solvent, the crude product was purified by silicagel chromatographie (pre-conditioned with n-heptane+0.5% NEt$_3$, 0 to 100% MTB-ether/DCM (1:1) in n-heptane), yielding 913 mg (87.3%) of the title compound (16e) as colourless solid.

1H-NMR (DMSO-d6, 400 MHz) δ[ppm]: 11.19 (s, 1H), 8.76, 8.74 (2×s, 1H), 8.61, 8.59 (2×s, 1H), 8.04 (d, J=8.09 Hz, 2H), 7.64 (t, J=7.37 Hz, 1H), 7.51-7.60 (m, 2H), 7.37 (m, 2H), 7.16-7.28 (m, 7H), 6.77-6.84 (m, 4H), 6.19 (m, 1H), 3.98-4.15 (m, 2H), 3.71 (2×s, 6H), 3.56-3.69 (m, 2H), 3.41-3.56 (m, 2H), 3.03-3.17 (m, 2H), 2.89-3.01 (m, 2H), 2.74-2.88 (m, 2H), 2.70 (t, J=6.15 Hz, 1H), 2.59 (m, 1H), 2.36 (m, 1H), 0.92-1.18 (m, 18H).

31P-NMR (DMSO-d6, 162 MHz) δ[ppm]: 147.0, 146.7.

16f: N-[1-[(2R,6S)-6-[[bis(4-methoxyphenyl)-phenyl-methoxy]methyl]-6-[[2-cyanoethoxy-(diisopropylamino)phosphanyl]oxymethyl]-4-isopropyl-morpholin-2-yl]-2-oxo-pyrimidin-4-yl]benzamide 550 mg (0.78 mmol) of the primary alcohol 15f were phosphitylated following the protocol described for 16e.

After chromatographic purification on silicagel (pre-conditioned with n-heptane+0.5% NEt$_3$, 0 to 100% MTB-ether/DCM (1:1) in n-heptane), 560 mg (79.3%) 16f were isolated as colourless foam.

1H-NMR (DMSO-d6, 400 MHz) δ[ppm]: 11.29 (br s, 1H), 8.12 (2×d, J=7.50 Hz, 1H), 7.98-8.04 (m, 2H), 7.63 (t, J=7.40 Hz, 1H), 7.48-7.55 (m, 2H), 7.36-7.45 (m, 3H), 7.21-7.35 (m, 7H), 6.88 (2×d, J=8.89 Hz, 4H), 5.95, 6.01 (2×m, 1H), 3.89-4.14 (m, 2H), 3.74, 3.75 (2×s, 6H), 3.55-3.72 (m, 2H), 3.39-3.55 (m, 2H), 3.24 (d, J=8.85 Hz, 1H), 2.93-3.05 (m, 2H), 2.68-2.87 (m, 3H), 2.55-2.64 (m, 1H), 2.10-2.23 (m, 2H), 0.90-1.22 (m, 18H).

31P-NMR (DMSO-d6, 162 MHz) δ[ppm]: 147.4, 146.7.

Example A.5

Synthetic Scheme 5

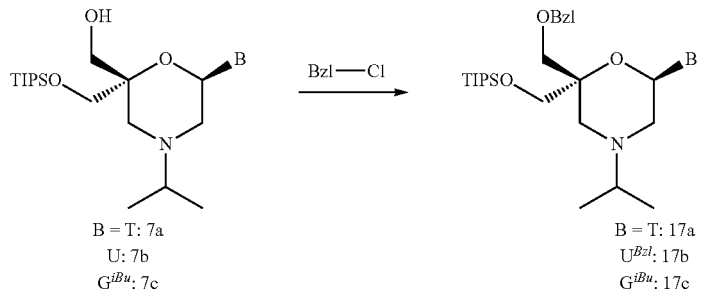

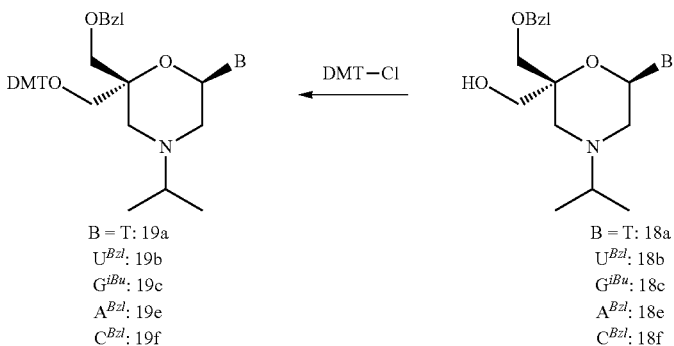

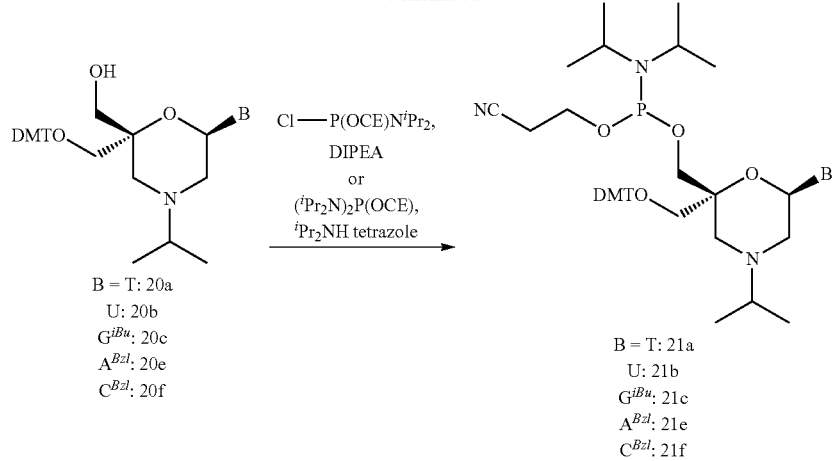

B = T: 20a
U: 20b
G<sup>iBu</sup>: 20c
A<sup>Bzl</sup>: 20e
C<sup>Bzl</sup>: 20f B = T: 21a
U: 21b
G<sup>iBu</sup>: 21c
A<sup>Bzl</sup>: 21e
C<sup>Bzl</sup>: 21f 17a: [(2S,6R)-4-isopropyl-6-(5-methyl-2,4-dioxo-pyrimidin-1-yl)-2-(triisopropylsilyloxy-methyl)morpholin-2-yl]methyl Benzoate 810 mg (1.7 mmol) of the free alcohol 7a were dissolved in 20 ml DCM. After adding 1.14 g (1.45 ml, 8.6 mmol) DIPEA and 294 mg (243 µl, 2.1 mmol) benzoyl chloride, the solution was stirred for 2 h at room temperature. To reach full conversion, another 0.2 equivalents of benzoyl chloride were added and stirring was continued for 18 hours. The reaction solution was directly transferred to a silicagel column, eluting with 0 to 65% EtOAc in n-heptane. 726 mg (73.3%) of the benzoylated product 17a were obtained as colourless foam.
LCMS-Method A:
UV-wavelength [nm]=220: $R_t$[min]=2.29
Ionization method: $ES^+$: $[M+H]^+$=574.3

17b: [(2S,6R)-6-(3-benzoyl-2,4-dioxo-pyrimidin-1-yl)-4-isopropyl-2-(triisopropylsilyloxy-methyl)morpholin-2-yl]methyl Benzoate 1.45 g (3.18 mmol) of the primary alcohol 7b were treated with benzoyl chloride as described in 17a, which led to a mixture of mono- and dibenzylated products. Therefore, the reaction mixture was evaporated and the crude product was dissolved in 30 ml pyridine. After adding 565 mg (3.98 mmol) benzoyl chloride and a catalytic amount of DMAP, the reaction solution was stirred at room temperature for 4 h. After evaporation of the solvent, the residue was dissolved in EtOAc and washed with 10% citric acid- and sat. NaCl-solution. The organic layer was dried with MgSO₄ and the solvent was removed. Final chromatography on silica (0 to 35% EtOAc in n-heptane) gave 1.64 g (77.8%) of the dibenzoylated product 17b.
LCMS-Method C:
UV-wavelength [nm]=220: $R_t$[min]=3.67
Ionization method: $ES^+$: $[M+H]^+$=664.4

17c: [(2S,6R)-4-isopropyl-6-[2-(2-methylpropanoylamino)-6-oxo-1H-purin-9-yl]-2-(triisopropylsilyloxymethyl)morpholin-2-yl]methyl Benzoate 0.89 g (1.58 mmol) of the starting compound 7c were dissolved in 30 ml pyridine. After adding 246 mg (203 µl, 1.73 mmol) benzoyl chloride, the reaction solution was stirred at room temperature overnight, when complete conversion was detected. The solvent was removed in vacuo and the residue was dissolved in EtOAc. After washing with H₂O, the organic phase was separated, dried with MgSO₄ and evaporated. Final purification on silica (0 to 5% MeOH in DCM) gave the title compound 17c as colourless foam (1.01 g, 95.4%).
LCMS-Method C:
UV-wavelength [nm]=220: $R_t$[min]=3.28
Ionization method: $ES^+$: $[M+H]^+$=669.2

18a: [(2R,6R)-2-(hydroxymethyl)-4-isopropyl-6-(5-methyl-2,4-dioxo-pyrimidin-1-yl)morpholin-2-yl]methyl Benzoate A solution of 720 mg (1.25 mmol) 17a in 15 ml THF was treated with 1.34 g (1.22 ml, 8.8 mmol) pyridine-hydrogen fluoride. After stirring for 1 h at room temperature, the reaction mixture was treated with sat. NaHCO₃-solution to reach a pH of 7.5. The solvent was concentrated under reduced pressure and the aqueous solution was extracted twice with DCM. The organic layers were dried with MgSO₄ and the solvent was removed. The crude product was codestilled twice with 50 ml of toluene and the remaining residue was purified by silicagel chromatography (0 to 100% EtOAc in n-heptane), which gave 502 mg (95.8%) of the desired product (18a) as colourless foam.
LCMS-Method A:
UV-wavelength [nm]=220: $R_t$[min]=1.30
Ionization method: $ES^+$: $[M+H]^+$=418.2

18b: [(2R,6R)-6-(3-benzoyl-2,4-dioxo-pyrimidin-1-yl)-2-(hydroxymethyl)-4-isopropyl-morpholin-2-yl]methyl Benzoate 1.64 g (2.47 mmol) of the silylether 17b were desilylated following the protocol described for 18a, which gave 1.33 g of the desired product 18b as crude product, which was used for the next steps without chromatographic purification.
LCMS-Method C:
UV-wavelength [nm]=220: $R_t$[min]=1.81
Ionization method: $ES^+$: $[M+H]^+$=508.2

18c: [(2R,6R)-2-(hydroxymethyl)-4-isopropyl-6-[2-(2-methylpropanoylamino)-6-oxo-1H-purin-9-yl]morpholin-2-yl]methyl Benzoate 1.0 g (1.49 mmol) of 17c were dissolved in 10 ml DMF. After adding 1.53 g (2.10 ml, 15.0 mmol) NEt$_3$ and 1.48 g (1.49 ml, 9.0 mmol) NEt$_3$.3HF, the reaction solution was stirred at 90° C. for 2 h. After the mixture was cooled to room temperature, 2.5 g NaHCO$_3$ and 10 ml H$_2$O were added and the reaction mixture was stirred for 2 h. The solvents were evaporated in vacuo and the residue was dissolved 25 ml DCM/iPrOH and washed with H$_2$O. The organic phase was separated, dried with MgSO$_4$ and evaporated. The crude product was purified on silica (0 to 10% MeOH in DCM), which gave 245 mg (32.0%) of the desilylated product 18c as colourless foam.
LCMS-Method C:
UV-wavelength [nm]=220: R$_t$[min]=1.45
Ionization method: ES$^+$: [M+H]$^+$=513.1

18e: [(2R,6R)-6-(6-benzamidopurin-9-yl)-2-(hydroxymethyl)-4-isopropyl-morpholin-2-yl]methyl Benzoate 1.23 g (1.79 mmol) of the silylether 13 were deprotected following the protocol described for 18a, which gave 939 mg (98.8%) of the title compound (18e) after silicagel chromatography (0 to 100% EtOAc in n-heptane).
LCMS-Method C:
UV-wavelength [nm]=220: R$_t$[min]=1.60
Ionization method: ES$^-$: [M−H]$^-$=529.3

18f: [(2R,6R)-6-(4-benzamido-2-oxo-pyrimidin-1-yl)-2-(hydroxymethyl)-4-isopropyl-morpholin-2-yl]methyl Benzoate 3.63 g (5.48 mmol) of the silylether 10 were deprotected following the protocol described for 18a, which gave 2.45 (88.4%) of the title compound (18f) after silicagel chromatography (5% MeOH in DCM).
LCMS-Method A:
UV-wavelength [nm]=220: R$_t$[min]=1.53
Ionization method: ES$^+$: [M+H]$^+$=507.3

19a: [(2R,6R)-2-[[bis(4-methoxyphenyl)-phenyl-methoxy]methyl]-4-isopropyl-6-(5-methyl-2,4-dioxo-pyrimidin-1-yl)morpholin-2-yl]methyl Benzoate 497 mg (1.2 mmol) of the starting compound 18a were dissolved in 15 ml DCM. After adding 502 mg (643 µl, 3.8 mmol) DIPEA and 659 mg (1.90 mmol) DMT-Cl, the reaction solution was stirred for 2 h at room temperature. The reaction mixture was evaporated i.vac. and the crude product was purified on silica gel (0 to 100% EtOAc in n-heptane). The DMT-protected product 19a was isolated as colourless foam (779 mg, 90.9%).
LCMS-Method A:
UV-wavelength [nm]=220: R$_t$[min]=2.14
Ionization method: ES$^+$: [M+H]$^+$=720.4

19b: [(2R,6R)-6-(3-benzoyl-2,4-dioxo-pyrimidin-1-yl)-2-[[bis(4-methoxyphenyl)-phenyl-methoxy]methyl]-4-isopropyl-morpholin-2-yl]methyl Benzoate 1.30 g (2.41 mmol) of the primary alcohol 18b and 492 mg (676 µl, 4.82 mmol) NEt$_3$ were dissolved in 20 ml DCM. After adding 925 mg (2.65 mmol) DMT-Cl, the reaction was stirred at room temperature for 6 h followed by the addition of another 925 mg (2.65 mmol) DMT-Cl. The reaction was stirred for 72 h. After adding 2.0 ml n-propanol, the solution was stirred for 10 min. The mixture was washed with H$_2$O and the organic layer was separated. After drying with MgSO$_4$, the solvent was removed i. vac. The crude product was purified by silicagel chromatography (0 to 25% EtOAc in n-heptane), yielding 1.74 g (89.2%) of the desired DMT-ether 19b.
LCMS-Method C:
UV-wavelength [nm]=220: R$_t$[min]=3.25
Ionization method: ES$^+$: [M+H]$^+$=810.3

19c: [(2R,6R)-2-[[bis(4-methoxyphenyl)-phenyl-methoxy]methyl]-4-isopropyl-6-[2-(2-methylpropanoylamino)-6-oxo-1H-purin-9-yl]morpholin-2-yl]methyl Benzoate 240 mg (468 µmol) of the starting alcohol 18c were dissolved in 5.0 ml DCM. After the addition of 95.7 mg (131.5 µl, 936 µmol) NEt$_3$ and 180 mg (515 µmol) DMT-Cl, the reaction was stirred at room temperature for 3 d to achieve complete conversion. After adding 2.0 ml n-propanol, the solution was stirred for 10 min. The mixture was washed with H$_2$O and the organic layer was separated. After drying with MgSO$_4$, the solvent was removed i. vac. The crude product was purified by silicagel chromatography (0 to 25% EtOAc in n-heptane), yielding 303 mg (79.4%) of the desired DMT-ether 19c.
LCMS-Method C:
UV-wavelength [nm]=220: R$_t$[min]=2.93
Ionization method: ES$^-$: [M−H]$^-$=813.2

19e: [(2R,6R)-6-(6-benzamidopurin-9-yl)-2-[[bis(4-methoxyphenyl)-phenyl-methoxy]methyl]-4-isopropyl-morpholin-2-yl]methyl Benzoate 934 mg (1.76 mmol) of the starting material 18e were dissolved in 20 ml DMC/pyridine (1:1). After adding 974 mg (2.82 mmol) DMT-Cl, the reaction solution was stirred for 17 h at room temperature. The solvents were removed i. vac. and the residue was dissolved in EtOAc and washed with H$_2$O, 2×10% citric acid-, sat. NaHCO$_3$- and NaCl-solution. The organic phase was dried with MgSO$_4$ and evaporated. The obtained crude product (1.77 g) was dissolved in 20 ml EtOAc/diethylether (1:2). After adding 40 ml of n-pentane, the precipitate was centrifuged and the supernatant was discarded. The precipitation procedure was repeated another two times, yielding the desired DMT-ether 19e as colourless solid.
LCMS-Method C:
UV-wavelength [nm]=220: R$_t$[min]=3.07
Ionization method: ES$^-$: [M−H]$^-$=831.5

19f: [(2R,6R)-6-(4-benzamido-2-oxo-pyrimidin-1-yl)-2-[[bis(4-methoxyphenyl)-phenyl-methoxy]methyl]-4-isopropyl-morpholin-2-yl]methyl Benzoate 2.45 g (4.84 mmol) 18f were dissolved in 40 ml pyridine. After adding 2.51 g (7.26 mmol) DMT-Cl, the reaction mixture was stirred at room temperature for 4 d. The solvent was removed i. vac. and the residue was dissolved in EtOAc and washed with H$_2$O, 2×10% citric acid-, sat. NaHCO$_3$- and NaCl-solution. The organic phase was dried with MgSO$_4$ and evaporated. The crude product was purified on silicagel (preconditioned with n-heptane+0.5% NEt₃, 0 to 100% EtOAc in n-heptane), yielding 3.69 g (94.3%) of the title compound 19f as colourless foam.

LCMS-Method A:
UV-wavelength [nm]=220: $R_t$[min]=2.14
Ionization method: ES⁻: [M–H]⁻=807.4

20a: 1-[(2R,6S)-6-[[bis(4-methoxyphenyl)-phenyl-methoxy]methyl]-6-(hydroxymethyl)-4-isopropyl-morpholin-2-yl]-5-methyl-pyrimidine-2,4-dione The benzoyl ester 19a (775 mg, 1.1 mmol) was dissolved in 20 ml THF-Methanol (4:1). At room temperature, 4.31 ml (8.6 mmol) of a 2 N aqueous NaOH-solution were added and the reaction was stirred for 90 minutes. By adding citric acid monohydrate, the pH was adjusted between 7 and 8, then the solvent was removed under reduced pressure. The residue was taken up in DCM and H₂O. The organic layer was separated and the aqueous phase was extracted with DCM. The combined organic phases were dried with MgSO₄ and evaporated. The crude product was purified by silicagel chromatography (5 to 100% EtOAc in n-heptane) yielding 663 mg (quant.) of the desired product (20a) as colourless foam.

LCMS-Method A:
UV-wavelength [nm]=220: $R_t$[min]=1.73
Ionization method: ES⁺: [M+H]⁺=616.3

1H-NMR (DMSO-d6, 400 MHz) δ[ppm]: 11.29 (s, 1H), 7.60 (d, J=1.10 Hz, 1H), 7.39 (d, J=6.93 Hz, 2H), 7.19-7.33 (m, 7H), 6.88 (d, J=8.68 Hz, 4H), 5.60 (dd, J=9.96, 2.87 Hz, 1H), 4.64 (t, J=5.93 Hz, 1H), 3.74 (m, 6H), 3.53-3.60 (m, 1H), 3.44-3.52 (m, 1H), 3.32-3.37 (m, 1H), 3.09 (d, J=8.56 Hz, 1H), 2.76 (br d, J=11.62 Hz, 1H), 2.61-2.72 (m, 2H), 2.37 (d, J=11.49 Hz, 1H), 2.10 (t, J=10.45 Hz, 1H), 1.78 (s, 3H), 0.84-0.96 (m, 6H).

20b: 1-[(2R,6S)-6-[[bis(4-methoxyphenyl)-phenyl-methoxy]methyl]-6-(hydroxymethyl)-4-isopropyl-morpholin-2-yl]pyrimidine-2,4-dione 1.40 g (1.73 mmol) of the starting compound 19b were dissolved in 80 ml MeOH. At room temperature, 13.83 ml (6.91 mmol) of a 0.5 M solution of NaOMe in MeOH were added and the reaction solution was stirred for 2 h, to achieve complete conversion. After adding 0.92 g citric acid, the solvent was removed. The residue was taken up in H₂O and the aqueous mixture was extracted 3× with DCM/iPrOH (4:1). The combined organic layers were dired with MgSO₄ and evaporated. to yield 0.85 g (81.2%, crude) of the desired compound 20b, which was used in the following step without further purification.

LCMS-Method C:
UV-wavelength [nm]=220: $R_t$[min]=2.04
Ionization method: ES⁺: [M+H]⁺=602.2

1H-NMR (DMSO-d6, 400 MHz) δ[ppm]: 11.31 (s, 1H), 7.75 (d, J=8.07 Hz, 1H), 7.39 (d, J=7.34 Hz, 2H), 7.10-7.33 (m, 8H), 6.88 (d, J=8.31 Hz, 4H), 5.55-5.64 (m, 2H), 4.66 (t, J=5.93 Hz, 1H), 3.74 (s, 6H), 3.57 (dd, J=11.31, 6.79 Hz, 1H), 3.46 (br dd, J=11.25, 5.14 Hz, 1H), 3.08 (d, J=8.56 Hz, 1H), 2.54-2.79 (m, 3H), 2.32-2.39 (m, 1H), 1.95-2.13 (m, 1H), 0.86-0.98 (m, 6H).

20c: N-[9-[(2R,6S)-6-[[bis(4-methoxyphenyl)-phenyl-methoxy]methyl]-6-(hydroxymethyl)-4-isopropyl-morpholin-2-yl]-6-oxo-1H-purin-2-yl]-2-methyl-propanamide 260 mg (319 μmol) of the starting material 19c were dissolved 10 ml EtOH. After adding 1.0 ml (1.0 mmol) of a 1 M NaOH-solution, the solution was stirred for 4 h at room temperature to achieve complete conversion. The solution was neutralized with 1 M HCl and the solvent was removed i. vac. The residue was dissolved in H₂O and extracted with DCM. The organic phase was separated, dried with MgSO₄ and evaporated. Final purification on silica (0 to 10% MeOH in DCM) gave 114 mg (50.3%) of the desired alcohol 20c as yellow solid.

LCMS-Method C:
UV-wavelength [nm]=220: $R_t$[min]=2.36
Ionization method: ES⁻: [M–H]⁻=709.3

1H-NMR (DMSO-d6, 400 MHz) δ[ppm]: 12.08 (s, 1H), 11.52 (s, 1H), 8.20 (s, 1H), 7.35-7.43 (m, 2H), 7.20-7.33 (m, 7H), 6.83-6.92 (m, 4H), 5.56 (dd, J=9.60, 2.75 Hz, 1H), 4.59-4.66 (m, 1H), 3.73 (2×s, 6H), 3.51-3.62 (m, 2H), 3.43-3.50 (m, 1H), 2.88-3.02 (m, 3H), 2.70-2.82 (m, 2H), 2.30-2.39 (m, 1H), 1.11 (m, 6H), 1.01 (d, J=6.48 Hz, 3H), 0.97 (d, J=6.48 Hz, 3H).

20e: N-[9-[(2R,6S)-6-[[bis(4-methoxyphenyl)-phenyl-methoxy]methyl]-6-(hydroxymethyl)-4-isopropyl-morpholin-2-yl]purin-6-yl]benzamide The starting compound 19e (1.27 g, 1.52 mmol) was dissolved in 14 ml EtOH/pyridine (1:1). At 0° C., 7.59 ml (15.19 mmol) of a 1 M NaOH-solution were added and the reaction mixture was stirred for 1.5 h at room temperature. After adjusting the pH to 7 by adding citric acid monohydrate (958 mg), 70 ml H₂O and EtOAc were added. The organic layer was separated and washed with 10% citric acid solution (3×), H₂O, sat. NaHCO₃- and NaCl-solution. After drying with MgSO₄, the organic phase was evaporated, yielding 1.08 g of the crude product as colourless foam, which was dissolved in 20 ml EtOAc/diethylether (1:1). After adding 40 ml of n-pentane, the precipitate was centrifuged and the supernatant was discarded. The precipitation procedure was repeated another two times, yielding 964 mg (87.1%) of the title compound (20e) as colourless foam.

LCMS-Method C:
UV-wavelength [nm]=220: $R_t$[min]=2.42
Ionization method: ES⁻: [M–H]⁻=727.5

1H-NMR (DMSO-d6, 400 MHz) δ[ppm]: 11.18 (s, 1H), 8.71 (s, 1H), 8.69 (s, 1H), 8.05 (d, J=7.34 Hz, 2H), 7.61-7.68 (m, 1H), 7.56 (t, J=7.58 Hz, 2H), 7.45 (d, J=7.46 Hz, 2H), 7.28-7.36 (m, 6H), 7.20-7.28 (m, 1H), 6.90 (dd, J=8.99, 2.26 Hz, 4H), 5.89 (dd, J=9.84, 2.63 Hz, 1H), 4.69 (t, J=5.99 Hz, 1H), 3.75 (s, 6H), 3.45-3.61 (m, 3H), 3.24-3.30 (m, 1H), 3.00 (br d, J=10.15 Hz, 1H), 2.85 (br d, J=11.62 Hz, 1H), 2.60-2.78 (m, 2H), 2.45-2.55 (m, 1H), 0.98 (br d, J=6.48 Hz, 3H), 0.95 (br d, J=6.48 Hz, 3H).

20f: N-[1-[(2R,6S)-6-[[bis(4-methoxyphenyl)-phenyl-methoxy]methyl]-6-(hydroxymethyl)-4-isopropyl-morpholin-2-yl]-2-oxo-pyrimidin-4-yl]benzamide 3.68 g (4.55 mmol) 19f were saponified following the procedure described for 20e. The crude product was purified by silicagel chromatography (20 to 100% EtOAc in n-heptane), which gave 1.72 g (53.5%) of 20f as light yellow foam.

LCMS-Method A:

UV-wavelength [nm]=220: R$_t$[min]=1.81

Ionization method: ES$^-$: [M−H]$^-$=703.3

1H-NMR (DMSO-d6, 400 MHz) δ[ppm]: 11.24 (s, 1H), 8.29 (d, J=7.46 Hz, 1H), 8.01 (d, J=7.46 Hz, 2H), 7.62 (t, J=7.40 Hz, 1H), 7.51 (t, J=7.70 Hz, 2H), 7.20-7.41 (m, 10H), 6.88 (dd, J=8.99, 2.38 Hz, 4H), 5.68 (dd, J=9.35, 2.38 Hz, 1H), 4.71 (t, J=6.11 Hz, 1H), 3.74 (s, 6H), 3.58-3.69 (m, 1H), 3.48-3.58 (m, 1H), 3.35-3.43 (m, 1H), 3.11 (d, J=8.56 Hz, 1H), 2.79-2.95 (m, 2H), 2.66-2.76 (m, 1H), 2.39-2.47 (m, 1H), 1.91-2.00 (m, 1H), 0.96 (d, J=6.54 Hz, 3H), 0.94 (d, J=6.54 Hz, 3H).

21a: 3-[[(2R,6R)-2-[[bis(4-methoxyphenyl)-phenyl-methoxy]methyl]-4-isopropyl-6-(5-methyl-2,4-di-oxo-pyrimidin-1-yl)morpholin-2-yl]methoxy-(diiso-propylamino)phosphanyl]-oxypropanenitrile 764 mg (1.2 mmol) of the starting material 20a were converted to the desired phosphoramidite 21a following the protocol for 16a (scheme 4). 842 mg (83.2%, mixture of diastereomers) were obtained as colourless foam.

1H-NMR (DMSO-d6, 400 MHz) δ[ppm]: 11.34, 11.32 (2×s, 1H), 7.59, 7.54 (2×d, J=1.10 Hz, 1H), 7.36-7.43 (m, 2H), 7.20-7.34 (m, 7H), 6.89 (m, 4H), 5.59-5.75 (m, 1H), 3.44-3.95 (m, 6H), 3.74 (s, 6H), 3.36 (m, 1H), 3.22 (m, 1H), 2.60-2.85 (m, 5H), 2.36 (m, 1H), 2.18 (m, 1H), 1.78 (2×d, J=8.69 Hz, 3H), 0.83-1.17 (m, 18H).

31P-NMR (DMSO-d6, 162 MHz) δ[ppm]: 148.6, 148.3.

21b: 3-[[(2R,6R)-2-[[bis(4-methoxyphenyl)-phenyl-methoxy]methyl]-6-(2,4-dioxopyrimidin-1-yl)-4-isopropyl-morpholin-2-yl]methoxy-(diisopropy-lamino)phosphanyl]oxypropanenitrile Following the protocol for 16b, the title compound 21b was synthesized, starting with 1.36 g (2.26 mmol) of the corresponding alcohol 20b. 1.09 g (60.1%) of the title compound were isolated as colourless foam.

LCMS-Method B-1:

UV-wavelength [nm]=220: R$_t$[min]=0.80

Ionization method: ES$^+$: [M-N$^i$Pr$_2$+OH+H]$^+$=718.3

1H-NMR (DMSO-d6, 400 MHz) δ[ppm]: 11.32 (br s, 1H), 7.71, 7.66 (2×s, J=8.13 Hz, 1H), 7.35-7.42 (m, 2H), 7.20-7.33 (m, 7H), 6.83-6.92 (m, 4H), 5.60-5.70 (m, 2H), 3.73 (s, 6H), 3.43-3.95 (m, 6H), 3.29-3.39 (m, 1H), 3.22 (m, 1H), 2.59-2.83 (m, 5H), 2.33 (m, 1H), 2.13 (m, 1H), 0.84-1.21 (m, 18H).

31P-NMR (DMSO-d6, 162 MHz) δ[ppm]: 148.5, 148.3.

21c: N-[9-[(2R,6R)-6-[[bis(4-methoxyphenyl)-phe-nyl-methoxy]methyl]-6-[[2-cyanoethoxy-(diisopro-pylamino)phosphanyl]oxymethyl]-4-isopropyl-mor-pholin-2-yl]-6-oxo-1H-purin-2-yl]-2-methyl-propanamide Following the protocol described for the synthesis of 16c, 40 mg (56 µmol) of the starting compound 20c gave 23 mg (44.9%) of the desired phosphoramidite 21c after silicagel chromatography (0 to 100% methyl-tert-butylether in n-heptane, column preconditioned with n-heptane+1% NEt$_3$).

LCMS-Method C:

UV-wavelength [nm]=220: R$_t$[min]=2.57

Ionization method: ES$^+$: [M-N$^i$Pr$_2$+OH+H]$^+$=828.2

1H-NMR (DMSO-d6, 400 MHz) δ[ppm]: 11.70-12.30 (b s, 1H), 11.53 (b s, 1H), 8.05 (s, 1H), 7.35-7.45 (m, 2H), 7.20-7.33 (m, 7H), 6.82-6.91 (m, 4H), 5.54-5.68 (m, 1H), 3.80-3.93 (m, 0.5H), 3.73, 3.72 (2×s, 6H), 3.68-3.76 (m, 1.5H), 3.60-3.67 (m, 2H), 3.35-3.60 (m, 4H), 3.12 (m, 1H), 2.57-2.98 (m, 7H), 0.92-1.13 (m, 24H).

31P-NMR (DMSO-d6, 162 MHz) δ[ppm]: 147.6, 147.4.

21e: N-[9-[(2R,6R)-6-[[bis(4-methoxyphenyl)-phe-nyl-methoxy]methyl]-6-[[2-cyanoethoxy-(diisopro-pylamino)phosphanyl]oxymethyl]-4-isopropyl-mor-pholin-2-yl]purin-6-yl]benzamide Starting with 950 mg (1.30 mmol) of 20e, the title compound was prepared following the protocol described for 16e (scheme 4), which gave 1.10 g (91.0%) of 21e as colourless foam.

1H-NMR (DMSO-d6, 400 MHz) δ[ppm]: 11.19 (br s, 1H), 8.73, 8.71 (2×s, 1H), 8.63, 8.59 (2×s, 1H), 8.04 (d, J=7.65 Hz, 2H), 7.64 (t, J=7.34 Hz, 1H), 7.55 (t, J=7.43 Hz, 2H), 7.44 (d, J=7.78 Hz, 2H), 7.21-7.35 (m, 7H), 6.86-6.93 (m, 4H), 5.89-5.99 (m, 1H), 3.80-4.15 (m, 1H), 3.74 (s, 6H), 3.63-3.72 (m, 2H), 3.31-3.60 (m, 5H), 3.01 (br d, J=10.79 Hz, 1H), 2.66-2.90 (m, 4H), 2.59-2.64 (m, 1H), 2.42-2.47 (m, 1H), 0.91-1.12 (m, 18H).

31P-NMR (DMSO-d6, 162 MHz) δ[ppm]: 147.6, 147.5.

21f: N-[1-[(2R,6R)-6-[[bis(4-methoxyphenyl)-phe-nyl-methoxy]methyl]-6-[[2-cyanoethoxy-(diisopro-pylamino)phosphanyl]oxymethyl]-4-isopropyl-mor-pholin-2-yl]-2-oxo-pyrimidin-4-yl]benzamide Starting with 620 mg (0.88 mmol) of 20f, the title compound was prepared following the protocol described for 16e (scheme 4), which gave 681 mg (85.5%) of 21f as colourless foam.

1H-NMR (DMSO-d6, 400 MHz) δ[ppm]: 11.28 (br s, 1H), 8.12-8.23 (2×d, J=7.47 Hz, 1H), 8.01 (d, J=7.65 Hz, 2H), 7.58-7.67 (m, 1H), 7.51 (t, J=7.58 Hz, 2H), 7.35-7.42 (m, 3H), 7.20-7.35 (m, 7H), 6.83-6.93 (m, 4H), 5.71-5.80 (2×dd, J=9.49, 2.54 Hz, 1H), 3.44-4.00 (m, 6H), 3.74 (s, 6H), 3.38 (m, 1H), 3.24-3.33 (m, 1H), 2.60-2.94 (m, 5H), 2.33-2.48 (m, 1H), 2.01-2.09 (m, 1H), 1.02-1.23 (m, 12H), 0.83-1.00 (m, 6H).

31P-NMR (DMSO-d6, 162 MHz) δ[ppm]: 147.5, 147.4.

Example A.6

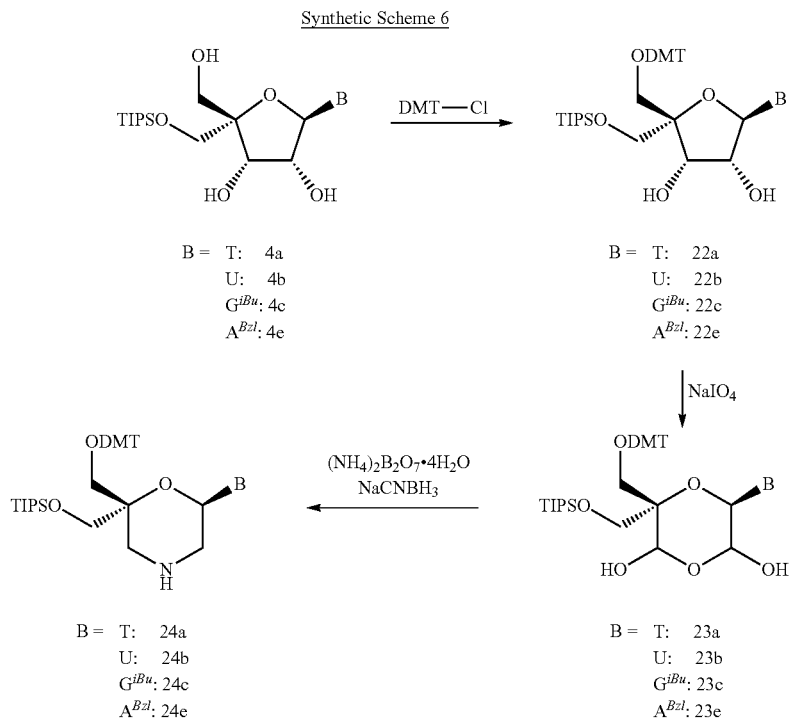

Synthetic Scheme 6

22a: 1-[(2R,3R,4S,5S)-5-[[bis(4-methoxyphenyl)-phenyl-methoxy]methyl]-3,4-dihydroxy-5-(triisopropylsilyloxymethyl)tetrahydrofuran-2-yl]-5-methyl-pyrimidine-2,4-dione To a solution of 23.7 g (53.4 mmol) of the starting compound 4a in 240 ml anhydrous pyridine were added 23.13 g (80 mmol) DMT-Cl at room temperature under $N_2$ atmosphere. After stirring for 12 h, the solvent was removed i.vac. and the residue was purified by silicagel column chromatography (PE/EtOAc 10:1 to 1:1), which gave 16.3 g, (41%) of the desired DMT-protected product (22a) as colourless solid.

1H-NMR (DMSO-d6, 400 MHz) δ[ppm]: 11.34 (s, 1H), 7.50 (d, J=0.75 Hz, 1H), 7.42-7.37 (m, 2H), 7.32 (t, J=7.53 Hz, 2H), 7.29-7.22 (m, 6H), 6.90 (dd, J=8.91, 2.13 Hz, 4H), 5.89 (d, J=7.28 Hz, 1H), 5.45 (d, J=6.53 Hz, 1H), 5.15 (d, J=5.02 Hz, 1H), 4.48-4.39 (m, 1H), 4.31 (t, J=5.14 Hz, 1H), 3.86-3.80 (m, 1H), 3.74 (s, 6H), 1.28 (s, 3H), 0.98-0.83 (m, 22H).

22b: 1-[(2R,3R,4S,5S)-5-[[bis(4-methoxyphenyl)-phenyl-methoxy]methyl]-3,4-dihydroxy-5-(triisopropylsilyloxymethyl)tetrahydrofuran-2-yl]pyrimidine-2,4-dione To a solution of compound 4b (75 g, 174 mmol) in 750 ml anhydrous pyridine was added DMT-Cl (70.8 g, 209 mmol) at room temperature under $N_2$ atmosphere. The mixture was stirred for 12 h to achieve complete conversion. The solvent was removed in vacuo, the residue was diluted with 500 ml of water and extracted with 3×500 ml EtOAc. The organic layers were washed with brine, dried over anhydrous $Na_2SO_4$, filtered and concentrated in vacuo. The obtained crude product was purified by flash chromatography on silicagel (PE/EtOAc 1:1 to EtOAc/MeOH 20:1) to give 80 g (62.6%) of 22b as a colourless foam.

1H-NMR (DMSO-d6, 400 MHz) δ[ppm]: 11.35 (s, 1H), 7.61 (d, J=8.28 Hz, 1H), 7.42-7.36 (m, 2H), 7.32 (t, J=7.65 Hz, 2H), 7.28-7.19 (m, 5H), 6.90 (d, J=8.03 Hz, 4H), 5.83 (d, J=6.53 Hz, 1H), 5.48 (d, J=6.02 Hz, 1H), 5.27 (d, J=8.03 Hz, 1H), 5.21 (d, J=5.27 Hz, 1H), 4.33-4.26 (m, 1H), 4.22 (q, J=6.02 Hz, 1H), 3.89-3.79 (m, 2H), 3.74 (s, 6H), 3.24 (d, J=10.04 Hz, 1H), 1.01-0.84 (m, 21H).

22c: N-[9-[(2R,3R,4S,5S)-5-[[bis(4-methoxyphenyl)-phenyl-methoxy]methyl]-3,4-dihydroxy-5-(triisopropylsilyloxymethyl)tetrahydrofuran-2-yl]-6-oxo-1H-purin-2-yl]-2-methyl-propanamide Following the protocol described for 22b, 55.8 g (103 mmol) of 4c were protected with DMT-Cl in pyridine, yielding 50.0 g (57.4%) of 22c as colourless solid.

1H-NMR (DMSO-d6, 400 MHz) δ[ppm]: 12.12 (br s, 1H), 11.67 (br s, 1H), 7.99-7.83 (m, 1H), 7.38 (br d, J=7.28 Hz, 2H), 7.32-7.13 (m, 8H), 6.84 (dd, J=8.78, 2.26 Hz, 4H), 5.86 (d, J=7.03 Hz, 1H), 5.70-5.45 (m, 1H), 5.18 (br s, 1H), 4.73-4.62 (m, 1H), 4.25 (br d, J=4.77 Hz, 1H), 3.97 (br d, J=10.29 Hz, 1H), 3.84 (br d, J=10.29 Hz, 1H), 3.73 (s, 6H), 3.20 (br d, J=10.04 Hz, 1H), 2.76 (dt, J=13.61, 6.87 Hz, 1H), 1.12 (d, J=6.78 Hz, 6H), 1.01-0.87 (m, 21H).

22e: N-[9-[(2R,3R,4S,5S)-5-[[bis(4-methoxyphenyl)-phenyl-methoxy]methyl]-3,4-dihydroxy-5-(triisopropylsilyloxymethyl)tetrahydrofuran-2-yl]purin-6-yl]benzamide Following the protocol described for 22b, 57.0 g (102 mmol) of 4e were protected with DMT-Cl in pyridine, yielding of 22e as colourless solid (70.0%).

1H-NMR (DMSO-d6, 400 MHz) δ[ppm]: 11.22 (s, 1H), 8.68-8.58 (m, 1H), 8.49 (s, 1H), 8.05 (d, J=7.28 Hz, 2H), 7.70-7.60 (m, 1H), 7.59-7.50 (m, 2H), 7.43 (d, J=7.28 Hz, 2H), 7.33-7.17 (m, 7H), 6.86 (dd, J=8.91, 1.38 Hz, 4H), 6.00 (d, J=7.28 Hz, 1H), 5.53 (d, J=6.78 Hz, 1H), 5.32 (d, J=4.89 Hz, 1H), 5.00-4.87 (m, 1H), 4.34 (t, J=4.89 Hz, 1H), 4.08-4.04 (m, 1H), 3.98 (d, J=10.79 Hz, 1H), 3.73 (s, 6H), 3.40 (d, J=9.54 Hz, 1H), 3.30 (br d, J=9.54 Hz, 1H), 1.12-0.93 (m, 21H).

23a: 1-[(2R,6S)-6-[[bis(4-methoxyphenyl)-phenyl-methoxy]methyl]-3,5-dihydroxy-6-(triisopropylsilyloxymethyl)-1,4-dioxan-2-yl]-5-methyl-pyrimidine-2,4-dione To a solution of 12.6 g (16.9 mmol) starting material 22a in 250 ml acetone/H$_2$O (3:1) was added dropwise an aqueous solution of 5.05 g (23.6 mmol) NaIO$_4$ in H$_2$O (60 ml) at room temperature. The mixture was stirred 12 h to reach complete conversion and was poured into 500 ml ice-water. The mixture was extracted 3× with 500 ml DCM. The organic layers were combined and washed with brine, dried over anhydrous Na$_2$SO$_4$, filtered and concentrated in vacuo to give 11.20 g (87%) of the desired product 23a as white foam, which was used in the next step without further purification.

1H-NMR (DMSO-d6, 400 MHz) δ[ppm]: 11.62-11.33 (m, 1H), 7.80-7.65 (m, 1H), 7.57-7.38 (m, 3H), 7.33-7.13 (m, 9H), 6.88-6.73 (m, 5H), 6.08-5.86 (m, 1H), 5.71-5.51 (m, 1H), 5.24-5.06 (m, 1H), 5.01-4.94 (m, 1H), 4.29-4.16 (m, 1H), 3.75-3.70 (m, 7H), 3.34-3.24 (m, 1H), 3.06-2.81 (m, 1H), 2.02-1.59 (m, 2H), 1.03 (m, 1H), 1.09-0.74 (m, 21H).

23b: 1-[(2R,6S)-6-[[bis(4-methoxyphenyl)-phenyl-methoxy]methyl]-3,5-dihydroxy-6-(triisopropylsilyloxymethyl)-1,4-dioxan-2-yl]pyrimidine-2,4-dione Following the protocol described for 23a, 77.0 g (105 mmol) of the diol 22b gave 80 g (quant., crude product) of the title compound 23b as yellow solid.

1H-NMR (DMSO-d6, 400 MHz) δ[ppm]: 11.67-11.36 (m, 1H), 7.87-7.77 (m, 1H), 7.76-7.67 (m, 1H), 7.55-7.41 (m, 2H), 7.39-7.20 (m, 8H), 6.94-6.81 (m, 4H), 5.94-5.87 (m, 1H), 5.78-5.63 (m, 1H), 5.59-5.51 (m, 1H), 5.25-5.08 (m, 1H), 5.07-4.99 (m, 1H), 4.32-4.20 (m, 1H), 3.82-3.70 (m, 6H), 3.34-3.26 (m, 1H), 3.15-3.04 (m, 1H), 2.95-2.86 (m, 1H), 1.14-0.81 (m. 22H).

23c: N-[9-[(2R,6S)-6-[[bis(4-methoxyphenyl)-phenyl-methoxy]methyl]-3,5-dihydroxy-6-(triisopropyl-silyloxymethyl)-1,4-dioxan-2-yl]-6-oxo-1H-purin-2-yl]-2-methyl-propanamide Following the protocol described for 23a, 50.0 g (59 mmol) of the diol 22c gave 47 g (96.1%, crude product) of the title compound 23c as yellow solid.

1H-NMR (DMSO-d6, 400 MHz) δ[ppm]: 12.25-12.06 (m, 1H), 11.78-11.55 (m, 1H), 8.19 (d, J=8.78 Hz, 1H), 7.44 (br d, J=7.28 Hz, 1H), 7.38 (br d, J=6.53 Hz, 1H), 7.34-7.14 (m, 10H), 6.99 (d, J=6.78 Hz, 1H), 6.90-6.71 (m, 5H), 6.05-5.98 (m, 1H), 5.74 (d, J=7.78 Hz, 1H), 5.61-5.53 (m, 1H), 5.48 (q, J=6.78 Hz, 1H), 5.24-5.17 (m, 1H), 5.06 (d, J=6.53 Hz, 1H), 4.35-4.22 (m, 1H), 3.83 (br d, J=11.54 Hz, 1H), 3.72 (d, J=3.26 Hz, 7H), 3.27 (br d, J=9.29 Hz, 1H), 3.29-3.23 (m, 1H), 3.12-3.04 (m, 1H), 2.91-2.75 (m, 1H), 1.22-0.76 (m, 29H).

23e: N-[9-[(2R,6S)-6-[[bis(4-methoxyphenyl)-phenyl-methoxy]methyl]-3,5-dihydroxy-6-(triisopropylsilyloxymethyl)-1,4-dioxan-2-yl]purin-6-yl]benzamide Following the protocol described for 23a, 78.0 g (90.6 mmol) of the diol 22e gave 75.2 g (94.6%, crude product) of the title compound 23e as white solid.

MS (m/z)=876.2 [M+H]$^+$

24a: 1-[(2R,6S)-6-[[bis(4-methoxyphenyl)-phenyl-methoxy]methyl]-6-(triisopropylsilyloxy-methyl)morpholin-2-yl]-5-methyl-pyrimidine-2,4-dione To a solution of 2.6 g (3.4 mmol) starting compound 23a in 44 ml anhydrous MeOH were added 0.98 g (3.7 mmol) (NH$_4$)$_2$B$_4$O$_7$.4H$_2$O at room temperature under N$_2$ atmosphere. The mixture was stirred for 2 hours, followed by the addition of 0.45 g (6.8 mmol) AcOH, 5.0 g 4 Å molecular sieves and 0.47 g (6.8 mmol) NaBH$_3$CN. After stirring for 12 h at room temperature, TLC showed that the starting material was consumed completely. The solvent was removed in vacuo, and the residue purified by silicagel chromatography (PE/EtOAc 4:1 to 1:1), yielding 1.59 g (64%) of the desired morpholine 24a as a white foam.

MS (m/z)=752.5 [M+Na]$^+$

1H-NMR (DMSO-d6, 400 MHz) δ[ppm]: 11.39 (s, 1H), 7.62 (s, 1H), 7.43 (br d, J=7.28 Hz, 2H), 7.33-7.23 (m, 8H), 6.84 (d, J=8.78 Hz, 5H), 5.86 (br dd, J=9.91, 2.64 Hz, 1H), 5.89-5.81 (m, 1H), 4.13 (br d, J=9.54 Hz, 1H), 3.96 (br d, J=9.54 Hz, 1H), 3.72 (d, J=0.75 Hz, 6H), 3.06 (br d, J=9.29 Hz, 1H), 2.97 (br d, J=9.03 Hz, 1H), 2.93-2.78 (m, 2H), 2.76-2.57 (m, 3H), 1.76 (s, 3H), 0.98-0.87 (m, 22H).

24b: 1-[(2R,6S)-6-[[bis(4-methoxyphenyl)-phenyl-methoxy]methyl]-6-(triisopropylsilyloxy-methyl)morpholin-2-yl]pyrimidine-2,4-dione To a solution of compound 23b (5.0 g, 6.7 mmol) in 85 ml anhydrous MeOH was added (NH$_4$)$_2$B$_4$O$_7$.4H$_2$O (1.93 g, 7.6 mmol) at 25° C. under N$_2$ atmosphere. The mixture was stirred for 2 h, followed by the addition of 0.80 g (13.4 mmol) AcOH, 10 g 4× molecular sieves and 0.84 g (13.4 mmol) NaBH$_3$CN. After stirring for 12 h the mixture was filtered and the filtrate was concentrated in vacuo. The residue was diluted with ice-water and extracted with 3× with 50 ml EtOAc. The organic layers were combined and washed with brine, dried over anhydrous Na$_2$SO$_4$, filtered and concentrated in vacuo. The crude product was purified by column chromatography on silica gel (PE/EtOAc 10:1 to 1:1), yielding the title compound 24b as white foam (94%).

MS (m/z)=738.5 [M+H]$^+$

1H-NMR (DMSO-d6, 400 MHz) δ[ppm]: 11.44 (br s, 1H), 7.75 (d, J=8.07 Hz, 1H), 7.45 (br d, J=7.34 Hz, 2H), 7.37-7.20 (m, 7H), 6.89 (d, J=8.80 Hz, 4H), 5.88 (br dd, J=10.03, 2.45 Hz, 1H), 5.73 (d, J=8.07 Hz, 1H), 4.17 (br d, J=9.78 Hz, 1H), 4.11-4.02 (m, 2H), 3.77 (d, J=0.73 Hz, 6H), 3.12 (br d, J=9.05 Hz, 1H), 3.02-2.83 (m, 3H), 2.70-2.58 (m, 2H), 1.06-0.90 (m, 21H).

24c: N-[9-[(2R,6S)-6-[[bis(4-methoxyphenyl)-phenyl-methoxy]methyl]-6-(triisopropylsilyl-oxymethyl)morpholin-2-yl]-6-oxo-1H-purin-2-yl]-2-methyl-propanamide Following the protocol described for 24b, 7.0 g (8.2 mmol) of the starting material 23c were converted to the morpholine compound 24c, which was isolated after silica-gel chromatography (PE/EtOAc 5:1 to 1:1) as colourless foam (73.2%).

MS (m/z)=825.2 [M+H]+

1H-NMR (DMSO-d6, 400 MHz) δ[ppm]: 12.12 (br s, 1H), 11.59 (s, 1H), 8.15 (s, 1H), 7.40 (br d, J=7.03 Hz, 2H), 7.30-7.12 (m, 7H), 6.81 (br d, J=7.78 Hz, 4H), 5.83 (dd, J=9.66, 3.14 Hz, 1H), 4.23 (br d, J=9.03 Hz, 1H), 3.92 (br d, J=9.03 Hz, 1H), 3.72 (d, J=2.76 Hz, 6H), 2.97-3.18 (m, 3H), 2.96-2.86 (m, 2H), 2.80 (dt, J=13.55, 6.78 Hz, 1H), MS (m/z)=843.1 [M+H]+

1H-NMR (DMSO-d6, 400 MHz) δ[ppm]: 11.22 (br s, 1H), 8.75 (s, 1H), 8.66 (s, 1H), 8.05 (d, J=7.34 Hz, 2H), 7.70-7.62 (m, 1H), 7.60-7.51 (m, 2H), 7.38 (br d, J=6.97 Hz, 2H), 7.26-7.16 (m, 7H), 6.78 (d, J=8.93 Hz, 4H), 6.16 (dd, J=10.03, 2.81 Hz, 1H), 4.26 (d, J=9.66 Hz, 1H), 4.10-3.98 (m, 1H), 3.71 (d, J=0.73 Hz, 6H), 3.28 (br d, J=10.64 Hz, 1H), 3.16 (br d, J=9.17 Hz, 1H), 3.06 (br d, J=9.17 Hz, 1H), 2.98-2.90 (m, 2H), 2.79 (br d, J=12.47 Hz, 1H), 1.10-0.82 (m, 21H).

Example A.7

Synthetic Scheme 7

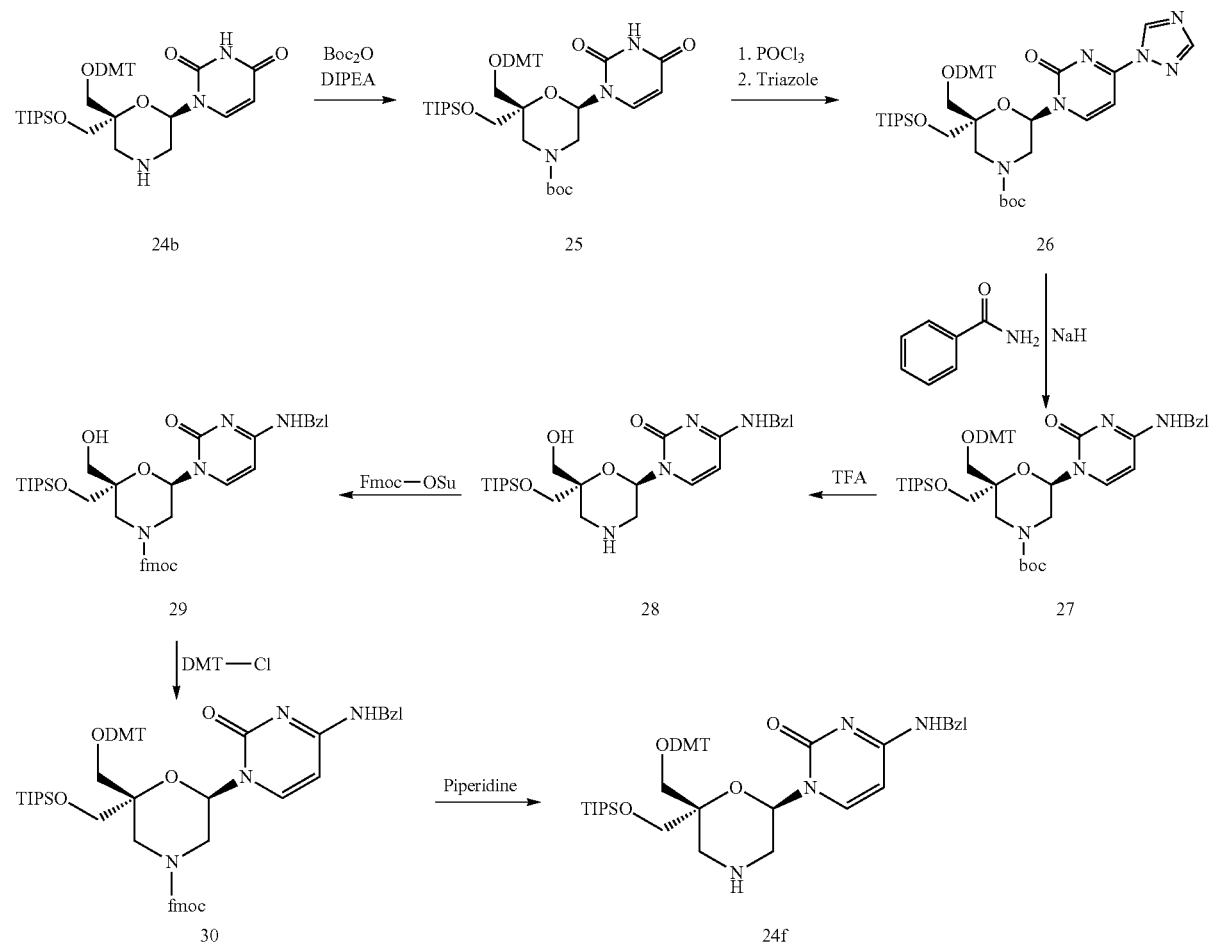

2.67 (br d, J=12.05 Hz, 1H), 1.13 (t, J=6.15 Hz, 6H), 1.03-0.82 (m, 22H).

24e: N-[9-[(2R,6S)-6-[[bis(4-methoxyphenyl)-phenyl-methoxy]methyl]-6-(triisopropylsilyl-oxymethyl)morpholin-2-yl]purin-6-yl]benzamide Following the protocol described for 24b, 5.0 g (5.7 mmol) of the starting material 23e were converted to the morpholine compound 24e, which was isolated after silica-gel chromatography (PE/EtOAc 1:4) as colourless foam (73.4%).

25: tert-butyl (2S,6R)-2-[[bis(4-methoxyphenyl)-phenyl-methoxy]methyl]-6-(2,4-dioxo-pyrimidin-1-yl)-2-(triisopropylsilyloxymethyl)morpholine-4-carboxylate To a mixture of the morpholine 24b (50 g, 69.8 mmol) and DIPEA (18 g, 139.7 mol) in 500 ml DCM was added Boc2O (22.9 g, 104.8 mol) dropwise at room temperature. After stirring 24 h, the solvent was removed in vacuo and the residue was purified by column chromatography (PE/EtOAc 1:1) to give compound 25 (60 g, yield 93%) as white foam.

1H-NMR (DMSO-d6, 400 MHz) δ[ppm]: 7.58 (d, J=8.0 Hz, 1H), 7.45 (d, J=7.2 Hz, 2H), 7.33-7.26 (m, 7H), 6.85-6.81 (m, 4H), 6.02-5.98 (dd, J=10.0 3.6 Hz, 1H), 5.77 (d, J=8.0 Hz, 1H), 4.24-4.11 (m, 2H), 3.99 (d, J=9.6 Hz, 1H), 3.80 (s, 1H), 3.75 (m, 1H), 3.28-3.20 (m, 2H), 3.08 (d, J=12.8 Hz, 1H), 2.69 (t, J=11.4 Hz, 1H), 1.48 (m, 9H), 1.03-0.95 (m, 21H).

26: tert-butyl (2S,6R)-2-[[bis(4-methoxyphenyl)-phenyl-methoxy]methyl]-6-[2-oxo-4-(1,2,4-triazol-1-yl)pyrimidin-1-yl]-2-(triisopropylsilyloxymethyl)morpholine-4-carboxylate To a mixture of 1H-1,2,4-triazole (65 g, 0.94 mol) in 650 ml ACN was added $POCl_3$ (49.79 g, 0.31 mol) dropwise at 30° C. After cooling to 0° C., DIPEA (198 g, 1.53 mol) was added dropwise and stirring was continued at 0° C. for 30 min. At the same temperature the starting material 25 (32 g, 39.21 mmol) was added to the mixture in one portion, the ice-bath was removed and the reaction was stirred at 30° C. for 3 h. The mixture was poured into 3 l of a mixed solvent of EtOAc/water (1:2). After separation, the organic layer was washed with 500 ml sat. $NaHCO_3$-solution and brine, dried over anhydrous $Na_2SO_4$, filtered and concentrated in vacuo to give crude compound 26 (40 g) as yellow oil, which was used for the next step without further purification.

MS (m/z)=867.5 $[M+H]^+$

27: tert-butyl-(2S,6R)-6-(4-benzamido-2-oxo-pyrimidin-1-yl)-2-[[bis(4-methoxyphenyl)-phenyl-methoxy]methyl]-2-(triisopropylsilyloxymethyl)morpholine-4-carboxylate To a mixture of benzamide (38 g, 0.31 mol) in 380 ml dioxane was added NaH (12.8 g, 0.31 mol) in portions at 0° C. After stirring at 30° C. for 30 min, triazole 26 (40 g, 39.21 mmol, crude) was added in one portion and the mixture was stirred at 30° C. for 1 h. The reaction was quenched with 24 l of sat. $NH_4Cl$-solution and extracted with 3 l EtOAc. The organic layer was washed with 2 l water and brine, dried over anhydrous $Na_2SO_4$, filtered and concentrated in vacuo to give 54 g of crude compound as yellow oil. Final silicagel chromatography (PE/EtOAc 2:1) gave 20.4 g (56.6%) of 27 as yellow foam.

1H-NMR (DMSO-d6, 400 MHz) δ[ppm]: 11.31 (br s, 1H), 8.20 (br d, J=7.21 Hz, 1H), 8.01 (br d, J=7.46 Hz, 2H), 7.70-7.59 (m, 1H), 7.58-7.48 (m, 2H), 7.47-7.36 (m, 3H), 7.34-7.16 (m, 7H), 6.87 (br d, J=7.70 Hz, 4H), 5.96 (br dd, J=10.09, 2.63 Hz, 1H), 4.12 (br d, J=11.25 Hz, 1H), 4.00-3.83 (m, 3H), 3.74 (s, 6H), 3.28-3.16 (m, 2H), 3.06 (br d, J=9.17 Hz, 2H), 1.55-1.32 (m, 9H), 1.11-0.80 (m, 21H).

28: N-[1-[(2R,6S)-6-(hydroxymethyl)-6-(triisopropylsilyloxymethyl)morpholin-2-yl]-2-oxo-pyrimidin-4-yl]benzamide To a solution of 27 (13.5 g, 14.70 mmol) in 93 ml DCM were added 31 ml of TFA dropwise at 0° C. The reaction was stirred at 30° C. for 16 h. After neutralization with sat. $NaHCO_3$— solution to pH=7-8, the organic layer was separated and the aqueous phase extracted 2× with 100 ml DCM. The combined organic layers were dried over anhydrous $Na_2SO_4$, filtered and concentrated in vacuo. The residue was purified by column chromatography (EtOAc/EtOH=30:1) to give 28 (2.7 g, yield 35.6%) as yellow foam and the corresponding trifluoro-aceticacidester as a side product (4.78 g, 53.1%) which was dissolved in a mixed solvent of 186 ml THF and 62 ml EtOH. At 0° C. 75.8 ml of a 1 M aqueous NaOH-solution were added. After stirring for 2 min, the solution was neutralized with sat. citric acid solution, diluted with 300 ml $H_2O$ and extracted with 300 ml EtOAc. The organic layer was washed with brine, dried with $Na_2SO_4$ and evaporated. Purification by silicagel chromatography (EtOAc/EtOH 30:1) gave 5.2 g (68.5%) of 28 as white solid.

MS (m/z)=517.4 $[M+H+]^+$

1H-NMR (DMSO-d6, 400 MHz) δ[ppm]: 11.26 (br s, 1H), 8.28 (d, J=7.53 Hz, 1H), 8.01 (d, J=7.28 Hz, 2H), 7.67-7.58 (m, 1H), 7.57-7.47 (m, 2H), 7.34 (d, J=7.40 Hz, 1H), 5.86 (dd, J=9.66, 2.64 Hz, 1H), 4.64 (br s, 1H), 4.01-3.90 (m, 2H), 3.46 (br s, 2H), 3.05 (dd, J=11.98, 2.57 Hz, 1H), 3.11-3.00 (m, 1H), 2.87-2.75 (m, 1H), 2.74-2.63 (m, 1H), 2.40-2.27 (m, 1H), 1.15-0.99 (m, 21H).

29: 9H-fluoren-9-ylmethyl (2S,6R)-6-(4-benzamido-2-oxo-pyrimidin-1-yl)-2-(hydroxymethyl)-2-(triisopropylsilyloxymethyl)morpholine-4-carboxylate To a solution of 7.0 g (13.55 mmol) of the morpholine 28 (13.55 mmol) in 70 ml in DMF were added 5.5 g (16.26 mmol) Fmoc-N-hydroxy-succinimide ester in portions at 0° C. After stirring for 16 h, the solution was poured into 100 ml of water and extracted 3× with 30 ml EtOAc. The combined organic layers were washed with brine, dried over anhydrous $Na_2SO_4$, filtered and concentrated in vacuo. Final purification on silica (PE/EtOAc 1:2) yielded 10.0 g (quant.) of compound 29 as yellow solid.

MS (m/z)=739.4 $[M+H]^+$

1H-NMR (DMSO-d6, 400 MHz) δ[ppm]: 11.26 (br s, 1H), 8.33 (br s, 1H), 8.02 (br d, J=7.46 Hz, 2H), 7.90 (d, J=7.58 Hz, 2H), 7.64 (br t, J=7.40 Hz, 3H), 7.57-7.49 (m, 2H), 7.48-7.40 (m, 3H), 7.39-7.30 (m, 2H), 6.11-5.79 (m, 1H), 4.98 (t, J=6.05 Hz, 1H), 4.52-4.12 (m, 4H), 3.89-3.69 (m, 2H), 3.54 (br s, 3H), 3.21-3.07 (m, 1H), 3.04-2.77 (m, 1H), 1.11-0.89 (m, 21H).

30: 9H-fluoren-9-ylmethyl-(2S,6R)-6-(4-benzamido-2-oxo-pyrimidin-1-yl)-2-[[bis(4-methoxyphenyl)-phenyl-methoxy]methyl]-2-(triisopropylsilyloxymethyl)morpholine-4-carboxylate To a solution of compound 29 (13.9 g, 18.83 mmol) in 140 ml pyridine were added 12.75 g (37.62 mmol) DMT-Cl at 25° C. The mixture was stirred at 25° C. for 16 h to achieve complete conversion. After evaporation of the solvent, the residue was dissolved in 200 ml EtOAc, washed with 100 ml water and brine. The organic phase was dried with $Na_2SO_4$, filtered and concentrated in vacuo. The residue was purified by column chromatography (PE/EtOAc 1:1) yielding 17.3 g (88.1%) of compound 30 as yellow foam.

1H-NMR (DMSO-d6, 400 MHz) δ[ppm]: 11.32 (br s, 1H), 8.21 (br s, 1H), 8.02 (br d, J=7.58 Hz, 2H), 7.88 (br s, 2H), 7.76-7.60 (m, 3H), 7.59-7.50 (m, 2H), 7.42 (br d, J=7.21 Hz, 5H), 7.38-7.19 (m, 9H), 6.89 (br d, J=8.44 Hz, 4H), 6.19-5.85 (m, 1H), 4.28 (br s, 4H), 3.91 (br d, J=8.80 Hz, 2H), 3.75 (s, 6H), 3.23 (br s, 1H), 3.10 (br d, J=9.05 Hz, 3H), 1.06-0.78 (m, 21H).

24f: N-[1-[(2R,6S)-6-[[bis(4-methoxyphenyl)-phenyl-methoxy]methyl]-6-(triisopropylsilyl-oxymethyl)morpholin-2-yl]-2-oxo-pyrimidin-4-yl]benzamide To a solution of 8.4 g (8.07 mmol) of 30 in 85 ml DCM were added 17 ml piperidine at room temperature. After complete conversion (approx. 20 min), the reaction solution was washed with sat. $NH_4Cl$-solution. The aqueous phase was extracted with DCM and the combined organic layers were dried with Na$_2$SO$_4$, filtered and concentrated in vacuo. The crude product was purified by column chromatography (PE/EtOAc 1:4), yielding 4.7 g (71.2%) of the title compound 24f as white foam.

MS (m/z)=819.4 [M+H]$^+$

1H-NMR (DMSO-d6, 400 MHz) δ[ppm]: 11.31 (br s, 1H), 8.18 (d, J=7.58 Hz, 1H), 8.01 (br d, J=7.34 Hz, 2H), 7.67-7.58 (m, 1H), 7.57-7.47 (m, 2H), 7.42 (br d, J=7.46 Hz, 3H), 7.34-7.15 (m, 7H), 6.86 (br d, J=8.56 Hz, 4H), 6.04-5.89 (m, 1H), 4.18 (br d, J=9.54 Hz, 1H), 4.07 (br d, J=9.54 Hz, 1H), 3.73 (d, J=1.34 Hz, 6H), 3.15 (br d, J=9.17 Hz, 1H), 3.05 (br d, J=10.15 Hz, 1H), 2.97 (br d, J=9.17 Hz, 1H), 2.88 (br d, J=12.47 Hz, 1H), 2.62 (br d, J=12.47 Hz, 1H), 2.46 (br s, 1H), 1.08-0.83 (m, 21H).

Example A.8

General Procedure A for the Reductive Amination Reaction to Prepare Compounds 31a-31f 1.0 g (1.4 mmol) of the morpholine 24a was dissolved in 25 ml MeOH followed by the addition of 2.0 g molecular sieves (4 Å), 560 mg (769 μl, 5.5 mmol) NEt$_3$, 827 mg (789 μl, 13.7 mmol) AcOH and 1.0 to 3.0 equivalents of the corresponding aldehyde or ketone. After stirring for 15 minutes, 344 mg (5.5 mmol) sodium cyanoboronhydride were added in four portions every 30 minutes and the reaction was stirred at room temperature for 6 h. After standing overnight, the mixture was filtered and the filtrate was diluted with 25 ml sat. NaHCO$_3$-solution. The MeO was evaporated and the aqueous phase was extracted with 50 ml DCM/iPrOH (5:1). After another filtration, the organic phase was separated, dried with MgSO$_4$ and evaporated. The obtained crude product was used in the next step without further purification.

Synthetic Scheme 8

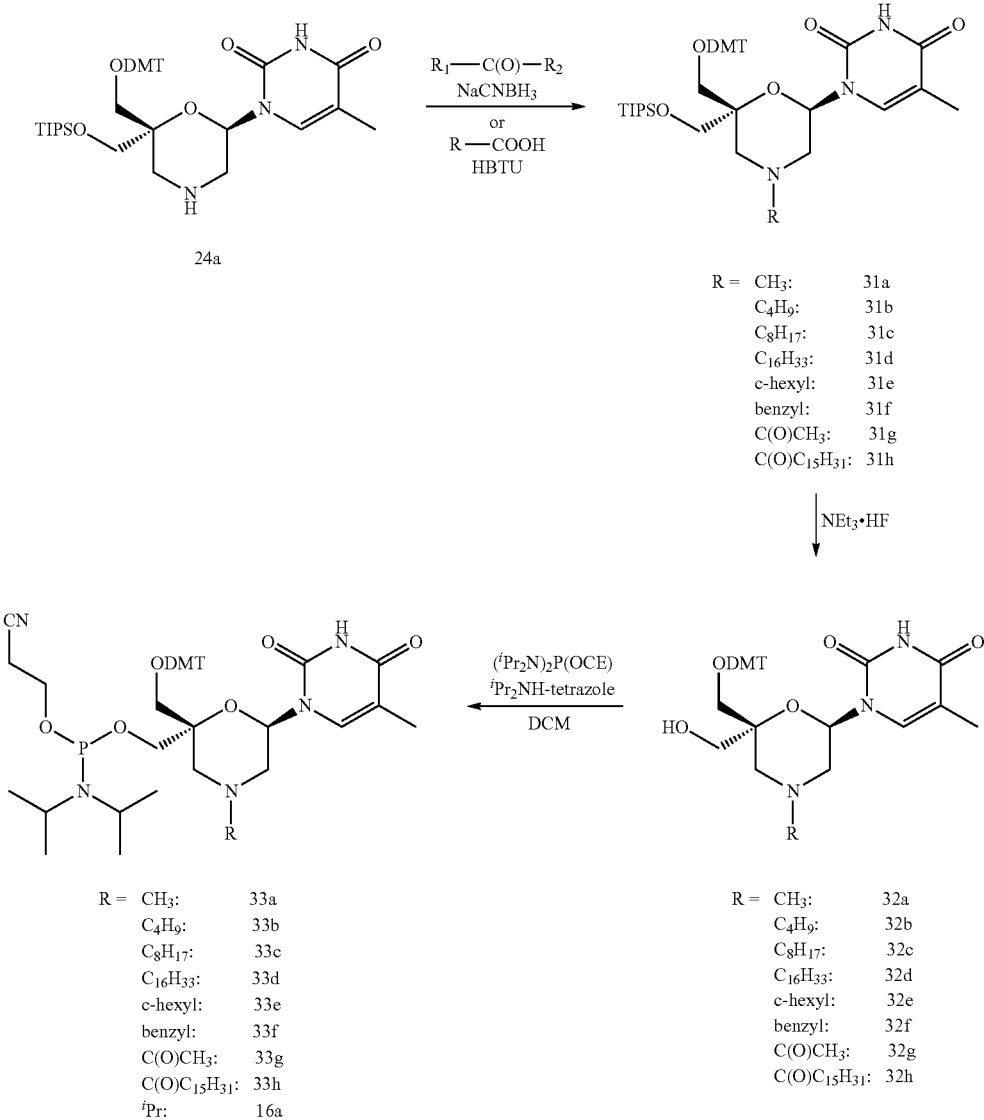

31a: 1-[(2R,6S)-6-[[bis(4-methoxyphenyl)-phenyl-methoxy]methyl]-4-methyl-6-(triiso-propylsilyloxymethyl)morpholin-2-yl]-5-methyl-pyrimidine-2,4-dione Following general procedure A, using 3.0 equivalents of formaldehyde (37% aqueous solution), 1.0 g of the title compound 31a was isolated as crude product and used without further purification.
LCMS-Method A:
UV-wavelength [nm]=220: $R_t$[min]=2.29
Ionization method: ES$^+$: [M+H]$^+$=744.3

31b: 1-[(2R,6S)-6-[[bis(4-methoxyphenyl)-phenyl-methoxy]methyl]-4-butyl-6-(triiso-propylsilyloxymethyl)morpholin-2-yl]-5-methyl-pyrimidine-2,4-dione Following general procedure A, using 2.0 equivalents of butyraldehyde, 1.19 g of the title compound 31b were isolated as crude product and used without further purification.
LCMS-Method A:
UV-wavelength [nm]=220: $R_t$[min]=2.41
Ionization method: ES$^+$: [M+H]$^+$=786.7

31c: 1-[(2R,6S)-6-[[bis(4-methoxyphenyl)-phenyl-methoxy]methyl]-4-octyl-6-(triiso-propylsilyloxymethyl)morpholin-2-yl]-5-methyl-pyrimidine-2,4-dione Following general procedure A, using 2.0 equivalents of octanal, 1.35 g of the title compound 31c were isolated as crude product and used without further purification.
LCMS-Method A:
UV-wavelength [nm]=220: $R_t$[min]=2.66
Ionization method: ES$^+$: [M+H]$^+$=842.7

31d: 1-[(2R,6S)-6-[[bis(4-methoxyphenyl)-phenyl-methoxy]methyl]-4-hexadecyl-6-(triiso-propylsilyloxymethyl)morpholin-2-yl]-5-methyl-pyrimidine-2,4-dione Following general procedure A, using 1.0 equivalent of hexadecanal, 1.58 g of the title compound 31d were isolated as crude product and used without further purification.

31e: 1-[(2R,6S)-6-[[bis(4-methoxyphenyl)-phenyl-methoxy]methyl]-4-cyclohexyl-6-(triiso-propylsilyloxymethyl)morpholin-2-yl]-5-methyl-pyrimidine-2,4-dione Following general procedure A, using 1.25 equivalents of cyclohexanone, 1.14 g of the title compound 31e were isolated as crude product and used without further purification.
LCMS-Method A:
UV-wavelength [nm]=220: $R_t$[min]=2.45
Ionization method: ES$^+$: [M+H]$^+$=812.5

31f: 1-[(2R,6S)-4-benzyl-6-[[bis(4-methoxyphenyl)-phenyl-methoxy]methyl]-6-(triisopropyl-silyloxymethyl)morpholin-2-yl]-5-methyl-pyrimidine-2,4-dione Following general procedure A, using 1.25 equivalents of benzaldehyde, 1.12 g of the title compound 31f were isolated as crude product and used without further purification.
LCMS-Method A:
UV-wavelength [nm]=220: $R_t$[min]=2.37
Ionization method: ES$^+$: [M+H]$^+$=821.4

31g: 1-[(2R,6S)-4-acetyl-6-[[bis(4-methoxyphenyl)-phenyl-methoxy]methyl]-6-(triiso-propylsilyloxymethyl)morpholin-2-yl]-5-methyl-pyrimidine-2,4-dione 1.0 g (1.4 mmol) of the starting compound 24a were dissolved in 25 ml DCM. After adding 103 mg (99 μl, 1.7 mmol) AcOH, 779 mg (2.1 mmol) HBTU and 903 mg (1.19 ml, 6.9 mmol) diisopropyl-ethylamine, the reaction mixture was stirred for 4 h at room temperature to achieve complete conversion. The reaction solution was washed with 25 ml H$_2$O and the organic layer was separated. After drying with MgSO$_4$, the solvent was evaporated and the crude product was purified by silicagel chromatography (0 to 5% MeOH in DCM), yielding 1.06 g (quant.) of the title compound 31g.
LCMS-Method A:
UV-wavelength [nm]=220: $R_t$[min]=2.20
Ionization method: ES$^-$: [M−H]$^-$=770.2

31h: 1-[(2R,6S)-6-[[bis(4-methoxyphenyl)-phenyl-methoxy]methyl]-4-hexadecanoyl-6-(triisopropylsilyloxymethyl)morpholin-2-yl]-5-methyl-pyrimidine-2,4-dione Following the protocol for 31g, 1.0 g (1.4 mmol) of the starting compound 24a and palmitic acid were converted to 1.14 g (86%) of the title compound 31h after silicagel chromatography (0 to 20% MeOH in DCM).

General Procedure B for the Desilylation Reaction to Prepare Compounds 32a-32 h

The crude products 31a-31 h were dissolved in 12 ml NMP. After the addition of 2.1 g (2.9 ml, 20.6 mmol) NEt$_3$ and 1.14 g (1.15 ml, 6.9 mmol) NEt$_3$ 3 HF, the reaction mixture was stirred for 2 hours at 90° C. After cooling down to room temperature, the solution was poured into sat. NaHCO$_3$-solution and extracted twice with EtOAc. The organic layers were dried with MgSO$_4$ and evaporated. The residue was dissolved in acetonitril/H$_2$O and lyophillized. The obtained crude products were purified by silicagel chromatography, which gave the desired compounds 32a-32 h.

32a: 1-[(2R,6R)-6-[[bis(4-methoxyphenyl)-phenyl-methoxy]methyl]-6-(hydroxymethyl)-4-methyl-morpholin-2-yl]-5-methyl-pyrimidine-2,4-dione Following general procedure B starting with crude product 31a, final silicagel purification (0 to 5% MeOH in DCM) delivered 543 mg (66.0%, two steps) of the title compound 32a.
LCMS-Method A:
UV-wavelength [nm]=220: $R_t$[min]=1.59
Ionization method: ES$^+$: [M+H]$^+$=588.3
1H-NMR (DMSO-d6, 400 MHz) δ[ppm]: 11.37 (s, 1H), 7.52 (s, 1H), 7.40 (d, J=7.46 Hz, 2H), 7.19-7.32 (m, 7H), 6.87 (d, J=8.80 Hz, 4H), 5.85 (dd, J=9.78, 2.93 Hz, 1H), 4.63 (t, J=5.32 Hz, 1H), 3.70-3.78 (m, 7H), 3.65 (m, 1H), 2.96-3.06 (m, 2H), 2.81 (br d, J=9.29 Hz, 1H), 2.63-2.74 (m, 1H), 2.21 (s, 3H), 2.06-2.16 (m, 1H), 1.97-2.04 (m, 1H), 1.67 (s, 3H).

32b: 1-[(2R,6R)-6-[[bis(4-methoxyphenyl)-phenyl-methoxy]methyl]-4-butyl-6-(hydroxy-methyl)morpholin-2-yl]-5-methyl-pyrimidine-2,4-dione Following general procedure B starting with crude product 31b, final silicagel purification (0 to 5% MeOH in DCM) delivered 753 mg (85.5%, two steps) of the title compound 32b.
LCMS-Method A:
UV-wavelength [nm]=220: $R_t$[min]=1.75
Ionization method: $ES^+$: $[M+H]^+$=630.3
1H-NMR (DMSO-d6, 400 MHz) δ[ppm]: 11.36 (s, 1H), 7.54 (s, 1H), 7.40 (d, J=7.46 Hz, 2H), 7.20-7.34 (m, 7H), 6.87 (d, J=8.68 Hz, 4H), 5.85 (dd, J=9.66, 2.93 Hz, 1H), 4.62 (t, J=5.14 Hz, 1H), 3.70-3.78 (m, 7H), 3.65 (m, 1H), 2.96-3.09 (m, 2H), 2.86 (br d, J=9.05 Hz, 1H), 2.71-2.80 (m, 1H), 2.31 (br t, J=7.15 Hz, 2H), 1.99-2.22 (m, 2H), 1.67 (s, 3H), 1.20-1.45 (m, 4H), 0.88 (m, 3H).

32c: 1-[(2R,6R)-6-[[bis(4-methoxyphenyl)-phenyl-methoxy]methyl]-6-(hydroxymethyl)-4-octyl-morpholin-2-yl]-5-methyl-pyrimidine-2,4-dione Following general procedure B starting with crude product 31c, final silicagel purification (0 to 5% MeOH in DCM) delivered 751 mg (78.2%, two steps) of the title compound 32c.
LCMS-Method A:
UV-wavelength [nm]=220: $R_t$[min]=1.99
Ionization method: $ES^+$: $[M+H]^+$=686.4
1H-NMR (DMSO-d6, 400 MHz) δ[ppm]: 11.36 (b s, 1H), 7.54 (s, 1H), 7.40 (d, J=7.34 Hz, 2H), 7.19-7.34 (m, 7H), 6.87 (d, J=8.68 Hz, 4H), 5.84 (dd, J=9.72, 2.87 Hz, 1H), 4.61 (t, J=5.14 Hz, 1H), 3.69-3.82 (m, 7H), 3.64 (m, 1H), 2.97-3.14 (m, 2H), 2.82-2.91 (m, 1H), 2.70-2.76 (m, 1H), 2.30 (br t, J=7.09 Hz, 2H), 1.98-2.21 (m, 2H), 1.67 (s, 3H), 1.33-1.46 (m, 2H), 1.26 (m, 10H), 0.81-0.92 (m, 3H).

32d: 1-[(2R,6R)-6-[[bis(4-methoxyphenyl)-phenyl-methoxy]methyl]-4-hexadecyl-6-(hydroxymethyl)morpholin-2-yl]-5-methyl-pyrimidine-2,4-dione Following general procedure B starting with crude product 31d, final silicagel purification (0 to 5% MeOH in DCM) delivered 677 mg (60.6%, two steps) of the title compound 32d.
LCMS-Method A:
UV-wavelength [nm]=220: $R_t$[min]=2.44
Ionization method: $ES^+$: $[M+H]^+$=798.5
1H-NMR (DMSO-d6, 400 MHz) δ[ppm]: 11.36 (s, 1H), 7.54 (s, 1H), 7.40 (d, J=7.46 Hz, 2H), 7.18-7.34 (m, 7H), 6.86 (m, 4H), 5.84 (m, 1H), 4.61 (m, 1H), 3.69-3.80 (m, 7H), 3.64 (m, 1H), 2.97-3.07 (m, 2H), 2.85 (br d, J=8.80 Hz, 1H), 2.68-2.77 (m, 1H), 2.24-2.35 (m, 2H), 1.99-2.20 (m, 2H), 1.67 (s, 3H), 1.35-1.46 (m, 2H), 1.23 (s, 26H), 0.82-0.88 (m, 3H).

32e: 1-[(2R,6R)-6-[[bis(4-methoxyphenyl)-phenyl-methoxy]methyl]-4-cyclohexyl-6-(hydroxymethyl)morpholin-2-yl]-5-methyl-pyrimidine-2,4-dione Following general procedure B starting with crude product 31e, final silicagel purification (0 to 5% MeOH in DCM) delivered 701 mg (76.4%, two steps) of the title compound 32e.
LCMS-Method A:
UV-wavelength [nm]=220: $R_t$[min]=1.75
Ionization method: $ES^+$: $[M+H]^+$=656.4
1H-NMR (DMSO-d6, 400 MHz) δ[ppm]: 11.35 (s, 1H), 7.55 (s, 1H), 7.40 (d, J=7.46 Hz, 2H), 7.18-7.33 (m, 7H), 6.87 (d, J=8.93 Hz, 4H), 5.81 (m, 1H), 4.59 (t, J=5.20 Hz, 1H), 3.72-3.78 (m, 7H), 3.66 (m, 1H), 3.03 (m, 2H), 2.84 (br d, J=9.41 Hz, 1H), 2.66-2.73 (m, 1H), 2.23-2.39 (m, 3H), 1.64-1.78 (m, 4H), 1.68 (s, 3H), 0.99-1.27 (m, 6H).

32f: 1-[(2R,6R)-4-benzyl-6-[[bis(4-methoxyphenyl)-phenyl-methoxy]methyl]-6-(hydroxy-methyl)morpholin-2-yl]-5-methyl-pyrimidine-2,4-dione Following general procedure B starting with crude product 31f, final silicagel purification (0 to 5% MeOH in DCM) delivered 591 mg (63.6%, two steps) of the title compound 32f.
LCMS-Method A:
UV-wavelength [nm]=220: $R_t$[min]=1.94
Ionization method: $ES^+$: $[M+H]^+$=664.3
1H-NMR (DMSO-d6, 400 MHz) δ[ppm]: 11.33 (s, 1H), 7.52 (s, 1H), 7.18-7.39 (m, 14H), 6.86 (d, J=8.80 Hz, 4H), 5.86 (dd, J=9.66, 2.93 Hz, 1H), 4.62 (t, J=5.20 Hz, 1H), 3.83 (dd, J=10.94, 4.46 Hz, 1H), 3.73 (s, 6H), 3.66 (dd, J=11.00, 5.99 Hz, 1H), 3.47-3.61 (m, 2H), 3.01 (s, 2H), 2.72-2.84 (m, 2H), 2.22-2.31 (m, 1H), 2.14-2.21 (m, 1H), 1.66 (s, 3H).

32g: 1-[(2R,6R)-4-acetyl-6-[[bis(4-methoxyphenyl)-phenyl-methoxy]methyl]-6-(hydroxy-methyl)morpholin-2-yl]-5-methyl-pyrimidine-2,4-dione Following general procedure B starting with crude product 31g, final silicagel purification (0 to 5% MeOH in DCM) delivered 600 mg (69.6%, two steps) of the title compound 32g.
LCMS-Method A:
UV-wavelength [nm]=220: $R_t$[min]=1.77
Ionization method: $ES^-$: $[M-H]^-$=614.2
1H-NMR (DMSO-d6, 400 MHz) δ[ppm]: 11.43 (s, 1H), 7.64 (s, 0.65H), 7.58 (s, 0.35H), 7.36-7.47 (m, 2H), 7.20-7.33 (m, 7H), 6.84-6.91 (m, 4H), 5.88 (dd, J=10.58, 2.75 Hz, 0.35H), 5.74-5.80 (m, 0.65H), 5.00 (t, J=4.40 Hz, 0.65H), 4.63 (t, J=4.83 Hz, 0.35H), 4.39 (br d, J=10.88 Hz, 0.65H), 4.22 (br d, J=13.33 Hz, 0.35H), 3.89 (m, 0.35H), 3.74 (s, 6.65H), 3.42-3.65 (m, 2H), 3.35-3.41 (m, 1H), 3.00-3.12 (m, 2H), 2.83-2.98 (m, 1H), 2.03 (m, 3H), 1.73 (s, 3H).

32h: 1-[(2R,6R)-6-[[bis(4-methoxyphenyl)-phenyl-methoxy]methyl]-4-hexadecanoyl-6-(hydroxymethyl)morpholin-2-yl]-5-methyl-pyrimidine-2,4-dione Following general procedure B starting with crude product 31 h, final silicagel purification (0 to 5% MeOH in DCM) delivered 874 mg (76.9%, two steps) of the title compound 32h.
LCMS-Method A:
UV-wavelength [nm]=220: $R_t$[min]=2.33
Ionization method: $ES^+$: $[M+H]^+$=304.3 ($DMT^+$)
1H-NMR (DMSO-d6, 400 MHz) δ[ppm]: 11.42 (br s, 1H), 7.61, 7.57 (2×s, 1H), 7.41 (m, 2H), 7.20-7.34 (m, 7H), 6.87 (m, 4H), 5.84 (m, 0.5H), 5.77 (m, 0.5H), 4.95 (m, 0.5H), 4.64 (m, 0.5H), 4.40 (m, 0.5H), 4.24 (m, 0.5H), 3.95 (m, 0.5H), 3.69-3.84 (m, 0.5H), 3.74 (s, 6H), 3.41-3.62 (m, 2H), 3.00-3.15 (m, 2H), 2.22-2.40 (m, 1H), 1.72 (s, 3H), 1.47 (br s, 2H), 1.23 (br s, 26H), 0.82-0.90 (m, 3H).

General Procedure C for the Preparation of Phosphoramidites 33a-33 h

The starting material 32a-32 h (1.0 mmol) and diisopropylammonium tetrazolide (3.0 mmol) were dissolved in 25 ml dry DCM. After adding 2-cyanoethyl N,N,N',N'-tetraisopropylphosphorodiamidite (1.5 mmol), the solution was stirred under an atmosphere of argon at room temperature. After 1.5 hours, the reaction solution was washed with 50 ml $H_2O$. The layers were separated and the aqeuous phase was extracted with DCM. The combined organic layers were dried with $MgSO_4$ and evaporated. The crude products were purified by silicagel chromatography (0 to 100% methyl-tert.-butylether in n-heptane, column preconditioned with n-heptane+1% $NEt_3$), yielding the final phosphoroamidites 33a-33 h.

33a: 3-[[(2S,6R)-2-[[bis(4-methoxyphenyl)-phenyl-methoxy]methyl]-4-methyl-6-(5-methyl-2,4-dioxo-pyrimidin-1-yl)morpholin-2-yl]methoxy-(diisopropylamino)phosphanyl]oxypropanenitrile Following general procedure C, 32a (540 mg, 0.92 mmol) was converted to the title compound 33a, which was isolated as colourless foam (568 mg, 78.5%).

1H-NMR (DMSO-d6, 400 MHz) δ[ppm]: 11.35 (br s, 1H), 7.54, 7.52 (2×s, 1H), 7.35-7.44 (m, 2H), 7.20-7.32 (m, 7H), 6.86 (d, J=8.85 Hz, 4H), 5.90 (m, 1H), 4.02 (m, 1H), 3.79-3.92 (m, 1H), 3.73 (s, 6H), 3.39-3.64 (m, 4H), 2.98-3.12 (m, 2H), 2.66-2.84 (m, 3H), 2.53-2.64 (m, 1H), 2.23, 2.21 (2×s, 3H), 1.99-2.18 (m, 2H), 1.72, 1.69 (2×s, 3H), 0.91-1.12 (m, 12H).

31P-NMR (DMSO-d6, 162 MHz) δ[ppm]: 147.9, 147.7.

33b: 3-[[(2S,6R)-2-[[bis(4-methoxyphenyl)-phenyl-methoxy]methyl]-4-butyl-6-(5-methyl-2,4-dioxo-pyrimidin-1-yl)morpholin-2-yl]methoxy-(diisopropylamino)phosphanyl]oxypropanenitrile Following general procedure C, 32b (750 mg, 0.98 mmol) was converted to the title compound 33b, which was isolated as colourless foam (569 mg, 70.2%).

1H-NMR (DMSO-d6, 400 MHz) δ[ppm]: 11.36 (br s, 1H), 7.57, 7.54 (2×s, 1H), 7.35-7.44 (m, 2H), 7.20-7.32 (m, 7H), 6.86 (d, J=8.78 Hz, 4H), 5.90 (m, 1H), 3.83-4.01 (m, 2H), 3.73 (s, 6H), 3.53-3.64 (m, 2H), 3.39-3.52 (m, 2H), 3.06-3.15 (m, 1H), 2.96-3.05 (m, 1H), 2.73-2.90 (m, 2H), 2.63-2.70 (m, 1H), 2.59 (m, 1H), 2.24-2.48 (m, 2H), 1.99-2.19 (m, 2H), 1.73, 1.70 (2×s, 3H), 1.27-1.42 (m, 4H), 0.95-1.18 (m, 12H), 0.87 (m, 3H).

31P-NMR (DMSO-d6, 162 MHz) δ[ppm]: 147.4, 147.0.

33c: 3-[[(2S,6R)-2-[[bis(4-methoxyphenyl)-phenyl-methoxy]methyl]-6-(5-methyl-2,4-dioxo-pyrimidin-1-yl)-4-octyl-morpholin-2-yl]methoxydiisopropylamino)phosphanyl]oxypropanenitrile Following general procedure C, 32c (745 mg, 1.0 mmol) was converted to the title compound 33c, which was isolated as colourless foam (537 mg, 60.6%).

1H-NMR (DMSO-d6, 400 MHz) δ[ppm]: 11.37, 11.36 (2×s, 1H), 7.56, 7.53 (2×s, 1H), 7.40 (m, 2H), 7.20-7.31 (m, 7H), 6.86 (d, J=8.72 Hz, 4H), 5.89 (m, 1H), 3.75-4.02 (m, 2H), 3.73 (s, 6H), 3.53-3.63 (m, 2H), 3.41-3.52 (m, 2H), 3.10 (m, 1H), 2.95-3.05 (m, 1H), 2.73-2.89 (m, 2H), 2.52- 2.69 (m, 2H), 2.23-2.41 (m, 2H), 1.98-2.18 (m, 2H), 1.73, 1.70 (2×s, 3H), 1.14-1.49 (m, 12H), 0.96-1.11 (m, 12H), 0.85 (m, 3H).

31P-NMR (DMSO-d6, 162 MHz) δ[ppm]: 147.3, 147.1.

33d: 3-[[(2S,6R)-2-[[bis(4-methoxyphenyl)-phenyl-methoxy]methyl]-4-hexadecyl-6-(5-methyl-2,4-dioxo-pyrimidin-1-yl)morpholin-2-yl]methoxy-(diisopropylamino)phosphanyl]-oxypropanenitrile Following general procedure C, 32d (675 mg, 0.77 mmol) was converted to the title compound 33d, which was isolated as colourless foam (608 mg, 79.1%).

1H-NMR (DMSO-d6, 400 MHz) [ppm]: 11.36 (br s, 1H), 7.56, 7.53 (2×s, 1H), 7.37-7.42 (m, 2H), 7.19-7.31 (m, 7H), 6.86 (d, J=8.85 Hz, 4H), 5.89 (m, 1H), 3.82-4.02 (m, 2H), 3.73 (s, 6H), 3.53-3.63 (m, 2H), 3.39-3.52 (m, 2H), 3.07-3.13 (m, 1H), 2.95-3.05 (m, 1H), 2.71-2.90 (m, 2H), 2.62-2.68 (m, 1H), 2.58 (m, 1H), 2.23-2.39 (m, 2H), 1.96-2.18 (m, 2H), 1.73, 1.70 (2×s, 3H), 1.13-1.45 (m, 28H), 0.96-1.13 (m, 12H), 0.82-0.88 (m, 3H).

31P-NMR (DMSO-d6, 162 MHz) δ[ppm]: 147.3, 147.1.

33e: 3-[[(2S,6R)-2-[[bis(4-methoxyphenyl)-phenyl-methoxy]methyl]-4-cyclohexyl-6-(5-methyl-2,4-dioxo-pyrimidin-1-yl)morpholin-2-yl]methoxy-(diisopropylamino)phosphanyl]oxy-propanenitrile Following general procedure C, 32e (695 mg, 0.86 mmol) was converted to the title compound 33e, which was isolated as colourless foam (560 mg, 76.2%).

1H-NMR (DMSO-d6, 400 MHz) δ[ppm]: 11.36, 11.35 (2×br s, 1H), 7.57, 7.54 (2×s, 1H), 7.37-7.43 (m, 2H), 7.21-7.31 (m, 7H), 6.86 (d, J=8.85 Hz, 4H), 5.86 (m, 1H), 3.87-4.02 (m, 2H), 3.73 (s, 6H), 3.53-3.65 (m, 2H), 3.40-3.52 (m, 2H), 3.12 (m, 1H), 3.00 (m, 1H), 2.79-2.88 (m, 1H), 2.64-2.77 (m, 2H), 2.54-2.63 (m, 1H), 2.23-2.41 (m, 3H), 1.64-1.73 (s, 7H), 0.91-1.25 (m, 18H).

31P-NMR (DMSO-d6, 162 MHz) δ[ppm]: 147.2, 146.7.

33f: 3-[[(2S,6R)-4-benzyl-2-[[bis(4-methoxyphenyl)-phenyl-methoxy]methyl]-6-(5-methyl-2,4-dioxo-pyrimidin-1-yl)morpholin-2-yl]methoxy-(diisopropylamino)phosphanyl]oxy-propanenitrile Following general procedure C, 32f (589 mg, 0.78 mmol) was converted to the title compound 33f, which was isolated as colourless foam (668 mg, 99.0%).

1H-NMR (DMSO-d6, 400 MHz) δ[ppm]: 11.34 (s, 1H), 7.54, 7.53 (2×s, 1H), 7.19-7.39 (m, 14H), 6.80-6.89 (m, 4H), 5.92 (m, 1H), 4.10 (dd, J=9.94, 7.56 Hz, 0.5H), 4.01 (m, 0.5H), 3.93 (m, 0.5H), 3.85 (m, 0.5H), 3.73 (s, 6H), 3.35-3.64 (m, 6H), 3.03-3.12 (m, 2H), 2.98 (d, J=9.10 Hz, 1H), 2.72-2.91 (m, 2H), 2.62-2.69 (m, 1H), 2.12-2.26 (m, 2H), 1.71, 1.70 (2×s, 3H), 0.97-1.10 (m, 9H), 0.91 (d, J=6.71 Hz, 3H).

31P-NMR (DMSO-d6, 162 MHz) δ[ppm]: 147.2.

33g: 3-[[(2S,6R)-4-acetyl-2-[[bis(4-methoxyphenyl)-phenyl-methoxy]methyl]-6-(5-methyl-2,4-dioxo-pyrimidin-1-yl)morpholin-2-yl]methoxy-(diisopropylamino)phosphanyl]oxy-propanenitrile Following general procedure C, 32g (598 mg, 0.89 mmol) was converted to the title compound 33g, which was isolated as colourless foam (728 mg, quant.). Purification of the crude product was done by dissolving in 10 ml tert.-butylmethylether and adding 40 ml of n-pentane. The precipitate was centrifuged and the supernatant was discarded. This washing procedure was repeated for another two times.

1H-NMR (DMSO-d6, 400 MHz) δ[ppm]: 11.41 (br s, 1H), 7.56-7.71 (m, 1H), 7.35-7.46 (m, 2H), 7.20-7.33 (m, 7H), 6.82-6.91 (m, 4H), 5.79-5.97 (m, 1H), 4.27-4.45 (m, 1H), 3.53-3.97 (m, 4H), 3.73 (s, 6H), 3.32-3.50 (m, 4H), 3.02-3.19 (m, 2H), 2.80-3.00 (m, 1H), 2.55-2.74 (m, 2H), 1.99-2.09 (m, 3H), 1.69-1.81 (m, 3H), 1.04-1.13 (m, 9H), 0.97-1.03 (m, 3H).

31P-NMR (DMSO-d6, 162 MHz) δ[ppm]: 147.9, 146.9, 146.8, 146.5.

3.53-3.65 (m, 2H), 3.37-3.52 (m, 2H), 3.02-3.25 (m, 2H), 2.82-3.00 (m, 1H), 2.67 (m, 1H), 2.58 (m, 1H), 2.21-2.48 (m, 2H), 1.69-1.80 (m, 3H), 1.49 (br s, 2H), 1.18-1.31 (m, 26H), 1.04-1.12 (m, 6H), 0.92-1.03 (m, 6H), 0.82-0.89 (m, 3H).

31P-NMR (DMSO-d6, 162 MHz) δ[ppm]: 147.7, 147.3, 147.2, 146.7.

Example A.9

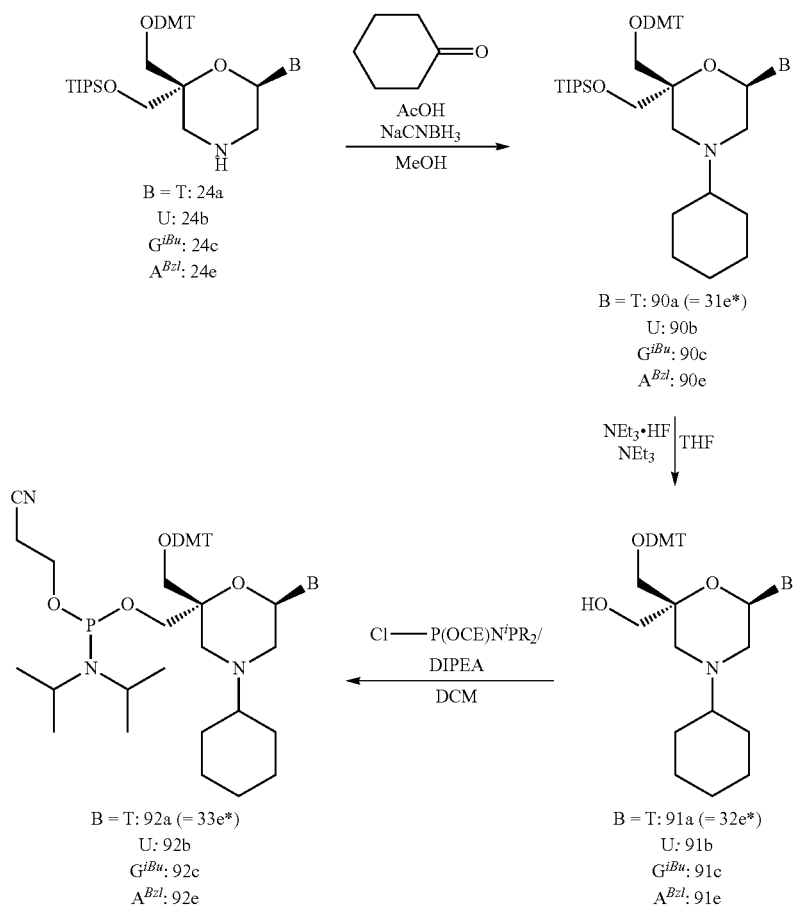

*: see Synthetic Scheme 8

33h: 3-[[(2S,6R)-2-[[bis(4-methoxyphenyl)-phenyl-methoxy]methyl]-4-hexadecanoyl-6-(5-methyl-2,4-dioxo-pyrimidin-1-yl)morpholin-2-yl]methoxy-(di-isopropylamino)phosphanyl]oxy-propanenitrile Following general procedure C, 32 h (872 mg, 1.03 mmol) was converted to the title compound 33h, which was isolated as colourless foam (915 mg, 87.7%).

1H-NMR (DMSO-d6, 400 MHz) δ[ppm]: 11.42, 11.40 (2×s, 1H), 7.55-7.71 (m, 1H), 7.40 (m, 2H), 7.18-7.34 (m, 7H), 6.82-6.91 (m, 4H), 5.73-5.99 (m, 1H), 4.27-4.50 (m, 1H), 3.98 (m, 0.5H), 3.75-3.85 (m, 1.5H), 3.73 (s, 6H), 90b: 1-[(2R,6S)-6-[[bis(4-methoxyphenyl)-phenyl-methoxy]methyl]-4-cyclohexyl-6-(triisopropylsily-loxymethyl)morpholin-2-yl]pyrimidine-2,4-dione To a mixture of 24b (25 g, 33 mmol), cyclohexanone (16.1 g, 165 mmol) and 4 Å MS (30 g) in MeOH (450 ml) was added AcOH, to adjust the pH between 5 and 6 at 25° C. After stirring at 40° C. for 1 h, NaBH₃CN (10.3 g, 165 mmol) was added portionwise at 40° C. Stirring was continued for 12 h to achieve complete conversion. The mixture was filtered and the filtrate was concentrated i. vac. The residue was diluted with EtOAc (1500 ml), washed with H₂O (2×500 ml) and sat. NaCl-solution (500 ml). The organic layer was dried with Na₂SO₄, filtered and concentrated i. vac. The residue was purified by column chromatography (PE/EtOAc 2:1) yielding 28 g (82%) of 90b as colourless foam.

1H-NMR (DMSO-d6, 400 MHz) δ[ppm]: 11.42 (br s, 1H), 7.71 (d, J=8.1 Hz, 1H), 7.41 (br d, J=7.5 Hz, 2H), 7.31-7.19 (m, 7H), 6.85 (d, J=8.8 Hz, 4H), 5.82 (br dd, J=2.6, 9.8 Hz, 1H), 5.73 (d, J=8.1 Hz, 1H), 4.14 (br d, J=8.9 Hz, 1H), 3.93 (br d, J=8.8 Hz, 1H), 3.74 (d, J=2.0 Hz, 6H), 3.13 (br d, J=9.4 Hz, 1H), 2.99-2.83 (m, 2H), 2.72 (br d, J=10.8 Hz, 1H), 2.31-2.17 (m, 3H), 1.78-1.48 (m, 5H), 1.32-1.09 (m, 6H), 1.01-0.83 (m, 21H).

91b: 1-[(2R,6R)-6-[[bis(4-methoxyphenyl)-phenyl-methoxy]methyl]-4-cyclohexyl-6-(hydroxymethyl)morpholin-2-yl]pyrimidine-2,4-dione To a solution of compound 90b (28 g, 35.1 mmol) in THF (280 ml) was added NEt$_3$ (35 g, 351 mmol) and NEt$_3$ 3 HF (56.3 g, 351 mmol) at room temperature. After stirring at 70° C. for 16 h under N$_2$-atmosphere, full deprotection could be detected by TLC. The mixture was concentrated i. vac. and the residue was diluted with EtOAc (500 ml). The organic solution was washed with water (2×200 ml) and sat. NaCl-solution (200 ml), dried with Na$_2$SO$_4$, filtered and concentrated i. vac. The crude product was purified by column chromatography (PE/EtOAc 1:2), which gave 20 g (88.8%) of the title compound 91b as colourless foam.

1H-NMR (DMSO-d6, 400 MHz) δ[ppm]: 11.41 (br s, 1H), 7.66 (d, J=8.1 Hz, 1H), 7.47-7.40 (m, 2H), 7.36-7.21 (m, 7H), 6.92 (br d, J=8.7 Hz, 4H), 5.84 (br dd, J=2.3, 9.4 Hz, 1H), 5.65 (br d, J=7.9 Hz, 1H), 4.67 (br s, 1H), 3.88 (br d, J=10.9 Hz, 1H), 3.78 (s, 6H), 3.72 (br d, J=10.5 Hz, 1H), 3.15 (br d, J=9.0 Hz, 1H), 3.10-2.96 (m, 2H), 2.91 (br d, J=9.8 Hz, 1H), 2.73 (br d, J=11.5 Hz, 1H), 2.35-2.18 (m, 3H), 1.73 (br s, 4H), 1.32-1.10 (m, 9H).

92b: 3-[[(2S,6R)-2-[[bis(4-methoxyphenyl)-phenyl-methoxy]methyl]-4-cyclohexyl-6-(2,4-dioxopyrimidin-1-yl)morpholin-2-yl]methoxy-(diisopropylamino)phosphanyl]-oxypropanenitrile To a solution of 91b (14 g, 22.4 mmol) in DCM (150 ml) was added DIPEA (11.5 g, 89.8 mmol) and 3-[chloro-(diisopropylamino)phosphanyl]oxypropanenitrile (6.9 g, 29.2 mmol) under an atmosphere of argon. The solution was stirred at 13° C. for 0.5 h to achieve complete conversion. The reaction mixture was concentrated i. vac. to a volume of approx. 50 ml and purified on silica (PE/EtOAc 2:1) yielding 12.0 g (65.5%) 92b as colourless foam.

LCMS-Method C:
UV-wavelength [nm]=220: R$_t$[min]=2.60
Ionization method: ES$^+$: [M+H-$^i$Pr$_2$N+OH]$^+$=759.5
1H-NMR (DMSO-d6, 400 MHz) 11.34 (br s, 1H), 7.59-7.69 (2×d, J=8.0 Hz, 1H), 7.35-7.44 (m, 2H), 7.20-7.32 (m, 7H), 6.87 (m, 4H), 5.84 (m, 1H), 5.59-5.68 (2×d, J=8.1 Hz, 1H), 3.99-4.09 (m, 1H), 3.93 (m, 1H), 3.73 (s, 6H), 3.54-3.68 (m, 2H), 3.40-3.53 (m, 2H), 3.16 (br d, J=8.9 Hz, 1H), 2.96 (t, J=9.5 Hz, 1H), 2.88 (m, 1H), 2.66-2.80 (m, 2H), 2.60 (m, 1H), 2.15-2.35 (m, 3H), 1.69 (m, 4H), 1.53 (m, 1H), 0.95-1.21 (m, 17H).
31P-NMR (DMSO-d6, 162 MHz) δ[ppm]: 147.4, 146.7.

90c: N-[9-[(2R,6S)-6-[[bis(4-methoxyphenyl)-phenyl-methoxy]methyl]-4-cyclohexyl-6-(triisopropylsilyloxymethyl)morpholin-2-yl]-6-oxo-1H-purin-2-yl]-2-methyl-propanamide Following the protocol, described for the synthesis of 90b, 35 g (42.4 mmol) of the starting material 24c gave, after silica gel purification (PE/EtOAc 1:1), 32 g (64.7%) of the desired product 90c as colourless foam.

LCMS-Method D:
UV-wavelength [nm]=220: R$_t$[min]=1.18
Ionization method: ES$^+$: [M+H]$^+$=907.5

91c: N-[9-[(2R,6R)-6-[[bis(4-methoxyphenyl)-phenyl-methoxy]methyl]-4-cyclohexyl-6-(hydroxymethyl)morpholin-2-yl]-6-oxo-1H-purin-2-yl]-2-methyl-propanamide Following the protocol, described for the synthesis of 91b, 32 g (35.3 mmol) of the starting material 90c gave, after silica gel chromatography (PE/EtOAc 1:2), 21 g (79%) of the desired product 91c as colourless foam.

1H-NMR (DMSO-d6, 400 MHz) δ[ppm]: 12.10 (s, 1H), 11.68 (s, 1H), 8.04 (s, 1H), 7.38 (d, J=7.3 Hz, 2H), 7.31-7.20 (m, 7H), 6.85 (d, J=8.7 Hz, 4H), 5.91 (dd, J=3.1, 8.8 Hz, 1H), 4.63 (t, J=5.2 Hz, 1H), 3.87-3.78 (m, 1H), 3.74 (s, 7H), 3.06-2.94 (m, 3H), 2.84-2.65 (m, 3H), 2.43 (d, J=11.6 Hz, 1H), 2.37-2.28 (m, 1H), 2.37-2.28 (m, 1H), 1.72 (br s, 4H), 1.56 (br d, J=10.8 Hz, 1H), 1.27-1.02 (m, 13H).

92c: N-[9-[(2R,6S)-6-[[bis(4-methoxyphenyl)-phenyl-methoxy]methyl]-6-[[2-cyanoethoxy-(diisopropylamino)phosphanyl]oxymethyl]-4-cyclohexyl-morpholin-2-yl]-6-oxo-1H-purin-2-yl]-2-methyl-propanamide Following the protocol, described for the synthesis of 92b, 20 g (26.6 mmol) of the starting material 91c gave, after a reaction time of 15 min at room temperature and silica gel chromatography (PE/EtOAc 1:1), 20 g (79%) of the desired product 92c as colourless foam.

LCMS-Method C:
UV-wavelength [nm]=220: R$_t$[min]=2.70, 2.73
Ionization method: ES$^+$: [M+H-$^i$Pr$_2$N+OH]$^+$=868.5
1H-NMR (DMSO-d6, 400 MHz) 12.08 (br s, 1H), 11.63 (br s, 1H), 8.07, 8.03 (2×s, 1H), 7.37 (d, J=8.2 Hz, 2H), 7.18-7.29 (m, 7H), 6.79-6.87 (m, 4H), 5.89 (m, 1H), 3.92-4.11 (m, 2H), 3.72-3.74 (m, 6H), 3.55-3.72 (m, 2H), 3.38-3.51 (m, 2H), 3.10 (m, 1H), 2.96-3.05 (m, 2H), 2.66-2.93 (m, 4H), 2.55-2.62 (m, 1H), 2.27-2.45 (m, 2H), 1.71 (m, 4H), 1.55 (m, 1H), 0.83-1.29 (m, 23H).
31P-NMR (DMSO-d6, 162 MHz) δ[ppm]: 147.5, 146.7.

90e: N-[9-[(2R,6S)-6-[[bis(4-methoxyphenyl)-phenyl-methoxy]methyl]-4-cyclohexyl-6-(triisopropylsilyloxymethyl)morpholin-2-yl]purin-6-yl]benzamide Following the protocol, described for the synthesis of 90b, 58 g (68.8 mmol) of the starting material 24e gave, after silica gel purification (PE/EtOAc 2:1), 49 g (77%) of the desired product 90e as colourless foam.

1H-NMR (DMSO-d6, 400 MHz) δ[ppm]: 11.21 (br s, 1H), 8.77 (s, 1H), 8.66 (s, 1H), 8.06 (br d, J=7.2 Hz, 2H), 7.68-7.61 (m, 1H), 7.60-7.52 (m, 2H), 7.38 (dd, J=1.6, 7.8 Hz, 2H), 7.26-7.15 (m, 7H), 6.76 (dd, J=3.1, 9.0 Hz, 4H), 6.16 (dd, J=3.1, 9.7 Hz, 1H), 4.29 (d, J=9.0 Hz, 1H), 3.95 (d, J=8.8 Hz, 1H), 3.70 (d, J=1.0 Hz, 6H), 3.17-3.02 (m, 3H), 2.94 (d, J=9.3 Hz, 1H), 2.83 (br d, J=11.1 Hz, 1H), 2.36-2.30 (m, 1H), 1.82-1.70 (m, 4H), 1.55 (br d, J=11.2 Hz, 1H), 1.34-1.15 (m, 8H), 1.04-0.91 (m, 23H).

91e: N-[9-[(2R,6R)-6-[[bis(4-methoxyphenyl)-phenyl-methoxy]methyl]-4-cyclohexyl-6-(hydroxymethyl)morpholin-2-yl]purin-6-yl]benzamide Following the protocol, described for the synthesis of 91b, 49 g (53.0 mmol) of the starting material 90e gave, after a reaction time of 12 h and silica gel chromatography (PE/EtOAc 1:2), 38 g (88%) of the desired product 91e as colourless foam.

LCMS-Method D:
UV-wavelength [nm]=220: $R_t$[min]=0.94
Ionization method: ES⁺: [M+H]⁺=769.4

92e: N-[9-[(2R,6S)-6-[[bis(4-methoxyphenyl)-phenyl-methoxy]methyl]-6-[[2-cyanoethoxy-(diisopropylamino)phosphanyl]oxymethyl]-4-cyclohexyl-morpholin-2-yl]purin-6-yl]benzamide Following the protocol, described for the synthesis of 92b, 22 g (31.2 mmol) of the starting material 91e gave, after a reaction time of 15 min at room temperature and silica gel chromatography (PE/EtOAc 1:1), 22.3 g (80.5%) of the desired product 92e as colourless foam.

LCMS-Method C:
UV-wavelength [nm]=220: $R_t$[min]=2.78
Ionization method: ES⁺: [M+H–$^i$Pr$_2$N+OH]⁺=886.6
1H-NMR (DMSO-d6, 400 MHz) 11.18 (s, 1H), 8.75, 8.73 (2×s, 1H), 8.59, 8.57 (2×s, 1H), 8.04 (d, J=7.8 Hz, 2H), 7.64 (t, J=7.3 Hz, 1H), 7.55 (t, J=7.6 Hz, 2H), 7.37 (m, 2H), 7.17-7.27 (m, 7H), 6.77-6.84 (m, 4H), 6.18 (m, 1H), 3.97-4.17 (m, 2H), 3.71 (m, 6H), 3.56-3.71 (m, 2H), 3.43-3.56 (m, 2H), 2.92-3.15 (m, 4H), 2.78-2.91 (m, 1H), 2.70 (t, J=6.0 Hz, 1H), 2.55-2.62 (m, 1H), 2.31-2.47 (m, 2H), 1.74 (m, 4H), 1.55 (m, 1H), 0.90-1.29 (m, 17H).
31P-NMR (DMSO-d6, 162 MHz) δ[ppm]: 147.0, 146.7.

Example A.10

93: 1-[(2R,6S)-6-[[bis(4-methoxyphenyl)-phenyl-methoxy]methyl]-4-cyclohexyl-6-(triisopropylsilyloxymethyl)morpholin-2-yl]-4-(1,2,4-triazol-1-yl)pyrimidin-2-one To a mixture of 1,2,4-triazole (41.5 g, 0.601 mol) in ACN (415 ml) was added POCl$_3$ (30.58 g, 0.20 mol) dropwise at 20° C. At 0° C., DIPEA (126 g, 0.977 mol) was added carefully and stirring was continued for 5 h at 0° C., followed by the addition of the starting material 90b (20 g, 25.0 mmol) in one portion. The solution was stirred for 3 h at 20° C. to achieve complete conversion. The reaction mixture was poured into EtOAc (500 ml) and water (1 l). The organic layer was separated and the aqueous phase was extracted with EtOAc (2×200 ml). The combined organic phases were washed with sat. NaHCO$_3$— (500 ml) and sat. NaCl-solution (500 ml), dried over anhydrous Na$_2$SO$_4$, filtered and concentrated i.vac., yielding the title compound 93 (29 g, crude) as yellow foam, which was used without further purification.

90f: N-[1-[(2R,6S)-6-[[bis(4-methoxyphenyl)-phenyl-methoxy]methyl]-4-cyclohexyl-6-(triisopropylsilyloxymethyl)morpholin-2-yl]-2-oxo-pyrimidin-4-yl]benzamide To a solution of benzamide (30.3 g, 0.251 mol) in dioxane (310 ml). was added NaH (10 g, 251 mmol) portionwise at 0° C. After stirring at 20° C. for 30 min, triazole 93 (29 g, crude product 25.0 mmol) was added and stirring was continued for 2 h to achieve complete conversion. The Synthetic Scheme 10

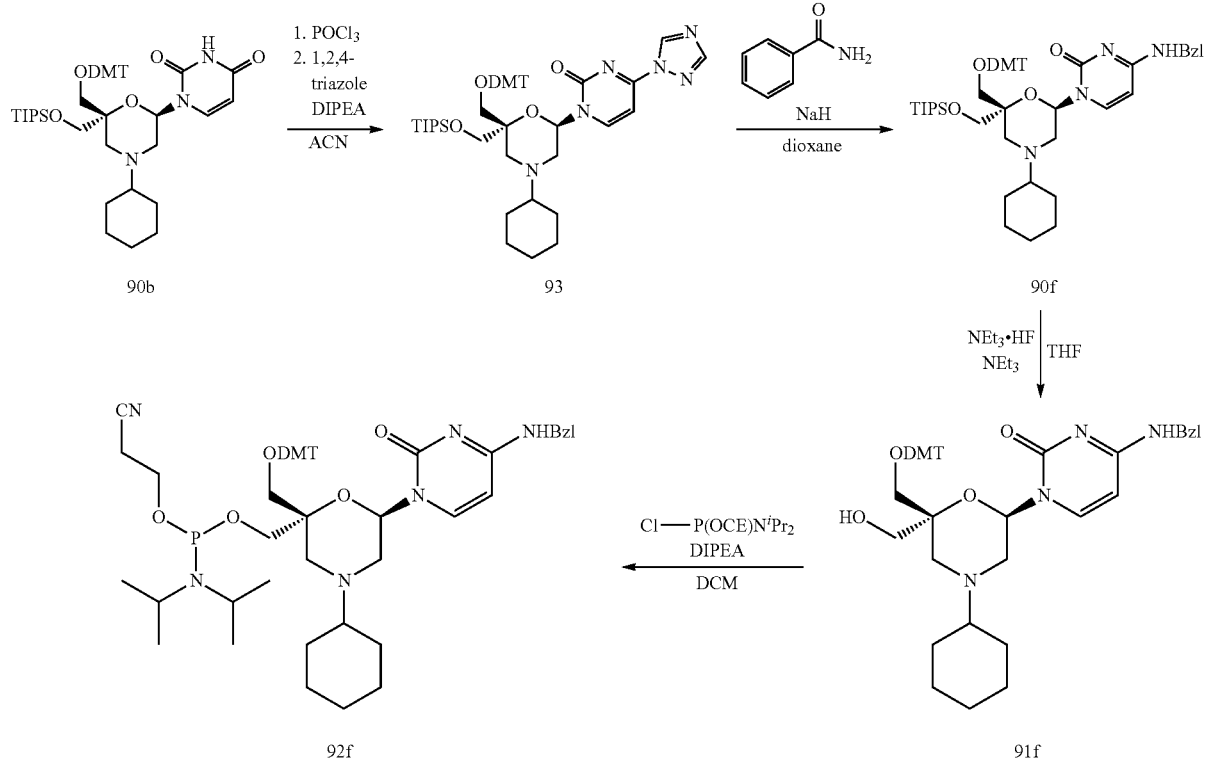

reaction mixture was poured into EtOAc (500 ml) and sat. NH₄Cl-solution (8 l). The aqueous layer was separated and extracted with EtOAc (2×500 ml). The combined organic phases were washed with water (2×500 ml) and sat. NaCl-solution (500 ml), dried over anhydrous $Na_2SO_4$ and concentrated i. vac. The residue was purified by column chromatography (PE/EA 5:1) to give 90f (16 g, 70.8%) as yellow foam.
LCMS-Method E:
UV-wavelength [nm]=220: $R_t$[min]=1.16
Ionization method: ES⁺: [M+H]⁺=901.6

91f: N-[1-[(2R,6R)-6-[[bis(4-methoxyphenyl)-phenyl-methoxy]methyl]-4-cyclohexyl-6-(hydroxymethyl)morpholin-2-yl]-2-oxo-pyrimidin-4-yl]benzamide Following the protocol, described for the synthesis of 91b, 40 g (44.4 mmol) of the starting material 90f gave, after a reaction time of 16 h and silica gel chromatography (PE/EtOAc 1:1), 24 g (72.7%) of the desired product 91f as colourless foam.
LCMS-Method E:
UV-wavelength [nm]=220: $R_t$[min]=0.92
Ionization method: ES⁺: [M+H]⁺=745.3

92f: N-[1-[(2R,6S)-6-[[bis(4-methoxyphenyl)-phenyl-methoxy]methyl]-6-[[2-cyanoethoxy-(diisopropylamino)phosphanyl]oxymethyl]-4-cyclohexyl-morpholin-2-yl]-2-oxo-pyrimidin-4-yl]benzamide Following the protocol, described for the synthesis of 92b, 16 g 22.8 mmol) of the starting material 91f gave, after a reaction time of 15 min at room temperature and silica gel chromatography (PE/EtOAc 1:1), 17 g (65.5%) of the desired product 92f as colourless foam.
LCMS-Method C:
UV-wavelength [nm]=220: $R_t$[min]=2.92
Ionization method: ES⁺: [M+H-$^i$Pr₂N+OH]⁺=862.5
1H-NMR (DMSO-d6, 400 MHz) 11.29, 11.26 (2×br s, 1H), 8.14, 8.09 (2×br d, J=7.6 Hz, 1H), 8.01 (br d, J=7.8 Hz, 2H), 7.63 (m, 1H), 7.51 (t, J=7.3 Hz, 2H), 7.35-7.45 (m, 3H), 7.21-7.34 (m, 7H), 6.88 (m, 4H), 5.96 (m, 1H), 3.94-4.15 (m, 2H), 3.74 (s, 6H), 3.55-3.69 (m, 2H), 3.41-3.53 (m, 2H), 3.19-3.28 (m, 1H), 2.95-3.08 (m, 2H), 2.66-2.92 (m, 2H), 2.52-2.64 (m, 1H), 2.32 (m, 1H), 2.13-2.28 (m, 2H), 1.70 (m, 4H), 1.54 (m, 1H), 0.91-1.27 (m, 17H).
31P-NMR (DMSO-d6, 162 MHz) [ppm]: 147.5, 146.7.

Example A.11

Synthetic Scheme 11

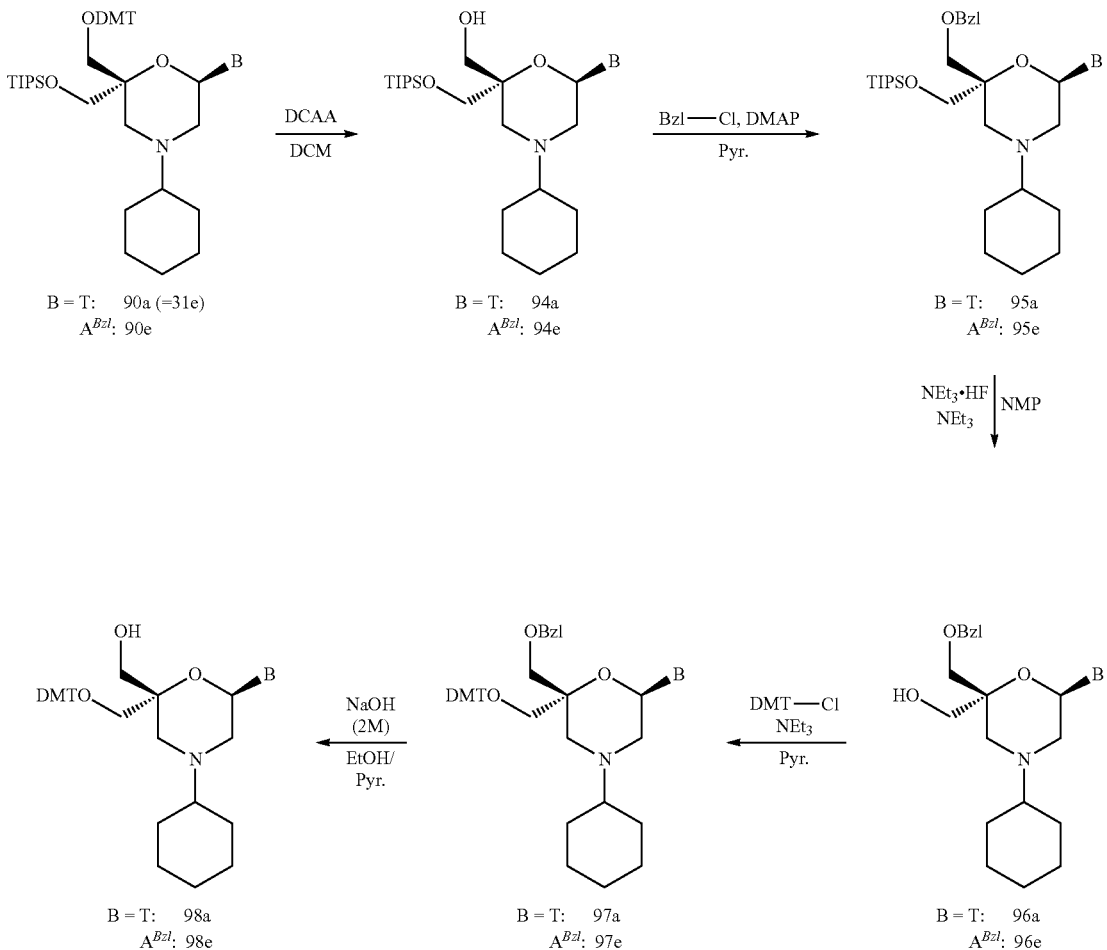

B = T:   90a (=31e)
A$^{Bzl}$: 90e

B = T:   94a
A$^{Bzl}$: 94e

B = T:   95a
A$^{Bzl}$: 95e

B = T:   98a
A$^{Bzl}$: 98e

B = T:   97a
A$^{Bzl}$: 97e

B = T:   96a
A$^{Bzl}$: 96e

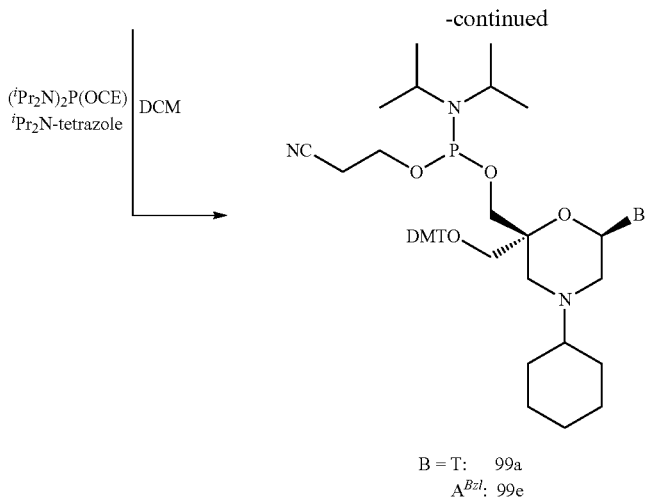

B = T: 99a
A^{Bzl}: 99e

94a: 1-[(2R,6S)-4-cyclohexyl-6-(hydroxymethyl)-6-(triisopropylsilyloxymethyl)-morpholin-2-yl]-5-methyl-pyrimidine-2,4-dione 5.09 g (6.26 mmol) of the DMT-ether 90a were deprotected with dichloroacetic acid, following the protocol, described for the synthesis of the dioxane analog 40e. After chromatographic purification on silica (0 to 10% MeOH in DCM) the desired product 94a was isolated as colourless foam (3.07 g, 96.0%).

LCMS-Method C:
UV-wavelength [nm]=220: $R_t$[min]=2.47
Ionization method: ES$^+$: [M+H]$^+$=510.3
1H-NMR (DMSO-d6, 400 MHz) δ[ppm]: 11.29 (s, 1H), 7.61 (s, 1H), 5.75 (dd, J=9.9, 2.7 Hz, 1H), 4.60 (t, J=6.0 Hz, 1H), 3.97 (d, J=9.3 Hz, 1H), 3.77 (d, J=9.3 Hz, 1H), 3.38-3.53 (m, 2H), 2.78 (m, 2H), 2.15-2.38 (m, 3H), 1.78 (s, 3H), 1.65-1.76 (m, 4H), 1.50-1.59 (m, 1H), 1.13-1.27 (m, 5H), 0.99-1.13 (m, 21H).

95a: [(2S,6R)-4-cyclohexyl-6-(5-methyl-2,4-dioxo-pyrimidin-1-yl)-2-(triiso-propylsilyloxy-methyl)morpholin-2-yl]methyl benzoate 3.05 g (6.0 mmol) of the starting material 94a were dissolved in 60 ml dry pyridine. At room temperature, 1.06 g (877.6 µl, 7.5 mmol) benzoyl chloride and 745.9 mg (6.0 mmol) DMAP were added and the solution was stirred for 4 h. After adding additional 212.0 mg (175.5 µl, 1.5 mmol) benzoyl chloride, the solution was stirred overnight, when complete conversion was detected. The solvent was removed i. vac. and the residue dissolved in EtOAc. The solution was washed with 5% citric acid-, sat. NaHCO$_3$- and sat. NaCl-solution, dried with MgSO$_4$ and evaporated. Purification on silica (0 to 5% MeOH in DCM) yielded 3.05 g (83.0%) of the benzoate 95a as colourless foam.

LCMS-Method C:
UV-wavelength [nm]=220: $R_t$[min]=3.57
Ionization method: ES$^+$: [M+H]$^+$=614.5
1H-NMR (DMSO-d6, 400 MHz) δ[ppm]: 11.32 (s, 1H), 7.97-8.02 (m, 2H), 7.68 (s, 1H), 7.52-7.58 (m, 2H), 7.47-7.49 (m, 1H), 5.80 (dd, J=9.9, 2.9 Hz, 1H), 4.40 (d, J=11.3 Hz, 1H), 4.31 (d, J=11.4 Hz, 1H), 4.17 (d, J=9.4 Hz, 1H), 3.95 (d, J=9.4 Hz, 1H), 2.95 (br d, J=11.5 Hz, 1H), 2.87 (br d, J=10.0 Hz, 1H), 2.44 (br d, J=11.4 Hz, 1H), 2.33 (m, 2H), 1.69-1.80 (m, 4H), 1.66 (s, 3H), 1.52-1.60 (m, 1H), 1.13-1.31 (m, 5H), 0.96-1.12 (m, 21H).

96a: [(2R,6R)-4-cyclohexyl-2-(hydroxymethyl)-6-(5-methyl-2,4-dioxo-pyrimidin-1-yl)-morpholin-2-yl]methyl Benzoate 3.0 g (4.89 mmol) of the silylether 95a were dissolved in 15 ml DMF. After adding 7.49 g (73.3 mmol, 10.29 ml) NEt$_3$ and 6.03 g (36.7 mmol, 6.10 ml) NEt$_3$.3HF, the solution was stirred at 75° C. for 2 h, to achieve complete conversion. The reaction was cooled to room temperature and washed with 100 ml 5%-NaHCO$_3$-solution. After filtration, the aqueous solution was extracted with DCM. The organic layer was separated, dried with MgSO$_4$ and evaporated. The crude product was purified by silicagel chromatography (0 to 10% MeOH in DCM), which gave 1.23 g (55.0%) of the desired deprotected product 96a, which contained about 20% of an isomeric impurity, which resulted from benzoylester migration to the free OH-group.

LCMS-Method C:
UV-wavelength [nm]=220: $R_t$[min]=1.63
Ionization method: ES$^+$: [M+H]$^+$=458.4

97a: [(2R,6R)-2-[[bis(4-methoxyphenyl)-phenyl-methoxy]methyl]-4-cyclo-hexyl-6-(5-methyl-2,4-dioxo-pyrimidin-1-yl)morpholin-2-yl]methyl Benzoate 2.05 g (4.48 mmol) of the starting material 96a were dissolved in 40 ml dry pyridine. AT room temperature, a solution of 1.64 g (4.70 mmol) DMT-Cl in 10 ml DCM was added dropwise and the reaction solution was stirred overnight. After adding 5 ml iPrOH, the reaction solution was evaporated and the residue dissolved in DCM. The organic solution was dried with MgSO4 and evaporated. The obtained crude product was purified by silicagel chromatography (0 to 10% MeOH in DCM), followed by a second purification by HPLC (column: Chiralcel OZ-H/140.250× 4.6 mm, 1.0 ml/min, 30° C.; eluent: MeOH/EtOH 1:1), which gave 1.05 g (30.8%) of the title compound 97a as colourless foam.

LCMS-Method C:
UV-wavelength [nm]=220: $R_t$[min]=3.17
Ionization method: ES$^-$: [M–H]$^-$=758.6

1H-NMR (DMSO-d6, 400 MHz) δ[ppm]: 11.31 (s, 1H), 7.73-7.79 (m, 2H), 7.63-7.71 (m, 1H), 7.46-7.54 (m, 3H), 7.35 (d, J=7.1 Hz, 2H), 7.16-7.28 (m, 7H), 6.79 (dd, J=8.9, 3.6 Hz, 4H), 5.65 (dd, J=9.9, 2.9 Hz, 1H), 4.50 (d, J=11.3 Hz, 1H), 4.40 (d, J=11.1 Hz, 1H), 3.69 (d, J=1.59 Hz, 6H), 3.55 (d, J=8.6 Hz, 1H), 3.01 (d, J=11.4 Hz, 1H), 2.81 (d, J=9.9 Hz, 1H), 2.66-2.69 (m, 1H), 2.23-2.39 (m, 2H), 1.61-1.78 (m, 4H), 1.68 (s, 3H), 1.51-1.60 (m, 1H), 0.98-1.30 (m, 5H).

98a: 1-[(2R,6S)-6-[[bis(4-methoxyphenyl)-phenyl-methoxy]methyl]-4-cyclohexyl-6-(hydroxy-methyl)morpholin-2-yl]-5-methyl-pyrimidine-2,4-dione 1.0 g (1.32 mmol) of the benzoylester 97a were dissolved in 12 ml EtOH/Pyr. (5:1). At 0° C. 6.58 ml (13.16 mmol) of a 2 M NaOH-solution were added. After removing the cooling bath, the reaction solution was stirred for 1 h at room temperature to achieve complete conversion. The solution was diluted with 50 ml $H_2O$ and extracted with EtOAc. The organic layer was separated and washed with 10% citric acid-s, 5% $NaHCO_3$- and sat. NaCl-solution. After drying with $MgSO_4$ and evaporation of the solvent, the crude product was purified on silica (0 to 50% EtOAc in n-heptane), which yielded 325 mg (37.7%) of the title compound 98a as colourless foam.

LCMS-Method C:

UV-wavelength [nm]=220: $R_t$[min]=2.33

Ionization method: $ES^+$: $[M+H]^+$=656.5

1H-NMR (DMSO-d6, 400 MHz) δ[ppm]: 11.28 (s, 1H), 7.58 (d, J=1.0 Hz, 1H), 7.39 (d, J=7.5 Hz, 2H), 7.19-7.32 (m, 7H), 6.87 (d, J=8.8 Hz, 4H), 5.56 (dd, J=9.9, 2.7 Hz, 1H), 4.65 (t, J=6.0 Hz, 1H), 3.73 (s, 6H), 3.58 (dd, J=11.4, 6.9 Hz, 1H), 3.50 (dd, J=11.3, 5.0 Hz, 1H), 3.35 (d, J=8.7 Hz, 1H), 3.10 (d, J=8.6 Hz, 1H), 2.68-2.83 (m, 2H), 2.42 (d, J=11.6 Hz, 1H), 2.22 (m, 1H), 2.14 (t, J=10.4 Hz, 1H), 1.78 (s, 3H), 1.58-1.71 (m, 4H), 1.53 (br d, J=12.2 Hz, 1H), 1.00-1.32 (m, 5H).

99a: 3-[[(2R,6R)-2-[[bis(4-methoxyphenyl)-phenyl-methoxy]methyl]-4-cyclo-hexyl-6-(5-methyl-2,4-dioxo-pyrimidin-1-yl)morpholin-2-yl]methoxy-(di-isopropylamino)-phosphanyl]-oxypropanenitrile 320 mg (488 μmol) of the starting material 98a were dissolved in 6 ml dry DCM. Under an argon atmosphere, 44 mg (244 μmol) $^iPr_2NH$-tetrazole and 190 mg (601 μmol) 2-cyanoethyl-N,N,N',N'-tetraisopropylphosphorodiamidite were added and the solution was stirred at room temperature overnight. After adding 50 ml $H_2O$ and DCM, the organic layer was separated, dried with $MgSO_4$ and evaporated. The crude product was purified by silicagel chromatography (preconditioned with n-heptane+1% $NEt_3$, 0 to 100% EtOAc in n-heptane), yielding 322 mg (78.6%) of the desired phosphoramidite 99a as colourless foam.

LCMS-Method B-2:

UV-wavelength [nm]=220: $R_t$[min]=0.83

Ionization method: $ES^+$: $[M+H-^iPr_2N+OH]^+$=773.3

1H-NMR (DMSO-d6, 400 MHz) δ[ppm]: 11.32, 11.30 (2×br s, 1H), 7.57, 7.52 (2×d, J=1.0 Hz, 1H), 7.38 (m, 2H), 7.19-7.32 (m, 7H), 6.84-6.91 (m, 4H), 5.68, 5.59 (2×m, 1H), 3.89 (m, 0.5H), 3.59-3.78 (m, 3.5H), 3.73 (s, 6H), 3.46-3.57 (m, 2H), 3.35 (m, 1H), 3.22 (m, 1H), 2.66-2.84 (m, 4H), 2.40 (m, 1H), 2.17-2.28 (m, 2H), 1.78, 1.76 (2×s, 3H), 1.56-1.72 (m, 4H), 1.47-1.56 (m, 1H), 1.00-1.31 (m, 17H).

31P-NMR (DMSO-d6, 162 MHz) δ[ppm]: 147.6, 147.5.

94e: N-[9-[(2R,6S)-4-cyclohexyl-6-(hydroxymethyl)-6-(triisopropylsilyloxymethyl)morpholin-2-yl]purin-6-yl]benzamide 2.18 g (2.36 mmol) of the DMT-ether 90e were deprotected with dichloroacetic acid, following the protocol, described for the synthesis of the dioxane analog 40e. After chromatographic purification on silica (0 to 100% EtOAc in n-heptane) the desired product 94e was isolated as colourless foam (1.14 g, 77.5%).

LCMS-Method C:

UV-wavelength [nm]=220: $R_t$[min]=2.94

Ionization method: $ES^+$: $[M+H]^+$=623.7

1H-NMR (DMSO-d6, 400 MHz) δ[ppm]: 11.17 (s, 1H), 8.74 (s, 1H), 8.70 (s, 1H), 8.04 (br d, J=7.3 Hz, 2H), 7.65 (m, 1H), 7.55 (t, J=7.1 Hz, 2H), 6.10 (m, 1H), 4.60 (m, 1H), 4.14 (m, 1H), 3.88 (m, 1H), 3.45 (br d, J=6.2 Hz, 2H), 3.12 (m, 1H), 2.77-2.93 (m, 2H), 2.45 (m, 1H), 2.35 (m, 1H), 1.76 (m, 4H), 1.56 (br d, J=11.5 Hz, 1H), 1.16-1.33 (m, 4H), 0.99-1.15 (m, 22H).

95e: [(2S,6R)-6-(6-benzamidopurin-9-yl)-4-cyclohexyl-2-(triisopropylsilyloxymethyl)-morpholin-2-yl]methyl Benzoate 1.13 g (1.8 mmol) of the starting material 94e were dissolved in 20 ml dry pyridine. At room temperature, 334.9 mg (276.5 μl, 2.4 mmol) benzoyl chloride and 223.9 mg (1.8 mmol) DMAP were added and the solution was stirred for 3 h. After adding additional 103.0 mg (85.1 μl, 0.7 mmol) benzoyl chloride, the solution was stirred until complete conversion was achieved. The solvent was removed i. vac. and the residue dissolved in EtOAc. The solution was washed with $H_2O$, 2×10% citric acid-, sat. $NaHCO_3$- and sat. NaCl-solution, dried with $MgSO_4$ and evaporated. Purification on silica (0 to 100% EtOAc in n-heptane) yielded 877 mg (66.5%) of the benzoate 95e as colourless foam.

LCMS-Method C:

UV-wavelength [nm]=220: $R_t$[min]=3.65

Ionization method: $ES^+$: $[M+H]^+$=727.8

1H-NMR (DMSO-d6, 400 MHz) δ[ppm]: 11.15 (m, 1H), 8.71 (s, 1H), 8.61 (s, 1H), 8.02 (d, J=7.3 Hz, 2H), 7.92 (d, J=7.4 Hz, 2H), 7.59-7.69 (m, 2H), 7.48-7.58 (m, 4H), 6.15 (m, 1H), 4.24-4.40 (m, 3H), 3.99 (m, 1H), 3.17 (m, 1H), 2.98-3.10 (m, 2H), 2.60 (m, 1H), 2.42 (m, 1H), 1.70-1.90 (m, 4H), 1.57 (br d, J=12.1 Hz, 1H), 1.16-1.32 (m, 4H), 0.99-1.14 (m, 22H).

96e: [(2R,6R)-6-(6-benzamidopurin-9-yl)-4-cyclohexyl-2-(hydroxymethyl)morpholin-2-yl]methyl Benzoate 870 mg (1.2 mmol) of the silylether 95e were deprotected following the protocol described for 45e. After chromatographic purification (0 to 100% EtOAc in n-heptane), 96e was isolated as colourless foam (616 mg, 90.2%).

LCMS-Method C:

UV-wavelength [nm]=220: $R_t$[min]=1.90

Ionization method: $ES^+$: $[M+H]^+$=571.5

1H-NMR (DMSO-d6, 400 MHz) δ[ppm]: 11.13 (s, 1H), 8.70 (s, 1H), 8.56 (s, 1H), 8.02 (br d, J=7.3 Hz, 2H), 7.93 (m, 2H), 7.65 (m, 1H), 7.48-7.59 (m, 4H), 6.16 (dd, J=8.7, 3.0 Hz, 1H), 4.97 (br s, 1H), 4.21-4.38 (m, 2H), 3.89 (br d, J=10.5 Hz, 1H), 3.80 (br d, J=10.2 Hz, 1H), 3.15 (m, 1H), 3.05 (m, 1H), 2.93 (br d, J=11.6 Hz, 1H), 2.63 (m, 1H), 2.37-2.44 (m, 1H), 1.65-1.82 (m, 4H), 1.57 (br d, J=11.7 Hz, 1H), 1.13-1.32 (m, 4H), 1.01-1.13 (m, 1H).

97e: [(2R,6R)-6-(6-benzamidopurin-9-yl)-2-[[bis(4-methoxyphenyl)-phenyl-methoxy]methyl]-4-cyclohexyl-morpholin-2-yl]methyl Benzoate 610 mg (1.1 mmol) of the starting material 96e were dissolved in 30 ml dry pyridine and evaporated. This procedure was repeated three times. The compound was then dissolved in 30 ml dry pyridine, followed by the addition of 162.7 mg (223.6 µl, 1.6 mmol) NEt$_3$ and 554.4 mg (1.6 mmol) DMT-Cl. The reaction solution was stirred at room temperature overnight, when complete conversion was achieved. The solvent was removed i. vac. and the residue dissolved in EtOAc. After washing with H$_2$O, 10%-citric acid-(2×), sat. NaHCO$_3$- and sat. NaCl-solution, the organic phase was dried with MgSO$_4$. Evaporation of the solvent and purification by silicagel chromatography (0 to 100% EtOAc in n-heptane) gave 807 mg (86.5%) of the DMT-ether 97e as colourless foam.

LCMS-Method C:
UV-wavelength [nm]=220: R$_t$[min]=3.26
Ionization method: ES$^+$: [M+H]$^+$=873.8
1H-NMR (DMSO-d6, 400 MHz) δ[ppm]: 11.17 (br s, 1H), 8.69 (s, 1H), 8.60 (s, 1H), 8.02 (m, 2H), 7.73 (m, 2H), 7.64 (m, 2H), 7.54 (m, 2H), 7.47 (m, 2H), 7.39 (m, 2H), 7.18-7.28 (m, 7H), 6.75-6.84 (m, 4H), 5.95 (dd, J=9.4, 2.9 Hz, 1H), 4.44 (m, 2H), 3.65-3.72 (m, 7H), 3.44 (m, 1H), 3.02-3.14 (m, 2H), 2.94 (br t, J=10.3 Hz, 1H), 2.67 (m, 1H), 2.41 (br d, J=7.7 Hz, 1H), 1.66-1.83 (m, 4H), 1.57 (br d, J=11.62 Hz, 1H), 1.13-1.29 (m, 4H), 1.01-1.12 (m, 1H).

98e: N-[9-[(2R,6S)-6-[[bis(4-methoxyphenyl)-phenyl-methoxy]methyl]-4-cyclohexyl-6-(hydroxymethyl)morpholin-2-yl]purin-6-yl]benzamide Following the protocol, described for compound 63e, 800 mg (0.9 mmol) 97e were saponified with 2 M NaOH-solution. After chromatographic purification (0 to 100% EtOAc in n-heptane), 634 mg (90.0%) of the desired compound 98e were isolated as colourless foam.

LCMS-Method C:
UV-wavelength [nm]=220: R$_t$[min]=2.69
Ionization method: ES$^-$: [M−H]$^-$=767.5
1H-NMR (DMSO-d6, 400 MHz) δ[ppm]: 11.18 (br s, 1H), 8.69 (s, 1H), 8.66 (s, 1H), 8.04 (d, J=7.7 Hz, 2H), 7.64 (m, 1H), 7.55 (t, J=7.6 Hz, 2H), 7.44 (d, J=7.5 Hz, 2H), 7.27-7.34 (m, 6H), 7.22 (m, 1H), 6.89 (dd, J=9.1, 2.6 Hz, 4H), 5.84 (dd, J=9.9, 2.7 Hz, 1H), 4.68 (br t, J=5.8 Hz, 1H), 3.74, 3.73 (2×s, 6H), 3.47-3.63 (m, 3H), 3.28 (m, 1H), 3.03 (br d, J=9.9 Hz, 1H), 2.86 (br d, J=11.6 Hz, 1H), 2.72 (t, J=10.5 Hz, 1H), 2.53 (m, 1H), 2.24-2.34 (m, 1H), 1.61-1.73 (m, 4H), 1.54 (br d, J=11.4 Hz, 1H), 1.00-1.30 (m, 5H).

99e: N-[9-[(2R,6R)-6-[[bis(4-methoxyphenyl)-phenyl-methoxy]methyl]-6-[[2-cyanoethoxy-(diisopropylamino)phosphanyl]oxymethyl]-4-cyclohexyl-morpholin-2-yl]purin-6-yl]-benzamide 625 mg (813 µmol) of the starting compound 98e were phosphitylated following the protocol described for 43e, which gave 710 mg (90.1%) of the desired phosphoramidite 99e as colourless solid.

LCMS-Method B-3:
UV-wavelength [nm]=220: R$_t$[min]=0.63
Ionization method: ES$^+$: [M+H-$^i$Pr$_2$N+OH-A$^{Bzl}$]$^+$=647.3
1H-NMR (DMSO-d6, 400 MHz) δ[ppm]: 11.16 (br s, 1H), 8.72, 8.70 (2×s, 1H), 8.60, 8.57 (2×s, 1H), 8.04 (d, J=8.1 Hz, 2H), 7.63 (m, 1H), 7.55 (m, 2H), 7.44 (m, 2H), 7.20-7.36 (m, 7H), 6.85-6.94 (m, 4H), 5.83-5.95 (m, 1H), 3.83-3.95 (m, 1H), 3.74 (s, 6H), 3.34-3.73 (m, 7H), 3.00-3.11 (m, 2H), 2.76-2.92 (m, 2H), 2.71, 2.62 (2×m, 2H), 2.23-2.39 (m, 1H), 1.59-1.77 (m, 4H), 1.47-1.58 (m, 1H), 0.99-1.30 (m, 14H), 0.90-0.97 (m, 3H).
31P-NMR (DMSO-d6, 162 MHz) δ[ppm]: 147.5, 147.3.

B. Synthesis of Nucleotide Analogs of Formula (I) Wherein X is O

Example B.1

Synthetic Scheme 12

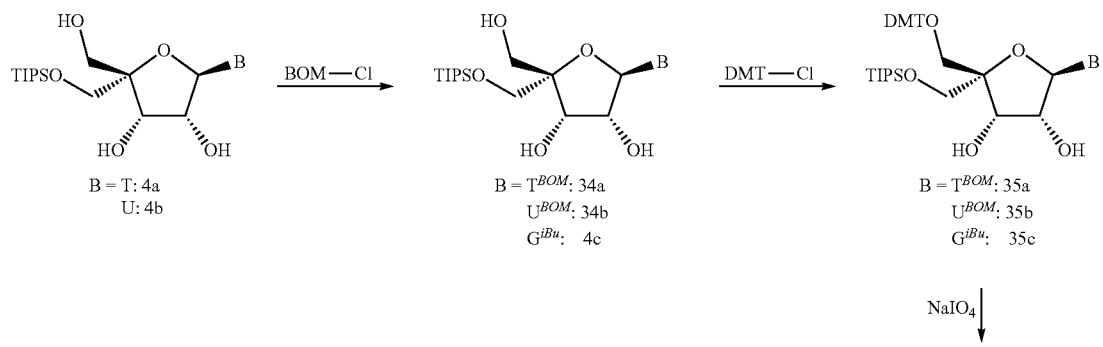

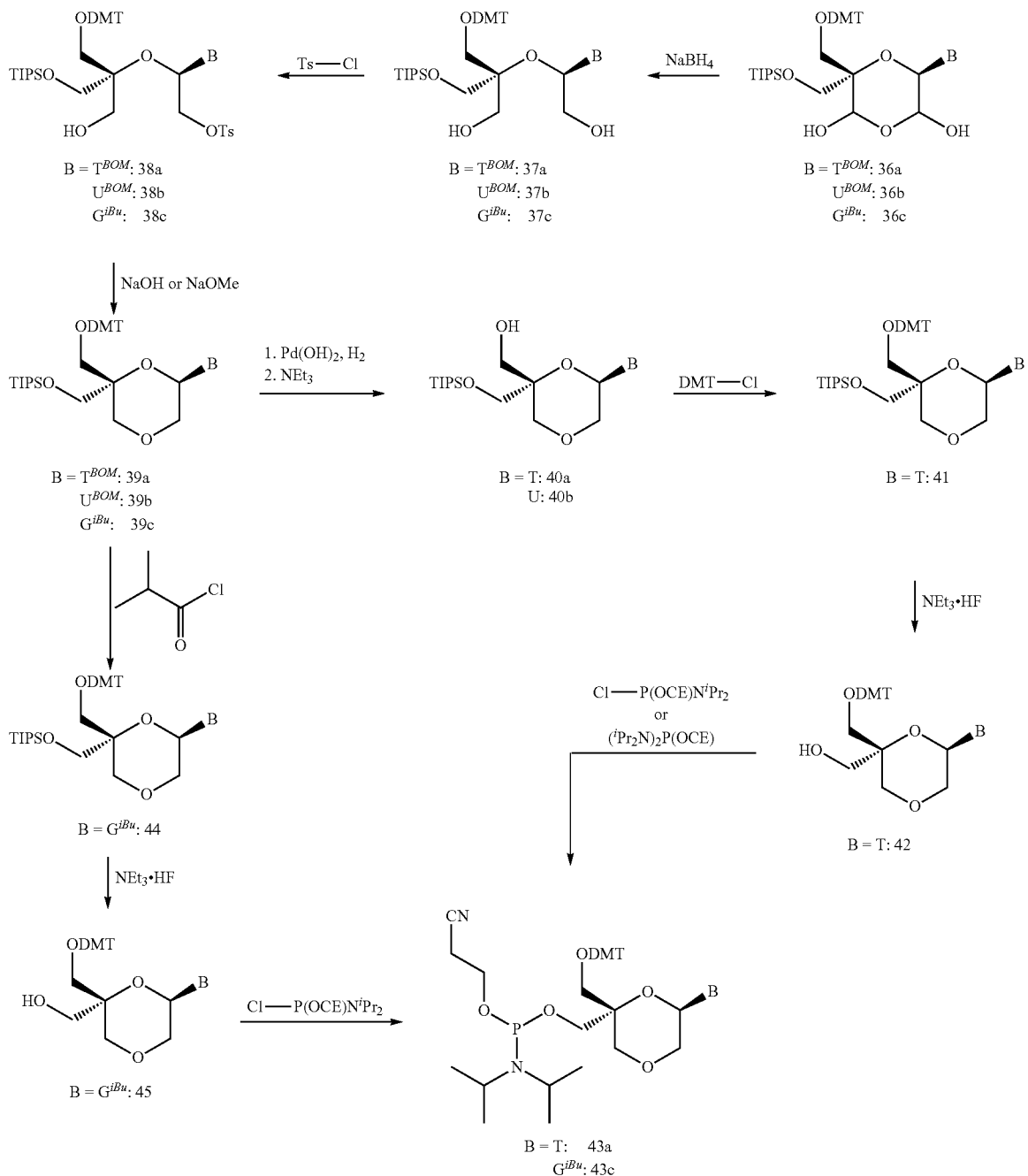

34a: 3-(benzyloxymethyl)-1-[(2R,3R,4S,5S)-3,4-dihydroxy-5-(hydroxymethyl)-5-(triisopropylsilyloxymethyl)tetrahydrofuran-2-yl]-5-methyl-pyrimidine-2,4-dione

To a mixture of compound 4a (72.75 g, 0.164 mmol) in 728 ml DMF were added 44.6 g BOM-Cl (0.285 mol) and 50 g DBU (0.327 mol) at −30° C. The mixture was stirred at −15° C. to −30° C. for 3 h to achieve complete conversion. The mixture was poured into sat. NaHCO$_3$— solution (2 l) and extracted with EtOAc (3×1 l). The combined organic layers were dried over anhydrous Na$_2$SO$_4$, filtered and concentrated in vacuo. The residue was purified by flash chromatography (DCM/MeOH 20:1) to give 62.7 g (67.7%) of the BOM-protected product 34a as yellow oil.

1H-NMR (CDC$_3$, 400 MHz) δ[ppm]: 8.67-8.55 (m, 4H), 7.70 (tt, J=7.64, 1.77 Hz, 2H), 7.52-7.20 (m, 10H), 5.69-5.62 (m, 1H), 5.52-5.44 (m, 1H), 4.74-4.54 (m, 2H), 4.51-4.42 (m, 1H), 4.11-3.63 (m, 6H), 2.01-1.84 (m, 4H), 1.30-0.85 (m, 21H).

34b: 3-(benzyloxymethyl)-1-[(2R,3R,4S,5S)-3,4-dihydroxy-5-(hydroxymethyl)-5-(triisopropylsilyloxymethyl)tetrahydrofuran-2-yl]pyrimidine-2,4-dione Following the protocol described for 34a, 24 g (0.056 mol) of the starting compound 4b gave 22.0 g (71.7%) of 34b after silicagel chromatography (DCM/MeOH 20:1 to 10:1) as colourless solid.

1H-NMR (CDC$_3$, 400 MHz) δ[ppm]: 8.02 (d, J=8.0 Hz, 1H), 7.34-7.31 (m, 5H), 5.95 (d, J=8.0 Hz, 1H), 5.85 (d, J=8.0 Hz, 1H), 5.35-5.32 (m, 3H), 5.08 (d, J=4.0 Hz, 1H), 4.59 (s, 2H), 4.50 (d, J=4.0 Hz, 1H), 4.24-4.19 (m, 2H), 4.09 (t, J=4.0 Hz, 1H), 3.83 (s, 2H), 3.65 (t, J=4.0 Hz, 2H), 1.03-1.02 (m, 21H).

35a: 3-(benzyloxymethyl)-1-[(2R,3R,4S,5S)-5-[[bis(4-methoxyphenyl)-phenyl-methoxy]-methyl]-3,4-dihydroxy-5-(triisopropylsilyloxymethyl)tetrahydrofuran-2-yl]-5-methyl-pyrimidine-2,4-dione 7.42 g (13.1 mmol) of the starting material 34a were co-distilled twice with 40 ml pyridine and dissolved in 150 ml DCM/pyridine (4:1). After adding 4.77 g (13.8 mmol) of DMT-Cl, the solution was stirred at room temperature for 65 h. The solution was washed twice with aqueous citric acid-solution (10%), followed by H$_2$O, sat. NaHCO$_3$- and NaCl-solution. The organic phase was separated, dried with MgSO$_4$ and purified by silicagel chromatography (0 to 100% EtOAc in n-heptane), to give 8.50 g (74.7%) of the desired product 35a as colourless foam.

LCMS-Method A:
UV-wavelength [nm]=220: R$_t$[min]=2.34
Ionization method: ES$^+$: [M+Na]$^+$=889.5

1H-NMR (CDCl$_3$, 400 MHz) δ[ppm]: 7.46-7.40 (m, 1H), 7.35-7.12 (m, 14H), 6.75 (d, J=7.91 Hz, 4H), 6.04 (d, J=5.52 Hz, 1H), 5.53-5.37 (m, 2H), 4.67-4.54 (m, 2H), 4.46-4.37 (m, 2H), 3.89 (d, J=10.29 Hz, 1H), 3.76-3.68 (m, 7H), 3.62 (d, J=10.16 Hz, 1H), 3.52 (br d, J=8.41 Hz, 1H), 3.40-3.33 (m, 1H), 3.17 (d, J=10.16 Hz, 1H), 1.44 (s, 3H), 1.05-0.85 (m, 21H).

35b: 3-(benzyloxymethyl)-1-[(2R,3R,4S,5S)-5-[[bis(4-methoxyphenyl)-phenyl-methoxy]-methyl]-3,4-dihydroxy-5-(triisopropylsilyloxymethyl)tetrahydrofuran-2-yl]pyrimidine-2,4-dione To a solution of compound 34b (21.0 g, 38 mmol) in 230 ml dry DMF was added DIPEA (9.8 g, 76 mmol) and DMT-Cl (15.4 g, 45.6 mmol) at room temperature. The reaction solution was stirred under N$_2$ atmosphere for 4 h. After adding 30 ml EtOH, the solvent was removed under reduced pressure and the residue was purified by column chromatography on silica gel (PE/EtOAc 10:1 to 1:1), which gave 19.0 g (58.5%) of 35b as yellow foam.

1H-NMR (DMSO-d6, 400 MHz) δ[ppm]: 7.72 (d, J=8.0 Hz, 1H), 6.90 (d, J=8.0 Hz, 4H), 7.39-7.24 (m, 14H), 5.89 (d, J=8.0 Hz, 1H), 3.51 (d, J=8.0 Hz, 1H), 5.37-5.24 (m, 4H), 4.58 (s, 2H), 4.34 (t, J=4.0 Hz, 1H), 4.24 (dd, J=12.0, 8.0 Hz, 1H), 3.73 (s, 6H), 3.40 (d, J=12.0 Hz, 1H), 3.29 (d, J=12.0 Hz, 1H), 1.19-0.86 (m, 21H).

35c: N-[9-[(2R,3R,4S,5S)-5-[[bis(4-methoxyphenyl)-phenyl-methoxy]methyl]-3,4-dihydroxy-5-(triisopropylsilyloxymethyl)tetrahydrofuran-2-yl]-6-oxo-1H-purin-2-yl]-2-methyl-propanamide To a solution of 4c (24 g, 44.5 mmol) in 314 ml anhydrous pyridine/DCM (1/4) was added DMT-Cl (18 g, 53.4 mmol) at 0° C. under N$_2$-atmosphere. After stirring for 2 h at 15° C., the mixture was poured into 500 ml ice-water and extracted with DCM (3×300 ml). The combined organic layers were washed with brine (300 ml), dried over anhydrous Na$_2$SO$_4$ and concentrated in vacuo. The crude product was purified by column chromatography on silica gel (DCM/MeOH 50:1 to 10:1), yielding 37.4 g (quant.) of 35c as yellow solid.

1H-NMR (DMSO-d6, 400 MHz) δ[ppm]: 12.09 (s, 1H), 11.65 (s, 1H), 7.93 (s, 1H), 7.37-7.34 (m, 2H), 7.27 (m, 7H), 6.85-6.83 (m, 4H), 5.86 (d, J=7.2 Hz, 1H), 5.60 (d, J=6.8 Hz, 1H), 5.20 (s, 1H), 4.67-4.64 (m, 1H), 4.26-4.24 (m, 1H), 3.98-3.95 (m, 111), 3.84 (d, J=10.4 Hz, 1H), 3.38-3.34 (m, 2H), 3.20-3.18 (m, 1H), 2.80-2.74 (m, 1H), 1.13-0.95 (m, 6H), 0.93-0.90 (m, 21H).

36a: 3-(benzyloxymethyl)-1-[(2R,6S)-6-[[bis(4-methoxyphenyl)-phenyl-methoxy]methyl]-3,5-dihydroxy-6-(triisopropylsilyloxymethyl)-1,4-dioxan-2-yl]-5-methyl-pyrimidine-2,4-dione To a solution of 35a (20 g, 23.07 mmol) in 400 ml acetone/water (3:1) was added a solution of NaIO$_4$ (6.9 g, 32.29 mmol) in 100 ml water at room temperature. After stirring for 16 h, the solvent was removed in vacuo and the residue was dissolved in EtOAc (300 ml) and washed with sat. NaHCO$_3$ (200 ml) and brine (200 ml). The organic layer was dried over anhydrous Na$_2$SO$_4$, filtered and concentrated in vacuo to give 36a as yellow foam, which was used for the next step without further purification.

LCMS-Method A:
UV-wavelength [nm]=220: R$_t$[min]=2.30, 2.32 (two isomers)
Ionization method: ES$^+$: [M+Na]$^+$=905.5

36b: 3-(benzyloxymethyl)-1-[(2R,6S)-6-[[bis(4-methoxyphenyl)-phenyl-methoxy]methyl]-3,5-dihydroxy-6-(triisopropylsilyloxymethyl)-1,4-dioxan-2-yl]pyrimidine-2,4-dione 20 g (23.5 mmol) of 35b were converted to the title compound 36b, following the protocol, described for 36a (18.6 g, crude).

LCMS-Method A:
UV-wavelength [nm]=220: R$_t$[min]=2.23, 2.25 (two isomers)
Ionization method: ES$^+$: [M+Na]$^+$=891.4

36c: N-[9-[(2R,6S)-6-[[bis(4-methoxyphenyl)-phenyl-methoxy]methyl]-3,5-dihydroxy-6-(triisopropylsilyloxymethyl)-1,4-dioxan-2-yl]-6-oxo-1H-purin-2-yl]-2-methyl-propanamide To a solution of 35c (30 g, 35.7 mmol) in 694 ml acetone/H$_2$O (5:1) was added a solution of NaIO$_4$ (10.62 g, 50 mmol) in 240 ml H$_2$O at 0° C. After stirring for 12 h at 15° C., the mixture was poured into 200 ml ice-water and extracted with DCM (3×200 ml). The organic layers were combined and washed with brine (300 ml), dried over anhydrous Na$_2$SO$_4$ and concentrated in vacuo to give 36c (30 g, crude) as a yellow foam, which was used in the next step without further purification.

37a: 3-(benzyloxymethyl)-1-[(1R)-1-[(1S)-1-[[bis(4-methoxyphenyl)-phenyl-methoxy]methyl]-1-(hydroxymethyl)-2-triisopropylsilyloxy-ethoxy]-2-hydroxy-ethyl]-5-methyl-pyrimidine-2,4-dione To a solution of compound 36a (crude product, 23.07 mmol) in 320 ml EtOH was added NaBH$_4$ (1.05 g, 27.68 mmol) portionwise at room temperature. The mixture was stirred overnight and the solvent was removed in vacuo. The residue was dissolved in EtOAc (500 ml) and washed with sat. NaHCO$_3$-solution (500 ml) and brine (500 ml). The organic layer was dried over anhydrous Na$_2$SO$_4$, filtered and concentrated in vacuo. After column chromatography (DCM/MeOH 20:1) 12.0 g of 37a (48%) were isolated as yellow foam.

LCMS-Method A:
UV-wavelength [nm]=220: R$_t$[min]=2.31
Ionization method: ES$^+$: [M+Na]$^+$=891.5
1H-NMR (CDCl$_3$, 400 MHz) δ[ppm]: 7.52-7.06 (m, 20H), 6.80-6.65 (m, 5H), 6.08 (dd, J=7.03, 3.76 Hz, 1H), 5.44-5.25 (m, 1H), 4.64-4.46 (m, 2H), 3.85-3.63 (m, 12H), 3.60-3.40 (m, 2H), 3.35, 3.22 (m, 2H), 2.95-2.66 (m, 2H), 1.80 (s, 3H), 1.51 (s, 3H), 1.03-0.81 (m, 23H).

37b: 3-(benzyloxymethyl)-1-[(JR)-1-[(1S)-1-[[bis(4-methoxyphenyl)-phenyl-methoxy]-methyl]-1-(hydroxymethyl)-2-triisopropylsilyloxy-ethoxy]-2-hydroxy-ethyl]pyrimidine-2,4-dione To a solution of 15.35 g (17.7 mmol, crude) 36b in 250 ml EtOH, were added 818 mg (21.2 mmol) NaBH$_4$ at room temperature. The reaction was stirred for 16 h, when complete conversion was detected. The solvent was removed i. vac. and the residue was dissolved in EtOAc. After the organic solution was washed with H$_2$O, sat. NaHCO$_3$- and sat. NaCl-solution, the organic layer was dried with MgSO$_4$ and evaporated, which gave 14.85 g (98.3%) of 37b as colourless foam, which was used without further purification.

LCMS-Method A:
UV-wavelength [nm]=220: R$_t$[min]=2.23
Ionization method: ES$^+$: [M]$^+$=303.2 (DMT)

37c: N-[9-[(1R)-1-[(1S)-1-[[bis(4-methoxyphenyl)-phenyl-methoxy]methyl]-1-(hydroxy-methyl)-2-triisopropylsilyloxy-ethoxy]-2-hydroxy-ethyl]-6-oxo-1H-purin-2-yl]-2-methyl-propanamide To a solution of 36c (30 g, 35 mmol) in 400 ml anhydrous EtOH was added NaBH$_4$ (1.6 g, 42 mmol) at 15-20° C. After stirring for 4 h, the pH was adjusted to 7 by using 10% citric acid solution (about 25 ml). The solvent was concentrated in vacuo and the residue was purified by column chromatography on silica gel (DCM/MeOH 20:1 to 10:1), which gave 22.0 g (74.5%) of 37c as a yellow solid.

1H-NMR (DMSO-d6, 400 MHz) δ[ppm]: 12.06 (s, 1H), 11.71 (s, 1H), 8.04 (s, 1H), 7.37-7.28 (m, 3H), 7.26-7.19 (m, 11H), 6.87-6.83 (m, 4H), 6.09 (d, J=5.6 Hz, J2=5.6 Hz, 1H), 5.22 (d, J=5.6 Hz, 1H), 4.75 (d, J$_1$=4.8 Hz, J$_2$=4.8 Hz, 1H), 3.85-3.84 (m, 2H), 3.74-3.70 (m, 9H), 3.68-3.49 (m, 2H), 3.14 (m, 1H), 2.99-2.81 (m, 1H), 1.15-1.12 (m, 6H), 0.80-0.79 (m, 21H).

38a: [(2R)-2-[3-(benzyloxymethyl)-5-methyl-2,4-dioxo-pyrimidin-1-yl]-2-[(1S)-1-[[bis(4-methoxy-phenyl)-phenyl-methoxy]methyl]-1-(hydroxymethyl)-2-triisopropylsilyloxy-ethoxy]ethyl] 4-methylbenzenesulfonate To a solution of 37a (10.8 g, 12.43 mmol), NEt$_3$ (3.14 g, 31.07 mmol) and DMAP (1.52 g, 12.43 mmol) in 108 ml DCM was added a solution of Ts-Cl (1.9 g, 9.94 mmol) in 54 ml DCM at 15° C. The mixture was stirred at 2 h, followed by the addition of another 500 mg Ts-Cl, dissolved in 5 ml DCM. After stirring for another 1 h at 15° C., the reaction mixture was washed with sat. NaHCO$_3$-solution (200 ml) and brine (200 ml), dried over anhydrous Na$_2$SO$_4$, filtered and concentrated in vacuo. The residue was purified by column chromatography (PE/EtOAc 2:1) to give 38a (10 g, 78.7%) as yellow oil.

1H-NMR (CDCl$_3$, 400 MHz) δ[ppm]: 7.74-7.43 (m, 2H), 7.34-7.00 (m, 18H) 6.84-6.64 (m, 4H), 6.42-6.24 (m, 1H), 5.43-5.15 (m, 2H), 5.00-4.72 (m, 1H), 4.63-4.47 (m, 2H), 4.21-3.90 (m, 2H), 3.83-3.56 (m, 10H), 3.29-3.11 (m, 1H), 2.44-2.19 (m, 4H), 1.89-1.64 (m, 3H), 1.07-0.71 (m, 21H).

38b: [(2R)-2-[3-(benzyloxymethyl)-2,4-dioxo-pyrimidin-1-yl]-2-[(1S)-1-[[bis(4-methoxy-phenyl)-phenyl-methoxy]methyl]-1-(hydroxymethyl)-2-triisopropylsilyloxy-ethoxy]ethyl] 4-methylbenzenesulfonate 3.0 g (3.5 mmol) 37b were converted to 38b, following the protocol for 38a by using 1.2 eq. Ts-Cl. After final purification on silicagel (PE/EtOAc 10:1 to 2:1), 2.0 g (57%) of the title compound (38b) were isolated as colourless foam.

1H-NMR (DMSO-d6, 400 MHz) δ[ppm]: 7.65-7.56 (m, 3H), 7.35-7.18 (m, 16H), 6.84-6.80 (m, 4H), 6.37-6.36 (m, 1H), 5.74 (s, 2H), 5.64 (d, J=12.0 Hz, 1H), 5.23-5.18 (m, 2H), 4.93-4.91 (m, 1H), 4.52 (s, 2H), 4.18-4.09 (m, 2H), 3.71 (s, 6H), 3.23-3.01 (m, 4H), 2.34 (s, 3H), 0.96-0.79 (m, 21H).

38c: [(2R)-2-[(S)-1-[[bis(4-methoxyphenyl)-phenyl-methoxy]methyl]-1-(hydroxymethyl)-2-triisopropyl-silyloxy-ethoxy]-2-[2-(2-methylpropanoylamino)-6-oxo-1H-purin-9-yl]ethyl] 4-methylbenzenesulfonate To a solution of 37c (31.5 g, 40.8 mmol) in 537 ml anhydrous DCM were added NEt$_3$ (10.3 g, 102 mmol) and DMAP (4.98 g, 40.8 mmol) at 0° C. under N$_2$-atmosphere. After 10 min, Ts-Cl (9.3 g, 49 mmol) was added to the mixture at 0° C. and stirring was continued at 15-20° C. for 6 h. The solvent was evaporated and the residue was purified by column chromatography (DCM/MeOH 20:1 to 10:1) to give 38c (30 g, 73.7%) as a yellow solid.

1H-NMR (DMSO-d6, 400 MHz) δ[ppm]: 12.03 (s, 1H), 11.59 (s, 1H), 8.11 (s, 2H), 7.09 (s, 1H), 7.50-7.49 (m, 2H), 7.31-7.16 (m, 12H), 6.87-6.86 (m, 4H), 6.59-6.58 (m, 2H), 6.31 (s, 1H), 4.96 (s, 1H), 4.62 (s, 1H), 4.37 (s, 1H), 4.04 (s, 2H), 3.66-3.61 (m, 4H), 3.59-3.51 (m, 1H), 3.12-3.03 (m, 2H), 2.95 (s, 6H), 2.79-2.61 (m, 1H), 2.33 (s, 3H), 1.20-1.11 (m, 7H), 0.86-0.79 (m, 21H).

39a: 3-(benzyloxymethyl)-1-[(2R,6S)-6-[[bis(4-methoxyphenyl)-phenyl-methoxy]methyl]-6-(triisopropylsilyloxymethyl)-1,4-dioxan-2-yl]-5-methyl-pyrimidine-2,4-dione To a mixture of compound 38a (10.5 g, 10.26 mmol) in 343 ml anhydrous THF and 343 ml MeOH was added a solution of 2 M NaOH (74 mL, 147.47 mmol) at 15° C. The mixture was stirred at 65° C. for 3 h, when full conversion was detected. The mixture was neutralized with aqueous citric acid (10%) and concentrated in vacuo. The residue was dissolved in EtOAc (700 ml) and washed with sat. NaHCO$_3$-solution (700 ml). The organic layer was dried over anhydrous Na$_2$SO$_4$, filtered and concentrated in vacuo. The residue was purified by column chromatography (PE/EtOAc 5:1) to give the title compound 39a (4.9 g, 49.1%) as yellow oil.

MS (m/z)=873.4 (M+Na)

1H-NMR (CDC$_3$, 400 MHz) δ[ppm]: 7.62-7.18 (m, 19H), 6.82 (br d, J=8.66 Hz, 4H), 6.10 (dd, J=10.04, 3.39 Hz, 1H), 5.53 (s, 1H), 4.74 (s, 1H), 4.26-4.15 (m, 1H), 4.04-3.88 (m, 2H), 3.81 (d, J=1.00 Hz, 7H), 3.72-3.59 (m, 1H), 3.31-3.12 (m, 3H), 1.94-1.80 (m, 3H), 1.17-0.78 (m, 23H).

39b: 3-(benzyloxymethyl)-1-[(2R,6S)-6-[[bis(4-methoxyphenyl)-phenyl-methoxy]methyl]-6-(triisopropylsilyloxymethyl)-1,4-dioxan-2-yl]pyrimidine-2,4-dione To a solution of compound 38b (1.0 g, 1.0 mmol) in 250 ml MeOH was added NaOMe (2.5 g, 45.0 mmol). The mixture was heated at 50° C. under N$_2$-atmosphere for 3 h, when TLC showed complete conversion. The solvent was removed under reduced pressure and the residue purified by column chromatography on silica gel (PE/EtOAc 10:1 to 3:1) to give 39b (0.27 g, 33%) as a white foam.

1H-NMR (CDC$_3$, 400 MHz) δ[ppm]: 7.54 (d, J=8.0 Hz, 1H), 7.39-7.37 (m, 2H), 7.35-7.30 (m, 6H), 7.28-7.26 (m, 3H), 7.24-7.22 (m, 1H), 6.85 (d, J=8.0 Hz, 4H), 6.05 (dd, J=12.0, 4.0 Hz, 1H), 5.79 (d, J=12.0 Hz, 1H), 5.49 (s, 2H), 4.72 (s, 2H), 4.20 (d, J=8.0 Hz, 1H), 4.0 (dd, J=12.0, 4.0 Hz, 1H), 3.94 (d, J=12.0 Hz, 1H), 3.86 (d, J=12.0 Hz, 1H), 3.79 (s, 6H), 3.56 (d, J=12.0 Hz, 1H), 3.22-3.12 (m, 3H), 1.10-0.95 (m, 21H).

39c: 2-amino-9-[(2R,6S)-6-[[bis(4-methoxyphenyl)-phenyl-methoxy]methyl]-6-(triisopropyl-silyloxymethyl)-1,4-dioxan-2-yl]-1H-purin-6-one To a solution of compound 38c (28 g, 28 mmol) in 616 ml MeOH was added dropwise 151 ml (758 mmol) of a 5 M NaOH at 15 to 20° C. The mixture was stirred between 60 and 70° C. for 30 min to achieve complete conversion. The mixture was cooled to 0° C. and the pH was adjusted to 7, using 10% citric acid solution (about 200 ml). The solvents were concentrated at 30° C. and the remaining aqueous phase was extracted with DCM (3×500 ml). The combined organic layers were washed with brine (500 ml), dried over anhydrous Na$_2$SO$_4$ and concentrated. The crude product was purified by column chromatography (DCM/MeOH 20:1 to 10:1) to give the 39c (18 g, 79%) as a yellow solid.

1H-NMR (DMSO-d6, 400 MHz) δ[ppm]: 10.71 (m, 1H), 7.91 (m, 1H), 7.41-7.40 (m, 2H), 7.27-7.20 (m, 12H), 6.82-6.50 (m, 6H), 6.50 (s, 1H), 5.88-5.85 (m, 1H), 4.17-4.14 (m, 1H), 3.96-3.89 (m, 1H), 3.80 (m, 2H), 3.74-3.72 (m, 10H), 3.69-3.61 (m, 1H), 3.10-3.08 (m, 1H), 2.41-2.58 (m, 1H), 0.94-0.91 (m, 21H).

40a: 1-[(2R,6R)-6-(hydroxymethyl)-6-(triisopropyl-silyloxymethyl)-1,4-dioxan-2-yl]-5-methyl-pyrimidine-2,4-dione To a solution of compound 39a (3.7 g, 4.35 mmol) in 55.5 ml EtOAc was added Pd(OH)$_2$/C (2 g, 20% on carbon and 50% in water) and trichloroacetic acid (1.42 g, 8.70 mmol). The reaction mixture was stirred at 15° C. under H$_2$ (15 psi) for 1 h to achieve complete conversion.

The mixture was filtered and the filtrate was concentrated in vacuo to give the crude debenzylated and detritylated intermediate as yellow oil, which was dissolved in 90 ml MeOH. After adding NEt$_3$ (1.14 g, 11.28 mmol) at 15° C., the solution was stirred overnight, when complete conversion was detected. The solvent was removed in vacuo and the residue was purified by column chromatography (DCM/MeOH 50:1), which gave 950 mg of the title compound 40a (51.0%) as white foam.

MS (m/z)=451.2 (M+Na)

1H-NMR (DMSO-d6, 400 MHz) δ[ppm]: 8.22 (s, 1H), 7.26-7.17 (m, 1H), 6.06-5.93 (m, 1H), 5.52 (d, J=8.16 Hz, 1H), 4.39-4.25 (m, 1H), 4.08 (d, J=11.92 Hz, 1H), 4.01-3.90 (m, 1H), 3.85 (d, J=9.29 Hz, 1H), 3.74 (s, 2H), 3.56-3.49 (m, 1H), 3.31 (dd, J=11.29, 10.29 Hz, 1H), 2.32-2.10 (m, 1H), 2.02-1.89 (m, 3H), 1.32-0.96 (m, 17H).

40b: 1-[(2R,6R)-6-(hydroxymethyl)-6-(triisopropyl-silyloxymethyl)-1,4-dioxan-2-yl]pyrimidine-2,4-dione Starting with 9.5 g (11.4 mmol) of 39b, the title compound 40b was synthesized following the protocol described for 40a. After purification on silica gel (PE/EtOAc 10:1 to 1:1), 4.0 g (86%) of 40b were isolated as white foam.

MS (m/z)=415.0 (M+H)

1H-NMR (DMSO-d6, 400 MHz) δ[ppm]: 8.74 (br. s., 1H), 7.47 (d, J=8.03 Hz, 1H), 6.02-5.97 (m, 1H), 5.85-5.78 (m, 1H), 5.50 (br. s., 1H), 4.32-4.26 (m, 1H), 4.08 (d, J=12.05 Hz, 1H), 4.03-3.96 (m, 1H), 3.85 (d, J=9.29 Hz, 1H), 3.73 (s, 2H), 3.51 (d, J=12.05 Hz, 1H), 3.27 (t, J=10.67 Hz, 1H), 1.19-1.09 (m, 21H).

41: 1-[(2R,6S)-6-[[bis(4-methoxyphenyl)-phenyl-methoxy]methyl]-6-(triisopropylsilyloxy-methyl)-1,4-dioxan-2-yl]-5-methyl-pyrimidine-2,4-dione The starting compound 40a (683 mg, 1.5 mmol) was dissolved in 30 ml dry DCM. At room temperature, 753 mg (1.03 ml, 7.4 mmol) NEt$_3$ and 616 mg (1.8 mmol) DMT-Cl were added and the reaction was stirred for 16 h, when the conversion of starting material was completed.

The reaction solution was evaporated and the crude product was purified by silicagel chromatography (0 to 100% EtOAc in n-heptane), which delivered 990 mg (91.0%) of the DMT-protected product 41 as light yellow foam.

LCMS-Method A:

UV-wavelength [nm]=220: R$_t$[min]=2.31

Ionization method: ES$^+$: [M+Na]$^+$=753.4

42: 1-[(2R,6S)-6-[[bis(4-methoxyphenyl)-phenyl-methoxy]methyl]-6-(hydroxymethyl)-1,4-dioxan-2-yl]-5-methyl-pyrimidine-2,4-dione 985 mg (1.35 mmol) of the starting material 41 were dissolved 40 ml THF. After adding 5.95 g (8.18 ml, 58.25 mmol) NEt$_3$ and 10.80 g (10.92 ml, 65.0 mmol) NEt$_3$.3HF, the reaction was stirred at 65° C. until complete conversion was detected (approx. 16 h). The solvent was removed and the residue was poured into 400 ml H$_2$O/sat-NaHCO$_3$-solution (1:2). The aqueous mixture was extracted twice with DCM (2×50 ml). The organic layers were dried with MgSO$_4$ and evaporated to yield 956 mg of a crude product, which was purified on silica (preconditioned with 1% NEt$_3$ in n-heptane, 10 to 100% EtOAc in n-heptane). 760 mg (98.2%) of the desired alcohol 42 were isolated as colourless foam.

LCMS-Method A:

UV-wavelength [nm]=220: R$_t$[min]=1.86

Ionization method: ES$^+$: [M]=303.1 (DMT)

1H-NMR (DMSO-d6, 400 MHz) δ[ppm]: 11.41 (s, 1H), 7.56-7.61 (m, 1H), 7.40 (d, J=7.34 Hz, 2H), 7.20-7.32 (m, 7H), 6.87 (d, J=8.56 Hz, 4H), 5.90 (dd, J=10.09, 3.36 Hz, 1H), 4.79 (t, J=5.20 Hz, 1H), 3.70-3.85 (m, 10H), 3.62 (d, J=11.74 Hz, 1H), 3.49 (t, J=10.76 Hz, 1H), 2.97-3.12 (m, 2H), 1.70 (s, 3H).

43a: 3-[[(2S,6R)-2-[[bis(4-methoxyphenyl)-phenyl-methoxy]methyl]-6-(5-methyl-2,4-dioxo-pyrimidin-1-yl)-1,4-dioxan-2-yl]methoxy-(diisopropylamino)phosphanyl]oxypropanenitrile 669 mg (1.2 mmol) of the starting material 42 and 415 mg (530 μl, 3.1 mmol) DIPEA were dissolved in 10 ml DCM. Under and atmosphere of argon, 384 mg (361 μl, 1.6 mmol) 2-cyanoethyl-N,N-diisopropylchlorophosphoramidite were added at 0° C. and the solution was stirred for 1 h, allowing to reach room temperature. To achieve complete conversion, additional 0.5 eq. DIPEA and 2-cyanoethyl-N,N-diisopropylchlorophosphoramidite were added and the reaction was stirred for another 2 h. After adding 200 μl n-butanol, the reaction was stirred for 10 minutes. The solution was washed with 50 ml of $H_2O$. The aqueous layer was separated and extracted with 50 ml DCM. The organic layers were dried with $MgSO_4$ and evaporated. The residue was dissolved in 30 ml diethylether and added dropwise in 100 ml n-pentane at −30° C. The precipitate was filtered and dried i.vac., to yield 723 mg (80.1%) of the desired product as colourless solid.

1H-NMR (DMSO-d6, 400 MHz) δ[ppm]: 11.40 (s, 1H), 7.63, 7.60 (2×s, 1H), 7.36-7.45 (m, 2H), 7.21-7.34 (m, 7H), 6.84-6.90 (m, 4H), 5.93-6.03 (m, 1H), 3.76-4.04 (m, 4H), 3.74 (s, 6H), 3.42-3.71 (m, 6H), 2.98-3.12 (m, 2H), 2.58-2.74 (m, 2H), 1.75, 1.72 (2×s, 3H), 0.95-1.14 (m, 12H).

31P-NMR (DMSO-d6, 162 MHz) δ[ppm]: 148.8, 148.7.

44: N-[9-[(2R,6S)-6-[[bis(4-methoxyphenyl)-phenyl-methoxy]methyl]-6-(triisopropylsilyl-oxymethyl)-1,4-dioxan-2-yl]-6-oxo-1H-purin-2-yl]-2-methyl-propanamide To a solution of 39c (14.18 g, 18.8 mmol) in 150 ml anhydrous pyridine was added TMSCl (15.22 g, 141 mmol) at 0° C. under $N_2$-atmosphere. After stirring for 2 h at room temperature, 2-methylpropanoyl chloride (2.18 g, 20.6 mmol) was added at 0° C. and stirring was continued for 2 h at room temperature, to achieve complete conversion. After adding 20 ml EtOH, the mixture was stirred for additional 10 min. The solution was poured into ice-water (500 ml) and extracted with DCM (3×500 ml). The combined organic layers were washed with 10% aqueous citric acid (2×500 ml), sat. $NaHCO_3$-solution (300 ml) and brine (200 ml), dried over anhydrous $Na_2SO_4$ and concentrated. The crude product was purified by preparative HPLC (0.1% FA/ACN), which gave 9.5 g (61.2%) of 44 as a white solid.

1H-NMR (DMSO-d6, 400 MHz) δ[ppm]: 8.08 (s, 2H), 7.39-7.26 (m, 2H), 7.25-7.19 (m, 8H), 6.80 (d, J=8.0 Hz, 4H), 5.79 (d, J=1.6 Hz, 1H), 4.18-4.12 (m, 1H), 3.99-3.81 (m, 4H), 3.72 (s, 7H), 3.69 (d, J=10 Hz, 1H), 3.11 (d, J=11.2 Hz, 1H), 2.93 (d, J=10.4 Hz, 1H), 2.72 (s, 1H), 1.11-1.08 (m, 7H), 1.01-0.91 (m, 21H).

45: N-[9-[(2R,6S)-6-[[bis(4-methoxyphenyl)-phenyl-methoxy]methyl]-6-(hydroxymethyl)-1,4-dioxan-2-yl]-6-oxo-1H-purin-2-yl]-2-methyl-propanamide 1.33 g (1.61 mmol) of 44 were dissolved in 16 ml DMF. After adding 1.65 g (2.26 ml, 16.1 mmol) $NEt_3$ and 1.32 g (1.34 ml, 8.05 mmol) $NEt_3 \cdot 3HF$, the solution was stirred for 2 h at 90° C. The reaction mixture was cooled to room temperature, followed by the addition of 2.5 g $NaHCO_3$ and 10 ml $H_2O$. After stirring for 2 h, the mixture was evaporated and the residue was dissolved in 25 ml DCM/iPrOH (4:1) and purified on silica (0 to 10% MeOH in DCM) to yield 0.83 g (76.5%) of the title compound 45.

LCMS-Method C:

UV-wavelength [nm]=220: $R_t$[min]=2.33

Ionization method: $ES^+$: $[M+H]^+$=670.2

1H-NMR (DMSO-d6, 400 MHz) δ[ppm]: 12.11 (br s, 1H), 11.66 (s, 1H), 8.11 (s, 1H), 7.37 (d, J=7.46 Hz, 2H), 7.18-7.29 (m, 7H), 6.84 (dd, J=8.93, 2.69 Hz, 4H), 5.98 (dd, J=8.31, 4.40 Hz, 1H), 4.81 (t, J=5.26 Hz, 1H), 3.90-4.02 (m, 2H), 3.67-3.86 (m, 4H), 3.72 (s, 6H), 3.04 (d, J=9.54 Hz, 1H), 2.96 (m, 1H), 2.75-2.81 (m, 1H), 1.11 (t, J=6.66 Hz, 6H).

43c: N-[9-[(2R,6S)-6-[[bis(4-methoxyphenyl)-phenyl-methoxy]methyl]-6-[[2-cyanoethoxy-(diisopropylamino)phosphanyl]oxymethyl]-1,4-dioxan-2-yl]-6-oxo-1H-purin-2-yl]-2-methyl-propanamide 100 mg (149 μmol) of the alcohol 45, 0.2 g molecular sieves (4 Å) and 13.5 mg (75 μmol) diisopropylammonium tetrazolide were dissolved in 2.5 ml dry DCM. Under an Ar-atmosphere, 45.5 mg (48 μl, 146 μmol) 2-cyanoethyl-N,N,N',N'-tetraisopropylphosphoro-diamidite were added and the solution was stirred for 2 h at room temperature to achieve complete conversion. After adding sat. $NaHCO_3$-solution, the organic phase was separated and the aqueous phase washed 1× with DCM. The combined organic layers were washed with sat. NaCl-solution, dried with $MgSO_4$ and evaporated. The crude product was purified on silica (pre-conditioned with DCM+0.5% $NEt_3$, 0 to 10% MeH in DCM), yielding 95 mg (73.1%) of the title compound (43c) as colourless foam.

LCMS-Method C:

UV-wavelength [nm]=220: $R_t$[min]=2.34, 2.36

Ionization method: $ES^+$: $[M]^+$=787.2 (M-iPr$_2$N+OH+H+)

1H-NMR (DMSO-d6, 400 MHz) δ[ppm]: 12.09 (br s, 1H), 11.61, 11.58 (2×s, 1H), 8.13, 8.08 (2×s, 1H), 7.35 (m, 2H), 7.18-7.28 (m, 7H), 6.80-6.85 (m, 4H), 5.97 (m, 1H), 3.95-4.07 (m, 4H), 3.56-3.94 (m, 4H), 3.72 (s, 6H), 3.36-3.54 (m, 2H), 2.96-3.11 (m, 2H), 2.68-2.82 (m, 2H), 2.59 (m, 1H), 0.96-1.15 (m, 12H), 0.83-0.90 (m, 6H).

31P-NMR (DMSO-d6, 162 MHz) δ[ppm]: 148.1, 147.9.

Example B.2

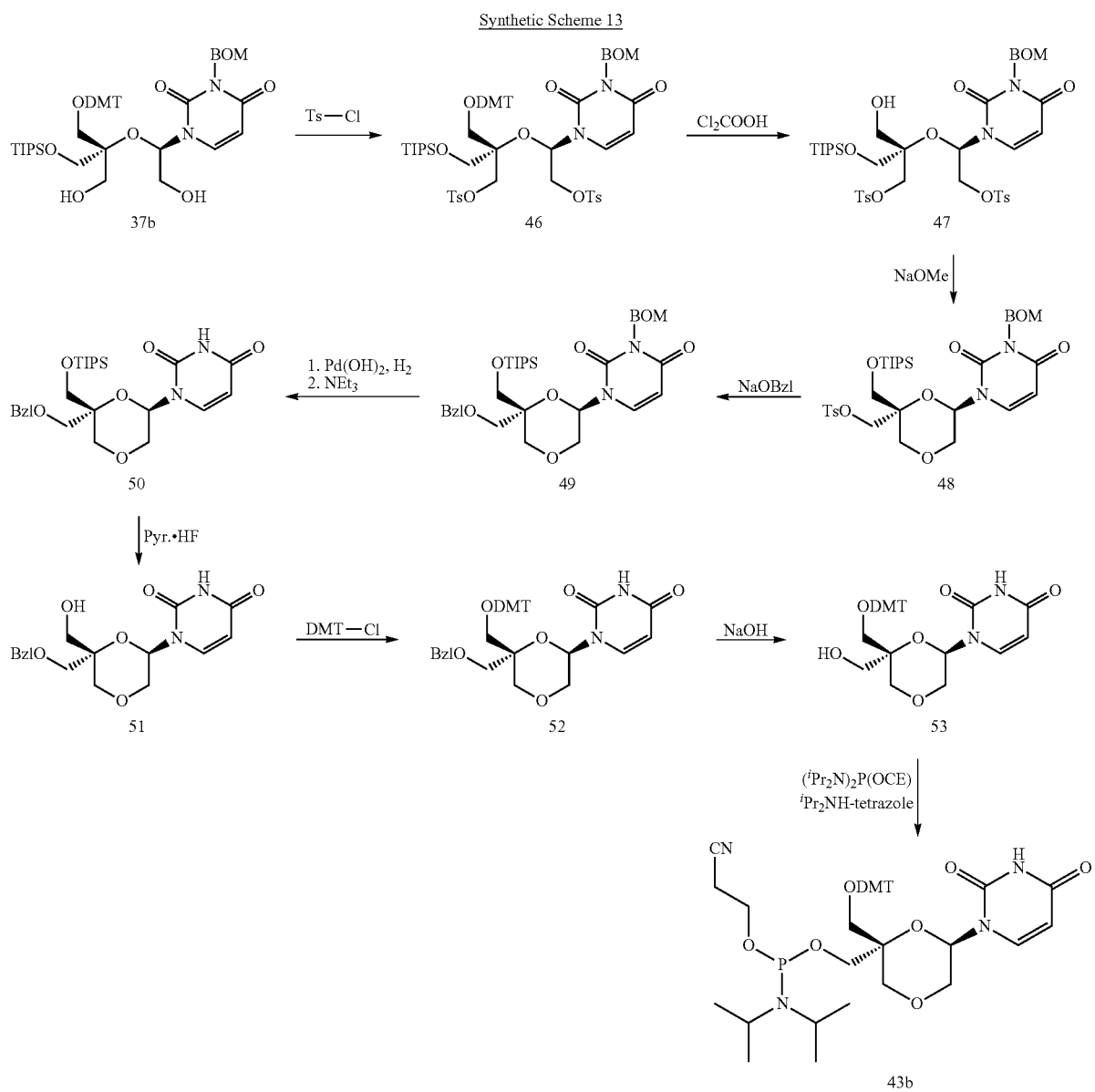

46: [(2R)-2-[3-(benzyloxymethyl)-2,4-dioxo-pyrimidin-1-yl]-2-[(1S)-1-[[bis(4-methoxy-phenyl)-phenylmethoxy]methyl]-1-(p-tolylsulfonyloxymethyl)-2-triisopropylsilyloxy-ethoxy]ethyl] 4-methylbenzenesulfonate 14.80 g (17.31 mmol) of the starting material 37b were dissolved in 120 ml dry pyridine. At room temperature, 13.33 g (69.23 mmol) Ts-Cl were added and the reaction was stirred at room temperature. After 23 h, 1.0 g (8.2 mmol) DMAP were added and stirring was continued for another 24 h. Additional 6.67 g (34.62 mmol) Ts-Cl were added and the reaction mixture was stirred for 48 h to achieve complete conversion. The solvent was removed and the residue was dissolved in EtOAc. The organic solution was washed with $H_2O$, aqueous citric acid (10%), sat. $NaHCO_3$-solution and brine. Drying over $MgSO_4$ and evaporation of the solvent, gave the crude product, which was purified on silica (pre-conditioned with n-heptane+0.5% $NEt_3$, 20 to 50% EtOAc in n-heptane), yielding 12.0 g (59.6%) of 46 as colourless foam.

LCMS-Method A:
UV-wavelength [nm]=220: $R_t$[min]=2.33
Ionization method: $ES^+$: $[M+Na]^+$=1185.5

47: [(2R)-2-[3-(benzyloxymethyl)-2,4-dioxo-pyrimidin-1-yl]-2-[(1S)-1-(hydroxymethyl)-1-(p-tolylsulfonyloxymethyl)-2-triisopropylsilyloxy-ethoxy]ethyl] 4-methylbenzenesulfonate A solution of 12.0 g (10.31 mmol) of 46 in 240 ml DCM was treated with 26.87 g (17.22 ml, 206.28 mmol) DCA. The solution was stirred at room temperature for 30 min to achieve complete conversion. The organic solution was washed with sat. NaHCO$_3$-solution and the layers were separated. The aqueous phase was washed 2× with DCM and the combined organic layers were dried with MgSO$_4$. After evaporation of the solvent, the crude product was purified on silica (0 to 100 EtOAc in n-heptane), yielding 7.84 g (88.3%) of the title compound 47 as orange oil.
LCMS-Method A:
UV-wavelength [nm]=220: R$_t$[min]=2.19
Ionization method: ES$^+$: [M+H]$^+$=861.3

48: [(2S,6R)-6-[3-(benzyloxymethyl)-2,4-dioxopyrimidin-1-yl]-2-(triisopropysilyloxy-methyl)-1,4-dioxan-2-yl]methyl-4-methylbenzenesulfonate 7.83 g (9.09 mmol) 47 were dissolved in 250 ml dry MeOH. After adding 22.11 g (409.18 mmol) sodium methoxide, the solution was stirred at 50° C. After 2.5 h, the solvent was removed and the residue dissolved in EtOAc. The organic solution was washed with H$_2$O, and brine, dried with MgSO$_4$ and evaporated. The crude product was purified on silica (20 to 100% ethyl in n-heptane), yielding the desired dioxane 48 as a colourless foam (3.84 g, 61.3%).
LCMS-Method A:
UV-wavelength [nm]=220: R$_t$[min]=2.20
Ionization method: ES$^+$: [M+H]=689.3

49: [(2R,6R)-6-[3-(benzyloxymethyl)-2,4-dioxopyrimidin-1-yl]-2-(triisopropylsilyloxy-methyl)-1,4-dioxan-2-yl]methyl benzoate 3.84 g (5.57 mmol) of starting compound 48 were dissolved in 200 ml DMF. After adding 2.03 g (13.94 mmol) sodium benzoate, the solution was stirred at 150° C. for 24 h, to achieve complete conversion. The reaction mixture was cooled to room temperature and the solvent was removed i.vac. The residue was dissolved in EtOAc and washed 2× with H$_2$O and brine. After drying over MgSO$_4$ and evaporation of the solvent, the crude product was purified on silica (0 to 100% EtOAc in n-heptane), yielding 2.63 g (73.8%) of 49 as colourless foam.
LCMS-Method A:
UV-wavelength [nm]=220: R$_t$[min]=2.24
Ionization method: ES$^+$: [M+H]$^+$=639.3

50: [(2R,6R)-6-(2,4-dioxopyrimidin-1-yl)-2-(triisopropylsilyloxymethyl)-1,4-dioxan-2-yl]methyl Benzoate To a solution of 2.62 g (4.10 mmol) 49 in 65 ml MeOH were added 144 mg (0.21 mmol) Pd(OH)$_2$ (20% on carbon) under an argon atmosphere. After the solution has been purged with H$_2$, the reaction mixture was stirred at room temperature under an atmosphere of H$_2$ at 4 bar. After 1 h, the catalyst was filtered and the filtrate was evaporated under reduced pressure. The crude product (2.11 g) was dissolved in 40 ml of MeOH and 3.63 g (5.0 ml, 35.87 mmol) NEt$_3$ were added. The solution was stirred for 30 min at room temperature, to achieve complete conversion. After adjusting the pH to 7, using aqueous citric acid (10%), the solvent was removed and the residue was dissolved in EtOAc. After washing with aqueous citric acid (10%) and sat. NaHCO$_3$-solution, the organic phase was dried with MgSO$_4$ and evaporated, yielding 1.97 g (99.3%, crude) of 50 as colourless foam.

LCMS-Method A:
UV-wavelength [nm]=220: R$_t$[min]=2.12
Ionization method: ES$^+$: [M+H]$^+$=519.3

51: [(2R,6R)-6-(2,4-dioxopyrimidin-1-yl)-2-(hydroxymethyl)-1,4-dioxan-2-yl]methyl Benzoate 980 mg (1.89 mmol) of 50 were dissolved in 35 ml dry THF. At room temperature, 7.20 g (6.55 ml, 47.24 mmol) pyridine-HF (65%) were added and the solution was stirred for 1.5 h. After adding another 7.20 g pyridine-HF (65%), stirring was continued for 5 h, when full conversion was detected. After adding solid NaHCO$_3$ (approx. 24 g), the reaction was stirred for 1.5 h. The inorganic salts were filtered off and the filtrate was evaporated. The crude product was purified on silica (0 to 5% MeO in DCM), yielding the title compound 51 (494 mg, 72.2%) as colourless foam.
LCMS-Method A:
UV-wavelength [nm]=220: R$_t$[min]=1.22
Ionization method: ES$^+$: [M+H]$^+$=363.1

52: [(2S,6R)-2-[[bis(4-methoxyphenyl)-phenylmethoxy]methyl]-6-(2,4-dioxopyrimidin-1-yl)-1,4-dioxan-2-yl]methyl Benzoate To a solution of 490 mg (1.35 mmol) 51 in 20 ml DCM were added 874 mg (1.18 ml, 6.76 mmol) DIPEA and 584 mg (1.69 mmol) DMT-Cl at room temperature. After stirring for 16 h, the solution was evaporated and the crude product was purified on silica (preconditioned with n-heptane+0.5% NEt$_3$, 0 to 100% EtOAc in n-heptane), yielding 894 mg (99.5%) of the desired DMT-ether 52 as colourless foam.
LCMS-Method A:
UV-wavelength [nm]=220: R$_t$[min]=1.96
Ionization method: ES$^+$: [M+Na]$^+$=687.2

53: 1-[(2R,6S)-6-[[bis(4-methoxyphenyl)-phenylmethoxy]methyl]-6-(hydroxymethyl)-1,4-dioxan-2-yl]pyrimidine-2,4-dione 888 mg (1.34 mmol) 52 were dissolved in 20 ml THF and 5 ml MeOH. At 0° C., 6.68 ml (13.36 mmol) of a 2 M NaOH solution were added and the solution was stirred for 1 h, allowing to reach room temperature. After cooling down to 0° C., 12 ml of an aqueous citric acid solution (10%) were added and the mixture was extracted with EtOAc. The organic layer was separated and washed with sat. NaHCO$_3$-solution. After drying with MgSO$_4$, the solvent was removed. The crude product was purified on silica (preconditioned with n-heptane+0.5% NEt$_3$, 0 to 100% (EtOAc+5% MeOH) in n-heptane), which gave 730 mg (97.5%) of 53 as colourless foam.
LCMS-Method A:
UV-wavelength [nm]=220: R$_t$[min]=1.78
Ionization method: ES$^-$: [M–H]$^-$=559.4
1H-NMR (DMSO-d6, 400 MHz) δ[ppm]: 11.42 (br s, 1H), 7.67 (d, J=8.07 Hz, 1H), 7.39 (d, J=6.95 Hz, 2H), 7.19-7.33 (m, 7H), 6.85-6.90 (m, 4H), 5.89 (dd, J=10.03, 3.18 Hz, 1H), 5.66 (d, J=8.07 Hz, 1H), 4.80 (t, J=5.26 Hz, 1H), 3.70-3.83 (m, 10H), 3.55 (d, J=11.62 Hz, 1H), 3.44 (m, 1H), 3.08 (d, J=9.41 Hz, 1H), 2.97 (d, J=9.41 Hz, 1H).

43b: 3-[[(2S,6R)-2-[[bis(4-methoxyphenyl)-phenylmethoxy]methyl]-6-(2,4-dioxopyrimidin-1-yl)-1,4-dioxan-2-yl]methoxy-(diisopropylamino)phosphanyl]oxypropanenitrile 725 mg (1.29 mmol) starting compound 53 and 122 mg (0.71 mmol) diisopropylammonium tetrazolide were dissolved in 20 ml dry DCM. Under an argon atmosphere, 429 mg (452 µl, 1.43 mmol) 2-cyanoethyl N,N,N',N'-tetraisopropylphosphoro-diamidite were added at room temperature and the solution was stirred for 16 h. After adding another 122 mg (0.71 mmol) diisopropylammonium tetrazolide and 429 mg (452 µl, 1.43 mmol) 2-cyanoethyl N,N,N',N'-tetraisopropylphosphorodiamidite, stirring was continued for 2 h, to achieve complete conversion. The solvent was removed and the residue was dissolved in EtOAc and washed with $H_2O$ and sat. $NaHCO_3$-solution. After drying with $MgSO_4$, the solvent was evaporated and the crude product was dissolved in 25 ml diethyl ether. Under stirring, the organic solution was dropped into 150 ml n-pentane. The precipitate was filtered and dried at 40° C. i. vac., yielding 751 mg (76.3%) of the title compound 43b as colourless solid.

1H-NMR (DMSO-d6, 400 MHz) δ[ppm]: 11.39 (br s, 1H), 7.65-7.73 (m, 1H), 7.34-7.43 (m, 2H), 7.19-7.34 (m, 7H), 6.84-6.90 (m, 4H), 5.95 (m, 1H), 5.66 (m, 1H), 3.92-4.10 (m, 2H), 3.78-3.91 (m, 2H), 3.73 (s, 6H), 3.41-3.68 (m, 6H), 3.11 (m, 1H), 2.98 (m, 1H), 2.70 (m, 1H), 2.61 (m, 1H), 0.94-1.14 (m, 12H).

31P-NMR (DMSO-d6, 162 MHz) δ[ppm]: 148.9, 148.7.

Example B.3

54: [(2S,6R)-6-(2,4-dioxopyrimidin-1-yl)-2-(triisopropylsilyloxymethyl)-1,4-dioxan-2-yl]methyl Benzoate 2.66 g (6.42 mmol) of 40b were dissolved in 35 ml dry pyridine. At room temperature, 1.37 g (1.13 ml, 9.62 mmol) benzoyl chloride were added dropwise and the solution was stirred for 16 h, to achieve complete conversion. The solvent was removed i. vac. and the residue was dissolved in EtOAc. After washing with 10% aqueous citric acid solution (2×), sat. $NaHCO_3$- and NaCl-solution, the organic layer was dried with $MgSO_4$ and evaporated. The crude product was purified on silica (0 to 100% EtOAc in n-heptane), yielding 2.0 g (60.0%) of 54 as colourless foam.

LCMS-Method C:
UV-wavelength [nm]=220: $R_t$[min]=3.02
Ionization method: $ES^+$: [M+H]=519.4

55: [(2S,6R)-6-(4-amino-2-oxo-pyrimidin-1-yl)-2-(triisopropylsilyloxymethyl)-1,4-dioxan-2-yl]methyl Benzoate To a solution of 1.99 g (3.61 mmol) 54 in dry ACN were added 6.28 g (8.63 ml, 61.43 mmol) $NEt_3$ and 3.06 g (43.36 mmol) 1H-1,2,4-triazole. The reaction mixture was cooled Synthetic Scheme 14

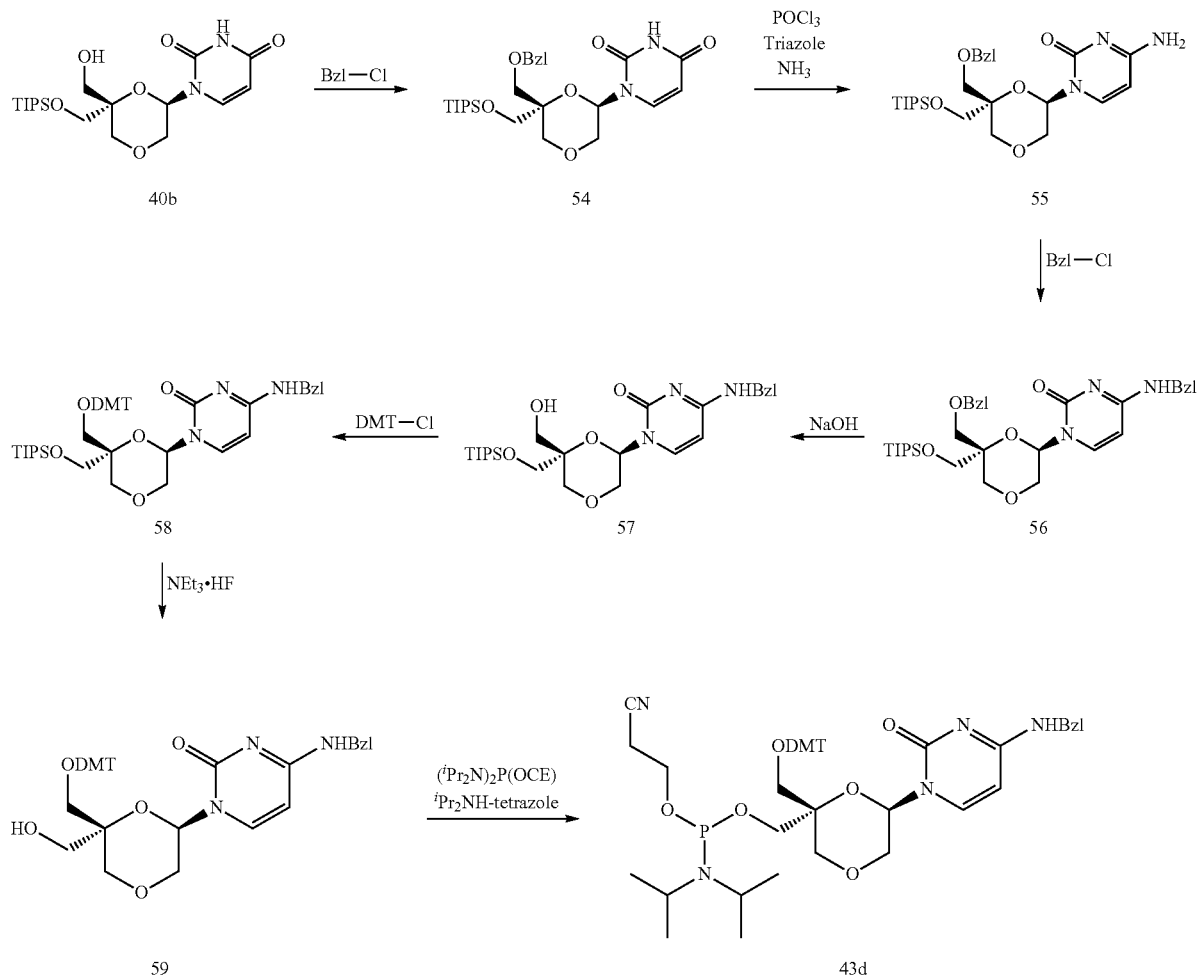

to 0° C. and a solution of 1.66 g (1.01 ml, 10.84 mmol) POCl₃ in 15 ml dry ACN was added dropwise under vigorous stirring. After 1 h, the solvent was removed i. vac. and to the residue were added 150 ml of a sat. NaHCO₃/H₂O-mixture (1:1). The aqueous mixture was extracted 3× with DCM and the combined organic layers were dried with MgSO4. After evaporation of the solvent, the crude product was dissolved in 50 ml dry ACN followed by the addition of 50 ml of an aqueous NH₃-solution (32%). After stirring overnight (17 h), the solution was concentrated and the remaining aqueous mixture was extracted with DCM (2×100 ml). The combined organic layers were dried with MgSO₄. Evaporation of the solvent gave 1.93 g (quant., crude product) 55 as light yellow foam, which was used without further purification.

LCMS-Method C:

UV-wavelength [nm]=220: $R_t$[min]=2.59

Ionization method: ES⁺: [M+H]⁺=518.4

56: [(2S,6R)-6-(4-benzamido-2-oxo-pyrimidin-1-yl)-2-(triisopropylsilyloxymethyl)-1,4-dioxan-2-yl]methyl Benzoate 1.93 g (3.72 mmol) of 55 were dissolved in 30 ml dry pyridine. At room temperature, 0.79 g (0.66 ml, 5.59 mmol) benzoyl chloride were added dropwise and the solution was stirred for 18 h, to achieve complete conversion. The solvent was removed i. vac. and the residue was dissolved in EtOAc. After washing with 10% aqueous citric acid solution (2×), sat. NaHCO₃- and NaCl-solution, the organic layer was dried with MgSO₄ and evaporated. The crude product was purified on silica (0 to 100% EtOAc in n-heptane), yielding 1.91 g (82.5%) of 56 as colourless foam.

LCMS-Method C:

UV-wavelength [nm]=220: $R_t$[min]=3.27

Ionization method: ES⁺: [M+H]⁺=622.5

57: N-[1-[(2R,6R)-6-(hydroxymethyl)-6-(triisopropylsilyloxymethyl)-1,4-dioxan-2-yl]-2-oxo-pyrimidin-4-yl]benzamide 952 mg (1.53 mmol) 56 were dissolved in 20 ml EtOH/pyridine (1:1). At 0° C., 9.19 ml (9.19 mmol) of a 1 M NaOH-solution were added and the solution was stirred at 0° C. for 3 h, when complete conversion was detected. The pH was brought to 6, using citric acid-monohydrate (approx. 650 mg, dissolved in 15 ml H₂O). After evaporation of the organic solvents, the aqueous layer was extracted with EtOAc. The organic phase was washed with aqueous citric acid (10%), H₂O and sat. NaCl-solution. After drying over MgSO₄ and evaporation, the crude product was purified on silica (0 to 100% EtOAc in n-heptane), yielding 678 mg (85.5%) of the title compound 57 as colourless foam.

LCMS-Method C:

UV-wavelength [nm]=220: $R_t$[min]=2.72

Ionization method: ES⁺: [M+H]⁺=518.2

58: N-[1-[(2R,6S)-6-[[bis(4-methoxyphenyl)-phenyl-methoxy]methyl]-6-(triisopropylsilyloxymethyl)-1,4-dioxan-2-yl]-2-oxo-pyrimidin-4-yl]benzamide 673 mg (1.30 mmol) 57 were dissolved in 20 ml DCM/pyridine (1:1). After adding 719 mg (2.08 mmol) DMT-Cl at room temperature, the solution was stirred for 2 h. The solvents were evaporated and the residue was dissolved in EtOAc. After washing with 2× aqueous citric acid (10%) and sat. NaHCO₃-solution, the organic layer was dried with MgSO₄ and concentrated i. vac. The crude product was purified on silica (preconditioned with n-heptane+0.5% NEt₃, 0 to 70% EtOAc in n-heptane), yielding 975 mg (91.5%) of the DMT-ether 58 as light yellow foam.

LCMS-Method C:

UV-wavelength [nm]=220: $R_t$[min]=3.61

Ionization method: ES⁻: [M−H]⁻=818.4

59: N-[1-[(2R,6S)-6-[[bis(4-methoxyphenyl)-phenyl-methoxy]methyl]-6-(hydroxymethyl)-1,4-dioxan-2-yl]-2-oxo-pyrimidin-4-yl]benzamide 970 mg (1.18 mmol) 58 and 1.68 g (2.31 ml, 16.56 mmol) NEt₃ were dissolved in 20 ml THF. After the addition of 3.15 g (3.18 ml, 18.93 mmol) NEt₃ 3 HF, the reaction was stirred at 65° C. for 48 h, to achieve complete conversion. After cooling to room temperature, the mixture was poured into 200 ml sat. NaHCO₃-solution and stirred for 1.5 h. After extraction with 2×100 ml DCM, the combined organic layers were dried with MgSO₄ and evaporated. Final purification on silica (0 to 100% EtOAc in n-heptane) gave 745 mg (94.9%) of 59 as colourless foam.

LCMS-Method C:

UV-wavelength [nm]=220: $R_t$[min]=2.61

Ionization method: ES⁺: [M+H]⁺=664.3

1H-NMR (DMSO-d6, 600 MHz) δ[ppm]: 11.31 (br s, 1H), 8.13 (br d, J=7.15 Hz, 1H), 8.00 (d, J=7.66 Hz, 2H), 7.63 (t, J=7.38 Hz, 1H), 7.51 (t, J=7.79 Hz, 2H), 7.36-7.42 (m, 3H), 7.22-7.33 (m, 7H), 6.87-6.91 (m, 4H), 6.03 (dd, J=9.72, 3.12 Hz, 1H), 4.84 (t, J=5.50 Hz, 1H), 3.94 (dd, J=11.19, 3.12 Hz, 1H), 3.84-3.89 (m, 1H), 3.72-3.81 (m, 8H), 3.56 (d, J=11.92 Hz, 1H), 3.33-3.38 (m, 1H), 3.16 (d, J=9.35 Hz, 1H), 3.02 (d, J=9.17 Hz, 1H).

43d: N-[1-[(2R,6S)-6-[[bis(4-methoxyphenyl)-phenyl-methoxy]methyl]-6-[[2-cyanoethoxy-(diisopropylamino)phosphanyl]oxymethyl]-1,4-dioxan-2-yl]-2-oxo-pyrimidin-4-yl]benzamide 715 mg (1.08 mmol) starting compound 59 and 559 mg (3.23 mmol) diisopropylammonium tetrazolide were dissolved in 20 ml dry DCM. Under an argon atmosphere, 502 mg (529 µl, 1.62 mmol) 2-cyanoethyl N,N,N',N'-tetraisopropylphosphoro-diamidite were added at room temperature and the solution was stirred for 16 h to achieve complete conversion. After adding 40 ml H₂O, the organic layer was separated and the aqueous phase was extracted with DCM. The combined organic layers were dried with MgSO₄ and evaporated. The crude product was purified on silica (preconditioned with n-heptane+1.0% NEt₃, 0 to 100% MTB-ether/DCM (1:1) in n-heptane), yielding 887 mg of title compound 43d as colourless foam.

1H-NMR (DMSO-d6, 400 MHz) [ppm]: 11.30 (br s, 1H), 8.15 (2×d, J=7.53 Hz, 1H), 8.00 (m, 2H), 7.63 (m, 1H), 7.51 (m, 2H), 7.20-7.44 (m, 10H), 6.89 (br d, J=8.72 Hz, 4H), 6.03-6.13 (m, 1H), 3.78-4.17 (m, 4H), 3.74 (s, 6H), 3.35-3.71 (m, 6H), 3.20 (m, 1H), 3.03 (m, 1H), 2.89 (m, 1H), 2.72 (m, 1H), 0.89-1.22 (m, 12H).

31P-NMR (DMSO-d6, 400 MHz) δ[ppm]: 148.2, 147.7.

Example B.4

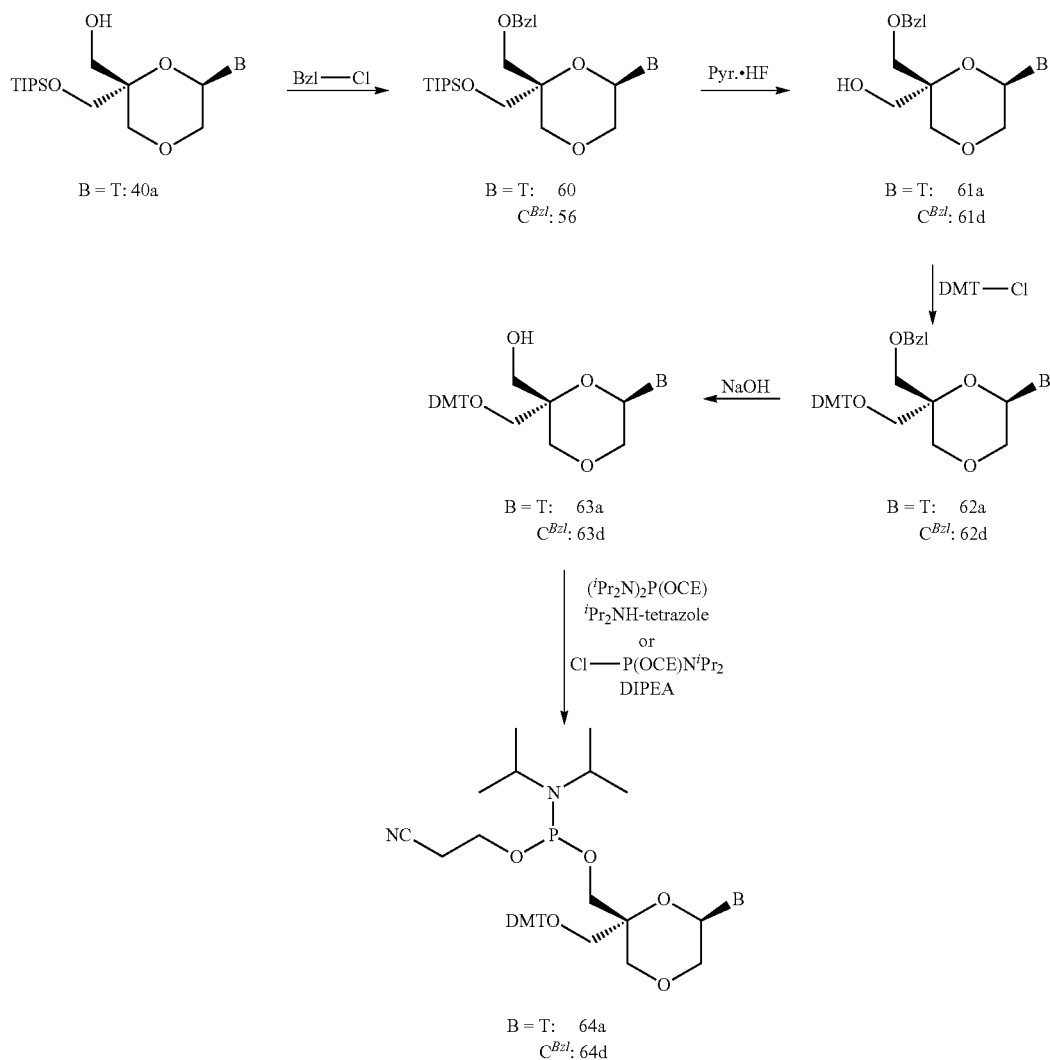

Synthetic Scheme 15

60: [(2S,6R)-6-(5-methyl-2,4-dioxo-pyrimidin-1-yl)-2-(triisopropylsilyloxymethyl)-1,4-dioxan-2-yl]methyl Benzoate Following the protocol, described for compound 54, 1.0 g (2.33 mmol) of 40a gave 1.24 g (86.4%) of the benzoylated product 60 after purification on silica (0 to 100% EtOAc in n-heptane) as colourless foam.
LCMS-Method C:
UV-wavelength [nm]=220: $R_t$[min]=3.10
Ionization method: ES⁻: [M−H]⁻=531.6

61a: [(2S,6R)-2-(hydroxymethyl)-6-(5-methyl-2,4-dioxo-pyrimidin-1-yl)-1,4-dioxan-2-yl]methyl Benzoate 1.07 g (2.01 mmol) of 60 were dissolved in 20 ml THF. At room temperature, 1.53 g (1.39 ml, 10.03 mmol) pyridine-HF (65%) were added and the mixture was stirred for 18 h. After adding another 3.06 g (2.78 ml, 20.06 mmol) pyridine-HF (65%), the solution was stirred at 65° C. for 5 h, when complete conversion was detected. The reaction mixture was poured into 250 ml sat. NaHCO₃-solution. After stirring for 1 h, the mixture was extracted with DCM (3×50 ml). The combined organic layers were dried with MgSO₄ and evaporated. The crude product was purified on silica (0 to 100% EtOAc in n-heptane), yielding 680 mg (90.0%) of 61a as colourless foam.
LCMS-Method C:
UV-wavelength [nm]=220: $R_t$[min]=1.46
Ionization method: ES⁻: [M−H]⁻=375.3

61d: [(2S,6R)-6-(4-benzamido-2-oxo-pyrimidin-1-yl)-2-(hydroxymethyl)-1,4-dioxan-2-yl]methyl Benzoate Following the protocol, described for compound 61a, using 10.0 eq. of pyridine-HF, 952 mg (1.53 mmol) of 56 gave 471 mg (66.1%) of 61d as colourless foam.
LCMS-Method C:
UV-wavelength [nm]=220: $R_t$[min]=1.89
Ionization method: ES⁺: [M+H]⁺=466.1

62a: [(2R,6R)-2-[[bis(4-methoxyphenyl)-phenyl-methoxy]methyl]-6-(5-methyl-2,4-dioxo-pyrimidin-1-yl)-1,4-dioxan-2-yl]methyl Benzoate 675 mg (1.79 mmol) 61a were dissolved in 10 ml DCM/pyridine (1:1). After adding a solution of 806 mg (2.33 mmol) DMT-Cl in 15 ml DCM, the reaction solution was stirred at room temperature for 5.5 h, followed by the addition of another 403 mg (1.17 mmol) DMT-Cl. Stirring was continued for 18 h, when complete conversion was detected. The solvents were evaporated and the residue was dissolved in EtOAc. After washing 2× with aqueous citric acid (10%) and sat. NaHCO$_3$-solution, the organic layer was dried with MgSO$_4$ and concentrated i. vac. The crude product was purified on silica (preconditioned with n-heptane+0.5% NEt$_3$, 0 to 100% EtOAc in n-heptane), yielding 1.15 g (94.1%) of the DMT-ether 62a as colourless foam.

LCMS-Method C:
UV-wavelength [nm]=220: R$_t$[min]=2.76
Ionization method: ES$^-$: [M–H]$^-$=677.3

62d: [(2R,6R)-6-(4-benzamido-2-oxo-pyrimidin-1-yl)-2-[[bis(4-methoxyphenyl)-phenyl-methoxy]methyl]-1,4-dioxan-2-yl]methyl Benzoate Following the protocol described for 62a, 467 mg (1.00 mmol) of starting compound 61d were DMT-protected, yielding 677 mg (87.9%) of 62d as colourless foam.

LCMS-Method C:
UV-wavelength [nm]=220: R$_t$[min]=2.95
Ionization method: ES$^-$: [M–H]$^-$=766.4

63a: 1-[(2R,6R)-6-[[bis(4-methoxyphenyl)-phenyl-methoxy]methyl]-6-(hydroxymethyl)-1,4-dioxan-2-yl]-5-methyl-pyrimidine-2,4-dione The starting compound 62a (580 mg, 0.85 mmol) was dissolved in 25 ml THF/MeOH (4:1). At room temperature, 4.27 ml (8.55 mmol) of a 2 M NaOH-solution were added and the reaction was stirred for 30 min. The pH was brought to 7 using solid citric acid-monohydrate and sat. NaHCO$_3$-solution. The organic solvents were removed i. vac. and the aqueous phase was extracted with DCM (2×30 ml). The combined organic layers were dried with MgSO$_4$. After evaporation, 481 mg (98.0%, crude) of the title compound 63a were obtained as colourless solid, which was used without further purification.

LCMS-Method A:
UV-wavelength [nm]=220: R$_t$[min]=1.82
Ionization method: ES$^-$: [M–H]$^-$=573.3
1H-NMR (DMSO-d6, 400 MHz) δ[ppm]: 11.35 (s, 1H), 7.63 (s, 1H), 7.39 (d, J=7.34 Hz, 2H), 7.20-7.33 (m, 7H), 6.89 (d, J=8.31 Hz, 4H), 5.75 (m, 1H), 4.83 (t, J=5.81 Hz, 1H), 3.74 (s, 6H), 3.57-3.72 (m, 4H), 3.51-3.56 (m, 2H), 3.20-3.29 (m, 2H), 1.79 (d, J=0.86 Hz, 3H).

63d: N-[1-[(2R,6R)-6-[[bis(4-methoxyphenyl)-phenyl-methoxy]methyl]-6-(hydroxymethyl)-1,4-dioxan-2-yl]-2-oxo-pyrimidin-4-yl]benzamide 672 mg (0.88 mmol) 62d were dissolved in 20 ml EtOH/pyridine (1:1). At 0° C., 5.25 ml (5.25 mmol) of a 1 M NaOH-solution were added and the reaction was stirred for 1 h. The pH was brought to 7, using an aqueous citric acid solution. After adding 200 ml EtOAc and H$_2$O, the organic phase was separated and washed 2× with aqueous citric acid solution (10%), H$_2$O and NaCl-solution. After drying with MgSO$_4$ and evaporation of the solvent, the crude product was purified on silica (preconditioned with n-heptane+0.5% NEt$_3$, 0 to 100% EtOAc in n-heptane), yielding 555 mg (95.5%) of the title compound 63d as colourless foam.

LCMS-Method C:
UV-wavelength [nm]=220: R$_t$[min]=2.49
Ionization method: ES$^-$: [M–H]$^-$=662.3
1H-NMR (DMSO-d6, 600 MHz) δ[ppm]: 11.28 (br s, 1H), 8.31 (br d, J=6.79 Hz, 1H), 8.00 (d, J=7.66 Hz, 2H), 7.63 (t, J=7.43 Hz, 1H), 7.52 (t, J=7.79 Hz, 2H), 7.39 (m, 3H), 7.21-7.33 (m, 7H), 6.87-6.91 (m, 4H), 5.80 (dd, J=9.81, 3.21 Hz, 1H), 4.89 (t, J=5.96 Hz, 1H), 3.85 (dd, J=11.19, 3.12 Hz, 1H), 3.79 (m, 1H), 3.74 (s, 6H), 3.64 (d, J=11.92 Hz, 1H), 3.59 (m, 2H), 3.26-3.30 (m, 2H), 3.20 (t, J=10.55 Hz, 1H).

64a: 3-[[(2R,6R)-2-[[bis(4-methoxyphenyl)-phenyl-methoxy]methyl]-6-(5-methyl-2,4-dioxo-pyrimidin-1-yl)-1,4-dioxan-2-yl]methoxy-(diisopropylamino)phosphanyl]oxypropanenitrile Following the protocol described for 43a, 380 mg (0.66 mmol) of the starting compound 63a were transferred to the phosphoroamidite 64a. After precipitation from diethylether/n-pentane, 342 mg (66.7%) of the title compound (64a) was isolated as colourless solid.

1H-NMR (DMSO-d6, 400 MHz) δ[ppm]: 11.40, 11.39 (2×s, 1H), 7.63, 7.61 (2×s, 1H), 7.40 (m, 2H), 7.21-7.35 (m, 7H), 6.83-6.96 (m, 4H), 5.77-5.87 (m, 1H), 3.36-3.90 (m, 17H), 3.12-3.28 (m, 1H), 2.66-2.77 (m, 2H), 1.81-1.79 (2×s, 3H), 1.02-1.17 (m, 12H).
31P-NMR (DMSO-d6, 162 MHz) δ[ppm]: 148.5, 148.1.

64d: N-[1-[(2R,6R)-6-[[bis(4-methoxyphenyl)-phenyl-methoxy]methyl]-6-[[2-cyanoethoxy-(diisopropylamino)phosphanyl]oxymethyl]-1,4-dioxan-2-yl]-2-oxo-pyrimidin-4-yl]benzamide Following the protocol described for 43d, 525 mg (0.79 mmol) of the starting material 63d were transferred to the phosphoroamidite 64d. After chromatographic purification on silica (preconditioned with n-heptane+1.0% NEt$_3$, 0 to 100% MTB-ether/DCM (1:1) in n-heptane), 620 mg (90.7%) of the title compound (64d) were isolated as colourless foam.

1H-NMR (DMSO-d6, 400 MHz) δ[ppm]: 11.31 (br s, 1H), 8.22 (m, 1H), 8.01 (d, J=7.59 Hz, 2H), 7.57-7.69 (m, 1H), 7.52 (m, 2H), 7.39 (m, 3H), 7.20-7.34 (m, 7H), 6.86-6.92 (m, 4H), 5.88 (m, 1H), 3.39-3.95 (m, 11H), 3.74 (s, 6H), 3.26-3.34 (m, 0.5H), 3.17-3.24 (m, 0.5H), 2.71-2.77 (m, 1H), 2.64-2.69 (m, 1H), 1.03-1.24 (m, 12H).
31P-NMR (DMSO-d6, 162 MHz) δ[ppm]: 147.5, 147.3.

Example B.5

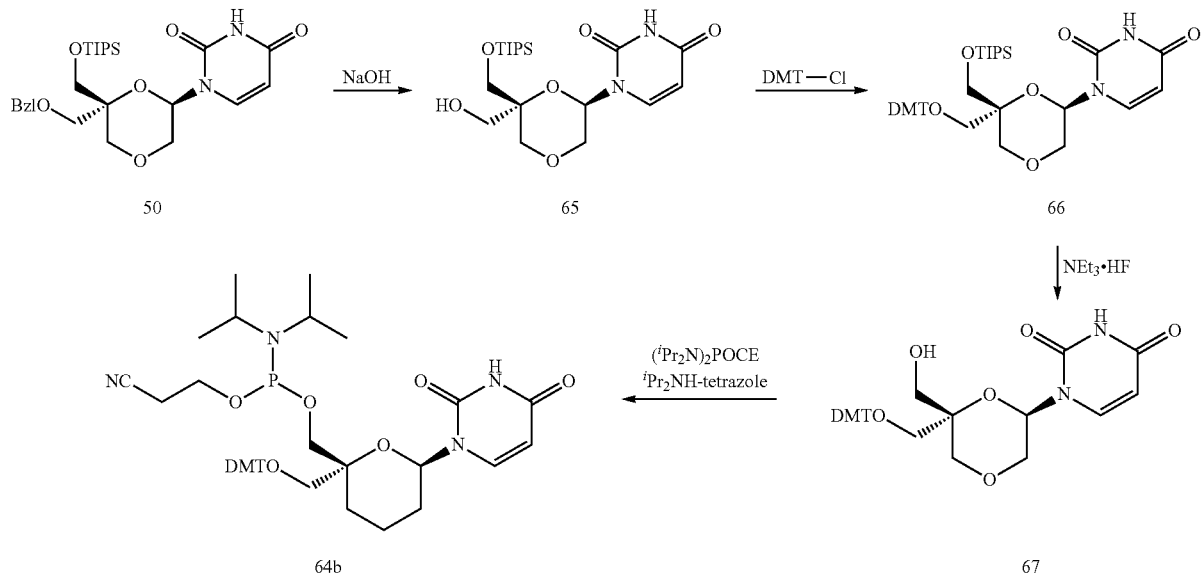

Synthetic Scheme 16

65: 1-[(2R,6S)-6-(hydroxymethyl)-6-(triisopropylsi-lyloxymethyl)-1,4-dioxan-2-yl]pyrimidine-2,4-dione 980 mg (1.89 mmol) of starting material 50 were dissolved in 40 ml THF/MeOH (4:1). At 0° C., 9.45 ml (18.90 mmol) of a 2 M NaOH-solution were added and the reaction was stirred at 0° C. for 1 h. The solution was brought to pH 7 by adding solid citric acid (approx. 1.33 g). The organic solvent were removed i. vac. and the aqueous residue was extracted with 100 ml EtOAc. The organic layer was separated and washed with sat. NaHCO$_3$-solution and dried with MgSO$_4$. After evaporation of the solvent, the crude product was purified on silica (0 to 5% MeOH in DCM), yielding 603 mg (77.0%) 65 as colourless foam.
LCMS-Method A:
UV-wavelength [nm]=220: R$_t$[min]=1.90
Ionization method: ES$^+$: [M+H]$^+$=415.3

66: 1-[(2R,6R)-6-[[bis(4-methoxyphenyl)-phenyl-methoxy]methyl]-6-(triisopropylsilyloxy-methyl)-1,4-dioxan-2-yl]pyrimidine-2,4-dione 597 mg (1.44 mmol) 65 and 931 mg (1.26 ml, 7.20 mmol) DIPEA were dissolved in 20 ml DCM. After adding 622 mg (1.80 mmol) DMT-Cl, the solution was stirred at room temperature for 22 h to achieve complete conversion. The solvent was removed i. vac. and the crude product purified on silica (preconditioned with n-heptane+0.5% NEt$_3$, 0 to 100% EtOAc in n-heptane), yielding 860 mg (83.3%) of the DMT-ether 66 as colourless foam.
LCMS-Method A:
UV-wavelength [nm]=220: R$_t$[min]=2.25
Ionization method: ES$^+$: [M+Na]$^+$=739.4

67: 1-[(2R,6R)-6-[[bis(4-methoxyphenyl)-phenyl-methoxy]methyl]-6-(hydroxymethyl)-1,4-dioxan-2-yl]pyrimidine-2,4-dione 854 mg (1.19 mmol) 66 was added to a solution of 5.26 g (7.23 ml, 51.49 mmol) NEt$_3$ and 9.55 g (9.66 ml, 57.46 mmol) NEt$_3$.3HF in 17 ml NMP. After stirring for 2 h at 65° C., the reaction was left at room temperature overnight. The reaction solution was poured into 450 ml H$_2$O/sat. NaHCO$_3$-solution (1:1) and the solution was extracted with 2×100 ml EtOAc. The combined organic layers were washed with H$_2$O and sat. NaCl-solution. After drying with MgSO$_4$, the crude product was purified on silica (preconditioned with n-heptane+0.5% NEt$_3$, 10 to 100% EtOAc in n-heptane), yielding 666 mg (99.7%) of the title compound 67 as colourless foam.
LCMS-Method A:
UV-wavelength [nm]=220: R$_t$[min]=1.76
Ionization method: ES$^+$: [M+Na]$^+$=583.3
1H-NMR (DMSO-d6, 400 MHz) δ[ppm]: 11.37 (s, 1H), 7.79 (d, J=8.07 Hz, 1H), 7.35-7.45 (m, 2H), 7.20-7.33 (m, 7H), 6.89 (2×d, J=8.93, 4H), 5.72 (dd, J=10.09, 3.24 Hz, 1H), 5.62-5.68 (m, 1H), 4.84 (t, J=5.75 Hz, 1H), 3.74 (s, 6H), 3.71 (m, 2H), 3.47-3.63 (m, 3H), 3.14-3.30 (m, 3H).

64b: 3-[[(2R,6R)-2-[[bis(4-methoxyphenyl)-phenyl-methoxy]methyl]-6-(2,4-dioxopyrimidin-1-yl)-1,4-dioxan-2-yl]methoxy-(diisopropylamino)phospha-nyl]oxypropanenitrile 650 mg (1.16 mmol) starting compound 67 and 110 mg (0.64 mmol) diisopropylammonium tetrazolide were dissolved in 16 ml dry DCM. Under an argon atmosphere, 396 mg (418 μl, 1.28 mmol) 2-cyanoethyl N,N,N',N'-tetraiso-propylphosphoro-diamidite were added at room temperature and the solution was stirred for 16 h. The solvent was removed and the residue was dissolved in EtOAc and washed with H$_2$O and sat. NaHCO$_3$-solution. After drying with MgSO$_4$, the solvent was evaporated and the crude product was dissolved in 15 ml methyl-tert.-butylether. Under stirring, the organic solution was dropped into 120 ml n-pentane. The precipitate was filtered and dried at 40° C. i. vac., yielding 827 mg (93.7%) of the title compound 64b as colourless solid.

1H-NMR (DMSO-d6, 400 MHz) δ[ppm]: 11.39 (br s, 1H), 7.74 (m, 1H), 7.35-7.44 (m, 2H), 7.18-7.35 (m, 7H), 6.84-6.92 (m, 4H), 5.73-5.86 (m, 1H), 5.67 (m, 1H), 3.54-3.89 (m, 7H), 3.74 (s, 6H), 3.35-3.53 (m, 4H), 3.12-3.28 (m, 1H), 2.62-2.76 (m, 2H), 1.02-1.16 (m, 12H).

31P-NMR (DMSO-d6, 162 MHz) δ[ppm]: 148.5, 148.1.

Example B.6

100% EtOAc in n-heptane) to yield 12.31 g (81.8%) of the title compound 1g as light yellow foam.

LCMS-Method C:

UV-wavelength [nm]=220: R$_t$[min]=2.57

Ionization method: ES⁻: [M–H+FA]⁻=625.1

1H-NMR (DMSO-d6, 400 MHz) δ[ppm]: 8.80 (s, 1H), 8.75 (s, 1H), 7.16-7.39 (m, 10H), 6.38 (d, J=4.2 Hz, 1H), 6.10 (dd, J=5.6, 4.3 Hz, 1H), 4.86 (d, J=5.7 Hz, 1H),

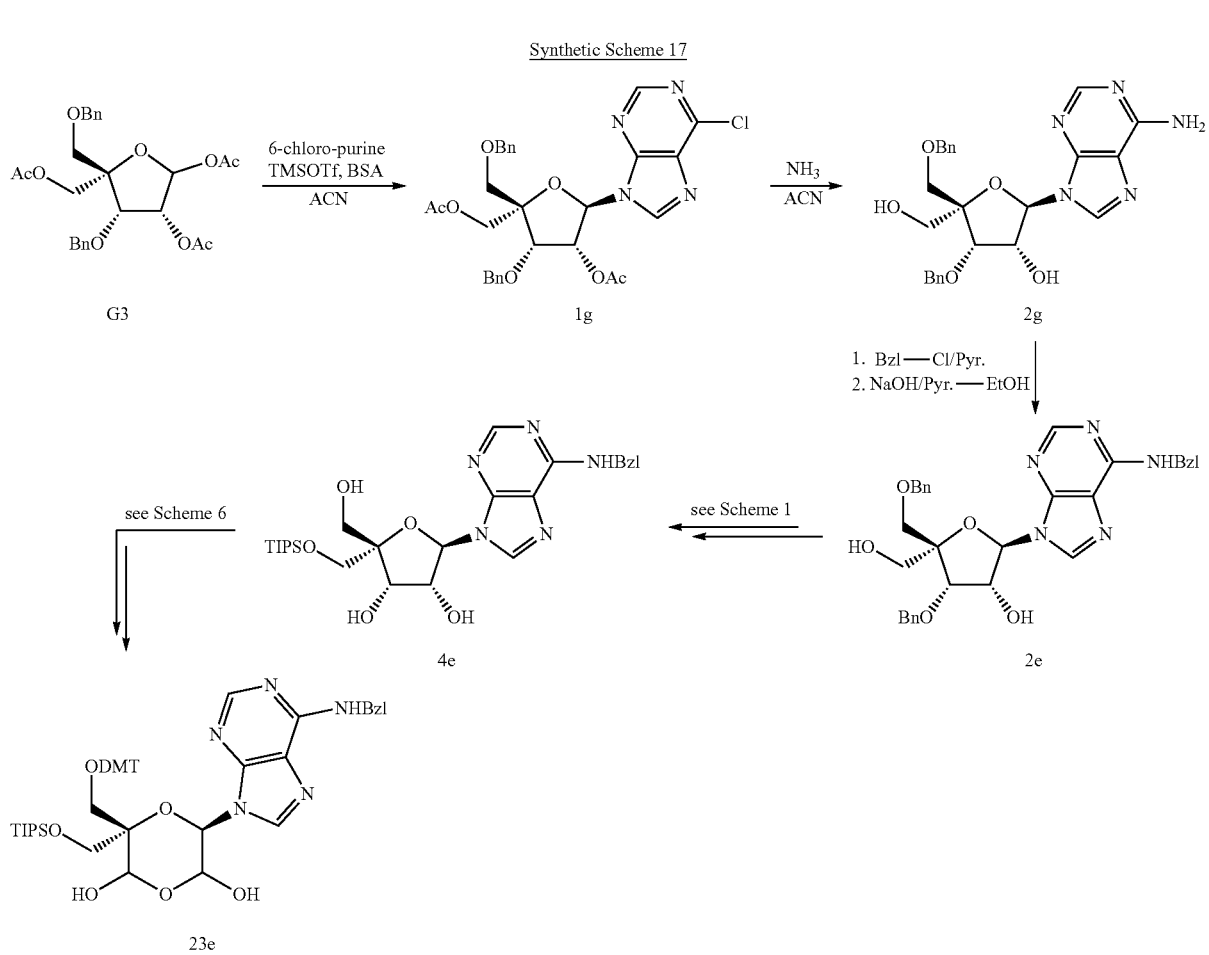

Synthetic Scheme 17

1g: [(2S,3S,4R,5R)-4-acetoxy-3-benzyloxy-2-(benzyloxymethyl)-5-(6-chloropurin-9-yl)tetra-hydrofuran-2-yl]methyl Acetate 12.60 g (25.9 mmol) of the carbohydrate building block G3 and 6.19 g (38.9 mmol) 6-chloropurine were dissolved in 175 ml dry ACN. Under an argon atmosphere, 12.07 g (11.84 ml, 77.7 mmol) DBU and 23.26 g (18.99 ml, 103.6 mmol) TMSOTf were added at 0° C. The ice bath was removed and the reaction was stirred for 1 h at room temperature and another h at 80° C., when complete conversion was detected. The solution was cooled to room temperature and poured into 500 ml sat. NaHCO$_3$-solution. After vigorous stirring for 1 h, the aqueous solution was extracted with 300 ml EtOAc. The organic layer was separated and washed with sat. NaHCO$_3$-solution/H$_2$O (1:1) and sat. NaCl-solution, dried with MgSO$_4$ and evaporated. The crude product (15.78 g) was purified on silica gel (10 to 4.54-4.68 (m, 2H), 4.37-4.47 (m, 3H), 4.24 (d, J=12.0 Hz, 1H), 3.69 (d, J=10.1 Hz, 1H), 3.60 (d, J=10.1 Hz, 1H), 2.05 (s, 3H), 1.99 (s, 3H).

2g: (2R,3R,4S,5R)-2-(6-aminopurin-9-yl)-4-benzyloxy-5-(benzyloxymethyl)-5-(hydroxy-methyl)tetrahydrofuran-3-ol 12.30 g (21.2 mmol) of the chloropurine riboside 1g were dissolved in 40 ml ACN. After adding 68.0 g (77.2 ml, 1.40 mol) aqueous ammonia (35%), the reaction solution was transferred in an autoclave and heated at 70° C. for 18 h. The reaction mixture was evaporated and the aqueous residue was extracted 3× with 150 ml DCM/isopropanol (4:1). The organic layers were combined, dried with MgSO$_4$ and evaporated, to yield 9.37 g crude product, which was recrystallized from 400 ml ACN, which gave 6.92 g (68.5%) of the adenosine analog 2g as colourless solid.

LCMS-Method C:
UV-wavelength [nm]=220: $R_t$[min]=1.69
Ionization method: ES$^+$: [M+H]$^+$=477.9
1H-NMR (DMSO-d6, 400 MHz) δ[ppm]: 8.22 (s, 1H), 8.12 (s, 1H), 7.24-7.42 (m, 12H), 6.01 (d, J=5.7 Hz, 1H), 5.72 (d, J=7.3 Hz, 1H), 5.01 (br t, J=5.1 Hz, 1H), 4.91-4.98 (m, 1H), 4.84 (d, J=11.9 Hz, 1H), 4.60 (d, J=11.7 Hz, 1H), 4.51 (s, 2H), 4.34 (d, J=5.3 Hz, 1H), 3.57-3.72 (m, 4H).

2e: N-[9-[(2R,3R,4S,5R)-4-benzyloxy-5-(benzyloxymethyl)-3-hydroxy-5-(hydroxymethyl)-tetrahydrofuran-2-yl]purin-6-yl]benzamide 6.91 g (14.5 mmol) of 2g were dissolved in 100 ml pyridine under an argon atmosphere. At room temperature, 10.17 g (8.41 ml, 72.4 mmol) benzoyl chloride were added and the reaction was stirred for 1 h. The solvent was removed i. vac. and the residue was dissolved in H$_2$O and extracted with EtOAc. The organic layer was separated and washed with 1 N HCl (2×250 ml), H$_2$O (1×200 ml), sat. NaHCO$_3$-solution (2×200 ml) and sat. NaCl-solution (1×200 ml). After drying with MgSO$_4$, the solvent was removed and the crude product (14.66 g, yellow foam) dissolved in 140 ml pyridine/EtOH (1:1). At room temperature, 108.5 ml (217.1 mmol) 2 N NaOH were added and the reaction mixture was stirred for 30 min. After adding 11 ml AcOH, the reaction solution was concentrated i.vac. The residue was treated with 200 ml H$_2$O and extracted with 200 ml EtOAc. The organic layer was washed with 1 N HCl (2×200 ml), H$_2$O (1×200 ml) and sat. NaHCO$_3$-solution (1×200 ml), dried with MgSO$_4$ and evaporated. Purification of the crude product (9.0 g) on silica (20 to 100% MeOH/EtOAc (9:1) in n-heptane) gave 7.25 g (86.1%) of the title compound 2e as colourless foam.
LCMS-Method C:
UV-wavelength [nm]=220: $R_t$[min]=2.12
Ionization method: ES$^+$: [M+H]$^+$=582.4
1H-NMR (DMSO-d6, 400 MHz) δ[ppm]: 11.19 (s, 1H), 8.72 (s, 1H), 8.58 (s, 1H), 8.05 (br d, J=7.3 Hz, 2H), 7.64 (br t, J=7.3 Hz, 1H), 7.52-7.60 (br t, 2H), 7.25-7.44 (m, 10H), 6.15 (d, J=5.6 Hz, 1H), 5.82 (d, J=7.5 Hz, 1H), 4.99-5.08 (m, 2H), 4.86 (d, J=11.9 Hz, 1H), 4.62 (d, J=11.9 Hz, 1H), 4.52 (s, 2H), 4.38 (d, J=5.1 Hz, 1H), 3.59-3.74 (m, 4H).

Example B.7

Synthetic Scheme 18

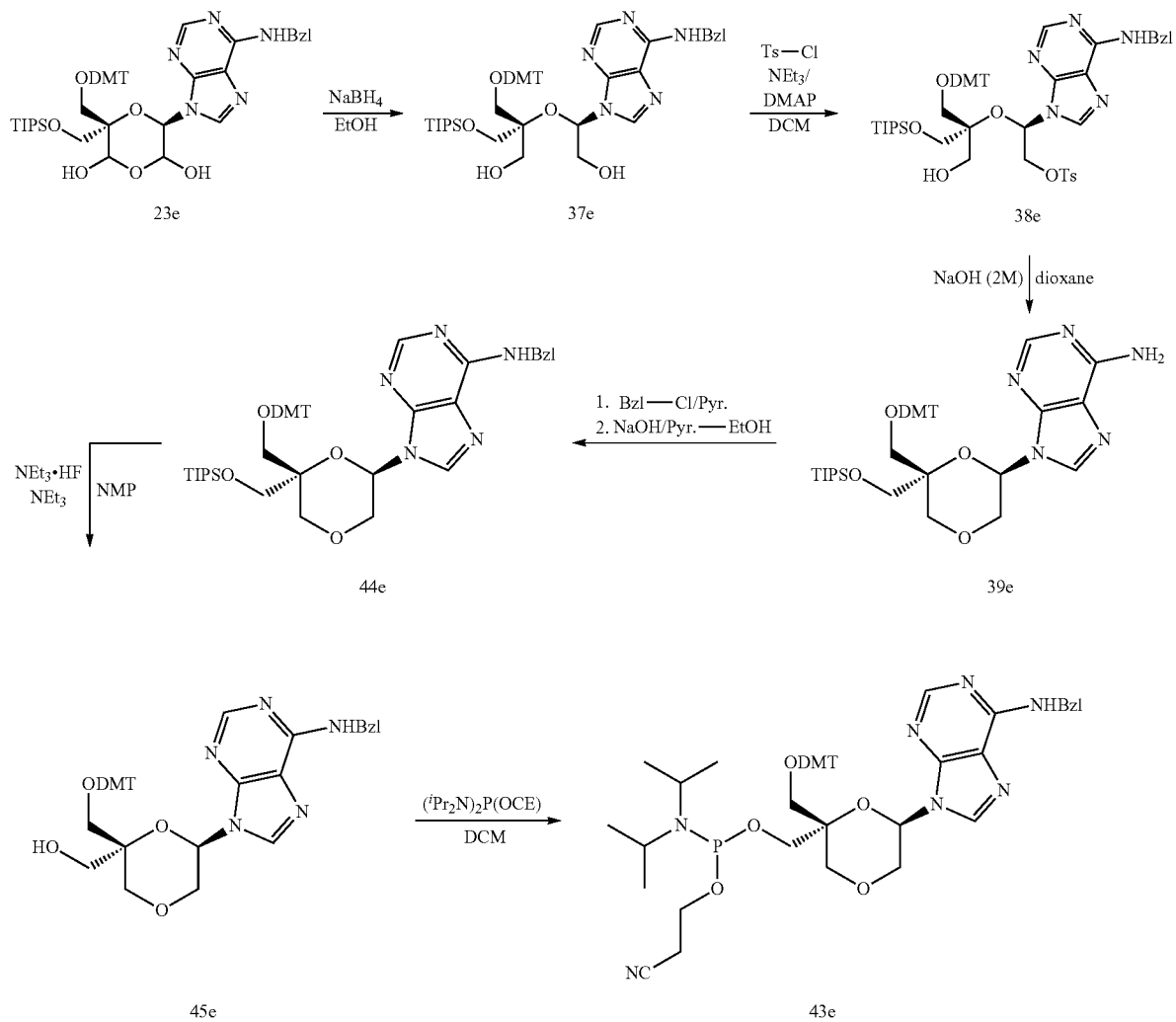

37e: N-[9-[(1R)-1-[(1S)-1-[[bis(4-methoxyphenyl)-phenyl-methoxy]methyl]-1-(hydroxymethyl)-2-triisopropylsilyloxy-ethoxy]-2-hydroxy-ethyl]purin-6-yl]benzamide 3.55 g (4.1 mmol) of the starting material 23e were dissolved in 60 ml ethanol. Under an argon atmosphere, 285.5 mg (7.4 mmol) sodium boron hydride were added and the mixture was stirred for 2 h at room temperature. After cooling the reaction mixture to 0° C., 50 ml citric acid were added, followed by the addition of sat. NaHCO$_3$-solution to achieve a pH of 7. The solvent was removed i. vac. and the aqueous residue was diluted with H$_2$O and extracted with EtOAc. The organic layer was separated and washed with sat. NaHCO$_3$- and sat. NaCl-solution. After drying with MgSO$_4$, the solvent was removed and the crude product purified on silica (0 to 5% MeOH in DCM), which gave 2.15 g of the desired diol 37e as light yellow foam.

LCMS-Method C:
UV-wavelength [nm]=220: R$_t$[min]=3.21
Ionization method: ES$^+$: [M+H]$^+$=862.7
1H-NMR (DMSO-d6, 400 MHz) δ[ppm]: 11.14 (s, 1H), 8.66 (s, 1H), 8.47 (s, 1H), 8.05 (br d, J=7.3 Hz, 2H), 7.61-7.67 (m, 1H), 7.51-7.60 (m, 2H), 7.36 (d, J=7.3 Hz, 2H), 7.27 (br t, J=7.6 Hz, 2H), 7.17-7.23 (m, 5H), 6.83 (dd, J=9.0, 3.0 Hz, 4H), 6.43 (t, J=5.7 Hz, 1H), 5.17 (t, J=5.7 Hz, 1H), 4.63 (t, J=4.7 Hz, 1H), 3.76-3.99 (m, 2H), 3.55-3.76 (m, 10H), 3.17-3.26 (m, 1H), 3.05 (d, J=9.7 Hz, 1H), 0.78-1.02 (m, 21).

38e: [(2R)-2-(6-benzamidopurin-9-yl)-2-[(S)-1-[[bis(4-methoxyphenyl)-phenyl-methoxy]methyl]-1-(hydroxymethyl)-2-triisopropylsilyloxy-ethoxy]ethyl] 4-methylbenzenesulfonate 2.15 g (2.5 mmol) of the diol 37e were dissolved in 60 ml DCM. At room temperature, 891.4 mg (1.22 ml, 8.7 mmol) NEt$_3$, 503.8 mg (2.6 mmol) p-toluene sulfonylchloride and 30.8 mg (0.25 mmol) DMAP were added and the solution was stirred for 0.5 h. After adding additional 167.9 mg (0.9 mmol) p-toluene sulfonylchloride after 2 and 4 h, the solution was stirred for another 15 h to achieve complete conversion. After the addition of 150 ml H$_2$O, the organic layer was separated and dried with MgSO$_4$. The solvent was removed and the obtained crude product (2.56 g) 38e used without further purification.

LCMS-Method C:
UV-wavelength [nm]=220: R$_t$[min]=3.46
Ionization method: ES$^-$: [M−H]$^-$=1014.8
1H-NMR (DMSO-d6, 400 MHz) δ[ppm]: 11.20 (br s, 1H), 8.53 (s, 1H), 8.43 (s, 1H), 8.04-8.10 (m, 2H), 7.62-7.70 (m, 1H), 7.54-7.60 (m, 2H), 7.43-7.48 (m, 2H), 7.12-7.35 (m, 11H), 6.77-6.86 (m, 4H), 6.58 (m, 1H), 4.80 (m, 1H), 4.59 (m, 1H), 4.35 (m, 1H), 3.73 (s, 3H), 3.72 (s, 3H), 3.50-3.67 (m, 4H), 3.21 (m, 1H), 3.09 (m, 1H), 2.35 (s, 3H), 0.82 (br s, 21H).

39e: 9-[(2R,6S)-6-[[bis(4-methoxyphenyl)-phenyl-methoxy]methyl]-6-(triisopropylsilyl-oxymethyl)-1,4-dioxan-2-yl]purin-6-amine To a solution of 2.45 g (2.4 mmol) of the tosylate 38e in 50 ml dioxane were added 36.16 ml (72.3 mmol) 2 M NaOH. After stirring for 2 h at 80° C., the reaction mixture was cooled to room temperature and the organic solvent was evaporated. To the aqueous residue, 250 ml H$_2$O and 150 ml DCM were added, followed by 4.5 ml acetic acid. The organic layer was separated and washed with sat. NaHCO$_3$-solution. After drying with MgSO$_4$, the solvent was removed and the crude product purified on silica (0 to 50% MeOH/EtOAc (1:1) in DCM), which gave 1.22 g of the dioxane 39e (68.6%) as light yellow foam.

LCMS-Method C:
UV-wavelength [nm]=220: R$_t$[min]=3.41
Ionization method: ES$^+$: [M+H]$^+$=740.6
1H-NMR (DMSO-d6, 400 MHz) δ[ppm]: 8.33 (s, 1H), 8.16 (s, 1H), 7.11-7.45 (m, 11H), 6.72-6.79 (m, 4H), 6.13 (m, 1H), 4.13-4.26 (m, 2H), 4.04 (m, 1H), 3.93 (m, 1H), 3.5 (m, 1H), 3.71 (s, 3H), 3.70 (s, 3H), 3.66 (br d, J=11.6 Hz, 1H), 3.06 (d, J=9.5 Hz, 1H), 2.92 (d, J=9.5 Hz, 1H), 0.88-0.95 (m, 21H).

44e: N-[9-[(2R,6S)-6-[[bis(4-methoxyphenyl)-phenyl-methoxy]methyl]-6-(triisopropylsilyl-oxymethyl)-1,4-dioxan-2-yl]purin-6-yl]benzamide 1.84 g (2.5 mmol) of the dioxane 39e were dissolved in 30 ml dry pyridine under an argon atmosphere. At room temperature, 1.05 g (867 μl, 7.5 mmol) benzoyl chloride were added and the reaction was stirred for 3 h. The solvent was removed i. vac. and the residue was dissolved in H$_2$O and extracted with EtOAc. The organic layer was separated and washed with citric acid solution (10%) (2×100 ml), H$_2$O (1×100 ml) and sat. NaHCO$_3$-solution (1×100 ml). After drying with MgSO$_4$, the solvent was removed and the crude product (2.61 g, yellow foam) dissolved in 40 ml pyridine/EtOH (1:1). At 0° C., 7.46 ml (14.9 mmol) 2 N NaOH were added and the reaction mixture was stirred for 30 min. After adding 864 μl AcOH, the reaction solution was concentrated i.vac. The residue was treated with 100 ml H$_2$O and extracted with 100 ml EtOAc. The organic layer was separated and washed with citric acid solution (10%) (2×100 ml), H$_2$O (1×100 ml), sat. NaHCO$_3$-solution (1×100 ml) and sat. NaCl-solution (1×100 ml), dried with MgSO$_4$ and evaporated. Purification of the crude product (2.19 g) on silica (0 to 70% EtOAc in n-heptane) gave 1.72 g (82.0%) of the title compound 44e as colourless foam.

LCMS-Method C:
UV-wavelength [nm]=220: R$_t$[min]=3.56
Ionization method: ES$^-$: [M−H]$^-$=842.8
1H-NMR (DMSO-d6, 400 MHz) δ[ppm]: 11.26 (br s, 1H), 8.77 (s, 1H), 8.68 (s, 1H), 8.05 (m, 2H), 7.64 (br t, J=7.3 Hz, 1H), 7.56 (m, 2H), 7.37 (dd, J=7.8, 1.5 Hz, 2H), 7.13-7.28 (m, 7H), 6.76 (dd, J=8.9, 1.7 Hz, 4H), 6.28 (dd, J=10.1, 3.4 Hz, 1H), 4.20-4.36 (m, 2H), 4.12 (m, 1H), 3.84-3.99 (m, 2H), 3.64-3.75 (m, 7H), 3.06 (m, 1H), 2.96 (m, 1H), 0.88-1.06 (m, 21H).

45e: N-[9-[(2R,6S)-6-[[bis(4-methoxyphenyl)-phenyl-methoxy]methyl]-6-(hydroxymethyl)-1,4-dioxan-2-yl]purin-6-yl]benzamide 1.10 g (1.3 mmol) of the silylether 44e were dissolved in 20 ml NMP. After adding 3.47 g (3.50 ml, 20.9 mmol) NEt$_3$·HF and 1.85 g (2.54 ml, 18.2 mmol) NEt$_3$, the reaction solution was stirred at 65° C. for 18 h. After cooling to room temperature, 250 ml sat. NaHCO$_3$— solution and 150 ml EtOAc were added and the mixture was stirred for 30 min. The organic layer was separated and washed with sat. NaHCO$_3$- and twice with sat. NaCl-solution. After drying with MgSO$_4$, the solvent was removed and the crude product purified by silicagel chromatography (preconditioned with 0.5% NEt$_3$, 0 to 100% EtOAc in n-heptane), yielding 852 mg (95.1%) of 45e as colourless foam.

LCMS-Method C:
UV-wavelength [nm]=220: $R_t$[min]=2.43
Ionization method: ES$^+$: [M+H]$^+$=688.3
1H-NMR (DMSO-d6, 400 MHz) δ[ppm]: 11.22 (br s, 1H), 8.75 (s, 1H), 8.59 (s, 1H), 8.04 (d, J=7.6 Hz, 2H), 7.64 (t, J=7.1 Hz, 1H), 7.55 (t, J=7.6 Hz, 2H), 7.38 (d, J=7.6 Hz, 2H), 7.14-7.32 (m, 7H), 6.80 (m, 4H), 6.26 (dd, J=9.8, 3.3 Hz, 1H), 4.85 (t, J=5.4 Hz, 1H), 4.29 (t, J=10.6 Hz, 1H), 4.09 (dd, J=11.1, 3.2 Hz, 1H), 3.73-3.90 (m, 4H), 3.72 (s, 3H), 3.71 (s, 3H), 3.03 (m, 1H), 2.95 (m, 1H).

43e: N-[9-[(2R,6S)-6-[[bis(4-methoxyphenyl)-phenyl-methoxy]methyl]-6-[[2-cyanoethoxy-(diisopropylamino)phosphanyl]oxymethyl]-1,4-dioxan-2-yl]purin-6-yl]benzamide 848 mg (1.2 mmol) of the starting material 45e and 640 mg (3.7 mmol) diisopropylammonium tetrazolide were dissolved in 25 ml dry DCM. Under an argon atmosphere, 574.7 mg (1.9 mmol) 2-cyanoethyl-N,N,N',N'-tertaisopropylphosphorodiamidite were added at room temperature. After 16 h, 50 ml H$_2$O were added. The organic layer was separated and the aqueous phase extracted with DCM. The combined organic layers were dried with MgSO$_4$ and the solvent was removed at 35° C. i. vac. The crude product was dissolved in 10 ml EtOAc/diethylether (1:1) and 40 ml n-pentane were added. The precipitate was collected by centrifugation and the solvents were discarded. The precipitation procedure was repeated three times, which gave after drying on a Speedvac 991 mg (90.5%) of the desired product 43e as colourless solid.

LCMS-Method B-3:
UV-wavelength [nm]=220: $R_t$[min]=0.61
Ionization method: ES$^+$: [M+H-$^i$Pr$_2$N+OH]$^+$=805.3
1H-NMR (DMSO-d6, 400 MHz) δ[ppm] 11.21 (br s, 1H), 8.76, 8.74 (2×s, 1H), 8.63, 8.61 (2×s, 1H), 8.04 (d, J=7.3 Hz, 2H), 7.65 (t, J=7.3 Hz, 1H), 7.55 (m, 2H), 7.37 (br d, J=8.3 Hz, 2H), 7.14-7.30 (m, 7H), 6.75-6.86 (m, 4H), 6.30 (m, 1H), 4.27 (m, 1H), 3.85-4.17 (m, 4H), 3.61-3.80 (m, 9H), 3.49 (m, 2H), 3.08 (m, 1H), 2.98 (dd, J=9.1, 7.1 Hz, 1H), 2.72 (m, 1H), 2.62 (m, 1H), 1.04-1.14 (m, 6H), 1.02 (m, 3H), 0.93 (d, J=6.8 Hz, 3H).
31P-NMR (DMSO-d6, 162 MHz) δ[ppm]: 147.7, 147.6.

Example B.8

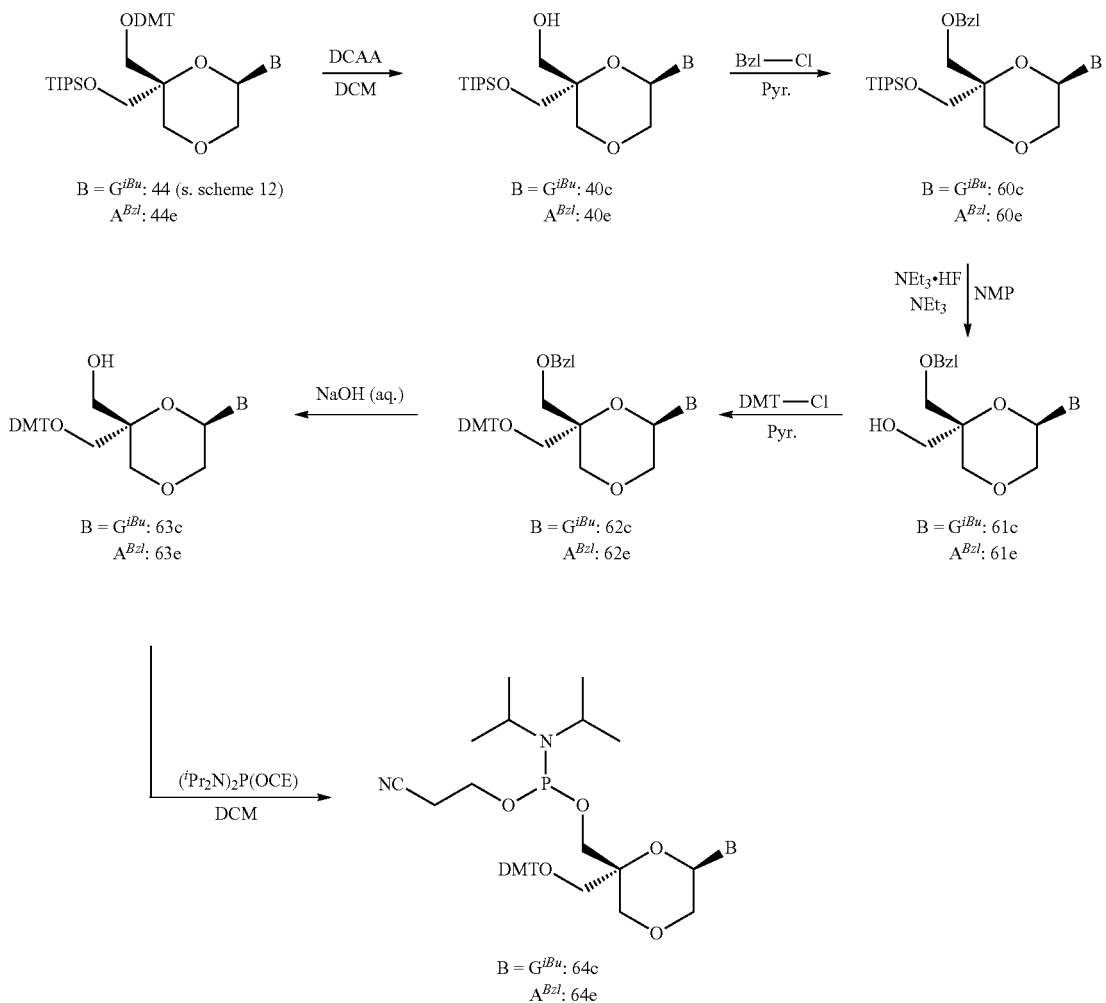

40c: N-[9-[(2R,6R)-6-(hydroxymethyl)-6-(triisopropylsilyloxymethyl)-1,4-dioxan-2-yl]-6-oxo-1H-purin-2-yl]-2-methyl-propanamide To a solution of DMT-ether 44 (9.5 g, 11.5 mmol; see synthetic scheme 12) in 190 ml anhydrous DCM, was added dropwise DCAA (29.7 g, 230 mmol) at 0° C. under $N_2$ atmosphere. After stirring at room temperature for 30 min, TLC showed complete conversion. The mixture was neutralized with sat. $NaHCO_3$-solution (100 ml) and extracted with DCM (3×200 ml). The organic layers were combined and washed with sat. NaCl-solution (200 ml). After drying with anhydrous $Na_2SO_4$, the organic solution was evaporated and the crude product was purified by preparative HPLC (ACN, 0.1% FA), yielding 9.5 g (61.2%) of the desired product 40c as white solid LCMS-Method C:

UV-wavelength [nm]=220: $R_t$[min]=2.68
Ionization method: $ES^+$: $[M+H]^+$=524.4
1H-NMR (DMSO-d6, 400 MHz) δ[ppm]: 12.10 (br s, 1H), 11.53 (br s, 1H), 8.21 (s, 1H), 5.88 (dd, J=9.8, 3.3 Hz, 1H), 4.75 (t, J=6.0 Hz, 1H), 4.06 (d, J=9.5 Hz, 1H), 3.98 (dd, J=11.4, 3.3 Hz, 1H), 3.86 (d, J=11.7 Hz, 1H), 3.74-3.83 (m, 2H), 3.61 (d, J=11.7 Hz, 1H), 3.46 (d, J=6.1 Hz, 2H), 2.79 (m, 1H), 1.00-1.16 (m, 27H).

60c: [(2S,6R)-6-[2-(2-methylpropanoylamino)-6-oxo-1H-purin-9-yl]-2-(triisopropylsilyloxy-methyl)-1,4-dioxan-2-yl]methyl Benzoate 2.80 g (5.35 mmol) of the starting material 40c were dissolved in 20 ml dry pyridine. After adding 949 mg (784 µl, 6.68 mmol) benzoyl chloride and 667 mg (5.35 mmol) DMAP, the reaction solution was stirred at room temperature for 4 h. Another 189 mg (157 µl, 1.37 mmol) benzoyl chloride were added and the reaction was stirred overnight to achieve complete conversion. The solvent was removed i. vac., the residue was dissolved in EtOAc and washed with 5% aqueous citric acid solution, 5% aqueous $NaHCO_3$- and sat. NaCl-solution. After drying with $MgSO_4$, the organic layer was evaporated and the crude product purified on silicagel (0 to 10% MeOH in DCM), yielding 3.33 g (99.2%) of the benzoylester 60c as colourless foam.

LCMS-Method C:
UV-wavelength [nm]=220: $R_t$[min]=3.06
Ionization method: $ES^+$: $[M+H]^+$=628.5
1H-NMR (DMSO-d6, 400 MHz) δ[ppm]: 11.84 (s, 1H), 11.58 (s, 1H), 8.09 (s, 1H), 7.79-7.86 (m, 2H), 7.56-7.64 (m, 1H), 7.41-7.49 (m, 2H), 5.89 (dd, J=5.9 Hz, 3.4 Hz, 1H), 4.18-4.32 (m, 3H), 4.07 (m, 1H), 3.77-4.02 (m, 4H), 2.79 (m, 1H), 0.93-1.21 (m, 27H).

61c: [(2S,6R)-2-(hydroxymethyl)-6-[2-(2-methylpropanoylamino)-6-oxo-1H-purin-9-yl]-1,4-dioxan-2-yl]methyl Benzoate 3.30 g (5.26 mmol) of the silylether 60c were dissolved in 33 ml DMF. After adding 8.06 g (78.9 mmol, 11.1 ml) $NEt_3$ and 6.49 g (39.4 mmol, 6.56 ml) $NEt_3$.3HF, the solution was stirred at 75° C. for 2 h, to achieve complete conversion. The reaction was cooled to room temperature and washed with 100 ml 5%-$NaHCO_3$-solution. After filtration, the aqueous solution was extracted with DCM. The organic layer was separated, dried with $MgSO_4$ and evaporated. The crude product was purified by HPLC (column: Chiralcel OD-H/74, 250×4.6 mm, 1.0 ml/min, 30° C.; eluent: heptane/EtOH 5:2), which gave 1.20 g (48.4%) of the desired product 61c as colourless solid.

LCMS-Method C:
UV-wavelength [nm]=220: $R_t$[min]=1.40
Ionization method: $ES^+$: $[M+H]^+$=472.3
1H-NMR (DMSO-d6, 400 MHz) δ[ppm]: 11.89 (s, 1H), 11.67 (s, 1H), 8.08 (s, 1H), 7.87 (d, J=7.7 Hz, 2H), 7.62 (t, J=7.2 Hz, 1H), 7.47 (t, J=7.6 Hz, 2H), 5.92 (dd, J=6.6, 3.3 Hz, 1H), 5.11 (t, J=5.7 Hz, 1H), 4.14-4.26 (m, 3H), 4.03 (dd, J=12.0, 3.4 Hz, 1H), 3.90 (d, J=12.0 Hz, 1H), 3.79 (d, J=12.0 Hz, 1H), 3.70 (m, 2H), 2.79 (spt, J=6.8 Hz, 1H), 1.15 (d, J=6.9 Hz, 3H), 1.11 (d, J=6.7 Hz, 3H).

62c: [(2R,6R)-2-[[bis(4-methoxyphenyl)-phenyl-methoxy]methyl]-6-[2-(2-methylpropanoyl-amino)-6-oxo-1H-purin-9-yl]-1,4-dioxan-2-yl]methyl Benzoate 1.20 g (2.55 mmol) of the primary alcohol 61c were dissolved in 25 ml dry pyridine. 647 mg (6.36 mmol, 891 µl) $NEt_3$ and 1.78 g (5.09 mmol) DMT-Cl were added and the solution was stirred for 1 h at room temperature, followed by 4 h at 80° C. After cooling to room temperature, 1 ml MeO was added and the solution was diluted with EtOAc. The organic solution was washed with 10% aqueous citric acid- and sat. NaCl-solution. After drying the organic phase with $MgSO_4$, the solvent was evaporated and the crude product purified by silicagel chromatography (0 to 5% MeOH in DCM), which gave 1.97 g (quant.) of the desired DMT-ether 62c as light yellow solid.

LCMS-Method C:
UV-wavelength [nm]=220: $R_t$[min]=2.75
Ionization method: $ES^+$: $[M+H]^+$=774.4
1H-NMR (DMSO-d6, 400 MHz) δ[ppm]: 11.78 (s, 1H), 11.53 (s, 1H), 8.06 (s, 1H), 7.50-7.55 (m, 2H), 7.31-7.41 (m, 5H), 7.14-7.29 (m, 7H), 6.81 (brd, J=8.9 Hz, 2H), 6.77 (d, J=8.9 Hz, 2H), 5.72 (m, 1H), 4.19-4.35 (m, 3H), 4.01-4.11 (m, 3H), 3.66 (s, 3H), 3.63 (s, 3H), 3.34 (d, J=8.8 Hz, 1H), 3.16 (d, J=8.7 Hz, 1H), 2.75 (m, 1H), 1.13 (d, J=6.9 Hz, 3H), 1.08 (d, J=6.7 Hz, 3H).

63c: N-[9-[(2R,6R)-6-[[bis(4-methoxyphenyl)-phenyl-methoxy]methyl]-6-(hydroxymethyl)-1,4-dioxan-2-yl]-6-oxo-1H-purin-2-yl]-2-methyl-propanamide 1.97 g (2.55 mmol) of the benzoylester 62c were dissolved in 40 ml EtOH/pyridine (3:1). After adding 12.9 ml (25.8 mmol) of a 2 M NaOH-solution, the mixture was stirred at room temperature for 30 min to achieve complete conversion. After neutralizing with citric acid (solid), the EtOH was removed i.vac. and the residue was diluted with 50 ml EtOAc and 25 ml $H_2O$. The precipitate was removed by filtration and from the filtrate, the organic layer was separated and washed with sat. NaCl-solution. After drying with $MgSO_4$, the solvent was removed and the crude product purified on silica (0 to 5% MeOH in DCM), yielding 0.99 g (58.0%) of the title compound 63c as colourless foam.

LCMS-Method C:
UV-wavelength [nm]=220: $R_t$[min]=2.46
Ionization method: $ES^+$: $[M+H]^+$=670.4
1H-NMR (DMSO-d6, 400 MHz) δ[ppm]: 12.10 (s, 1H), 11.52 (s, 1H), 8.19 (s, 1H), 7.20-7.42 (m, 9H), 6.85-6.93 (m, 4H), 5.62 (dd, J=9.7, 3.3 Hz, 1H), 4.81 (br t, 1H), 3.91-3.99 (m, 2H), 3.74 (s, 3H), 3.73 (s, 3H), 3.65-3.76 (m, 1H), 3.41-3.59 (m, 4H), 3.15 (d, J=9.1 Hz, 1H), 2.77 (m, 1H), 1.13 (m, 6H).

64c: N-[9-[(2R,6R)-6-[[bis(4-methoxyphenyl)-phenyl-methoxy]methyl]-6-[[2-cyanoethoxy-(diisopropylamino)phosphanyl]oxymethyl]-1,4-dioxan-2-yl]-6-oxo-1H-purin-2-yl]-2-methyl-propanamide 985 mg (1.47 mmol) of the starting material 63c were dissolved in 30 ml dry DCM. Under an argon atmosphere, 133 mg (735 µmol) $^i$Pr$_2$NH-tetrazole and 571 mg (1.84 mmol, 602 µl) 2-cyanoethyl-N,N,N',N'-tetraisopropylphosphorodiamidite were added and the solution was stirred at room temperature overnight. After adding 50 ml H$_2$O and DCM, the organic layer was separated, dried with MgSO$_4$ and evaporated. The crude product was purified by silicagel chromatography (preconditioned with n-heptane+1% NEt$_3$, 0 to 100% EtOAc in n-heptane), yielding 1.07 g (83.8%) of the desired phosphoramidite 64c as colourless foam.

LCMS-Method C:
UV-wavelength [nm]=220: R$_t$[min]=2.42
Ionization method: ES$^+$: [M+H-$^i$Pr$_2$N+OH]$^+$=787.4
1H-NMR (DMSO-d6, 400 MHz) δ[ppm]: 12.08 (br s, 1H), 11.55 (br s, 1H), 8.06, 8.05 (2×s, 1H), 7.18-7.44 (m, 9H), 6.82-6.94 (m, 4H), 5.65 (m, 1H), 3.66-4.01 (m, 3H), 3.73 (s, 3H), 3.72 (s, 3H), 3.35-3.65 (m, 6H), 3.21-3.29 (m, 1H), 2.72-2.83 (m, 1H), 2.59-2.72 (m, 2H), 0.90-1.22 (m, 20H).
31P-NMR (DMSO-d6, 162 MHz) δ[ppm]: 147.7, 147.3.

40e: N-[9-[(2R,6R)-6-(hydroxymethyl)-6-(triisopropylsilyloxymethyl)-1,4-dioxan-2-yl]purin-6-yl]benzamide 615 mg (729 µmol) of the DMT-ether 44e were dissolved in 25 ml DCM. After adding 949 mg (608 µl, 7.3 mmol) dichloroacetic acid, the reaction mixture was stirred for 1 min to achieve complete conversion. The reaction solution was washed with 100 ml sat. NaHCO$_3$— solution. The organic layer was separated and the aqueous phase extracted twice with 35 ml DCM. The combined organic extracts were dried with MgSO$_4$ and evaporated. The crude product was purified by silica gel chromatography (0 to 100% EtOAc in n-heptane), yielding 302 mg (76.5%) of the desired product 40e as colourless foam.

LCMS-Method C:
UV-wavelength [nm]=220: R$_t$[min]=2.70
Ionization method: ES$^+$: [M+H]$^+$=542.5
1H-NMR (DMSO-d6, 400 MHz) δ[ppm]: 11.20 (s, 1H), 8.75 (s, 1H), 8.69 (s, 1H), 8.04 (d, J=7.5 Hz, 2H), 7.65 (m, 1H), 7.55 (m, 2H), 6.23 (m, 1H), 4.75 (t, J=6.1 Hz, 1H), 4.01-4.12 (m, 3H), 3.94 (d, J=9.9 Hz, 1H), 3.86 (d, J=11.9 Hz, 1H), 3.65 (d, J=11.7 Hz, 1H), 3.44 (m, 2H), 1.10-1.17 (m, 3H), 1.04-1.09 (m, 18H).

60e: [(2S,6R)-6-[6-(dibenzoylamino)purin-9-yl]-2-(triisopropylsilyloxymethyl)-1,4-dioxan-2-yl]methyl Benzoate To a solution of 299 mg (552 µmol) of the free alcohol 40e in 10 ml dry pyridine were added 94.0 mg (77.7 µl, 662.3 µmol) of benzoyl chloride at room temperature. After 18 h, the solvent was concentrated to a volume of 5 ml and another 94.0 mg of benzoyl chloride were added. Additional 282 mg benzoyl chloride were added after another 60 min at room temperature and the solution was stirred overnight. The solvent was removed and the residue was treated with H$_2$O and EtOAc. The organic layer was separated and washed twice with citric acid-solution (10%), sat. NaHCO$_3$- and sat. NaCl-solution. After drying with MgSO$_4$, the solvent was removed and the crude product was purified on silica (0 to 100% EtOAc in n-heptane), which gave 405 mg (97.8%) of 60e as colourless foam.

LCMS-Method C:
UV-wavelength [nm]=220: R$_t$[min]=3.49
Ionization method: ES$^+$: [M+H]$^+$=750.7
1H-NMR (DMSO-d6, 400 MHz) δ[ppm]: 8.74 (s, 1H), 8.62 (s, 1H), 7.92-7.97 (m, 2H), 7.74-7.79 (m, 4H), 7.42-7.67 (m, 9H), 6.28 (dd, J=9.4, 3.4 Hz, 1H), 4.22-4.35 (m, 4H), 4.16 (m, 1H), 4.01 (m, 2H), 3.78 (m, 1H), 1.06-1.14 (m, 3H), 0.97-1.05 (m, 18H).

61e: [(2S,6R)-6-[6-(dibenzoylamino)purin-9-yl]-2-(hydroxymethyl)-1,4-dioxan-2-yl]methyl Benzoate 402 mg (536 µmol) of the silylether 60e were deprotected using the protocol described for 45e. After chromatographic purification on silica (0 to 100% EtOAc in n-heptane), 194 mg (61.0%) of the desired product 61e were isolated as colourless foam.

LCMS-Method C:
UV-wavelength [nm]=220: R$_t$[min]=2.22
Ionization method: ES$^+$: [M+H]$^+$=594.5
1H-NMR (DMSO-d6, 400 MHz) δ[ppm]: 8.71 (s, 1H), 8.59 (s, 1H), 7.97 (m, 2H), 7.77 (m, 4H), 7.43-7.67 (m, 9H), 6.27 (m, 1H), 5.14 (m, 1H), 4.20-4.36 (m, 3H), 4.12 (m, 1H), 3.95 (m, 1H), 3.75-3.91 (m, 3H).

62e: [(2R,6R)-2-[[bis(4-methoxyphenyl)-phenyl-methoxy]methyl]-6-[6-(dibenzoylamino)-purin-9-yl]-1,4-dioxan-2-yl]methyl Benzoate 190 mg (320 µmol) of the starting material 61e were dissolved in 10 ml dry pyridine and evaporated. This procedure was repeated three times. The compound was then dissolved in 10 ml dry pyridine, followed by the addition of 48.7 mg (66.9 µl, 480 µmol) NEt$_3$ and 166 mg (480 µmol) DMT-Cl. After stirring overnight at room temperature, another 97.4 mg NEt$_3$ and 332 mg DMT-Cl were added and the solution was stirred for additional 18 h to achieve complete conversion. The solvent was removed i. vac. and the residue dissolved in EtOAc. After washing with H$_2$O, citric acid solution (2×), sat. NaHCO$_3$- and sat. NaCl-solution, the organic phase was dried with MgSO$_4$. Evaporation of the solvent and purification by silicagel chromatography (0 to 100% EtOAc in n-heptane) gave 216 mg (75.3%) of the DMT-ether 62e as light yellow foam.

LCMS-Method C:
UV-wavelength [nm]=220: R$_t$[min]=3.17
Ionization method: ES$^+$: [M+H]$^+$=896.5
1H-NMR (DMSO-d6, 400 MHz) 8.75 (s, 1H), 8.61 (s, 1H), 7.73-7.80 (m, 7H), 7.65 (m, 1H), 7.58 (m, 2H), 7.42-7.50 (m, 6H), 7.36-7.41 (m, 2H), 7.22-7.29 (m, 6H), 6.78-6.84 (m, 4H), 6.07 (m, 1H), 4.36 (m, 2H), 4.22 (m, 1H), 3.99-4.14 (m, 2H), 3.84 (d, J=11.9 Hz, 1H), 3.68 (s, 6H), 3.44-3.57 (m, 2H).

63e: N-[9-[(2R,6R)-6-[[bis(4-methoxyphenyl)-phenyl-methoxy]methyl]-6-(hydroxymethyl)-1,4-dioxan-2-yl]purin-6-yl]benzamide The starting material 62e (213 mg, 238 µmol) was dissolved in 8 ml EtOH/pyridine (3:1).

After the addition of 1.19 ml (2.4 mmol) 2 M NaOH at 0° C., the solution was stirred for 10 min at 0° C. and 60 min at room temperature to achieve complete conversion. 166 mg citric acid-monohydrate were added, followed by the addition of 50 ml $H_2O$ and 50 ml EtOAc. The organic layer was separated and washed with 10% citric acid-solution (2×), $H_2O$, sat. $NaHCO_3$- and sat. NaCl-solution. After drying with $MgSO_4$, the crude product was purified on silica (0 to 100% acetone in DCM), yielding 134 mg (82.0%) of 63e as colourless foam.

LCMS-Method C:

UV-wavelength [nm]=220: $R_t$[min]=2.44

Ionization method: $ES^+$: $[M+H]^+$=688.4

1H-NMR (DMSO-d6, 400 MHz) 11.21 (br s, 1H), 8.72 (s, 1H), 8.67 (s, 1H), 8.04 (m, 2H), 7.65 (m, 1H), 7.55 (m, 2H), 7.45 (m, 2H), 7.29-7.37 (m, 6H), 7.23 (m, 1H), 6.91 (dd, J=9.0, 2.0 Hz, 4H), 6.01 (m, 1H), 4.84 (t, J=5.9 Hz, 1H), 3.94-4.02 (m, 2H), 3.83 (m, 1H), 3.74 (s, 6H), 3.68-3.73 (m, 1H), 3.49-3.55 (m, 2H), 3.38 (m, 2H).

64e: N-[9-[(2R,6R)-6-[[bis(4-methoxyphenyl)-phenyl-methoxy]methyl]-6-[[2-cyanoethoxy-(diisopropylamino)phosphanyl]oxymethyl]-1,4-dioxan-2-yl]purin-6-yl]benzamide 131 mg (190 μmol) of the starting compound 63e were phosphitylated following the protocol described for its stereoisomer 43e, which gave the desired phosphoramidite 64e in quantitative yield.

LCMS-Method B-3:

UV-wavelength [nm]=220: $R_t$[min]=0.61

Ionization method: $ES^+$: $[M+H-^iPr_2N+OH]^+$=805.3

1H-NMR (DMSO-d6, 400 MHz) δ[ppm] 11.20 (br s, 1H), 8.74, 8.73 (2×s, 1H), 8.62, 8.60 (2×s, 1H), 8.05 (d, J=7.4 Hz, 2H), 7.65 (m, 1H), 7.55 (m, 2H), 7.45 (d, J=7.3 Hz, 2H), 7.29-7.36 (m, 6H), 7.24 (m, 1H), 6.91 (m, 4H), 6.06 (m, 1H), 3.99-4.14 (m, 2H), 3.62-3.90 (m, 11H), 3.37-3.62 (m, 5H), 2.71 (m, 1H), 2.64 (m, 1H), 1.06-1.13 (m, 6H), 1.03 (d, J=6.7 Hz, 3H), 0.97 (m, 3H).

31P-NMR (DMSO-d6, 162 MHz) δ[ppm]: 147.7, 147.6.

Synthesis of Targeted Nucleotide Analogs of Formula (III)

Example C.1

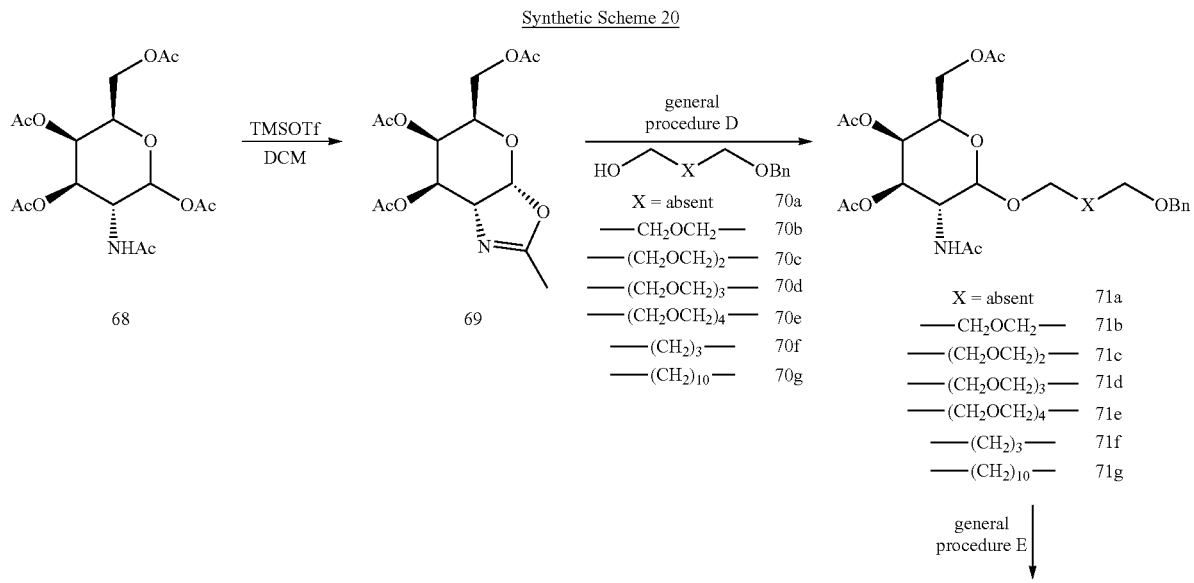

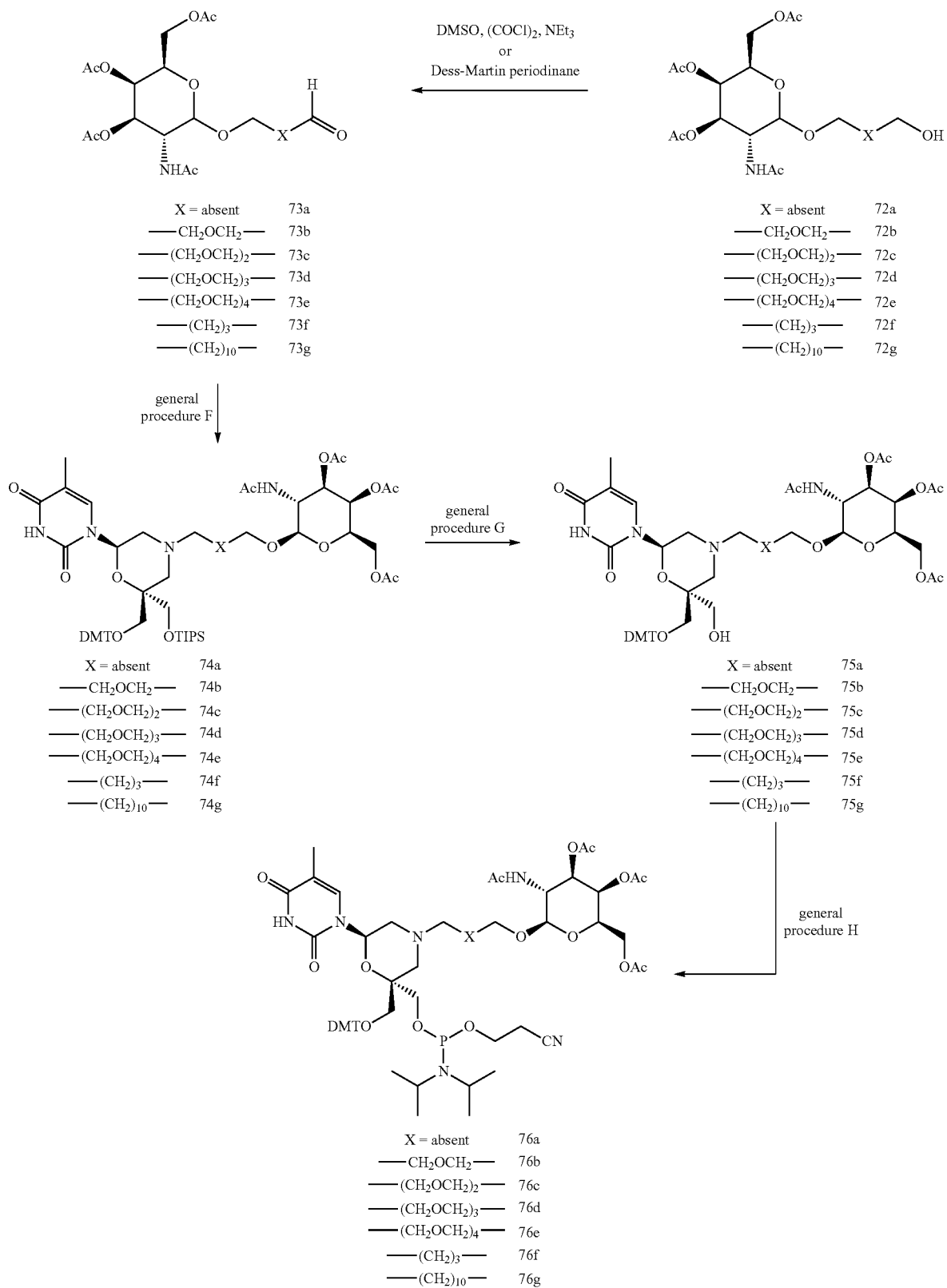

69: [(3aR,5R,6R,7R,7aR)-6,7-diacetoxy-2-methyl-5,6,7,7a-tetrahydro-3aH-pyrano[3,2-d]oxazol-5-yl]methyl Acetate To a solution of 20.0 g (51.4 mmol) D-galactosamine pentaacetate (68) in 200 ml DCE was added 17.1 g (77.1 mmol) TMSOTf dropwise at 30° C. The mixture was heated to 50° C. for 2 h. After standing overnight at room temperature, complete conversion was detected. The mixture was quenched by a solution of NaHCO$_3$ (8.63 g, 102.8 mmol) in 1 l water and extracted with 2×500 ml DCM. The combined organic layers were dried over anhydrous Na$_2$SO$_4$, filtered and concentrated in vacuo, yielding 19.0 g of the title compound 69 (crude), which were used without further purification.

LCMS-Method A:
ELSD: R$_t$[min]=0.90
Ionization method: ES$^+$: [M+H]$^+$=330.1

70g: 12-benzyloxydodecan-1-ol 14.05 g (68.76 mmol) 1,12-dodecanediol were dissolved in 150 ml dry DMF. At 0° C., 2.75 g (68.76 mmol) NaH (60%) were added over a period of 30 min in four portions. The ice bath was removed and the solution was stirred for 3 h at room temperature, followed by the addition of a solution of 10.0 g (6.99 ml, 57.33 mmol) benzylbromide in 50 ml dry DMF at 0° C. The reaction was stirred overnight at room temperature. After adding another 1.99 g (49.8 mmol) of NaH (60%), stirring was continued for 4 h. The reaction mixture was poured into 500 ml ice-water and extracted with diethylether and EtOAc. The organic layers were washed with sat. NaCl-solution, dried with MgSO$_4$ and evaporated. The crude product was purified on silica (0 to 60% EtOAc in n-heptane) to yield 6.91 g (41.2%) of the title compound 70g as white solid.

LCMS-Method A:
UV-wavelength [nm]=220: R$_t$[min]=2.09
Ionization method: ES$^+$: [M+H]$^+$=293.3

General Procedure D for the Preparation of Compounds 71a to 71g

To a solution of oxazoline 69 (1.0 eq.) in dry DCE (200 ml/50.0 mmol) and the alcohol 70a-70g (1.10 eq.) were added molecular sieves 4 Å (20.0 g). At room temperature, TMSOTf (0.5 eq.) was added dropwise and the solution was stirred until complete conversion was achieved. The reaction was quenched by adding a solution of NaHCO$_3$ (2.0 eq.) in 400 ml H$_2$O. The organic phase was separated and the aqueous layer was extracted with 2×100 ml DCM. The combined organic extracts were dried with Na$_2$SO$_4$ and concentrated i. vac. The crude products were purified by silicagel chromatography to yield the glycosides 71a to 70g.

71a: [(2R,3R,4R,5R,6R)-5-acetamido-3,4-diacetoxy-6-(2-benzyloxyethoxy)tetrahydropyran-2-yl]methyl Acetate Following general procedure D, 17.0 g (51.37 mmol) 69 and 8.6 g (56.56 mmol) 70a gave 18.87 g (76.4%) of the title compound 71a after silicagel chromatography (PE/EtOAc 1:2) as yellow oil.

1H-NMR (DMSO-d6, 400 MHz) δ[ppm]: 7.83 (d, J=9.29 Hz, 1H), 7.41-7.20 (m, 5H), 5.22 (d, J=3.30 Hz, 1H), 4.98 (dd, J=11.25, 3.42 Hz, 1H), 4.58 (d, J=8.44 Hz, 1H), 4.52-4.43 (m, 2H), 4.03 (s, 2H), 3.96-3.80 (m, 2H), 3.69-3.49 (m, 3H), 2.12-2.08 (m, 3H), 1.99 (s, 3H), 1.89 (s, 3H), 1.74 (s, 3H).

71b: [(2R,3R,4R,5R,6R)-5-acetamido-3,4-diacetoxy-6-[2-(2-benzyloxyethoxy)ethoxy]-tetrahydropyran-2-yl]methyl Acetate Following general procedure D, 14.0 g (42.5 mmol) 69 and 7.5 g (38.2 mmol) 70b gave 10.6 g (48%) of the title compound 71b after silicagel chromatography as yellow oil.

MS: Ionization method: ES$^+$: [M+H]$^+$=526.3

71c: [(2R,3R,4R,5R,6R)-5-acetamido-3,4-diacetoxy-6-[2-[2-(2-benzyloxyethoxy)ethoxy]-ethoxy]tetrahydropyran-2-yl]methyl Acetate Following general procedure D, 16.0 g (48.6 mmol) 69 and 14.0 g (58.3 mmol) 70c gave 15.6 g (57%) of the title compound 71c after silicagel chromatography as colourless oil.

MS: Ionization method: ES$^+$: [M+H]$^+$=570.1

71d: [(2R,3R,4R,5R,6R)-5-acetamido-3,4-diacetoxy-6-[2-[2-[2-(2-benzyloxyethoxy)-ethoxy]ethoxy]ethoxy]tetrahydropyran-2-yl]methyl acetate Following general procedure D, 19.0 g (51.4 mmol) 69 and 17.5 g (61.7 mmol) 70d gave 10.0 g (32%) of the title compound 71d after silicagel chromatography as colourless oil.

1H-NMR (DMSO-d6, 400 MHz) δ[ppm]: 7.79 (d, J=9.3 Hz, 1H), 7.40-7.25 (m, 5H), 5.27-5.20 (m, 1H), 5.22 (d, J=3.3 Hz, 1H), 4.98 (dd, J=3.4, 11.2 Hz, 1H), 4.49 (s, 2H), 4.08-3.99 (m, 3H), 3.94-3.75 (m, 2H), 3.62-3.43 (m, 16H), 2.15-2.07 (m, 3H), 2.00 (s, 3H), 1.90 (s, 3H), 1.78 (s, 3H).

71e: [(2R,3R,4R,5R,6R)-5-acetamido-3,4-diacetoxy-6-[2-[2-[2-[2-(2-benzyloxyethoxy)-ethoxy]ethoxy]ethoxy]ethoxy]tetrahydropyran-2-yl]methyl Acetate Following general procedure D, 35.0 g (64.2 mmol, 60% purity) 69 and 23.2 g (70.6 mmol) 70e gave 13.4 g (32%) of the title compound 71e after silicagel chromatography as yellow oil.

1H-NMR (CDC$_3$, 400 MHz) δ[ppm]: 7.44-7.29 (m, 5H), 6.63 (d, J=9.29 Hz, 1H), 5.33 (d, J=2.76 Hz, 1H), 5.01 (dd, J=11.17, 3.39 Hz, 1H), 4.80 (d, J=8.66 Hz, 1H), 4.58 (s, 2H), 4.33-4.01 (m, 4H), 3.98-3.80 (m, 3H), 3.77-3.54 (m, 20H), 2.18-2.16 (m, 3H) 1.99 (s, 6H) 1.87 (s, 3H).

71f: [(2R,3R,4R,5R,6R)-5-acetamido-3,4-diacetoxy-6-(5-benzyloxypentoxy)tetrahydropyran-2-yl]methyl Acetate Following general procedure D, 1.69 g (5.13 mmol) 69 and 1.10 g (1.09 ml, 5.39 mmol) 70f gave 2.60 g (96.7%) of the title compound 71f after silicagel chromatography (0 to 10% MeOH in DCM) as colourless oil.

1H-NMR (CDC$_3$, 400 MHz) δ[ppm]: 7.36-7.28 (m, 6H), 5.24 (d, J=12.0 Hz, 1H), 5.37 (d, J=2.4 Hz, 1H), 5.34-5.31 (m, 1H), 4.71 (d, J=8.0 Hz, 1H), 4.51 (s, 2H), 4.17-4.14 (m, 2H), 3.93-3.90 (m, 3H), 3.50-3.47 (m, 3H), 2.15 (s, 3H), 2.06 (s, 3H), 1.92 (s, 3H), 1.68 (s, 3H), 1.66-1.61 (m, 4H), 1.48-1.44 (m, 2H).

71g: [(2R,3R,4R,5R,6R)-5-acetamido-3,4-diacetoxy-6-(12-benzyloxydodecoxy)tetrahydro-pyran-2-yl]methyl Acetate Following general procedure D, 4.16 g (12.62 mmol) 69 and 4.43 g (15.14 mmol) 70g gave 5.69 g (72.6%) of the title compound 71g after silicagel chromatography (10 to 100% DCM in EtOAc) as light yellow oil.

LCMS-Method A:
UV-wavelength [nm]=220: $R_t$[min]=2.07
Ionization method: $ES^+$: $[M+H]^+$=622.4

General Procedure E for the Preparation of Compounds 72a to 72g

The benzylethers 71a-g were dissolved in THF (40 mmol in 370 ml). After adding 5 g Pd/C (10%, containing 50% $H_2O$), the mixture was stirred at room temperature under an atmosphere of $H_2$ (15 psi) until complete debenzylation was observed. The mixture was filtered and the filtrate was evaporated i. vac. Final purification on silica gave the desired title compounds 72a-g.

72a: [(2R,3R,4R,5R,6R)-5-acetamido-3,4-diacetoxy-6-(2-hydroxyethoxy)tetrahydropyran-2-yl]methyl Acetate Following general procedure E, 18.87 g (39.19 mmol) 71a gave 11.6 g (75.8%) 72a after purification on silica (EtOAc/MeOH 10:1) as colourless solid.

1H-NMR (DMSO-d6, 400 MHz) δ[ppm]: 7.81 (br d, J=9.03 Hz, 1H), 5.22 (br d, J=2.38 Hz, 1H), 4.98 (br dd, J=10.98, 2.57 Hz, 1H), 4.66-4.44 (m, 2H), 4.04 (s, 3H), 3.94-3.79 (m, 1H), 3.68 (br d, J=4.64 Hz, 1H), 3.49 (br s, 3H), 2.11 (s, 3H), 2.01 (s, 3H), 1.90 (s, 3H), 1.78 (s, 3H).

72b: [(2R,3R,4R,5R,6R)-5-acetamido-3,4-diacetoxy-6-[2-(2-hydroxyethoxy)ethoxy]-tetrahydropyran-2-yl]methyl Acetate Following general procedure E, 10.6 g (20.1 mmol) 71b gave 8.0 g (92.0%) 72b without additional purification as colourless oil.

1H-NMR (DMSO-d6, 400 MHz) δ[ppm]: 7.80 (d, J=9.2 Hz, 1H), 5.22 (d, J=3.3 Hz, 1H), 4.98 (dd, J=3.4, 11.3 Hz, 1H), 4.64-4.53 (m, 2H), 4.11-4.00 (m, 3H), 3.94-3.83 (m, 1H), 3.82-3.73 (m, 1H), 3.61 (dt, J=3.2, 7.1 Hz, 1H), 3.56-3.46 (m, 4H), 3.44-3.38 (m, 2H), 2.11 (s, 3H), 2.01 (s, 3H), 1.90 (s, 3H), 1.78 (s, 3H).

72c: [(2R,3R,4R,5R,6R)-5-acetamido-3,4-diacetoxy-6-[2-[2-(2-hydroxyethoxy)ethoxy]-ethoxy]tetrahydropyran-2-yl]methyl Acetate Following general procedure E, 15.6 g (27.4 mmol) 71c were hydrogenated in a mixed solvent of 200 ml EtOAc/THF (1:1), which gave 11.0 g (84.6%) 72c without additional purification as colourless oil.

1H-NMR (DMSO-d6, 400 MHz) [ppm]: 7.80 (d, J=9.2 Hz, 1H), 5.22 (d, J=3.3 Hz, 1H), 4.98 (dd, J=3.4, 11.2 Hz, 1H), 4.62-4.52 (m, 2H), 4.09-4.00 (m, 4H), 3.89 (td, J=8.9, 11.0 Hz, 1H), 3.82-3.74 (m, 1H), 3.63-3.56 (m, 1H), 3.55-3.46 (m, 8H), 3.45-3.39 (m, 2H), 2.11 (s, 3H), 2.01 (s, 3H), 1.91-1.88 (m, 3H), 1.78 (s, 3H), 1.18 (t, J=7.1 Hz, 1H).

72d: [(2R,3R,4R,5R,6R)-5-acetamido-3,4-diacetoxy-6-[2-[2-[2-(2-hydroxyethoxy)ethoxy]-ethoxy]ethoxy]tetrahydropyran-2-yl]methyl Acetate (Following general procedure E, 10.0 g (16.3 mmol) 71d were hydrogenated in 100 EtOAc, yielding 8.7 g (93.0%) 72d without additional purification as colourless oil.

1H-NMR (DMSO-d6, 400 MHz) δ[ppm]: 7.80 (d, J=9.2 Hz, 1H), 5.22 (d, J=3.3 Hz, 1H), 4.97 (dd, J=3.4, 11.2 Hz, 1H), 4.62-4.53 (m, 2H), 4.09-3.98 (m, 4H), 3.89 (td, J=9.0, 10.9 Hz, 1H), 3.82-3.75 (m, 1H), 3.63-3.56 (m, 1H), 3.55-3.46 (m, 12H), 3.42 (d, J=5.0 Hz, 2H), 2.11 (s, 3H), 2.00 (s, 3H), 1.92-1.87 (m, 3H), 1.78 (s, 3H).

72e: [(2R,3R,4R,5R,6R)-5-acetamido-3,4-diacetoxy-6-[2-[2-[2-[2-(2-hydroxyethoxy)ethoxy]-ethoxy]ethoxy]ethoxy]tetrahydropyran-2-yl]methyl Acetate Following general procedure E, 12.4 g (18.9 mmol) 71e were hydrogenated in 250 EtOAc, yielding 9.7 g (83.9%) 72e after final purification on silica (DCM/MeOH 15:1) as yellow oil.

1H-NMR (CDCl3, 400 MHz) δ[ppm]: 6.96 (br d, J=9.29 Hz, 1H), 5.35-5.32 (m, 1H), 5.05 (dd, J=11.17, 3.39 Hz, 1H), 5.09-5.02 (m, 1H), 4.74 (d, J=8.66 Hz, 1H), 4.27 (dt, J=11.04, 8.97 Hz, 1H), 4.20-4.11 (m, 2H), 4.01-3.91 (m, 3H), 3.84-3.59 (m, 21H), 2.95 (br s, 2H), 2.17-2.15 (m, 3H), 2.05 (s, 3H), 2.01-1.98 (m, 6H).

72f: [(2R,3R,4R,5R,6R)-5-acetamido-3,4-diacetoxy-6-(5-hydroxypentoxy)tetrahydropyran-2-yl]methyl Acetate 2.50 g (4.77 mmol) 71f were hydrogenated in 13 ml THF in the presence of 168 mg (239 μmol) Pd(OH)$_2$/C (20%) at room temperature under 4 bar H$_2$-atmosphere until complete conversion was achieved. The reaction mixture was filtered and the filtrate evaporated, yielding 2.08 g (quant., crude) of the title compound 72f.

LCMS-Method A:
ELSD: $R_t$[min]=1.15
Ionization method: $ES^-$: $[M-H+formic\ acid]^-$=478.2

72g: [(2R,3R,4R,5R,6R)-5-acetamido-3,4-diacetoxy-6-(12-hydroxydodecoxy)tetrahydro-pyran-2-yl]methyl Acetate 5.69 g (9.14 mmol) of the benzylether 71g were hydrogenated following the protocol described for 72f, yielding 4.79 g (98.5%) of the title compound 72g as colourless oil, which crystallized to white needles.

LCMS-Method A:
ELSD: $R_t$[min]=1.72
Ionization method: $ES^+$: $[M-H+]^+$=532.3

73a: [(2R,3R,4R,5R,6R)-5-acetamido-3,4-diacetoxy-6-(2-oxoethoxy)tetrahydropyran-2-yl]methyl Acetate To a solution of 0.75 g (1.92 mmol) of the starting material 72a in 10 ml DCM, were added 6.77 g (4.97 ml, 2.40 mmol) 1,1,1-Triacetoxy-1,1-dihydro-1,2-benziodoxol-3(1H)-on (Dess-Martin periodinane). After the solution was stirred for 2 h at room temperature, the solvent was removed and the residue purified on silica (EtOAc/DCM 1:1 to EtOAc/DCM/MeOH 5:5:2), yielding 591 mg (79.2%) of the title compound 73a.
LCMS-Method C:
ELSD $R_t$[min]=0.86
Ionization method: ES$^+$: [M+H]$^+$=390.2

73b: [(2R,3R,4R,5R,6R)-5-acetamido-3,4-diacetoxy-6-[2-(2-oxoethoxy)ethoxy]tetrahydro-pyran-2-yl]methyl Acetate Following the protocol described for 73a, 1.0 g (2.30 mmol) of 72b were oxidized with 8.12 g (5.96 ml, 2.87 mmol) 1,1,1-Triacetoxy-1,1-dihydro-1,2-benziodoxol-3 (1H)-on (Dess-Martin periodinane). Final purification on silica (EtOAc/DCM 1:1 to EtOAc/DCM/MeOH 5:5:2) gave 1.0 g (quant.) of the title compound 73b.
LCMS-Method B2:
MS TIC $R_t$[min]=0.35
Ionization method: ES$^+$: [M+H]$^+$=434.1

73c: [(2R,3R,4R,5R,6R)-5-acetamido-3,4-diacetoxy-6-[2-[2-(2-oxoethoxy)ethoxy]ethoxy]-tetrahydropyran-2-yl]methyl Acetate 596 mg (542 µl, 7.59 mmol) DMSO were dissolved in 11 ml dry DCM. After cooling to −60° C., 1.75 ml (3.50 mmol) of a 2 M solution of oxalylchloride in dry DCM were added and stirring was continued for 10 minutes, followed by the addition of a solution of 1.40 g (2.92 mmol) of the alcohol 72c in 11 ml dry DCM. The mixture was stirred for another 10 minutes at −60° C. and 2.97 g (4.08 ml, 29.2 mmol) NEt$_3$ were added. The cooling bath was removed and the reaction mixture was allowed to reach room temperature. After complete conversion, the solution was diluted with 25 ml DCM and washed with sat. NaHCO$_3$-solution. The organic layer was separated, dried with MgSO$_4$ and the solvent was removed, which gave 1.27 g (91.1%, crude) of the desired aldehyde (73c) as colourless oil, which was used without further purification.
LCMS-Method B2:
ELSD $R_t$[min]=1.66
Ionization method: ES$^+$: [M+H]$^+$=478.2

73d: [(2R,3R,4R,5R,6R)-5-acetamido-3,4-diacetoxy-6-[2-[2-[2-(2-oxoethoxy)ethoxy]ethoxy]-ethoxy]tetrahydropyran-2-yl]methyl Acetate Following the protocol described for 73c, 1.10 g (2.10 mmol) of the alcohol 72d were oxidized, yielding 0.99 g (90.3%, crude) of the aldehyde 73d as colourless oil.
LCMS-Method C:
ELSD $R_t$[min]=1.69
Ionization method: ES$^+$: [M+H]$^+$=522.2

73e: [(2R,3R,4R,5R,6R)-5-acetamido-3,4-diacetoxy-6-[2-[2-2-[2-(2-oxoethoxy)ethoxy]-ethoxyethoxy]ethoxy]tetrahydropyran-2-yl]methyl Acetate Following the protocol described for 73c, 1.10 g (1.94 mmol) of the alcohol 72e were oxidized, yielding 1.10 g (quant., crude) of the aldehyde 73e as colourless oil.
LCMS-Method A:
ELSD $R_t$[min]=1.50
Ionization method: ES$^+$: [M+H]$^+$=566.4

73f: [(2R,3R,4R,5R,6R)-5-acetamido-3,4-diacetoxy-6-(5-oxopentoxy)tetrahydropyran-2-yl]methyl Acetate Following the protocol described for 73c, 2.05 g (4.73 mmol) of the alcohol 72f were oxidized, yielding 2.05 g (quant., crude) of the aldehyde 73f as colourless oil.
LCMS-Method A:
ELSD $R_t$[min]=1.19
Ionization method: ES$^-$: [M−H+formic acid]−=476.2

73g: [(2R,3R,4R,5R,6R)-5-acetamido-3,4-diacetoxy-6-(12-oxododecoxy)tetrahydropyran-2-yl] methyl Acetate Following the protocol described for 73c, 2.20 g (4.14 mmol) of the alcohol 72g were oxidized, yielding 2.19 g (99.9%, crude) of the aldehyde 73g as colourless oil.
LCMS-Method A:
ELSD $R_t$[min]=1.79
Ionization method: ES$^-$: [M−H+formic acid]−=574.3

General procedure F for the syntheses of compounds 74a to 74g 1.0 eq. of the starting aldehyde 73a to 73e was dissolved in MeO (20 ml/1.0 mmol). At room temperature, 5 g molecular sieves (4 Å), 4.0 eq. NEt$_3$ and 10.0 eq. AcOH were added, followed by the addition of 1.0 eq. of the morpholine 24a. The reaction solution was stirred for 15 minutes and 4.0 eq. of sodium cyanoboronhydride were added over a period of 2 h (4 portions). The reaction was stirred at room temperature overnight to achieve complete conversion. The mixture was filtered and the filtrate was poured into 50 ml of sat. NaHCO$_3$— solution. The MeO was evaporated and the aqueous mixture was extracted twice with DCM. The organic layers were dried with MgSO$_4$, the solvent was removed i.vac. and the crude product purified by silicagel chromatography to yield the title compounds 74a to 74g.

74a: [(2R,3R,4R,5R,6R)-5-acetamido-3,4-diacetoxy-6-[2-[(2S,6R)-2-[[bis(4-methoxyphenyl)-phenyl-methoxy]methyl]-6-(5-methyl-2,4-dioxo-pyrimidin-1-yl)-2-(triisopropylsilyloxy-methyl)morpholin-4-yl]ethoxy]tetrahydropyran-2-yl]methyl Acetate 580 mg (745 µmol) of the starting aldehyde 73a gave 510 mg (62.1%) of the title compound 74a, following general procedure F and final purification on silica (0 to 10% MeOH in DCM) as colourless foam.
LCMS-Method C:
UV-wavelength [nm]=220: $R_t$[min]=3.30
Ionization method: ES$^+$: [M+H]$^+$=1104.0

74b: [(2R,3R,4R,5R,6R)-5-acetamido-3,4-diacetoxy-6-[2-[2-[(2S,6R)-2-[[bis(4-methoxy-phenyl)-phenyl-methoxy]methyl]-6-(5-methyl-2,4-dioxo-pyrimidin-1-yl)-2-(triisopropyl-silyloxymethyl)morpholin-4-yl]ethoxy]ethoxy]tetrahydropyran-2-yl] methyl Acetate 500 mg (577 µmol) of the starting aldehyde 73b gave 352 mg (53.2%) of the title compound 74b, following general procedure F and final purification on silica (EtOAc/DCM 1:1 to EtOAc/DCM/MeOH 5:5:1) as colourless foam.
LCMS-Method C:
UV-wavelength [nm]=220: $R_t$[min]=3.27
Ionization method: ES$^+$: [M+H]$^+$=1148.0

74c: [(2R,3R,4R,5R,6R)-5-acetamido-3,4-diacetoxy-6-[2-[2-[2-[(2S,6R)-2-[[bis(4-methoxy-phenyl)-phenyl-methoxy]methyl]-6-(5-methyl-2,4-dioxo-pyrimidin-1-yl)-2-(triisopropylsilyl-oxymethyl)morpholin-4-yl]ethoxy]ethoxy]ethoxy]tetrahydropyran-2-yl] methyl Acetate 900 mg (1.88 mmol) of the starting aldehyde 73c gave 1.34 g (59.5%) of the title compound 74c, following general procedure F and final purification on silica (0 to 10% MeO in DCM) as colourless foam.

LCMS-Method C:
UV-wavelength [nm]=220: $R_t$[min]=3.29
Ionization method: ES⁻: [M−H]⁻=1189.9

74d: [(2R,3R,4R,5R,6R)-5-acetamido-3,4-diacetoxy-6-[2-[2-[2-[2-[(2S,6R)-2-[[bis(4-methoxyphenyl)-phenyl-methoxy]methyl]-6-(5-methyl-2,4-dioxo-pyrimidin-1-yl)-2-(triiso-propylsilyloxymethyl)morpholin-4-yl]ethoxy]ethoxy]ethoxy]ethoxy] tetrahydropyran-2-yl]methyl Acetate 840 mg (1.61 mmol) of the starting aldehyde 73d gave 835 mg (42.0%) of the title compound 74d, following general procedure F and final purification on silica (0 to 10% MeO in DCM) as colourless foam.

LCMS-Method C:
UV-wavelength [nm]=220: $R_t$[min]=3.30
Ionization method: ES⁺: [M+H]⁺=1235.8

74e: [(2R,3R,4R,5R,6R)-5-acetamido-3,4-diacetoxy-6-[2-[2-[2-[2-[2-[(2S,6R)-2-[[bis(4-methoxyphenyl)-phenyl-methoxy]methyl]-6-(5-methyl-2,4-dioxo-pyrimidin-1-yl)-2-(triiso-propylsilyloxymethyl)morpholin-4-yl]ethoxy]ethoxy]ethoxy]ethoxy]ethoxy]tetrahydropyran-2-yl]methyl Acetate 1.09 g (1.54 mmol, purity 80%) of the starting aldehyde 73e gave 1.12 g (56.8%) of the title compound 74e, following general procedure F and final purification on silica (0 to 10% MeOH in DCM) as colourless foam.

LCMS-Method A:
UV-wavelength [nm]=220: $R_t$[min]=2.20
Ionization method: ES⁺: [M+H]⁺=1279.9

74f: [(2R,3R,4R,5R,6R)-5-acetamido-3,4-diacetoxy-6-[5-[(2S,6R)-2-[[bis(4-methoxyphenyl)-phenyl-methoxy]methyl]-6-(5-methyl-2,4-dioxo-pyrimidin-1-yl)-2-(triisopropylsilyloxy-methyl)morpholin-4-yl]pentoxy]tetrahydropyran-2-yl]methyl Acetate 1.0 g (2.32 mmol) of the starting aldehyde 73f gave 2.18 g (82.1%) of the title compound 74f, following general procedure F and final purification on silica (0 to 10% MeOH in DCM) as colourless foam.

1H-NMR (DMSO-d6, 400 MHz) δ[ppm]: 11.44 (s, 1H), 7.84-7.77 (m, 1H), 7.62 (s, 1H), 7.42 (d, J=7.6 Hz, 2H), 7.33-7.18 (m, 8H), 6.84 (d, J=8.8 Hz, 4H), 5.88 (dd, J=2.4, 10.0 Hz, 1H), 5.22 (d, J=3.6 Hz, 1H), 4.98 (dd, J=3.2, 11.2 Hz, 1H), 4.52-4.47 (m, 1H), 4.11 (d, J=9.6 Hz, 1H), 4.07-3.97 (m, 4H), 3.93-3.83 (m, 2H), 3.80-3.65 (m, 8H), 3.47-3.38 (m, 1H), 3.11 (d, J=9.2 Hz, 1H), 2.97 (d, J=9.2 Hz, 1H), 2.90 (d, J=8.8 Hz, 1H), 2.79 (d, J=11.2 Hz, 1H), 2.29 (t, J=7.2 Hz, 2H), 2.14-2.04 (m, 5H), 2.02-1.95 (m, 3H), 1.90 (s, 3H), 1.82-1.73 (m, 6H), 1.57-1.22 (m, 6H), 1.01-0.83 (m, 21H).

74g: [(2R,3R,4R,5R,6R)-5-acetamido-3,4-diacetoxy-6-[12-[(2S,6R)-2-[[bis(4-methoxy-phenyl)-phenyl-methoxy]methyl]-6-(5-methyl-2,4-dioxo-pyrimidin-1-yl)-2-(triisopropyl-silyloxymethyl)morpholin-4-yl]dodecoxy]tetrahydropyran-2-yl] methyl Acetate 2.19 g (4.13 mmol) of the starting aldehyde 73g gave 4.84 g (94.3%) of the title compound 74g, following general procedure F and final purification on silica (0 to 100% MeOH/EtOAc (9:1) in n-heptane) as colourless foam.

LCMS-Method B-2:
UV-wavelength [nm]=220: $R_t$[min]=1.14
Ionization method: ES⁺: [(M+2H)/2]⁺=622.5

General Procedure G for the Synthesis of Compounds 75a-g and 81a-e 1.0 eq. of the TIPS-protected starting compounds 74a-e (80a-e, see Scheme 22) were dissolved in NMP (14 ml/1.0 mmol). After adding 15.0 eq. triethyl amine and 6.0 eq. NEt₃·3HF, the reaction mixture was stirred at 90° C. until complete conversion was achieved. After the solution was cooled to room temperature, sat. NaHCO₃-solution was added and the mixture was extracted three times with EtOAc. The combined organic layers were washed with sat. NaCl-solution and dried with MgSO₄. After evaporation of the solvent, the crude product was purified on silica, yielding the deprotected products 75a-g (81a-e, s. Scheme 22).

75a: [(2R,3R,4R,5R,6R)-5-acetamido-3,4-diacetoxy-6-[2-[(2R,6R)-2-[[bis(4-methoxyphenyl)-phenyl-methoxy]methyl]-2-(hydroxymethyl)-6-(5-methyl-2,4-dioxo-pyrimidin-1-yl)morpholin-4-yl]ethoxy] tetrahydropyran-2-yl]methyl Acetate Following general procedure G, 850 mg (770 μmol) of the TIPS-ether 74a were deprotected, yielding 401 mg (55.0%) of the title compound 75a after silicagel chromatography (EtOAc/DCM 1:1 to EtOAc/DCM/MeOH 5:5:1).

LCMS-Method C:
UV-wavelength [nm]=220: $R_t$[min]=2.16
Ionization method: ES⁺: [M+H]⁺=947.8
1H-NMR (DMSO-d6, 600 MHz) δ[ppm]: 11.37 (s, 1H), 7.78 (d, J=9.17 Hz, 1H), 7.53 (s, 1H), 7.40 (d, J=7.52 Hz, 2H), 7.18-7.32 (m, 7H), 6.87 (d, J=8.99 Hz, 4H), 5.85 (dd, J=9.90, 3.12 Hz, 1H), 5.20 (d, J=3.48 Hz, 1H), 4.96 (dd, J=11.19, 3.48 Hz, 1H), 4.57 (t, J=5.32 Hz, 1H), 4.52 (d, J=8.44 Hz, 1H), 3.99-4.06 (m, 3H), 3.79-3.91 (m, 2H), 3.72-3.76 (m, 7H), 3.66 (dd, J=11.10, 5.78 Hz, 1H), 3.59 (dt, J=11.51, 5.52 Hz, 1H), 3.00 (s, 2H), 2.90 (br d, J=9.35 Hz, 1H), 2.76 (br d, J=11.55 Hz, 1H), 2.51-2.60 (m, 2H), 2.25 (d, J=11.37 Hz, 1H), 2.17 (t, J=10.64 Hz, 1H), 2.04 (m, 3H), 1.97 (m, 3H), 1.88 (s, 3H), 1.70 (s, 3H), 1.69 (s, 3H).

75b: [(2R,3R,4R,5R,6R)-5-acetamido-3,4-diacetoxy-6-[2-[2-[(2R,6R)-2-[[bis(4-methoxy-phenyl)-phenyl-methoxy]methyl]-2-(hydroxymethyl)-6-(5-methyl-2,4-dioxo-pyrimidin-1-yl)morpholin-4-yl]ethoxy]ethoxy]tetrahydropyran-2-yl]methyl Acetate Following general procedure G, 720 mg (635 μmol) of the TIPS-ether 74b were deprotected, yielding 527 mg (83.7%)

of the title compound 75b after silicagel chromatography (EtOAc/DCM 1:1 to EtOAc/DCM/MeOH 5:5:1).
LCMS-Method C:
UV-wavelength [nm]=220: R$_t$[min]=2.12
Ionization method: ES$^+$: [M+H]$^+$=991.9
1H-NMR DMSO-d6, 600 MHz) δ[ppm]: 11.36 (s, 1H), 7.79 (d, J=9.17 Hz, 1H), 7.55 (s, 1H), 7.40 (d, J=7.70 Hz, 2H), 7.21-7.31 (m, 7H), 6.87 (d, J=8.80 Hz, 4H), 5.85 (br d, J=7.34 Hz, 1H), 5.21 (d, J=3.30 Hz, 1H), 4.98 (dd, J=11.19, 3.30 Hz, 1H), 4.61 (br s, 1H), 4.54 (d, J=8.62 Hz, 1H), 3.99-4.04 (m, 3H), 3.83-3.90 (m, 1H), 3.72-3.79 (m, 8H), 3.55-3.67 (m, 2H), 3.48-3.55 (m, 4H), 3.01 (s, 2H), 2.90 (br d, J=10.09 Hz, 1H), 2.80 (br d, J=12.10 Hz, 1H), 2.51-2.55 (m, 2H), 2.27 (br d, J=11.74 Hz, 1H), 2.15-2.21 (m, 1H), 2.09 (s, 3H), 1.98 (s, 3H), 1.89 (s, 3H), 1.76 (s, 3H), 1.67 (s, 3H).

75c: [(2R,3R,4R,5R,6R)-5-acetamido-3,4-diacetoxy-6-[2-[2-[2-[(2R,6R)-2-[[bis(4-methoxyphenyl)-phe-nyl-methoxy]methyl]-2-(hydroxymethyl)-6-(5-methyl-2,4-dioxo-pyrimidin-1-yl)morpholin-4-yl] ethoxy]ethoxy]ethoxy]tetrahydropyran-2-yl]methyl Acetate Following general procedure G, 1.25 g (1.05 mmol) of the TIPS-ether 74c were deprotected, yielding 630 mg (58.0%) of the title compound 75c after silicagel chroma-tography (EtOAc/DCM 1:1 to EtOAc/DCM/MeOH 5:5:1).
LCMS-Method C:
UV-wavelength [nm]=220: R$_t$[min]=2.11
Ionization method: ES$^+$: [M+H]$^+$=1035.6
1H-NMR (DMSO-d6, 600 MHz) δ[ppm]: 11.36 (s, 1H), 7.77 (d, J=9.17 Hz, 1H), 7.55 (s, 1H), 7.40 (d, J=7.34 Hz, 2H), 7.20-7.31 (m, 7H), 6.87 (d, J=8.62 Hz, 4H), 5.85 (dd, J=9.72, 3.12 Hz, 1H), 5.21 (d, J=3.48 Hz, 1H), 4.97 (dd, J=11.19, 3.30 Hz, 1H), 4.60 (t, J=5.41 Hz, 1H), 4.54 (d, J=8.62 Hz, 1H), 4.00-4.06 (m, 3H), 3.84-3.91 (m, 1H), 3.71-3.77 (m, 8H), 3.59-3.67 (m, 1H), 3.42-3.57 (m, 9H), 3.01 (s, 2H), 2.92 (br d, J=9.54 Hz, 1H), 2.80 (br d, J=11.55 Hz, 1H), 2.51-2.56 (m, 2H), 2.27 (d, J=11.55 Hz, 1H), 2.17 (t, J=10.45 Hz, 1H), 2.10 (s, 3H), 1.99 (s, 3H), 1.89 (s, 3H), 1.76 (m, 3H), 1.67 (m, 3H).

75d: [(2R,3R,4R,5R,6R)-5-acetamido-3,4-diac-etoxy-6-[2-[2-[2-[2-[(2R,6R)-2-(hydroxy-methyl)-2-[[(4-hydroxyphenyl)-(4-methoxyphenyl)-phenyl-methoxy]methyl]-6-(5-methyl-2,4-dioxo-pyrimidin-1-yl)morpholin-4-yl]ethoxy]ethoxy]ethoxy]ethoxy] tetrahydropyran-2-yl]methyl Acetate Following general procedure G, 780 mg (631 µmol) of the TIPS-ether 74d were deprotected, yielding 450 mg (66.1%) of the title compound 75d after silicagel chromatography (EtOAc/DCM 1:1 to EtOAc/DCM/MeOH 5:5:1).
LCMS-Method C:
UV-wavelength [nm]=220: R$_t$[min]=2.12
Ionization method: ES$^+$: [M+H]$^+$=1079.7
1H-NMR (DMSO-d6, 600 MHz) δ[ppm]: 11.36 (s, 1H), 7.77 (d, J=9.17 Hz, 1H), 7.55 (s, 1H), 7.40 (d, J=7.34 Hz, 2H), 7.20-7.31 (m, 7H), 6.87 (d, J=8.80 Hz, 4H), 5.84 (dd, J=9.72, 3.12 Hz, 1H), 5.21 (d, J=3.48 Hz, 1H), 4.97 (dd, J=11.28, 3.39 Hz, 1H), 4.60 (t, J=5.32 Hz, 1H), 4.55 (d, J=8.44 Hz, 1H), 4.00-4.06 (m, 3H), 3.85-3.91 (m, 1H), 3.72-3.78 (m, 8H), 3.61-3.66 (m, 1H), 3.55-3.60 (m, 1H), 3.43-3.54 (m, 12H), 3.00 (s, 2H), 2.92 (br d, J=8.99 Hz, 1H), 2.81 (br d, J=11.19 Hz, 1H), 2.51-2.56 (m, 2H), 2.28 (d, J=11.74 Hz, 1H), 2.15-2.21 (m, 1H), 2.10 (s, 3H), 1.99 (s, 3H), 1.89 (m, 3H), 1.77 (s, 3H), 1.67 (s, 3H).

75e: [(2R,3R,4R,5R,6R)-5-acetamido-3,4-diacetoxy-6-[2-[2-[2-[2-[2-[(2R,6R)-2-[[bis(4-methoxyphenyl)-phenyl-methoxy]methyl]-2-(hydroxymethyl)-6-(5-methyl-2,4-dioxo-pyrimidin-1-yl)morpholin-4-yl] ethoxy]ethoxy]ethoxy]ethoxy]ethoxy] tetrahydropyran-2-yl]methyl Acetate Following general procedure G, 1.10 g (860 µmol) of the TIPS-ether 74e were deprotected, yielding 437 mg (45.3%) of the title compound 75e after silicagel chroma-tography (0 to 5% MeOH in DCM).
LCMS-Method A:
UV-wavelength [nm]=220: R$_t$[min]=1.72
Ionization method: ES$^-$: [M−H]$^-$=1121.6
1H-NMR (DMSO-d6, 400 MHz) δ[ppm]: 11.36 (s, 1H), 7.77 (d, J=9.17 Hz, 1H), 7.53-7.56 (m, 1H), 7.40 (d, J=7.34 Hz, 2H), 7.19-7.31 (m, 7H), 6.87 (d, J=8.93 Hz, 4H), 5.85 (dd, J=9.66, 2.93 Hz, 1H), 5.21 (d, J=3.42 Hz, 1H), 4.97 (dd, J=11.25, 3.42 Hz, 1H), 4.53-4.62 (m, 2H), 4.03 (s, 3H), 3.83-3.93 (m, 1H), 3.72-3.82 (m, 8H), 3.44-3.66 (m, 18H), 2.98-3.04 (m, 2H), 2.92 (br d, J=8.80 Hz, 1H), 2.77-2.86 (m, 1H), 2.52-2.57 (m, 2H), 2.25-2.32 (m, 1H), 2.18 (br t, J=10.51 Hz, 1H), 2.10 (m, 3H), 1.99 (m, 3H), 1.89 (s, 3H), 1.77 (s, 3H), 1.67 (s, 3H).

75f: [(2R,3R,4R,5R,6R)-5-acetamido-3,4-diacetoxy-6-[5-[(2R,6R)-2-[[bis(4-methoxyphenyl)-phenyl-methoxy]methyl]-2-(hydroxymethyl)-6-(5-methyl-2,4-dioxo-pyrimidin-1-yl)morpholin-4-yl]pentoxy] tetrahydropyran-2-yl]methyl Acetate Following general procedure G, 2.15 g (1.88 mmol) of the TIPS-ether 74f were deprotected, yielding 1.21 g (65.0%) of the title compound 75f after silicagel chroma-tography (0 to 5% MeOH in DCM).
LCMS-Method A:
UV-wavelength [nm]=220: R$_t$[min]=1.69
Ionization method: ES$^+$: [M+H]$^+$=989.5
1H-NMR (DMSO-d6, 400 MHz) δ[ppm]: 11.36 (s, 1H), 7.79 (d, J=9.29 Hz, 1H), 7.51-7.58 (m, 1H), 7.40 (d, J=7.34 Hz, 2H), 7.19-7.32 (m, 7H), 6.87 (d, J=8.44 Hz, 4H), 5.84 (dd, J=9.90, 2.93 Hz, 1H), 5.21 (d, J=3.42 Hz, 1H), 4.96 (dd, J=11.25, 3.42 Hz, 1H), 4.58-4.65 (m, 1H), 4.48 (d, J=8.44 Hz, 1H), 3.98-4.06 (m, 3H), 3.80-3.94 (m, 1H), 3.63-3.78 (m, 9H), 3.34-3.45 (m, 1H), 2.97-3.08 (m, 2H), 2.87 (br d, J=9.05 Hz, 1H), 2.74 (br d, J=11.49 Hz, 1H), 2.24-2.33 (m, 2H), 2.01-2.17 (m, 5H), 1.98 (s, 3H), 1.89 (s, 3H), 1.76 (s, 3H), 1.67 (s, 3H), 1.35-1.54 (m, 4H), 1.23-1.35 (m, 2H).

75g: [(2R,3R,4R,5R,6R)-5-acetamido-3,4-diac-etoxy-6-[12-[(2R,6R)-2-[[bis(4-methoxy-phenyl)-phenyl-methoxy]methyl]-2-(hydroxymethyl)-6-(5-methyl-2,4-dioxo-pyrimidin-1-yl)morpholin-4-yl] dodecoxy]tetrahydropyran-2-yl]methyl Acetate Following general procedure G, 4.83 g (3.88 mmol) of the TIPS-ether 74g were deprotected, yielding 3.03 g (71.7%) of the title compound 75g without additional purification.
LCMS-Method A:
UV-wavelength [nm]=220: R$_t$[min]=1.89
Ionization method: ES$^-$: [M−H]$^-$=1085.5
1H-NMR (DMSO-d6, 400 MHz) δ[ppm]: 11.36 (s, 1H), 7.79 (d, J=9.29 Hz, 1H), 7.54 (s, 1H), 7.40 (d, J=7.46 Hz, 2H), 7.19-7.32 (m, 7H), 6.87 (d, J=8.80 Hz, 4H), 5.84 (dd, J=9.72, 2.87 Hz, 1H), 5.21 (d, J=3.30 Hz, 1H), 4.96 (dd, J=11.25, 3.30 Hz, 1H), 4.61 (t, J=5.14 Hz, 1H), 4.48 (d, J=8.44 Hz, 1H), 3.98-4.07 (m, 3H), 3.82-3.91 (m, 1H), 3.61-3.78 (m, 9H), 3.35-3.44 (m, 1H), 2.96-3.08 (m, 2H), 2.86 (br d, J=9.17 Hz, 1H), 2.66-2.77 (m, 1H), 2.30 (br t, J=7.09 Hz, 2H), 2.01-2.16 (m, 5H), 1.99 (s, 3H), 1.89 (m, 3H), 1.76 (m, 3H), 1.67 (m, 3H), 1.36-1.48 (m, 4H), 1.20-1.31 (br s, 16H).

General Procedure H for the Syntheses of Compounds 76a-g and 82a-e 1.0 eq. of the starting alcohols 75a-e (81a-e, see Scheme 22) and 6.0 eq. diisopropylammonium tetrazolide were dissolved dry DCM (33 ml/1.0 mmol). Under an atmosphere of argon, 3.0 eq. 2-cyanoethyl-N,N,N',N'-tetraisopropyl phosphorodiamidite were added dropwise at room temperature and the solution was stirred until complete conversion was achieved. The reaction was quenched with H$_2$O (25 ml) and the organic layer was separated. The aqueous phase was extracted with DCM and the combined organic extracts were dried with MgSO$_4$. After evaporation of the solvent, the crude product was dissolved in approx. 10 ml ethylacetate/diethylether (1:1) and 40 ml of n-pentane were added. The precipitate was centrifuged (2 minutes, 10° C., 4400 upm) and the liquid layer was decanted. The purification of the precipitate was repeated three times. After drying on a speedvac, the title compounds 76a-g (82a-e, see Scheme 22) were isolated as colourless solids.

76a: [(2R,3R,4R,5R,6R)-5-acetamido-3,4-diacetoxy-6-[2-[(2S,6R)-2-[[bis(4-methoxyphenyl)-phenyl-methoxy]methyl]-2-[[2-cyanoethoxy-(diisopropylamino)phosphanyl]oxymethyl]-6-(5-methyl-2,4-dioxo-pyrimidin-1-yl)morpholin-4-yl]ethoxy]tetrahydropyran-2-yl]methyl Acetate Following general procedure H, 401 mg (423 µmol) of the starting alcohol 75a were phosphitylated, yielding 430 mg (88.5%) of the title compound 76a.

1H-NMR (DMSO-d6, 400 MHz) δ[ppm]: 11.35 (br s, 1H), 7.78 (d, J=9.03 Hz, 1H), 7.52, 7.55 (2×s, 1H), 7.35-7.44 (m, 2H), 7.19-7.32 (m, 7H), 6.81-6.90 (m, 4H), 5.86-5.92 (m, 1H), 5.20 (m, 1H), 4.95 (2×t, 3.12 Hz, 1H), 4.50 (m, 1H), 3.96-4.08 (m, 4H), 3.77-3.93 (m, 3H), 3.73 (s, 6H), 3.38-3.67 (m, 5H), 2.87-3.11 (m, 3H), 2.72-2.83 (m, 1H), 2.52-2.70 (m, 4H), 2.13-2.36 (m, 2H), 1.93-2.04 (m, 6H), 1.85-1.91 (m, 3H), 1.67-1.76 (m, 6H), 0.94-1.13 (m, 12H).

31P-NMR (DMSO-d6, 162 MHz) δ[ppm]: 147.7, 147.5.

76b: [(2R,3R,4R,5R,6R)-5-acetamido-3,4-diacetoxy-6-[2-[2-[(2S,6R)-2-[[bis(4-methoxy-phenyl)-phenyl-methoxy]methyl]-2-[[2-cyanoethoxy-(diisopropylamino)phosphanyl]oxymethyl]-6-(5-methyl-2,4-dioxo-pyrimidin-1-yl)morpholin-4-yl]ethoxy]ethoxy]tetrahydro-pyran-2-yl]methyl Acetate Following general procedure H, 527 mg (532 µmol) of the starting alcohol 75b were phosphitylated, yielding 528 mg (83.4%) of the title compound 76b.

1H-NMR (DMSO-d6, 400 MHz) δ[ppm]: 11.35 (br s, 1H), 7.79 (d, J=9.16, 1H), 7.55 (2×s, 1H), 7.35-7.43 (m, 2H), 7.19-7.32 (m, 7H), 6.82-6.90 (m, 4H), 5.84-5.93 ((m, 1H), 5.21 (m, 1H), 4.98 (m, 1H), 4.54 (m, 1H), 3.95-4.09 (m, 5H), 3.71-3.92 (m, 3H), 3.73 (s, 6H), 3.39-3.64 (m, 9H), 2.96-3.12 (m, 2H), 2.77-2.96 (m, 2H), 2.63-2.73 (m, 1H), 2.52-2.63 (m, 2H), 2.16-2.35 (m, 2H), 2.09 (s, 3H), 1.98, 1.99 (2×s, 3H), 1.89 (s, 3H), 1.76 (s, 3H) 1.72, 1.69 (2×s, 3H), 0.91-1.14 (m, 12H).

31P-NMR (DMSO-d6, 162 MHz) δ[ppm]: 147.6, 147.4.

76c: [(2R,3R,4R,5R,6R)-5-acetamido-3,4-diacetoxy-6-[2-[2-[2-[(2S,6R)-2-[[bis(4-methoxyphenyl)-phenyl-methoxy]methyl]-2-[[2-cyanoethoxy-(diisopropylamino)-phosphanyl]oxymethyl]-6-(5-methyl-2,4-dioxo-pyrimidin-1-yl)morpholin-4-yl]ethoxy]-ethoxy]ethoxy]tetrahydropyran-2-yl]methyl Acetate Following general procedure H, 630 mg (609 µmol) of the starting alcohol 75c were phosphitylated, yielding 698 mg (92.8%) of the title compound 76c.

1H-NMR (DMSO-d6, 400 MHz) δ[ppm]: 11.35 (br s, 1H), 7.76 (m, 1H), 7.56, 7.53 (2×s, 1H), 7.39 (m, 2H), 7.19-7.33 (m, 7H), 6.82-6.91 (m, 4H), 5.84-5.93 (m, 1H), 5.21 (m, 1H), 4.97 (m, 1H), 4.55 (m, 1H), 3.96-4.09 (m, 4H), 3.70-3.91 (m, 4H), 3.73 (s, 6H), 3.40-3.63 (m, 13H), 2.98-3.08 (m, 2H), 2.79-2.96 (m, 2H), 2.64-2.73 (m, 1H), 2.52-2.62 (m, 2H), 2.17-2.34 (m, 2H), 2.10 (s, 3H), 1.99 (m, 3H), 1.89 (m, 3H), 1.78 (m, 3H), 1.72, 1.70 (2×s, 3H), 0.91-1.25 (m, 12H).

31P-NMR (DMSO-d6, 162 MHz) δ[ppm]: 147.6, 147.4.

76d: [(2R,3R,4R,5R,6R)-5-acetamido-3,4-diacetoxy-6-[2-[2-[2-[2-[(2S,6R)-2-[[bis(4-methoxyphenyl)-phenyl-methoxy]methyl]-2-[[2-cyanoethoxy-(diisopropylamino)-phosphanyl]oxymethyl]-6-(5-methyl-2,4-dioxo-pyrimidin-1-yl)morpholin-4-yl]ethoxy]-ethoxy]ethoxy]ethoxy]tetrahydropyran-2-yl]methyl Acetate Following general procedure H, 450 mg (417 µmol) of the starting alcohol 75d were phosphitylated, yielding 460 mg (86.2%) of the title compound 76d.

1H-NMR (DMSO-d6, 400 MHz) δ[ppm]: (br s, 1H), 7.77 (d, J=9.22 Hz, 1H), 7.56, 7.53 (2×s, 1H), 7.35-7.43 (m, 2H), 7.19-7.33 (m, 7H), 6.82-6.90 (m, 4H), 5.84-5.93 (m, 1H), 5.22 (m, 1H), 4.97 (m, 1H), 4.56 (m, 1H), 3.97-4.09 (m, 4H), 3.68-3.96 (m, 4H), 3.73 (s, 6H), 3.37-3.66 (m, 17H), 2.79-3.08 (m, 4H), 2.64-2.71 (m, 1H), 2.52-2.62 (m, 2H), 2.17-2.35 (m, 2H), 2.10 (s, 3H), 1.99 (s, 3H), 1.89 (s, 3H), 1.77 (s, 3H), 1.72, 1.69 (2×s, 3H), 0.89-1.22 (m, 12H).

31P-NMR (DMSO-d6, 162 MHz) δ[ppm]: 147.6, 147.4.

76e: [(2R,3R,4R,5R,6R)-5-acetamido-3,4-diacetoxy-6-[2-[2-[2-[2-[2-[(2S,6R)-2-[[bis(4-methoxyphenyl)-phenyl-methoxy]methyl]-2-[[2-cyanoethoxy-(diisopropylamino)-phosphanyl]oxymethyl]-6-(5-methyl-2,4-dioxo-pyrimidin-1-yl)morpholin-4-yl]ethoxy]-ethoxy]ethoxy]ethoxy]tetrahydropyran-2-yl]methyl Acetate Following general procedure H, 495 mg (441 µmol) of the starting alcohol 75e were phosphitylated, yielding 589 mg (quant.) of the title compound 76e.

1H-NMR (DMSO-d6, 400 MHz) δ[ppm]: 11.35 (br s, 1H), 7.77 (d, J=9.16 Hz, 1H), 7.56, 7.53 (2×s, 1H), 7.35-7.43 (m, 2H), 7.18-7.33 (m, 7H), 6.86 (br d, J=8.78 Hz, 4H), 5.84-5.93 (m, 1H), 5.22 (dm, 1H), 4.97 (m, 1H), 4.56 (m, 1H), 3.96-4.10 (m, 4H), 3.72-3.95 (m, 4H), 3.73 (s, 6H), 3.41-3.63 (m, 21H), 2.79-3.08 (m, 4H), 2.64-2.72 (m, 1H), 2.53-2.61 (m, 2H), 2.14-2.33 (m, 2H), 2.10 (s, 3H), 1.99 (s, 3H), 1.89 (s, 3H), 1.77 (s, 3H), 1.72, 1.69 (2×s, 3H), 0.93-1.12 (m, 12H).

31P-NMR (DMSO-d6, 162 MHz) δ[ppm]: 147.6, 147.4.

76f: [(2R,3R,4R,5R,6R)-5-acetamido-3,4-diacetoxy-6-[5-[(2S,6R)-2-[[bis(4-methoxyphenyl)-phenyl-methoxy]methyl]-2-[[2-cyanoethoxy-(diisopropy-lamino)phosphanyl]oxymethyl]-6-(5-methyl-2,4-dioxo-pyrimidin-1-yl)morpholin-4-yl]pentoxy]tetrahydropyran-2-yl]methyl Acetate Following general procedure H, 1.17 g (1.18 mmol) of the starting alcohol 75f were phosphitylated, yielding 1.32 g (94.1%) of the title compound 76f.

1H-NMR (DMSO-d6, 400 MHz) δ[ppm]: 11.36 (br s, 1H), 7.78 (2×d, J=9.19, 1H), 7.57, 7.54 (2×s, 1H), 7.36-7.44 (m, 2H), 7.19-7.32 (m, 7H), 6.86 (brd, J=8.78 Hz, 4H), 5.89 (m, 1H), 5.21 (m, 1H), 4.96 (m, 1H), 4.48 (m, 1H), 3.94-4.09 (m, 4H), 3.81-3.93 (m, 2H), 3.66-3.75 (m, 1H), 3.73 (s, 6H), 3.53-3.66 (m, 2H), 3.37-3.51 (m, 3H), 3.07-3.13 (m, 1H), 2.95-3.05 (m, 1H), 2.84-2.92 (m, 1H), 2.77 (m, 1H), 2.63-2.71 (m, 1H), 2.52-2.62 (m, 1H), 2.23-2.39 (m, 2H), 2.02-2.16 (m, 2H), 2.10 (s, 3H), 1.99, 1.98 (2×s, 3H), 1.89 (s, 3H), 1.76 (s, 3H), 1.73, 1.70 (2×s, 3H), 1.35-1.56 (m, 4H), 1.22-1.33 (m, 2H), 0.93-1.13 (m. 12H).

31P-NMR (DMSO-d6, 162 MHz) δ[ppm]: 147.4, 147.1.

76g: [(2R,3R,4R,5R,6R)-5-acetamido-3,4-diac-etoxy-6-[12-[(2S,6R)-2-[[bis(4-methoxy-phenyl)-phenyl-methoxy]methyl]-2-[[2-cyanoethoxy-(diiso-propylamino)phosphanyl]oxymethyl]-6-(5-methyl-2,4-dioxo-pyrimidin-1-yl)morpholin-4-yl]dodecoxy]tetrahydropyran-2-yl]methyl Acetate Following general procedure H, 1.52 g (1.40 mmol) of the starting alcohol 75g were phosphitylated, yielding 1.55 g (86.3%) of the title compound 76g.

1H-NMR (DMSO-d6, 400 MHz) δ[ppm]: 11.37 (br s, 1H), 7.80 (d, J=9.22 Hz, 1H), 7.57, 7.54 (2×s, 1H), 7.36-7.45 (m, 2H), 7.20-7.32 (m, 7H), 6.86 (d, J=8.85 Hz, 4H), 5.86-5.93 (m, 1H), 5.22 (m, 1H), 4.97 (m, 1H), 4.49 (m, 1H), 3.82-4.09 (m, 6H), 3.74 (s, 6H), 3.65-3.72 (m, 1H), 3.54-3.64 (m, 2H), 3.36-3.52 (m, 3H), 3.06-3.14 (m, 1H), 2.96-3.06 (m, 1H), 2.73-2.91 (m, 2H), 2.64-2.71 (m, 1H), 2.53-2.61 (m, 1H), 2.20-2.39 (m, 2H), 2.03-2.16 (m, 2H), 2.11 (s, 3H), 1.99 (s, 3H), 1.90 (s, 3H), 1.77 (s, 3H), 1.73, 1.71 (2×s, 3H), 1.35-1.52 (m, 4H), 1.17-1.32 (m, 16H), 0.97-1.14 (m, 12H).

31P-NMR (DMSO-d6, 162 MHz) δ[ppm]: 147.3, 147.1.

Example C.2

Synthetic Scheme 21

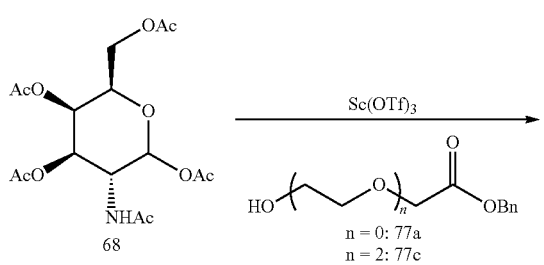

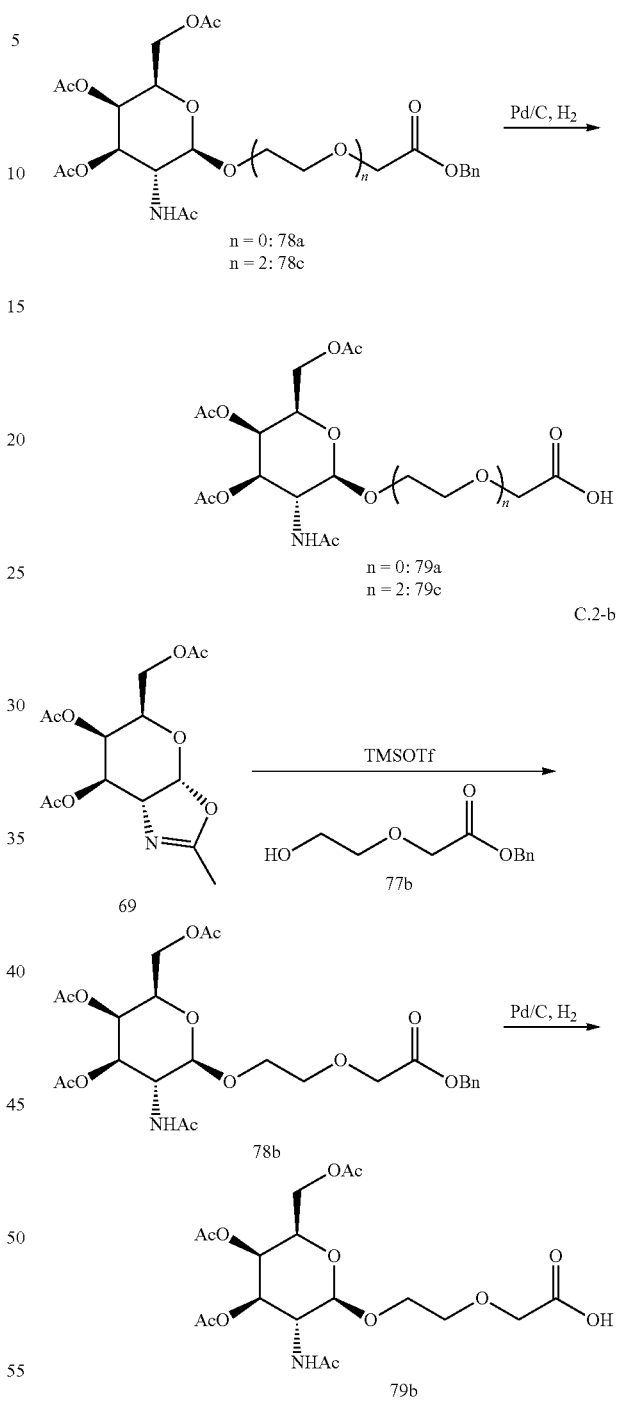

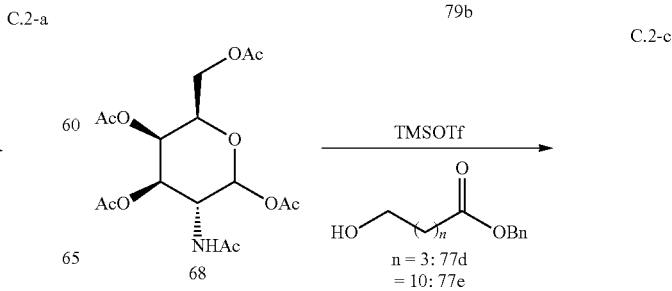

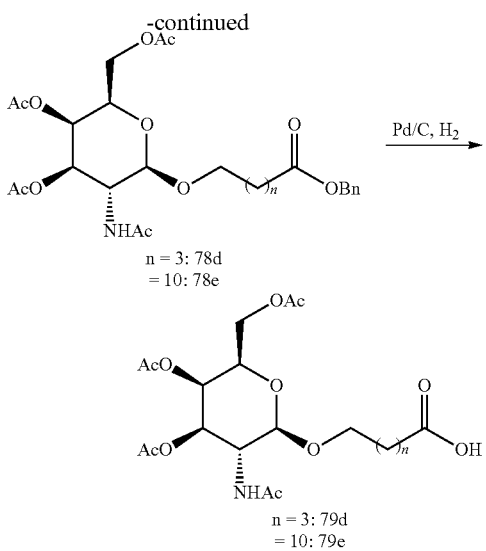

78a: benzyl 2-[(2R,3R,4R,5R,6R)-3-acetamido-4,5-diacetoxy-6-(acetoxymethyl)tetrahydro-pyran-2-yl]oxyacetate To a mixture of starting compound 68 (16 g, 41.1 mmol) and benzyl 2-hydroxy-acetate 77a (13.6 g, 82.2 mmol) in 160 ml DCE was added Sc(OTf)$_3$ (1.41 g, 2.88 mmol). The solution was stirred at 90° C. for 16 h to achieve complete conversion. The reaction mixture was poured into 200 ml sat. NaHCO$_3$ and extracted with 3×100 ml DCM. The combined organic phases were dried over anhydrous Na$_2$SO$_4$, filtered and the filtrate was concentrated in vacuo. The residue was purified by column chromatography (PE:EtOAc 1:1) and then reverse flash chromatography (neutral), yielding 12.0 g (60%) of the title compound 78a as yellow oil.

MS [M+H]$^+$ (m/z)=496.0

79a: 2-[(2R,3R,4R,5R,6R)-3-acetamido-4,5-diacetoxy-6-(acetoxymethyl)tetrahydropyran-2-yl]oxyacetic Acid To the mixture of compound 78a (12 g, 24.2 mmol) in 150 ml EtOAc was added Pd/C (3 g, 10% on carbon and 50% of water content) at 25° C. The mixture was stirred at room temperature for 12 h under H$_2$-atmosphere (15 psi) until complete conversion was achieved. The mixture was filtered and the filtrate was concentrated in vacuo to give 79a (9.2 g, 93%) as colourless foam.

1H-NMR (DMSO-d6, 400 MHz) δ[ppm]: 7.93 (br d, J=8.7 Hz, 1H), 5.22 (d, J=3.4 Hz, 1H), 5.01 (dd, J=3.3, 11.1 Hz, 1H), 4.63 (d, J=8.5 Hz, 1H), 4.10 (br d, J=4.9 Hz, 2H), 4.05-3.99 (m, 3H), 3.94-3.85 (m, 2H), 2.14-2.10 (m, 3H), 2.02-1.99 (m, 3H), 1.89 (s, 3H), 1.79 (s, 3H).

78c: benzyl 2-[2-[2-[(2R,3R,4R,5R,6R)-3-acetamido-4,5-diacetoxy-6-(acetoxymethyl)tetra-hydro-pyran-2-yl]oxyethoxy]ethoxy]acetate Following the protocol described for compound 78a, 14.6 g (37.6 mmol) of 68 and 19.1 g (75.2 mmol) benzyl 2-[2-(2-hydroxyethoxy)ethoxy]acetate 77c gave 12.0 g (54.8%) of the title compound 78c as light yellow oil.

1H-NMR (DMSO-d6, 400 MHz) δ[ppm]: 7.75 (d, J=9.17 Hz, 1H), 7.50-7.27 (m, 5H), 5.21 (d, J=3.30 Hz, 1H,) 5.15 (s, 2H), 4.97 (dd, J=11.19, 3.36 Hz, 1H), 4.57 (d, J=8.44 Hz, 1H), 4.19 (s, 2H), 4.04-4.00 (m, 3H), 3.88 (dt, J=10.97, 8.94 Hz, 1H), 3.81-3.71 (m, 1H), 3.63-3.48 (m, 7H), 2.10 (s, 3H), 1.99 (s, 3H), 1.89 (s, 3H), 1.77 (s, 3H).

79c: 2-[2-[2-[(2R,3R,4R,5R,6R)-3-acetamido-4,5-diacetoxy-6-(acetoxymethyl)tetrahydro-pyran-2-yl]oxyethoxy]ethoxy]acetic Acid To a solution of benzylester 78c (12.0 g, 20.6 mmol) in 400 ml EtOAc was added Pd/C (2 g, 10% on carbon and 50% of water content). The mixture was stirred at room temperature under H$_2$-atmosphere (15 psi) for 12 h. The reaction mixture was filtered and the filtrate was concentrated in vacuum to give 8.5 g (83.7%) 79c as a colorless oil.

1H-NMR (DMSO-d6, 400 MHz) [ppm]: 7.78 (d, J=9.17 Hz, 1H), 5.22 (d, J=3.42 Hz, 1H), 4.98 (dd, J=11.13, 3.42 Hz, 1H), 4.59 (d, J=8.44 Hz, 1H), 4.10-3.98 (m, 5H), 3.89 (dt, J=11.00, 8.93 Hz, 1H), 3.78 (dt, J=11.16, 4.63 Hz, 1H), 3.65-3.46 (m, 7H), 2.11 (s, 3H), 2.01 (s, 3H), 1.90 (s, 3H), 1.78 (s, 3H).

78b: benzyl 2-[2-[(2R,3R,4R,5R,6R)-3-acetamido-4,5-diacetoxy-6-(acetoxymethyl)tetrahydro-pyran-2-yl]oxyethoxy]acetate To the mixture of compound 77b (7.0 g, 21.2 mmol) and oxazoline 69 (6.7 g, 31.9 mmol) in 100 ml DCE was added 4 Å sieves (10 g) at 25° C. The mixture was stirred for 1.5 h, followed by the addition of TMSOTf (2.3 g, 10.6 mmol). After stirring for 12 h at room temperature, the reaction solution was poured into 200 ml sat. NaHCO$_3$-solution and extracted with 3×100 ml DCM. The combined organic phases were dried over anhydrous Na$_2$SO$_4$, filtered and concentrated in vacuo. The residue was purified by reverse flash chromatography to give compound 78b (4.0 g, 36%) as yellow oil.

1H-NMR (DMSO-d6, 400 MHz) δ[ppm]: 7.68 (d, J=9.2 Hz, 1H), 7.29-7.16 (m, 5H), 5.12-5.05 (m, 1H), 5.02 (s, 2H), 4.89-4.79 (m, 1H), 4.43 (d, J=8.4 Hz, 1H), 4.06 (d, J=1.6 Hz, 2H), 3.92-3.85 (m, 3H), 3.81-3.64 (m, 2H), 3.55-3.41 (m, 3H), 1.97 (s, 3H), 1.87-1.84 (m, 3H), 1.78-1.74 (m, 3H), 1.65-1.57 (m, 3H).

79b: 2-[2-[(2R,3R,4R,5R,6R)-3-acetamido-4,5-diacetoxy-6-(acetoxymethyl)tetrahydropyran-2-yl]oxyethoxy]acetic Acid To the mixture of compound 78b (6.0 g, 11.1 mmol) in 100 ml EtOAc was added Pd/C (0.6 g, 10% on carbon and 50% of water content) at room temperature. The mixture was stirred at for 12 h under H$_2$ (15 psi) to achieve complete conversion. The reaction mixture was filtered and the filtrate was concentrated in vacuo to give 5.0 g (96%) of the title compound 79b as white foam.

1H-NMR (DMSO-d6, 400 MHz) δ[ppm]: 7.83 (d, J=9.3 Hz, 1H), 5.22 (d, J=3.4 Hz, 1H), 4.97 (dd, J=3.4, 11.2 Hz, 1H), 4.57 (d, J=8.6 Hz, 1H), 4.06-4.02 (m, 3H), 4.01 (s, 2H), 3.89 (td, J=8.9, 11.1 Hz, 1H), 3.83-3.77 (m, 1H), 3.66-3.52 (m, 3H), 2.13-2.07 (m, 3H), 2.02-1.98 (m, 3H), 1.89 (s, 3H), 1.78 (s, 3H).

78d: benzyl 5-[(2R,3R,4R,5R,6R)-3-acetamido-4,5-diacetoxy-6-(acetoxymethyl)tetrahydro-pyran-2-yl]oxypentanoate To a solution of (D)-2-desoxy-2-amino-galactosyl-pentaacetate 68 (387 g, 0.968 mol) in 4 l DCE, was added TMSOTf (322 g, 1.452 mol) dropwise at 15° C. The mixture was heated at 50° C. for 1.5 h and then stirred at 30° C. overnight. The reaction mixture was poured into 4 l sat. NaHCO$_3$-solution and extracted twice with 1 l DCM. The combined organic layers were dried over anhydrous Na$_2$SO$_4$, filtered and concentrated in vacuo. The residue was dissolved in 4 l DCE, benzyl-5-hydroxypentanoate 77d (302 g, 1.452 mol) and 300 g powdered molecular sieves (4 Å) were added at 15° C. After stirring for 1 h, TMSOTf (107.4 g, 0.484 mol) was added dropwise at 15° C. The suspension was stirred at 15° C. overnight, to achieve complete conversion. The reaction mixture was poured into 4 l sat. NaHCO$_3$-solution, filtered and extracted twice with 1 l DCM. The combined organic layers were dried over Na$_2$SO$_4$, filtered and concentrated in vacuo. The residue was purified by column chromatography (PE/EtOAc 3:1) to give the desired product (240 g, 46%) as colorless oil.

1H-NMR (CDCl$_3$, 400 MHz) δ[ppm]: 7.47-7.30 (m, 5H), 5.74 (br d, J=8.5 Hz, 1H), 5.36 (d, J=2.8 Hz, 1H), 5.30-5.23 (m, 1H), 5.17-5.07 (m, 2H), 4.65 (d, J=8.4 Hz, 1H), 4.20-4.08 (m, 3H), 4.02-3.94 (m, 1H), 3.94-3.85 (m, 2H), 3.50 (td, J=6.1, 9.9 Hz, 1H), 2.49-2.32 (m, 2H), 2.15 (s, 3H), 2.05 (s, 3H), 2.01 (s, 3H), 1.92 (s, 3H), 1.78-1.56 (m, 4H).

79d: 5-[(2R,3R,4R,5R,6R)-3-acetamido-4,5-diacetoxy-6-(acetoxymethyl)tetrahydropyran-2-yl]oxypentanoic Acid To a solution of benzylester 78d (240 g, 0.447 mol) in 2.5 l MeOH was added Pd/C (24 g, 10% on carbon, 50% water content). The mixture was stirred at 15° C. under H$_2$ (15 psi) overnight. The reaction mixture was filtered and the filtrate was concentrated i. vac., yielding 196 g (97%) of 79d as white solid.

1H-NMR (CDC$_3$, 400 MHz) δ[ppm]: 6.19 (d, J=8.8 Hz, 1H), 5.37 (d, J=3.1 Hz, 1H), 5.30 (dd, J=3.4, 11.2 Hz, 1H), 4.69 (d, J=8.3 Hz, 1H), 4.16 (m, 1H), 3.98-3.92 (m, 2H), 3.57-3.48 (m, 2H), 2.40-2.30 (m, 2H), 2.18-2.15 (s, 3H), 2.06 (s, 3H), 2.02 (s, 3H), 1.99-1.94 (s, 3H), 1.76-1.59 (m, 4H).

77e: benzyl 12-hydroxydodecanoate 5.0 g (22.4 mmol) 12-hydroxydodecanoic acid were dissolved in 100 ml DMF. After adding 4.5 g (3.15 ml, 25.8 mmol) benzylbromide and 3.37 g (33.6 mmol) potassium bicarbonate, the mixture was stirred for 20 h. The solvent was removed i. vac. and the residue was dissolved in diethyl ether. After washing with H$_2$O, the aqueous phase was separated and extracted with diethyl ether. The combined organic layers were dried with MgSO$_4$ and purified by silicagel chromatography (0 to 30% EtOAc in n-heptane), yielding 5.70 g (82.9%) of the desired benzylester.

LCMS-Method A:
UV-wavelength [nm]=220: R$_t$[min]=2.04
Ionization method: ES$^+$: [M+H]$^+$=307.2

78e: benzyl 12-[(2R,3R,4R,5R,6R)-3-acetamido-4,5-diacetoxy-6-(acetoxymethyl)tetrahydro-pyran-2-yl]oxydodecanoate Starting with 2.20 g (5.7 mmol) 68, 2.0 g (55.9%) of the title compound 78e were synthesized, following the protocol described for 78d. Complete glycosylation with 77e was achieved after stirring for 4 h at 70° C. and additional 16 h at room temperature. Final purification was done on silicagel, eluting with 0 to 100% EtOAc/DCM (1:1) in n-heptane.

LCMS-Method A:
UV-wavelength [nm]=220: R$_t$[min]=1.99
Ionization method: ES$^+$: [M+H]$^+$=636.5

79e: 12-[(2R,3R,4R,5R,6R)-3-acetamido-4,5-diacetoxy-6-(acetoxymethyl)tetrahydropyran-2-yl]oxydodecanoic Acid 2.0 g (3.2 mmol) of benzylester 78e were dissolved in 20 ml THF. After adding 167 mg (157 μmol) of Pd (10% on carbon), the reaction mixture was purged with H$_2$ and hydrogenated at an H$_2$-pressure of 4 bar. After 4 h, the Pd-catalyst was filtered off and the filtrate was evaporated i. vac. The crude product was purified by silicagel chromatography (0 to 20% MeOH in DCM, 10% AcOH), which gave 1.67 g (97.3%) of carboxylic acid 79e.

LCMS-Method A:
ELSD: R$_t$[min]=1.68
Ionization method: ES$^+$: [M+H]$^+$=546.4

1H-NMR (DMSO-d6, 400 MHz) δ[ppm]: 11.79 (br s, 1H), 7.67 (d, J=9.17 Hz, 1H), 5.08 (d, J=3.42 Hz, 1H), 4.83 (dd, J=11.25, 3.42 Hz, 1H), 4.35 (d, J=8.44 Hz, 1H), 3.84-3.95 (m, 3H), 3.73 (m, 1H), 3.56 (m, 1H), 3.44-3.51 (m, 1H), 3.28 (m, 1H), 1.97 (s, 3H), 1.87 (s, 3H), 1.76 (s, 3H), 1.63 (s, 3H), 1.28-1.39 (m, 4H), 1.11 (s, 14H).

Example C.3

Synthetic Scheme 22

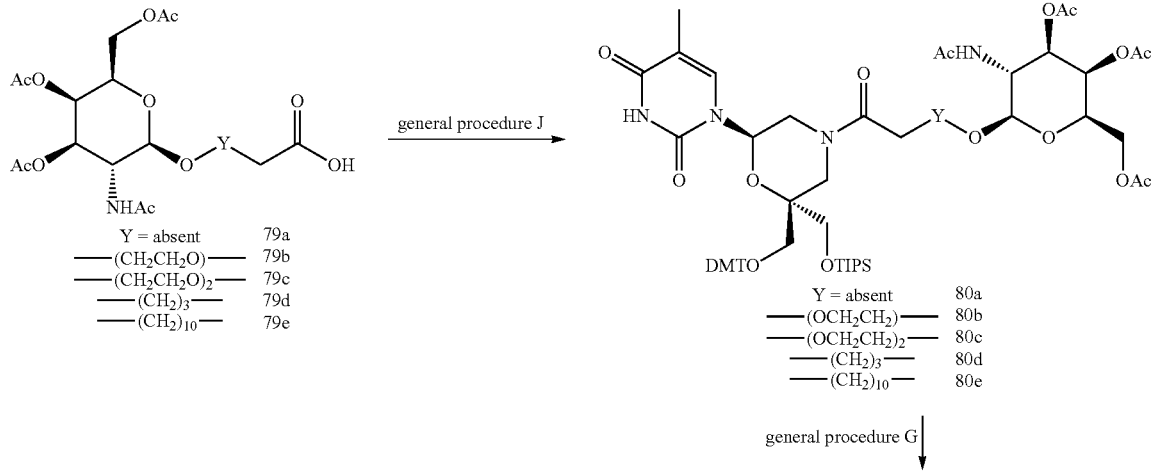

general procedure J

| Y = absent | 79a |
| (CH$_2$CH$_2$O) | 79b |
| (CH$_2$CH$_2$O)$_2$ | 79c |
| (CH$_2$)$_3$ | 79d |
| (CH$_2$)$_{10}$ | 79e |

| Y = absent | 80a |
| (OCH$_2$CH$_2$) | 80b |
| (OCH$_2$CH$_2$)$_2$ | 80c |
| (CH$_2$)$_3$ | 80d |
| (CH$_2$)$_{10}$ | 80e | general procedure G

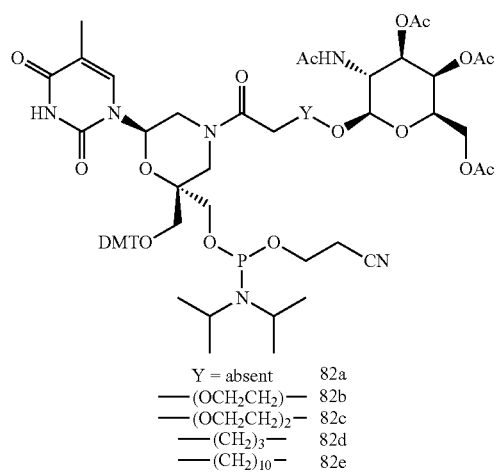

Y = absent 82a
—(OCH₂CH₂)— 82b
—(OCH₂CH₂)₂— 82c
—(CH₂)₃— 82d
—(CH₂)₁₀— 82e

-continued general procedure H

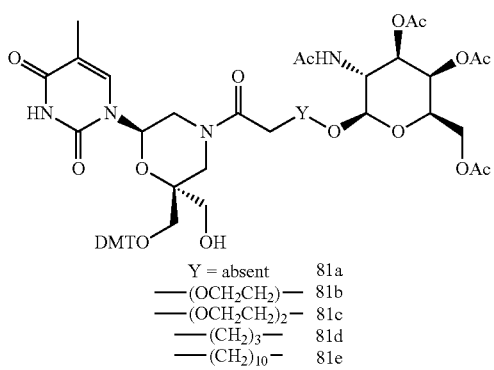

Y = absent 81a
—(OCH₂CH₂)— 81b
—(OCH₂CH₂)₂— 81c
—(CH₂)₃— 81d
—(CH₂)₁₀— 81e

General Procedure J for the Syntheses of Compounds 80a to 80e

The carboxylic acid (79a-e, 1.0 to 1.2 eq.) and of the morpholine compound 24a (1.0 eq.) were dissolved in DCM (20 ml./1.0 mmol). After adding 1.5 eq. HBTU and 3.0 eq. DIPEA, the reaction was stirred for 18 h at room temperature, to achieve complete conversion. The reaction solution was washed with sat. NaCHO₃- and sat. NaCl-solution. The organic layer was dried with MgSO₄ and the solvent was evaporated. Purification of the crude product on silica gave the desired amides as colourless solids.

80a: [(2R,3R,4R,5R,6R)-5-acetamido-3,4-diacetoxy-6-[2-[(2S,6R)-2-[[bis(4-methoxyphenyl)-phenyl-methoxy]methyl]-6-(5-methyl-2,4-dioxo-pyrimidin-1-yl)-2-(triisopropylsilyloxy-methyl)morpholin-4-yl]-2-oxo-ethoxy]tetrahydropyran-2-yl]methyl Acetate Following general procedure J, 400 mg (986 μmol, 1.2 eq.) of the carboxylic acid 79a gave 530 mg (57.7%) of the title compound 80a after purification on silica (0 to 10% DCM/EtOAc/MeOH 10:10:1 in DCM/EtOAc 1:1).
LCMS-Method C:
UV-wavelength [nm]=220: $R_t$[min]=3.15
Ionization method: ES⁻: [M−H]⁻=1115.9

80b: [(2R,3R,4R,5R,6R)-5-acetamido-3,4-diacetoxy-6-[2-[2-[(2S,6R)-2-[[bis(4-methoxy-phenyl)-phenyl-methoxy]methyl]-6-(5-methyl-2,4-dioxo-pyrimidin-1-yl)-2-(triisopropyl-silyloxymethyl)morpholin-4-yl]-2-oxo-ethoxy]ethoxy]tetrahydropyran-2-yl]methyl Acetate Following general procedure J, 406 mg (904 μmol, 1.1 eq.) of the carboxylic acid 79b gave 590 mg (61.8%) of the title compound 80b after purification on silica (0 to 10% DCM/EtOAc/MeOH 10:10:1 in DCM/EtOAc 1:1).
LCMS-Method C:
UV-wavelength [nm]=220: $R_t$[min]=3.16
Ionization method: ES⁻: [M−H]⁻=1160.0

80c: [(2R,3R,4R,5R,6R)-5-acetamido-3,4-diacetoxy-6-[2-[2-[2-[(2S,6R)-2-[[bis(4-methoxy-phenyl)-phenyl-methoxy]methyl]-6-(5-methyl-2,4-dioxo-pyrimidin-1-yl)-2-(triisopropylsilyl-oxymethyl)morpholin-4-yl]-2-oxo-ethoxy]ethoxy]ethoxy]tetrahydropyran-2-yl]methyl Acetate Following general procedure J, 406 mg (822 μmol, 1.2 eq.) of the carboxylic acid 79c gave 413 mg (50.0%) of the title compound 80c after purification on silica (0 to 10% DCM/EtOAc/MeOH 10:10:1 in DCM/EtOAc 1:1).
LCMS-Method C:
UV-wavelength [nm]=220: $R_t$[min]=3.17
Ionization method: ES⁻: [M−H]⁻=1204.0

80d: [(2R,3R,4R,5R,6R)-5-acetamido-3,4-diacetoxy-6-[5-[(2S,6R)-2-[[bis(4-methoxy-phenyl)-phenyl-methoxy]methyl]-6-(5-methyl-2,4-dioxo-pyrimidin-1-yl)-2-(triisopropylsilyl-oxymethyl)morpholin-4-yl]-5-oxo-pentoxy]tetrahydropyran-2-yl]methyl Acetate Following general procedure J, 750 mg (1.68 mmol, 1.0 eq.) of the carboxylic acid 79d gave 1.76 g (90.6%) of the title compound 80d after purification on silica (0 to 5% MeOH in DCM).
LCMS-Method A:
UV-wavelength [nm]=220: $R_t$[min]=2.16
Ionization method: ES⁻: [M−H]⁻=1157.5

80e: [(2R,3R,4R,5R,6R)-5-acetamido-3,4-diacetoxy-6-[12-[(2S,6R)-2-[[bis(4-methoxy-phenyl)-phenyl-methoxy]methyl]-6-(5-methyl-2,4-dioxo-pyrimidin-1-yl)-2-(triisopropylsilyl-oxymethyl)morpholin-4-yl]-12-oxo-dodecoxy]tetrahydropyran-2-yl]methyl Acetate Following general procedure J, 897 mg (1.64 mmol, 1.2 eq.) of the carboxylic acid 79e gave 1.46 g (84.5%) of the title compound 80e after purification on silica (0 to 5% MeOH in DCM).
LCMS-Method A:
UV-wavelength [nm]=220: $R_t$[min]=2.25
Ionization method: ES⁻: [M−H]⁻=1255.6

81a: [(2R,3R,4R,5R,6R)-5-acetamido-3,4-diacetoxy-6-[2-[(2R,6R)-2-[[bis(4-methoxyphenyl)-phenyl-methoxy]methyl]-2-(hydroxymethyl)-6-(5-methyl-2,4-dioxo-pyrimidin-1-yl)morpholin-4-yl]-2-oxo-ethoxy]tetrahydropyran-2-yl]methyl Acetate Following general procedure G (see scheme 20), 530 mg (474 µmol) of the TIPS-ether 80a were deprotected, yielding 380 mg (83.4%) of the title compound 81a after silicagel chromatography (0 to 10% DCM/EtOAc/MeOH 5:5:1 in DCM/EtOAc 1:1).
LCMS-Method C:
UV-wavelength [nm]=220: $R_t$[min]=2.29
Ionization method: ES⁻: [M−H]⁻=959.9
1H-NMR (DMSO-d6, 600 MHz) δ[ppm]: 11.44 (br s, 1H), 7.83-7.88 (m, 0.4H), 7.78 (br d, J=9.17 Hz, 0.6H), 7.64 (s, 1H), 7.39-7.44 (m, 2H), 7.21-7.32 (m, 7H), 6.85-6.90 (m, 4H), 5.88-5.93 (m, 0.4H), 5.83 (m, 0.6H), 5.19-5.23 (m, 1H), 4.90-5.02 (m, 1.6H), 4.53-4.62 (m, 1.4H), 21 4.42 (br d, J=14.12 Hz, 0.6H), 4.32-4.39 (m, 1H), 4.20-4.31 (m, 1.4H), 3.81-4.07 (m, 6H), 3.72-3.79 (m, 7H), 3.47-3.65 (m, 2H), 2.99-3.11 (m, 2H), 2.88-2.97 (m, 1H), 2.10, 2.04 (2×s, 3H), 1.99, 1.97 (2×s, 3H), 1.88 (s, 3H), 1.73, 1.72 (m, 6H).

81b: [(2R,3R,4R,5R,6R)-5-acetamido-3,4-diacetoxy-6-[2-[2-[(2R,6R)-2-[[bis(4-methoxy-phenyl)-phenyl-methoxy]methyl]-2-(hydroxymethyl)-6-(5-methyl-2,4-dioxo-pyrimidin-1-yl)morpholin-4-yl]-2-oxo-ethoxy]ethoxy]tetrahydropyran-2-yl]methyl Acetate Following general procedure G (see scheme 20), 670 mg (577 µmol) of the TIPS-ether 80b were deprotected, yielding 504 mg (86.9%) of the title compound 81b after silicagel chromatography (0 to 10% DCM/EtOAc/MeOH 5:5:1 in DCM/EtOAc 1:1).
LCMS-Method C:
UV-wavelength [nm]=220: $R_t$[min]=2.30
Ionization method: ES⁻: [M−H]⁻=1003.9
1H-NMR (DMSO-d6, 600 MHz) δ[ppm]: 11.42 (br s, 1H), 7.80 (d, J=9.35 Hz, 1H), 7.64, 7.60 (2×s, 1H), 7.39-7.44 (m, 2H), 7.19-7.35 (m, 7H), 6.85-6.90 (m, 4H), 5.87-5.93 (m, 0.4H), 5.82 (br d, J=8.07 Hz, 0.6H), 5.21 (br s, 1H), 4.94-5.00 (m, 1.6H), 4.64-4.70 (m, 0.4H), 4.54-4.58 (m, 1H), 4.33-4.39 (m, 0.6H), 4.11-4.26 (m, 2.4H), 4.00-4.05 (m, 3.4H), 3.78-3.94 (m, 2.6H), 3.74 (m, 6H), 3.42-3.70 (m, 6H), 3.07-3.11 (m, 1H), 2.89-3.05 (m, 2H), 2.04-2.12 (m, 3H), 1.97-2.01 (m, 3H), 1.89 (s, 3H), 1.71-1.78 (m, 6H).

81c: [(2R,3R,4R,5R,6R)-5-acetamido-3,4-diacetoxy-6-[2-[2-[2-[(2R,6R)-2-[[bis(4-methoxy-phenyl)-phenyl-methoxy]methyl]-2-(hydroxymethyl)-6-(5-methyl-2,4-dioxo-pyrimidin-1-yl)-morpholin-4-yl]-2-oxo-ethoxy]ethoxy]ethoxy]tetrahydropyran-2-yl] methyl Acetate Following general procedure G (see scheme 20), 410 mg (340 µmol) of the TIPS-ether 80c were deprotected, yielding 285 mg (79.9%) of the title compound 81c after silicagel chromatography (0 to 10% DCM/EtOAc/MeOH 5:5:1 in DCM/EtOAc 1:1).
LCMS-Method C:
UV-wavelength [nm]=220: $R_t$[min]=2.31
Ionization method: ES⁻: [M−H]⁻=1047.9
1H-NMR (DMSO-d6, 600 MHz) δ[ppm]: 11.43 (br s, 1H), 7.76 (m, 1H), 7.57-7.65 (m, 1H), 7.42 (m, 2H), 7.21-7.32 (m, 7H), 6.85-6.90 (m, 4H), 5.88-5.94 (m, 0.4H), 5.82 (m, 0.6H), 5.21 (m, 1H), 4.94-4.99 (m, 1.6H), 4.63-4.69 (m, 0.4H), 4.57 (m, 1H), 4.36 (m, 0.6H), 4.16-4.26 (m, 2H), 4.09-4.15 (m, 0.4H), 3.99-4.05 (m, 3H), 3.85-3.92 (m, 2H), 3.69-3.79 (m, 8H), 3.45-3.62 (m, 9H), 3.06-3.10 (m, 1H), 2.88-3.06 (m, 2H), 2.10 (s, 3H), 1.99 (s, 3H), 1.88 (s, 3H), 1.76 (br s, 3H), 1.73 (s, 3H).

81d: [(2R,3R,4R,5R,6R)-5-acetamido-3,4-diacetoxy-6-[5-[(2R,6R)-2-[[bis(4-methoxyphenyl)-phenyl-methoxy]methyl]-2-(hydroxymethyl)-6-(5-methyl-2,4-dioxo-pyrimidin-1-yl)morpholin-4-yl]-5-oxo-pentoxy]tetrahydropyran-2-yl]methyl Acetate Following general procedure G (see scheme 20), 1.75 g (1.51 mmol) of the TIPS-ether 80d were deprotected, yielding 1.17 g (77.3%) of the title compound 81d after silicagel chromatography (0 to 10% MeOH in DCM).
LCMS-Method A:
UV-wavelength [nm]=220: $R_t$[min]=1.80
Ionization method: ES⁻: [M−H]⁻=1001.4
1H-NMR (DMSO-d6, 400 MHz) δ[ppm]: 11.43 (s, 1H), 7.78 (m, 1H), 7.64, 7.58 (2×bs, 1H), 7.41 (m, 2H), 7.20-7.33 (m, 7H), 6.88 (m, 4H), 5.85 (m, 0.4H), 5.77 (m, 0.6H), 5.21 (m, 1H), 4.92-5.01 (m, 1.6H), 4.61-4.67 (m, 0.4H), 4.45-4.52 (m, 1H), 4.37-4.45 (m, 0.6H), 4.21-4.29 (m, 0.4H), 3.67-4.07 (m, 12H), 3.32-3.64 (m, 4H), 2.81-3.14 (m, 3H), 2.27-2.38 (m, 2H), 2.06-2.12 (m, 3H), 1.96-2.01 (m, 3H), 1.89 (m, 3H), 1.76 (m, 3H), 1.72 (m, 3H), 1.49 (br s, 4H).

81e: [(2R,3R,4R,5R,6R)-5-acetamido-3,4-diacetoxy-6-[12-[(2R,6R)-2-[[bis(4-methoxy-phenyl)-phenyl-methoxy]methyl]-2-(hydroxymethyl)-6-(5-methyl-2,4-dioxo-pyrimidin-1-yl)-morpholin-4-yl]-12-oxo-dodecoxy]tetrahydropyran-2-yl]methyl Acetate Following general procedure G (see scheme 20), 1.45 g (1.15 mmol) of the TIPS-ether 80e were deprotected, yielding 1.10 g (86.6%) of the title compound 81e after silicagel chromatography (0 to 5% MeOH in DCM).
LCMS-Method A:
UV-wavelength [nm]=220: $R_t$[min]=1.96
Ionization method: ES⁻: [M−H]⁻=1099.6
1H-NMR (DMSO-d6, 400 MHz) δ[ppm]: 11.42 (br s, 1H), 7.79 (d, J=9.29 Hz, 1H), 7.63, 7.57 (2×s, 1H), 7.41 (m, 2H), 7.20-7.34 (m, 7H), 6.87 (m, 4H), 5.84 (m, 0.4H), 5.77 (m, 0.6H), 5.21 (m, 1H), 4.91-5.01 (m, 1.6H), 4.61-4.68 (m, 0.4H), 4.48 (m, 1H), 4.39 (m, 0.6H), 4.24 (m, 0.4H), 3.98-4.06 (m, 3H), 3.66-3.90 (m, 3H), 3.74 (s, 6H), 3.56 (m, 1H), 3.36-3.50 (m, 2H), 2.77-3.16 (m, 2H), 2.22-2.39 (m, 2H), 2.10 (m, 3H), 1.99 (m, 3H), 1.89 (m, 3H), 1.76 (m, 3H), 1.72 (m, 3H), 1.39-1.56 (m, 4H), 1.18-1.32 (br s, 16H).

82a: [(2R,3R,4R,5R,6R)-5-acetamido-3,4-diacetoxy-6-[2-[(2S,6R)-2-[[bis(4-methoxyphenyl)-phenyl-methoxy]methyl]-2-[[2-cyanoethoxy-(diisopropylamino)phosphanyl]oxymethyl]-6-(5-methyl-2,4-dioxo-pyrimidin-1-yl)morpholin-4-yl]-2-oxo-ethoxy]tetrahydropyran-2-yl]methyl Acetate Following general procedure H (see Scheme 20), 380 mg (395 µmol) of the starting alcohol 81a gave 434 mg (94.4%) of the title compound 82a.
1H-NMR (DMSO-d6, 400 MHz) δ[ppm]: 11.41 (b s, 1H), 7.72-7.90 (m, 1H), 7.60-7.71 (m, 1H), 7.35-7.48 (m, 2H), 7.17-7.33 (m, 7H), 6.82-6.95 (m, 4H), 5.78-6.05 (m, 1H), 5.16-5.26 (m, 1H), 4.91-5.03 (m, 1H), 4.55-4.64 (m, 1H), 4.10-4.54 (m, 3H), 3.52-4.08 (m, 16H), 3.36-3.50 (m, 2H), 2.85-3.18 (m, 3H), 2.57-2.72 (m, 2H), 2.07 (m, 3H), 1.98 (m, 3H), 1.88 (m, 3H), 1.68-1.78 (m, 6H), 0.89-1.22 (m, 12H).

31P-NMR (DMSO-d6, 162 MHz) δ[ppm]: 148.2, 147.1, 146.8, 146.3.

82b: [(2R,3R,4R,5R,6R)-5-acetamido-3,4-diacetoxy-6-[2-[2-[(2S,6R)-2-[[bis(4-methoxy-phenyl)-phenyl-methoxy]methyl]-2-[[2-cyanoethoxy-(diisopropylamino)phosphanyl]oxymethyl]-6-(5-methyl-2,4-dioxo-pyrimidin-1-yl)morpholin-4-yl]-2-oxo-ethoxy]ethoxy]tetra-hydropyran-2-yl]methyl Acetate Following general procedure H (see Scheme 20), 500 mg (497 μmol) of the starting alcohol 81b gave 575 mg (95.9%) of the title compound 82b.

1H-NMR (DMSO-d6, 400 MHz) δ[ppm]: 11.40 (br s, 1H), 7.79 (br d, J=9.22 Hz, 1H), 7.63 (m, 1H), 7.40 (br s, 2H), 7.20-7.34 (m, 7H), 6.83-6.91 (m, 4H), 5.80-6.03 (m, 1H), 5.22 (m, 1H), 4.96 (m, 1H), 4.56 (m, 1H), 4.08-4.43 (m, 4H), 4.03 (s, 3H), 3.52-3.91 (m, 16H), 3.38-3.50 (m, 2H), 2.86-3.18 (m, 3H), 2.52-2.75 (m, 2H), 2.07 (m, 3H), 1.99 (m, 3H), 1.90 (m, 3H), 1.68-1.81 (m, 6H), 0.89-1.22 (m, 12H).

31P-NMR (DMSO-d6, 162 MHz) δ[ppm]: 148.2, 147.2, 147.13, 147.06.

82c: [(2R,3R,4R,5R,6R)-5-acetamido-3,4-diacetoxy-6-[2-[2-[2-[(2S,6R)-2-[[bis(4-methoxy-phenyl)-phenyl-methoxy]methyl]-2-[[2-cyanoethoxy-(diisopropylamino)phosphanyl]oxymethyl]-6-(5-methyl-2,4-dioxo-pyrimidin-1-yl)morpholin-4-yl]-2-oxo-ethoxy]ethoxy]-ethoxy]tetrahydropyran-2-yl]methyl Acetate Following general procedure H (see Scheme 20), 285 mg (272 μmol) of the starting alcohol 81c gave 317 mg (93.5%) of the title compound 82c.

1H-NMR (DMSO-d6, 400 MHz) δ[ppm]: 11.40 (br s, 1H), 7.77 (m, 1H), 7.60-7.71 (m, 1H), 7.40 (m, 2H), 7.21-7.33 (m, 7H), 6.87 (m, 4H), 5.82-5.99 (m, 1H), 5.21 (m, 1H), 4.97 (m, 1H), 4.57 (m, 1H), 4.09-4.39 (m, 3H), 3.97-4.08 (m, 3H), 3.34-3.95 (m, 20H), 2.90-3.18 (m, 3H), 2.56-2.73 (m, 2H), 2.10 (m, 3H), 2.07 (m, 3H), 1.99 (m, 3H), 1.89 (m, 3H), 1.71-1.80 (m, 6H), 0.89-1.22 (m, 12H).

31P-NMR (DMSO-d6, 162 MHz) δ[ppm]: 148.1, 147.3, 147.2, 147.0.

82d: [(2R,3R,4R,5R,6R)-5-acetamido-3,4-diacetoxy-6-[5-[(2S,6R)-2-[[bis(4-methoxyphenyl)-phenyl-methoxy]methyl]-2-[[2-cyanoethoxy-(diisopropylamino)phosphanyl]oxymethyl]-6-(5-methyl-2,4-dioxo-pyrimidin-1-yl)morpholin-4-yl]-5-oxo-pentoxy]tetrahydropyran-2-yl]methyl Acetate Following general procedure H (see Scheme 20), 1.0 g (997 μmol) of the starting alcohol 81d gave 1.19 g (99.2%) of the title compound 82d.

1H-NMR (DMSO-d6, 400 MHz) δ[ppm]: 11.41 (br s, 1H), 7.74-7.81 (m, 1H), 7.58-7.70 (m, 1H), 7.40 (m, 2H), 7.20-7.33 (m, 7H), 6.87 (m, 4H), 5.79-5.93 (m, 1H), 5.21 (br s, 1H), 4.96 (m, 1H), 4.31-4.52 (m, 2H), 3.96-4.08 (m, 4H), 3.53-3.94 (m, 6H), 3.73 (s, 6H), 3.34-3.50 (m, 4H), 3.02-3.19 (m, 1H), 2.83-3.01 (m, 1H), 2.56-2.74 (m, 2H), 2.52-2.54 (m, 1H), 2.26-2.43 (m, 2H), 2.10, 2.08 (2×s, 3H), 1.99 (s, 3H), 1.89 (m, 3H), 1.71-1.79 (m, 6H), 1.41-1.69 (m, 4H), 0.89-1.12 (m, 12H).

31P-NMR (DMSO-d6, 162 MHz) δ[ppm]: 147.9, 147.1, 147.0, 146.7.

82e: [(2R,3R,4R,5R,6R)-5-acetamido-3,4-diacetoxy-6-[12-[(2S,6R)-2-[[bis(4-methoxy-phenyl)-phenyl-methoxy]methyl]-2-[[2-cyanoethoxy-(diisopropylamino)phosphanyl]oxymethyl]-6-(5-methyl-2,4-dioxo-pyrimidin-1-yl)morpholin-4-yl]-12-oxo-dodecoxy]tetra-hydropyran-2-yl]methyl Acetate Following general procedure H (see Scheme 20), 557 mg (506 μmol) of the starting alcohol 81e gave 396 mg (60.2%) of the title compound 82e.

1H-NMR (DMSO-d6, 400 MHz) δ[ppm]: 11.35-11.48 (m, 1H), 7.76-7.84 (m, 1H), 7.56-7.70 (m, 1H), 7.33-7.45 (m, 2H), 7.21-7.33 (m, 7H), 6.87 (m, 4H), 5.77-5.96 (m, 1H), 5.21 (m, 1H), 4.93-5.01 (m, 1H), 4.31-4.51 (m, 2H), 3.94-4.11 (m, 4H), 3.53-3.92 (m, 4H), 3.73 (m, 6H), 3.33-3.49 (m, 3H), 3.03-3.21 (m, 2H), 2.83-2.99 (m, 1H), 2.62-2.72 (m, 1H), 2.21-2.48 (m, 2H), 2.10 (m, 3H), 1.99 (m, 3H), 1.89 (m, 3H), 1.71-1.82 (m, 6H), 1.45 (br s, 4H), 1.14-1.30 (m, 18H), 0.83-1.13 (m, 12H).

31P-NMR (DMSO-d6, 162 MHz) δ[ppm]: 147.7, 147.3, 147.2, 146.7.

C. Synthesis of Solid Support Building Blocks for Oligonucleotide Synthesis

Synthetic Scheme 23

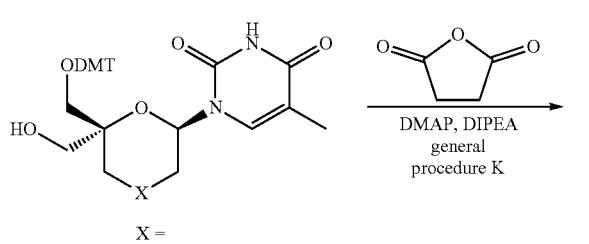

X =
N$^{iPr}$: 15a
O: 42

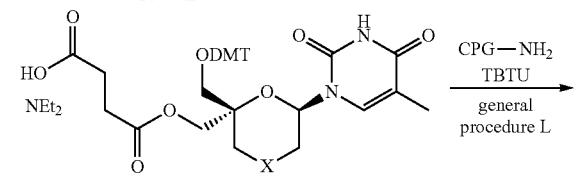

X =
N$^{iPr}$: 83a
O: 83b

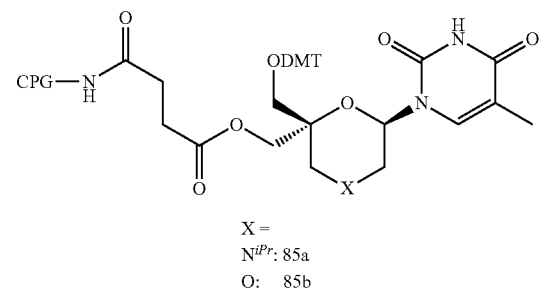

X =
N$^{iPr}$: 85a
O: 85b

-continued

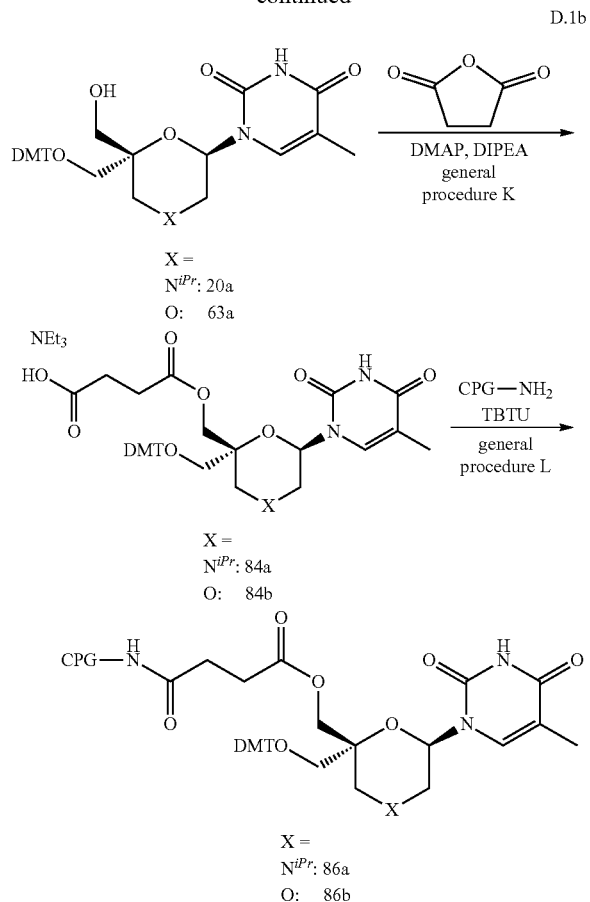

General Procedure K for the Preparation of Succinates 83a-b and 84a-b

The starting compounds (15a, 42, 20a, 63a, 1.0 eq.), DIPEA (5.0 eq.) and DMAP (0.25 eq.) were dissolved in dry DCM (20 ml/1.0 mmol). After adding 5.0 eq. succinic anhydride, the solution was stirred at room temperature overnight (approx. 16 h) to achieve complete conversion. After adding H$_2$O, the organic layer was separated and washed 1× with aqueous solution of citric acid (10%) and sat. NaHCO$_3$-solution. After drying with MgSO$_4$, the crude products were purified by silicagel chromatography. The product fractions were collected and 1.0 eq. NEt$_3$ was added. After evaporation of the solvent i.vac., the product was isolated as colourless foams (NEt$_3$-salt).

83a: 4-[[(2S,6R)-2-[[bis(4-methoxyphenyl)-phenyl-methoxy]methyl]-4-isopropyl-6-(5-methyl-2,4-di-oxo-pyrimidin-1-yl)morpholin-2-yl]methoxy]-4-oxo-butanoic acid (NEt$_3$ salt)

Following general procedure K, 146 mg (237 µmol) of 15a gave 112 mg (57.9%, NEt$_3$-salt) of the desired succinate 83a after purification on silica (preconditioned with DCM/NEt$_3$ 99.5:0.5, 0 to 20% MeOH in DCM).
LCMS-Method A:
UV-wavelength [nm]=220: R$_t$[min]=1.85
Ionization method: ES$^+$: [M+H]$^+$=716.2
1H-NMR (DMSO-d6, 400 MHz) δ[ppm]: 11.34 (br s, 1H), 7.57 (s, 1H), 7.20-7.39 (m, 9H), 6.88 (dd, J=8.99, 2.75 Hz, 4H), 5.81 (dd, J=9.84, 2.75 Hz, 1H), 4.57 (d, J=11.00 Hz, 1H), 4.32 (d, J=11.13 Hz, 1H), 3.73 (s, 6H), 3.08 (d, J=9.05 Hz, 1H), 2.95 (d, J=8.93 Hz, 1H), 2.76 (m, 3H), 2.40-2.48 (m, 6H), 2.22-2.37 (m, 6H), 1.74 (s, 3H), 0.76-0.97 (m, 15H).

83b: 4-[[(2S,6R)-2-[[bis(4-methoxyphenyl)-phenyl-methoxy]methyl]-6-(5-methyl-2,4-dioxo-pyrimidin-1-yl)-1,4-dioxan-2-yl]methoxy]-4-oxo-butanoic Acid Following general procedure K, 75 mg (131 µmol) of 42 gave 73 mg (71.9%, partial NEt$_3$-salt) of the desired succinate 83b, which used in the next step without additional purification.
LCMS-Method A:
UV-wavelength [nm]=220: R$_t$[min]=1.85
Ionization method: ES$^-$: [M-H]$^-$=673.4
1H-NMR (DMSO-d6, 400 MHz) [ppm]: 11.38 (br s, 1H), 7.58 (s, 1H), 7.20-7.38 (m, 9H), 6.88 (dd, J=8.93, 3.06 Hz, 4H), 5.89 (dd, J=10.03, 3.30 Hz, 1H), 4.62 (d, J=11.61 Hz, 1H), 4.33 (d, J=11.74 Hz, 1H), 3.76-3.92 (m, 2H), 3.73 (s, 6H), 3.51-3.63 (m, 2H), 3.03 (d, J=9.17 Hz, 1H), 2.95 (d, J=9.05 Hz, 1H), 2.58-2.68 (m, 2H), 2.31-2.41 (m, 2H), 1.73 (s, 3H).

84a: 4-[[(2R,6R)-2-[[bis(4-methoxyphenyl)-phenyl-methoxy]methyl]-4-isopropyl-6-(5-methyl-2,4-di-oxo-pyrimidin-1-yl)morpholin-2-yl]methoxy]-4-oxo-butanoic Acid (NEt$_3$ Salt)

Following general procedure K, 78 mg (127 µmol) of 20a gave 50 mg (48.3%, NEt$_3$-salt) of the desired succinate 84a after purification on silica (preconditioned with DCM/NEt$_3$ 99.5:0.5, 0 to 20% MeOH in DCM).
LCMS-Method A:
UV-wavelength [nm]=220: R$_t$[min]=1.86
Ionization method: ES$^+$: [M+H]$^+$=716.2
1H-NMR (DMSO-d6, 400 MHz) δ[ppm]: 11.32 (br s, 1H), 7.54-7.58 (m, 1H), 7.20-7.39 (m, 9H), 6.89 (d, J=8.80 Hz, 4H), 5.64 (dd, J=10.03, 2.93 Hz, 1H), 4.19 (d, J=11.25 Hz, 1H), 4.09 (d, J=11.13 Hz, 1H), 3.74 (s, 6H), 3.42 (br d, J=8.80 Hz, 2H), 3.15 (m, 1H), 2.86 (br d, J=11.37 Hz, 1H), 2.69-2.77 (m, 2H), 2.44 (q, J=7.13 Hz, 6H), 2.28-2.40 (m, 5H), 2.16-2.25 (m, 1H), 1.78 (s, 3H), 0.89-0.98 (m, 15H).

84b: 4-[[(2R,6R)-2-[[bis(4-methoxyphenyl)-phenyl-methoxy]methyl]-6-(5-methyl-2,4-dioxo-pyrimidin-1-yl)-1,4-dioxan-2-yl]methoxy]-4-oxo-butanoic Acid Following general procedure K, 69 mg (119 µmol) of 63a gave 63 mg (68.2%, partial NEt$_3$-salt) of the desired succinate 84b, which used in the next step without additional purification.
LCMS-Method A:
UV-wavelength [nm]=220: R$_t$[min]=1.82
Ionization method: ES$^-$: [M-H]$^-$=673.3
1H-NMR (DMSO-d6, 400 MHz) δ[ppm]: 11.39 (br s, 1H), 7.62 (s, 1H), 7.20-7.39 (m, 9H), 6.90 (d, J=8.93 Hz, 4H), 5.78 (dd, J=10.21, 3.36 Hz, 1H), 4.23 (d, J=11.25 Hz, 1H), 4.10 (d, J=11.25 Hz, 1H), 3.68-3.80 (m, 8H), 3.51-3.59 (m, 1H), 3.20-3.51 (m, 5H), 2.45-2.52 (m, 2H), 1.79 (s, 3H).

General Procedure L for the Preparation of CPG-Solid Supports 85a-b and 86a-b

The CPG solid support material was dried i. vac. for 2 h at 35° C. A solution of 1.0 eq. of the succinates (83a, 83b, 84a, 84b), 1.2 eq. TBTU and 1.2 eq. N-ethyl-morpholine in DMF (8 ml, 0.125 mmol) was stirred at room temperature for 1 h and was then transferred into a falcon tube, containing 1.0 eq. CPG-solid support (30 μmol/g free amino, 500 Å). After diluting with 20 ml DMF, the mixture was shaken for 24 h at room temperature. The solid support was filtered and washed with 30 ml MeOH (3×), 30 ml acetone (3×) and 30 ml diethyl ether (3×). After drying, the solid support was treated in a falcon tube with 15 ml capping reagent A (THF, 2,6-lutidine, acetic anhydride 8:1:1 v/v/v) and 15 ml capping reagent B (N-Methylimidazole, THF 1:9 v/v) for 1 h. After filtration and washing as above, the solid material was dried i. vac. at 35° C. for 2 hours. The loading was determined photometrically.

85a: Solid Support on CPG of Succinate 83a 105 mg (128.5 μmol) of the succinate 83a were immobilized to 4.28 g CPG-solid support (30 μmol/g free amine) following general procedure L. The final loading was determined to be 30.1 μmol/g solid support 85a (4.25 g).

85b: Solid Support on CPG of Succinate 83b 63 mg (81 μmol) of the succinate 83b were immobilized to 2.32 g CPG-solid support (30 μmol/g free amine) following general procedure L. The final loading was determined to be 32.8 μmol/g solid support 85b (2.31 g).

86a: Solid Support on CPG of Succinate 84a 44 mg (54 μmol) of the succinate 84a were immobilized to 1.80 g CPG-solid support (30 μmol/g free amine) following general procedure L. The final loading was determined to be 30.4 μmol/g solid support 86a (1.76 g).

86b: Solid Support on CPG of Succinate 84b 54 mg (70 μmol) of the succinate 84b were immobilized to 1.99 g CPG-solid support (30 μmol/g free amine) following general procedure L. The final loading was determined to be 36.1 μmol/g solid support 86b (2.00 g).

Example D.2

Synthetic Scheme 24

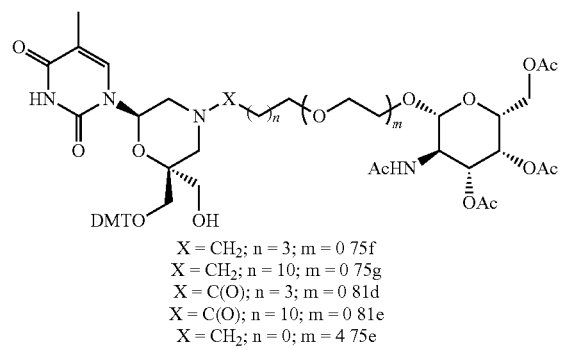

X = CH₂; n = 3; m = 0 75f
X = CH₂; n = 10; m = 0 75g
X = C(O); n = 3; m = 0 81d
X = C(O); n = 10; m = 0 81e
X = CH₂; n = 0; m = 4 75e

↓ general procedure M

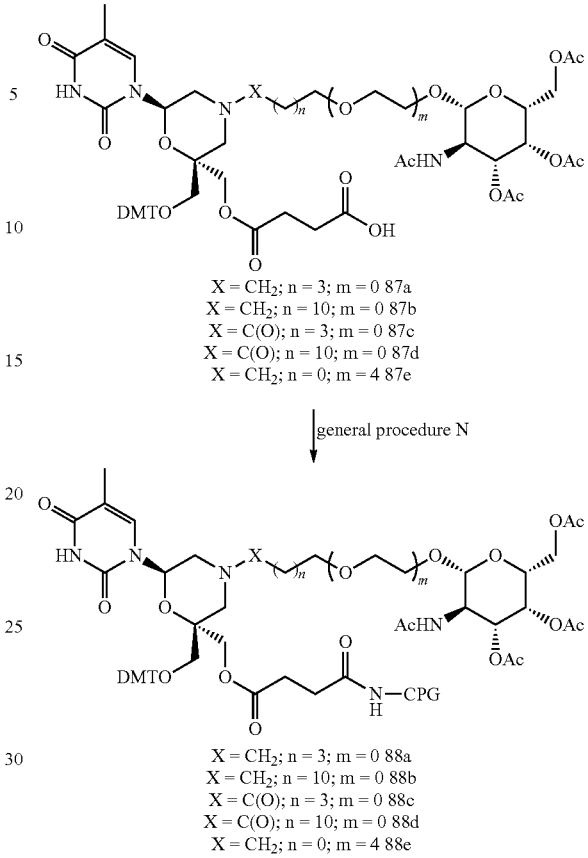

X = CH₂; n = 3; m = 0 87a
X = CH₂; n = 10; m = 0 87b
X = C(O); n = 3; m = 0 87c
X = C(O); n = 10; m = 0 87d
X = CH₂; n = 0; m = 4 87e

↓ general procedure N

X = CH₂; n = 3; m = 0 88a
X = CH₂; n = 10; m = 0 88b
X = C(O); n = 3; m = 0 88c
X = C(O); n = 10; m = 0 88d
X = CH₂; n = 0; m = 4 88e

General Procedure M for the Syntheses of Succinates 87a-e

The starting compounds (75f, 75g, 75e, 81d, 81e, 1.0 eq.) were dissolved in dry DCM (120 ml, 1.0 mmol). After adding 2.0 eq. of succinic anhydride and 3.0 eq. DMAP, the solutions were stirred at room temperature until complete conversion was achieved. A cold aqueous solution of citric acid (10%) was added and the organic phase was separated, dried with MgSO₄ and evaporated. The crude product was dissolved in ACN/H₂O (1:1) and lyophilized to yield the crude products as colourless foams, which were used without further purification.

87a: 4-[[(2S,6R)-4-[5-[(2R,3R,4R,5R,6R)-3-acetamido-4,5-diacetoxy-6-(acetoxymethyl)tetra-hydropyran-2-yl]oxypentyl]-2-[[bis(4-methoxyphenyl)-phenyl-methoxy]methyl]-6-(5-methyl-2,4-dioxopyrimidin-1-yl)morpholin-2-yl]methoxy]-4-oxobutanoic Acid Following general procedure M, 50 mg (51 μmol) of 75f gave 54 mg (98.1%, crude) of the desired succinate 87a.
LCMS-Method A:
UV-wavelength [nm]=220: $R_t$[min]=1.82
Ionization method: ES⁺: [M+H]⁺=1089.7
1H-NMR (DMSO-d6, 400 MHz): 12.19 (br s, 1H), 11.33 (s, 1H), 7.79 (d, J=9.17 Hz, 1H), 7.54 (s, 1H), 7.19-7.39 (m, 9H), 6.81-6.91 (m, 4H), 5.82 (dd, J=9.78, 2.57 Hz, 1H), 5.21 (d, J=3.30 Hz, 1H), 4.96 (dd, J=11.25, 3.30 Hz, 1H), 4.61 (d, J=11.25 Hz, 1H), 4.49 (d, J=8.44 Hz, 1H), 4.27 (d, J=11.49

Hz, 1H), 3.96-4.08 (m, 3H), 3.82-3.95 (m, 1H), 3.68-3.76 (m, 7H), 3.36-3.49 (m, 2H), 3.05 (d, J=8.80 Hz, 1H), 2.96 (d, J=8.93 Hz, 1H), 2.81-2.92 (m, 2H), 2.25-2.41 (m, 5H), 2.05-2.17 (m, 5H), 1.98 (s, 3H), 1.88 (s, 3H), 1.77 (s, 3H), 1.72 (s, 3H), 1.36-1.56 (m, 4H), 1.22-1.34 (m, 2H).

87b: 4-[[(2S,6R)-4-[12-[(2R,3R,4R,5R,6R)-3-acet-amido-4,5-diacetoxy-6-(acetoxymethyl)-tetrahydro-pyran-2-yl]oxydodecyl]-2-[[bis(4-methoxyphenyl)-phenyl-methoxy]methyl]-6-(5-methyl-2,4-dioxo-pyrimidin-1-yl)morpholin-2-yl]methoxy]-4-oxo-butanoic Acid Following general procedure M, 50 mg (46 µmol) of 75g gave 55 mg (99.8%, crude) of the desired succinate 87b.
LCMS-Method A:
UV-wavelength [nm]=220: R$_t$[min]=2.03
Ionization method: ES$^+$: [M+H]$^+$=1187.8
1H-NMR (DMSO-d6, 400 MHz): 12.20 (br s, 1H), 11.33 (s, 1H), 7.79 (d, J=9.29 Hz, 1H), 7.53 (s, 1H), 7.20-7.39 (m, 9H), 6.88 (dd, J=8.99, 2.87 Hz, 4H), 5.81 (dd, J=9.78, 2.69 Hz, 1H), 5.21 (d, J=3.30 Hz, 1H), 4.96 (dd, J=11.19, 3.48 Hz, 1H), 4.60 (d, J=11.37 Hz, 1H), 4.48 (d, J=8.56 Hz, 1H), 4.26 (d, J=11.25 Hz, 1H), 3.97-4.06 (m, 3H), 3.82-3.91 (m, 1H), 3.66-3.75 (m, 7H), 3.37-3.45 (m, 2H), 3.04 (br d, J=8.80 Hz, 1H), 2.93-2.99 (m, 1H), 2.80-2.88 (m, 2H), 2.25-2.41 (m, 5H), 2.05-2.20 (m, 5H), 1.99 (s, 3H), 1.89 (s, 3H), 1.76 (s, 3H), 1.72 (s, 3H), 1.44 (m, 4H), 1.24 (br s, 16H).

87c: 4-[[(2S,6R)-4-[5-[(2R,3R,4R,5R,6R)-3-acet-amido-4,5-diacetoxy-6-(acetoxymethyl)tetra-hydro-pyran-2-yl]oxypentanoyl]-2-[[bis(4-methoxyphe-nyl)-phenyl-methoxy]methyl]-6-(5-methyl-2,4-dioxo-pyrimidin-1-yl)morpholin-2-yl]methoxy]-4-oxo-butanoic Acid Following general procedure M, 150 mg (150 µmol) of 81d gave 95 mg (57.6%, crude) of the desired succinate 87c.
LCMS-Method A:
UV-wavelength [nm]=220: R$_t$[min]=1.78
Ionization method: ES$^-$: [M−H]$^-$=1101.4
1H-NMR (DMSO-d6, 400 MHz): 12.20 (br s, 1H), 11.37-11.43 (m, 1H), 7.74-7.81 (m, 1H), 7.58-7.65 (m, 1H), 7.18-7.42 (m, 9H), 6.90 (m, 4H), 5.75-5.92 (m, 1H), 5.21 (m, 1H), 4.96 (m, 1H), 4.50 (m, 1H), 4.07-4.46 (m, 3H), 4.02 (s, 3H), 3.81-3.99 (m, 2H), 3.74 (s, 7H), 3.36-3.49 (m, 2H), 3.15 (m, 1H), 2.93-3.08 (m, 2H), 2.31-2.43 (m, 8H), 2.10, 2.07 (2×s, 3H), 1.99 (s, 3H), 1.89 (s, 3H), 1.72-1.79 (m, 6H), 1.51 (br s, 4H).

87d: 4-[[(2S,6R)-4-[12-[(2R,3R,4R,5R,6R)-3-acet-amido-4,5-diacetoxy-6-(acetoxymethyl)-tetrahydro-pyran-2-yl]oxydodecanoyl]-2-[[bis(4-methoxyphe-nyl)-phenyl-methoxy]methyl]-6-(5-methyl-2,4-dioxo-pyrimidin-1-yl)morpholin-2-yl]methoxy]-4-oxo-butanoic Acid Following general procedure M, 150 mg (150 µmol) of 81e gave 102 mg (62.3%, crude) of the desired succinate 87d.
LCMS-Method A:
UV-wavelength [nm]=220: R$_t$[min]=1.92
Ionization method: ES$^-$: [M−H]$^-$=1199.5
1H-NMR (DMSO-d6, 400 MHz): 12.17 (br s, 1H), 11.36-11.45 (m, 1H), 7.79 (d, J=9.17 Hz, 1H), 7.58-7.65 (m, 1H), 7.17-7.45 (m, 9H), 6.84-6.94 (m, 4H), 5.76-5.89 (m, 1H), 5.21 (m, 1H), 4.96 (m, 1H), 4.48 (m, 1H), 4.08-4.45 (m, 3H), 3.97-4.05 (m, 3H), 3.80-3.97 (m, 2H), 3.63-3.79 (m, 7H), 3.34-3.46 (m, 2H), 2.87-3.20 (m, 3H), 2.29-2.44 (m, 8H), 2.06-2.14 (m, 3H), 1.99 (s, 3H), 1.84-1.94 (m, 3H), 1.68-1.84 (m, 6H), 1.45 (br s, 4H), 1.24 (br s, 12H).

87e: 4-[[(2S,6R)-4-[2-[2-[2-[2-[2-[(2R,3R,4R,5R,6R)-3-acetamido-4,5-diacetoxy-6-(acetoxy- methyl)tetrahydropyran-2-yl]oxyethoxy]ethoxy]ethoxy]ethoxy]ethyl]-2-[[bis(4-methoxy-phenyl)-phenyl-methoxy]methyl]-6-(5-methyl-2,4-dioxo-pyrimidin-1-yl)morpholin-2-yl]-methoxy]-4-oxo-butanoic Acid Following general procedure M, 50 mg (44.5 µmol) of 75e gave 54 mg (99.2%, crude) of the desired succinate 87e.
LCMS-Method A:
UV-wavelength [nm]=220: R$_t$[min]=1.81
Ionization method: ES$^-$: [M−H]$^-$=1221.7
1H-NMR (DMSO-d6, 400 MHz): 12.19 (b s, 1H), 11.33 (s, 1H), 7.77 (d, J=9.17 Hz, 1H), 7.54 (s, 1H), 7.20-7.39 (m, 9H), 6.88 (dd, J=8.93, 3.18 Hz, 4H), 5.81 (dd, J=9.90, 2.69 Hz, 1H), 5.21 (d, J=3.30 Hz, 1H), 4.97 (dd, J=11.25, 3.42 Hz, 1H), 4.62 (d, J=11.49 Hz, 1H), 4.56 (d, J=8.56 Hz, 1H), 4.26 (d, J=11.49 Hz, 1H), 4.03 (s, 3H), 3.83-3.95 (m, 1H), 3.71-3.82 (m, 7H), 3.42-3.58 (m, 16H), 2.88-3.04 (m, 4H), 2.53-2.62 (m, 2H), 2.23-2.41 (m, 7H), 2.10 (s, 3H), 1.99 (s, 3H), 1.89 (s, 3H), 1.77 (s, 3H), 1.71 (s, 3H).

General Procedure N for the Preparation of CPG-Solid Supports 88a-e

The CPG solid support material was dried i. vac. for 2 h at 35° C. A solution of 1.0 eq. of the succinates (87a-e) 1.5 eq. HBTU and 5.0 eq. DIPEA in DMF (10 ml/0.100 mmol) was stirred at room temperature for 10 min followed by the addition of 1.0 eq. CPG-solid support (30 µmol/g free amino, 500 Å). The mixture was shaken for 24 h at room temperature. The solid support was filtered and washed 2× with 20 ml DCM, DCM/MeOH (10:1) and 30 ml diethyl ether. After drying, the solid support was treated in a falcon tube with 15 ml capping reagent A (THF, 2,6-lutidine, acetic anhydride 8:1:1 v/v/v) and 15 ml capping reagent B (N-Methylimidazole, THF 1:9 v/v) for 1 h. After filtration and washing as above, the solid material was dried i. vac. at 35° C. for 2 h. The loading was determined photometrically.

88a: Solid Support on CPG of Succinate 87a 50 mg (46 µmol) of the succinate 87a were immobilized to 1.53 g CPG-solid support (30 µmol/g free amine) following general procedure N. The final loading was determined to be 24.2 µmol/g solid support 88a.

88b: Solid Support on CPG of Succinate 87b 52 mg (44 µmol) of the succinate 87b were immobilized to 1.45 g CPG-solid support (30 µmol/g free amine) following general procedure N. The final loading was determined to be 22.3 µmol/g solid support 88b.

88c: Solid Support on CPG of Succinate 87c 90 mg (82 µmol) of the succinate 87c were immobilized to 2.72 g CPG-solid support (30 µmol/g free amine) following general procedure N. The final loading was determined to be 28.7 µmol/g solid support 88c.

88d: Solid Support on CPG of Succinate 87d 100 mg (83 µmol) of the succinate 87d were immobilized to 2.76 g CPG-solid support (30 µmol/g free amine) following general procedure N. The final loading was determined to be 32.0 µmol/g solid support 88d.

88e: Solid Support on CPG of Succinate 87e 55 mg (45 µmol) of the succinate 87e were immobilized to 1.50 g CPG-solid support (30 µmol/g free amine) following general procedure N. The final loading was determined to be 29.2 µmol/g solid support 88e.

The chemical structures of some examples of compounds according to the present specification are illustrated in the following tables; correspondence with the specification and the schemes is indicated, as well as stereochemistry. Table A shows some examples of phosphoramidite nucleotide analogs for oligonucleotide synthesis; Table B shows some solid support of nucleotide analogs for oligonucleotide synthesis.

In the (2S,6R) diastereomeric series, the phosphoramidites as nucleotide precursors are abbreviated with a "pre-1", the nucleotide analogs are abbreviated with an "1", followed by the nucleobase and a number, which specifies the group Y in formulas (I) and (II). To distinguish both stereochemistries, the analogues (2R,6R)-diastereoisomers are indicated with an additional "b". For solid supports, the abbreviation "CPG-1" is used with the additional information as described above. Targeted nucleotide precursors, targeted nucleotide analogs and solid supports are abbreviated as described above, but with an "lg" instead of the "l".

TABLE A

| N° | structure | text number | Synthetic scheme | name | name in oligo-sequence | Stereochemistry: |
|---|---|---|---|---|---|---|
| 1 | 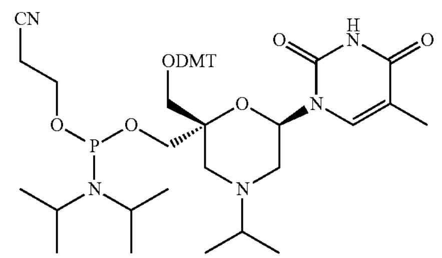 | 16a | 4 | pre-lT3 | lT3 | (2S,6R) |
| 2 | 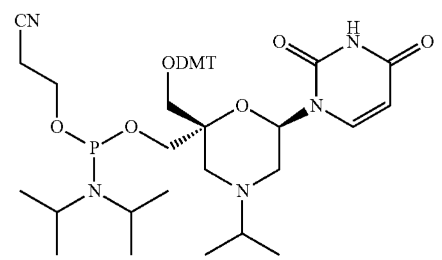 | 16b | 4 | pre-lU3 | lU3 | (2S,6R) |
| 3 | 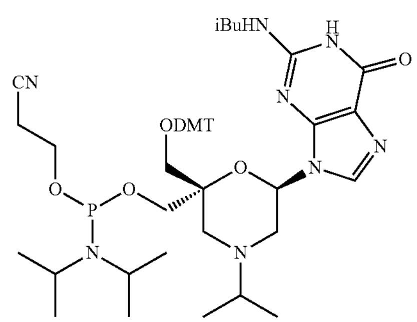 | 16c | 4 | pre-lG3 | lG3 | (2S,6R) |
| 4 | 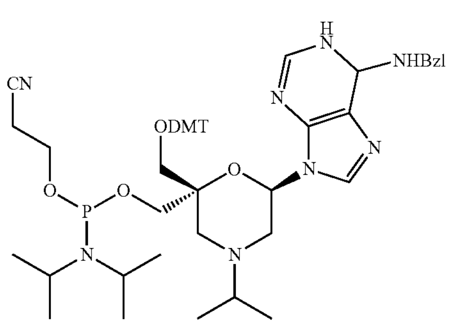 | 16e | 4 | pre-lA3 | lA3 | (2S,6R) |

TABLE A-continued

| N° | structure | text number | Synthetic scheme | name | name in oligo-sequence | Stereo-chemistry: |
|---|---|---|---|---|---|---|
| 5 | 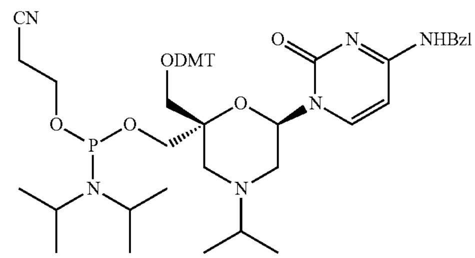 | 16f | 4 | pre-lC3 | lC3 | (2S,6R) |
| 6 | 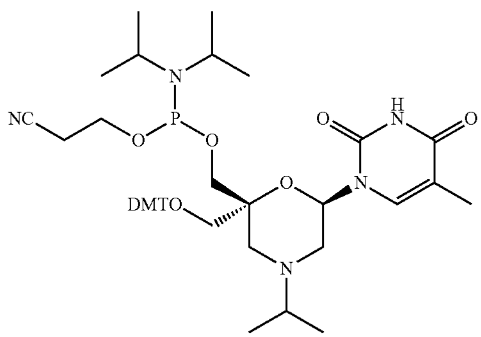 | 21a | 5 | pre-lT3b | lT3b | (2R,6R) |
| 7 | 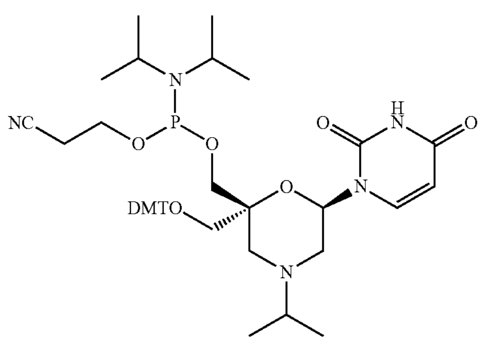 | 21b | 5 | pre-lU3b | lU3b | (2R,6R) |
| 8 | 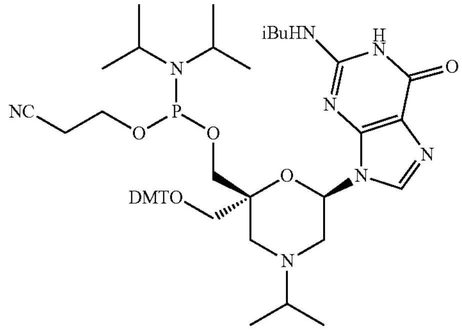 | 21c | 5 | pre-lG3b | lG3b | (2R,6R) |

TABLE A-continued

| N° | structure | text number | Synthetic scheme | name | name in oligo-sequence | Stereo-chemistry: |
|---|---|---|---|---|---|---|
| 9 | 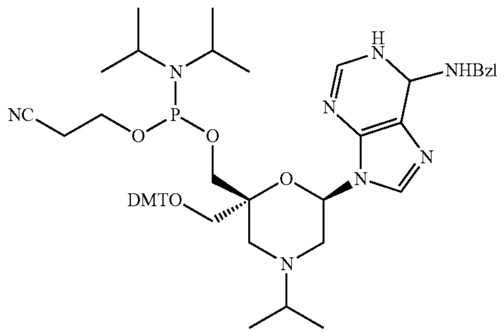 | 21e | 5 | pre-lA3b | lA3b | (2R,6R) |
| 10 | 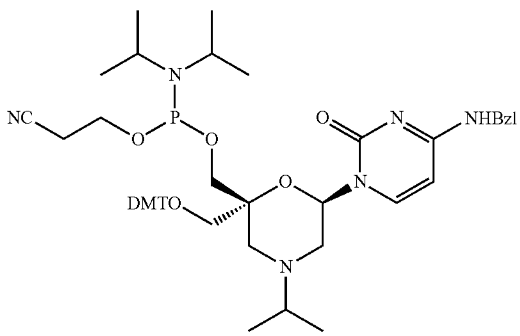 | 21f | 5 | pre-lC3b | lC3b | (2R,6R) |
| 11 | 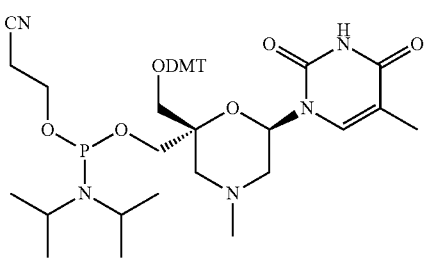 | 33a | 8 | pre-lT2 | lT2 | (2S,6R) |
| 12 | 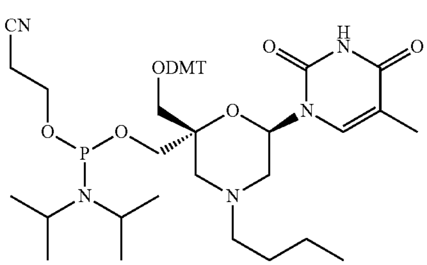 | 33b | 8 | pre-lT6 | lT6 | (2S,6R) |
| 13 | 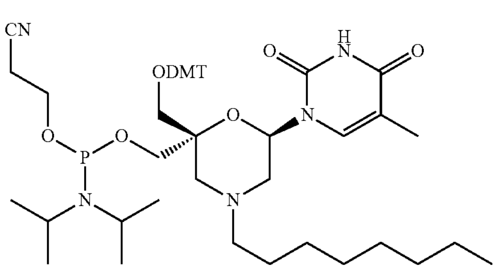 | 33c | 8 | pre-lT7 | lT7 | (2S,6R) |

TABLE A-continued

| N° | structure | text number | Synthetic scheme | name | name in oligo-sequence | Stereo-chemistry: |
|---|---|---|---|---|---|---|
| 14 | 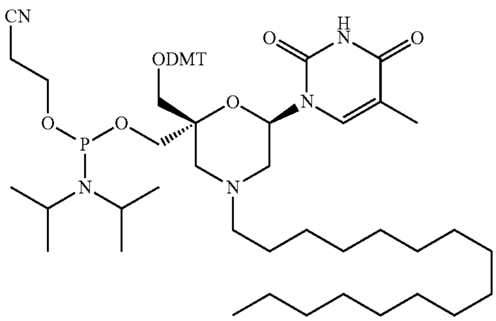 | 33d | 8 | pre-IT8 | IT8 | (2S,6R) |
| 15 | 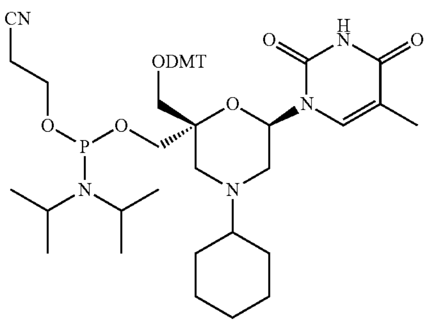 | 33e | 8 | pre-IT4 | IT4 | (2S,6R) |
| 16 | 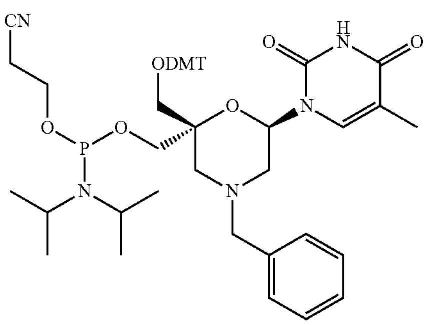 | 33f | 8 | pre-It5 | IT5 | (2S,6R) |
| 17 | 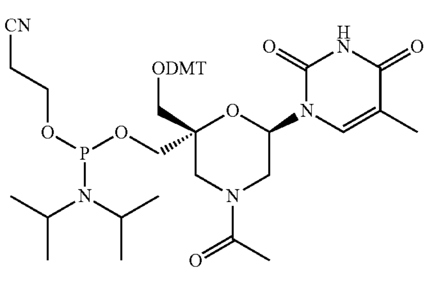 | 33g | 8 | pre-IT9 | IT9 | (2S,6R) |
| 18 | 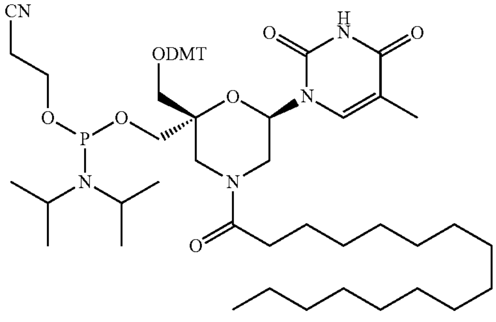 | 33h | 8 | pre-IT10 | IT10 | (2S,6R) |

TABLE A-continued

| N° | structure | text number | Synthetic scheme | name | name in oligo-sequence | Stereo-chemistry: |
|---|---|---|---|---|---|---|
| 19 | 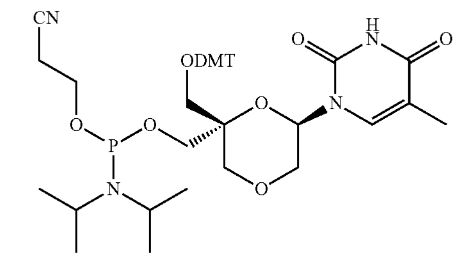 | 43a | 12 | pre-lT1 | lT1 | (2S,6R) |
| 20 | 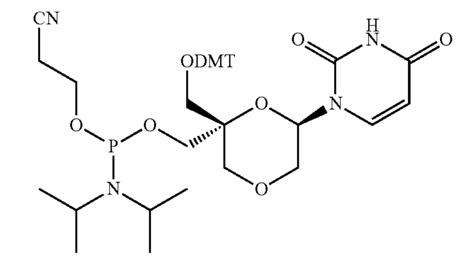 | 43b | 13 | pre-lU1 | lU1 | (2S,6R) |
| 21 | 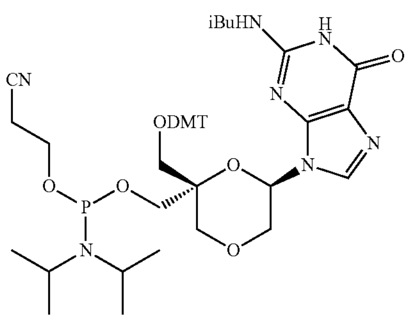 | 43c | 12 | pre-lG1 | lG1 | (2S,6R) |
| 22 | 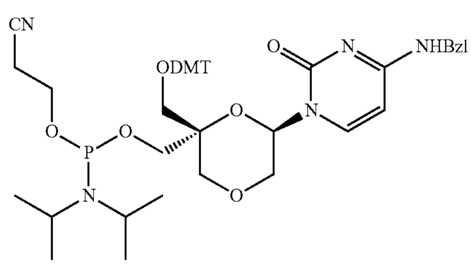 | 43d | 14 | pre-lC1 | lC1 | (2S,6R) |
| 23 | 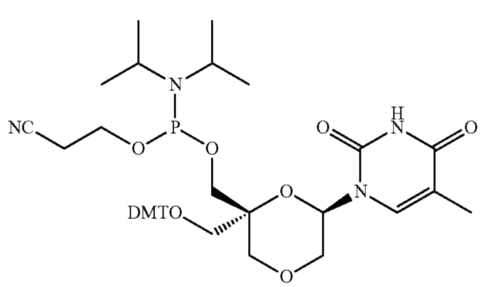 | 64a | 15 | pre-lT1b | lT1b | (2R,6R) |

TABLE A-continued

| N° | structure | text number | Synthetic scheme | name | name in oligo-sequence | Stereo-chemistry: |
|---|---|---|---|---|---|---|
| 24 | 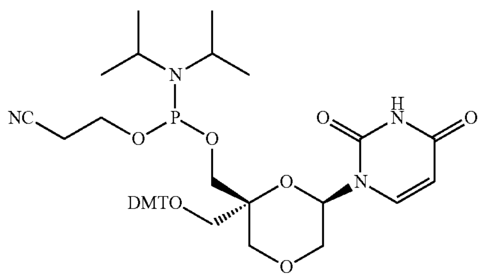 | 64b | 16 | pre-lU1b | lU1b | (2R,6R) |
| 25 | 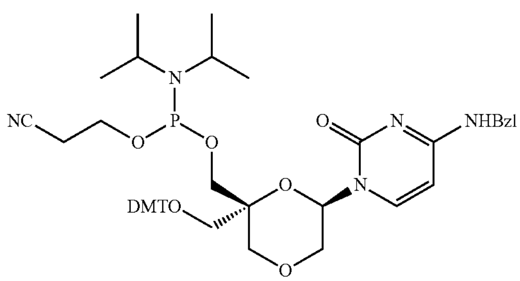 | 64d | 15 | pre-lC1b | lC1b | (2R,6R) |
| 26 | 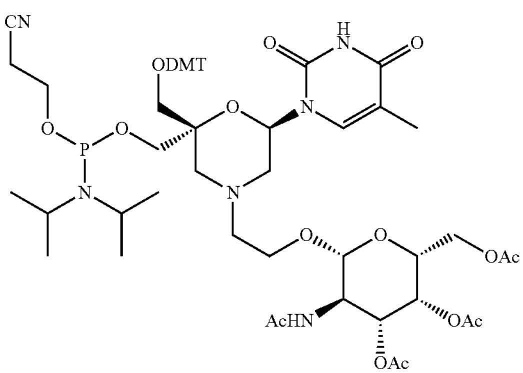 | 76a | 20 | pre-lgT9 | lgT9 | (2S,6R) |
| 27 | 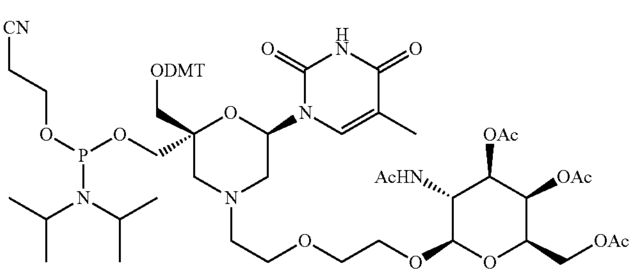 | 76b | 20 | pre-lgT8 | lgT8 | (2S,6R) |

TABLE A-continued

| N° | structure | text number | Synthetic scheme | name | name in oligo-sequence | Stereo-chemistry: |
|---|---|---|---|---|---|---|
| 28 | 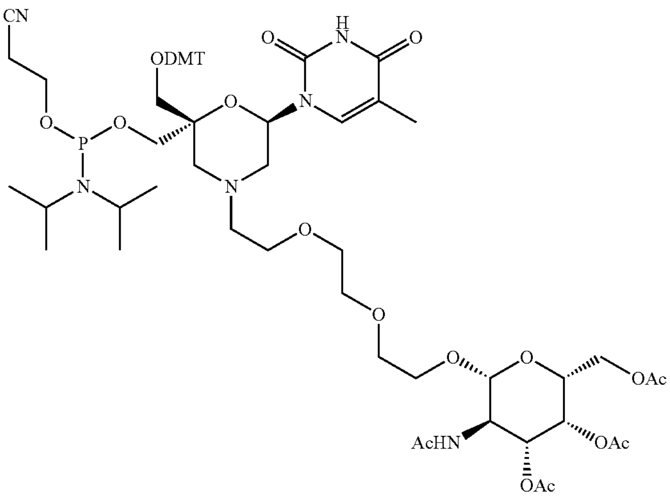 | 76c | 20 | pre-lgT7 | lgT7 | (2S,6R) |
| 29 | 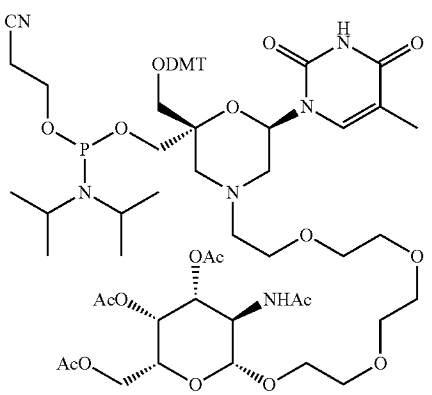 | 76d | 20 | pre-lgT6 | lgT6 | (2S,6R) |
| 30 | 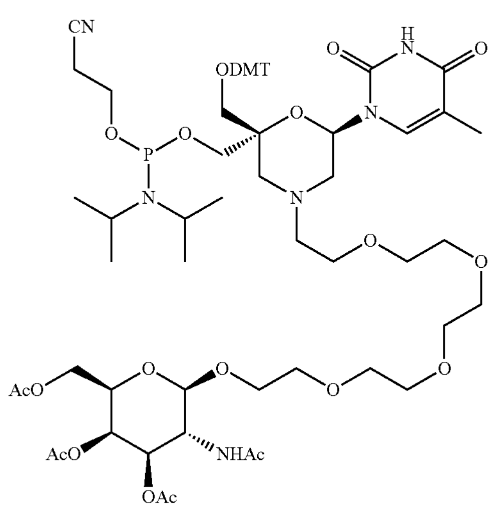 | 76e | 20 | pre-lgT5 | lgT5 | (2S,6R) |

TABLE A-continued

| N° | structure | text number | Synthetic scheme | name | name in oligo-sequence | Stereo-chemistry: |
|---|---|---|---|---|---|---|
| 31 | 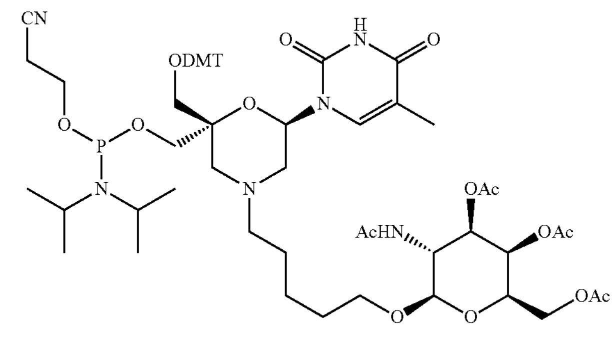 | 76f | 20 | pre-lgT3 | lgT3 | (2S,6R) |
| 32 | 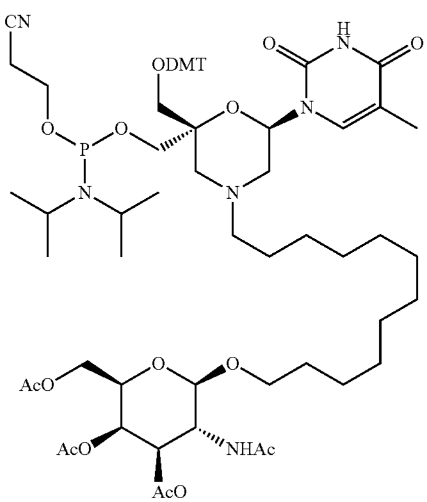 | 76g | 20 | pre-lgT4 | lgT4 | (2S,6R) |
| 33 | 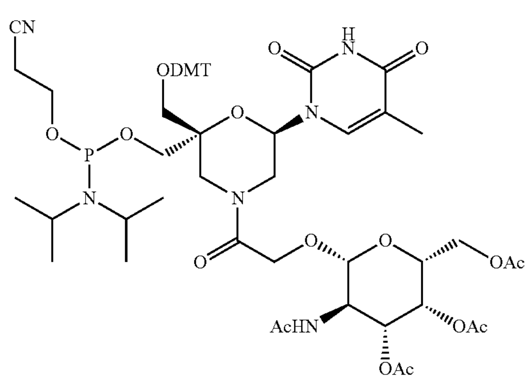 | 82a | 22 | pre-lgT12 | lgT12 | (2S,6R) |
| 34 | 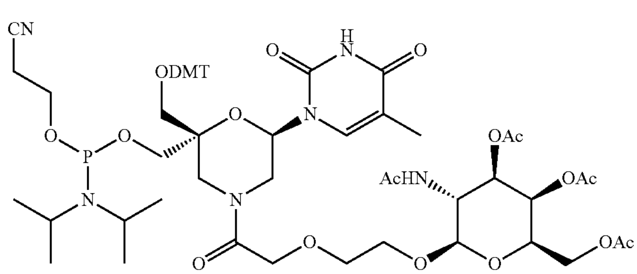 | 82b | 22 | pre-lgT11 | lgT11 | (2S,6R) |

TABLE A-continued

| N° | structure | text number | Synthetic scheme | name | name in oligo-sequence | Stereo-chemistry: |
|---|---|---|---|---|---|---|
| 35 | 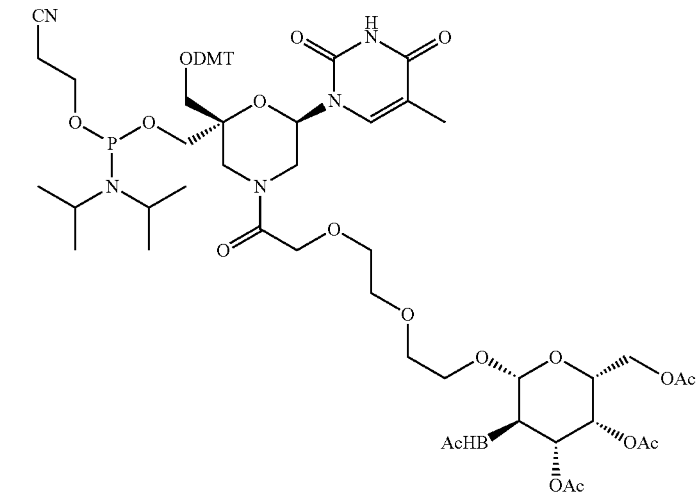 | 82c | 22 | pre-lgT10 | lgT10 | (2S,6R) |
| 36 | 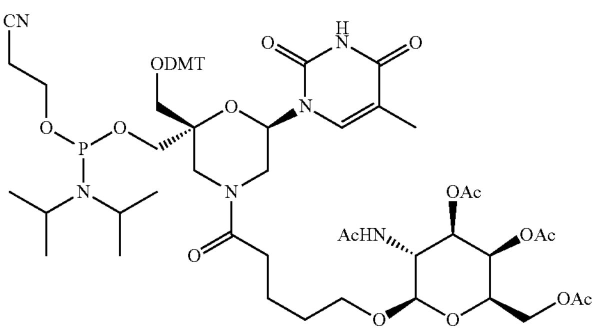 | 82d | 22 | pre-lgT1 | lgT1 | (2S,6R) |
| 37 | 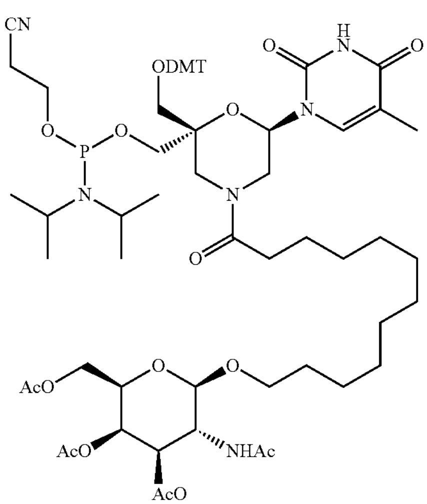 | 82e | 22 | pre-lgT2 | lgT2 | (2S,6R) |

TABLE A-continued

| N° | structure | text number | Synthetic scheme | name | name in oligo-sequence | Stereo-chemistry: |
|---|---|---|---|---|---|---|
| 38 | 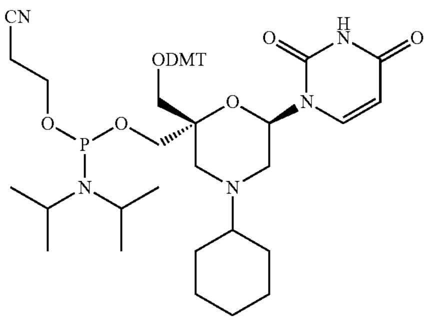 | 92b | 9 | pre-lU4 | lU4 | (2S,6R) |
| 39 | 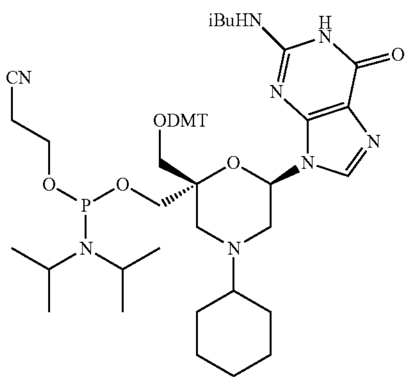 | 92c | 9 | pre-lG4 | lG4 | (2S,6R) |
| 40 | 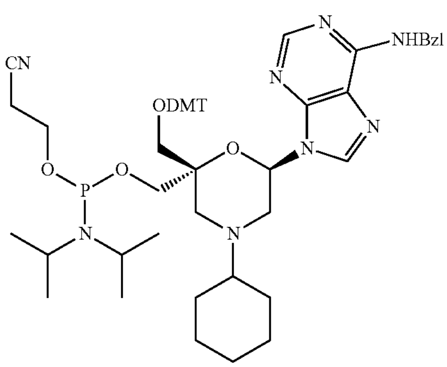 | 92e | 9 | pre-lA4 | lA4 | (2S,6R) |
| 41 | 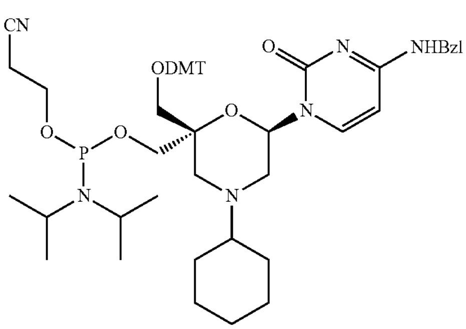 | 92f | 10 | pre-lC4 | lC4 | (2S,6R) |

TABLE A-continued

| N° | structure | text number | Synthetic scheme | name | name in oligo-sequence | Stereo-chemistry: |
|---|---|---|---|---|---|---|
| 42 | 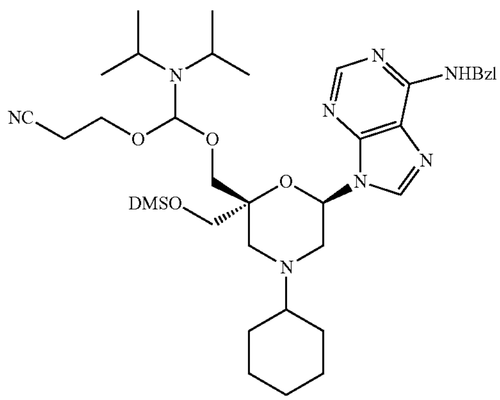 | 99e | 11 | pre-1A4b | 1A4b | (2R,6R) |
| 43 | 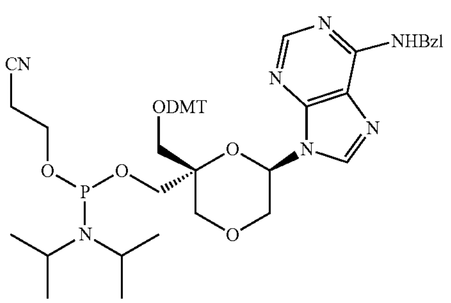 | 43e | 18 | pre-1A1 | 1A1 | (2S,6R) |
| 44 | 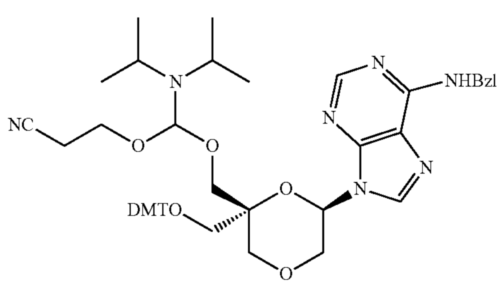 | 64e | 19 | pre-1A1b | 1A1b | (2R,6R) |
| 45 | 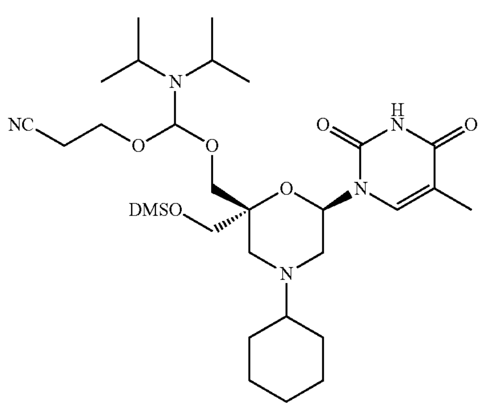 | 99a | 11 | pre-1T4b | 1T4b | (2R,6R) |

TABLE A-continued
| N° | structure | text number | Synthetic scheme | name | name in oligo-sequence | Stereo-chemistry: |
|---|---|---|---|---|---|---|
| 46 | 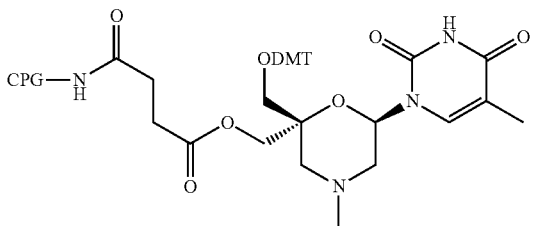 | 64c | 19 | pre-lG1b | lG1b | (2R,6R) |
TABLE B
| N° | structure | text number | Synthetic scheme | name | name in oligo-sequence | Stereo-chemistry |
|---|---|---|---|---|---|---|
| 1 | 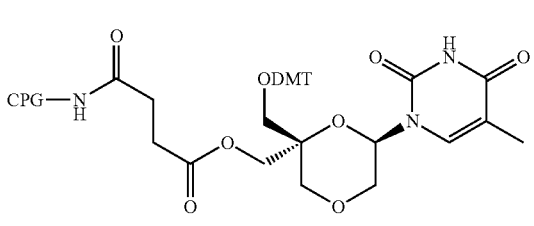 | 85a | 23 | cpg-lT3 | lT3 | (2S,6R) |
| 2 | 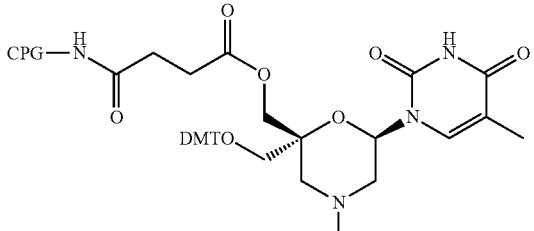 | 85b | 23 | cpg-lT1 | lT1 | (2S,6R) |
| 3 | 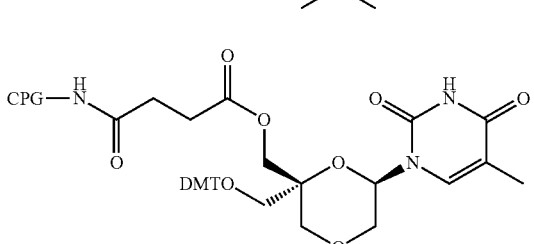 | 86a | 23 | cpg-lT3b | lT3b | (2R,6R) |
| 4 | 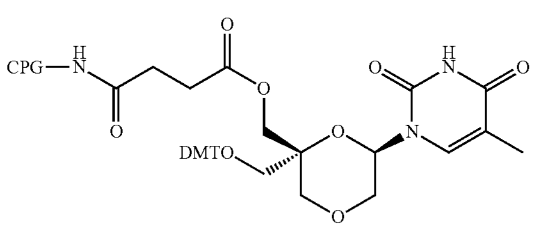 | 86b | 23 | cpg-lT1b | lT1b | (2R,6R) |

TABLE B-continued

| N° | structure | text number | Synthetic scheme | name | name in oligo-sequence | Stereo-chemistry |
|---|---|---|---|---|---|---|
| 5 | 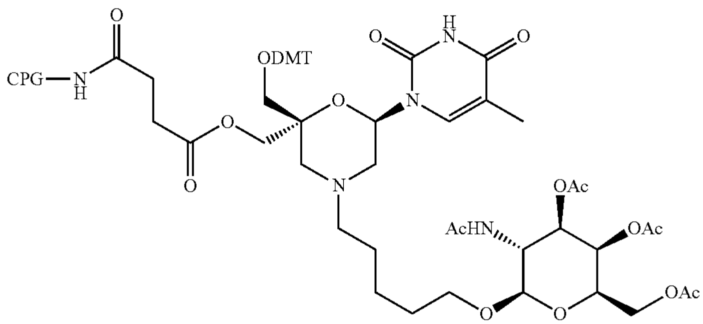 | 88a | 24 | cpg-lgT3 | lgT3 | (2S,6R) |
| 6 | 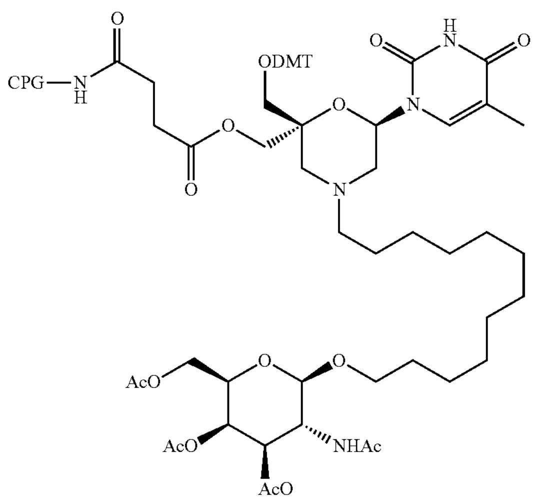 | 88b | 24 | cpg-lgT4 | lgT4 | (2S,6R) |
| 7 | 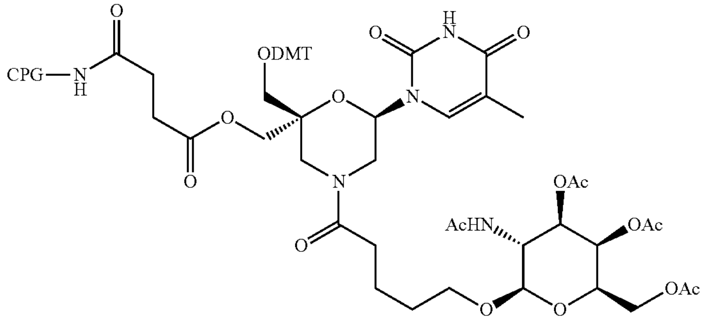 | 88c | 24 | cpg-lgT1 | lgT1 | (2S,6R) |

TABLE B-continued

| N° | structure | text number | Synthetic scheme | name | name in oligo-sequence | Stereo-chemistry |
|---|---|---|---|---|---|---|
| 8 | 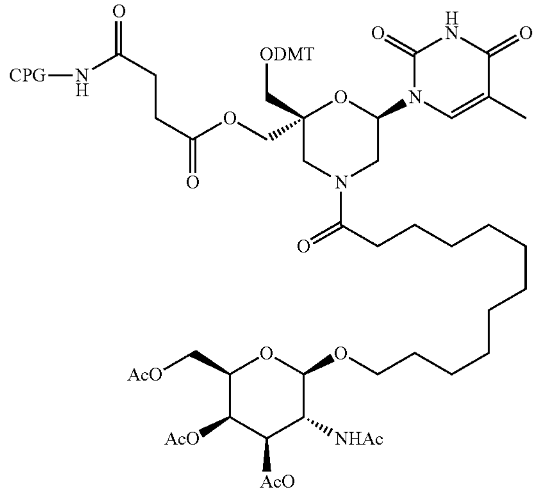 | 88d | 24 | cpg-lgT2 | lgT2 | (2S,6R) |
| 9 | 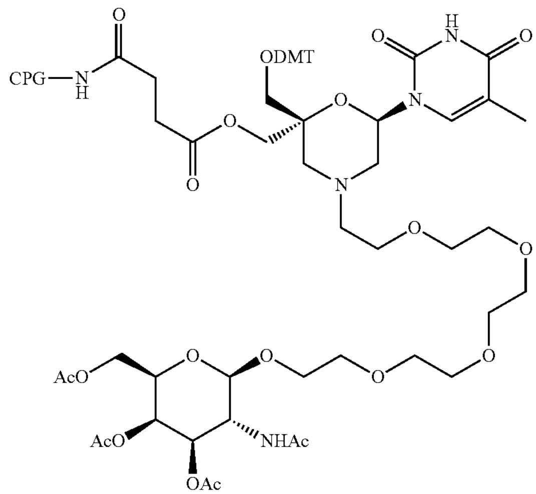 | 88e | 24 | cpg-lgT5 | lgT5 | (2S,6R) |

Synthesis of siRNAs Comprising Nucleotide Analogs and Targeted Nucleotide and Analogs Oligonucleotide Synthesis and siRNA Preparation All oligonucleotides were synthesized on a ABI394 synthesizer. Commercially available (Sigma Aldrich) DNA-, RNA-, 2'-OMe-RNA and 2'-desoxy-F-RNA-phosphoramidites with standard protecting groups as 5'-O-dimethoxytrityl-thymidine-3'-O—(N,N-diisopropyl-2-cyanoethyl-phosphoramidite, 5'-O-dimethoxytrityl-2'-O-tert-butyldimethylsilyl-uracile-3'-O—(N,N-diisopropyl-2-cyanoethyl)-phosphoramidite, 5'-O-dimethoxytrityl-2'-O-tert-butyldimethylsilyl-N4-cytidine-3'-O—(N,N-diisopropyl-2-cyanoethyl)-phosphoramidite, 5'-O-dimethoxytrityl-2'-O-tert-butyldimethylsilyl-N6-benzoyl-adenosine-3'-(N,N-diisopropyl-2-cyanoethyl)-phosphoramidite, 5'-O-dimethoxytrityl-2'-O-tert-butyldimethylsilyl-N2-isobutyryl-guanosine-3'-O—(N,N-diisopropyl-2-cyanoethyl)-phosphoramidite, 5'-O-dimethoxytrityl-2'-O-methyl-uracile-3'-O—(N,N-diisopropyl-2-cyanoethyl)-phosphoramidite, 5'-O-dimethoxytrityl-2'-O-methyl-N4-cytidine-3'-O—(N,N-diisopropyl-2-cyanoethyl)-phosphoramidite, 5'-O-dimethoxytrityl-2'-O-methyl-N6-benzoyl-adenosine-3'-O—(N,N-diisopropyl-2-cyanoethyl)-phosphoramidite, 5'-O-dimethoxytrityl-2'-O-methyl-N2-isobutyryl-guanosine-3'-O—(N,N-diisopropyl-2-cyanoethyl)-phosphoramidite, 5'-O-dimethoxytrityl-2'-desoxy-fluoro-uracile-3'-O—(N,N-diisopropyl-2-cyanoethyl)-phosphoramidite, 5'-O-dimethoxytrityl-2'-desoxy-fluoro-N4-cytidine-3'-O—(N,N-diisopropyl-2-cyanoethyl)-phosphoramidite, 5'-O-dimethoxytrityl-2'-desoxy-fluoro-N6-benzoyl-adenosine-3'-O—(N,N-diisopropyl-2-cyanoethyl)-phosphoramidite andand 5'-O-dimethoxytrityl-2'-desoxy-fluoro-N2-isobutyryl-guanosine-3'-O—(N,N-diisopropyl-2-cyanoethyl)-phosphoramidite as well as the corresponding solid support materials (CPG-500 Å, loading 40 µmol/g, ChemGenes) were used for automated oligonucleotide synthesis. For 3'-end cholesterol conjugates, solid support 3'-Cholesterol SynBase™ CPG1000 (link technologies) 32 mol/g was used.

Phosphoramidite building blocks were used as 0.1 M solutions in acetonitrile and activated with 5-(bis-3,5-trifluoromethylphenyl)-1H-tetrazole (activator 42, 0.25 M in acetonitrile, Sigma Aldrich). Reaction times of 200 s were used for standard phosphoramidite couplings. In case of herein described phosphoramidites, listed in Table A, coupling times of 300 s were applied. As capping reagents, acetic anhydride in THF (capA for ABI, Sigma Aldrich) and N-methylimidazole in THF (capB for ABI, Sigma Aldrich) were used. As oxidizing reagent, iodine in THF/pyridine/water (0.02 M; oxidizer for ABI, Sigma Aldrich) was used. Alternative, PS-oxidation was achieved with a 0.05 M solution of 3-((N,N-dimethyl-aminomethylidene)amino)-3H-1,2,4-dithiazole-5-thione (DDTT) in pyridine/acetonitrile (1:1). Deprotection of the DMT-protecting group was done using dichloroacetic acid in DCM (DCA deblock, Sigma Aldrich). Final cleavage from solid support and deprotection (acyl- and cyanoethyl-protecting groups) was achieved with $NH_3$ (32% aqueous solution/ethanol, v/v 3:1). Treatment with $NMP/NEt_3/NEt_3.3HF$ (3:1.5:2) was applied for TBDMS-deprotection.

Oligonucleotides with herein described morpholino- or dioxane building blocks at the 3'-end were synthesized on solid support materials shown in Table B or on universal linker-solid support (CPG-500 Å, loading 39 μmol/g, AM Chemicals LLC) and the corresponding phosphoramidites shown in Table A.

Crude products were analyzed by HPLC and purification of the single strands was performed by ion exchange or preparative HPLC-methods.

Ion exchange: ÄKTA purifier, (Thermo Fisher Scientific DNAPac PA200 semi prep ion exchange column, 8 μm particles, width 22 mm×length 250 mm).

buffer A: 1.50 l $H_2O$, 2.107 g $NaClO_4$, 438 mg EDTA, 1.818 g TRIS, 540.54 g urea, pH 7.4.

buffer B: 1.50 l $H_2O$, 105.34 g $NaClO_4$, 438 mg EDTA, 1.818 g TRIS, 540.54 g urea, pH 7.4.

Isolation of the oligonucleotides was achieved by precipitation, induced by the addition of 4 volumes of ethanol and storing at −20° C.

Preparative HPLC: Agilent 1100 series prep HPLC, (Waters XBridge®BEH C18 OBD™ Prep Column 130 Å, 5 μm, 10 mm×100 mm). Eluent: Triethylammonium acetate (0.1 M) in acetonitrile/water. After lyophilization, the products were dissolved in 1.0 ml 2.5 M NaCl-solution and 4.0 ml $H_2O$. The corresponding $Na^+$-salts were isolated after precipitation by adding 20 ml ethanol and storing at −20° C. for 18 h.

Final analysis of the single strands was done by LC/MS-TOF methods. Results are shown in table C.

For double strand formation, equimolar amounts of sense- and antisense strands were mixed in 1×PBS-buffer and heated to 85° C. for 10 min and slowly cooled down to room temperature. Final analysis of the siRNA-double strands was done by LC/MS-TOF methods. Results are shown in table D.

Materials and Methods of In Vitro Biological Assays $T_m$-Determination 1.0 μM solutions of the siRNAs in PBS-buffer (1×PBS) were heated in a spectrophotometer (Jasco V-650) from 20 to 90° C. with a heating rate of 1° C./min. The absorption was measured at 260 nm and plotted versus the corresponding temperature. After reaching 90° C., the solution was cooled down to 20° C. with the same rate of 1° C./min and the heating cooling cycle was repeated. The melting temperature was calculated as mean value of the inflection points of the two heating curves.

Cells and Tissue Culture

Human HepG2 cells were grown at 37° C., 5% $CO_2$ and 95% RH, and cultivated in MEM medium (ThermoFisher, cat. no. 41090) supplemented with 10% FBS.

Primary hepatocytes from female C57BL/6 mice were isolated freshly before the experiments based on a protocol adapted from Seglen, P.O. (1976): Preparation of Isolated Rat Liver Cells; Methods in Cell Biology, 13: 29-83. Plating of isolated hepatocytes was done for 3-5 hours at 37° C., 5% C02 and 95% RH in Williams' E medium (ThermoFisher, cat. no. 22551) supplemented with 2 mM glutamin (ThermoFisher, cat. no. 25030), 100 U/ml Penicillin-Streptomycin (ThermoFisher, cat. no. 15140), 1 μg/ml Dexamethason (Sigma, cat. no. D1756), 1×ITS solution (ThermoFisher, cat. no. 41400) and 5% FBS. After plating, the medium was changed to cultivation medium that was identical to plating medium except supplement of 1% FBS. No further medium change was done during the incubation period of 48 or 72 hours.

Human peripheral blood mononuclear cells (PBMCs) were isolated from approximately 16 mL of blood from three healthy donors that were collected in Vacutainer tubes coated with sodium heparin (BD, Heidelberg Germany) according to manufacturer's instructions.

siRNA Transfections

For knock-down experiments in HepG2 cells, 20,000 cells/well were used in a Collagen-I coated 96-well plate (Corning, cat. no. 356407). The cells were transfected with the indicated concentration of AHA-1 siRNAs using 0.2 μl/well of Lipofectamine RNAiMAX transfection reagent (ThermoFisher) according to the manufacturer's protocol in a reverse transfection setup and incubated for 48 h without medium change. Usually, N=4 technical replicates were carried out per test sample.

For transfection of human PBMCs, 100 nM of the siRNAs were reverse transfected into $1×10^5$ PBMCs with 0.3 μL Lipofectamine 2000 per 96-well (N=2) in a total volume of 150 μL serum-free RPMI medium (ThermoFisher, cat. no. 11875) for 24 hours.

$IC_{50}$ Measurements

For $IC_{50}$ measurements in primary fresh mouse hepatocytes, 30,000 cells in Collagen-I coated 96-well plates were incubated for 48 hours under free uptake conditions with the siRNAs at concentrations ranging from 1 μM-1 pM using 10-fold dilution steps. The half maximal inhibitory concentration ($IC_{50}$) for each siRNA was calculated by applying a Biostat-Speed statistical calculation tool. Results were obtained using the 4-parameter logistic model according to Ratkovsky and Reedy (1986). The adjustment was obtained by non-linear regression using the Levenberg-Marquardt algorithm in SAS v9.1.3 software.

mRNA Expression Analysis 48 hours after siRNA transfection or free siRNA uptake, the cellular RNA was harvested by usage of Promega's SV96 total RNA isolation system (cat. no. Z3500) according to the manufacturer's protocol including a DNase step during the procedure.

For cDNA synthesis the Reverse Transcriptase kit (cat. no. N8080234) was used from ThermoFisher. cDNA synthesis from 30 ng RNA was performed using 1.2 μl 10×RT buffer, 2.64 μl $MgCl_2$ (25 mM), 2.4 μl dNTPs (10 mM), 0.6 μl random hexamers (50 μM), 0.6 μl Oligo(dT)16 (50 μM), 0.24 μl RNase inhibitor (20 U/μl) and 0.3 μl Multiscribe (50 U/μl) in a total volume of 12 μl. Samples were incubated at 25° C. for 10 minutes and 42° C. for 60 minutes. The reaction was stopped by heating to 95° C. for 5 minutes.

Human AHA-land mouse TTR mRNA levels were quantified by qPCR using the ThermoFisher TaqMan Universal PCR Master Mix (cat. no. 4305719) and the TaqMan Gene Expression assays Hs00201602_m1 and Mm00443267_m1, respectively. PCR was performed in technical duplicates with the ABI Prism 7900 under the following PCR conditions: 2 minutes at 50° C., 10 minutes at 95° C., 40 cycles with 95° C. for 15 seconds and 1 minute at 60° C. PCR was set up as a simplex PCR detecting the target gene in one reaction and the housekeeping gene (human/mouse RPL37A) for normalization in a second reaction. The final volume for the PCR reaction was 12.5 µl in a 1×PCR master mix, RPL37A primers were used in a final concentration of 50 nM and the probe of 200 nM. The ΔΔCt method was applied to calculate relative expression levels of the target transcripts. Percentage of target gene expression was calculated by normalization based on the levels of the LV2 or LV3 non-silencing siRNA control sequence.

IFNα Determination

IFNα protein concentration was quantified in the supernatant of human PBMCs as follows: 25 µL of the cell culture supernatant was used for measurement of IFNα concentration applying a self-established electrochemiluminescence assay based on MesoScale Discovery's technology, and using a pan IFNα monoclonal capture antibody (MT1/3/5, Mabtech). Alternatively, human IFNα2a isoform-specific assay (cat. no. K151VHK) was applied based on MesoScale's U-PLEX platform and according to the supplier's protocol.

Cytotoxicity

Cytotoxicity of mouse TTR siRNAs was measured 72 hours after incubation with 30,000 primary fresh mouse hepatocytes under free uptake conditions by determining the ratio of cellular viability/toxicity in each sample. Cell viability was measured by determination of the intracellular ATP content using the CellTiter-Glo assay (Promega, cat. no. G7570) according to the manufacturer's protocol. Cell toxicity was measured in the supernatant using the LDH assay (Sigma, cat. no. 11644793001) according to the manufacturer's protocol.

Nuclease Stability

The siRNAs were tested for nuclease stability in 50% mouse serum. For this purpose, 160 µL mouse serum (Sigma, cat. no. M5905) was incubated at 37° C. for 0, 8, 24, 32, 48, 56, 72, 80 and 96 hours. At each time point, 21 µL of the reaction was taken out and quenched with 23 µL stop solution (for 3,000 µL stop solution: 1123 µL Tissue & Cell Lysis Solution (Epicentre, cat. no. MTC096H), 183 µL 20 mg/mL Proteinase K (Sigma, cat. no. P2308), 1694 µL water) at 65° C. for 30 minutes. Prior to HPLC analysis on a Waters 2695 Separation Module and a 2487 Dual Absorbance Detector, 33 µL of RNase-free water was added to each sample. 50 µL of the solution was analyzed by HPLC using a DNAPac PA200 analytical column (Thermo Scientific, cat. no. 063000), and the following gradient:

| Time (min) | Flow (mL/min) | % Buffer A* | % Buffer B** |
|---|---|---|---|
| 0 | 1 | 75 | 25 |
| 20 | 1 | 35 | 65 |

*Buffer A: 20 mM sodium phosphate (Sigma, cat. No. 342483), pH 11;
**Buffer B: 20 mM sodium phosphate (Sigma, cat. No. 342483), 1M sodium bromide (Sigma, cat. No. 02119), pH 11.

Example 1: Stability of Exemplary siRNAs as Measured by Melting Point

In a siRNA-sequence, targeting AHA-1 (siRNA-1), all rU-nucleotides of the sense strand were successively replaced by iPr-morpholine-U nucleotide analogs lU3 and lU3b. Successive replacement, starting at the 3'-end of the sense strand, using pre-lU3b as phosphoramidite building block, gave the modified sense strands ss2 (1 lU3b) to ss6 (5 lU3b), which were annealed with the unmodified antisense strand as1, yielding the lU3b-modified double strands siRNA-2 to siRNA-6 (Tables 1-3). The analogue diastereomeric series using pre-lU3 as nucleotide precursor gave the corresponding double strands siRNA-9 to siRNA13 (Tables 1-3).

TABLE 1 sense strands (5'→3')

| sense strand # | Sense strands sequence | SEQ ID NO. |
|---|---|---|
| ss1 | rG-rG-rA-rU-rG-rA-rA-rG-rU-rG-rG-rA-rG-rA-rU-rU-rA-rG-rU-dT*dT | 1 |
| ss2 | rG-rG-rA-rU-rG-rA-rA-rG-rU-rG-rG-rA-rG-rA-rU-rU-rA-rG-1U3b-dT*dT | 2 |
| ss3 | rG-rG-rA-rU-rG-rA-rA-rG-rU-rG-rG-rA-rG-rA-rU-1U3b-rA-rG-1U3b-dT*dT | 3 |
| ss4 | rG-rG-rA-rU-rG-rA-rA-rG-rU-rG-rG-rA-rG-rA-1U3b-1U3b-rA-rG-1U3b-dT*dT | 4 |
| ss5 | rG-rG-rA-rU-rG-rA-rA-rG-1U3b-rG-rG-rA-rG-rA-1U3b-1U3b-rA-rG-1U3b-dT*dT | 5 |
| ss6 | rG-rG-rA-1U3b-rG-rA-rA-rG-1U3b-rG-rG-rA-rG-rA-1U3b-1U3b-rA-rG-1U3b-dT*dT | 6 |
| ss7 | rG-rG-rA-mU-rG-rA-rA-rG-mU-rG-rG-rA-rG-rA-mU-mU-rA-rG-mU-dT*dT | 7 |
| ss8 | rG-rG-rA-rU-rG-rA-rA-rG-rU-rG-rG-rA-rG-rA-rU-rU-rA-rG-1U3-dT*dT | 8 |
| ss9 | rG-rG-rA-rU-rG-rA-rA-rG-rU-rG-rG-rA-rG-rA-rU-1U3-rA-rG-1U3-dT*dT | 9 |
| ss10 | rG-rG-rA-rU-rG-rA-rA-rG-rU-rG-rG-rA-rG-rA-1U3-1U3-rA-rG-1U3-dT*dT | 10 |
| ss11 | rG-rG-rA-rU-rG-rA-rA-rG-1U3-rG-rG-rA-rG-rA-1U3-1U3-rA-rG-1U3-dT*dT | 11 |
| ss12 | rG-rG-rA-1U3-rG-rA-rA-rG-1U3-rG-rG-rA-rG-rA-1U3-1U3-rA-rG-1U3-dT*dT | 12 |

TABLE 2 antisense strands (5'→3')

| antisense strand # | Sense strands sequence | SEQ ID NO. |
|---|---|---|
| as1 | rA-rC-rU-rA-rA-rU-rC-rU-rC-rC-rA-rC-rU-rU-rC-rA-rU-rC-rC-dT*dT | 13 |
| as2 | rA-rC-mU-rA-rA-rU-rC-rU-rC-mC-rA-rC-rU-rU-mC-rA-rU-rC-rC-dT*dT | 14 |

TABLE 3

Tm-values measured for some siRNAs

| siRNA # | Sense strand # | Antisense strand # | # of lU3b | # of lU3 | Tm [° C.] |
|---|---|---|---|---|---|
| siRNA-1 | ss1 | as1 | 0 | 0 | 73.6 |
| siRNA-2 | ss2 | as1 | 1 | 0 | 72.7 |
| siRNA-3 | ss3 | as1 | 2 | 0 | 70.2 |
| siRNA-4 | ss4 | as1 | 3 | 0 | 68.6 |
| siRNA-5 | ss5 | as1 | 4 | 0 | 60.1 |
| siRNA-6 | ss6 | as1 | 5 | 0 | 50.2 |
| siRNA-7 | ss7 | as2 | 0 | 0 | 76.8 |
| siRNA-8 | ss6 | as2 | 5 | 0 | 50.1 |
| siRNA-9 | ss8 | as1 | 0 | 1 | 72.5 |
| siRNA-10 | ss9 | as1 | 0 | 2 | 70.3 |
| siRNA-11 | ss10 | as1 | 0 | 3 | 68.8 |
| siRNA-12 | ss11 | as1 | 0 | 4 | 60.3 |
| siRNA-13 | ss12 | as1 | 0 | 5 | 50.7 |
| siRNA-14 | ss12 | as2 | 0 | 5 | 50.6 |

Tm values of the siRNAs were measured according the Materials and Methods specified in the present disclosure. The melting point of the unmodified siRNA-1 was measured at 73.6° C. Using a 2'-OMe modified antisense strand gave an expected, slightly increased melting temperature of 76.8° C. (siRNA-7). Replacing the first rU-nucleotide by a lU3b-analog led to a small decrease in the Tm-value. The data in Table 3 show that with every additional lU3b-incorporation, the melting temperature was further decreased, resulting in a Tm-value of 50.2° C. for siRNA-6 with five lU3b-building blocks incorporated. Changing the antisense strand in siRNA-6 to the 2'-OMe analog (siRNA-8) did not result in an increased melting temperature.

In the lU3-series with opposite stereochemistry at the 2-position of the morpholine, similar results were obtained. The data in Table 3 show that the melting temperatures in both series were almost identical, comparing to those siRNAs with equal number of lU3b- or lU3-building blocks incorporated into the sense strand of the corresponding siRNAs (siRNA-2 and siRNA-9, siRNA-3 and siRNA-10, siRNA-4 and siRNA-11, siRNA-5 and siRNA-12, siRNA-6 and siRNA-13 and siRNA-8 and siRNA-14).

These results demonstrate that the $^i$Pr-morpholine-U based building blocks lU3b and lU3 lead to a decrease in the melting temperature of the corresponding siRNAs compared to their unmodified counterparts. An increasing number of lU3b- or lU3-nucleotides leads to an increased reduction in the Tm-value. There is no significant difference between the two diastereomeric orientations at the morpholine-scaffold, leading to lU3b- and lU3-structures.

Similar evaluations were performed using the uridine analog in the dioxane series (Tables 4-6). Based on a luciferase sequence, the melting temperature of an unmodified siRNA (siRNA-15) was determined at 74° C. In the sense strand (ss3) all rU-nucleotides were successively replaced by:

lU1b-nucleotides, leading to the double strands siRNA-16 to siRNA-21, with 1 to 6 lU1b-building blocks in the sense strands (ss14 to ss19) or lU1-nucleotides, leading to the double strands siRNA-22 to siRNA-27, with 1 to 6 lU1-building blocks in the sense strands (ss20 to ss25).

TABLE 4 sense strands (5'→3')

| sense strand # | Sense strands sequence | SEQ ID NO. |
|---|---|---|
| ss13 | mC-mU-mU-rA-mC-rG-mC-mU-rG-rA-rG-mU-rA-mC-mU-mU-mC-rG-rA*dT*dT | 15 |
| ss14 | mC-mU-mU-rA-mC-rG-mC-mU-rG-rA-rG-mU-rA-mC-mU-1U1b-mC-rG-rA*dT*dT | 16 |
| ss15 | mC-mU-mU-rA-mC-rG-mC-mU-rG-rA-rG-mU-rA-mC-1U1b-1U1b-mC-rG-rA*dT*dT | 17 |
| ss16 | mC-mu-mu-rA-mC-rG-mC-mu-rG-rA-rG-1U1b-rA-mC-1U1b-1U1b-mC-rG-rA*dT*dT | 18 |
| ss17 | mC-mu-mu-rA-mC-rG-mC-1U1b-rG-rA-rG-1U1b-rA-mC-1U1b-1U1b-mC-rG-rA*dT*dT | 19 |
| ss18 | mC-mu-1U1b-rA-mC-rG-mC-1U1b-rG-rA-rG-1U1b-rA-mC-1U1b-1U1b-mC-rG-rA*dT*dT | 20 |
| ss19 | mC-1U1b-1U1b-rA-mC-rG-mC-1U1b-rG-rA-rG-1U1b-rA-mC-1U1b-1U1b-mC-rG-rA*dT*dT | 21 |
| ss20 | mC-mu-mu-rA-mC-rG-mC-mu-rG-rA-rG-mu-rA-mC-mu-1U1-mC-rG-rA*dT*dT | 22 |
| ss21 | mC-mu-mu-rA-mC-rG-mC-mu-rG-rA-rG-mu-rA-mC-1U1-1U1-mC-rG-rA*dT*dT | 23 |
| ss22 | mC-mu-mu-rA-mC-rG-mC-mu-rG-rA-rG-1U1-rA-mC-1U1-1U1-mC-rG-rA*dT*dT | 24 |
| ss23 | mC-mu-mu-rA-mC-rG-mC-1U1-rG-rA-rG-1U1-rA-mC-1U1-1U1-mC-rG-rA*dT*dT | 25 |
| ss24 | mC-mu-1U1-rA-mC-rG-mC-1U1-rG-rA-rG-1U1-rA-mC-1U1-1U1-mC-rG-rA*dT*dT | 26 |
| ss25 | mC-1U1-1U1-rA-mC-rG-mC-1U1-rG-rA-rG-1U1-rA-mC-1U1-1U1-mC-rG-rA*dT*dT | 27 |

TABLE 5 antisense strands (5'→3')

| antisense strand # | Sense strands sequence | SEQ ID NO. |
|---|---|---|
| as3 | rU-rC-rG-rA-rA-rG-rU-rA-rC-rU-rC-rA-rG-rC-rG-rU-rA-rA-rG-dT*dT | 28 |

TABLE 6

Tm-values measured for some siRNAs

| siRNA # | Sense strand # | Antisense strand # | # of lU1b | # of lU1 | Tm [° C.] |
|---|---|---|---|---|---|
| siRNA-15 | ss13 | as3 | 0 | 0 | 74.0 |
| siRNA-16 | ss14 | as3 | 1 | 0 | 66.3 |
| siRNA-17 | ss15 | as3 | 2 | 0 | 63.7 |
| siRNA-18 | ss16 | as3 | 3 | 0 | 56.2 |
| siRNA-19 | ss17 | as3 | 4 | 0 | 49.6 |
| siRNA-20 | ss18 | as3 | 5 | 0 | 42.3 |
| siRNA-21 | ss19 | as3 | 6 | 0 | 42.0 |
| siRNA-22 | ss20 | as3 | 0 | 1 | 66.0 |
| siRNA-23 | ss21 | as3 | 0 | 2 | 64.3 |
| siRNA-24 | ss22 | as3 | 0 | 3 | 55.3 |
| siRNA-25 | ss23 | as3 | 0 | 4 | 46.8 |
| siRNA-26 | ss24 | as3 | 0 | 5 | 37.2 |
| siRNA-27 | ss25 | as3 | 0 | 6 | 37.0 |

The data in Table 6 show that with an increasing number of dioxane-based nucleotide building blocks lU1b or lU1 in the sense strands, the resulting siRNAs had successive reduction of the corresponding melting temperatures, with the lowest values for siRNA-21 in the lU1b-series and siRNA-27 in the lU1-modified siRNAs.

The results in Tables 3 and 6 demonstrate, that the incorporation of $^i$Pr-morpholine-U- or dioxane-U-nucleotides (lU3b, lU3, lU1b and lU1) into an siRNA-sense strand leads to a reduction in the double strand stability, which leads to reduced melting temperature. The higher the number of $^i$Pr-morpholine- or dioxane-U building blocks is, the lower the Tm-value and duplex stability of the siRNA molecules are. There is no significant dependency on the stereochemistry in both series (lU3b vs. lU3 and lU1b vs. lU1).

Example 2: Stability of Exemplary siRNAs in Time

Tables 7 to 10 contain the control sequences that have been used.

TABLE 7 sense strands controls (5'→3')

| sense strand # | Sense strands sequence | SEQ ID NO. |
|---|---|---|
| ss7 | rG-rG-rA-mU-rG-rA-rA-rG-mU-rG-rG-rA-rG-rA-mU-mU-rA-rG-mU-dT*dT | 7 |
| ss26 | rG-rG-rA-mU-rG-rA-rA-rG-mU-rG-rG-rA-rG-rA-mU-mU-rA-rG-mU-dT-dT | 29 |

TABLE 8 antisense strands controls (5'→3')

| antisense strand # | Sense strands sequence | SEQ ID NO. |
|---|---|---|
| as2 | rA-rC-mU-rA-rA-rU-rC-rU-rC-mC-rA-rC-rU-rU-mC-rA-rU-rC-rC-dT*dT | 14 |
| as5 | rA-rC-mU-rA-rA-rU-rC-rU-rC-mC-rA-rC-rU-rU-mC-rA-rU-rC-rC-dT-dT | 30 |

TABLE 9 control-siRNAs with dT-dT-overhangs

| siRNA # | Sense strand # | Antisense strand # | 3'-end sense | 3'-end antisense |
|---|---|---|---|---|
| siRNA-7 | ss7 | as2 | dT*dT | dT*dT |
| siRNA-28 | ss26 | as2 | dT-dT | dT*dT |
| siRNA-56 | ss26 | as5 | dT-dT | dT-dT |

Both diastereomeric isomers of $^i$Pr-morpholine-T- and dioxane-T building blocks (pre-T3, pre-lT3b, pre-lT1 and pre-lT1b) have been attached as overhangs at the 3'- and 5'-end of the sense strand as well as the 3'-end of the antisense strand in an AHA-sequence. The single sense- and antisense strand sequences are listed in Tables 10 and 11 respectively. The corresponding siRNAs are shown in Table 12. As control siRNAs, the standard dT-PS-dT-stabilized molecule (siRNA-7) has been used. For direct comparison with the PO-linked modified siRNAs (Table 9), the analogues controls (siRNA-28 and siRNA-56) with partial or full PO-bridged overhangs have been synthesized.

The stabilities in mouse serum of the modified siRNAs (siRNA-58 to siRNA-79) have been compared to standard dT-PS-dT-overhangs (siRNA-7) as well as the partial PO-bridged analogs siRNA-28 and -56. Stabilities were determined by the amount of antisense strand, which could be detected after 24 h incubation in 50% mouse serum by HPLC-methods and is listed as %-value of the initial amount at 0 h-incubation. The resulting antisense strand amounts (%) are listed in table 13.

TABLE 10 sense strands with 1T3-, 1T3b-, 1T1- and 1T1b- overhangs (5'→3')

| sense strand # | Sense strands sequence | Stereo-chemistry | SEQ ID NO. |
|---|---|---|---|
| ss44 | rG-rG-rA-mU-rG-rA-rA-rG-mU-rG-rG-rA-rG-rA-mU-mU-rA-rG-mU-1T3 | (2S, 6R) | 31 |
| ss27 | rG-rG-rA-mU-rG-rA-rA-rG-mU-rG-rG-rA-rG-rA-mU-mU-rA-rG-mU-1T3-1T3 | (2S, 6R) | 32 |
| ss45 | 1T3-1T3-rG-rG-rA-mU-rG-rA-rA-rG-mU-rG-rG-rA-rG-rA-mU-mU-rA-rG-mU-1T3-1T3 | (2S, 6R) | 33 |
| ss46 | rG-rG-rA-mU-rG-rA-rA-rG-mU-rG-rG-rA-rG-rA-mU-mU-rA-rG-mU-1T3b | (2R, 6R) | 34 |
| ss37 | rG-rG-rA-mU-rG-rA-rA-rG-mU-rG-rG-rA-rG-rA-mU-mU-rA-rG-mU-1T3b-1T3b | (2R, 6R) | 35 |
| ss47 | 1T3b-1T3b-rG-rG-rA-mU-rG-rA-rA-rG-mU-rG-rG-rA-rG-rA-mU-mU-rA-rG-mU-1T3b-1T3b | (2R, 6R) | 36 |
| ss48 | rG-rG-rA-mU-rG-rA-rA-rG-mU-rG-rG-rA-rG-rA-mU-mU-rA-rG-mU-1T1 | (2S, 6R) | 37 |
| ss49 | rG-rG-rA-mU-rG-rA-rA-rG-mU-rG-rG-rA-rG-rA-mU-mU-rA-rG-mU-1T1-1T1 | (2S, 6R) | 38 |

TABLE 10-continued sense strands with 1T3-, 1T3b-, 1T1- and 1T1b- overhangs (5'→3')

| sense strand # | Sense strands sequence | Stereochemistry | SEQ ID NO. |
|---|---|---|---|
| ss50 | 1T1-1T1-rG-rG-rA-mU-rG-rA-rA-rG-mU-rG-rG-rA-rG-rA-mU-mU-rA-rG-mU-1T1-1T1 | (2S, 6R) | 39 |
| ss51 | rG-rG-rA-mU-rG-rA-rA-rG-mU-rG-rG-rA-rG-rA-mU-mU-rA-rG-mU-1T1b | (2R, 6R) | 40 |
| ss52 | rG-rG-rA-mU-rG-rA-rA-rG-mU-rG-rG-rA-rG-rA-mU-mU-rA-rG-mU-1T1b-1T1b | (2R, 6R) | 41 |
| ss53 | 1T1b-1T1b-rG-rG-rA-mU-rG-rA-rA-rG-mU-rG-rG-rA-rG-rA-mU-mU-rA-rG-mU-1T1b-1T1b | (2R, 6R) | 42 |

TABLE 11 antisense strands with 1T3-, 1T3b-, 1T1- and 1T1b -overhangs (5'→3')

| antisense strand # | Sense strands sequence | Stereochemistry | SEQ ID NO. |
|---|---|---|---|
| as6 | rA-rC-mU-rA-rA-rU-rC-rU-rC-mC-rA-rC-rU-rU-mC-rA-rU-rC-rC-1T3 | (2S, 6R) | 43 |
| as7 | rA-rC-mU-rA-rA-rU-rC-rU-rC-mC-rA-rC-rU-rU-mC-rA-rU-rC-rC-1T3b | (2R, 6R) | 44 |
| as8 | rA-rC-mU-rA-rA-rU-rC-rU-rC-mC-rA-rC-rU-rU-mC-rA-rU-rC-rC-1T1 | (2S, 6R) | 45 |
| as9 | rA-rC-mU-rA-rA-rU-rC-rU-rC-mC-rA-rC-rU-rU-mC-rA-rU-rC-rC-1T1b | (2R, 6R) | 46 |
| as10 | rA-rC-mU-rA-rA-rU-rC-rU-rC-mC-rA-rC-rU-rU-mC-rA-rU-rC-rC-1T3-1T3 | (2S, 6R) | 47 |
| as 11 | rA-rC-mU-rA-rA-rU-rC-rU-rC-mC-rA-rC-rU-rU-mC-rA-rU-rC-rC-1T3b-1T3b | (2R, 6R) | 48 |
| as12 | rA-rC-mU-rA-rA-rU-rC-rU-rC-mC-rA-rC-rU-rU-mC-rA-rU-rC-rC-1T1-1T1 | (2S, 6R) | 49 |
| as13 | rA-rC-mU-rA-rA-rU-rC-rU-rC-mC-rA-rC-rU-rU-mC-rA-rU-rC-rC-1T1b-1T1b | (2R, 6R) | 50 |

TABLE 12 siRNAs with with morpholine- and dioxane-overhangs at ss & as

| siRNA-# | ss-# | as-# | stereochemistry |
|---|---|---|---|
| siRNA-58 | ss44 | as2 | (2S, 6R) |
| siRNA-29 | ss27 | as2 | (2S, 6R) |
| siRNA-59 | ss45 | as2 | (2S, 6R) |
| siRNA-60 | ss44 | as6 | (2S, 6R) |
| siRNA-61 | ss27 | as10 | (2S, 6R) |
| siRNA-62 | ss45 | as10 | (2S, 6R) |
| siRNA-63 | ss46 | as2 | (2R, 6R) |
| siRNA-45 | ss37 | as2 | (2R, 6R) |
| siRNA-64 | ss47 | as2 | (2R, 6R) |
| siRNA-65 | ss46 | as7 | (2R, 6R) |
| siRNA-66 | ss37 | as11 | (2R, 6R) |
| siRNA-67 | ss47 | as11 | (2R, 6R) |
| siRNA-68 | ss48 | as2 | (2S, 6R) |
| siRNA-69 | ss49 | as2 | (2S, 6R) |
| siRNA-70 | ss50 | as2 | (2S, 6R) |
| siRNA-71 | ss48 | as8 | (2S, 6R) |
| siRNA-72 | ss49 | as12 | (2S, 6R) |
| siRNA-73 | ss50 | as12 | (2S, 6R) |
| siRNA-74 | ss51 | as2 | (2R, 6R) |
| siRNA-75 | ss52 | as2 | (2R, 6R) |
| siRNA-76 | ss53 | as2 | (2R, 6R) |
| siRNA-77 | ss51 | as9 | (2R, 6R) |
| siRNA-78 | ss52 | as13 | (2R, 6R) |
| siRNA-79 | ss53 | as13 | (2R, 6R) |

TABLE 13

Stabilities: amount of antisense strand detected after 24 h compared to 0 h-value

| siRNA # | ss-# | as-# | 3'-end sense | 3'-end antisense | amount of antisense [%] |
|---|---|---|---|---|---|
| siRNA-7 | ss7 | as2 | dT*dT | dT*dT | 15 |
| siRNA-28 | ss26 | as2 | dT-dT | dT*dT | 0 |
| siRNA-56 | ss26 | as5 | dT-dT | dT-dT | 0 |

| siRNA # | ss-# | as-# | Stereochemistry | amount of antisense [%] |
|---|---|---|---|---|
| siRNA-58 | ss44 | as2 | (2S, 6R) | 17 |
| siRNA-29 | ss27 | as2 | (2S, 6R) | 17 |
| siRNA-59 | ss45 | as2 | (2S, 6R) | 35 |
| siRNA-60 | ss44 | as6 | (2S, 6R) | n.d. |
| siRNA-61 | ss27 | as10 | (2S, 6R) | 27 |
| siRNA-62 | ss45 | as10 | (2S, 6R) | 33 |
| siRNA-63 | ss46 | as2 | (2R, 6R) | 16 |
| siRNA-45 | ss37 | as2 | (2R, 6R) | 19 |
| siRNA-64 | ss47 | as2 | (2R, 6R) | 25 |
| siRNA-65 | ss46 | as7 | (2R, 6R) | n.d. |
| siRNA-66 | ss37 | as11 | (2R, 6R) | 26 |
| siRNA-67 | ss47 | as11 | (2R, 6R) | 32 |
| siRNA-68 | ss48 | as2 | (2S, 6R) | 17 |
| siRNA-69 | ss49 | as2 | (2S, 6R) | 21 |
| siRNA-70 | ss50 | as2 | (2S, 6R) | 22 |
| siRNA-71 | ss48 | as8 | (2S, 6R) | n.d. |
| siRNA-72 | ss49 | as12 | (2S, 6R) | 33 |
| siRNA-73 | ss50 | as12 | (2S, 6R) | 24 |
| siRNA-74 | ss51 | as2 | (2R, 6R) | 13 |
| siRNA-75 | ss52 | as2 | (2R, 6R) | 19 |
| siRNA-76 | ss53 | as2 | (2R, 6R) | 18 |
| siRNA-77 | ss51 | as9 | (2R, 6R) | n.d. |
| siRNA-78 | ss52 | asl3 | (2R, 6R) | 22 |
| siRNA-79 | ss53 | asl3 | (2R, 6R) | 23 |

As can be seen in Table 13, under the test conditions, among the control siRNAs, only siRNA-7, which has two phosphothioate-stabilized dT-dT overhangs, showed a significant amount of antisense (15%) after 24 h of incubation. The analog molecules, siRNA-28, which has only one PS-group in the antisense strand (as2), and siRNA-56, which has no PS-group, showed no detectable amount of antisense strand at the selected time point.

In contrast, all lTlT-modified siRNAs (siRNA-58 to -79), showed significant amounts of antisense strand after 24 h.

The amounts were comparable to the amount observed with control molecule siRNA-7, although the IT-modified double strands were all synthesized without additional PS-stabilization in the ITIT-overhangs (IT=IT3, IT3b, IT1 and IT1b). Moreover some of the siRNA-modifications showed an antisense amount that was about twice as much as the amount observed with the dT-PS-dT-stabilized control compound siRNA-7. Examples are siRNA-61, -66 and -72, which all have double T-overhangs (IT3, IT3b and IT1) at the sense and the antisense strand and without any PS-groups in the whole siRNA sequences. Additionally, it has to be emphasized that the IT3-stabilized molecules siRNA-59 and siRNA-62 showed unexpected high stabilities, where siRNA-59 contains IT3-overhangs at the 3'- and 5'-end of the sense strand and a dT-PS-dT-stabilized antisense strand (as2), whereas siRNA-62 has the same sense strand, but is additionally stabilized with IT3-overhangs at the 3'-end of the antisense strand (as10). Similar stabilization is achieved in siRNA-67 with the corresponding IT3b-modifications.

The results in Table 13 demonstrate that replacing standard dT-PS-dT (siRNA-7) 3'-overhangs with IT-IT-overhangs (IT=IT3, IT3b, IT1 and somewhat less pronounced IT1b) leads to a significant increase in siRNA stability without additional PS-groups within the IT-overhangs. An additional increase in compound stability can still be achieved by also using IT-IT-overhangs at the 5'-end of the sense strand.

As can be seen in FIG. 1, all compounds were still potent in human HepG2-cells excepted those with a single IT-overhang at the 3'-end of the antisense strand (siRNA-60, -65, -71 and -77). All siRNAs (siRNA29 to siRNA55) with IT1, IT1b, IT3- or IT3b-overhangs were tested with in IFNα- and cytotoxicity assay and did not show any effects on immune stimulation or cell viability.

Example 3: In Vitro Inhibition of a Target Gene with Modified siRNAs According to the Present Disclosure The sequences contained in tables 14 to 18 have been used (AHA-sequences synthesized with overhangs containing nucleotide analogs IT3 and IT3b.

TABLE 14

Sense strands (5'→3')

| sense strand # | Sense strands sequence | SEQ ID NO. |
|---|---|---|
| ss7 | rG-rG-rA-mU-rG-rA-rA-rG-mU-rG-rG-rA-rG-rA-mU-mU-rA-rG-mU-dT*dT | 7 |
| ss26 | rG-rG-rA-mU-rG-rA-rA-rG-mU-rG-rG-rA-rG-rA-mU-mU-rA-rG-mU-dT-dT | 29 |
| ss27 | rG-rG-rA-mU-rG-rA-rA-rG-mU-rG-rG-rA-rG-rA-mU-mU-rA-rG-mU-1T3-1T3 | 32 |
| ss28 | rG-rG-rA-mU-rG-rA-rA-rG-mU-rG-rG-rA-rG-rA-mU-mU-rA-rG-mU-1T3-1T3-1T3-1T3 | 51 |
| ss29 | rG-rG-rA-mU-rG-rA-rA-rG-mU-rG-rG-rA-rG-rA-mU-mU-rA-rG-mU-1T3-1T3-1T3-1T3-1T3 | 52 |
| ss30 | rG-rG-rA-mU-rG-rA-rA-rG-mU-rG-rG-rA-rG-rA-mU-mU-rA-rG-mU-1T3-1T3-1T3-1T3-1T3-1T3 | 53 |

TABLE 14-continued

Sense strands (5'→3')

| sense strand # | Sense strands sequence | SEQ ID NO. |
|---|---|---|
| ss31 | rG-rG-rA-mU-rG-rA-rA-rG-mU-rG-rG-rA-rG-rA-mU-mU-rA-rG-mU-1T3-1T3-1T3-1T3-1T3-1T3-1T3 | 54 |
| ss32 | rG-rG-rA-mU-rG-rA-rA-rG-mU-rG-rG-rA-rG-rA-mU-mU-rA-rG-mU-1T3-1T3-1T3-1T3-1T3-1T3-1T3-1T3 | 55 |
| ss33 | rG-rG-rA-mU-rG-rA-rA-rG-mU-rG-rG-rA-rG-rA-mU-mU-rA-rG-mU-1T3-1T3-Chol | 56 |
| ss34 | rG-rG-rA-mU-rG-rA-rA-rG-mU-rG-rG-rA-rG-rA-mU-mU-rA-rG-mU-1T3-1T3-1T3-1T3-Chol | 57 |
| ss35 | rG-rG-rA-mU-rG-rA-rA-rG-mU-rG-rG-rA-rG-rA-mU-mU-rA-rG-mU-1T3-1T3-1T3-1T3-1T3-Chol | 58 |
| ss36 | rG-rG-rA-mU-rG-rA-rA-rG-mU-rG-rG-rA-rG-rA-mU-mU-rA-rG-mU-1T3-1T3-1T3-1T3-1T3-1T3-1T3-Chol | 59 |

TABLE 15

Antisense strands (5'→3')

| antisense strand # | Sense strands sequence | SEQ ID NO. |
|---|---|---|
| as2 | rA-rC-mU-rA-rA-rU-rC-rU-rC-mC-rA-rC-rU-rU-mC-rA-rU-rC-rC-dT*dT | 14 |
| as4 | rA-rC-mU-rA-rA-rU-rC-rU-rC-mC-rA-rC-rU-rU-mC-rA-rU-rC-rC-dT*dT-Chol | 60 |

TABLE 16 siRNAs with overhangs containing nucleotide analogs

| siRNA # | Sense strand # | Antisense strand # | # of 1T3 |
|---|---|---|---|
| siRNA-7 | ss7 | as2 | 0 |
| siRNA-28 | ss26 | as2 | 0 |
| siRNA-29 | ss27 | as2 | 2 |
| siRNA-30 | ss28 | as2 | 4 |
| siRNA-31 | ss29 | as2 | 5 |
| siRNA-32 | ss30 | as2 | 6 |
| siRNA-33 | ss31 | as2 | 7 |
| siRNA-34 | ss32 | as2 | 8 |
| siRNA-35 | ss33 | as2 | 2 |
| siRNA-36 | ss27 | as4 | 2 |
| siRNA-37 | ss34 | as2 | 4 |
| siRNA-38 | ss28 | as4 | 4 |
| siRNA-39 | ss35 | as2 | 6 |
| siRNA-40 | ss30 | as4 | 6 |
| siRNA-41 | ss36 | as2 | 8 |
| siRNA-42 | ss32 | as4 | 8 |
| siRNA-43 | ss29 | as4 | 5 |
| siRNA-44 | ss31 | as4 | 7 |

TABLE 17

Sense strands (5'→3')

| sense strand # | Sense strands sequence | SEQ ID NO. |
|---|---|---|
| ss7 | rG-rG-rA-mU-rG-rA-rA-rG-mU-rG-rG-rA-rG-rA-mU-mU-rA-rG-mU-dT*dT | 7 |
| ss26 | rG-rG-rA-mU-rG-rA-rA-rG-mU-rG-rG-rA-rG-rA-mU-mU-rA-rG-mU-dT-dT | 29 |
| ss37 | rG-rG-rA-mU-rG-rA-rA-rG-mU-rG-rG-rA-rG-rA-mU-mU-rA-rG-mU-1T3b-1T3b | 35 |
| ss38 | rG-rG-rA-mU-rG-rA-rA-rG-mU-rG-rG-rA-rG-rA-mU-mU-rA-rG-mU-1T3b-1T3b-1T3b-1T3b | 61 |
| ss39 | rG-rG-rA-mU-rG-rA-rA-rG-mU-rG-rG-rA-rG-rA-mU-mU-rA-rG-mU-1T3b-1T3b-1T3b-1T3b-1T3b-1T3b | 62 |
| ss40 | rG-rG-rA-mU-rG-rA-rA-rG-mU-rG-rG-rA-rG-rA-mU-mU-rA-rG-mU-1T3b-1T3b-1T3b-1T3b-1T3b-1T3b-1T3b-1T3b | 63 |
| ss41 | rG-rG-rA-mU-rG-rA-rA-rG-mU-rG-rG-rA-rG-rA-mU-mU-rA-rG-mU-1T3b-1T3b-Chol | 64 |
| ss42 | rG-rG-rA-mU-rG-rA-rA-rG-mU-rG-rG-rA-rG-rA-mU-mU-rA-rG-mU-1T3b-1T3b-1T3b-1T3b-Chol | 65 |
| ss43 | rG-rG-rA-mU-rG-rA-rA-rG-mU-rG-rG-rA-rG-rA-mU-mU-rA-rG-mU-1T3b-1T3b-1T3b-1T3b-1T3b-1T3b-Chol | 66 |

TABLE 18 siRNAs with overhangs containing nucleotide analogs

| siRNA # | Sense strand # | Antisense strand # | # of lT3b |
|---|---|---|---|
| siRNA-45 | ss37 | as2 | 2 |
| siRNA-46 | ss38 | as2 | 4 |
| siRNA-47 | ss39 | as2 | 6 |
| siRNA-48 | ss40 | as2 | 8 |
| siRNA-49 | ss41 | as2 | 2 |
| siRNA-50 | ss37 | as4 | 2 |
| siRNA-51 | ss42 | as2 | 4 |
| siRNA-52 | ss38 | as4 | 4 |
| siRNA-53 | ss43 | as2 | 6 |
| siRNA-54 | ss39 | as4 | 6 |
| siRNA-55 | ss40 | as4 | 8 |

Description

Based on an AHA-1 sequence, 3'-end overhangs at the sense strand were attached using pre-lT3- or pre-lT3b-nucleotide precursors. For both nucleotide analogs, up to eight lT3- or lT3b-nucleotides were attached to the sense strand, in some example compounds with an additional cholesterol substituent (see chapter of oligonucleotide syntheses). The synthesized sense strands for both series are listed in Table 14 (lT3-containing 3'-overhangs) and Table 17 (lT3b-containing 3'-overhangs).

The above described sense strands were combined with the antisense strands as2 and as4 (see Table 15), yielding the corresponding double strands siRNA-29-siRNA-44 (lT3-overhangs, Table 16) and siRNA-45-siRNA-55 (lT3b-overhangs, Table 18).

The obtained siRNAs were transfected in human HepG2 cells at 5 nM concentrations. The AHA1-mRNA concentration was determined after 48 h.

Figure 2:
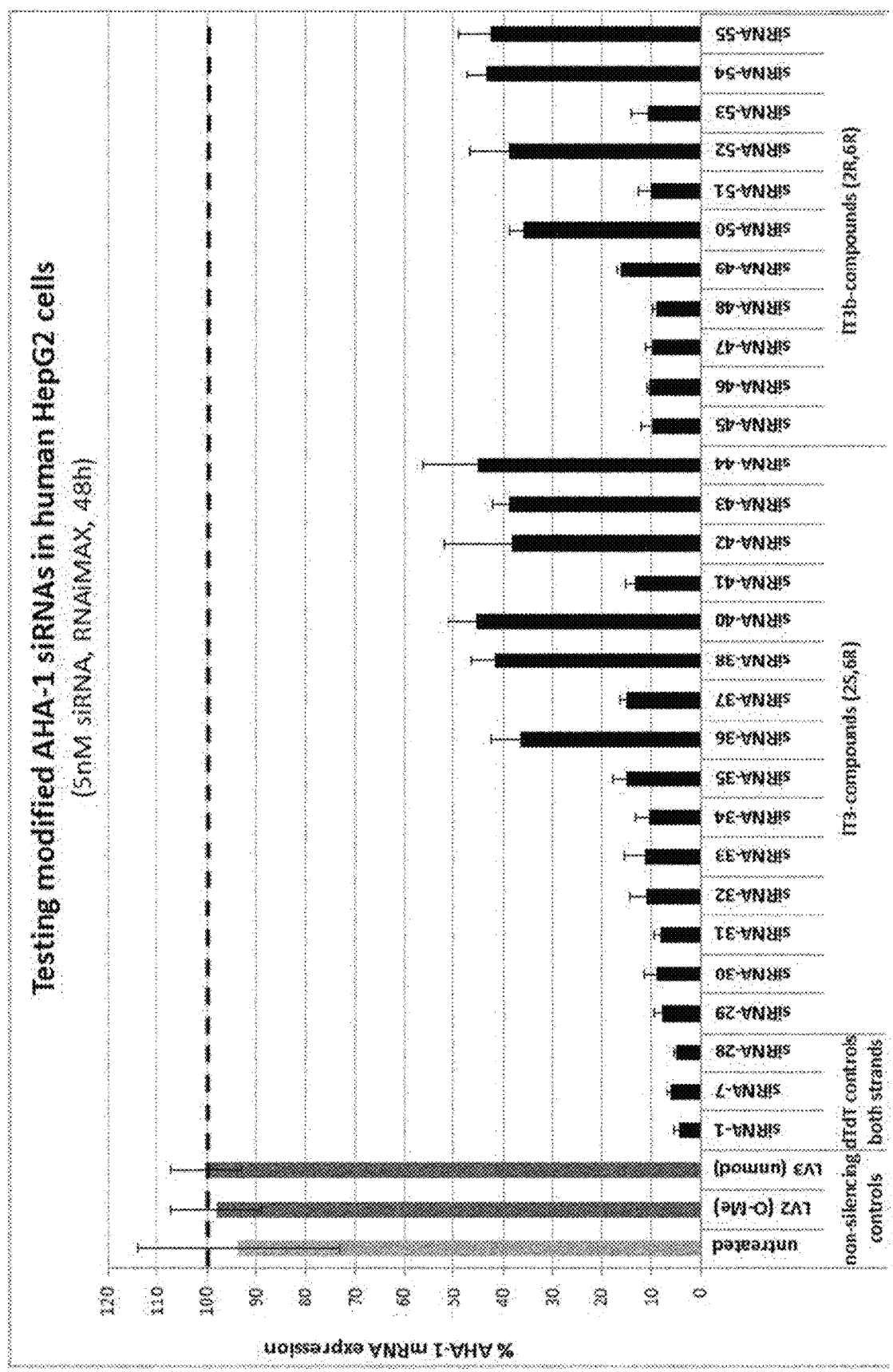
FIG. 2: In vitro knock-down of siRNAs 29 to 55 with IT3- and IT3b-overhangs with or without additional cholesterol-substitution
  Ordinate: percent AHA-1 expression in transfected HepG2 cells relative to the control
  Abscissa: siRNA-#

As can be seen in FIG. 2, the AHA-1 control siRNAs, siRNA-7 and siRNA-28 show a similar mRNA-knock down between 90 and 95%. Compared to these molecules, almost all siRNAs with lT3- or lT3b-modifications still show satisfying knock-down behaviour with inhibitions >85%. Only those siRNAs with as4 as antisense strand with an additional cholesterol-substituent at the 3'-end show a significant loss of inhibitory potency, whereas all siRNAs with modified sense strands still show very high in-vitro knock-down. Surprisingly, the number of lT3- or lT3b-nucleotides does not make a difference on the inhibitory potency of then corresponding siRNAs. Even the siRNAs with 8 lT3- or lT3b-nucleotides as3'-overhangs (siRNA-34 and siRNA-48) show a robust down regulation of the AHA1-mRNA. Also the attachment of an additional cholesterol substituent in the 3'-overhangs at the sense strands does not show a significant change in the potency of the molecules.

All siRNAs (siRNA29 to siRNA55) with lT3- or lT3b-overhangs were tested with in IFNα- and cytotoxicity assay and did not show any effects on immune stimulation or cell viability.

Example 4: In Vivo Inhibition of a Target Gene Expression with Modified siRNAs According to the Present Disclosure The sequences contained in tables 19 to 21 have been used

TABLE 19 sense strands (5'→3') with lgT-overhangs

| ss-# | Sense strands sequence | SEQ ID NO. |
|---|---|---|
| ss1-1 | 1gT2-1gT2-1gT2-fA-mA-fC-mA-fG-mU-fG-mU-fU-fC-fU-mU-fG-mC-fU-mC-fU-mA-fU-mA-fA | 67 |
| ss1-2 | fA*mA*fC-mA-fG-mU-fG-mU-fU-fC-fU-mU-fG-mC-fU-mC-fU-mA-fU-mA-fA-1gT2-1gT2-1gT2 | 68 |
| ss1-3 | 1gT5-1gT5-1gT5-fA-mA-fC-mA-fG-mU-fG-mU-fU-fC-fU-mU-fG-mC-fU-mC-fU-mA-fU-mA-fA | 69 |
| ss1-4 | fA*mA*fC-mA-fG-mU-fG-mU-fU-fC-fU-mU-fG-mC-fU-mA-fU-mA-fA-1gT5-1gT5-1gT5 | 70 |
| ss1-5 | 1gT1-1gT1-1gT1-fA-mA-fC-mA-fG-mU-fG-mU-fU-fC-fU-mU-fG-mC-fU-mC-fU-mA-fU*mA*fA | 71 |
| ss1-6 | 1gT1-1gT1-1gT1-fA-mA-fC-mA-fG-mU-fG-mU-fU-fC-fU-mU-fG-mC-fU-mC-fU-mA-fU-mA-fA | 72 |
| ss1-7 | fA*mA*fC-mA-fG-mU-fG-mU-fU-fC-fU-mU-fG-mC-fU-mC-fU-mA-fU-mA-fA-1gT1-1gT1-1gT1 | 73 |
| ss1-8 | 1gT3-1gT3-1gT3-fA-mA-fC-mA-fG-mU-fG-mU-fU-fC-fU-mU-fG-mC-fU-mC-fU-mA-fU*mA*fA | 74 |
| ss1-9 | 1gT3-1gT3-1gT3-fA-mA-fC-mA-fG-mU-fG-mU-fU-fC-fU-mU-fG-mC-fU-mC-fU-mA-fU-mA-fA | 75 |
| ss1-10 | fA*mA*fC-mA-fG-mU-fG-mU-fU-fC-fU-mU-fG-mC-fU-mC-fU-mA-fU-mA-fA-1gT3-1gT3-1gT3 | 76 |

TABLE 19-continued sense strands (5'→3') with 1gT-overhangs

| ss-# | Sense strands sequence | SEQ ID NO. |
|---|---|---|
| ss1-11 | 1gT4-1gT4-1gT4-fA-mA-fC-mA-fG-mU-fG-mU-fU-fC-fU-mU-fG-mC-fU-mC-fU-mA-fU*mA*fA | 77 |
| ss1-12 | fA*mA*fC-mA-fG-mU-fG-mU-fU-fC-fU-mU-fG-mC-fU-mC-fU-mA-fU-mA-fA-1gT4-1gT4-1gT4 | 78 |

TABLE 20 antisense strand (5'→3')

| as-# | Sense strands sequence | SEQ ID NO. |
|---|---|---|
| as1-1 | mU*fU*mA-fU-mA-fG-mA-fG-mC-fA-mA-mG-mA-fA-mC-fA-mC-fU-mG-fU-mU*mU*mU | 79 |

TABLE 21 siRNAs with IT-GalNAc-overhangs

| siRNA-# | ss-# | as-# |
|---|---|---|
| siRNA1-1 | ss1-1 | as1-1 |
| siRNA1-2 | ss1-2 | as1-1 |
| siRNA1-3 | ss1-3 | as1-1 |
| siRNA1-4 | ss1-4 | as1-1 |
| siRNA1-5 | ss1-5 | as1-1 |
| siRNA1-6 | ss1-6 | as1-1 |
| siRNA1-7 | ss1-7 | as1-1 |
| siRNA1-8 | ss1-8 | as1-1 |
| siRNA1-9 | ss1-9 | as1-1 |
| siRNA1-10 | ss1-10 | as1-1 |
| siRNA1-11 | ss1-11 | as1-1 |
| siRNA1-12 | ss1-12 | as1-1 |

In Vivo Example 4.1

Demonstration of in vivo activity of GalNAc-siRNA conjugates and comparison of impact of different siRNA building blocks for GalNAc attachment on RNA interfering activity Methods:

C57BL/6N mice (female 20-22 g; Charles River, Germany) were treated subcutaneously with a single dose of 2.5 mpk of siRNA1-1 to siRNA1-12 or PBS (mock control) in groups of n=5. Sequences and chemical composition of administered compounds are listed in Table 19 to Table 21. Blood samples were drawn pre- and post-dosing as indicated in FIG. 1.1. siRNA target TTR was quantified from serum by a commercially available ELISA assay (Alpco Diagnostics, Cat. no.: 41-PALMS-E01).

Results

Figure 3A:
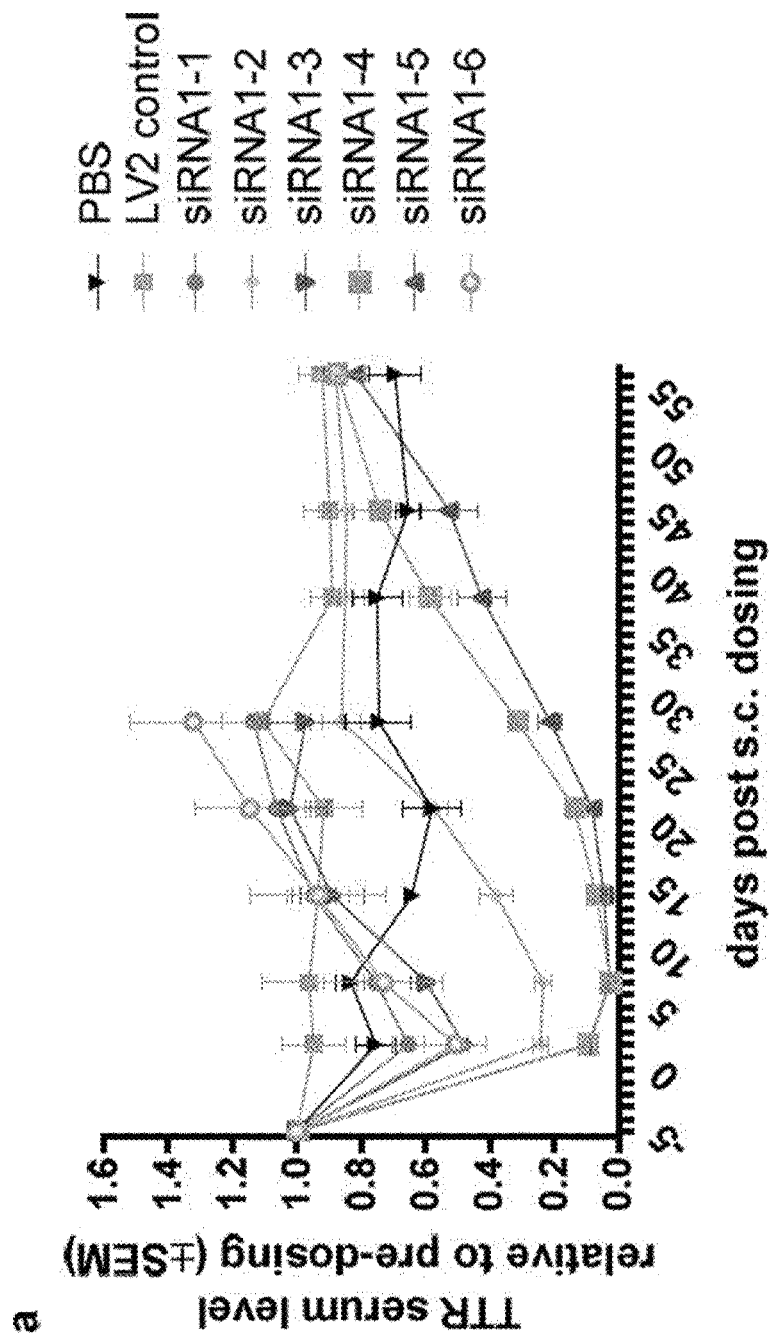
FIGS. 3a and 3b: Relative TTR protein serum levels at blood sampling time points pre-/post s.c. dosing of substances as indicated in X-axis labels
  Ordinate: TTR serum level relative to pre-dosing+/−SEM
  Abscissa: days post-subcutaneous dosing
Figure 3B:
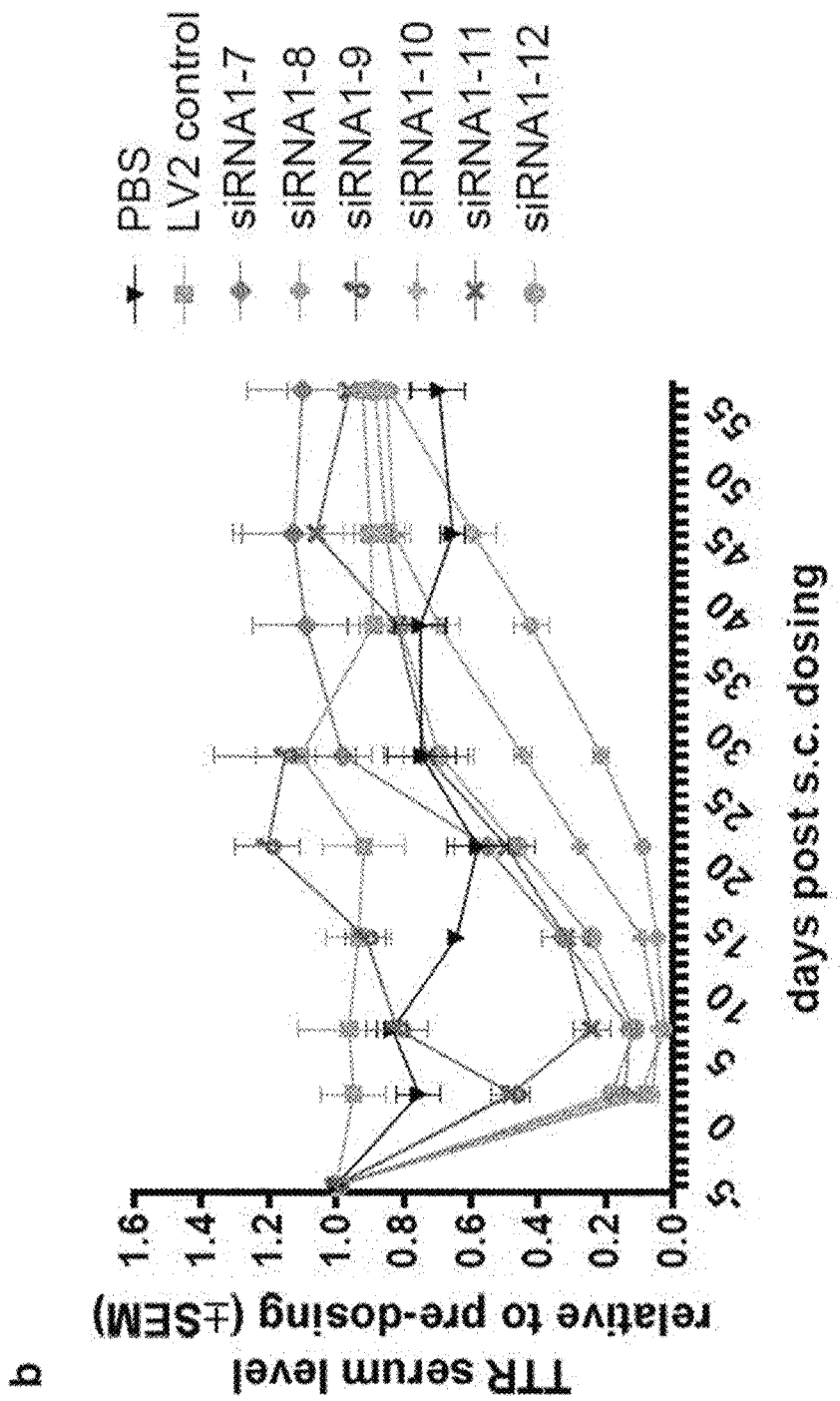

As can be seen from FIGS. 3a/b, the siRNAs without a double PS-stabilized 3'-end of the sense strand (siRNA1-1, siRNA1-3, siRNA1-6 and siRNA1-9) show only very weak knock-down and return to baseline within approximately 2 weeks.

In contrast, in all remaining molecules the attachment of three lgT-nucleotides (lgT=lgT1, lgT2, lgT3, lgT4 and lgT5) lead to a robust knock-down of the TTR-target mRNA and therefore to a robust delivery into the hepatocytes. Quite unexpectedly, the lgT-siRNA-conjugates show an interesting SAR between their in vivo duration of action and the linker unit, by which the GalNAc-targeting ligand is attached to the morpholine nitrogen atom of the lgT-scaffold. In addition, an interesting correlation between the attachment site of the lgT-scaffolds to the sense strand can be deduced (3'-vs. 5'-end).

There is a clear advantage of 5'-end attachment over the 3'-end conjugates. As it is shown in FIGS. 3a/b, the 5'-end attachment of e.g. lgT1 and lgT3 (siRNA1-5 and siRNA1-8) show a significant longer duration of action as their 3'-end analogs (siRNA1-7 and siRNA1-10 respectively).

In addition it was found that longer linkers between the morpholine- and the GalNAc perform weaker than their shorter analogs e. g. siRNA1-11, which has a C12-alkyl-linked lgT4-scaffold shows shorter duration of action times than the analogs siRNA1-8 with a C5-alkyl linker in the lgT3-building block. When both are attached at the 5'-end of the sense strand, there is a clear benefit by using the shorter lgT3-nucleotide analog.

In addition, the lgT5-containing siRNA1-4, with a PEG-type linker between the morpholine- and the GalNAc-moiety showed a very attractive in vivo potency and duration of action.

In Vivo Example 4.2

Dose dependent in vivo activity and acute toxicity assessment of selected compounds from in vivo example 4.1

Methods

Animal Study

C57BL/6N mice (female 20-22 g; Charles River, Germany) were treated subcutaneously with a single dose of 0.5, 2.5 or 20 mpk of siRNA or PBS (mock control) in groups of n=6 (for 0.5 and 2.5 mpk) or n=4 (for 20 mpk). Sequences and chemical composition of administered compounds are referenced in Table 19 to Table 21. Animals were taken down 48 h post treatment, blood drawn for hematology analysis, clinical chemistry and organs harvested and weighed. Blood count was performed on a scil Vet animal blood counter and clinical chemistry analysis on a Roche Cobas system.

Post Study Analysis siRNA target TTR was quantified from serum by a commercially available ELISA assay (Alpco Diagnostics, Cat. no.: 41-PALMS-E01).

Liver tissue was processed for RT-qPCR analysis by total RNA extraction including DNase digest (RNAeasy Mini Kit, Qiagen). TTR (TaqMan assay ID Mm00443267_m1) and reference mRNA (Actb (TaqMan assay ID 4352341E), Gapdh (TaqMan assay ID 4308313)) was quantified by qPCR on an ABI Prism 7900 system following Oligo-dT and Random Hexamer primed cDNA synthesis. The ΔΔCt method was applied to calculate relative expression levels of the target transcripts.

The upper right liver lobe, spleen and kidneys of 20 mpk treatment groups (+PBS) were Formalin fixed and pathologically evaluated for abnormalities following standard H&E staining.

Figure 4:
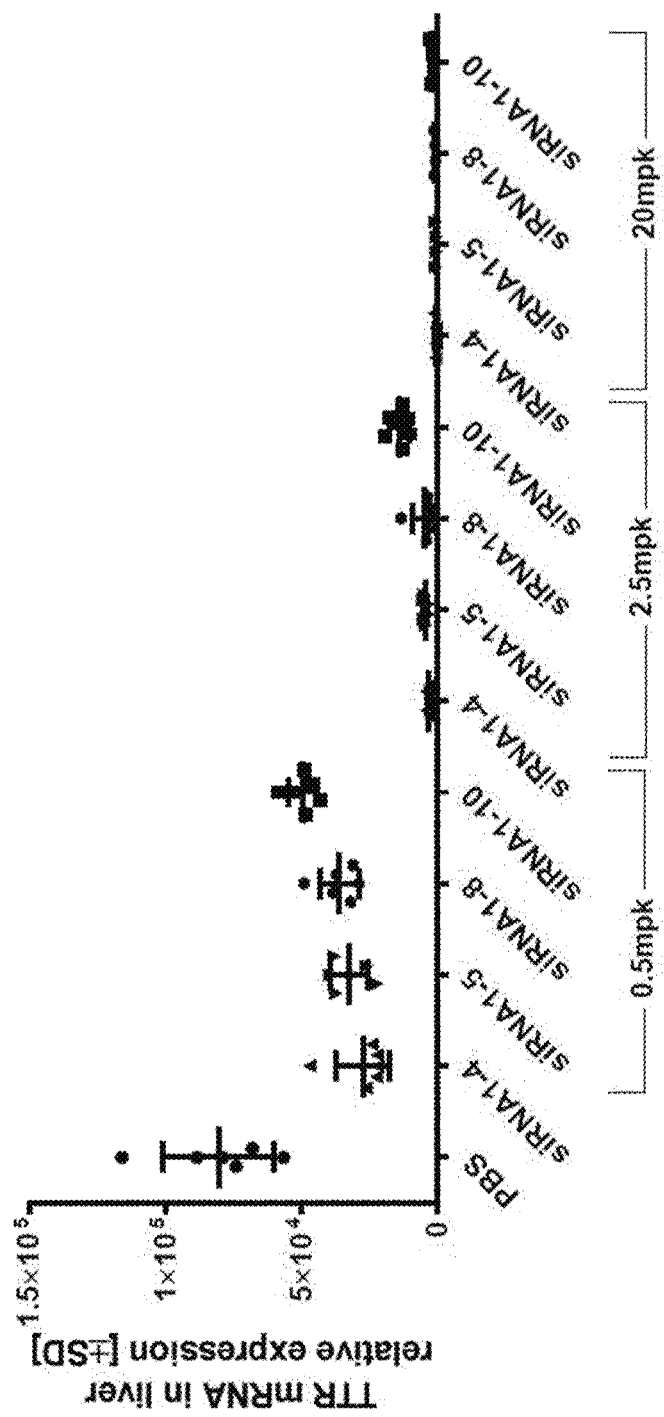
FIG. 4: Relative TTR mRNA expression levels in liver at study take-down 48 h post s.c. dosing of substances as indicated in X-axis labels
  Ordinate: TTR mRNA in liver relative expression+/−SD
  Abscissa: siRNA-#, dose
Figure 5:
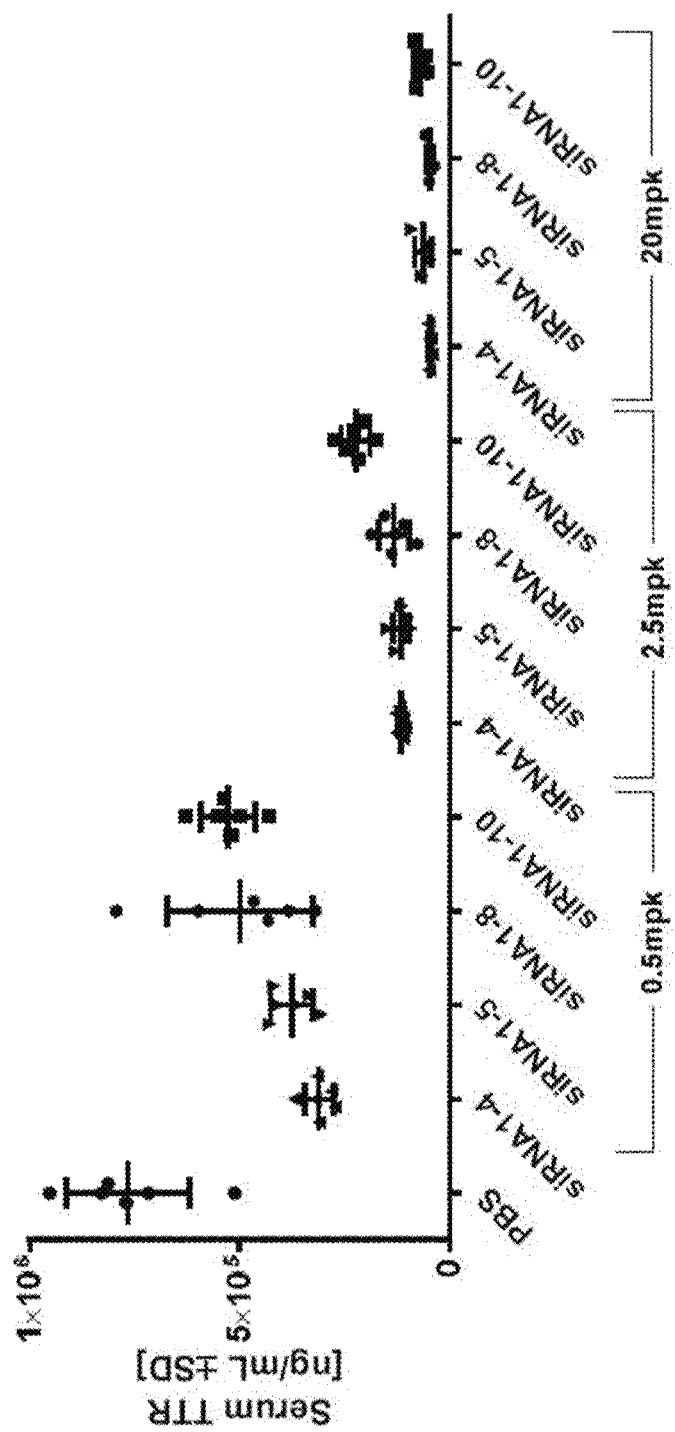
FIG. 5: TTR protein serum levels at study take-down 48 h post s.c. dosing of substances as indicated in X-axis labels
  Ordinate: serum TTR concentration as expressed in ng/ml+/−SD
  Abscissa: siRNA-#, dose

Results (See FIGS. 4 and 5)

Both protein and mRNA levels were reduced by all tested active siRNAs in a dose dependent manner at 48 h post dosing. mRNA and protein reduction occurred in a paralleled fashion. Within the tested active substances, no significant differences were observed between siRNA1-4, 1-5 and 1-8, while siRNA1-10 displayed a slightly less pronounced efficacy compared to the former ones, particularly at 0.5 and 2.5 mpk treatment doses. This matches the observations from the longitudinal study shown in Figure. 4.

No treatment and dose dependent effects were observed in standard hematology and liver/kidney clinical chemistry assays. Also, no significant treatment dependent alterations of serum cytokines and effects on organ or body weight were observed at take down. All deviations were within normal physiological range or normal inter-animal variability. Histopathology evaluation of liver, spleen and kidneys were without findings.

The in vitro knock-down results in primary mouse hepatocytes of the compounds siRNA1-1 to siRNA1-12 are summarized in Table 22:

TABLE 22

$IC_{50}$-data of siRNAs 1-1 to 1-12 in primary mouse hepatocytes

| siRNA-# | $IC_{50}$ (pM) | Imax % |
| --- | --- | --- |
| siRNA1-1 | 1160 | 96.5% |
| siRNA1-2 | 595 | 98.6% |
| siRNA1-3 | 468 | 97.9% |
| siRNA1-4 | 106 | 99.5% |
| siRNA1-5 | 74 | 100.2% |
| siRNA1-6 | 180 | 99.4% |
| siRNA1-7 | 31 | 99.9% |
| siRNA1-8 | 99 | 100.1% |
| siRNA1-9 | 194 | 99.1% |
| siRNA1-10 | 84 | 98.9% |
| siRNA1-11 | 1550 | 98.7% |
| siRNA1-12 | 1920 | 97.2% |

All siRNAs (siRNA1-1 to siRNA1-12) with 1gT-overhangs were tested with in IFNα- and cytotoxicity assay and did not show any effects on immune stimulation or cell viability.

Example 5: In Vivo Inhibition of a Target Gene Expression with Modified siRNAs According to the Present Disclosure In Vivo Example 5.1

Demonstration of in vivo activity of GalNAc-siRNA conjugates and comparison of impact of different double strand layouts and combinations on RNA interfering activity.

Methods

C57BL/6N mice (female 20-22 g; Charles River, Germany) were treated subcutaneously with a single dose of 1 mpk of GalNAc-siRNA (+2.5 mpk for siRNA1-8 for comparison to in vivo example 1) or PBS (mock control) in groups of n=5. Sequences and chemical composition of administered compounds are listed in Table 23 to Table 25. Blood samples were drawn pre- and post-dosing as indicated in FIG. 6. SiRNA target TTR was quantified from serum by a commercially available ELISA assay (Alpco Diagnostics, Cat. no.: 41-PALMS-E01).

TABLE 23 sense strands (5'→3') with 1gT- and 1T-overhangs

| ss-# | Sense strands sequence | remark | SEQ ID NO. |
| --- | --- | --- | --- |
| ss2-0 | 1gT3-1gT3-1gT3-fA-mU-fC-mG-fU-mA-fC-mG-fU-mA-fC-mC-fG-mU-fC-mG-fU*mA*fU | LV-2 neg. control | 80 |
| ss1-8 | 1gT3-1gT3-1gT3-fA-mA-fC-mA-fG-mU-fG-mU-fU-fC-fU-mU-fG-mC-fU-mC-fU-mA-fU*mA*fA | pos. control | 74 |
| ss2-2 | 1gT3-1gT3-1gT3-fA-mA-fC-mA-fG-mU-fG-mU-fU-fC-fU-mU-fG-mC-fU-mC-fU-mA-fU-mA-fA-1T1-1T1 | | 81 |
| ss2-3 | 1gT3-1gT3-1gT3-fA-mA-fC-mA-fG-mU-fG-mU-fU-fC-fU-mU-fG-mC-fU-mC-fU-mA-fU-mA-fA-1T2-1T2 | | 82 |
| ss2-4 | 1gT3-1gT3-1gT3-fA-mA-fC-mA-fG-mU-fG-mU-fU-fC-fU-mU-fG-mC-fU-mC-fU-mA-fU-mA-fA-1T3-1T3 | | 83 |
| ss2-5 | 1gT3-1gT3-1gT3-fA-mA-fC-mA-fG-mU-fG-mU-fU-fC-fU-mU-fG-mC-fU-mC-fU-mA-fU-mA4A-1T4-1T4 | | 84 |
| ss2-6 | 1gT3-1gT3-1gT3-fA-mA-fC-mA-fG-mU-fG-mU-fU-fC-fU-mU-fG-mC-fU-mC-fU-mA-fU-mA4A-1T5-1T5 | | 85 |
| ss2-7 | 1gT3-1gT3-1gT3-fA-mA-fC-mA-fG-mU-fG-mU-fU-fC-fU-mU-fG-mC-fU-mC-fU-mA-fU-mA-fA-1T6-1T6 | | 86 |
| ss2-8 | 1gT3-1gT3-1gT3-fA-mA-fC-mA-fG-mU-fG-mU-fU-fC-fU-mU-fG-mC-fU-mC-fU-mA-fU-mA4A-1T7-1T7 | | 87 |
| ss2-9 | 1gT3-1gT3-1gT3-fA-mA-fC-mA-fG-mU-fG-mU-fU-fC-fU-mU-fG-mC-fU-mC-fU-mA-fU-mA-fA-1T8-1T8 | | 88 |
| ss2-10 | 1gT3-1gT3-1gT3-fA-mA-fC-mA-fG-mU-fG-mU-fU-fC-fU-mU-fG-mC-fU-mC-fU-mA-fU-mA-fA-1T9-1T9 | | 89 |
| ss2-11 | 1gT3-1gT3-1gT3-fA-mA-fC-mA-fG-mU-fG-mU-fU-fC-fU-mU-fG-mC-fU-mC-fU-mA-fU-mA-fA-1T10-1T10 | | 90 |

TABLE 24 antisense strands (5'→3') with 1T-overhangs

| as-# | Sense strands sequence | remark | SEQ ID NO. |
| --- | --- | --- | --- |
| as2-0 | fA*fU*mA-fC-mG-fA-mC-fG-mG-fU-mA-fC-mG-fU-mA-fC-mG-fA-mU*dT*dT | LV-2 | 91 |
| as1-1 | mU*fU*mA-fU-mA-fG-mA-fG-mC-fA-mA-mG-mA-fA-mC-fA-mC-fU-mG-fU-mU*mU*mU | | 79 |
| as2-2 | mU*fU*mA-fU-mA-fG-mA-fG-mC-fA-mA-mG-mA-fA-mC-fA-mC-fU-mG-fU-mU-1T1-1T1 | | 92 |

TABLE 24-continued antisense strands (5'→3') with 1T-overhangs

| as-# | Sense strands sequence | re-mark | SEQ ID NO. |
|---|---|---|---|
| as2-3 | mU*fU*mA-fU-mA-fG-mA-fG-mC-fA-mA-mG-mA-fA-mC-fA-mC-fU-mG-fU-mU-1T2-1T2 | | 93 |
| as2-4 | mU*fU*mA-fU-mA-fG-mA-fG-mC-fA-mA-mG-mA-fA-mC-fA-mC-fU-mG-fU-mU-1T3-1T3 | | 94 |
| as2-5 | mU*fU*mA-fU-mA-fG-mA-fG-mC-fA-mA-mG-mA-fA-mC-fA-mC-fU-mG-fU-mU-1T4-1T4 | | 95 |
| as2-6 | mU*fU*mA-fU-mA-fG-mA-fG-mC-fA-mA-mG-mA-fA-mC-fA-mC-fU-mG-fU-mU-1T5-1T5 | | 96 |
| as2-7 | mU*fU*mA-fU-mA-fG-mA-fG-mC-fA-mA-mG-mA-fA-mC-fA-mC-fU-mG-fU-mU-1T6-1T6 | | 97 |
| as2-8 | mU*fU*mA-fU-mA-fG-mA-fG-mC-fA-mA-mG-mA-fA-mC-fA-mC-fU-mG-fU-mU-1T7-1T7 | | 98 |
| as2-9 | mU*fU*mA-fU-mA-fG-mA-fG-mC-fA-mA-mG-mA-fA-mC-fA-mC-fU-mG-fU-mU-1T9-1T9 | | 99 |

TABLE 25 siRNAs with lgT- and 1T-overhangs

| siRNA-# | ss-# | as-# | remark |
|---|---|---|---|
| siRNA2-0 | ss2-0 | as2-0 | neg. control |
| siRNA1-8 | ss1-8 | as1-1 | pos. control |
| siRNA2-2 | ss2-2 | as1-1 | |
| siRNA2-3 | ss2-2 | as2-2 | |
| siRNA2-4 | ss2-3 | as2-3 | |
| siRNA2-5 | ss2-4 | as1-1 | |
| siRNA2-6 | ss2-4 | as2-4 | |
| siRNA2-7 | ss2-5 | as2-5 | |
| siRNA2-8 | ss2-6 | as2-6 | |
| siRNA2-9 | ss2-7 | as2-7 | |
| siRNA2-10 | ss2-8 | as2-8 | |
| siRNA2-11 | ss2-9 | as2-4 | |
| siRNA2-12 | ss2-10 | as2-9 | |
| siRNA2-13 | ss2-11 | as2-4 | |

Results

Figure 6A:
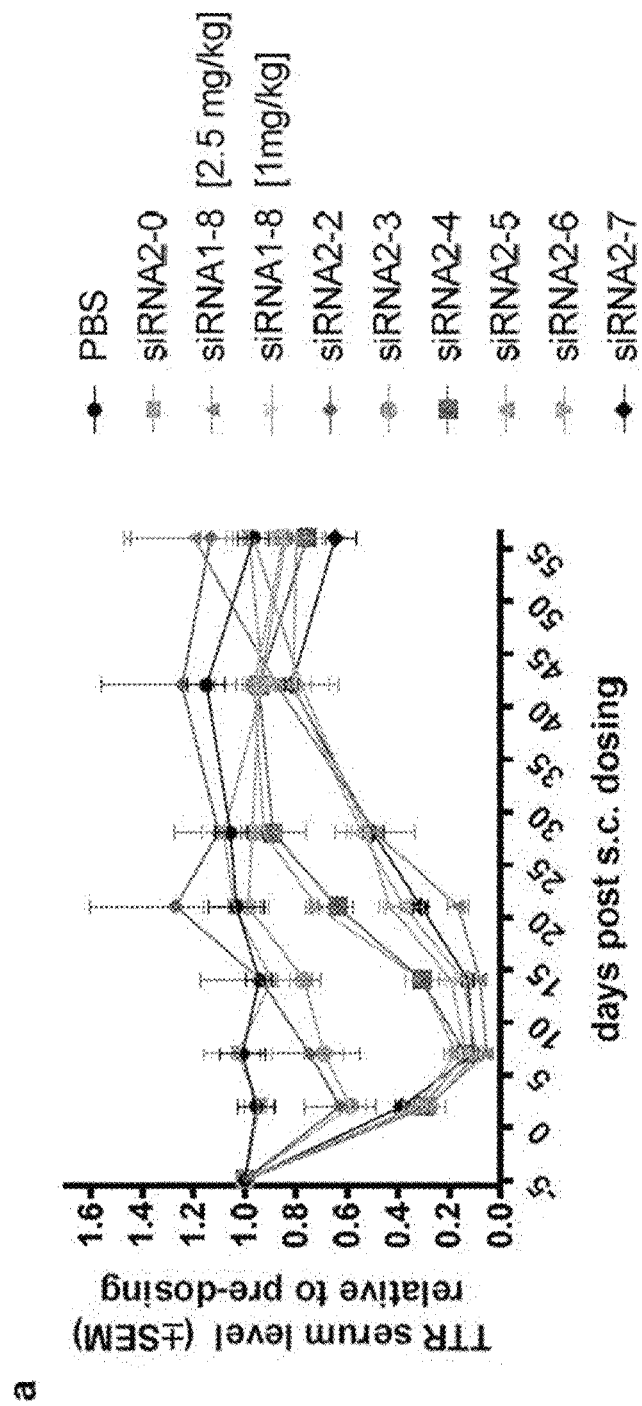
FIGS. 6a and 6b: Relative TTR protein serum levels at blood sampling time points post s.c. dosing of substances as indicated in X-axis labels
  Ordinate: TTR serum level relative to pre-dosing+/−SEM
  Abscissa: days post-subcutaneous dosing
Figure 6B:
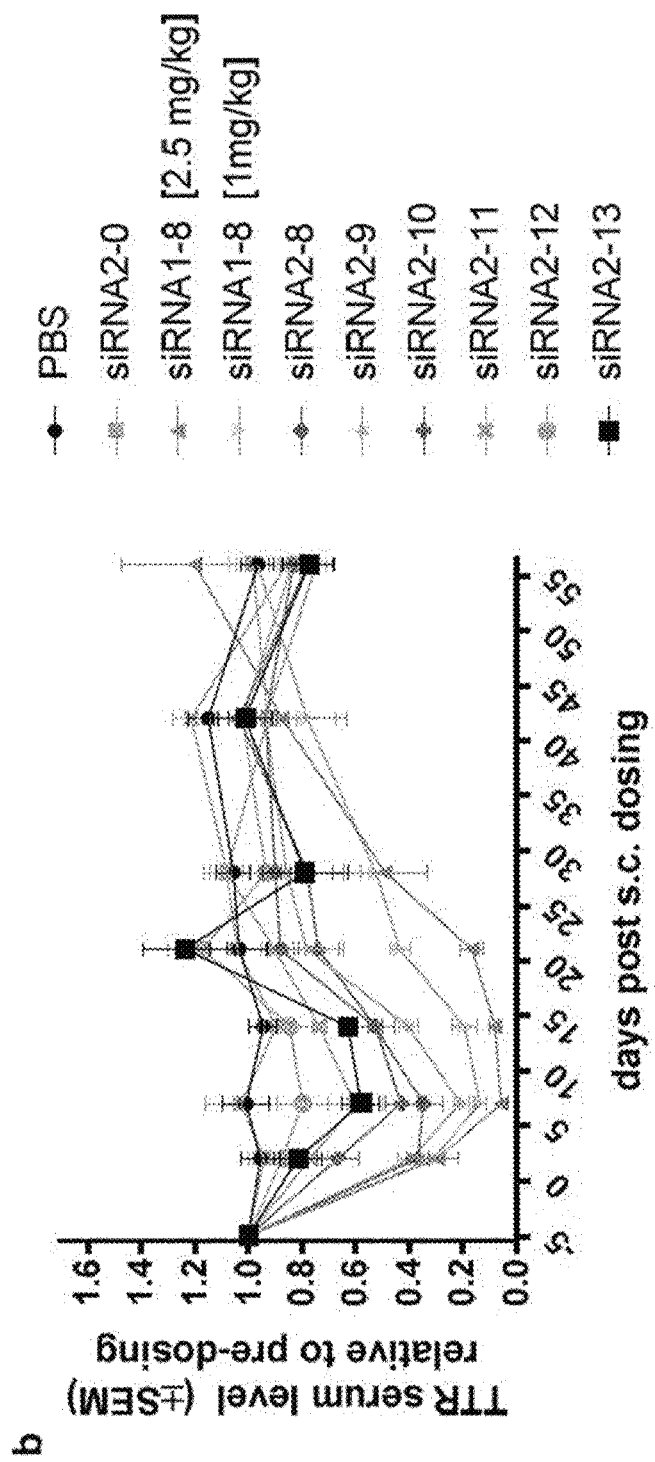

Compared to the control siRNA-8, which only has the lgT3-overhang at the 5'-end of the sense strand and no additional 1T-overhangs (1T=1T1 to 1T9) at the 3'-end of sense- or antisense strand, FIGS. 6a/b show, that siRNA2-5 with additional attachment of 1T3 at the 3'-end of the sense strand shows an equal in vivo performance than the control siRNA1-8, using a sense strand without any PS-groups, neither at the 5'-end nor at the 3'-end, where siRNA1-8 still has two PS-groups at the 3'-end.

An additional progress could be achieved with siRNA2-7, with a 1T4-1T4-overhang at the 3'-end of the sense strand and at the 3'-end of the antisense strand, again with a reduction of two PS-groups at the 1T4-attachment site of antisense strand as 2-5. SiRNA2-7 again shows equal in vivo potency and duration of action as siRNA1-8 with common PS-stabilization pattern at the sense and antisense strand.

In Vivo Example 5.2

Dose dependent in vivo activity and acute toxicity assessment have been determined for compounds selected from in vivo example 5.1.

Methods

Animal Study

C57BL/6N mice (female 20-22 g; Charles River, Germany) were treated subcutaneously with a single dose of 0.5, 2.5 or 25 mpk of siRNA or PBS (mock control) in groups of n=6 (for 0.5 and 2.5 mpk) or n=5 (for 25 mpk). Sequences and chemical composition of administered compounds are referenced in Table 23 to Table 25. Animals were taken down 48 h post treatment, blood drawn for hematology analysis, clinical chemistry and organs harvested and weighed. Hematology blood count was performed on a scil Vet animal blood counter and clinical chemistry analysis on a Roche Cobas system.

Post Study Analysis siRNA target TTR was quantified from serum by a commercially available ELISA assay (Alpco Diagnostics, Cat. no.: 41-PALMS-E01).

Liver tissue was processed for RT-qPCR analysis by total RNA extraction including DNase digest (RNAeasy Mini Kit, Qiagen). TTR (TaqMan assay ID Mm00443267_m1) and reference mRNA (Actb (TaqMan assay ID 4352341E), Gapdh (TaqMan assay ID 4308313)) was quantified by qPCR on an ABI Prism 7900 system following Oligo-dT and Random Hexamer primed cDNA synthesis. The $\Delta\Delta Ct$ method was applied to calculate relative expression levels of the target transcripts.

The upper right liver lobe, spleen and kidneys of 25 mpk treatment groups (+PBS) were Formalin fixed and pathologically evaluated for abnormalities following standard H&E staining.

Figure 7:
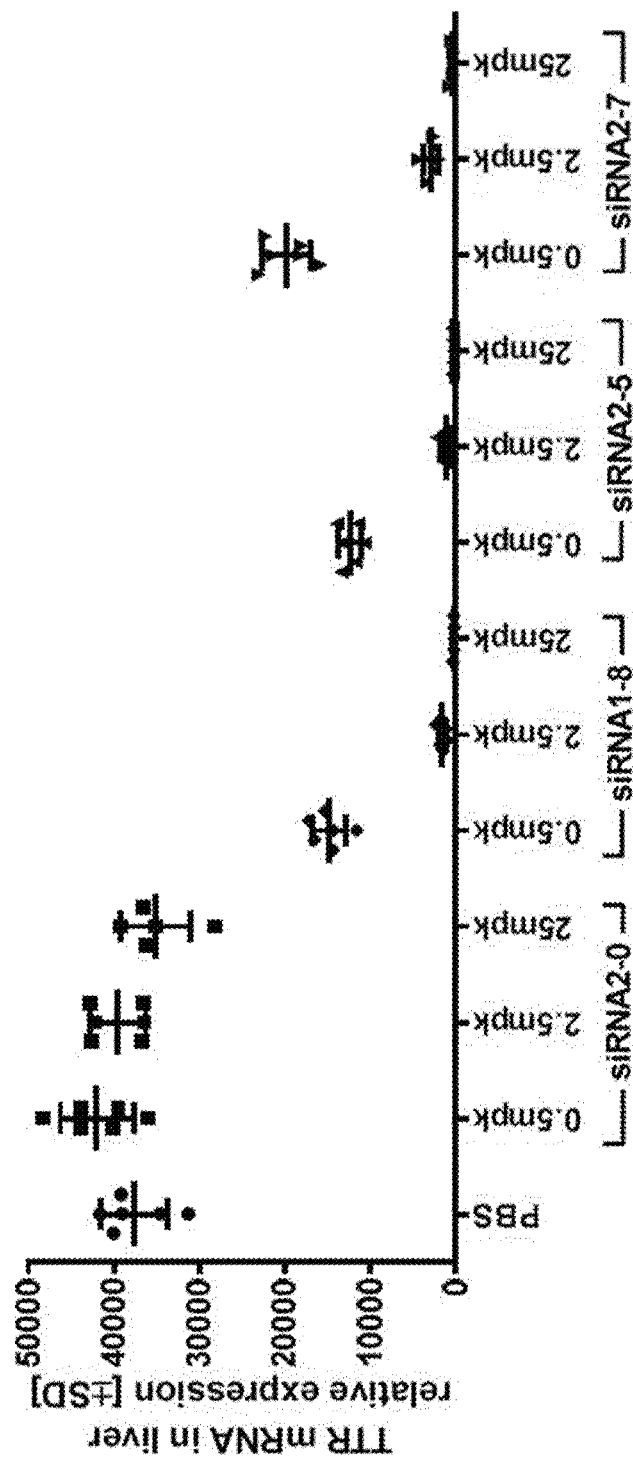
FIG. 7: Relative TTR mRNA expression levels in liver at study take-down 48 h post s.c. dosing of substances as indicated in X-axis labels
  Ordinate: TTR mRNA in liver relative expression+/−SD
  Abscissa: siRNA-#, dose
Figure 8:
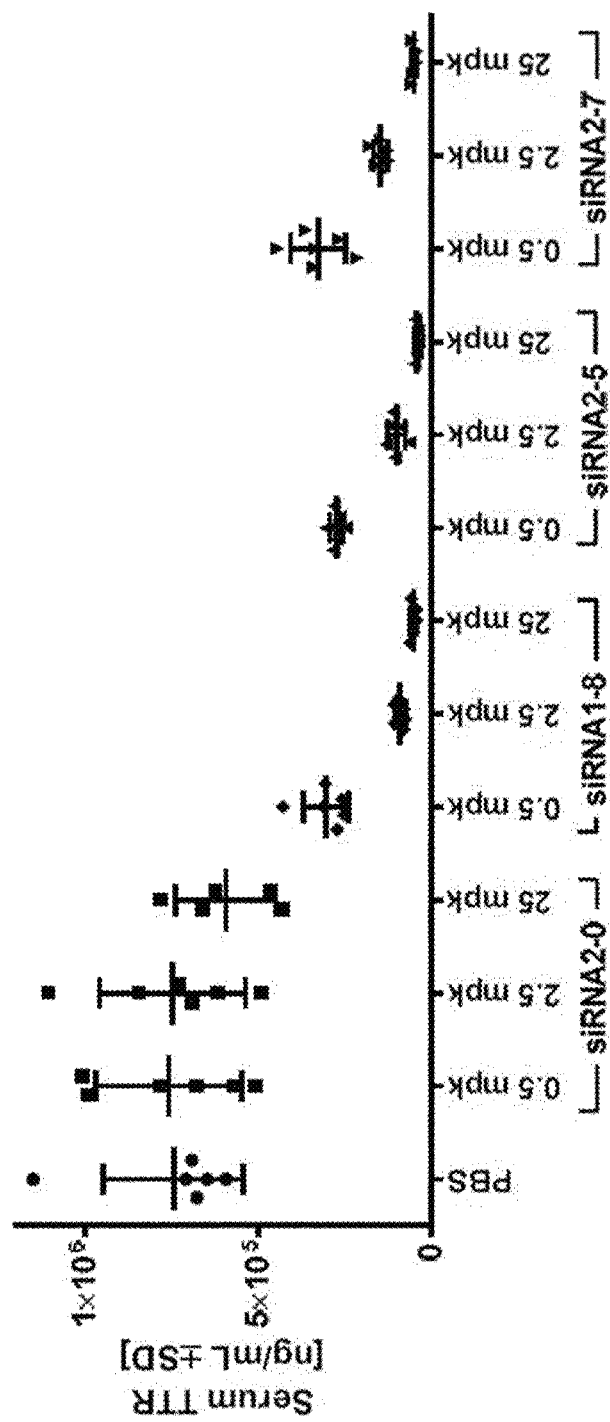
FIG. 8: TTR protein serum levels at study take-down 48 h post s.c. dosing of substances as indicated in X-axis labels
  Ordinate: serum TTR concentration as expressed in ng/ml+/−SD
  Abscissa: siRNA-#, dose

Results (See FIGS. 7 and 8)

Both protein and mRNA levels were reduced by all tested siRNAs in a dose dependent manner at 48 h post dosing. mRNA and protein reduction occurred in a paralleled fashion. Within the tested active substances, no significant differences were observed between siRNA1-8 and 2-5, while siRNA2-7 displayed a trend towards a slightly less pronounced efficacy compared to the former ones, particularly at 0.5 and 2.5 mpk treatment doses.

No treatment dose dependent effects were observed in standard hematology and liver/kidney clinical chemistry assays. Also, no significant treatment dependent alterations of serum cytokines and effects on organ or body weight were observed at take down. All deviations were within normal physiological range or normal inter-animal variability. Histopathology evaluation of liver and spleen were without findings.

The in vitro knock-down results obtained in primary mouse hepatocytes for the compounds siRNA2-2 to siRNA2-13 are summarized in Table 26:

TABLE 26

$IC_{50}$-data of siRNAs 2-2 to 2-13 in primary mouse hepatocytes

| siRNA-# | $IC_{50}$ (pM) | Imax % |
|---|---|---|
| siRNA1-8 | 24 | 98.8% |
| siRNA2-2 | 57 | 98.8% |
| siRNA2-3 | 170 | 97.3% |
| siRNA2-4 | 90 | 98.0% |
| siRNA2-5 | 39 | 98.7% |
| siRNA2-6 | 81 | 98.2% |

TABLE 26-continued

IC$_{50}$-data of siRNAs 2-2 to 2-13 in primary mouse hepatocytes

| siRNA-# | IC$_{50}$ (pM) | Imax % |
|---|---|---|
| siRNA2-7 | 177 | 97.4% |
| siRNA2-8 | 94 | 98.5% |
| siRNA2-9 | 136 | 97.3% |
| siRNA2-10 | 983 | 98.3% |
| siRNA2-11 | 4010 | 93.4% |
| siRNA2-12 | 220 | 97.0% |
| siRNA2-13 | 4010 | 99.1% |

All siRNAs (siRNA-8, siRNA2-2 to siRNA2-13) with lgT- and 1T-overhangs were tested with in IFNα- and cytotoxicity assay and did not show any effects on immune stimulation or cell viability.

In Vitro Stabilities

As it is shown in Table 27, the replacement of PS-stabilized sense- or antisense 3'-ends by the attachment of 1T-overhangs is leading to increased in vitro stability.

TABLE 27

| siRNA# | 0 h | 4 h | 8 h | 16 h | 24 h | 32 h | 48 h | 56 h | 72 h | 80 h | 96 h |
|---|---|---|---|---|---|---|---|---|---|---|---|
| siRNA1-8 | | | | | | | X | X | X | X | X |
| siRNA2-2 | | | | | | | X | X | X | X | X |
| siRNA2-3 | | | | | | | X | X | X | X | X |
| siRNA2-4 | | | | | | | | X | X | X | X |
| siRNA2-5 | | | | | | | | | X | X | X |
| siRNA2-6 | | | | | | | X | X | X | X | X |
| siRNA2-7 | | | | | | | | X | X | X | X |
| siRNA2-8 | | | | | | | X | X | X | X | X |
| siRNA2-9 | | | | | | | | | X | X | X |
| siRNA2-10 | | | | | | | X | X | X | X | X |
| siRNA2-11 | | | | | | | | | | | X |
| siRNA2-12 | | | | | | | X | X | X | X | X |
| siRNA2-13 | | | | | | | | | | | X |

In Table 27, "X" means that the remaining amount of one of both strands is less than 50%.

All 1T-modified siRNAs show at least the same stability as the control compound siRNA1-8 of 32 h. Again, those ends in siRNAs 42-2 to 2-13, where 1T-overhangs are attached do not contain any additional PS-stabilization. Changing the 3'-end modification of the sense strand from PS-stabilization to a double 1T3-overhang (siRNA2-5) increases the stability significantly from 32 h to 56 h. Even the attachment of an 1T4-overhang at the 3'-end of both strands increases the siRNA2-7 to 48 h.

Example 6: In Vivo Inhibition of a Target Gene Expression with Modified siRNAs According to the Present Disclosure

TABLE 28 sense strands (5'→3') with 1gT- and 1T-overhangs

| ss-# | Sense strands sequence | re-mark | SEQ ID NO. |
|---|---|---|---|
| ss2-0 | 1gT3-1gT3-1gT3-fA-mU-fC-mG-fU-mA-fC-mG-fU-mA-fC-mC-fG-mU-fC-mG-fU*mA*fU | negative control | 80 |

TABLE 28-continued sense strands (5'→3') with 1gT- and 1T-overhangs

| ss-# | Sense strands sequence | re-mark | SEQ ID NO. |
|---|---|---|---|
| ss1-8 | 1gT3-1gT3-1gT3-fA-mA-fC-mA-fG-mU-fG-mU-fU-fC-fU-mU-fG-mC-fU-mC-fU-mA-fU*mA*fA | positive control | 74 |
| ss3-1 | fA*mA*fC-mA-fG-mU-fG-mU-fU-fC-fU-mU-fG-mC-fU-mC-fU-mA-fU-mA-fA-1gT5-1gT5-1gT5 | =ss1-4 | 100 |
| ss3-2 | fA*mA*fC-mA-fG-mU-fG-mU-fU-fC-fU-mU-fG-mC-fU-mC-fU-mA-fU-mA-fA-1gT6-1gT6-1gT6 | | 101 |
| ss3-3 | fA*mA*fC-mA-fG-mU-fG-mU-fU-fC-fU-mU-fG-mC-fU-mC-fU-mA-fU-mA-fA-1gT7-1gT7-1gT7 | | 102 |
| ss3-4 | fA*mA*fC-mA-fG-mU-fG-mU-fU-fC-fU-mU-fG-mC-fU-mC-fU-mA-fU-mA-fA-1gT8-1gT8-1gT8 | | 103 |
| ss3-5 | fA*mA*fC-mA-fG-mU-fG-mU-fU-fC-fU-mU-fG-mC-fU-mC-fU-mA-fU-mA-fA-1gT9-1gT9-1gT9 | | 104 |
| ss3-6 | 1gT5-1gT5-1gT5-fA-mA-fC-mA-fG-mU-fG-mU-fU-fC-fU-mU-fG-mC-fU-mC-fU-mA-fU*mA*fA | | 105 |
| ss3-7 | 1gT6-1gT6-1gT6-fA-mA-fC-mA-fG-mU-fG-mU-fU-fC-fU-mU-fG-mC-fU-mC-fU-mA-fU*mA*fA | | 106 |
| ss3-8 | 1gT7-1gT7-1gT7-fA-mA-fC-mA-fG-mU-fG-mU-fU-fC-fU-mU-fG-mC-fU-mC-fU-mA-fU*mA*fA | | 107 |
| ss3-9 | 1gT8-1gT8-1gT8-fA-mA-fC-mA-fG-mU-fG-mU-fU-fC-fU-mU-fG-mC-fU-mC-fU-mA-fU*mA*fA | | 108 |

TABLE 28-continued sense strands (5'→3') with lgT- and
1T-overhangs

| ss-# | Sense strands sequence | re-mark | SEQ ID NO. |
|---|---|---|---|
| ss3-10 | lgT9-lgT9-lgT9-fA-mA-fC-mA-fG-mU-fG-mU-fU-fC-fU-mU-fG-mC-fU-mC-fU-mA-fU*mA*fA | | 109 |
| ss3-11 | lgT3-lgT3-lgT3-fA-mU-fC-mG-fU-mA-fC-mG-fU-mA-fC-mC-fG-mU-fC-mG-fU-mA-fU-mA-fA-1T4-1T4 | =ss2-5 | 110 |

TABLE 29 antisense strands (5'→3')

| as-# | Sense strands sequence | SEQ ID NO. |
|---|---|---|
| as2-0 | fA*fU*mA-fC-mG-fA-mC-fG-mG-fU-mA-fC-mG-fU-mA-fC-mG-fA-mU*dT*dT | 91 |
| as1-1 | mU*fU*mA-fU-mA-fG-mA-fG-mC-fA-mA-mG-mA-fA-mC-fA-mC-fU-mG-fU-mU*mU*mU | 79 |

TABLE 30 siRNAs with lgT- and 1T-overhangs

| siRNA-# | ss-# | as-# | remark |
|---|---|---|---|
| siRNA2-0 | ss2-0 | as2-0 | negative control |
| siRNA1-8 | ss1-8 | as1-1 | positive control |
| siRNA3-1 | ss3-1 | as1-1 | = siRNA1-4 |
| siRNA3-2 | ss3-2 | as1-1 | |
| siRNA3-3 | ss3-3 | as1-1 | |
| siRNA3-4 | ss3-4 | as1-1 | |
| siRNA3-5 | ss3-5 | as1-1 | |
| siRNA3-6 | ss3-6 | as1-1 | |
| siRNA3-7 | ss3-7 | as1-1 | |
| siRNA3-8 | ss3-8 | as1-1 | |
| siRNA3-9 | ss3-9 | as1-1 | |
| siRNA3-10 | ss3-10 | as1-1 | |
| siRNA3-11 | ss3-11 | as1-1 | |

In Vivo Example 6.1

Demonstration of in vivo activity of PEG-GalNAc-siRNA conjugates and comparison of impact of different PEG-GalNAc building blocks on RNA interfering activity.

Methods

C57BL/6N mice (female 20-22 g; Charles River, Germany) were treated subcutaneously with a single dose of 5 mpk of PEG-GalNAc-siRNA or PBS (mock control) in groups of n=6. Sequences and chemical composition of administered compounds are listed in Table 28 to Table 30. Blood samples were drawn pre- and post-dosing as indicated in FIGS. 9a/b. siRNA target TTR was quantified from serum by a commercially available ELISA assay (Alpco Diagnostics, Cat. no.: 41-PALMS-E01).

Figure 9A:
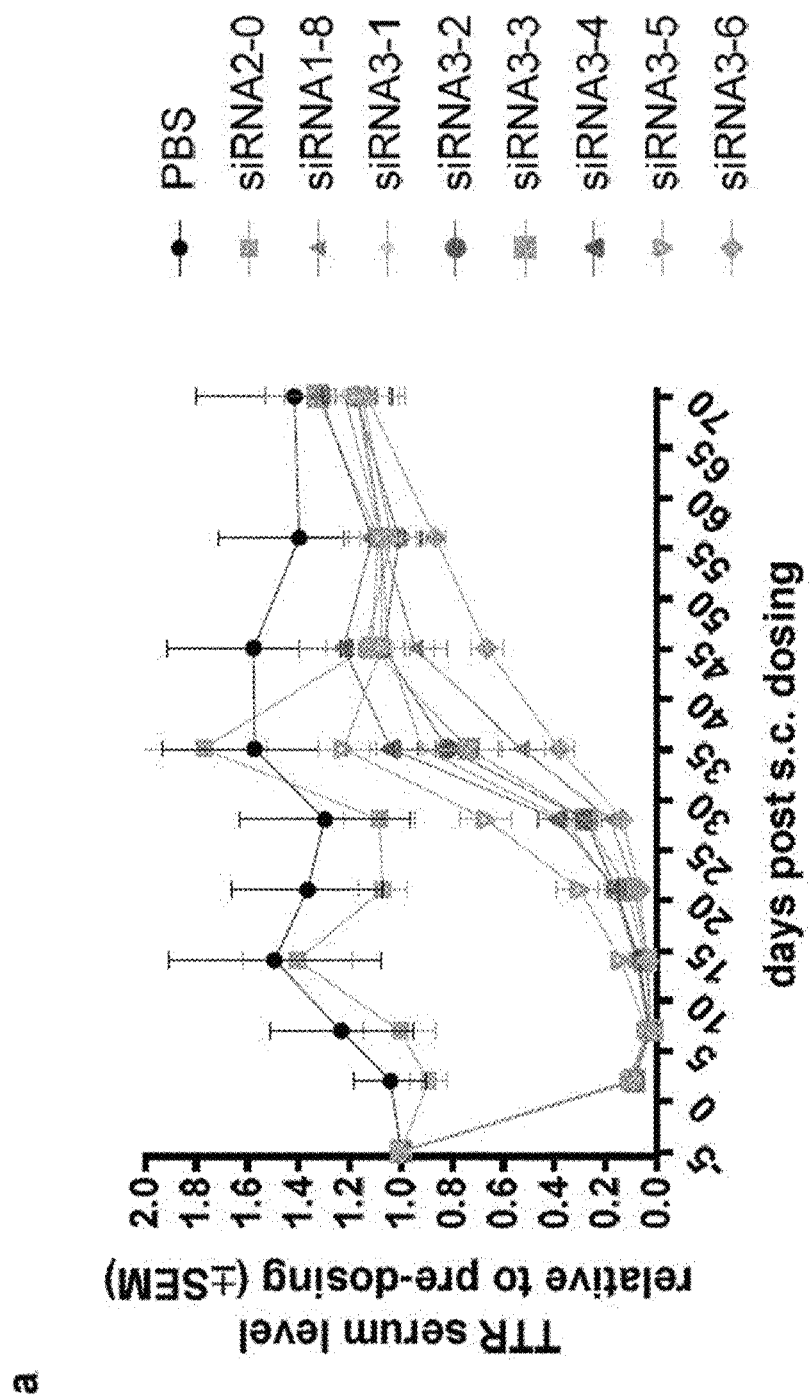
FIGS. 9a and 9b: Relative TTR protein serum levels at blood sampling time points post s.c. dosing of substances as indicated in legend
  Ordinate: TTR serum level relative to pre-dosing+/−SEM
  Abscissa: days post-subcutaneous dosing
Figure 9B:
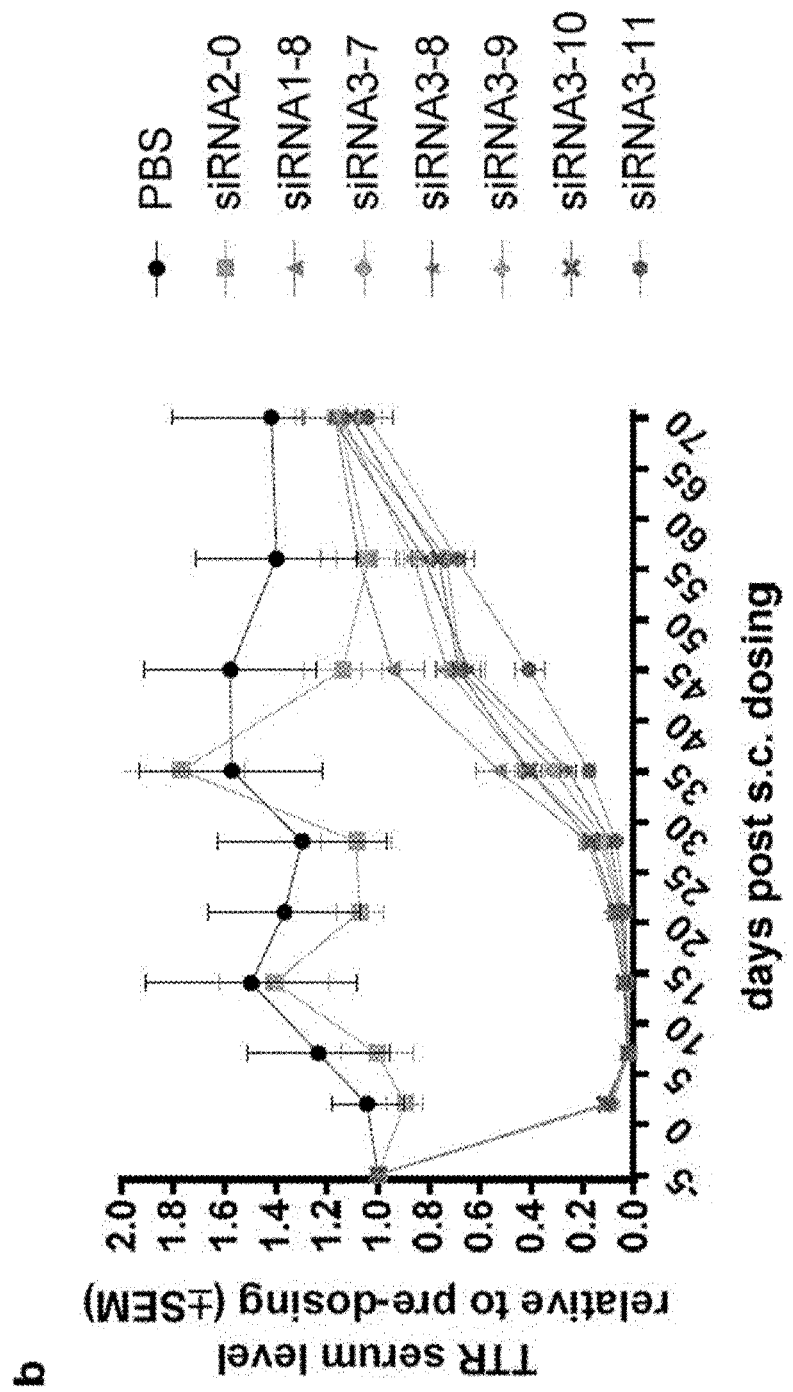

Results (see FIGS. 9a/b)

Again, there is a clear benefit on the attachment of the lgT-building blocks (lgT=lgT5, lgT6, lgT7, lgT8 and lgT9) at the 5'-end (siRNA3-6 to siRNA3-10) over the analogs 3'-end counterparts (siRNA3-1 to siRNA3-5). Compared to the lgT3-containing siRNA1-8, which already shows a clear knock-down of the TTR-mRNA, the PEG-type analogs siRNA3-7 and siRNA3-8 show an improved duration of action after day 30. This is an unexpected result, since lgT6 and lgT7 contain longer linkers between the morpholine-N and the GalNAc-moiety. The PEG-structure of the linking units seems to have a positive effect on the in vivo potency of the corresponding siRNAs.

A further improvement of the duration of action was achieved by combining the lgT3-attachment at the 5'-end of the sense strand (ss-8) with an additional 1T4-1T4-overhang at the 3'-end (ss3-11). Without any remaining PS-groups in the sense strand, the corresponding siRNA3-11 shows an additional improvement in the duration of action and was the most potent compound in the above in vivo study.

These results clearly show that the morpholine-nucleotide analogs display beneficial properties in vivo, when used as GalNAc-substituted nucleotide analogs (lgTs) for hepatic siRNA-targeting. An additional benefit can be achieved when these three-fold lgT-substituted siRNAs are modified with double 1T-overhangs at the 3'-end of the same sense strand. This second modification leads to a clearly improved duration of action (see siRNA1-8 vs. siRNA3-11).

In Vivo Example 6.2

Dose dependent in vivo activity and acute toxicity assessment of compounds selected from in vivo example 6.1

Methods

Animal Study

C57BL/6N mice (female 20-22 g; Charles River, Germany) were treated subcutaneously with a single dose of 0.5, 2.5 or 25 mpk of siRNA or PBS (mock control) in groups of n=6 (for 0.5 and 2.5 mpk) or n=5 (for 25 mpk). Sequences and chemical composition of administered compounds are referenced in Table 25 to Table 27. Animals were taken down 48 h post treatment, blood drawn for hematology analysis, clinical chemistry and organs harvested and weighed. Hematology blood count was performed on a scil Vet animal blood counter and clinical chemistry analysis on a Roche Cobas system.

Post Study Analysis siRNA target TTR was quantified from serum by a commercially available ELISA assay (Alpco Diagnostics, Cat. no.: 41-PALMS-E01).

Liver tissue was processed for RT-qPCR analysis by total RNA extraction including DNase digest (RNAeasy Mini Kit, Qiagen). TTR (TaqMan assay ID Mm00443267_m1) and reference mRNA (Actb (TaqMan assay ID 4352341E), Gapdh (TaqMan assay ID 4308313)) was quantified by qPCR on an ABI Prism 7900 system following Oligo-dT and Random Hexamer primed cDNA synthesis. The ΔΔCt method was applied to calculate relative expression levels of the target transcripts.

The upper right liver lobe, spleen and kidneys of 25 mpk treatment groups (+PBS) were Formalin fixed and pathologically evaluated for abnormalities following standard H&E staining.

Figure 10:
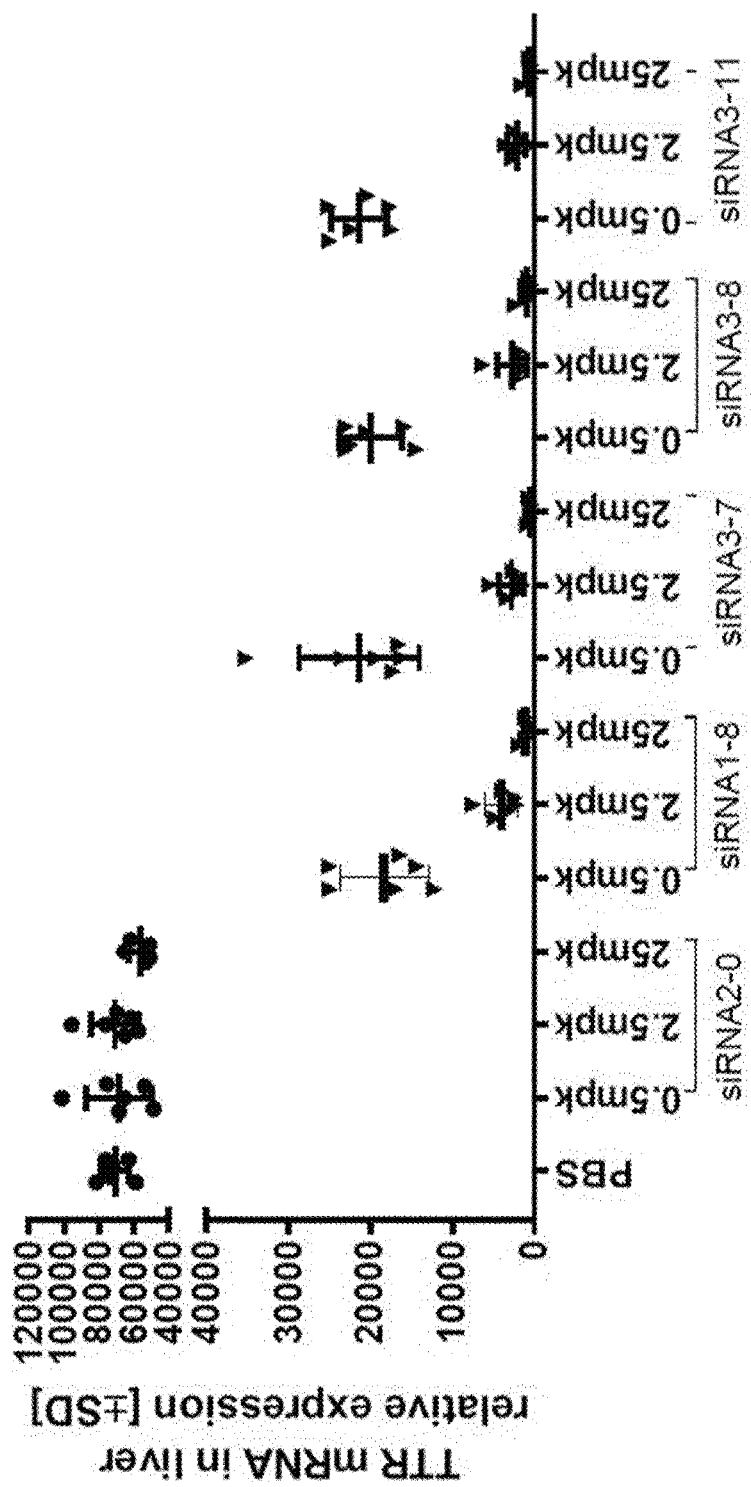
FIG. 10: Relative TTR mRNA expression levels in liver at study take-down 48 h post s.c. dosing of substances as indicated in X-axis labels
  Ordinate: TTR mRNA in liver relative expression+/−SD
  Abscissa: siRNA-#, dose
Figure 11:
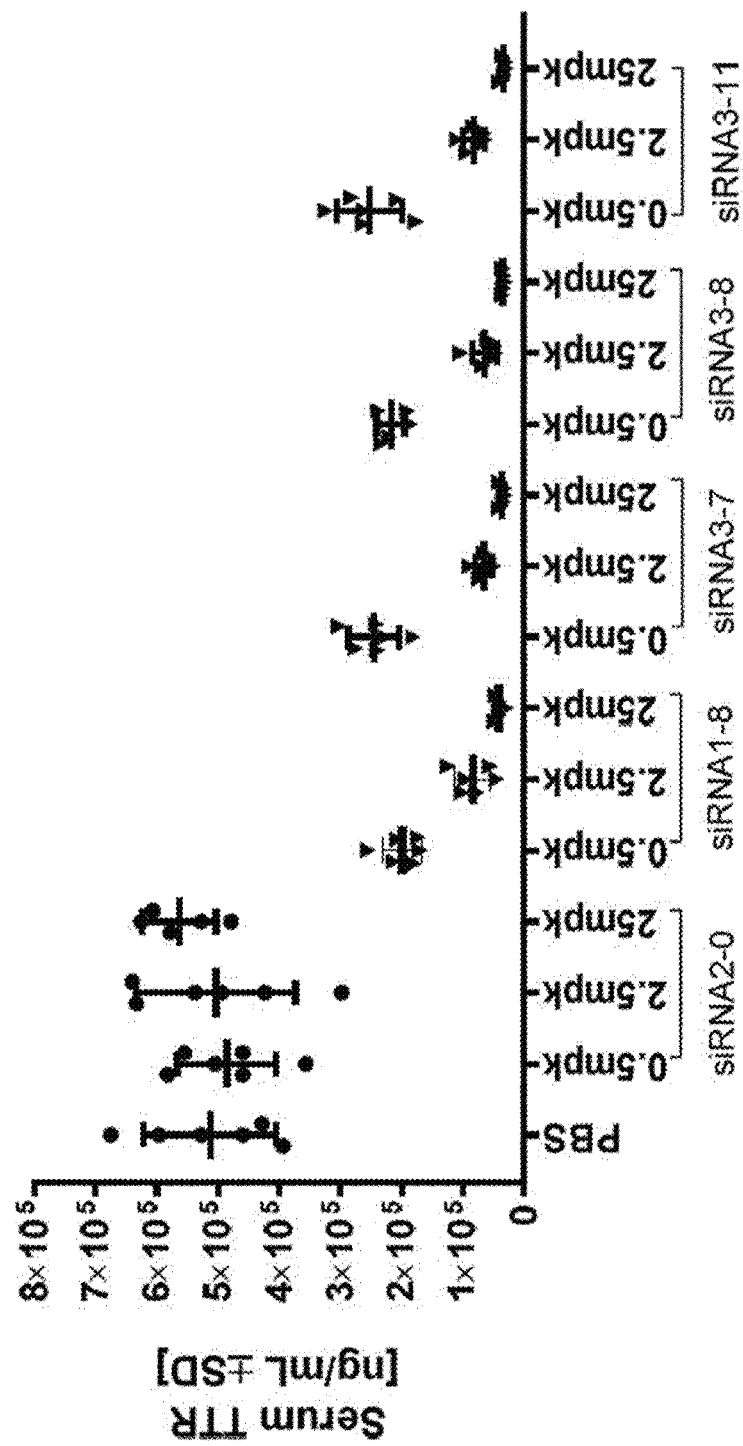
FIG. 11: TTR protein serum levels at study take-down 48 h post s.c. dosing of substances as indicated in X-axis labels
  Ordinate: serum TTR concentration as expressed in ng/ml+/−SD
  Abscissa: siRNA-#, dose

Results (See FIGS. 10 and 11)

Both protein and mRNA levels were reduced by all tested active siRNAs in a dose dependent manner at 48 h post dosing. mRNA and protein reduction occurred in a paralleled fashion. Within the tested active substances, no significant differences were observed either on the protein or mRNA level at any dose.

The in vitro knock-down results in primary mouse hepatocytes of the compounds siRNA3-1 to siRNA3-11 are summarized in Table 31.

No treatment dose dependent effects were observed in standard hematology and liver/kidney clinical chemistry assays. Also, no significant treatment dependent alterations of serum cytokines and effects on organ or body weight were observed at take down. All deviations were within normal physiological range or normal inter-animal variability. Histopathology evaluation of liver and spleen were without findings.

TABLE 31

IC$_{50}$-data of siRNAs 3-1 to 3-11 in primary mouse hepatocytes

| siRNA-# | IC$_{50}$ (pM) | Imax % |
|---|---|---|
| siRNA1-8 | 48 | 99.4% |
| siRNA3-1 | 19 | 100.1% |
| siRNA3-2 | 17 | 100.0% |
| siRNA3-3 | 15 | 100.3% |
| siRNA3-4 | 24 | 99.9% |
| siRNA3-5 | 74 | 100.8% |
| siRNA3-6 | 14 | 100.4% |
| siRNA3-7 | 18 | 100.2% |
| siRNA3-8 | 10 | 100.2% |
| siRNA3-9 | 18 | 100.3% |
| siRNA3-10 | 56 | 99.8% |
| siRNA3-11 | 60 | 99.9% |

All siRNAs (siRNA1-8, siRNA3-1 to siRNA3-11) with lgT- or lgT- and lT-overhangs were tested with in IFNα- and cytotoxicity assay and did not show any effects on immune stimulation or cell viability.

Example 7: In Vivo Inhibition of a Target Gene Expression with Modified siRNAs According to the Present Disclosure In Vivo Example 7.1

TABLE 32 sense strands (5'→3') with lgT- and 1T- or 1A-3'-ends

| ss-# | Sense strands sequence | re-mark | SEQ ID NO. |
|---|---|---|---|
| ss2-0 | lgT3-lgT3-lgT3-fA-mU-fC-mG-fU-mA-fC-mG-fU-mA-fC-mC-fG-mU-fC-mG-fU*mA*fU | LV-2 | 80 |
| ss4-1 | lgT3-lgT3-lgT3-fA-mA-fC-mA-fG-mU-fG-mU-fU-fC-fU-mU-fG-mC-fU-mC-fU-mA-fU*mA*fA | =ss1-8 | 74 |
| ss4-2 | lgT3-lgT3-lgT3-fA-mA-fC-mA-fG-mU-fG-mU-fU-fC-fU-mU-fG-mC-fU-mC-fU-mA-fU-mA-fA-1T4-1T4 | =ss2-5 | 84 |
| ss4-3 | lgT6-lgT6-lgT6-fA-mA-fC-mA-fG-mU-fG-mU-fU-fC-fU-mU-fG-mC-fU-mC-fU-mA-fU-mA-fA-1T4-1T4 | | 111 |
| ss4-4 | lgT7-lgT7-lgT7-fA-mA-fC-mA-fG-mU-fG-mU-fU-fC-fU-mU-fG-mC-fU-mC-fU-mA-fU-mA-fA-1T4-1T4 | | 112 |
| ss4-5 | lgT7-lgT7-lgT7-fA-mA-fC-mA-fG-mU-fG-mU-fU-fC-fU-mU-fG-mC-fU-mC-fU-mA-fU-mA-fA*1T4*1T4 | | 113 |

TABLE 32-continued sense strands (5'→3') with lgT- and 1T- or 1A-3'-ends

| ss-# | Sense strands sequence | re-mark | SEQ ID NO. |
|---|---|---|---|
| ss4-6 | lgT7-lgT7-lgT7-fA-mA-fC-mA-fG-mU-fG-mU-fU-fC-fU-mU-fG-mC-fU-mC-fU-mA-fU-1T4-1T4 | | 114 |
| ss4-7 | lgT7-lgT7-lgT7-fA-mA-fC-mA-fG-mU-fG-mU-fU-fC-fU-mU-fG-mC-fU-mC-fU-mA-fU*1T4*1T4 | | 115 |
| ss4-8 | lgT7-lgT7-lgT7-fA-mA-fC-mA-fG-mU-fG-mU-fU-fC-fU-mU-fG-mC-fU-mC-fU-mA-fU-1A4-1A4 | | 116 |
| ss4-9 | lgT7-lgT7-lgT7-fA-mA-fC-mA-fG-mU-fG-mU-fU-fC-fU-mU-fG-mC-fU-mC-fU-mA-fU*1A4*1A4 | | 117 |

TABLE 33 antisense strands (5'→3')

| as-# | Sense strands sequence | re-mark | SEQ ID NO. |
|---|---|---|---|
| as2-0 | fA*fU*mA-fC-mG-fA-mC-fG-mG-fU-mA-fC-mG-fU-mA-fC-mG-fA-mU*dT*dT | LV-2 | 91 |
| as1-1 | mU*fU*mA-fU-mA-fG-mA-fG-mC-fA-mA-mG-mA-fA-mC-fA-mC-fU-mG-fU-mU*mU*mU | | 79 |
| as2-5 | mU*fU*mA-fU-mA-fG-mA-fG-mC-fA-mA-mG-mA-fA-mC-fA-mC-fU-mG-fU-mU-1T4-1T4 | | 95 |

TABLE 34 siRNAs with lgT- and lT-overhangs

| siRNA-# | ss-# | as-# | remark |
|---|---|---|---|
| siRNA2-0 | ss2-0 | as2-0 | LV-2; neg. cntrl. |
| siRNA4-1 | ss4-1 | as1-1 | siRNA1-8; pos. ctrl. |
| siRNA4-2 | ss4-2 | as1-1 | siRNA3-11; pos. ctrl. |
| siRNA4-3 | ss4-3 | as1-1 | |
| siRNA4-4 | ss4-4 | as1-1 | |
| siRNA4-5 | ss4-5 | as1-1 | |
| siRNA4-6 | ss4-6 | as1-1 | |
| siRNA4-7 | ss4-7 | as1-1 | |
| siRNA4-8 | ss4-8 | as1-1 | |
| siRNA4-9 | ss4-9 | as1-1 | |
| siRNA4-10 | ss4-4 | as2-5 | |
| siRNA4-11 | ss4-1 | as2-5 | |

Methods

C57BL/6N mice (female 20-22 g; Charles River, Germany) were treated subcutaneously with a single dose of 1 mpk of siRNA or PBS (mock control) in groups of n=6. Sequences and chemical composition of administered compounds are listed in Table 32 to Table 34. Blood samples were drawn pre- and post-dosing as indicated in FIGS. 12a/b. siRNA target TTR was quantified from serum by a commercially available ELISA assay (Alpco Diagnostics, Cat. no.: 41-PALMS-E01).

Figure 12A:
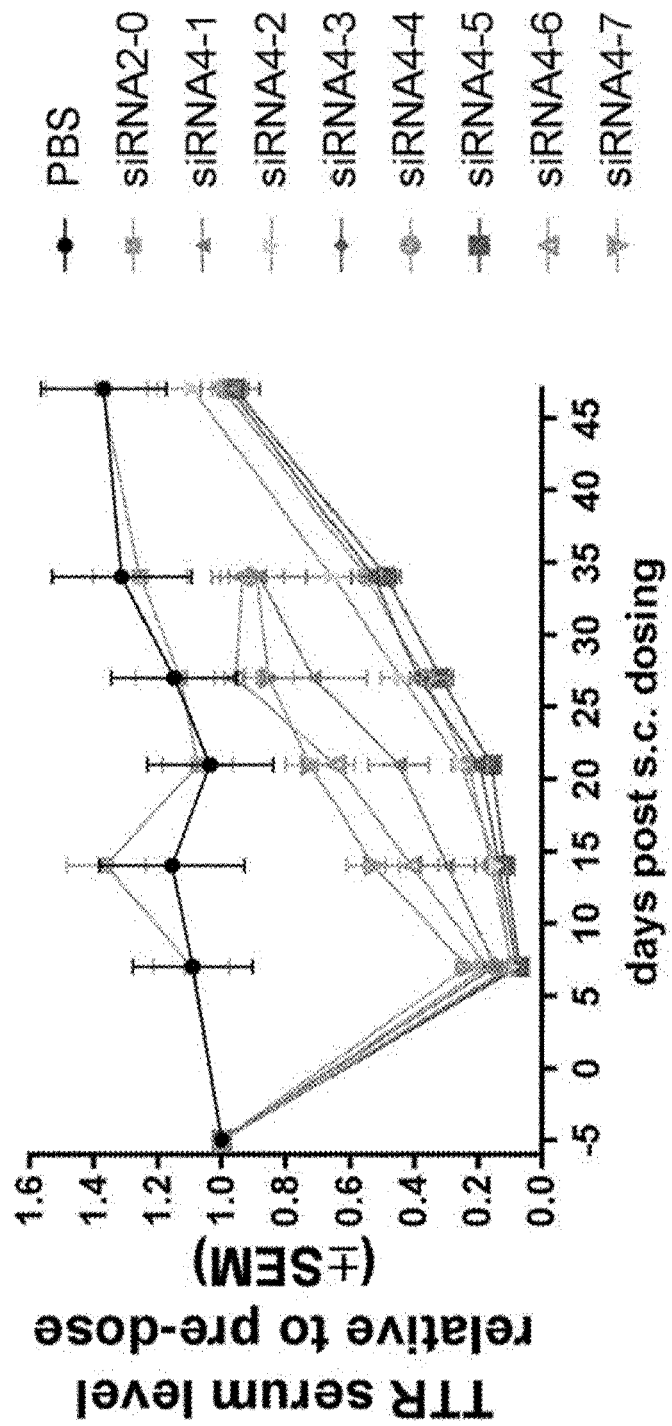
FIGS. 12a and 12b: Relative TTR protein serum levels at blood sampling time points post s.c. dosing of substances as indicated in legend
  Ordinate: TTR serum level relative to pre-dosing+/−SEM
  Abscissa: days post-subcutaneous dosing
Figure 12B:
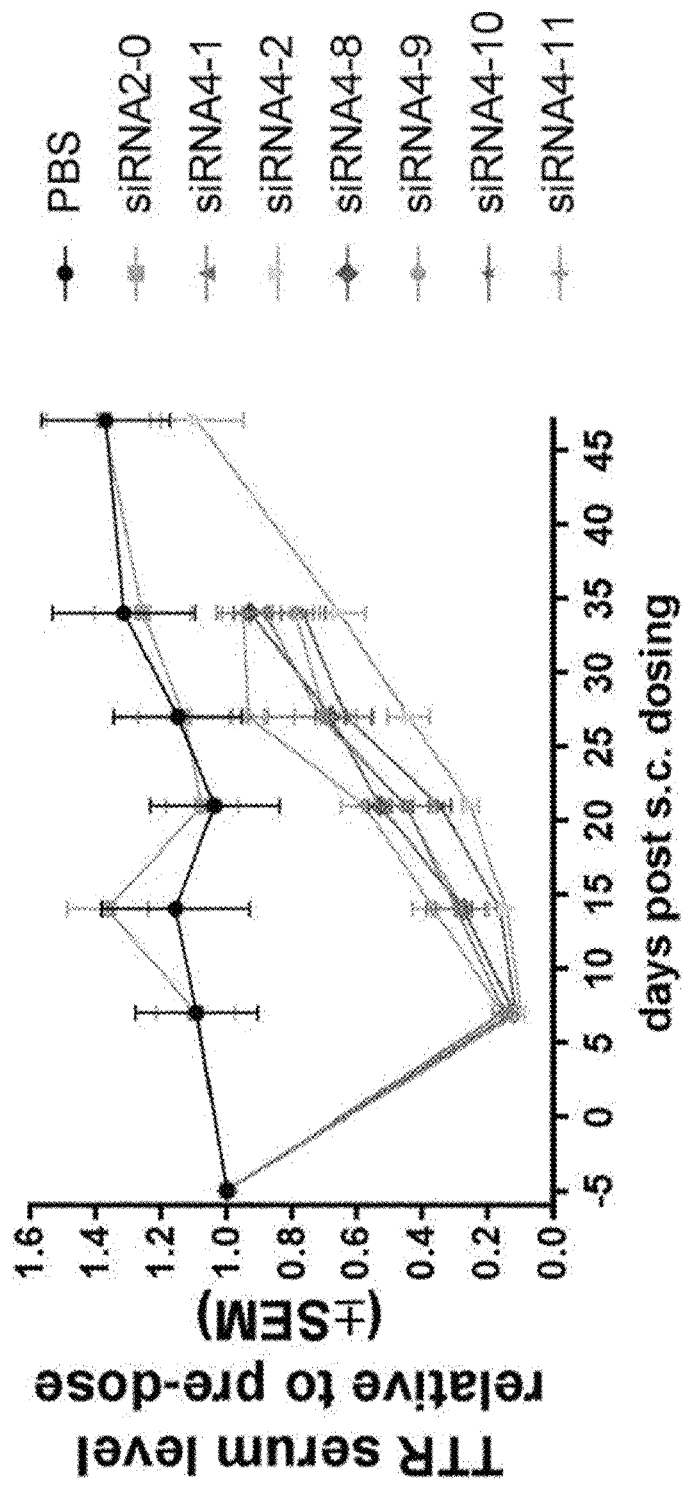

Demonstration of in-vivo activity of siRNA-conjugates listed in Table 34 and comparison of their RNAi activity Results (See FIGS. 12a/12b)

Comparing the two positive controls, siRNA4-1 and siRNA4-2, confirms that there is a clear benefit of the 1T4-1T4-overhang at the 3'-end of the sense strand compared to the initial phosphothioate stabilization.

The durations of action could still be improved by exchanging the three lgT3-building blocks in siRNA4-1 to lgT6- or lgT7-analogs with PEG-type linkers between the morpholine ring and the GalNAc-targeting moiety (see siRNA4-3 and siRNA4-4).

Unexpectedly, the comparison between siRNA4-4 and siRNA4-5 shows that there is no additional increase in the duration of action, when the T4-1T4-3'-end-stabilization of the sense strand has additional phosphothioate groups at these positions (see ss4-5).

In Vivo Example 7.2

Dose dependent in-vivo activity and acute toxicity assessment of selected compounds from in-vivo example 7.1

Methods

Animal Study

C57BL/6N mice (female 20-22 g; Charles River, Germany) were treated subcutaneously with a single dose of 0.5, 2.5 or 25 mpk of siRNA or PBS (mock control) in groups of n=6 (for 0.5 and 2.5 mpk) or n=5 (for 25 mpk). Sequences and chemical composition of administered compounds are referenced in Table 32 to Table 34. Animals were taken down 48 h post treatment, blood drawn for hematology analysis, clinical chemistry and organs harvested and weighed. Hematology blood count was performed on a scil Vet animal blood counter and clinical chemistry analysis on a Roche Cobas system.

Post Study Analysis siRNA target TTR was quantified from serum by a commercially available ELISA assay (Alpco Diagnostics, Cat. no.: 41-PALMS-E01).

Liver tissue was processed for RT-qPCR analysis by total RNA extraction including DNase digest (RNAeasy Mini Kit, Qiagen). TTR (TaqMan assay ID Mm00443267_m1) and reference mRNA (Actb (TaqMan assay ID 4352341E), Gapdh (TaqMan assay ID 4308313)) was quantified by qPCR on an ABI Prism 7900 system following Oligo-dT and Random Hexamer primed cDNA synthesis. The ΔΔCt method was applied to calculate relative expression levels of the target transcripts.

The upper right liver lobe, spleen and kidneys of 25 mpk treatment groups (+PBS) were Formalin fixed and pathologically evaluated for abnormalities following standard H&E staining.

Figure 13:
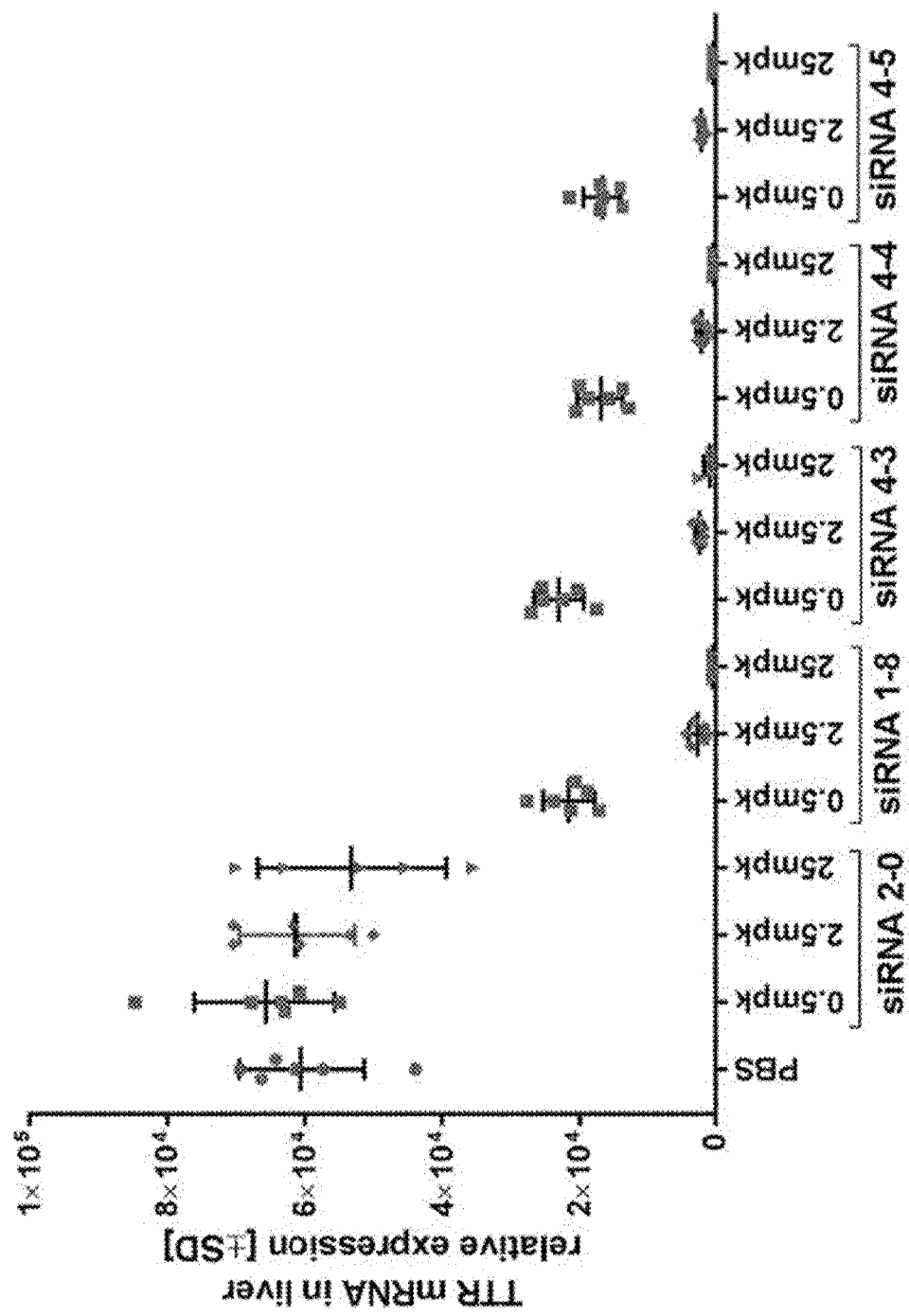
FIG. 13: Relative TTR mRNA expression levels in liver at study take-down 48 h post s.c. dosing of substances as indicated in X-axis labels
  Ordinate: TTR mRNA in liver relative expression+/−SD
  Abscissa: siRNA-#, dose
Figure 14:
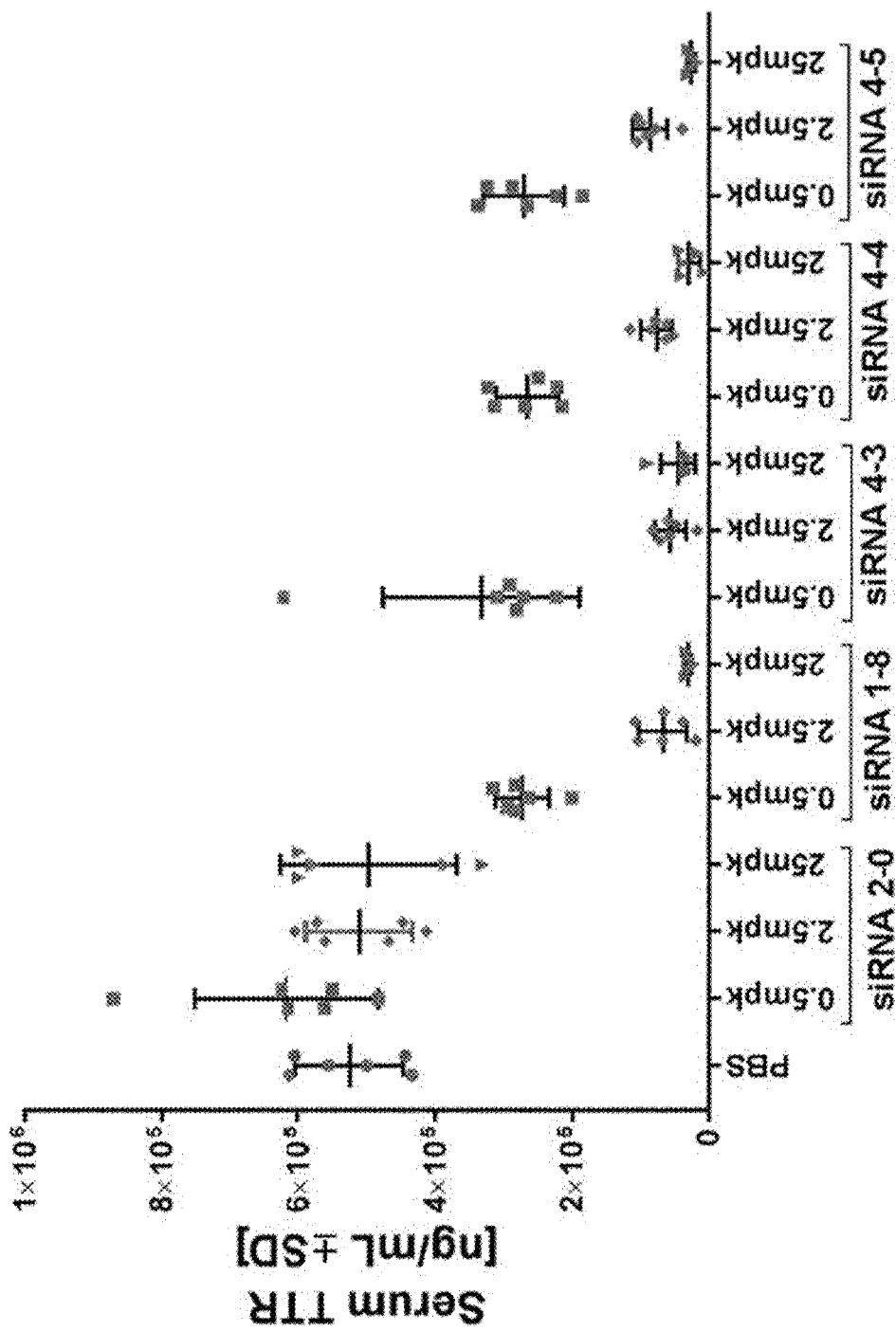
FIG. 14: TTR protein serum levels at study take-down 48 h post s.c. dosing of substances as indicated in X-axis labels
  Ordinate: serum TTR concentration as expressed in ng/ml+/−SD
  Abscissa: siRNA-#, dose

Results (See FIGS. 13 and 14):

Both protein and mRNA levels were reduced by all tested active siRNAs in a dose dependent manner at 48 h post dosing. mRNA and protein reduction occurred in a paralleled fashion. Within the tested active substances, no significant differences were observed either on the protein or mRNA level at any dose.

No treatment dose dependent effects were observed in standard hematology and liver/kidney clinical chemistry assays. Also, no significant treatment dependent alterations of serum cytokines and effects on organ or body weight were observed at take down. All deviations were within normal physiological range or normal inter-animal variability. Histopathology evaluation of liver and spleen were without findings.

The in-vitro knock-down results in primary mouse hepatocytes of the compounds siRNA4-1 to siRNA4-11 are summarized in Table 35:

TABLE 35

$IC_{50}$-data of siRNAs 4-1 to 4-11 in primary mouse hepatocytes

| siRNA-# | $IC_{50}$ (pM) | Imax % |
|---|---|---|
| siRNA4-1 | 160 | 99.5 |
| siRNA4-2 | 558 | 100.7 |
| siRNA4-3 | 389 | 99.5 |
| siRNA4-4 | 242 | 99.3 |
| siRNA4-5 | 545 | 100.8 |
| siRNA4-6 | 111 | 99.6 |
| siRNA4-7 | 295 | 99.7 |
| siRNA4-8 | 166 | 99.3 |
| siRNA4-9 | 273 | 99.8 |
| siRNA4-10 | 490 | 100.0 |
| siRNA4-11 | 378 | 99.7 |

Compared to the positive controls siRNA4-1 (=siRNA1-8) and siRNA4-2 (=siRNA3-11), which show $IC_{50}$-values of 160 and 558 μM respectively, the new analogs, siRNA4-3 to siRNA4-11 show in-vitro potencies in the same range, between 111p M (siRNA4-6) and 545 pM (siRNA4-5). All siRNAs (siRNA4-1 to siRNA4-11) with lgT- with or without lT- or lA-overhangs were tested with in IFNα- and cytotoxicity assay and did not show any effects on immune stimulation or cell viability.

Based on all collected data (in-vivo and in-vitro), the nucleotide analogs lgT7 and lT4 were selected for hepatic targeting and 3'-end stabilization of the corresponding siRNAs.

Example 8: Analytic Data of the Modified Oligonucleotides Described in the Present Disclosure 8.1. Analytic Results of the Single Strand Oligonucleotides 8.1.1.—Sense Strands

TABLE C

| ss-# | MW(ss) calc. | MW(ss) found (m/z) | z |
|---|---|---|---|
| ss1 | 6830.2 | 2276.6 | 3 |
| ss2 | 6885.3 | 2294.8 | 3 |
| ss3 | 6940.4 | 6939.6 | 1 |
| ss4 | 6995.6 | 6995.1 | 1 |
| ss5 | 7050.7 | 7049.8 | 1 |
| ss6 | 7105.8 | 7105.1 | 1 |
| ss7 | 6900.3 | 6899.5 | 1 |
| ss8 | 6885.3 | 6884.7 | 1 |
| ss9 | 6940.4 | 6939.8 | 1 |
| ss10 | 6995.6 | 2331.6 | 3 |
| ss11 | 7050.7 | 7049.8 | 1 |
| ss12 | 7105.8 | 7105.0 | 1 |
| ss13 | 6639.2 | 6638.9 | 1 |
| ss14 | 6653.1 | 6652.8 | 1 |
| ss15 | 6667.1 | 6666.9 | 1 |
| ss16 | 6681.1 | 6680.9 | 1 |
| ss17 | 6695.2 | 6694.9 | 1 |
| ss18 | 6709.2 | 6708.9 | 1 |
| ss19 | 6723.2 | 6722.9 | 1 |
| ss20 | 6653.1 | 6652.9 | 1 |
| ss21 | 6667.1 | 6666.9 | 1 |
| ss22 | 6681.1 | 6680.9 | 1 |
| ss23 | 6695.2 | 6694.9 | 1 |
| ss24 | 6709.2 | 6708.8 | 1 |
| ss25 | 6723.2 | 6722.9 | 1 |

TABLE C-continued

| ss-# | MW(ss) calc. | MW(ss) found (m/z) | z |
|---|---|---|---|
| ss26 | 6884.3 | 6884.0 | 1 |
| ss27 | 7026.5 | 7026.2 | 1 |
| ss28 | 7777.1 | 7776.4 | 1 |
| ss29 | 8152.5 | 8152.5 | 1 |
| ss30 | 8527.8 | 8527.6 | 1 |
| ss31 | 8903.1 | 8902.7 | 1 |
| ss32 | 9278.4 | 9277.9 | 1 |
| ss33 | 7734.4 | 7733.6 | 1 |
| ss34 | 8485.1 | 8484.9 | 1 |
| ss35 | 9235.7 | 9235.1 | 1 |
| ss36 | 9986.3 | 9985.3 | 1 |
| ss37 | 7026.5 | 7026.2 | 1 |
| ss38 | 7777.1 | 7776.4 | 1 |
| ss39 | 8527.8 | 8527.6 | 1 |
| ss40 | 9278.4 | 9277.9 | 1 |
| ss41 | 7734.4 | 7733.6 | 1 |
| ss42 | 8485.1 | 8484.9 | 1 |
| ss43 | 9235.7 | 9235.1 | 1 |
| ss44 | 6651.2 | 6651.0 | 1 |
| ss45 | 7777.2 | 7776.4 | 1 |
| ss46 | 6651.2 | 6651.1 | 1 |
| ss47 | 7777.2 | 7776.4 | 1 |
| ss48 | 6610.1 | 6610.0 | 1 |
| ss49 | 6944.4 | 6944.1 | 1 |
| ss50 | 7612.8 | 7612.2 | 1 |
| ss51 | 6610.1 | 6610.0 | 1 |
| ss52 | 6944.4 | 6944.1 | 1 |
| ss53 | 7612.8 | 7612.2 | 1 |

TABLE D

| ss-# | MW(ss) calc. | MW(ss) found (m/z) | z |
|---|---|---|---|
| ss1-1 | 8973.3 | 8972.7 | 1 |
| ss1-2 | 9005.2 | 9004.6 | 1 |
| ss1-3 | 9039.2 | 9038.5 | 1 |
| ss1-4 | 9071.3 | 9070.5 | 1 |
| ss1-5 | 8710.9 | 8710.3 | 1 |
| ss1-6 | 8678.8 | 8678.3 | 1 |
| ss1-7 | 8710.9 | 8710.2 | 1 |
| ss1-8 | 8668.9 | 8668.3 | 1 |
| ss1-9 | 8636.8 | 8636.3 | 1 |
| ss1-10 | 8668.9 | 8668.3 | 1 |
| ss1-11 | 8963.5 | 8962.9 | 1 |
| ss1-12 | 8963.5 | 8962.9 | 1 |
| ss2-0 | 8044.6 | 8044.7 | 1 |
| ss2-2 | 9305.3 | 9304.9 | 1 |
| ss2-3 | 9331.3 | 9330.7 | 1 |
| ss2-4 | 9387.5 | 9387.0 | 1 |
| ss2-5 | 9467.6 | 9467.1 | 1 |
| ss2-6 | 9483.5 | 9483.0 | 1 |
| ss2-7 | 9415.5 | 9414.9 | 1 |
| ss2-8 | 9527.7 | 9527.2 | 1 |
| ss2-9 | 9752.2 | 9751.2 | 1 |
| ss2-10 | 9387.4 | 9386.9 | 1 |
| ss2-11 | 9780.1 | 9779.2 | 1 |
| ss3-1 | 9071.3 | 9070.9 | 1 |
| ss3-2 | 8939.2 | 8938.8 | 1 |
| ss3-3 | 8807.0 | 8806.7 | 1 |
| ss3-4 | 8674.9 | 8674.6 | 1 |
| ss3-5 | 8542.7 | 8542.5 | 1 |
| ss3-6 | 9071.3 | 9070.9 | 1 |
| ss3-7 | 8939.2 | 8938.8 | 1 |
| ss3-8 | 8807.0 | 8806.7 | 1 |
| ss3-9 | 8674.9 | 8674.7 | 1 |
| ss3-10 | 8542.7 | 8542.5 | 1 |
| ss3-11 | 9467.6 | 9467.1 | 1 |
| ss4-1 | 8668.9 | 8668.8 | 1 |
| ss4-2 | 9467.6 | 9467.0 | 1 |
| ss4-3 | 9737.8 | 9737.1 | 1 |
| ss4-4 | 9605.7 | 9605.0 | 1 |
| ss4-5 | 9637.8 | 9637.0 | 1 |
| ss4-6 | 8931.2 | 8930.9 | 1 |

TABLE D-continued

| | | | |
|---|---|---|---|
| ss4-7 | 8963.3 | 8962.9 | 1 |
| ss4-8 | 8949.3 | 8948.9 | 1 |
| ss4-9 | 8981.4 | 8981.0 | 1 |

8.1.2. Antisense Strands

| as-# | MW(as) calc. | MW(as) found (m/z) | z |
|---|---|---|---|
| as1 | 6487.0 | 6486.3 | 1 |
| as2 | 6529.0 | 2176.1 | 3 |
| as3 | 6709.1 | 6708.9 | 1 |
| as4 | 7237.0 | 7236.3 | 1 |
| as5 | 6513.0 | 6512.9 | 1 |
| as6 | 6279.9 | 6278.9 | 1 |
| as7 | 6279.9 | 6279.0 | 1 |
| as8 | 6238.8 | 6237.9 | 1 |
| as9 | 6238.8 | 6237.9 | 1 |
| as10 | 6655.3 | 6655.1 | 1 |
| as11 | 6655.3 | 6655.1 | 1 |
| as12 | 6573.1 | 6573.0 | 1 |
| as13 | 6573.1 | 6573.0 | 1 |
| as1-1 | 7596.0 | 7595.0 | 1 |
| as2-0 | 6903.5 | 6903.0 | 1 |
| as2-2 | 7591.9 | 7591.3 | 1 |
| as2-3 | 7618.0 | 7617.2 | 1 |
| as2-4 | 7674.1 | 7673.4 | 1 |
| as2-5 | 7754.2 | 7753.5 | 1 |
| as2-6 | 7770.2 | 7769.4 | 1 |
| as2-7 | 7702.1 | 7701.4 | 1 |
| as2-8 | 7814.4 | 7813.6 | 1 |
| as2-9 | 7674.0 | 7673.3 | 1 |

8.2. Analytic Results of the Double Strand Oligonucleotides

| siRNA # | ss-# | as-# | MW (ss) found | MW (as) found |
|---|---|---|---|---|
| siRNA-7 | ss7 | as2 | 6900.0 | 6528.9 |
| siRNA-28 | ss26 | as2 | 6884.0 | 6527.9 |
| siRNA-29 | ss27 | as2 | 7026.2 | 6528.9 |
| siRNA-30 | ss28 | as2 | 7776.4 | 6528.9 |
| siRNA-31 | ss29 | as2 | 8151.5 | 6528.9 |
| siRNA-32 | ss30 | as2 | 8527.7 | 6528.9 |
| siRNA-33 | ss31 | as2 | 8902.8 | 6528.9 |
| siRNA-34 | ss32 | as2 | 9277.9 | 6528.9 |
| siRNA-35 | ss33 | as2 | 7733.6 | 6528.9 |
| siRNA-36 | ss27 | as4 | 7026.2 | 7236.3 |
| siRNA-37 | ss34 | as2 | 8484.9 | 6528.9 |
| siRNA-38 | ss28 | as4 | 7776.4 | 7236.4 |
| siRNA-39 | ss35 | as2 | 9235.1 | 6528.9 |
| siRNA-40 | ss30 | as4 | 8526.7 | 7236.4 |
| siRNA-41 | ss36 | as2 | 9986.3 | 6527.9 |
| siRNA-42 | ss32 | as4 | 9277.9 | 7236.4 |
| siRNA-43 | ss29 | as4 | 8151.5 | 7236.4 |
| siRNA-44 | ss31 | as4 | 8902.8 | 7236.4 |
| siRNA-45 | ss37 | as2 | 7026.2 | 6528.9 |
| siRNA-46 | ss38 | as2 | 7776.4 | 6527.9 |
| siRNA-47 | ss39 | as2 | 8527.7 | 6528.9 |
| siRNA-48 | ss40 | as2 | 9277.9 | 6528.9 |
| siRNA-49 | ss41 | as2 | 7733.6 | 6528.9 |
| siRNA-50 | ss37 | as4 | 7026.2 | 7236.4 |
| siRNA-51 | ss42 | as2 | 8484.9 | 6528.9 |
| siRNA-52 | ss38 | as4 | 7776.4 | 7236.3 |
| siRNA-53 | ss43 | as2 | 9235.1 | 6527.9 |
| siRNA-54 | ss39 | as4 | 8527.6 | 7236.4 |
| siRNA-55 | ss40 | as4 | 9277.9 | 7236.4 |
| siRNA-56 | ss26 | as5 | 6884.0 | 6511.9 |
| siRNA-58 | ss44 | as2 | 6651.0 | 6528.9 |
| siRNA-59 | ss45 | as2 | 7776.4 | 6528.9 |
| siRNA-60 | ss44 | as6 | 6651.0 | 6278.9 |
| siRNA-61 | ss27 | as10 | 7026.1 | 6655.0 |
| siRNA-62 | ss45 | as10 | 7776.4 | 6655.1 |
| siRNA-63 | ss46 | as2 | 6651.0 | 6528.9 |

| siRNA # | ss-# | as-# | | |
|---|---|---|---|---|
| siRNA-64 | ss47 | as2 | 7776.4 | 6528.9 |
| siRNA-65 | ss46 | as7 | 6651.1 | 6278.5 |
| siRNA-66 | ss37 | as11 | 7026.2 | 6655.1 |
| siRNA-67 | ss47 | as11 | 7776.4 | 6655.1 |
| siRNA-68 | ss48 | as2 | 6609.0 | 6528.9 |
| siRNA-69 | ss49 | as2 | 6944.1 | 6528.9 |
| siRNA-70 | ss50 | as2 | 7612.2 | 6528.9 |
| siRNA-71 | ss48 | as8 | 6609.0 | 6237.9 |
| siRNA-72 | ss49 | as12 | 6944.0 | 6572.9 |
| siRNA-73 | ss50 | as12 | 7612.1 | 6571.9 |
| siRNA-74 | ss51 | as2 | 6609.0 | 6528.9 |
| siRNA-75 | ss52 | as2 | 6944.0 | 6528.9 |
| siRNA-76 | ss53 | as2 | 7612.1 | 6528.9 |
| siRNA-77 | ss51 | as9 | 6609.0 | 6237.9 |
| siRNA-78 | ss52 | as13 | 6944.0 | 6572.9 |
| siRNA-79 | ss53 | as13 | 7612.1 | 6572.9 |
| siRNA1-1 | ss1-1 | as1-1 | 8972.9 | 7595.0 |
| siRNA1-2 | ss1-2 | as1-1 | 9004.8 | 7595.1 |
| siRNA1-1 | ss1-1 | as1-1 | 8972.9 | 7595.0 |
| siRNA1-3 | ss1-3 | as1-1 | 9038.8 | 7595.1 |
| siRNA1-4 | ss1-4 | as1-1 | 9070.8 | 7595.1 |
| siRNA1-5 | ss1-5 | as1-1 | 8710.5 | 7595.1 |
| siRNA1-6 | ss1-6 | as1-1 | 8677.5 | 7595.0 |
| siRNA1-7 | ss1-7 | as1-1 | 8710.5 | 7595.1 |
| siRNA1-8 | ss1-8 | as1-1 | 8668.6 | 7595.1 |
| siRNA1-9 | ss1-9 | as1-1 | 8636.7 | 7595.1 |
| siRNA1-10 | ss1-10 | as1-1 | 8668.4 | 7595.1 |
| siRNA1-11 | ss1-11 | as1-1 | 8962.8 | 7596.0 |
| siRNA1-12 | ss1-12 | as1-1 | 8962.8 | 7595.0 |
| siRNA2-2 | ss2-2 | as1-1 | 9304.5 | 7594.9 |
| siRNA2-3 | ss2-2 | as2-2 | 9304.5 | 7592.0 |
| siRNA2-4 | ss2-3 | as2-3 | 9330.6 | 7617.0 |
| siRNA2-5 | ss2-4 | as1-1 | 9386.6 | 7594.9 |
| siRNA2-6 | ss2-4 | as2-4 | 9386.6 | 7673.1 |
| siRNA2-7 | ss2-5 | as2-5 | 9466.7 | 7753.1 |
| siRNA2-8 | ss2-6 | as2-6 | 9482.6 | 7769.1 |
| siRNA2-9 | ss2-7 | as2-7 | 9414.7 | 7701.1 |
| siRNA2-10 | ss2-8 | as2-8 | 9526.8 | 7814.2 |
| siRNA2-11 | ss2-9 | as2-4 | 9750.9 | 7673.0 |
| siRNA2-12 | ss2-10 | as2-9 | 9386.6 | 7673.0 |
| siRNA2-13 | ss2-11 | as2-4 | 9778.9 | 7673.0 |

| siRNA # | ss-# | as-# | MW(siRNA) calc. | MW(siRNA) found (m/z) | z |
|---|---|---|---|---|---|
| siRNA2-0 | ss2-0 | as2-0 | 14948.1 | 2490.2; 2988.5 | 6; 5 |
| siRNA3-1 | ss3-1 | as1-1 | 16667.3 | 2776.8 | 6 |
| siRNA3-2 | ss3-2 | as1-1 | 16535.2 | 2754.8 | 6 |
| siRNA3-3 | ss3-3 | as1-1 | 16403.0 | 2732.8 | 6 |
| siRNA3-4 | ss3-4 | as1-1 | 16270.9 | 2710.7 | 6 |
| siRNA3-5 | ss3-5 | as1-1 | 16138.7 | 2688.7 | 6 |
| siRNA3-6 | ss3-6 | as1-1 | 16667.3 | 2776.8 | 6 |
| siRNA3-7 | ss3-7 | as1-1 | 16535.2 | 2754.8 | 6 |
| siRNA3-8 | ss3-8 | as1-1 | 16403.0 | 2732.8 | 6 |
| siRNA3-9 | ss3-9 | as1-1 | 16270.9 | 2710.7 | 6 |
| siRNA3-10 | ss3-10 | as1-1 | 16138.7 | 2688.7 | 6 |
| siRNA3-11 | ss2-5 | as1-1 | 17063.6 | 2842.8 | 6 |
| siRNA4-1 | ss4-1 | as1-1 | 16264.9 | 2709.8 | 6 |
| siRNA4-2 | ss4-2 | as1-1 | 17063.5 | 2842.8 | 6 |
| siRNA4-3 | ss4-3 | as1-1 | 17333.8 | 2887.9 | 6 |
| siRNA4-4 | ss4-4 | as1-1 | 17201.6 | 2865.8 | 6 |
| siRNA4-5 | ss4-5 | as1-1 | 17233.7 | 2871.2 | 6 |
| siRNA4-6 | ss4-6 | as1-1 | 16527.2 | 2753.5 | 6 |
| siRNA4-7 | ss4-7 | as1-1 | 16559.3 | 2759.0 | 6 |
| siRNA4-8 | ss4-8 | as1-1 | 16565.5 | 2756.5 | 6 |
| siRNA4-9 | ss4-9 | as1-1 | 16577.3 | 2761.8 | 6 |
| siRNA4-10 | ss4-4 | as2-5 | 17359.9 | 2892.4 | 6 |
| siRNA4-11 | ss4-1 | as2-5 | 16423.2 | 2736.2 | 6 |
| siRNA2-0 | ss2-0 | as2-0 | 14948.1 | 2490.3 | 6 |

The invention claimed is:
1. A compound of formula (I):

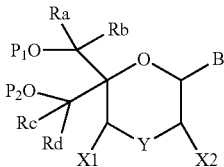

wherein:
B is a heterocyclic nucleobase;
P1 and P2 are each, independently, H, a reactive phosphorus group or a protecting group;
Y is O, NH, NR1 or N—C(=O)—R1, wherein R1 is:
a (C1-C20) alkyl group,
a (C3-C8) cycloalkyl group, or
a group —[C(=O)]m-R2-(O—CH$_2$-CH$_2$)p-R3, wherein:
m is an integer of 0 or 1,
p is an integer ranging from 0 to 10,
R2 is a (C1-C20) alkylene group,
and
R3 is selected from the group consisting of a hydrogen atom, a (C1-C6) alkyl group, a (C1-C6) alkoxy group, a (C3-C8) cycloalkyl group, a (C3-C14) heterocycle, a (C6-C14) aryl group, and a (C5-C14) heteroaryl group,
or
R3 is a cell targeting moiety,
X1 and X2 are each, independently, a hydrogen atom, or a (C1-C6) alkyl group, and
each of Ra, Rb, Rc and Rd is, independently, H or a (C1-C6) alkyl group.

2. The compound of formula (I) according to claim 1, wherein Y is NR1, and wherein R1 is a (C1-C20) alkyl group or a (C3-C8) cycloalkyl group, and P1, P2, Ra, Rb, Rc, Rd, X1, X2 and B are as defined for the general formula (I).

3. The compound of formula (I) according to claim 1, wherein Y is N—C(=O)—R1, and wherein R1 is a (C1-C20) alkyl group,
and P1, P2, Ra, Rb, Rc, Rd, X1, X2 and B have the same meaning as defined for the general formula (I).

4. The compound of formula (I) according to claim 1, wherein Y is NR1 with R1 being —[C(=O)]m-R2-(O—CH2-CH2)p-R3, wherein:
m is an integer of 0 or 1,
p is an integer ranging from 0 to 10,
R2 is a (C1-C20) alkylene group,
and
R3 is a cell targeting moiety,
X1 and X2 are each, independently, a hydrogen atom, or a (C1-C6) alkyl group, and
each of Ra, Rb, Rc and Rd is, independently, H or a (C1-C6) alkyl group.

5. The compound of formula (I) according to claim 4, wherein R1 is the group —[C(=O)]m-R2-(O—CH2-CH2)p-R3, m is 0, p is 0, 1, 2, 3 or 4, R3 is a cell targeting moiety, B, P1, P2, Ra, Rb, Rc, Rd, X1, X2, and R2 are as in the general definition of the compound of formula (I).

6. The compound of formula (I) according to claim 4, wherein:

R2 is an ethylene group, p is 0, or
R2 is a pentylene group, or
R2 is a (C12) alkylene group,
and X1 and X2 are both an hydrogen atom.

7. The compound of formula (I) according to claim 4, wherein R2 is an ethylene group, p is 1, 2, 3, or 4, and X1 and X2 are both an hydrogen atom.

8. The compound of formula (I) according to claim 4, wherein m is 1, p is 0, 1, or 2, R3 is a cell targeting moiety, and R2, B, P1, P2, Ra, Rb, Rc, Rd, X1, X2, are as in the general definition of the compound of formula (I).

9. The compound of formula (I) according to claim 8, wherein R2
is a butylene,
a (C11) alkylene, or
a methylene; wherein
X1 and X2 both represent a hydrogen atom,
and B, P1, P2, Ra, Rb, Rc and Rd are as defined for the general formula (I).

10. The compound of formula (I) according to claim 4, wherein R2 is a methylene group, p is 1 or 2, R3 is a cell targeting moiety, and B, P1, P2, Ra, Rb, Rc, Rd, X1, X2 are as defined for the general formula (I).

11. The compound of formula (I) according to claim 4, wherein R3 is a compound of formula (III):

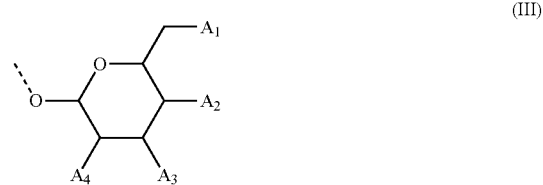

wherein A1, A2 and A3 are O—C(=O)—R4, wherein R4 is a (C1-C6) alkyl or a (C6-C10) aryl group;
A4 is O—C(=O)—R4 or NHC(=O)—R5, wherein R4 is defined as above and R5 is a (C1-C6) alkyl group.

12. The compound of formula (I) according to claim 11, wherein R3 is 3,4,6-Tri-O-acetyl-D-N-Acetylgalactosylamine.

13. The compound of formula (I) according to claim 1, wherein B is selected from the group consisting of a pyrimidine, a substituted pyrimidine, a purine and a substituted purine.

14. The compound of formula (I) according to claim 1, wherein:
one of P1 or P2 is a O-4,4'-dimethoxytrityl group and the other of P1 and P2 is H, a reactive phosphorus group or a protecting group, or
one of P1 and P2 is a 2-cyanoethyl-N,N-diisopropylphosphoramidite group and the other of P1 and P2 is a protecting group, or
one of P1 and P2 is a 2-cyanoethyl-N,N-diisopropylphosphoramidite group and the other of P1 and P2 is 0-4,4'-dimethoxytrityl group,
and Y, B, X1, X2, Ra, Rb, Rc and Rd are as defined in claim 1.

15. A method for preparing a compound of formula (I-A),

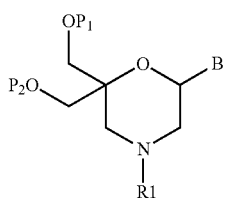
(I-A)

comprising the steps of:
a) oxidation of a compound of formula (X),

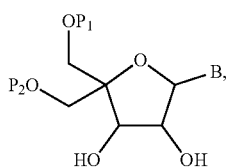
(X)

wherein B is a heterocyclic nucleobase and P1 and P2 each represents independently a protecting group as defined in the general formula (I) according to claim 1, by reaction of the compound of formula (X) with an oxidizing reagent, whereby the following compound of formula (XI) is obtained:

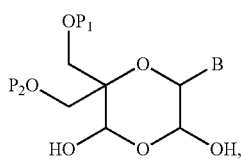
(XI)

and
b) subjecting the compound of formula (XI) to a step of reductive amination in the presence of the compound of formula (XII)

$R1-NH_2$ (XII)

wherein R1 is as defined in the general formula (I) according to claim 1,
for obtaining the compound of formula (I-A):

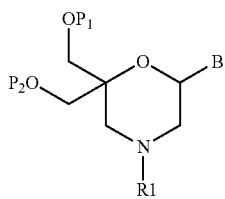
(I-A)

wherein B is a heterocyclic nucleobase and P1 and P2 each represent independently a protecting group as defined in the general formula (I) according to claim 1.

16. A method for preparing a compound of formula (I-E) comprising the steps of:

a) reducing the compound of formula (XI)

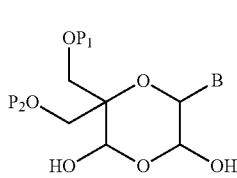
(XI)

wherein P1, P2 and B are as defined in the general formula (I) according to claim 1, so as to obtain a compound of formula (XVII)

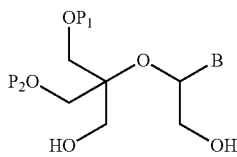
(XVII)

b) transferring the compound of formula (XVII) in the presence of a sulfonylating agent, so as to obtain the compound of formula (XVIII)

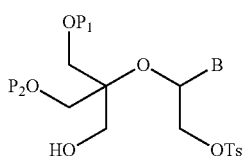
(XVIII)

wherein Ts represents a tosyl group, and
c) subjecting the compound of formula (XVIII) to a basic condition, so as to obtain the compound of formula (I-E)

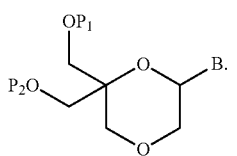
(I-E)

17. A method for preparing a compound of formula (I-E) comprising the steps of:
a) transferring the compound of formula (XVII)

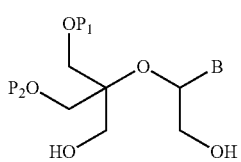
(XVII)

wherein P1, P2 and B are as defined in the general formula (I) according to claim 1, in the presence of an excess of a sulfonylating agent so as to obtain the compound of formula (XIX)

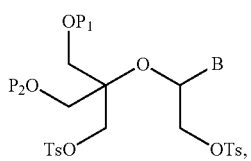

(XIX)

wherein Ts represents a tosyl group,
b) deprotecting the compound of formula (XIX) by removal of group P1 for obtaining the compound of formula (XX)

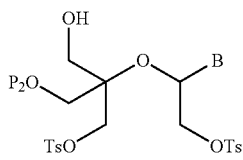

(XX)

c) subjecting the compound of formula (XX) to a basic condition, so as to obtain the compound of formula (XXI)

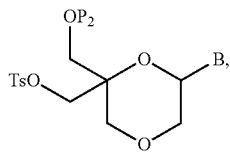

(XXI)

and
d) replacing the tosyl group by the protecting group P1, so as to obtain the compound of formula (I-E)

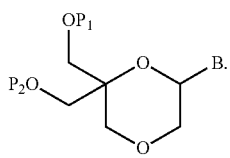

(I-E)

18. A compound of formula (I'):

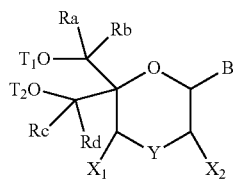

(I')

wherein T1 and T2 are each independently a protecting group, —C(=O)(CH2)r-COOH, or —C(=O)(CH2)r-C(=O)NH—R7, Wherein R7 represents a solid support material, r is an integer selected from 2, 3 and 4, and wherein:

B is a heterocyclic nucleobase;

Y is O, NH, NR1 or N—C(=O)—R1, wherein R1 is:
  a (C1-C20) alkyl group,
  a (C3-C8) cycloalkyl group, or
  a group —[C(=O)]m-R2-(O—CH2-CH2)p-R3, wherein:
    m is an integer of 0 or 1,
    p is an integer ranging from 0 to 10,
    R2 is a (C1-C20) alkylene group,
    and
    R3 is selected from the group consisting of a hydrogen atom, a (C1-C6) alkyl group, a (C1-C6) alkoxy group, a (C3-C8) cycloalkyl group, a (C3-C14) heterocycle, a (C6-C14) aryl group, and a (C5-C14) heteroaryl group,
    or
    R3 is a cell targeting moiety, X1 and X2 are each, independently, a hydrogen atom, or a (C1-C6) alkyl group, and each of Ra, Rb, Rc and Rd is, independently, H or a (C1-C6) alkyl group.

19. The compound of formula (I') according to claim 18, wherein one of T1 and T2 is C(=O)(CH2)r-C(=O)NH—R7,
  wherein R7 is a CPG solid support or a polystyrene solid support,
  and the other one of T1 and T2 is a protecting group, and r is 2.

* * * * *

UNITED STATES PATENT AND TRADEMARK OFFICE
CERTIFICATE OF CORRECTION

| | |
|---|---|
| PATENT NO. | : 11,897,911 B2 |
| APPLICATION NO. | : 16/978603 |
| DATED | : February 13, 2024 |
| INVENTOR(S) | : Armin Hofmeister et al. |

It is certified that error appears in the above-identified patent and that said Letters Patent is hereby corrected as shown below:

In the Claims

At Column 545, Claim number 4, Line number 50, delete "CH2-CH2" and insert -- $CH_2$-$CH_2$ --.

At Column 545, Claim number 5, Line number 62, delete "CH2-CH2" and insert -- $CH_2$-$CH_2$ --.

At Column 546, Claim number 6, Line number 5, delete "an hydrogen atom." and insert -- a hydrogen atom. --.

At Column 546, Claim number 7, Line number 8, delete "an hydrogen atom." and insert -- a hydrogen atom. --.

At Column 550, Claim number 18, Line number 14, delete "C(=O)(CH2)r-COOH, or -C(=O)(CH2)r" and insert -- C(=O)($CH_2$)r-COOH, or -C(=O)($CH_2$)r --.

At Column 550, Claim number 18, Line number 22, delete "[C(=O)]m-R2-(O-CH2-CH2)p-R3," and insert -- [C(=O)]m-R2-(O-$CH_2$-$CH_2$)p-R3, --.

At Column 550, Claim number 19, Line number 41, delete "C(=O)(CH2)r-C(=O)NH" and insert -- C(=O)($CH_2$)r-C(=O)NH --.

Signed and Sealed this
Twelfth Day of November, 2024

Katherine Kelly Vidal
*Director of the United States Patent and Trademark Office*